US012617866B2

(12) United States Patent
Spriggs et al.

(10) Patent No.: US 12,617,866 B2
(45) Date of Patent: May 5, 2026

(54) HUMANIZED ANTIBODIES TO MUCIN-16 AND METHODS OF USE THEREOF

(71) Applicants: MEMORIAL SLOAN KETTERING CANCER CENTER, New York, NY (US); EUREKA THERAPEUTICS, INC., Emeryville, CA (US)

(72) Inventors: David Spriggs, New York, NY (US); Dharmarao Thapi, New York, NY (US); Su Yan, College Station, PA (US); Cheng Liu, Emeryville, CA (US)

(73) Assignees: Memorial Sloan Kettering Cancer Center, New York, NY (US); Eureka Therapeutics, Inc., Emeryville, CA (US)

( * ) Notice: Subject to any disclaimer, the term of this patent is extended or adjusted under 35 U.S.C. 154(b) by 1026 days.

(21) Appl. No.: 17/609,053

(22) PCT Filed: May 7, 2020

(86) PCT No.: PCT/US2020/031886
§ 371 (c)(1),
(2) Date: Nov. 5, 2021

(87) PCT Pub. No.: WO2020/227538
PCT Pub. Date: Nov. 12, 2020

(65) Prior Publication Data
US 2022/0235143 A1     Jul. 28, 2022

Related U.S. Application Data

(60) Provisional application No. 62/845,065, filed on May 8, 2019.

(51) Int. Cl.
| | |
|---|---|
| *C07K 16/30* | (2006.01) |
| *A61K 38/17* | (2006.01) |
| *A61K 39/00* | (2006.01) |
| *A61K 39/395* | (2006.01) |
| *A61K 40/11* | (2025.01) |
| *A61K 40/31* | (2025.01) |
| *A61K 40/42* | (2025.01) |
| *A61K 47/68* | (2017.01) |
| *A61K 51/10* | (2006.01) |
| *A61P 35/00* | (2006.01) |
| *A61P 35/04* | (2006.01) |
| *C07K 14/705* | (2006.01) |
| *C07K 14/725* | (2006.01) |
| *C07K 16/28* | (2006.01) |
| *C12N 5/0783* | (2010.01) |
| *G01N 33/574* | (2006.01) |

(52) U.S. Cl.
CPC ........ *C07K 16/3092* (2013.01); *A61K 38/177* (2013.01); *A61K 38/1774* (2013.01); *A61K 39/39558* (2013.01); *A61K 40/11* (2025.01); *A61K 40/31* (2025.01); *A61K 40/4257*

(2025.01); *A61K 47/6851* (2017.08); *A61K 51/1045* (2013.01); *A61P 35/00* (2018.01); *A61P 35/04* (2018.01); *C07K 14/7051* (2013.01); *C07K 14/70517* (2013.01); *C07K 14/70578* (2013.01); *C07K 16/2809* (2013.01); *C12N 5/0636* (2013.01); *G01N 33/57496* (2013.01); *A61K 2039/505* (2013.01); *A61K 2239/31* (2023.05); *A61K 2239/38* (2023.05); *A61K 2239/59* (2023.05); *C07K 2317/24* (2013.01); *C07K 2317/31* (2013.01); *C07K 2317/34* (2013.01); *C07K 2317/565* (2013.01); *C07K 2317/567* (2013.01); *C07K 2317/622* (2013.01); *C07K 2317/73* (2013.01); *C07K 2317/77* (2013.01); *C07K 2317/92* (2013.01); *C07K 2319/02* (2013.01); *C07K 2319/03* (2013.01); *C07K 2319/30* (2013.01); *C07K 2319/33* (2013.01); *C12N 2510/00* (2013.01); *G01N 2333/4725* (2013.01)

(58) Field of Classification Search
None
See application file for complete search history.

(56) References Cited

U.S. PATENT DOCUMENTS

| | | | |
|---|---|---|---|
| 9,133,532 B2 | 9/2015 | Park et al. | |
| 11,066,480 B2 | 7/2021 | Spriggs et al. | |
| 2013/0171152 A1 | 7/2013 | Spriggs et al. | |
| 2016/0045551 A1* | 2/2016 | Brentjens | A61P 35/02 |

(Continued)

FOREIGN PATENT DOCUMENTS

| | | |
|---|---|---|
| CN | 107667120 A | 2/2018 |
| JP | 2013-529061 A | 7/2013 |
| JP | 2018-509907 A | 4/2018 |

(Continued)

OTHER PUBLICATIONS

Aithal, et al., Expert Opin Ther Targ, 2018, 675-686 (Year: 2018).*

(Continued)

*Primary Examiner* — Michael Szperka
*Assistant Examiner* — Samantha Lake Hopkins
(74) *Attorney, Agent, or Firm* — Foley & Lardner LLP

(57) ABSTRACT

Provided herein are compositions, methods, and uses involving anti-Mucin-16 (MUC16) agents that immunospecifically bind an epitope of Mucin-16 (MUC16). Also provided herein are uses and methods for managing, treating, or preventing disorders, such as cancer and diseases associated with positive MUC16 expression.

12 Claims, 30 Drawing Sheets

Specification includes a Sequence Listing.

(56)                    References Cited

U.S. PATENT DOCUMENTS

2018/0258048  A1      9/2018  Coburn et al.

FOREIGN PATENT DOCUMENTS

| WO | WO-2016/149368 A1 | 9/2016 | |
|----|----|----|----|
| WO | WO-2017/172981 A2 | 10/2017 | |
| WO | WO-2018067331 A1 * | 4/2018 | ........... A61K 39/395 |
| WO | WO-2018/231759 A1 | 12/2018 | |
| WO | WO-2019/079357 A1 | 4/2019 | |

OTHER PUBLICATIONS

International Search Report and Written Opinion on PCT PCT/US2020/031886 dated Oct. 14, 2020.
Liu J.F. et al.: "Phase I study of safety and pharmacokinetics of the anti-MUC16 antibody-drug conjugate DMUC5754A in patients with platinum-resistant ovarian cancer or unresectable pancreatic cancer", Annals of Oncology, vol. 27, No. 11, Nov. 1, 2016 (Nov. 1, 2016), pp. 2124-2130, XP93002159, NL ISSN: 0923-7534, DOI: 10.1093/annonc/mdw401 * abstract *.

* cited by examiner

4H11 and 9C9 MUC16-BINDING FOOTPRINT

(1) Control (Non-Specific Binding)
$[^{89}Zr]$Zr-DFO-mu4H11

(2) Unblocked
+ MUC16 Peptide-2
+ $[^{89}Zr]$Zr-DFO-mu4H11

(3) Blocked
+ MUC16 Peptide-2
+ $[^{89}Zr]$Zr-DFO-mu4H11
+ Excess Unlabeled 9C9

DFO Conjugation of hu4H11

~ 1 DFO per Ab

Flow Cytometry to Assess Binding

Unstained SKOV3 Cells

SKOV3+ Cells + Sec Ab

SKOV3 Cells + Sec Ab

Unstained SKOV3+ Cells

SKOV3 Cells + DFO-hu4H11 + Sec Ab

DFO-hu4H11-bound SKOV3+ Cells

SKOV3+ Cells + DFO-hu4H11 + Sec Ab

PE-Texas Red

$^{89}$Zr-labeling of DFO-hu4H11

[$^{89}$Zr]Zr-DFO-hu4H11

H&E

SKOV3 Tumor

SKOV3+ Tumor

[⁸⁹Zr]Zr-DFO-hu4H11 PET OvCa PDX

FACS analysis of OVCAR3 or SKOV3 or A2780 transfectant cell lines with or without 4H11 or 18C6 mAbs - % PE Positives FACS analysis of OVCAR3, SKOV3 or A2780 transfectant cell lines with pQD-hu-4H11-Alexa647 or pQD-hu18C6-Alexa-647 mAb - Geometric Mean Fluorescence

HUMANIZED ANTIBODIES TO MUCIN-16 AND METHODS OF USE THEREOF

CROSS-REFERENCE TO RELATED APPLICATIONS

This application is a U.S. National Stage Application under 35 U.S.C. § 371 of International Patent Application No. PCT/US2020/031886, filed on May 7, 2020, which claims the benefit of and priority to U.S. Provisional Patent Application No. 62/845,065, filed May 8, 2019, the entire contents of each of which are incorporated herein by reference.

STATEMENT OF GOVERNMENT SUPPORT

This invention was made with government support under P01 CA190174-01, P01 CA190174-02, and P01 CA190174-03, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 12, 2020, is named 115872-0832_SL.txt and is 545,591 bytes in size.

BACKGROUND

Mucins are important biomolecules for cellular homeostasis and protection of epithelial surfaces. Changes in expression of mucins in cancers, such as ovarian cancer, are useful as a biomarker for diagnosis, prognosis and treatment (Singh A P, et al., *Lancet Oncol* 2008; 9(11): 1076-85). MUC16 is a mucin that is over expressed on most ovarian carcinoma cells and is an established surrogate serum marker (CA-125) for the detection and progression of ovarian cancers (Badgwell D, et al., *Dis Markers* 23(5-6):397410 (2007); Bast RC, Jr, et al., *Int J Gynecol Cancer* 15 Suppl 3:274-81 (2005); Fritsche H A, et al., *Clin Chem* 44(7): 1379-80 (1998); and Krivak T C et al., *Gynecol Oncol* 115(1):81-5 (2009)).

MUC16 is a highly glycosylated mucin composed of a large extracellular domain (CA-125), which is cleaved and released, and a retained domain (MUC-CD) (FIG. 1). MUC-CD comprises a non-repeating extracellular domain (MUC16 ectodomain) proximal to a cleavage site, a transmembrane domain, and a cytoplasmic tail with potential phosphorylation sites. Distal to the cleavage site, the released extracellular domain (CA-125) contains 16-20 tandem repeats of 156 amino acids, each with many potential glycosylation sites (O'Brien T J, et al., *Tumor Biol* 22(6): 348-66 (2001)). Since the MUC16 antigen is otherwise expressed only at low levels in normal tissues of the uterus, endometrium, fallopian tubes, ovaries, and serosa of the abdominal and thoracic cavities, MUC16 is a potentially attractive target for immune-based therapies, including the targeting and treatment of cancer.

A significant portion of the extracellular domain of MUC16 is cleaved and secreted (i.e., CA-125), which limits the utility of this portion of MUC16 to be used as a target antigen on ovarian carcinomas. Many reported MUC16 monoclonal antibodies bind to epitopes present on the large secreted CA-125 fraction of the glycoprotein, and not to the retained MUC16 ectodomain (Bellone S *Am J Obstet Gyne-*

*col* 200(1):75 el-10 (2009), Berek J S. *Expert Opin Biol Ther.* 4(7): 1159-65 (2004); O'Brien T J, et al., *Int J Biol Markers* 13(4): 188-95 (1998)). Thus, the generation of new antibodies to the region of MUC16 that is not shed are needed for diagnostic and therapeutic purposes.

SUMMARY OF THE PRESENT TECHNOLOGY

Provided herein are compositions, methods, and uses of anti-Mucin 16 (MUC16) constructs that comprise antibody moieties that immunospecifically bind to Mucin 16 (MUC16), and modulate expression and/or activity of MUC16 for managing or treating MUC16-mediated disorders, such as cancer.

Provided herein, in certain embodiments, are anti-mucin 16 (MUC16) constructs comprising an antibody moiety that immunospecifically recognizes a mucin 16 (MUC16) polypeptide, wherein the antibody moiety comprises a humanized heavy chain variable domain and a humanized light chain variable domain of a 4H11 or 18C6 murine monoclonal antibody. In some embodiments, the antibody moiety comprises (a) (i) a variable heavy (VH) chain comprising a heavy chain complementarity determining region 1 (HC-CDR1), HC-CDR2, and HC-CDR3 of SEQ ID NOS: 17, 18, and 19, respectively, and a heavy chain framework region 1 (HC-FW1), HC-FW2, and HC-FW3 of SEQ ID NOS: 136, 137, and 138, respectively, wherein one or more amino acids selected from amino acid positions 1, 3, 5, 11 and 19 of SEQ ID NO: 136, amino acid positions 5, 7, 8, and 9 of SEQ ID NO: 137, and amino acid positions 12, 14, 18, 22, and 23 of SEQ ID NO: 138 is humanized relative to a mouse HC-FW1, HC-FW2, and HC-FW3 of SEQ ID NOS: 124, 125, and 126, respectively; (ii) a variable light (VL) chain comprising a light chain complementarity determining region 1 (LC-CDR1), LC-CDR2, and LC-CDR3 of SEQ ID NOS: 14, 15, and 16, respectively, and a light chain framework region 1 (LC-FW1), LC-FW2, LC-FW3, and LC-FW4 of SEQ ID NOS: 120, 121, 122, and 123, respectively, wherein one or more amino acids selected from positions 3, 9, 15, 18, and 22 of SEQ ID NO: 120, amino acid positions 7 and 27 of SEQ ID NO: 122, and amino acid positions 3 and 9 of SEQ ID NO: 123, is humanized relative to a mouse LC-FW1, LC-FW2, LC-FW3, and LC-FW4 of SEQ ID NOS: 104, 105, 106 and 107, respectively; or (b)(i) a variable heavy (VH) chain comprising SEQ ID NO: 4 or 5; and (ii) a variable light (VL) chain comprising SEQ ID NO: 2 or 3; or (c) (i) a variable heavy (VH) chain comprising a heavy chain complementarity determining region 1 (HC-CDR1), HC-CDR2, and HC-CDR3 of SEQ ID NOS: 35, 36, and 37, respectively, and a heavy chain framework region 1 (HC-FW1), HC-FW2, HC-FW3, and HC-FW4 of SEQ ID NOS: 175, 176, 177 and 178, respectively, wherein one or more amino acids selected from amino acid positions 10, 11, 12, 13, 15, 19, and 23 of SEQ ID NO: 175, amino acid positions 5, 14, 16, 18, 22, and 23 of SEQ ID NO: 177, and amino acid position 6 of SEQ ID NO: 178 is humanized relative to a mouse HC-FW1, HC-FW2, HC-FW3, and HC-FW4 of SEQ ID NOS: 159, 160, 161, and 162, respectively; and (ii) a variable light (VL) chain comprising a light chain complementarity determining region 1 (LC-CDR1), LC-CDR2, and LC-CDR3 of SEQ ID NOS: 32, 33, and 34, respectively, and a light chain framework region 1 (LC-FW1), LC-FW2, LC-FW3, and LC-FW4 of SEQ ID NOS: 155, 156, 157, and 158, respectively, wherein one or more amino acids selected from positions 7, 9, 11, and 18 of SEQ ID NO: 155, amino acid position 5 of SEQ ID NO: 156, and amino acid positions 9 and 18 of SEQ ID NO: 157, is humanized relative to a mouse LC-FW1, LC-FW2, LC-FW3, and LC-FW4 of SEQ ID NOS: 139, 140, 141, and 142, respectively; or (d) (i) a variable heavy (VH) chain comprising SEQ ID NO: 22 or 23; and (ii) a variable light (VL) chain comprising SEQ ID NO: 20 or 21.

In some embodiments, the HC-FW1 of (a)(i) comprises SEQ ID NO: 130; the HC-FW2 of (a)(i) comprises SEQ ID NO: 131; the HC-FW3 of (a)(i) comprises SEQ ID NO: 132; the LC-FW1 of (a)(ii) comprises SEQ ID NO: 112; the LC-FW2 of (a)(ii) comprises SEQ ID NO: 113; the LC-FW3 of (a)(ii) comprises SEQ ID NO: 114; and/or the LC-FW4 of (a)(ii) comprises SEQ ID NO: 115. In some embodiments, the HC-FW1 of (a)(i) comprises SEQ ID NO: 133; the HC-FW2 of (a)(i) comprises SEQ ID NO: 134; the HC-FW3 of (a)(i) comprises SEQ ID NO: 135; the LC-FW1 of (a)(ii) comprises SEQ ID NO: 116; the LC-FW2 of (a)(ii) comprises SEQ ID NO: 117; the LC-FW3 of (a)(ii) comprises SEQ ID NO: 118; and/or the LC-FW4 of (a)(ii) comprises SEQ ID NO: 119.

In some embodiments, the HC-FW1 of (c)(i) comprises SEQ ID NO: 167; the HC-FW2 of (c)(i) comprises SEQ ID NO: 168; the HC-FW3 of (c)(i) comprises SEQ ID NO: 169; the HC-FW4 of (c)(i) comprises SEQ ID NO: 170; the LC-FW1 of (c)(ii) comprises SEQ ID NO: 147; the LC-FW2 of (c)(ii) comprises SEQ ID NO: 148; the LC-FW3 of (c)(ii) comprises SEQ ID NO: 149; and/or the LC-FW4 of (c)(ii) comprises SEQ ID NO: 150. In some embodiments, the HC-FW1 of (c)(i) comprises SEQ ID NO: 171; the HC-FW2 of (c)(i) comprises SEQ ID NO: 172; the HC-FW3 of (c)(i) comprises SEQ ID NO: 173; the HC-FW4 of (c)(i) comprises SEQ ID NO: 174; the LC-FW1 of (c)(ii) comprises SEQ ID NO: 151; the LC-FW2 of (c)(ii) comprises SEQ ID NO: 152; the LC-FW3 of (c)(ii) comprises SEQ ID NO: 153; and/or the LC-FW4 of (c)(ii) comprises SEQ ID NO: 154.

In some embodiments, the antibody moiety immunospecifically recognizes a human MUC16. In some embodiments, the antibody moiety immunospecifically recognizes a human MUC16 peptide of SEQ ID NO: 53. In some embodiments, the antibody moiety immunospecifically binds to a MUC16 c114 polypeptide comprising the amino acid sequence of SEQ ID NO: 44 or 180. In some embodiments, the MUC16 is glycosylated. In some embodiments, the MUC16 is N-glycosylated at Asn1800 or Asn1806. In some embodiments, the antibody moiety of the anti-mucin 16 (MUC16) constructs provided herein comprises (a)(i) a heavy chain comprising SEQ ID NO: 12 or 13 and (ii) a light chain comprising SEQ ID NO: 10 or 11; or (b)(i) a heavy chain comprising SEQ ID NO: 30 or 31 and (ii) a light chain comprising SEQ ID NO: 28 or 29.

In some embodiments, the antibody moiety of the anti-mucin 16 (MUC16) constructs provided herein immunospecifically binds to the ectodomain of MUC16. In some embodiments, the antibody moiety is a full-length antibody, a Fab, a Fab', a F(ab')2, an Fv, or a single chain Fv (scFv). In some embodiments, the antibody moiety is a single chain Fv (scFv), and the scFv comprises any one of SEQ ID NOs: 53-68. In some embodiments, the VH chain and the VL chain are human VH chain and VL chain. In some embodiments, the antibody moiety is a monoclonal antibody.

In some embodiments, the anti-MUC16 constructs provided herein inhibit in vitro invasion of a tumor cell that expresses MUC16 in a Matrigel invasion assay. In some embodiments, the tumor cell is an ovarian tumor cell.

In some embodiments, the antibody moiety comprises human-derived heavy and light chain constant regions. In some embodiments, the heavy chain constant region has an isotype selected from the group consisting of gamma 1, gamma 2, gamma 3, and gamma 4. In some embodiments, the light chain constant region has an isotype selected from the group consisting of kappa and lambda. In some embodiments, the antibody moiety is an immunoglobulin comprising two identical heavy chains and two identical light chains. In some embodiments, the immunoglobulin is an IgG.

In some embodiments, the anti-MUC16 construct provided herein is monospecific. In some embodiments, the anti-MUC16 construct provided herein is multispecific. In some embodiments, the anti-MUC16 construct provided herein is bispecific. In some embodiments, the anti-MUC16 construct provided herein is a tandem scFv, a diabody (Db), a single chain diabody (scDb), a dual-affinity retargeting (DART) antibody, a F(ab')2, a dual variable domain (DVD) antibody, a knob-into-hole (KiH) antibody, a dock and lock (DNL) antibody, a chemically cross-linked antibody, a heteromultimeric antibody, or a heteroconjugate antibody. In some embodiments, the anti-MUC16 construct provided herein is a tandem scFv comprising two scFvs linked by a peptide linker. In some embodiments, the antibody moiety that immunospecifically recognizes MUC16 is a first antibody moiety, and wherein the anti-MUC16 construct further comprises a second antibody moiety that immunospecifically recognizes a second antigen. In some embodiments, the second antigen is an antigen on the surface of a T cell. In some embodiments, the second antigen is a CD3. In some embodiments, the second antigen is selected from the group consisting of CD3γ, CD3δ, CD3ε, and CD3ζ. In some embodiments, the second antigen is CD3ε. In some embodiments, a multispecific or bispecific anti-MUC16 construct comprises an anti-CD3 antibody moiety. In some embodiments, a multispecific or bispecific anti-MUC16 construct comprises any one of SEQ ID NOS: 42, 69-75, and 88-95.

In some embodiments, the anti-MUC16 construct provided herein is a chimeric antigen receptor (CAR). In some embodiments, the CAR comprises a co-stimulatory domain. In some embodiments, the CAR comprises a CD3 zeta (ζ) chain cytoplasmic signaling domain. In some embodiments, the CAR comprises an scFv of any one of SEQ ID NOS: 53-68. In some embodiments, the CAR comprises any one of SEQ ID NOS: 80-87 and 97-103.

In some embodiments, the anti-MUC16 construct provided herein is further conjugated to a peptide agent, a detection agent, an imaging agent, a therapeutic agent, or a cytotoxic agent.

Also provided herein, in certain embodiments, are polypeptides comprising an amino acid sequence of one or more of SEQ ID NOs: 2-5, 10-13, 20-23 and 28-31, or an amino acid of an anti-MUC16 construct provided herein.

Also provided herein, in certain embodiments, are polynucleotides comprising a nucleic acid sequence encoding one or more polypeptides comprising an amino acid sequence of one or more of SEQ ID NOs: 2-5, 10-13, 20-23 and 28-31, or an amino acid of an anti-MUC16 construct provided herein. Provided herein, in certain embodiments, are vectors comprising the polynucleotide provided herein operably linked to a promoter.

Also provided herein, in certain embodiments, are cells comprising the anti-MUC16 construct provided herein, a polypeptide provided herein, a polynucleotide provided herein, or a vector provided herein. In some embodiments, the cell is a mammalian cell. In some embodiments, the cell is an immune cell. In some embodiments, the cell is a lymphocyte. In some embodiments, the cell is a T cell or a B cell.

Also provided herein, in certain embodiments, are pharmaceutical compositions comprising: a therapeutically effective amount of the anti-MUC16 construct provided herein, a polypeptide provided herein, polynucleotide provided herein, or a vector provided herein; and a pharmaceutically acceptable carrier.

Also provided herein, in certain embodiments, are methods of treating a MUC16-associated disease or disorder in a patient in need thereof, comprising administering to said patient a pharmaceutical composition comprising a therapeutically effective amount of the anti-MUC16 construct provided herein, a polypeptide provided herein, polynucleotide provided herein, or a vector provided herein. In some embodiments, the MUC16-associated disease or disorder is a cancer. In some embodiments, the cancer is a cancer of the ovary, lung, pancreas, breast, uterine, fallopian tube, or primary peritoneum. In some embodiments, the cancer is a metastatic cancer. In some embodiments, the pharmaceutical composition inhibits or reduces metastasis in the patient. In some embodiments, the patient is a human patient.

Also provided herein, in certain embodiments, are methods for producing an effector cell, comprising genetically modifying a cell with one or more nucleic acids encoding the anti-MUC16 construct provided herein.

Also provided herein, in certain embodiments, are methods of comprising introducing one or more nucleic acids encoding the anti-MUC16 construct provided herein into one or more primary cells isolated from a patient and administering cells comprising the one or more nucleic acids to the patient. In some embodiments, the method further comprises expanding the cells prior to administering the cells to the patient. In some embodiments, the primary cells are lymphocytes. In some embodiments, the primary cells are T cells.

In some embodiments, the methods of treatment provided herein further comprises administering a therapeutically effective amount of an additional therapeutic agent to the patient. In some embodiments, the therapeutic agent is an anti-cancer agent. In some embodiments, the therapeutic agent is a chemotherapeutic agent.

Also provided herein, in certain embodiments, are methods of detecting MUC16 in a sample, comprising: (a) contacting the sample with the anti-MUC16 construct provided herein; and (b) detecting the binding, directly or indirectly, between the anti-MUC16 construct and MUC16 that is present in the sample. In some embodiments, the anti-MUC16 construct is conjugated to a detectable label. In some embodiments, the detectable label is a chromogenic, enzymatic, radioisotopic, isotopic, fluorescent, toxic, chemiluminescent, nuclear magnetic resonance contrast agent. In some embodiments, the binding between the anti-MUC16 construct and any MUC16 in the sample is detected directly by detecting the detectable label. In some embodiments, the binding between the anti-MUC16 construct and any MUC16 in the sample is detected indirectly using a secondary antibody.

Also provided herein, in certain embodiments, are methods of diagnosing an individual suspected of having a MUC16-associated disease or disorder, comprising a) administering an effective amount of the anti-MUC16 construct provided herein to the individual; and b) determining the level of the binding, directly or indirectly, between the anti-MUC16 construct and any MUC16 in the individual, wherein a level of the binding above a threshold level indicates that the individual has the MUC16-associated disease or disorder. In some embodiments, the anti-MUC16 construct is conjugated to a detectable label. In some embodiments, the detectable label is a chromogenic, enzymatic, radioisotopic, isotopic, fluorescent, toxic, chemiluminescent, nuclear magnetic resonance contrast agent. In some embodiments, the binding between the anti-MUC16 construct and any MUC16 in the sample is detected directly by detecting the detectable label. In some embodiments, the binding between the anti-MUC16 construct and any MUC16 in the sample is detected indirectly using a secondary antibody.

A method of diagnosing an individual suspected of having a MUC16-associated disease or disorder, comprising a) contacting a sample comprising cells derived from the individual with the anti-MUC16 construct provided herein; and b) determining the number of cells in the sample bound to the anti-MUC16 construct, wherein a value for the number of cells bound to the anti-MUC16 construct above a threshold level indicates that the individual has the MUC16-associated disease or disorder. In some embodiments, the anti-MUC16 construct is conjugated to a detectable label. In some embodiments, the detectable label is a chromogenic, enzymatic, radioisotopic, isotopic, fluorescent, toxic, chemiluminescent, nuclear magnetic resonance contrast agent. In some embodiments, the binding between the anti-MUC16 construct and any MUC16 in the sample is detected directly by detecting the detectable label. In some embodiments, the binding between the anti-MUC16 construct and any MUC16 in the sample is detected indirectly using a secondary antibody.

Also provided herein, in certain embodiments, are uses of anti-MUC16 constructs, anti-MUC16 polypeptides, polynucleotides encoding anti-MUC16 constructs or anti-MUC16 polypeptides, vectors comprising the polynucleotides, or cells comprising any the polypeptides and polynucleotides thereof provided herein for the treatment of a disease or disorder associated with positive MUC16 expression. In some embodiments, the disease or disorder associated with positive MUC16 expression is a cancer.

Also provided herein, in certain embodiments, are uses of the anti-MUC16 constructs, anti-MUC16 polypeptides, polynucleotides encoding anti-MUC16 constructs or anti-MUC16 polypeptides, vectors comprising the polynucleotides, or cells comprising any the polypeptides and polynucleotides thereof provided herein in the manufacture of a medicament for the treatment of a disease or disorder associated with positive MUC16 expression. In some embodiments, the disease or disorder associated with positive MUC16 expression is a cancer.

Also provided herein, in certain embodiments, are uses of anti-MUC16 constructs, anti-MUC16 polypeptides, polynucleotides encoding anti-MUC16 constructs or anti-MUC16 polypeptides, vectors comprising the polynucleotides, or cells comprising any the polypeptides and polynucleotides thereof provided herein for the diagnosis of a disease or disorder associated with positive MUC16 expression. In some embodiments, the disease or disorder associated with positive MUC16 expression is a cancer

BRIEF DESCRIPTION OF THE DRAWINGS

FIG. 1B shows schematic and amino acid sequence of the truncated form of MUC16, called MUC16 c114 (SEQ ID NO: 44), which includes the 58 amino acid ectodomain, the 25 amino acid transmembrane domain, and the 31 amino acid cytoplasmic tail. Numbering in figure is based on original publication identifying Muc16, Yin and Lloyd (2001) *J Biol Chem* 276: 27371-27375.

FIG. 2 shows an amino acid alignment between wildtype MUC16-C114 (SEQ ID NO: 180) and the N30 mutant MUC16-C114 (SEQ ID NO: 181) ectodomains. Figure also discloses SEQ ID NO: 182.

FIG. 3A shows a cartoon representation of the molecular layout of the MUC16 superstructure highlighting the 4 distinct regions: N-terminal domain, tandem repeat [TR] region, SEA (Sperm protein, Enterokinase and Agrin) domains, and carboxy-terminus domain including the juxtamembrane [JM] region or ectodomain and the transmembrane [TM] region. The sequence of MUC16 peptide-2 (SEQ ID NO: 183), which is found within the ectodomain region and is the target-binding site for antibodies tested in this study, is shown. FIG. 3B provides graphs showing results from the saturation binding assays for radiolabeled variants of the two lead antibody candidates. The binding affinity curves for [$^{89}$Zr]Zr-DFO-9C9 (left) and [$^{89}$Zr]Zr-DFO-4H11 (right) (solid lines) versus control antibodies (dashes) are shown. FIG. 3C illustrates the cellular internalization profiles of [$^{89}$Zr]Zr-DFO-4H11 versus [$^{89}$Zr]Zr-DFO-9C9 showing minimum uptake of either antibody at 4° C., but relatively rapid uptake of [$^{89}$Zr]Zr-DFO-4H11 at 37° C. compared to the slow uptake of [$^{89}$Zr]Zr-DFO-9C9 in SKOV3$^{c114}$ cells; FIG. 3D provides a graphic representation showing comparable in vitro serum stability of [$^{89}$Zr]Zr-DFO-4H11 versus [$^{89}$Zr]Zr-DFO-9C9. FIG. 3E provides a graphic representation showing blockade of [$^{89}$Zr]Zr-DFO-4H11 binding to biotinylated MUC16 peptide-2 captured on a streptavidin-functionalized magnetic beads in presence of an excess of unlabeled 9C9 antibody (compare Unblocked (middle bar) to Blocked (right bar); control sample without MUC16 peptide-2 is also shown (left bar)).

FIG. 4A provides representative serial PET images [top: coronal slice; bottom: maximum intensity projection (MIP)] of [$^{89}$Zr]Zr-DFO-9C9 (170-200 μCi; 6.29-7.4 MBq suspended in 200 μL of chelex-treated PBS injected via the lateral tail vein) in SKOV3$^{c114}$ xenografts showing tumor (T) delineation at 24 h post-injection (p.i.) and progressively increasing uptake of activity in the tumor up to 96 h p.i. High concentrations of activity visible in the liver (L) and kidneys (K) at early time points, but gradually reduced at later time points. FIG. 4B provides representative serial PET images [top: coronal slice; bottom: maximum intensity projection (MIP)] of [$^{89}$Zr]Zr-DFO-4H11 (170-200 μCi; 6.29-7.4 MBq suspended in 200 μL of chelex-treated PBS injected via the lateral tail vein) in SKOV3$^{c114}$ xenografts delineating the tumor (T) and lymph nodes (LN) at 24 h post-injection (p.i.), with the PET signal intensity in the tumor increasing progressively up to 96 h p.i. High contrast PET images were obtained with [$^{89}$Zr]Zr-DFO-4H11 and liver (L) and lymph nodes (LN) were the only non-tumor tissues displaying background activity at later time points. FIG. 4C provides a graphical representation of the in vivo biodistribution of [$^{89}$Zr]Zr-DFO-9C9 and [$^{89}$Zr]Zr-DFO-4H11 in SKOV3$^{c114}$ xenografts showing high and comparable tumoral uptake of activity associated with both the radioimmunoconjugates. The uptake of [$^{89}$Zr]Zr-DFO-9C9 and [$^{89}$Zr]Zr-DFO-4H11 in SKOV3$^{c114}$ tumors could be blocked in the presence of an excess of the unlabeled antibody co-injected with the respective radiolabeled variants of the antibody, and was significantly higher than that of the isotype control. Differences between the in vivo activity concentrations in non-tumor tissues were most notable between the kidneys and axillary lymph nodes (LN). [$^{89}$Zr]Zr-DFO-9C9 displayed significantly higher activity concentration in the kidney than [$^{89}$Zr]Zr-DFO-4H11 and the isotype control whereas [$^{89}$Zr]Zr-DFO-4H11 displayed significantly higher activity concentration in the LN of mice injected with [$^{89}$Zr]Zr-DFO-9C9 or isotype control.  indicates p-value 0.005; * indicates p-value 0.0005; * indicates p-value 0.00005. FIG. 4D** provides a bar graph displaying a comparison between the in vivo radiopharmacologic profiles of [$^{89}$Zr]Zr-DFO-9C9 versus [$^{89}$Zr]Zr-DFO-4H11 as evaluated from the tumor-to-background (T:B) ratios of the activity concentration in vital organs of interest.

FIG. 5A provides a cartoon representation of DFO-conjugated humanized 4H11 antibody (DFO-hu4H11). FIG. 5B provides a histogram from flow cytometry analysis showing the binding of DFO-hu4H11 to SKOV3$^{c114}$ cells (or SKOV3+ cells, solid lines) versus lack of binding to SKOV3 cells (dotted lines); FIG. 5C provides a cartoon representation of $^{89}$Zr-labeled hu4H11 antibody ([$^{89}$Zr]Zr-DFO-hu4H11). FIG. 5D provides a quality control of [$^{89}$Zr]Zr-DFO-hu4H11 showing high radiochemical purity on instant thin layer chromatograph analysis of crude labeling reaction versus size-exclusion purified radioimmunoconjugate; FIG. 5E provides a graphical representation of the low non-specific binding and high (>90%) immunoreactive fraction of [$^{89}$Zr]Zr-DFO-hu4H11 to biotinylated MUC16 peptide-2 captured on streptavidin-functionalized DynaBeads. Specificity of target-binding was established by virtue of blockade of [$^{89}$Zr]Zr-DFO-hu4H11 binding to MUC16 peptide-2 on magnetic beads in presence of a huge excess of unlabeled DFO-hu4H11.

FIG. 6A provides representative serial PET images [top: coronal slices; bottom: maximum intensity projection (MIP)] of [$^{89}$Zr]Zr-DFO-hu4H11 (200 μCi; 7.4 MBq suspended in 200 μL of chelex-treated PBS injected via the lateral tail vein) in SKOV3$^{c114}$ xenografts showing clear delineation of the tumor (T) at 36 h followed by the gradual accretion of a vast majority of injected activity in the tumor at 96 h p.i.; FIG. 6B illustrates in vivo biodistribution of [$^{89}$Zr]Zr-DFO-hu4H11 showing high activity concentration in the tumor, with most non-tumor background organs having 8% ID/g except the bone and axillary lymph nodes. The tumoral uptake of activity could be blocked by co-injection of a 40-fold excess of unlabeled DFO-hu4H11.  indicates p-value 0.005; FIG. 6C** provides a bar graph displaying the in vivo radiopharmacologic profile of [$^{89}$Zr]Zr-DFO-hu4H11 as evaluated from the tumor-to-background (T:B) ratios of the activity concentration in vital organs of interest.

FIG. 7A provides representative serial PET images [top: coronal slices; middle: transverse slice; bottom: PET-CT overlay of the maximum intensity projection (MIP)] of [$^{89}$Zr]Zr-DFO-hu4H11 (250 μCi; 9.25 MBq suspended in 200 μL of chelex-treated PBS injected via the lateral tail vein) in bilateral xenografts (left shoulder: SKOV3$^{c114}$ tumor; right shoulder: SKOV3 tumor) showing preferential and targeted uptake in SKOV3$^{c114}$ tumors. FIG. 7B provides representative autoradiography images from the ex vivo analysis of the harvested bilateral tumors (from mouse shown in 7A) revealing higher and heterogeneous distribution of signal in SKOV3$^{c114}$ tumor (dashed circle: high activity hot spot dashed triangle: low-no activity cold spot) in comparison to a near absence of any signal in the SKOV3 tumor exposed for autoradiography in the same cassette. FIG. 7C provides hematoxylin and eosin (H&E) staining of the tumor sections (shown in 7B) revealing areas of necrosis (dashed triangle) versus areas with nests of actively dividing tumor cells (dashed circle). FIG. 7D provides comparative H&E staining of formalin-fixed paraffin-embedded SKOV3$^{c114}$ (left) versus SKOV3 (right) tumors showing distinct differences in the tumor architecture and morphology of cells comprising the tumors.

FIG. 8A provides representative PET image [left: coronal slice; right maximum intensity projection (MIP)] of [$^{89}$Zr]Zr-DFO-hu4H11 (150 µCi; 5.55 MBq suspended in 200 µL of chelex-treated PBS injected via the lateral tail vein) at 72 h p.i. in nude mice bearing subcutaneously xenografted MUC16-positive OVCAR3 tumor on the right shoulder. FIG. 8B provides representative PET images [MIPs] of [$^{89}$Zr]Zr-DFO-hu4H11 (150 µCi; 5.55 MBq suspended in 200 µL of chelex-treated PBS injected via the lateral tail vein) at 72 h p.i. in two mice bearing PDXs of HGSOC tumor on the right shoulder and showing high activity concentration in the tumors (T) and some persistent activity in the blood pool (BP) including the heart and descending aorta.

FIG. 9A shows mean fluorescence for binding of the 4H11 and 18C6 mouse mAbs antibodies to the assayed cell lines. FIG. 9B shows fluorescence percentage positive cells for binding of the 4H11 and 18C6 mouse mAbs antibodies to the assayed cell lines. FIG. 9C shows mean fluorescence for binding of the 4H11 and 18C6 humanized antibodies to the assayed cell lines. FIG. 9D shows fluorescence percentage positive cells for binding of the 4H11 and 18C6 humanized antibodies to the assayed cell lines.

DETAILED DESCRIPTION

Figure 1A:
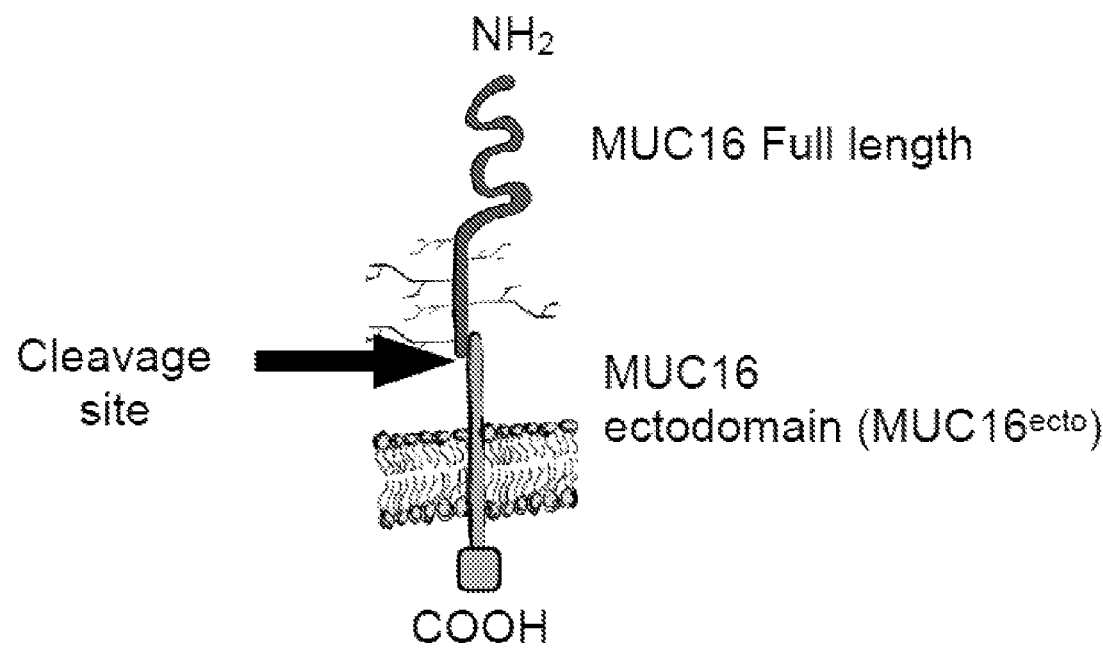
FIG. 1A shows a schematic illustration of the structure of MUC16.

The present application in one aspect provides anti-MUC16 antibody agents, such as anti-MUC16 constructs that comprise an antibody moiety that specifically recognizes an epitope of MUC16, such as an epitope of the retained extracellular domain of MUC16 (MUC16 ectodomain).

Using phage display technology, scFvs that are specific for the retained extracellular domain of human MUC16 were identified. Flow cytometry assays demonstrated that these antibodies recognize MUC16-expressing cancer cell lines. The present application thus provides anti-MUC16 antibody agents, such as anti-MUC16 constructs that comprise an antibody moiety that immunospecifically binds MUC16. The anti-MUC16 antibody agents include, for example, anti-MUC16 antibodies, e.g., full-length anti-MUC16 antibodies and antigen-binding fragments thereof, anti-MUC16 scFvs, anti-MUC16 antibody fusion proteins (e.g., anti-MUC16 Fc fusion proteins and chimeric antigen receptors (CAR)), multi-specific antibodies, e.g., bispecific antibodies, and anti-MUC16 antibody conjugates (i.e., anti-MUC16 immunoconjugates) thereof.

In another aspect, provided are nucleic acids encoding the anti-MUC16 antibody agents, such as anti-MUC16 antibodies, e.g., full-length anti-MUC16 antibodies and antigen-binding fragments thereof, anti-MUC16 scFvs, anti-MUC16 antibody fusion proteins (e.g., anti-MUC16 Fc fusion proteins and chimeric antigen receptors (CAR)), multi-specific antibodies, e.g., bispecific antibodies, and anti-MUC16 antibody conjugates (i.e., anti-MUC16 immunoconjugates) thereof.

In another aspect, provided are compositions, such as pharmaceutical compositions, comprising an anti-MUC16 antibody agent, such as full-length anti-MUC16 antibodies and antigen-binding fragments thereof, anti-MUC16 scFvs, anti-MUC16 antibody fusion proteins (e.g., anti-MUC16 Fc fusion proteins and chimeric antigen receptors (CAR)), multi-specific antibodies, e.g., bispecific antibodies, and anti-MUC16 antibody conjugates (i.e., anti-MUC16 immunoconjugates) thereof.

Also provided are methods of making and using the anti-MUC16 antibody agents and antibodies, such as for treating cancer, as well as kits and articles of manufacture useful for such methods.

Also disclosed herein are kits for the detection and/or treatment of MUC16-associated pathologies, comprising at least one anti-MUC16 antibody agent of the present technology, or a functional variant (e.g., substitutional variant) thereof and instructions for use. In certain embodiments, the anti-MUC16 antibody agent is coupled to one or more detectable labels. In one embodiment, the one or more detectable labels comprise a radioactive label, a fluorescent label, or a chromogenic label.

Additionally or alternatively, in some embodiments, the kit further comprises a secondary antibody that specifically binds to an anti-MUC16 antibody agent described herein. In some embodiments, the secondary antibody is coupled to at least one detectable label selected from the group consisting of a radioactive label, a fluorescent label, or a chromogenic label.

Definitions

Unless defined otherwise, all technical and scientific terms used herein have the meaning commonly understood by a person skilled in the art to which this disclosure belongs. The following references provide one of skill with a general definition of many of the terms used in the present technology: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al., (eds.), Springer Verlag (1991); and Hale & Marham, The Harper Collins Dictionary of Biology (1991). As used herein, the following terms have the meanings ascribed to them below, unless specified otherwise. The terminology used herein is for the purpose of describing particular embodiments only and is not intended to be limiting of the disclosure.

As used herein, the term "MUC16" or "MUC16 polypeptide" or "MUC16 peptide" refers to the MUC16 tethered mucin protein as described in Yin B W and Lloyd K O, 2001, *J Biol Chem.* 276(29):27371-5. GenBank™ accession number NP_078966.2 (SEQ ID NO: 1) provides an exemplary human MUC16 nucleic acid sequence. GenBank™ accession number NP 078966.2 (SEQ ID NO: 1) provides an exemplary human MUC16 amino acid sequence. Native MUC16 comprises an intracellular domain, a transmembrane domain, an ectodomain proximal to the putative cleavage site, and a large, heavily glycosylated region of 12-20 repeats, each 156 amino acids long (FIG. 1A). "Immature" MUC16 refers to SEQ ID NO: 1, which comprises the MUC16 signal sequence (amino acid residues 1-60 of SEQ ID NO: 1). "Mature MUC16" refers to native MUC16 as expressed on the cell surface, i.e., where the signal sequence has been removed by cellular processing, for example, SEQ ID NO: 51, where the first 60 amino acid residues of SEQ ID NO: 1 have been removed (i.e., SEQ ID NO: 1 is the "immature" form of MUC16).

Figure 1B:
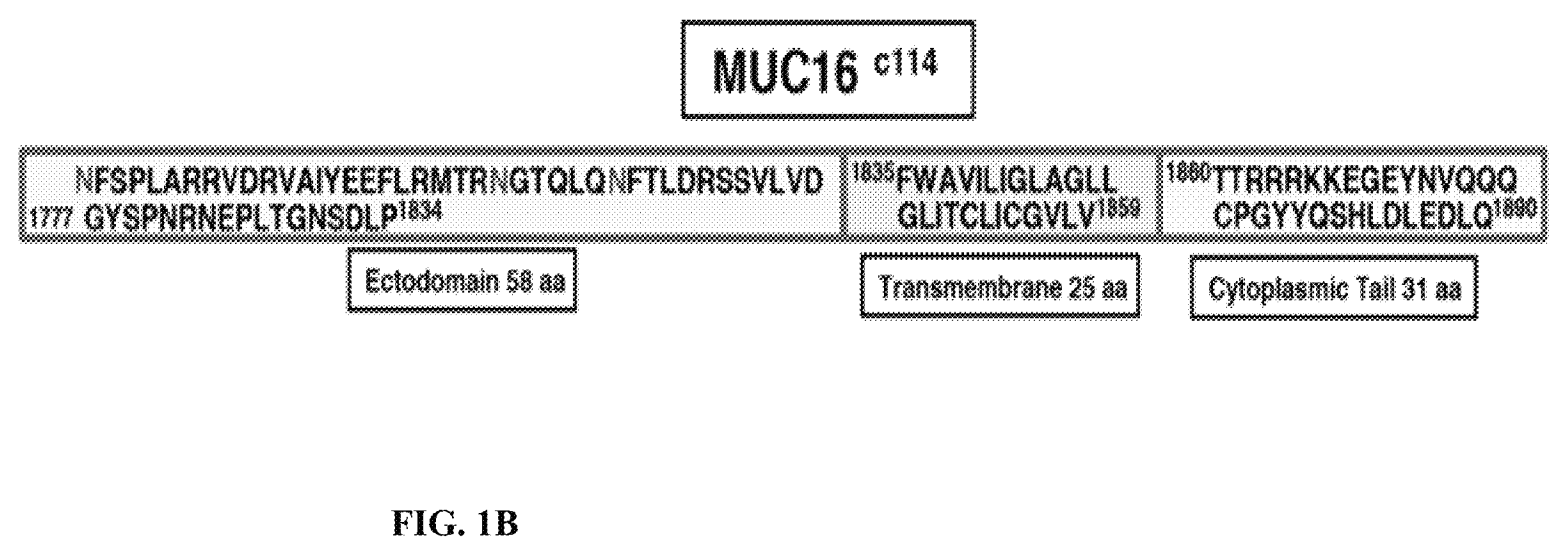

The polypeptide represented by the amino acid sequence of SEQ ID NO: 44 or 180 is referred to herein as MUC16 C114 and consists of the C-terminal 114 amino acid residues of mature MUC16 (SEQ ID NO: 51 being the sequence of mature MUC16). MUC16 C114 comprises a 58 amino acid ectodomain, a 25 amino acid transmembrane domain and a 31 amino acid cytoplasmic tail (FIG. 1). MUC16c114 is capable of being N-glycosylated at the asparagine amino acid residues at positions 1, 24, and 30 of SEQ ID NO: 44 or 180 (also referred to as amino acid positions Asnl777, Asnl800, and Asnl806 according the original MUC16 publication Yin B W and Lloyd K O, 2001, *J Biol Chem.* 276(29):27371-5).

As used herein, the singular forms "a", "an" and "the" are intended to include the plural forms as well, unless the context clearly indicates otherwise.

As used herein, the terms "about" when used to modify a numeric value or numeric range, indicate that deviations of 5% to 10% above and 5% to 10% below the value or range remain within the intended meaning of the recited value or range.

As used herein, the term "administration" of an agent to a subject includes any route of introducing or delivering the agent to a subject to perform its intended function. Administration can be carried out by any suitable route, including, but not limited to, intravenously, intramuscularly, intraperitoneally, subcutaneously, and other suitable routes as described herein. Administration includes self-administration and the administration by another.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form and a second plurality are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter code.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments that lack the Fc fragment of intact antibody, clear more rapidly from the circulation, and may have less non-specific tissue binding of an intact antibody (Wahl et al., *J. Nucl. Med.* 24:316-325 (1983)). The antibodies of the present technology comprise whole native antibodies, monoclonal antibodies, human antibodies, humanized antibodies, camelised antibodies, multispecific antibodies, bispecific antibodies, chimeric antibodies, Fab, Fab', single chain V region fragments (scFv), single domain antibodies (e.g., nanobodies and single domain camelid antibodies), $V_{NAR}$ fragments, Bi-specific T-cell engager antibodies, minibodies, disulfide-linked Fvs (sdFv), and anti-idiotypic (anti-Id) antibodies, intrabodies, fusion polypeptides, unconventional antibodies and antigen-binding fragments of any of the above. In particular, antibodies include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgA1 and IgA2) or subclass.

In certain embodiments, an antibody is a glycoprotein comprising at least two heavy (H) chains and two light (L) chains inter-connected by disulfide bonds. Each heavy chain is comprised of a heavy chain variable region (abbreviated herein as $V_H$) and a heavy chain constant ($C_H$) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Cl q) of the classical complement system. As used herein interchangeably, the terms "antigen-binding portion", "antigen-binding fragment", or "antigen-binding region" of an antibody, refer to the region or portion of an antibody that binds to the antigen and which confers antigen specificity to the antibody; fragments of antigen-binding proteins, for example, antibodies includes one or more fragments of an antibody that retain the ability to specifically bind to an antigen (e.g., an peptide/HLA complex). It has been shown that the antigen-binding function of an antibody can be performed by fragments of a full-length antibody. Examples of antigen-binding portions encompassed within the term "antibody fragments" of an antibody include a Fab fragment, a monovalent fragment consisting of the $V_L$, $V_H$, $C_L$ and CHI domains; a $F(ab)_2$ fragment, a bivalent fragment comprising two Fab fragments linked by a disulfide bridge at the hinge region; a Fd fragment consisting of the $V_H$ and CHI domains; a Fv fragment consisting of the $V_L$ and $V_H$ domains of a single arm of an antibody; a dAb fragment (Ward et al., *Nature* 341: 544-546 (1989)), which consists of a $V_H$ domain; and an isolated complementarity determining region (CDR).

Antibodies and antibody fragments can be wholly or partially derived from mammals (e.g., humans, non-human primates, goats, guinea pigs, hamsters, horses, mice, rats, rabbits and sheep) or non-mammalian antibody producing animals (e.g., chickens, ducks, geese, snakes, urodele amphibians). The antibodies and antibody fragments can be produced in animals or produced outside of animals, such as from yeast or phage (e.g., as a single antibody or antibody fragment or as part of an antibody library).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fv (scFv); see e.g., Bird et al., *Science* 242:423-426 (1988); and Huston et al., *Proc. Natl. Acad. Sci.* 85: 5879-5883 (1988). These antibody fragments are obtained using conventional techniques known to those of ordinary skill in the art, and the fragments are screened for utility in the same manner as are intact antibodies.

An "isolated antibody" or "isolated antigen-binding protein" is one which has been identified and separated and/or recovered from a component of its natural environment. "Synthetic antibodies" or "recombinant antibodies" are generally generated using recombinant technology or using peptide synthetic techniques known to those of skill in the art.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$:$V_L$ heterodimer. The heavy ($V_H$) and light chains ($V_L$) are either joined directly or joined by a peptide-encoding linker (e.g., about 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain.

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al., *Proc. Nat. Acad. Sci. USA*, 85:5879-5883 (1988)). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., *Hybridoma* (Larchmt) 27(6):455-51 (2008); Peter et al., *J Cachexia Sarcopenia Muscle* (2012); Shieh et al., *J Imunol* 183(4):2277-85 (2009); Giomarelli et al., *Thromb Haemost* 97(6):955-63 (2007); Fife et al., *J Clin Invst* 116(8):2252-61 (2006); Brocks et al., *Immunotechnology* 3(3): 173-84 (1997); Moosmayer et al., *Ther Immunol* 2(10):31-40 (1995) Agonistic scFvs having stimulatory activity have been described (see, e.g., Peter et al., *J Biol Chem* 25278(38):36740-7 (2003); Xie et al., *Nat Biotech* 15(8):768-71 (1997); Ledbetter et al., *Crit Rev Immunol* 17(5-6):427-55 (1997); Ho et al., *Bio Chim Biophys Acta* 1638(3):257-66 (2003)).

As used herein, an "antigen" refers to a molecule to which an antibody (or antigen binding fragment thereof) can selectively bind. The target antigen may be a protein, carbohydrate, nucleic acid, lipid, hapten, or other naturally occurring or synthetic compound. In some embodiments, the target antigen may be a polypeptide (e.g., a MUC16 polypeptide). An antigen may also be administered to an animal to generate an immune response in the animal.

The term "antigen binding fragment" refers to a fragment of the whole immunoglobulin structure which possesses a part of a polypeptide responsible for binding to antigen. Examples of the antigen binding fragment useful in the present technology include scFv, $(scFv)_2$, scFvFc, Fab, Fab' and $F(ab')_2$, but are not limited thereto.

As used herein, the term "biological sample" or "sample" means sample material derived from living cells. Biological samples may include tissues, cells, protein or membrane extracts of cells, and biological fluids (e.g., ascites fluid or cerebrospinal fluid (CSF)) isolated from a subject, as well as tissues, cells and fluids present within a subject. Biological samples of the present technology include, but are not limited to, samples taken from breast tissue, renal tissue, the uterine cervix, the endometrium, the head or neck, the gallbladder, parotid tissue, the prostate, the brain, the pituitary gland, kidney tissue, muscle, the esophagus, the stomach, the small intestine, the colon, the liver, the spleen, the pancreas, thyroid tissue, heart tissue, lung tissue, the bladder, adipose tissue, lymph node tissue, the uterus, ovarian tissue, adrenal tissue, testis tissue, the tonsils, thymus, blood, hair, buccal, skin, serum, plasma, CSF, semen, prostate fluid, seminal fluid, urine, feces, sweat, saliva, sputum, mucus, bone marrow, lymph, and tears. Biological samples can also be obtained from biopsies of internal organs or from cancers. Biological samples can be obtained from subjects for diagnosis or research or can be obtained from non-diseased individuals, as controls or for basic research. Samples may be obtained by standard methods including, e.g., venous puncture and surgical biopsy. In certain embodiments, the biological sample is a tissue sample obtained by needle biopsy.

"Bispecific antibody" or "BsAb", as used herein, refers to an antibody that can bind simultaneously to two targets that have a distinct structure, e.g., two different target antigens, or two different epitopes on the same target antigen. A variety of different bispecific antibody structures are known in the art. In some embodiments, each antigen binding moiety in a bispecific antibody includes $V_H$ and/or $V_L$ regions; in some such embodiments, the $V_H$ and/or $V_L$ regions are those found in a particular monoclonal antibody. In some embodiments, the bispecific antibody contains two antigen binding moieties, each including $V_H$ and/or $V_L$ regions from different monoclonal antibodies. In some embodiments, the bispecific antibody contains two antigen binding moieties, wherein one of the two antigen binding moieties includes an immunoglobulin molecule having $V_H$ and/or $V_L$ regions that contain CDRs from a first monoclonal antibody, and the other antigen binding moiety includes an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

As used herein, the term "conjugated" refers to the association of two molecules by any method known to those in the art. Suitable types of associations include chemical bonds and physical bonds. Chemical bonds include, for example, covalent bonds and coordinate bonds. Physical bonds include, for instance, hydrogen bonds, dipolar interactions, van der Waal forces, electrostatic interactions, hydrophobic interactions and aromatic stacking.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term "consensus FR" means a framework (FR) antibody region in a consensus immunoglobulin sequence. The FR regions of an antibody do not contact the antigen.

As used herein, the term "effective amount" refers to a quantity sufficient to achieve a desired therapeutic and/or prophylactic effect, e.g., an amount which results in the prevention of, or a decrease in a disease or condition described herein or one or more signs or symptoms associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression can include splicing of the mRNA in a eukaryotic cell. The expression level of a gene can be determined by measuring the amount of mRNA or protein in a cell or tissue sample. In one aspect, the expression level of a gene from one sample can be directly compared to the expression level of that gene from a control or reference sample. In another aspect, the expression level of a gene from one sample can be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell.

The term "linker" refers to synthetic sequences (e.g., amino acid sequences) that connect or link two sequences, e.g., that link two polypeptide domains. In some embodiments, the linker contains 1, 2, 3, 4, 5, 6, 7, 8, 9, or 10 of amino acid sequences.

As used herein, "humanized" forms of non-human (e.g., murine) antibodies are chimeric antibodies which contain minimal sequence derived from non-human immunoglobulin. For the most part, humanized antibodies are human immunoglobulins in which hypervariable region residues of the recipient are replaced by hypervariable region residues from a non-human species (donor antibody) such as mouse, rat, rabbit or nonhuman primate having the desired specificity, affinity, and capacity. In some embodiments, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance such as binding affinity. Generally, the humanized antibody will comprise substantially all of at least one, and typically two, variable domains (e.g., Fab, Fab', F(ab')$_2$, or Fv), in which all or substantially all of the hypervariable loops correspond to those of a non-human immunoglobulin and all or substantially all of the FR regions are those of a human immunoglobulin consensus FR sequence although the FR regions may include one or more amino acid substitutions that improve binding affinity. The number of these amino acid substitutions in the FR are typically no more than 6 in the H chain, and in the L chain, no more than 3. The humanized antibody optionally may also comprise at least a portion of an immunoglobulin constant region (Fc), typically that of a human immunoglobulin. For further details, see Jones et al., *Nature* 321: 522-525 (1986); Reichmann et al., *Nature* 332:323-329 (1988); and Presta, *Curr. Op. Struct. Biol.* 2:593-596 (1992). See e.g., Ahmed & Cheung, *FEBS Letters* 588(2):288-297 (2014).

As used herein, the term "hypervariable region" refers to the amino acid residues of an antibody which are responsible for antigen-binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, MD. (1991)) and/or those residues from a "hypervariable loop" (e.g., residues 26-32 (L1), 50-52 (L2)

and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')$_2$" refers to an antibody fragment generated by pepsin digestion of whole IgG antibodies, wherein this fragment has two antigen binding (ab') (bivalent) regions, wherein each (ab$^1$) region comprises two separate amino acid chains, a part of a H chain and a light (L) chain linked by an S—S bond for binding an antigen and where the remaining H chain portions are linked together. A "F(ab')$_2$" fragment can be split into two individual Fab' fragments.

As used herein, "CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U. S. Department of Health and Human Services, National Institutes of Health (1987). Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat system (Kabat, E. A., et al., Sequences of Proteins of Immunological Interest, Fifth Edition, U.S. Department of Health and Human Services, NIH Publication No. 91-3242(1991)).

As used herein, the term "constant region" or "constant domain" is interchangeable and has its meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, an "epitope" is a term in the art and can refer to a localized region of an antigen to which an antibody can immunospecifically bind. An epitope can be, e.g., contiguous amino acids of a polypeptide (linear or contiguous epitope) or an epitope can, e.g., come together from two or more noncontiguous regions of a polypeptide or polypeptides (conformational, non-linear, discontinuous, or noncontiguous epitope).

As used herein, the term "ligand" refers to a molecule that binds to a receptor. In particular, the ligand binds a receptor on another cell, allowing for cell-to-cell recognition and/or interaction.

As used herein, the term "affinity" is meant a measure of binding strength. Without being bound to theory, affinity depends on the closeness of stereochemical fit between antibody combining sites and antigen determinants, on the size of the area of contact between them, and on the distribution of charged and hydrophobic groups. Affinity also includes the term "avidity," which refers to the strength of the antigen-antibody bond after formation of reversible complexes (e.g., either monovalent or multivalent). Methods for calculating the affinity of an antibody for an antigen are known in the art, comprising use of binding experiments to calculate affinity. Antibody activity in functional assays (e.g., flow cytometry assay) is also reflective of antibody affinity. Antibodies and affinities can be phenotypically characterized and compared using functional assays (e.g., flow cytometry assay). Nucleic acid molecules useful in the presently disclosed subject matter include any nucleic acid molecule that encodes a polypeptide or a fragment thereof. In certain embodiments, nucleic acid molecules useful in the presently disclosed subject matter include nucleic acid molecules that encode an antibody or an antigen-binding portion thereof. Such nucleic acid molecules need not be 100% identical with an endogenous nucleic acid sequence, but will typically exhibit substantial identity. Polynucleotides having "substantial homology" or "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger, *Methods Enzymol.* 152:399 (1987); Kimmel, A. R., *Methods Enzymol.* 152:507 (1987)).

As used herein, the terms "immunospecifically binds," "immunospecifically recognizes," "specifically binds," and "specifically recognizes" are analogous terms in the context of antibodies and refer to antibodies and antigen-binding fragments thereof that bind to an antigen (e.g., epitope or immune complex) via the antigen-binding sites as understood by one skilled in the art, and does not exclude cross-reactivity of the antibody or antigen-binding fragment with other antigens.

The terms "substantially homologous" or "substantially identical" mean a polypeptide or nucleic acid molecule that exhibits at least 50% or greater homology or identity to a reference amino acid sequence (for example, any one of the amino acid sequences described herein) or nucleic acid sequence (for example, any one of the nucleic acid sequences described herein). For example, such a sequence is at least about 60%, about 65%, about 70%, about 75%, about 80%, about 85%, about 90%, about 95% or about 99% homologous or identical at the amino acid level or nucleic acid to the sequence used for comparison (e.g., a wild-type, or native, sequence). In some embodiments, a substantially homologous or substantially identical polypeptide contains one or more amino acid amino acid substitutions, insertions, or deletions relative to the sequence used for comparison. In some embodiments, a substantially homologous or substantially identical polypeptide contains one or more non-natural amino acids or amino acid analogs, including, D-amino acids and retroinverso amino acids, to replace homologous sequences.

Sequence homology or sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between $e^{-3}$ and $e^{-100}$ indicating a closely related sequence.

As used herein, the term "analog" refers to a structurally related polypeptide or nucleic acid molecule having the function of a reference polypeptide or nucleic acid molecule.

As used herein, the term "a conservative sequence modification" refers to an amino acid modification that does not significantly affect or alter the binding characteristics of the presently disclosed anti-MUC16 antibody agent or an antigen-binding fragment thereof comprising the amino acid sequence. Conservative modifications can include amino acid substitutions, additions and deletions. Modifications can be introduced into the human scFv of the presently disclosed anti-MUC16 antibody or an antigen-binding fragment thereof by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, and histidine; negatively-charged amino acids include aspartic acid and glutamic acid; neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, and aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (l) above) using the functional assays described herein. In certain embodiments, no more than one, no more than two, no more than three, no more than four, no more than five residues within a specified sequence or a CDR region are altered.

As used herein, the term "heterologous nucleic acid molecule or polypeptide" refers to a nucleic acid molecule (e.g., a cDNA, DNA or RNA molecule) or polypeptide that is not normally present in a cell or sample obtained from a cell. This nucleic acid may be from another organism, or it may be, for example, an mRNA molecule that is not normally expressed in a cell or sample.

As used herein, the term "modulate" refers positively or negatively alter. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%), 1%), 0.5%), or 0.1%) of other material, e.g., cellular material, culture medium, other nucleic acid molecules, chemical precursors and/or other chemicals.

As used herein, the term "isolated cell" refers to a cell that is separated from the molecular and/or cellular components that naturally accompany the cell.

As used herein, the term "neoplasia" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasia can affect a variety of cell types, tissues, or organs, including but not limited to an organ selected from the group consisting of bladder, colon, bone, brain, breast, cartilage, glia, esophagus, fallopian tube, gallbladder, heart, intestines, kidney, liver, lung, lymph node, nervous tissue, ovaries, pleura, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasia include cancers, such as sarcomas, carcinomas, or plasmacytomas (malignant tumor of the plasma cells).

As used herein, the term "pharmaceutically acceptable carrier" is intended to include any and all solvents, dispersion media, coatings, antibacterial and antifungal compounds, isotonic and absorption delaying compounds, and the like, compatible with pharmaceutical administration. Pharmaceutically acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, Pa.).

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, for example, recombinant cells express genes that are not found within the native (non-recombinant) form of the cell or express native genes that are otherwise abnormally expressed, under expressed or not expressed at all.

As used herein, the term "separate" therapeutic use refers to an administration of at least two active ingredients at the same time or at substantially the same time by different routes.

As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

As used herein, the term "simultaneous" therapeutic use refers to the administration of at least two active ingredients by the same route and at the same time or at substantially the same time.

As used herein, the terms "subject," "individual", or "patient" can be an individual organism, a vertebrate, a mammal, or a human. In some embodiments, the individual, patient or subject is a human.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of disorders as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Anti-Muc16 Antibody Agents

Provided herein are anti-MUC16 antibody agents that immunospecifically bind to MUC16. In some embodiments, the anti-MUC16 antibody agent immunospecifically binds to the retained extracellular domain of MUC16. In some embodiments, the anti-MUC16 antibody agent is an anti-MUC16 construct that comprises an antibody moiety that immunospecifically binds to MUC16. In some embodiments, the anti-MUC16 antibody agent is an anti-MUC16 antibody (e.g., a full-length anti-MUC16 antibody or an antigen binding fragment thereof). In some embodiments, the anti-MUC16 antibody agent binds to an MUC16-expressing cell (e.g., an MUC16-expressing cancer cell).

Anti-MUC16 antibody agents, such as anti-MUC16 antibodies or antigen-binding fragments thereof, can include, e.g., monoclonal antibodies, polyclonal antibodies, recombinantly produced antibodies, monospecific antibodies, multispecific antibodies (including bispecific antibodies (BsAb)), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, single domain antibodies, monovalent antibodies, single chain antibodies or single-chain variable fragments (scFv), camelized antibodies, affybodies, and disulfide-linked Fvs (dsFv), Fc fusion proteins, immunoconjugates, or fragments thereof. Such antibodies and antigen-binding fragments can be made by methods known in the art.

In some embodiments, the anti-MUC16 antibody agent is a full-length antibody (e.g., full-length IgG) or antigen-binding fragment thereof, which specifically binds to MUC16.

In some embodiments, reference to an antibody agent that immunospecifically binds to MUC16 means that the antibody agent binds to MUC16 with an affinity that is at least about 10 times (including for example at least about any of 10, $10^2$, $10^3$, $10^4$, $10^5$, $10^6$, or $10^7$ times) its binding affinity for non-target. In some embodiments, the non-target is an antigen that is not MUC16. Binding affinity can be determined by methods known in the art, such as ELISA, fluorescence activated cell sorting (FACS) analysis, or radioimmunoprecipitation assay (RIA). $K_d$ can be determined by methods known in the art, such as surface plasmon resonance (SPR) assay utilizing, for example, Biacore instruments, or kinetic exclusion assay (KinExA) utilizing, for example, Sapidyne instruments.

Although anti-MUC16 antibody agents containing human sequences (e.g., human heavy and light chain variable domain sequences comprising human CDR sequences) are extensively discussed herein, non-human anti-MUC16 antibody agents are also contemplated. In some embodiments, non-human anti-MUC16 antibody agents comprise human CDR sequences from an anti-MUC16 antibody agent as described herein and non-human framework sequences. Non-human framework sequences include, in some embodiments, any sequence that can be used for generating synthetic heavy and/or light chain variable domains using one or more human CDR sequences as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. In some embodiments, a non-human anti-MUC16 antibody agent includes an anti-MUC16 antibody agent generated by grafting one or more human CDR sequences as described herein onto a non-human framework sequence (e.g., a mouse or chicken framework sequence).

The complete amino acid sequence of an exemplary human MUC16 comprises or consists of the amino acid sequence of SEQ ID NO: 1. In some embodiments, the anti-MUC16 antibody agent described herein specifically recognizes an epitope within human MUC16. In some embodiments, the anti-MUC16 antibody agent described herein specifically recognizes an epitope within the retained extracellular domain of human MUC16. In some embodiments, the anti-MUC16 antibody agent described herein immunospecifically binds to that MUC16 ectodomain (FIG. 1). In some embodiments, the anti-MUC16 antibody agent described herein immunospecifically binds to a cell expressing human MUC16. In some embodiments, the anti-MUC16 antibody agent described herein immunospecifically binds to a cell expressing a recombinant MUC16 polypeptide. In some embodiments, the MUC16 polypeptide is MUC16-c344 having the amino acid sequence set forth in SEQ ID NO: 43. In some embodiments, the MUC16 polypeptide is MUC16-c114 having the amino acid sequence set forth in SEQ ID NO: 44 or 180.

In some embodiments, the anti-MUC16 antibody agent cross-reacts with MUC16 polypeptide from a species other than human. In some embodiments, the anti-MUC16 antibody agent is completely specific for human MUC16 and does not exhibit species or other types of non-human cross-reactivity.

In some embodiments, the anti-MUC16 antibody agent specifically recognizes MUC16 expressed on the cell surface of a cancer cell (such as solid tumor). In some embodiments, the anti-MUC16 antibody agent specifically recognizes MUC16 expressed on the cell surface of one or more of ovarian cancer cells, breast cancer cells, prostate cancer cells, colon cancer cells, lung cancer cells, brain cancer cells, pancreatic cancer cells, kidney cancer cells, fallopian tube cancer cells, uterine (e.g., endometrial) cancer cells, primary peritoneum cancer cells or cancer cells of any other tissue that expresses MUC16. In some embodiments, the anti-MUC16 antibody agent specifically recognizes MUC16 expressed on the cell surface of a cancer cell line, e.g. ovarian cancer cell lines, such as OVCAR3, OVCA-432, OVCA-433 and CAOV3.

In some embodiments, the anti-MUC16 antibody agent cross-reacts with at least one allelic variant of the MUC16 protein, or fragments thereof. In some embodiments, the allelic variant has up to about 30, such as about any of 1, 2, 3, 4, 5, 6, 7, 8, 9, 10, 15, 20, 25, or 30, amino acid substitutions, such as a conservative amino acid substitution, when compared to the naturally occurring MUC16, or fragments thereof. In some embodiments, the anti-MUC16 antibody agent does not cross-react with any allelic variant of the MUC16 protein, or fragments thereof.

In some embodiments, the anti-MUC16 antibody agent cross-reacts with at least one interspecies variant of the MUC16 protein. In some embodiments, for example, the MUC16 protein, or fragments thereof is human MUC16 and the interspecies variant of the MUC16 protein, or fragments thereof, is a mouse or rat variant thereof. In some embodiments, the anti-MUC16 antibody agent does not cross-react with any interspecies variant of the MUC16 protein.

In some embodiments, according to any of the anti-MUC16 antibody agents described herein, the anti-MUC16 antibody agent comprises an anti-MUC16 antibody moiety that specifically binds to MUC16.

In some embodiments, the anti-MUC16 antibody moiety comprises an antibody heavy chain variable domain and an antibody light chain variable domain. In some embodiments, the anti-MUC16 antibody moiety comprises an antibody heavy chain variable domain and/or an antibody light chain variable domain of a humanized 18C6 anti-MUC16 antibody.

Humanized 4H11 Anti-MUC16 Antibody Agents

In some embodiments, an anti-MUC16 antibody agent described herein comprises an antibody heavy chain variable domain and/or an antibody light chain variable domain of a 4H11 anti-MUC16 antibody (PCT Pub. No. WO2011/119979), where one or more amino acid residues of one or more framework regions of the 4H11 anti-MUC16 heavy chain variable domain and/or an antibody light chain variable domain are modified to a corresponding amino acid in a human antibody heavy chain framework region (HC-FW) or a light chain framework region (LC-FW).

In some embodiments, 1, 2, 3, 4, 5, 6, 7, 8, 9, 10, 11, 12, 13, 14, 15, 16, 17, 18, 19, 20, 21, 22, 23, 24, 25, or more amino acid residues of the framework regions of the mouse 4H11 anti-MUC16 heavy chain variable domain and/or an antibody light chain variable domain are modified to a corresponding amino acid in a human antibody HC-FW and/or LC-FW. In some embodiments, the human LC-FW is from an Immunoglobulin Kappa Variable 4-1 (IGKV4-1) gene or an Immunoglobulin Kappa Joining 2 (IGKJ2) gene. In some embodiments, the human HC-FW is from an Immunoglobulin Heavy Variable 3-21 (IGHV3-21) gene. In some embodiments, the anti-MUC16 antibody agent described herein is more mouse-like, meaning that about 10 or fewer amino acid residues the framework regions of the mouse 4H11 anti-MUC16 heavy chain variable domain and/or an antibody light chain variable domain are modified to a corresponding amino acid in a human antibody HC-FW or LC-FW. In some embodiments, the anti-MUC16 antibody agent described herein is more human-like, meaning that 10 or more amino acid residues the framework regions of the mouse 4H11 anti-MUC16 heavy chain variable domain and/or an antibody light chain variable domain are modified to a corresponding amino acid in a human antibody HC-FW or LC-FW. In some embodiments, the more human amino acid substitutions that are made with respect to the mouse 4H11 anti-MUC16 antibody sequence, a lower the immunogenicity is expected for the anti-MUC16 antibody agent when administered to a human. In some embodiments, one or more amino acids are may be unmodified with respect to the mouse sequence in order to maintain structure and/or activity of the antibody.

In some embodiments, the anti-MUC16 antibody moiety comprises a heavy chain variable domain comprising one, two or three HC-CDRs of SEQ ID NO: 4 or 5. In some embodiments, the anti-MUC16 antibody moiety comprises a heavy chain variable domain comprising HC-CDR1, HC-CDR2 and HC-CDR3 of the heavy chain variable domain of SEQ ID NOS: 4 or 5. In some embodiments, the anti-MUC16 antibody moiety comprises a heavy chain variable domain comprising a HC-CDR1, HC-CDR2 and HC-CDR3 set forth in SEQ ID NOS: 17, 18, and 19, respectively.

In some embodiments, the anti-MUC16 antibody moiety comprises a heavy chain variable domain comprising a heavy chain framework region 1 (HC-FW1), HC-FW2, and HC-FW3 set forth in SEQ ID NOS: 124, 125, and 126, respectively, where one or more amino acid residues in the HC-FW1, HC-FW2, and/or HC-FW3 are modified to a corresponding amino acid in a human HC-FW1, HC-FW2, and/or HC-FW3, respectively. In some embodiments, the anti-MUC16 antibody moiety comprises a heavy chain variable domain comprising a heavy chain framework region 1 (HC-FW1), HC-FW2, and HC-FW3 of SEQ ID NOS: 124, 125, and 126, respectively, where one or more amino acid residues in the HC-FW1, HC-FW2, and/or HC-FW3 are modified to a corresponding amino acid in a human HC-FW1, HC-FW2, and/or HC-FW3 set forth in SEQ ID NOS: 127, 128, and 129, respectively.

Additionally or alternatively, in some embodiments, the anti-MUC16 antibody moiety comprises a heavy chain variable domain comprising a HC-FW1, HC-FW2, and HC-FW3 set forth in SEQ ID NOS: 136, 137, and 138, respectively, where X at position 1 of SEQ ID NO: 136 is S or E, X at position 3 of SEQ ID NO: 136 is K or Q, X at position 5 of SEQ ID NO: 136 is Q or V, X at position 11 of SEQ ID NO: 136 is F or L, X at position 19 of SEQ ID NO: 136 is K or R; X at position 5 of SEQ ID NO: 137 is S or A, X at position 7 of SEQ ID NO: 137 is E or G, X at position 8 of SEQ ID NO: 137 is M or K, X at position 9 of SEQ ID NO: 137 is R or G; X at position 12 of SEQ ID NO: 138 is T or S, X at position 14 of SEQ ID NO: 138 is H or Y, X at position 18 of SEQ ID NO: 138 is G or N, X at position 22 of SEQ ID NO: 138 is S or A, and/or X at position 23 of SEQ ID NO: 138 is G or E.

In some embodiments, the anti-MUC16 antibody moiety comprises a heavy chain variable domain comprising a HC-FW1, HC-FW2, and HC-FW3 of SEQ ID NOS: 130, 131, and 132, respectively. In some embodiments, the anti-MUC16 antibody moiety comprises a heavy chain variable domain comprising a HC-FW1, HC-FW2, and HC-FW3 of SEQ ID NOS: 130, 131, and 132, respectively, or variants thereof comprising up to about 5 (such as about any of 1, 2, 3, 4, or 5) amino acid substitutions or having at least about 95% (for example at least about any of 96%, 97%, 98%, or 99%) sequence identity to SEQ ID NOS: 130, 131, and 132. In some embodiments, the anti-MUC16 antibody moiety comprises a heavy chain variable domain comprising a HC-FW1, HC-FW2, and HC-FW3 of SEQ ID NOS: 133, 134, and 135, respectively. In some embodiments, the anti-MUC16 antibody moiety comprises a heavy chain variable domain comprising a HC-FW1, HC-FW2, and HC-FW3 of SEQ ID NOS: 133, 134, and 135, respectively, or variants thereof comprising up to about 5 (such as about any of 1, 2, 3, 4, or 5) amino acid substitutions or having at least about 95% (for example at least about any of 96%, 97%, 98%, or 99%) sequence identity to SEQ ID NOS: 133, 134, and 135.

In some embodiments, the anti-MUC16 antibody moiety comprises a heavy chain variable domain comprising SEQ ID NO: 4 or 5. In some embodiments, the anti-MUC16 antibody moiety comprises a heavy chain variable domain set forth in SEQ ID NO: 4 or 5.

In some embodiments, the anti-MUC16 antibody moiety comprises a light chain variable domain comprising one, two or three LC-CDRs of SEQ ID NO: 2 or 3. In some embodiments, the anti-MUC16 antibody moiety comprises a light chain variable domain comprising LC-CDR1, LC-CDR2 and LC-CDR3 of the light chain variable domain of SEQ ID NO: 2 or 3. In some embodiments, the anti-MUC16 antibody moiety comprises a light chain variable domain comprising a LC-CDR1, LC-CDR2 and LC-CDR3 set forth in SEQ ID NOS: 14, 15, and 16, respectively. In some embodiments, the anti-MUC16 antibody moiety comprises a light chain variable domain comprising SEQ ID NO: 2 or 3. In some embodiments, the anti-MUC16 antibody moiety comprises a light chain variable domain set forth in SEQ ID NO: 2 or 3.

In some embodiments, the anti-MUC16 antibody moiety comprises a light chain variable domain comprising a light chain framework region 1 (LC-FW1), LC-FW2, LC-FW3, and LC-FW4 set forth in SEQ ID NOS: 104, 105, 106, and 107, respectively, where one or more amino acid residues in the LC-FW1, LC-FW2, LC-FW3, and/or LC-FW4 are modified to a corresponding amino acid in a human LC-FW1, LC-FW2, LC-FW3, and/or LC-FW4, respectively. In some embodiments, the anti-MUC16 antibody moiety comprises a light chain variable domain comprising a LC-FW1, LC-FW2, LC-FW3, and LC-FW4 of SEQ ID NOS: 104, 105, 106, and 107, respectively, where one or more amino acid residues in the LC-FW1, LC-FW2, LC-FW3, and/or LC-FW4 are modified to a corresponding amino acid in a human LC-FW1, LC-FW2, LC-FW3, and/or LC-FW4 set forth in SEQ ID NOS: 108, 109, 110, and 111, respectively.

In some embodiments, the anti-MUC16 antibody moiety comprises a light chain variable domain comprising a LC-FW1, LC-FW2, LC-FW3, and LC-FW4 set forth in SEQ ID NOS: 120, 121, 122, and 123, respectively, where X at position 3 of SEQ ID NO: 120 is E or V, X at position 9 of SEQ ID NO: 120 is S or D, X at position 15 of SEQ ID NO: 120 is A or L, X at position 18 of SEQ ID NO: 120 is K or R, X at position 22 of SEQ ID NO: 120 is S or N; X at position 7 of SEQ ID NO: 122 is T or S, X at position 27 of SEQ ID NO: 122 is L or V, X at position 3 of SEQ ID NO: 123 is P or Q, and/or X at position 9 of SEQ ID NO: 123 is V or I.

In some embodiments, the anti-MUC16 antibody moiety comprises a light chain variable domain comprising a LC-FW1, LC-FW2, LC-FW3, and LC-FW4 of SEQ ID NOS: 112, 113, 114 and 115, respectively. In some embodiments, the anti-MUC16 antibody moiety comprises a light chain variable domain comprising a LC-FW1, LC-FW2, LC-FW3, and LC-FW4 of SEQ ID NOS: 112, 113, 114 and 115, respectively, or variants thereof comprising up to about 5 (such as about any of 1, 2, 3, 4, or 5) amino acid substitutions or having at least about 95% (for example at least about any of 96%, 97%, 98%, or 99%) sequence identity to SEQ ID NOS: 112, 113, 114 and 115. In some embodiments, the anti-MUC16 antibody moiety comprises a light chain variable domain comprising a LC-FW1, LC-FW2, LC-FW3, and LC-FW4 of SEQ ID NOS: 116, 117, 118 and 119, respectively. In some embodiments, the anti-MUC16 antibody moiety comprises a light chain variable domain comprising a LC-FW1, LC-FW2, LC-FW3, and LC-FW4 of SEQ ID NOS: 116, 117, 118 and 119, respectively, or variants thereof comprising up to about 5 (such as about any of 1, 2, 3, 4, or 5) amino acid substitutions or having at least about 95% (for example at least about any of 96%, 97%, 98%, or 99%) sequence identity to SEQ ID NOS: 116, 117, 118 and 119.

In some embodiments, the anti-MUC16 antibody moiety comprises a heavy chain variable domain comprising HC-CDR1, HC-CDR2 and HC-CDR3 of the heavy chain variable domain of SEQ ID NO: 4 or 5, and a light chain variable domain comprising LC-CDR1, LC-CDR2 and LC-CDR3 of the light chain variable domain of SEQ ID NO: 2 or 3. In some embodiments, the anti-MUC16 antibody moiety comprises a heavy chain variable domain comprising HC-CDR1, HC-CDR2 and HC-CDR3 set forth in SEQ ID NOS: 17, 18, and 19, respectively, and a light chain variable domain comprising LC-CDR1, LC-CDR2 and LC-CDR3 set forth in SEQ ID NOS: 14, 15, and 16, respectively. In some embodiments, the anti-MUC16 antibody moiety comprises a heavy chain variable domain comprising SEQ ID NO: 4 or 5, and a light chain variable domain comprising SEQ ID NO: 2 or 3. In some embodiments, the anti-MUC16 antibody moiety comprises a heavy chain variable domain set forth in SEQ ID NO: 4 or 5, and a light chain variable domain set forth in SEQ ID NO: 2 or 3.

In some embodiments, the anti-MUC16 antibody moiety comprises a heavy chain variable domain comprising a HC-FW1 set forth in SEQ ID NO: 130, a HC-FW2 set forth in SEQ ID NO: 131, a HC-FW3 set forth in SEQ ID NO: 132, a LC-FW1 set forth in SEQ ID NO: 112, a LC-FW2 set forth in SEQ ID NO: 113, a LC-FW3 set forth in SEQ ID NO: 114, and/or a LC-FW4 set forth in SEQ ID NO: 115.

In some embodiments, the anti-MUC16 antibody moiety comprises a heavy chain variable domain comprising a HC-FW1 set forth in SEQ ID NO: 133, a HC-FW2 set forth in SEQ ID NO: 134, a HC-FW3 set forth in SEQ ID NO: 135, a LC-FW1 set forth in SEQ ID NO: 116, a LC-FW2 set forth in SEQ ID NO: 117, a LC-FW3 set forth in SEQ ID NO: 118, and/or a LC-FW4 set forth in SEQ ID NO: 119.

In some embodiments, the anti-MUC16 antibody moiety comprises a heavy chain variable domain comprising HC-CDR1, HC-CDR2, and HC-CDR3 set forth in SEQ ID NOS: 17, 18, and 19, respectively, and a HC-FW1, HC-FW2, and HC-FW3, set forth in SEQ ID NOS: 130, 131, and 132, respectively; and a light chain variable domain comprising LC-CDR1, LC-CDR2 and LC-CDR3 set forth in SEQ ID NOS: 14, 15, and 16, respectively, and a LC-FW1, LC-FW2, LC-FW3, and a LC-FW4 set forth in SEQ ID NOS: 112, 113, 114, and 115, respectively.

In some embodiments, the anti-MUC16 antibody moiety comprises a heavy chain variable domain comprising HC-CDR1, HC-CDR2, and HC-CDR3 set forth in SEQ ID NOS: 17, 18, and 19, respectively, and a HC-FW1, HC-FW2, and HC-FW3, set forth in SEQ ID NOS: 133, 134, and 135, respectively; and a light chain variable domain comprising LC-CDR1, LC-CDR2 and LC-CDR3 set forth in SEQ ID NOS: 14, 15, and 16, respectively, and a LC-FW1, LC-FW2, LC-FW3, and a LC-FW4 set forth in SEQ ID NOS: 116, 117, 118, and 119, respectively.

In some embodiments, the antibody heavy chain variable domain comprises the amino acid sequence of SEQ ID NO: 4 or 5, or a variant thereof comprising up to about 5 (such as about any of 1, 2, 3, 4, or 5) amino acid substitutions or having at least about 95% (for example at least about any of 96%, 97%, 98%, or 99%) sequence identity to SEQ ID NO: 4 or 5. In some embodiments, the light chain variable domain comprises the amino acid sequence of SEQ ID NO: 2 or 3, or a variant thereof comprising up to about 5 (such as about any of 1, 2, 3, 4, or 5) amino acid substitutions or having at least about 95% (for example at least about any of 96%, 97%, 98%, or 99%) sequence identity to SEQ ID NO: 2 or 3.

Humanized 18C6 Anti-MUC16 Antibody Agents

In some embodiments, an anti-MUC16 antibody agent described herein comprises an antibody heavy chain variable domain and/or an antibody light chain variable domain of a 18C6 anti-MUC16 antibody (PCT Pub. No. WO2016/149368), where one or more amino acid residues of one or more framework regions of the 18C6 anti-MUC16 heavy chain variable domain and/or an antibody light chain variable domain are modified to a corresponding amino acid in a human antibody heavy chain framework region (HC-FW) or a light chain framework region (LC-FW).

In some embodiments, 1, 2, 3, 4, 5, 6, 7, 8, 9, 10, 11, 12, 13, 14, 15, 16, 17, 18, 19, 20, 21, 22, 23, 24, 25 or more amino acid residues of the framework regions of the mouse 18C6 anti-MUC16 heavy chain variable domain and/or an antibody light chain variable domain are modified to a corresponding amino acid in a human antibody HC-FW and/or LC-FW. In some embodiments, the human LC-FW is from an Immunoglobulin Kappa Variable 2-28 (IGKV2-28) gene or an Immunoglobulin Kappa Joining 4 (IGKJ4) gene. In some embodiments, the human HC-FW is from an Immunoglobulin Heavy Variable 2-5 (IGHV2-5) gene. In some embodiments, the anti-MUC16 antibody agent described herein is more mouse-like, meaning that about 10 or fewer amino acid residues the framework regions of the mouse 18C6 anti-MUC16 heavy chain variable domain and/or an antibody light chain variable domain are modified to a corresponding amino acid in a human antibody HC-FW or LC-FW. In some embodiments, the anti-MUC16 antibody agent described herein is more human-like, meaning that 10 or more amino acid residues the framework regions of the mouse 18C6 anti-MUC16 heavy chain variable domain and/or an antibody light chain variable domain are modified to a corresponding amino acid in a human antibody HC-FW or LC-FW. In some embodiments, the more human amino acid substitutions that are made with respect to the mouse 18C6 anti-MUC16 antibody sequence, a lower the immunogenicity is expected for the anti-MUC16 antibody agent when administered to a human. In some embodiments, one or more amino acids are may be unmodified with respect to the mouse sequence in order to maintain structure and/or activity of the antibody.

In some embodiments, the anti-MUC16 antibody moiety comprises a heavy chain variable domain comprising one, two or three HC-CDRs of SEQ ID NO: 22 or 23. In some embodiments, the anti-MUC16 antibody moiety comprises a heavy chain variable domain comprising HC-CDR1, HC-CDR2 and HC-CDR3 of the heavy chain variable domain of SEQ ID NO: 22 or 23. In some embodiments, the anti-MUC16 antibody moiety comprises a heavy chain variable domain comprising a HC-CDR1, HC-CDR2 and HC-CDR3 set forth in SEQ ID NOS: 35, 36, and 37, respectively.

In some embodiments, the anti-MUC16 antibody moiety comprises a heavy chain variable domain comprising a heavy chain framework region 1 (HC-FW1), HC-FW2, HC-FW3 and HC-FW4 set forth in SEQ ID NOS: 159, 160, 161, and 162, respectively, where one or more amino acid residues in the HC-FW1, HC-FW2, HC-FW3 and/or HC-FW4 are modified to a corresponding amino acid in a human HC-FW1, HC-FW2, HC-FW3 and/or HC-FW4, respectively. In some embodiments, the anti-MUC16 antibody moiety comprises a heavy chain variable domain comprising a heavy chain framework region 1 (HC-FW1), HC-FW2, HC-FW3 and HC-FW4 of SEQ ID NOS: 159, 160, 161, and 162, respectively, where one or more amino acid residues in the HC-FW1, HC-FW2, HC-FW3 and/or HC-FW4 are modified to a corresponding amino acid in a human HC-FW1, HC-FW2, HC-FW3 and/or HC-FW4 set forth in SEQ ID NOS: 163, 164, 165, and 166, respectively.

In some embodiments, the anti-MUC16 antibody moiety comprises a heavy chain variable domain comprising a heavy chain framework region 1 (HC-FW1), HC-FW2, HC-FW3 and HC-FW4 set forth in SEQ ID NOS: 175, 176, 177 and 178, respectively, where X at position 10 of SEQ ID NO: 175 is G or T, X at position 11 of SEQ ID NO: 175 is I or L, X at position 12 of SEQ ID NO: 175 is L or V, X at position 13 of SEQ ID NO: 175 is Q or K, X at position 15 of SEQ ID NO: 175 is S or T, X at position 19 of SEQ ID NO: 175 is S or T, X at position 23 of SEQ ID NO: 175 is S or T; X at position 5 of SEQ ID NO: 177 is S or T, X at position 14 of SEQ ID NO: 177 is F or V, X at position 16 of SEQ ID NO: 177 is K or T, X at position 18 of SEQ ID NO: 177 is A or T, X at position 22 of SEQ ID NO: 177 is T or P, X at position 23 of SEQ ID NO: 177 is A or V; and/or X at position 6 of SEQ ID NO: 178 is S or L.

In some embodiments, the anti-MUC16 antibody moiety comprises a heavy chain variable domain comprising a HC-FW1, HC-FW2, HC-FW3 and HC-FW4 of SEQ ID NOS: 167, 168, 169, and 170, respectively. In some embodiments, the anti-MUC16 antibody moiety comprises a heavy chain variable domain comprising a HC-FW1, HC-FW2, HC-FW3 and HC-FW4 of SEQ ID NOS: 167, 168, 169, and 170, respectively, or variants thereof comprising up to about 5 (such as about any of 1, 2, 3, 4, or 5) amino acid substitutions or having at least about 95% (for example at least about any of 96%, 97%, 98%, or 99%) sequence identity to SEQ ID NOS: 167, 168, 169, and 170. In some embodiments, the anti-MUC16 antibody moiety comprises a heavy chain variable domain comprising a HC-FW1, HC-FW2, HC-FW3 and HC-FW4 of SEQ ID NOS: 171, 172, 173 and 174, respectively. In some embodiments, the anti-MUC16 antibody moiety comprises a heavy chain variable domain comprising a HC-FW1, HC-FW2, HC-FW3 and HC-FW4 of SEQ ID NOS: 171, 172, 173 and 174, respectively, or variants thereof comprising up to about 5 (such as about any of 1, 2, 3, 4, or 5) amino acid substitutions or having at least about 95% (for example at least about any of 96%, 97%, 98%, or 99%) sequence identity to SEQ ID NOS: 171, 172, 173 and 174.

In some embodiments, the anti-MUC16 antibody moiety comprises a heavy chain variable domain comprising SEQ ID NO: 22 or 23. In some embodiments, the anti-MUC16 antibody moiety comprises a heavy chain variable domain set forth in SEQ ID NO: 22 or 23.

In some embodiments, the anti-MUC16 antibody moiety comprises a light chain variable domain comprising one, two or three LC-CDRs of SEQ ID NO: 20 or 21. In some embodiments, the anti-MUC16 antibody moiety comprises a light chain variable domain comprising LC-CDR1, LC-CDR2 and LC-CDR3 of the light chain variable domain of SEQ ID NO: 20 or 21. In some embodiments, the anti-MUC16 antibody moiety comprises a light chain variable domain comprising a LC-CDR1, LC-CDR2 and LC-CDR3 set forth in SEQ ID NOS: 32, 33, and 34, respectively. In some embodiments, the anti-MUC16 antibody moiety comprises a light chain variable domain comprising SEQ ID NO: 20 or 21. In some embodiments, the anti-MUC16 antibody moiety comprises a light chain variable domain set forth in SEQ ID NO: 20 or 21.

In some embodiments, the anti-MUC16 antibody moiety comprises a light chain variable domain comprising a light chain framework region 1 (LC-FW1), LC-FW2, LC-FW3, and LC-FW4 set forth in SEQ ID NOS: 139, 140, 141, and 142, respectively, where one or more amino acid residues in the LC-FW1, LC-FW2, LC-FW3, and/or LC-FW4 are modified to a corresponding amino acid in a human LC-FW1, LC-FW2, LC-FW3, and/or LC-FW4, respectively. In some embodiments, the anti-MUC16 antibody moiety comprises a light chain variable domain comprising a LC-FW1, LC-FW2, LC-FW3, and LC-FW4 of SEQ ID NOS: 139, 140, 141, and 142, respectively, where one or more amino acid residues in the LC-FW1, LC-FW2, LC-FW3, and/or LC-FW4 are modified to a corresponding amino acid in a human LC-FW1, LC-FW2, LC-FW3, and/or LC-FW4 set forth in SEQ ID NOS: 143, 144, 145, and 146, respectively.

In some embodiments, the anti-MUC16 antibody moiety comprises a light chain variable domain comprising a LC-FW1, LC-FW2, LC-FW3, and LC-FW4 set forth in SEQ ID NOS: 155, 156, 157, and 158, respectively, where X at position 7 of SEQ ID NO: 155 is A or S, X at position 9 of SEQ ID NO: 155 is P or L, X at position 11 of SEQ ID NO: 155 is V or L, X at position 18 of SEQ ID NO: 155 is S or P, X at position 5 of SEQ ID NO: 156 is R or K, X at position 9 of SEQ ID NO: 157 is R or S, and/or X at position 18 of SEQ ID NO: 157 is R or K.

In some embodiments, the anti-MUC16 antibody moiety comprises a light chain variable domain comprising a LC-FW1, LC-FW2, LC-FW3, and LC-FW4 of SEQ ID NOS: 147, 148, 149 and 150, respectively. In some embodiments, the anti-MUC16 antibody moiety comprises a light chain variable domain comprising a LC-FW1, LC-FW2, LC-FW3, and LC-FW4 of SEQ ID NOS: 147, 148, 149 and 150, respectively, or variants thereof comprising up to about 5 (such as about any of 1, 2, 3, 4, or 5) amino acid substitutions or having at least about 95% (for example at least about any of 96%, 97%, 98%, or 99%) sequence identity to SEQ ID NOS: 147, 148, 149 and 150. In some embodiments, the anti-MUC16 antibody moiety comprises a light chain variable domain comprising a LC-FW1, LC-FW2, LC-FW3, and LC-FW4 of SEQ ID NOS: 151, 152, 153 and 154, respectively. In some embodiments, the anti-MUC16 antibody moiety comprises a light chain variable domain comprising a LC-FW1, LC-FW2, LC-FW3, and LC-FW4 of SEQ ID NOS: 151, 152, 153 and 154, respectively, or variants thereof comprising up to about 5 (such as about any of 1, 2, 3, 4, or 5) amino acid substitutions or having at least about 95% (for example at least about any of 96%, 97%, 98%, or 99%) sequence identity to SEQ ID NOS: 151, 152, 153 and 154.

In some embodiments, the anti-MUC16 antibody moiety comprises a heavy chain variable domain comprising HC-CDR1, HC-CDR2 and HC-CDR3 of the heavy chain variable domain of SEQ ID NO: 22 or 23, and a light chain variable domain comprising LC-CDR1, LC-CDR2 and LC-CDR3 of the light chain variable domain of SEQ ID NO: 20 or 21. In some embodiments, the anti-MUC16 antibody moiety comprises a heavy chain variable domain comprising HC-CDR1, HC-CDR2 and HC-CDR3 set forth in SEQ ID NOS: 35, 36, and 37, respectively, and a light chain variable domain comprising LC-CDR1, LC-CDR2 and LC-CDR3 set forth in SEQ ID NOS: 32, 33, and 34, respectively. In some embodiments, the anti-MUC16 antibody moiety comprises a heavy chain variable domain comprising SEQ ID NO: 22 or 23, and a light chain variable domain comprising SEQ ID NO: 20 or 21. In some embodiments, the anti-MUC16 antibody moiety comprises a heavy chain variable domain set forth in SEQ ID NO: 22 or 23, and a light chain variable domain set forth in SEQ ID NO: 20 or 21.

In some embodiments, the anti-MUC16 antibody moiety comprises a heavy chain variable domain comprising a HC-FW1 set forth in SEQ ID NO: 167, a HC-FW2 set forth in SEQ ID NO: 168, a HC-FW3 set forth in SEQ ID NO: 169, a HC-FW4 set forth in SEQ ID NO: 170, a LC-FW1 set forth in SEQ ID NO: 147, a LC-FW2 set forth in SEQ ID NO: 148, a LC-FW3 set forth in SEQ ID NO: 149, and/or a LC-FW4 set forth in SEQ ID NO: 150.

In some embodiments, the anti-MUC16 antibody moiety comprises a heavy chain variable domain comprising a HC-FW1 set forth in SEQ ID NO: 171, a HC-FW2 set forth in SEQ ID NO: 172, a HC-FW3 set forth in SEQ ID NO: 173, a HC-FW4 set forth in SEQ ID NO: 174, a LC-FW1 set forth in SEQ ID NO: 151, a LC-FW2 set forth in SEQ ID NO: 152, a LC-FW3 set forth in SEQ ID NO: 153, and/or a LC-FW4 set forth in SEQ ID NO: 154.

In some embodiments, the anti-MUC16 antibody moiety comprises a heavy chain variable domain comprising HC-CDR1, HC-CDR2, and HC-CDR3 set forth in SEQ ID NOS: 35, 36, and 37, respectively, and a HC-FW1, HC-FW2, HC-FW3, and a HC-FW4 set forth in SEQ ID NOS: 167, 168, 169, and 170, respectively; and a light chain variable domain comprising LC-CDR1, LC-CDR2 and LC-CDR3 set forth in SEQ ID NOS: 32, 33, and 34, respectively, and a LC-FW1, LC-FW2, LC-FW3, and a LC-FW4 set forth in SEQ ID NOS: 147, 148, 149, and 150, respectively.

In some embodiments, the anti-MUC16 antibody moiety comprises a heavy chain variable domain comprising HC-CDR1, HC-CDR2, and HC-CDR3 set forth in SEQ ID NOS: 35, 36, and 37, respectively, and a HC-FW1, HC-FW2, HC-FW3, and a HC-FW4 set forth in SEQ ID NOS: 171, 172, 173, and 174, respectively; and a light chain variable domain comprising LC-CDR1, LC-CDR2 and LC-CDR3 set forth in SEQ ID NOS: 32, 33, and 34, respectively, and a LC-FW1, LC-FW2, LC-FW3, and a LC-FW4 set forth in SEQ ID NOS: 151, 152, 153, and 154, respectively.

In some embodiments, the antibody heavy chain variable domain comprises the amino acid sequence of SEQ ID NO: 22 or 23, or a variant thereof comprising up to about 5 (such as about any of 1, 2, 3, 4, or 5) amino acid substitutions or having at least about 95% (for example at least about any of 96%, 97%, 98%, or 99%) sequence identity to SEQ ID NO: 22 or 23. In some embodiments, the light chain variable domain comprises the amino acid sequence of SEQ ID NO: 20 or 21, or a variant thereof comprising up to about 5 (such as about any of 1, 2, 3, 4, or 5) amino acid substitutions or having at least about 95% (for example at least about any of 96%, 97%, 98%, or 99%) sequence identity to SEQ ID NO: 20 or 21.

Exemplary antibody sequences of the humanized 4H11 and 18C6 antibody agents provided herein are shown in the Tables below. The exemplary CDR sequences in Table 1 are predicted using the IgBLAST algorithm. See, for example, Ye J. et al., *Nucleic Acids Research* 41:W34-W40 (2013), the disclosure of which is incorporated herein by reference in its entirety. Those skilled in the art will recognize that many algorithms are known for prediction of CDR positions in antibody heavy chain and light chain variable regions, and antibody agents comprising CDRs from antibodies described herein, but based on prediction algorithms other than IgBLAST, are within the scope of the present technology.

The exemplary antibody heavy chain and light chain variable region sequences are delimited according to the INTERNATIONAL IMMUNOGENETICS INFORMATION SYSTEM® (IMGT). See, for example, Lefranc, M.-P. et al., Nucleic Acids Res., 43:D413-422 (2015), the disclosure of which is incorporated herein by reference in its entirety. Those skilled in the art will recognize that antibody agents comprising $V_H$ or $V_L$ sequences from antibodies described herein, but based on algorithms other than IMGT, are within the scope of the present technology.

TABLE 1

Exemplary anti-MUC16 antibody CDR sequences.

| Antibody ID | HC-CDR1 | HC-CDR2 | HC-CDR3 |
|---|---|---|---|
| 4H11 | GFTFSSYA (SEQ ID NO: 17) | ISSAGGYI (SEQ ID NO: 18) | ARQGFGNYGDYYAMDY (SEQ ID NO: 19) |
| 18C6 | GFSLSTVGMG (SEQ ID NO: 35) | IWWDDEDK (SEQ ID NO: 36) | TRIGTAQATDALDY (SEQ ID NO: 37) |

| Antibody ID | LC-CDR1 | LC-CDR2 | LC-CDR3 |
|---|---|---|---|
| 4H11 | QSLLNSRTRKNQ (SEQ ID NO: 14) | WAS (SEQ ID NO: 15) | QQSYNLLT (SEQ ID NO: 16) |
| 18C6 | KSLLHSNGNTY (SEQ ID NO: 32) | YMS (SEQ ID NO: 33) | MQSLEYPLT (SEQ ID NO: 34) |

TABLE 2

Exemplary anti-MUC16 antibody VH and VL domain sequences.

| Clone ID | Description | Sequence |
|---|---|---|
| 4H11 | VH Domain (H1) | EVKLQESGGGFVKPGGSLRVSCAASGFTFSSYAMSWVRLAPEMRL EWVATISSAGGYIFYSDSVQGRFTISRDNAKNSLHLQMGSLRSGDT AMYYCARQGFGNYGDYYAMDYWGQGTTVTVSS (SEQ ID NO: 4) |
| 4H11 | VH Domain (H2) | EVQLVESGGGLVKPGGSLRVSCAASGFTFSSYAMSWVRLAPGKGL EWVATISSAGGYIFYSDSVQGRFTISRDNAKNSLYLQMNSLRAEDT AMYYCARQGFGNYGDYYAMDYWGQGTLVTVSS (SEQ ID NO: 5) |
| 4H11 | VL Domain (L1) | DIELTQSPSSLAVSAGERVTMNCKSSQSLLNSRTRKNQLAWYQQKP GQSPELLIYWASTRQSGVPDRFSGSGSGTDFTLTISSVQAEDVAVYY CQQSYNLLTFGPGTKLEIKR (SEQ ID NO: 2) |
| 4H11 | VL Domain (L2) | DIVLTQSPDSLAVSLGERVTMNCKSSQSLLNSRTRKNQLAWYQQK PGQSPELLIYWASTRQSGVPDRFSGSGSGTDFTLTISSVQAEDVAVY YCQQSYNLLTFGQGTKLEIKR (SEQ ID NO: 3) |
| 18C6 | VH Domain (H1) | QVTLKESGPGILQPTQTLTLTCTFSGFSLSTVGMGVGWSRQPSGKG LEWLAHIWWDDEDKYYNPALKSRLTITKDTSKNQVFLKITNVDTA DTATYYCTRIGTAQATDALDYWGQGTLVTVSS (SEQ ID NO: 22) |
| 18C6 | VH Domain (H2) | QVTLKESGPTLVKPTQTLTLTCTFSGFSLSTVGMGVGWSRQPSGKG LEWLAHIWWDDEDKYYNPALKSRLTITKDTSKNQVVLTITNVDPV DTATYYCTRIGTAQATDALDYWGQGTLVTVSS (SEQ ID NO: 23) |
| 18C6 | VL Domain (L1) | DIVMTQSAPSVPVTPGESVSISCRSSKSLLHSNGNTYLYWFLQKPGQ SPQRLIYYMSNLASGVPDRFSGRGSGTDFTLKISRVEAEDVGVYYC MQSLEYPLTFGGGTKLEIKR (SEQ ID NO: 20) |
| 18C6 | VL Domain (L2) | DIVMTQSALSLPVTPGEPVSISCRSSKSLLHSNGNTYLYWFLQKPGQ SPQRLIYYMSNLASGVPDRFSGSGSGTDFTLKISRVEAEDVGVYYC MQSLEYPLTFGGGTKLEIKR (SEQ ID NO: 21) |

In some embodiments, the anti-MUC16 antibody moiety comprises an antibody heavy chain constant region and an antibody light chain constant region.

In some embodiments, the anti-MUC16 antibody moiety comprises an IgG1 heavy chain constant region. In some embodiments, the anti-MUC16 antibody moiety comprises an IgG2 heavy chain constant region. In some embodiments, the anti-MUC16 antibody moiety comprises an IgG3 heavy chain constant region.

In some embodiments, the anti-MUC16 antibody moiety comprises an IgG1 heavy chain constant region. In some embodiments, the heavy chain constant region comprises or consists of the amino acid sequence of SEQ ID NO: 8, 9, 26, 27, or 47.

In some embodiments, the anti-MUC16 antibody moiety comprises an IgG4 heavy chain constant region. In some embodiments, the IgG4 heavy chain constant region comprises or consists of the amino acid sequence of SEQ ID NO: 48.

In some embodiments, the anti-MUC16 antibody moiety comprises a lambda light chain constant region. In some embodiments, the light chain constant region comprises or consists of the amino acid sequence of SEQ ID NO: 6, 7, 24, 25, or 49.

In some embodiments, the anti-MUC16 antibody moiety comprises a kappa light chain constant region.

Full-length anti-MUC16 antibody

The anti-MUC16 antibody agent in some embodiments is a full-length anti-MUC16 antibody. In some embodiments, the full-length anti-MUC16 antibody is an IgA, IgD, IgE, IgG, or IgM. In some embodiments, the full-length anti-MUC16 antibody comprises IgG constant domains, such as constant domains of any of IgG1, IgG2, IgG3, and IgG4 including variants thereof. In some embodiments, the full-length anti-MUC16 antibody comprises a lambda light chain constant region. In some embodiments, the full-length anti-MUC16 antibody comprises a kappa light chain constant region. In some embodiments, the full-length anti-MUC16 antibody is a full-length human anti-MUC16 antibody. In some embodiments, the full-length anti-MUC16 antibody comprises an Fc sequence of a mouse immunoglobulin. In some embodiments, the full-length anti-MUC16 antibody comprises an Fc sequence that has been altered or otherwise changed so that it has enhanced antibody dependent cellular cytotoxicity (ADCC) or complement dependent cytotoxicity (CDC) effector function.

Thus, for example, in some embodiments, there is provided a full-length anti-MUC16 antibody comprising IgG1 or IgG4 constant domains, wherein the anti-MUC16 antibody specifically binds to MUC16 on a tumor cell. In some embodiments, the IgG1 is human IgG1. In some embodiments, the IgG1 is human IgG4. In some embodiments, the anti-MUC16 heavy chain constant region comprises or consists of the amino acid sequence of SEQ ID NO: 8, 9, 26, or 27. In some embodiments, the anti-MUC16 light chain constant region comprises or consists of the amino acid sequence of SEQ ID NO: 6, 7, 24, or 25. In some embodiments, the anti-MUC16 heavy chain constant region comprises or consists of the amino acid sequence of SEQ ID NO: 8, 9, 26, or 27 and the anti-MUC16 light chain constant region comprises or consists of the amino acid sequence of SEQ ID NO: 6, 7, 24, or 25. In some embodiments, binding of the anti-MUC16 antibody to an MUC16-expressing cell (e.g., an MUC16-expressing cancer cell) inhibits tumor growth or metastasis of a tumor or induces regression of a tumor. In some embodiments, binding of the anti-MUC16 antibody to an MUC16-expressing cell (e.g., an MUC16-expressing cancer cell) inhibits Matrigel invasion in vitro of the MUC16-expressing cells.

In some embodiments, there is provided a full-length anti-MUC16 antibody comprising IgG1 or IgG4 constant domains, wherein the anti-MUC16 antibody comprises a) a heavy chain variable domain comprising SEQ ID NO: 4 or 5; and b) a light chain variable domain comprising SEQ ID NO: 2 or 3. In some embodiments, the IgG1 is human IgG1. In some embodiments, the IgG4 is human IgG4. In some embodiments, the anti-MUC16 heavy chain constant region comprises or consists of the amino acid sequence of SEQ ID NO: 8 or 9. In some embodiments, the anti-MUC16 light chain constant region comprises or consists of the amino acid sequence of SEQ ID NO: 6 or 7. In some embodiments, the anti-MUC16 antibody comprises a heavy chain comprising SEQ ID NO: 12 or 13 and a light chain comprising SEQ ID NO: 10 or 11.

In some embodiments, there is provided a full-length anti-MUC16 antibody comprising IgG1 or IgG4 constant domains, wherein the anti-MUC16 antibody comprises a) a heavy chain variable domain comprising SEQ ID NO: 22 or 23; and b) a light chain variable domain comprising SEQ ID NO: 20 or 21. In some embodiments, the IgG1 is human IgG1. In some embodiments, the IgG4 is human IgG4. In some embodiments, the anti-MUC16 heavy chain constant region comprises or consists of the amino acid sequence of SEQ ID NO: 26 or 27. In some embodiments, the anti-MUC16 light chain constant region comprises or consists of the amino acid sequence of SEQ ID NO: 24 or 25. In some embodiments, the anti-MUC16 antibody comprises a heavy chain comprising SEQ ID NO: 30 or 31 and a light chain comprising SEQ ID NO: 28 or 29.

Chimeric Anti-MUC16 Constructs

In some embodiments, the anti-MUC16 antibody agent is an anti-MUC16 chimeric antigen receptor (CAR) or variant thereof that specifically binds to MUC16. In some embodiments, the anti-MUC16 antibody agent is an anti-MUC16 CAR. CARs are well known in the art, and the anti-MUC16 antibody agent can be a CAR according to any CAR known in the art, such as described in Sadelain et al., Nature 545: 423-431 (2017), the disclosure of which is explicitly incorporated herein for use in the present technology.

The term "chimeric antigen receptor (CAR)" as used herein refers to an artificially constructed hybrid single-chain protein or single-chain polypeptide containing a single-chain variable fragment (scFv) as a part of the extra-cellular antigen-binding domain, linked directly or indirectly to a transmembrane domain (e.g., an immune cell co-stimulatory signaling molecule transmembrane domain), which is in turn linked directly or indirectly to an intracel-lular immune cell (e.g., T cell or NK cell) signaling domain. The intracellular signaling domain (ISD) comprises a pri-mary signaling sequence, or primary immune cell signaling sequence, from an antigen-dependent, TCR-associated T cell activation molecule, e.g., a portion of the intracellular domain of CD3ζ, TCRζ, FcRγ, FcRβ, CD3γ, CD3δ, CD3ε, CD5, CD22, CD79a, CD79b, or CD66d). The ISD can further comprise a co-stimulatory signaling sequence; e.g., a portion of the intracellular domain of an antigen-indepen-dent, co-stimulatory molecule such as CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, or the like. Characteristics of CARs include their ability to redirect immune cell (e.g., T cell or NK cell) specificity and reactivity toward a selected target in either MHC-restricted (in cases of TCR-mimic antibodies) or non-MHC-restricted (in cases of antibodies against cell surface proteins) manners, exploiting the antigen-binding properties of monoclonal antibodies. The non-MHC-restricted antigen recognition gives immune cells (e.g., T cells or NK cells) expressing CARs the ability to recognize antigen independent of antigen processing, thus bypassing a major mechanism of tumor escape.

In some embodiments, the anti-MUC16 CAR comprises an anti-MUC16 antibody moiety according to any of the anti-MUC16 antibody moieties described herein. For example, in some embodiments, there is provided an anti-MUC16 CAR comprising an anti-MUC16 antibody moiety. In some embodiments, the anti-MUC16 antibody moiety of an anti-MUC16 CAR comprises a) a heavy chain variable domain comprising SEQ ID NO: 4 or 5; and b) a light chain variable domain comprising SEQ ID NO: 2 or 3. In some embodiments, the heavy chain variable domain comprises the amino acid sequence of SEQ ID NO: 4 or 5, or a variant thereof having at least about 95% (for example at least about any of 96%, 97%, 98%, or 99%) sequence identity, and the light chain variable domain comprises the amino acid sequence of SEQ ID NO: 2 or 3, or a variant thereof having at least about 95% sequence identity. In some embodiments, the anti-MUC16 CAR comprises a sequence selected from among SEQ ID NOS: 80-83 or 97-99.

In some embodiments, the anti-MUC16 antibody moiety of an anti-MUC16 CAR comprises a) a heavy chain variable domain comprising SEQ ID NO: 22 or 23; and b) a light chain variable domain comprising SEQ ID NO: 20 or 21. In some embodiments, the heavy chain variable domain comprises the amino acid sequence of SEQ ID NO: 22 or 23, or a variant thereof having at least about 95% (for example at least about any of 96%, 97%, 98%, or 99%) sequence identity, and the light chain variable domain comprises the amino acid sequence of SEQ ID NO: 20 or 21, or a variant thereof having at least about 95% sequence identity. In some embodiments, the anti-MUC16 CAR comprises a sequence selected from among SEQ ID NOS: 84-87 or 100-103.

In some embodiments, the anti-MUC16 antibody agent is an anti-MUC16 chimeric receptor comprising T cell receptor (TCR) transmembrane domains. For example, in some embodiments, the anti-MUC16 antibody agent is an anti-body-T cell receptor (abTCR) as described in PCT Patent Application Publication No. WO2017070608, the disclosure of which is explicitly incorporated herein for use in the present technology and for possible inclusion in one or more claims herein. In some embodiments, the anti-MUC16 abTCR comprises an anti-MUC16 antibody moiety according to any of the anti-MUC16 antibody moieties described herein. For example, in some embodiments, there is provided an anti-MUC16 abTCR comprising an anti-MUC16 antibody moiety.

In some embodiments, the anti-MUC16 antibody moiety of an anti-MUC16 abTCR comprises a) a heavy chain variable domain comprising SEQ ID NO: 4 or 5; and b) a light chain variable domain comprising SEQ ID NO: 2 or 3. In some embodiments, the heavy chain variable domain of an anti-MUC16 abTCR comprises the amino acid sequence of SEQ ID NO: 4 or 5, or a variant thereof having at least about 95% (for example at least about any of 96%, 97%, 98%, or 99%) sequence identity, and the light chain variable domain comprises the amino acid sequence of SEQ ID NO: 2 or 3, or a variant thereof having at least about 95% sequence identity.

In some embodiments, the anti-MUC16 antibody moiety of an anti-MUC16 abTCR comprises a) a heavy chain variable domain comprising SEQ ID NO: 22 or 23; and b) a light chain variable domain comprising SEQ ID NO: 20 or 21. In some embodiments, the heavy chain variable domain of an anti-MUC16 abTCR comprises the amino acid sequence of SEQ ID NO: 22 or 23, or a variant thereof having at least about 95% (for example at least about any of 96%, 97%, 98%, or 99%) sequence identity, and the light chain variable domain comprises the amino acid sequence of SEQ ID NO: 20 or 21, or a variant thereof having at least about 95% sequence identity.

In some embodiments, the anti-MUC16 antibody agent is a chimeric co-stimulatory receptor comprising an anti-MUC16 antibody moiety that specifically binds to MUC16 and a co-stimulatory signaling domain. In some embodiments, the anti-MUC16 chimeric co-stimulatory receptor is capable of stimulating an immune cell on the surface of which it is functionally expressed upon binding MUC16. In some embodiments, the anti-MUC16 chimeric co-stimulatory receptor lacks a functional primary immune cell signaling sequence. In some embodiments, the anti-MUC16 chimeric co-stimulatory receptor lacks any primary immune cell signaling sequence. In some embodiments, the anti-MUC16 chimeric co-stimulatory receptor comprises a single polypeptide chain comprising the anti-MUC16 antibody moiety, a transmembrane domain, and the co-stimulatory signaling domain. In some embodiments, the anti-MUC16 chimeric co-stimulatory receptor comprises a first polypeptide chain and a second polypeptide chain, wherein the first and second polypeptide chains together form the anti-MUC16 antibody moiety, a transmembrane module, and co-stimulatory signaling module comprising the co-stimulatory signaling domain. In some embodiments, the first and second polypeptide chains are separate polypeptide chains, and the anti-MUC16 chimeric co-stimulatory receptor is a multimer, such as a dimer. In some embodiments, the first and second polypeptide chains are covalently linked, such as by a peptide linkage, or by another chemical linkage, such as a disulfide linkage. In some embodiments, the first polypeptide chain and the second polypeptide chain are linked by at least one disulfide bond. In some embodiments, the anti-MUC16 antibody moiety is a Fab, a Fab', a (Fab')2, an Fv, or a single chain Fv (scFv). In some embodiments, the anti-MUC16 scFv comprise a sequence selected from any one of SEQ ID NOS: 53-68.

Examples of co-stimulatory immune cell signaling domains for use in the anti-MUC16 chimeric co-stimulatory receptors of the present technology include the cytoplasmic sequences of co-receptors of the T cell receptor (TCR), which can act in concert with a chimeric receptor (e.g., a CAR or abTCR) to initiate signal transduction following chimeric receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of intracellular signaling sequence: those that initiate antigen-dependent primary activation through the TCR (referred to herein as "primary immune cell signaling sequences") and those that act in an antigen-independent manner to provide a secondary or co-stimulatory signal (referred to herein as "co-stimulatory immune cell signaling sequences").

Primary immune cell signaling sequences that act in a stimulatory manner may contain signaling motifs which are known as immunoreceptor tyrosine-based activation motifs or ITAMs. Examples of ITAM-containing primary immune cell signaling sequences include those derived from TCRζ, FcRγ, FcRβ, CD3γ, CD3δ, CD3ε, CD5, CD22, CD79a, CD79b, and CD66d. A "functional" primary immune cell signaling sequence is a sequence that is capable of transducing an immune cell activation signal when operably coupled to an appropriate receptor. "Non-functional" primary immune cell signaling sequences, which may comprise fragments or variants of primary immune cell signaling sequences, are unable to transduce an immune cell activation signal. The anti-MUC16 chimeric co-stimulatory receptors described herein lack a functional primary immune cell signaling sequence, such as a functional signaling sequence comprising an ITAM. In some embodiments, the anti-MUC16 chimeric co-stimulatory receptors lack any primary immune cell signaling sequence.

The co-stimulatory immune cell signaling sequence can be a portion of the intracellular domain of a co-stimulatory molecule including, for example, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like.

In some embodiments, the anti-MUC16 antibody moiety of an anti-MUC16 chimeric co-stimulatory receptor comprises a) a heavy chain variable domain comprising SEQ ID NO: 4 or 5; and b) a light chain variable domain comprising SEQ ID NO: 2 or 3. In some embodiments, the heavy chain variable domain comprises the amino acid sequence of SEQ ID NO: 4 or 5, or a variant thereof having at least about 95% (for example at least about any of 96%, 97%, 98%, or 99%) sequence identity, and the light chain variable domain comprises the amino acid sequence of SEQ ID NO: 2 or 3, or a variant thereof having at least about 95% sequence identity.

In some embodiments, the anti-MUC16 antibody moiety of an anti-MUC16 chimeric co-stimulatory receptor comprises a) a heavy chain variable domain comprising SEQ ID NO: 22 or 23; and b) a light chain variable domain comprising SEQ ID NO: 20 or 21. In some embodiments, the heavy chain variable domain comprises the amino acid sequence of SEQ ID NO: 22 or 23, or a variant thereof having at least about 95% (for example at least about any of 96%, 97%, 98%, or 99%) sequence identity, and the light chain variable domain comprises the amino acid sequence of SEQ ID NO: 20 or 21, or a variant thereof having at least about 95% sequence identity.

In some embodiments, the anti-MUC16 chimeric co-stimulatory receptor is expressed in an immune cell. In some embodiments, the anti-MUC16 chimeric co-stimulatory receptor is expressed in an immune cell that expresses another chimeric receptor. In some embodiments, the other chimeric receptor is a CAR or an abTCR. In some embodiments, the other chimeric receptor binds to MUC16. In some embodiments, the other chimeric receptor does not bind to MUC16. In some embodiments, the other chimeric receptor binds to an antigen associated with a cancer characterized by high expression of MUC16 and/or high aerobic glycolysis. In some embodiments, the other chimeric receptor binds to an antigen associated with any of the cancers described herein (such as kidney cancer, cervical cancer, prostate cancer, breast cancer, colon cancer, brain cancer, or pancreatic cancer). In some embodiments, the other chimeric receptor binds to an antigen associated with kidney cancer. In some embodiments, the kidney cancer is renal cell carcinoma (RCC). In some embodiments, the RCC is metastatic RCC. In some embodiments, the immune cell is a T cell. In some embodiments, expression of the anti-MUC16 chimeric co-stimulatory receptor in the immune cell is inducible. In some embodiments, the expression of the anti-MUC16 chimeric co-stimulatory receptor in the immune cell is inducible upon signaling through the other chimeric receptor.

Binding Affinity

Binding affinity can be indicated by $K_d$, $K_{off}$, $K_{on}$, or $K_a$. The term "$K_{off}$", as used herein, is intended to refer to the off-rate constant for dissociation of an antibody agent from the antibody agent/antigen complex, as determined from a kinetic selection set up. The term "$K_{on}$", as used herein, is intended to refer to the on-rate constant for association of an antibody agent to the antigen to form the antibody agent/antigen complex. The term equilibrium dissociation constant "$K_d$", as used herein, refers to the dissociation constant of a particular antibody agent-antigen interaction, and describes the concentration of antigen required to occupy one half of all of the antibody-binding domains present in a solution of antibody agent molecules at equilibrium, and is equal to $K_{off}/K_{on}$. The measurement of $K_d$ presupposes that all binding agents are in solution. In the case where the antibody agent is tethered to a cell wall, e.g., in a yeast expression system, the corresponding equilibrium rate constant is expressed as EC50, which gives a good approximation of $K_d$. The affinity constant, $K_a$, is the inverse of the dissociation constant, $K_d$.

The dissociation constant ($K_d$) is used as an indicator showing affinity of antibody moieties to antigens. For example, easy analysis is possible by the Scatchard method using antibody agents marked with a variety of marker agents, as well as by using Biacore (made by Amersham Biosciences), analysis of biomolecular interactions by surface plasmon resonance, according to the user's manual and attached kit. The $K_d$ value that can be derived using these methods is expressed in units of M (Mols). An antibody agent that specifically binds to a target may have a $K_d$ of, for example, $\leq 10^{-7}$ M, $\leq 10^{-8}$ M, $\leq 10^{-9}$ M, $\leq 10^{-10}$ M, $\leq 10^{-11}$ M, $\leq 10^{-12}$ M, or $\leq 10^{-13}$ M.

Binding specificity of the antibody agent can be determined experimentally by methods known in the art. Such methods comprise, but are not limited to, Western blots, ELISA-, RIA-, ECL-, IRMA-, EIA-, BIAcore-tests and peptide scans. In some embodiments, the binding affinity of the anti-MUC16 antibody agent is measured by testing the binding affinity of the anti-MUC16 antibody agent to cells expressing MUC16 on the surface (e.g., HepG2 cells).

In some embodiments, the anti-MUC16 antibody agent specifically binds to a target MUC16 (e.g., nMUC16) with a $K_d$ of about $10^{-7}$M to about $10^{-13}$ M (such as about $10^{-7}$ M to about $10^{-13}$ M, about $10^{-9}$ M to about $10^{-13}$ M, or about $10^{-10}$ M to about $10^{-12}$ M). Thus in some embodiments, the $K_d$ of the binding between the anti-nMUC16 antibody agent and nMUC16, the $K_d$ of the binding between the anti-sMUC16 antibody agent and sMUC16, or the $K_d$ of the binding between the anti-MUC16 antibody agent and MUC16 (any format), is about $10^{-7}$M to about $10^{-13}$ M, about $1 \times 10^{-7}$ M to about $5 \times 10^{-13}$ M, about $10^{-7}$M to about $10^{-12}$ M, about $10^{-7}$ M to about $10^{-11}$ M, about $10^{-7}$ M to about $10^{-10}$ M, about $10^{-7}$ M to about $10^{-9}$M, about $10^{-8}$ M to about $10^{-13}$ M, about $1 \times 10^{-8}$ M to about $5 \times 10^{-13}$ M, about $10^{-8}$ M to about $10^{-12}$ M, about $10^{-8}$ M to about $10^{-11}$ M, about $10^{-8}$ M to about $10^{-10}$ M, about $10^{-8}$ M to about $10^{-9}$ M, about $5 \times 10^{-9}$ M to about $1 \times 10^{-13}$ M, about $5 \times 10^{-9}$ M to about $1 \times 10^{-12}$ M, about $5 \times 10^{-9}$ M to about $1 \times 10^{-11}$ M, about $5 \times 10^{-9}$ M to about $1 \times 10^{-10}$ M, about $10^{-9}$ M to about $10^{-13}$ M, about $10^{-9}$ M to about $10^{-12}$ M, about $10^{-9}$ M to about $10^{-10}$ M, about $10^{-9}$ M to about $10^{-10}$ M, about $5\times10^{-10}$ M to about $1\times10^{-13}$ M, about $5\times10^{-10}$ M to about $1\times10^{-12}$ M, about $5\times10^{-10}$ M to about $1\times10^{-11}$ M, about $10^{-10}$ M to about $10^{-13}$ M, about $1\times10^{-10}$ M to about $5\times10^{-13}$ M, about $1\times10^{-10}$ M to about $1\times10^{-12}$ M, about $1\times10^{-10}$ M to about $5\times10^{-12}$ M, about $1\times10^{-10}$ M to about $1\times10^{-11}$ M, about $10^{-11}$ M to about $10^{-13}$ M, about $1\times10^{-11}$ M to about $5\times10^{-13}$ M, about $10^{-11}$ M to about $10^{-12}$M, or about $10^{-12}$M to about $10^{-13}$ M. In some embodiments, the $K_d$ of the binding between the anti-nMUC16 antibody agent and an nMUC16 is about $10^{-7}$ M to about $10^{-13}$ M.

In some embodiments, the $K_d$ of the binding between the anti-MUC16 antibody agent and a non-target is more than the $K_d$ of the binding between the anti-MUC16 antibody agent and the target, and is herein referred to in some embodiments as the binding affinity of the anti-MUC16 antibody agent to the target (e.g., cell surface-bound MUC16) is higher than that to a non-target. In some embodiments, the non-target is an antigen that is not MUC16. In some embodiments, the $K_d$ of the binding between the anti-MUC16 antibody agent (against nMUC16) and a non-MUC16 target can be at least about 10 times, such as about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^{11}$-$10^{12}$ times of the $K_d$ of the binding between the anti-MUC16 antibody agent and a target MUC16.

In some embodiments, the anti-MUC16 antibody agent binds to a non-target with a $K_d$ of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M). In some embodiments, the non-target is an antigen that is not MUC16. Thus in some embodiments, the $K_d$ of the binding between the anti-MUC16 antibody agent and a non-MUC16 target is about $10^{-1}$ M to about $10^{-6}$ M, about $1\times10^{-1}$ M to about $5\times10^{-6}$ M, about $10^{-1}$ M to about $10^{-5}$ M, about $1\times10^{-1}$ M to about $5\times10^{-5}$ M, about $10^{-1}$ M to about $10^{-4}$ M, about $1\times10^{-1}$ M to about $5\times10^{-4}$ M, about $10^{-1}$ M to about $10^{-3}$ M, about $1\times10^{-1}$ M to about $5\times10^{-3}$ M, about $10^{-1}$ M to about $10^{-2}$ M, about $10^{-2}$ M to about $10^{-6}$ M, about $1\times10^{-2}$ M to about $5\times10^{-6}$ M, about $10^{-2}$ M to about $10^{-5}$ M, about $1\times10^{-2}$ M to about $5\times10^{-5}$ M, about $10^{-2}$M to about $10^{-4}$ M, about $1\times10^{-2}$ M to about $5\times10^{-4}$ M, about $10^{-2}$ M to about $10^{-3}$ M, about $10^{-3}$ M to about $10^{-6}$ M, about $1\times10^{-3}$ M to about $5\times10^{-6}$ M, about $10^{-3}$ M to about $10^{-5}$ M, about $1\times10^{-3}$ M to about $5\times10^{-5}$ M, about $10^{-3}$ M to about $10^{-4}$ M, about $10^{-4}$ M to about $10^{-6}$ M, about $1\times10^{-4}$ M to about $5\times10^{-6}$ M, about $10^{-4}$ M to about $10^{-5}$ M, or about $10^{-5}$ M to about $10^{-6}$ M.

In some embodiments, when referring to that the anti-MUC16 antibody agent specifically recognizes a target MUC16 (e.g., cell surface-bound MUC16) at a high binding affinity, and binds to a non-target at a low binding affinity, the anti-MUC16 antibody agent will bind to the target MUC16 (e.g., cell surface-bound MUC16) with a $K_d$ of about $10^{-7}$ M to about $10^{-13}$ M (such as about $10^{-7}$ M to about $10^{-13}$ M, about $10^{-9}$ M to about $10^{-13}$ M, or about $10^{-10}$ M to about $10^{-12}$ M), and will bind to the non-target with a $K_d$ of about $10^{-1}$ M to about $10^{-6}$ M (such as about $10^{-1}$ M to about $10^{-6}$ M, about $10^{-1}$ M to about $10^{-5}$ M, or about $10^{-2}$ M to about $10^{-4}$ M).

In some embodiments, when referring to that the anti-MUC16 antibody agent specifically recognizes a cell surface-bound MUC16, the binding affinity of the anti-MUC16 antibody agent is compared to a control anti-MUC16 antibody agent. In some embodiments, the $K_d$ of the binding between the control anti-MUC16 antibody agent and a cell surface-bound MUC16 can be at least about 2 times, such as about 2 times, about 3 times, about 4 times, about 5 times, about 6 times, about 7 times, about 8 times, about 9 times, about 10 times, about 10-100 times, about 100-1000 times, about $10^3$-$10^4$ times, about $10^4$-$10^5$ times, about $10^5$-$10^6$ times, about $10^6$-$10^7$ times, about $10^7$-$10^8$ times, about $10^8$-$10^9$ times, about $10^9$-$10^{10}$ times, about $10^{10}$-$10^{11}$ times, or about $10^1$-$10^{12}$ times of the $K_d$ of the binding between the anti-nMUC16 antibody agent described herein and a cell surface-bound MUC16.

Functional Activities of Anti-Muc16 Antibody Agents

In certain embodiments, an anti-MUC16 antibody agent or an antigen-binding fragment thereof described herein inhibits Matrigel invasion in vitro of cells recombinantly expressing a MUC16 polypeptide. In some embodiments the MUC16 comprises SEQ ID NO: 44 or 180 (MUC16 c114). In certain embodiments, the cells recombinantly expressing glycosylated MUC16 c114 are SKOV3 cells. In certain embodiments, the MUC16 polypeptide is glycosylated. In certain embodiments, the glycosylated form of MUC16 polypeptide is N-glycosylated at amino acid residue Asn30 (corresponding to Asnl806 of mature MUC16 (SEQ ID NO: 1)). In certain embodiments, MUC16 polypeptide is N-glycosylated at amino acid residues Asn24 and Asn30 (corresponding to Asnl800 and Asnl806, respectively, of mature MUC16 (SEQ ID NO: 1)). In certain embodiments, the MUC16 polypeptide is N-glycosylated at amino acid residues Asn1, Asn24, and Asn30 of SEQ ID NO: 44 or 180 (also referred to as Asn1777, Asn1800, and Asn1806, respectively, in Yin and Lloyd (2001) *J Biol Chem* 276: 27371-27375). In certain embodiments, the glycosylation comprises N-linked chitobiose. In certain embodiments, the glycosylation consists of an N-linked chitobiose. In certain embodiments, Matrigel invasion is inhibited by at least 1.25, 1.5, 1.75, 2, 3, 4, 5, 6, 7, 8, 9, or 10-fold as compared to Matrigel invasion in vitro of the cells wherein the cells are treated with a control antibody (e.g., an antibody that does not target MUC16). In certain embodiments, Matrigel invasion is inhibited by about 1.25, 1.5, 1.75, 2, 3, 4, 5, 6, 7, 8, 9, or 10-fold as compared to Matrigel invasion in vitro of the cells wherein the cells are treated with a control antibody (e.g., an antibody that does not target MUC16).

Assays to determine the MUC16 anti-MUC16 antibody agent or antigen-binding fragment-mediated inhibition of Matrigel invasion are known to a person skilled in the art. For example, BD BioCoat™ Matrigel™ Invasion Inserts or Chambers (catalog #354480 in 24 well plate) and Control Inserts (catalog #354578 in 24 well plate) can be purchased from BD Biosciences, MA. Matrigel Invasion assay can be performed as per manufacturer's protocol. Briefly, the Matrigel chambers in 24 well plates (stored at −20° C.) and control inserts (stored at 4° C.) are allowed to come to room temperature. Both inserts are rehydrated with 0.5 mL of serum free medium in the insert as well as in the outside well of the 24 well plate, for 2 hours at 37° C. 5% $CO_2$ humidified incubator. Cultured SKOV3 cells are trypsinized and washed with culture medium. A million cells are separated into another centrifuge tube and washed 3 times with serum free medium. These cells are later adjusted to give 5,000 cells in 0.5 mL serum free medium. The medium in the rehydrated inserts are removed and the insert was transferred into a new 24 well plate containing 0.75 mL of 10% Fetal Bovine Serum (FBS) containing culture medium in the well which serves as a chemo attractant. Immediately, 0.5 mL of the cells (5,000 cells) in serum free medium is added to the insert. Proper care is taken to see that there is no air bubble is trapped in the insert and the outside well. The 24 well plate is incubated at 37° C. 5% C02 humidified incubator for 48 hrs. After incubation, the non-invading cells are removed from the upper surface of the membrane by "scrubbing" by inserting a cotton tipped swab into Matrigel or control insert and gently applied pressure while moving the tip of the swab over the membrane surface. The scrubbing is repeated with a second swab moistened with medium. Then the inserts are stained in a new 24 well plate containing 0.5 mL of 0.5% crystal violet stain in distilled water for 30 minutes. Following staining the inserts are rinsed in 3 beakers of distilled water to remove excess stain. The inserts are air dried for in a new 24 well plate. The invaded cells are hand counted under an inverted microscope at 200× magnification. Several fields of triplicate membranes were counted and recorded in the figure.

In certain embodiments, an anti-MUC16 antibody agent or an antigen-binding fragment thereof described herein is capable of inhibiting or reducing metastasis, inhibiting tumor growth or inducing tumor regression in mouse model studies. For example, tumor cell lines can be introduced into athymic nude mice, and the athymic mice can be administered an anti-MUC16 antibody agent or an antigen-binding fragment thereof described herein one or more times, and tumor progression of the injected tumor cells can be monitored over a period of weeks and/or months. In some cases, administration of an anti-MUC16 antibody agent or an antigen-binding fragment thereof to the athymic nude mice can occur prior to introduction of the tumor cell lines. In a certain embodiment, SKOV3 cells expressing MUC16 c114 are utilized for the mouse xenograft models described herein.

In some embodiments, an anti-MUC16 antibody agent or an antigen-binding fragment thereof described herein inhibits tumor growth or induce tumor regression in a mouse model by at least about 5%, 10%, 15%, 20%, 25%, 30%, 35%, 40%, 45%, 50%, 55%, 60%, 65%, 70%, 75%, 80%, 85%, 90%, 95%, 98%, 99%, or 100% as assessed by methods described herein or known to one of skill in the art, as compared to mock-treated mice. In some embodiments, an anti-MUC16 antibody agent or an antigen-binding fragment thereof described herein inhibits tumor growth or induce tumor regression in a mouse model by at least about 25% or 35%), optionally to about 75%, as assessed by methods described herein or known to one of skill in the art, as compared to mock-treated mice. In some embodiments, an anti-MUC16 antibody agent or an antigen-binding fragment thereof described herein inhibit tumor growth or induce tumor regression in a mouse model by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, as compared to mock-treated mice. Mock-treated mice can, for example, be treated with phosphate buffered saline or a control (e.g., anti-IgG antibody).

Determining tumor growth inhibition or tumor regression can be assessed, for example, by monitoring tumor size over a period of time, such as by physical measurement of palpable tumors, or other visual detection methods. For example, tumor cell lines can be generated to recombinantly express a visualization agent, such as green fluorescent protein (GFP) or luciferase, then in vivo visualization of GFP can be carried out by microscopy, and in vivo visualization of luciferase can be carried out by administering luciferase substrate to the xenograft mice and detecting luminescent due to the luciferase enzyme processing the luciferase substrate. The degree or level of detection of GFP or luciferase correlates to the size of the tumor in the xenograft mice.

In certain embodiments, an anti-MUC16 antibody agent or an antigen-binding fragment thereof described herein can increase survival of animals in tumor xenograft models as compared to mock-treated mice. In some embodiments, an anti-MUC16 antibody agent or an antigen-binding fragment thereof described herein increases survival of mice in tumor xenograft models by at least about 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein or known to one of skill in the art, as compared to mock-treated mice. In some embodiments, an anti-MUC16 antibody agent or an antigen-binding fragment thereof described herein increases survival of mice in tumor xenograft models by at least about 25% or 35%, optionally to about 75%), as assessed by methods described herein or known to one of skill in the art, as compared to mock-treated mice in tumor xenograft models. In some embodiments, an anti-MUC16 antibody agent or an antigen-binding fragment thereof described herein increases survival of mice in tumor xenograft models by at least about 1 fold, 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein or known to one of skill in the art, as compared to mock-treated mice in tumor xenograft models. Survival can, for example, be determined by plotting a survival curve of number of surviving mice against time (e.g., days or weeks) after tumor cell line injection. Mock-treated mice can, for example, be treated with phosphate buffered saline or a control (e.g., anti-IgG antibody).

In certain embodiments, an anti-MUC16 antibody agent or an antigen-binding fragment thereof described herein is internalized into a cell expressing a MUC16 polypeptide upon contacting the cell with the anti-MUC16 antibody agent or an antigen-binding fragment thereof. "Internalized" or "internalization," when in reference to a molecule that is internalized by a cell, refers to passage of the molecule that is in contact with the extracellular surface of a cell membrane across the cell membrane to the intracellular surface of the cell membrane and/or into the cell cytoplasm. In certain embodiments, the cells recombinantly expressing glycosylated MUC16 c114 are SKOV3 cells. In certain embodiments, the glycosylated form of MUC16 c114 is N-glycosylated, e.g., at Asn1, Asn24, and Asn30 of SEQ ID NO: 44 or 180 (also referred to as Asn1777, Asn1800, and Asn1806, respectively, in Yin and Lloyd (2001) *J Biol Chem* 276: 27371-27375). In certain embodiments, the glycosylation comprises N-linked chitobiose. In certain embodiments, the glycosylation consists of an N-linked chitobiose.

Assays to determine internalization of an anti-MUC16 antibody agent or an antigen-binding fragment thereof described herein to a cell, such as, for example, using radiolabeled antibodies, are known to a person skilled in the art. For example, internalization of $^{89}$Zr-labeled antibody can be investigated on SKOV3 cells expressing MUC16 c114. Briefly, approximately $1\times10^5$ cells are seeded in a 12-well plate and incubated overnight at 37° C. 5% $CO_2$ incubator. A volume of radiolabeled protein is added to each well and the plates are incubated at 37° C. and 4° C. for 1, 5, 12, and 24 hours. Following each incubation period, the medium is collected and the cells are rinsed with 1 mL of phosphate buffered saline (PBS). Surface-bound activity is collected by washing the cells in 1 mL of 100 mM acetic acid with 100 mM glycine (1:1, pH 3.5) at 4° C. The adherent cells are then lysed with 1 mL of 1 M NaOH. Each wash is collected and counted for activity. The ratio of activity of the final wash to the total activity of all the washes is used to determine the % internalized. In certain embodiments, the assay is performed at 37° C. In certain embodiments, the anti-MUC16 antibody agent or an antigen-binding fragment thereof is internalized in at least 1, 2, 3, 5, 6, 7, 8, 9, or 10 percent of cells incubated with the anti-MUC16 antibody agent or an antigen-binding fragment thereof. In certain embodiments, the anti-MUC16 antibody agent or an antigen-binding fragment thereof is internalized in about 1, 2, 3, 5, 6, 7, 8, 9, or 10 percent of cells incubated with the anti-MUC16 antibody agent or an antigen-binding fragment thereof. In certain embodiments, the anti-MUC16 antibody agent or an antigen-binding fragment thereof is internalized within 1, 2, 3, 4, 8, 12, 16, 20, or 24 hours of contacting the cells with the anti-MUC16 antibody agent or an antigen-binding fragment thereof.

Nucleic Acids

Nucleic acid molecules encoding the anti-MUC16 antibody agents or an antigen-binding fragment thereof (such as anti-MUC16 antibodies, e.g., full-length anti-MUC16 antibodies) are also contemplated. In some embodiments, there is provided a nucleic acid (or a set of nucleic acids) encoding a full-length anti-MUC16 antibody, including any of the full-length anti-MUC16 antibodies described herein, or an antigen-binding fragment thereof. In some embodiments, the nucleic acid (or a set of nucleic acids) encoding the anti-MUC16 antibody agent described herein may further comprises a nucleic acid sequence encoding a peptide tag (such as protein purification tag, e.g., His-tag, HA tag).

Also contemplated here are isolated host cells comprising an anti-MUC16 antibody agent, an isolated nucleic acid encoding the polypeptide components of the anti-MUC16 antibody agent, or a vector comprising a nucleic acid encoding the polypeptide components of the anti-MUC16 antibody agent described herein.

The present application also includes variants to these nucleic acid sequences. For example, the variants include nucleotide sequences that hybridize to the nucleic acid sequences encoding the anti-MUC16 antibody agents (such as anti-MUC16 antibodies, e.g., full-length anti-MUC16 antibodies), antigen-binding fragments thereof, or anti-MUC16 antibody moieties of the present application under at least moderately stringent hybridization conditions.

The present technology also provides vectors in which a nucleic acid of the present technology is inserted.

In brief summary, the expression of an anti-MUC16 antibody agent (e.g., full-length anti-MUC16 antibody) or an antigen-binding fragment thereof by a natural or synthetic nucleic acid encoding the anti-MUC16 antibody agent can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present technology may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the present technology provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Green and Sambrook (2013, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter.

Further, the present technology should not be limited to the use of constitutive promoters. Inducible promoters are also contemplated as part of the present technology. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the expression of the anti-MUC16 antibody agent is inducible. In some embodiments, a nucleic acid sequence encoding the anti-MUC16 antibody agent is operably linked to an inducible promoter, including any inducible promoter described herein.

Inducible Promoters

The use of an inducible promoter provides a molecular switch capable of turning on expression of the polynucleotide sequence which it is operatively linked when such expression is desired, or turning off the expression when expression is not desired. Exemplary inducible promoter systems for use in eukaryotic cells include, but are not limited to, hormone-regulated elements (e.g., see Mader, S. and White, J. H. *Proc. Natl. Acad. Sci. USA* 90:5603-5607 (1993)), synthetic ligand-regulated elements (see, e.g., Spencer, D. M. et al 1993) Science 262: 1019-1024) and ionizing radiation-regulated elements (e.g., see Manome, Y. et al., *Biochemistry* 32: 10607-10613 (1993); Datta, R. et al., *Proc. Natl. Acad. Sci. USA* 89: 1014-10153 (1992)). Further exemplary inducible promoter systems for use in in vitro or in vivo mammalian systems are reviewed in Gingrich et al., *Annual Rev. Neurosci* 21:377-405 (1998). In some embodiments, the inducible promoter system for use to express the anti-MUC16 antibody agent is the Tet system. In some embodiments, the inducible promoter system for use to express the anti-MUC16 antibody agent is the lac repressor system from *E. coli.*

An exemplary inducible promoter system for use in the present technology is the Tet system. Such systems are based on the Tet system described by Gossen et al., (1993). In an exemplary embodiment, a polynucleotide of interest is under the control of a promoter that comprises one or more Tet operator (TetO) sites. In the inactive state, Tet repressor (TetR) will bind to the TetO sites and repress transcription from the promoter. In the active state, e.g., in the presence of an inducing agent such as tetracycline (Tc), anhydrotetracycline, doxycycline (Dox), or an active analog thereof, the inducing agent causes release of TetR from TetO, thereby allowing transcription to take place. Doxycycline is a member of the tetracycline family of antibiotics having the chemical name of 1-dimethylamino-2,4a,5,7,12-pentahydroxy-11-methyl-4,6-dioxo-1,4a,11,11a,12,12a-hexahydro-tetracene-3-carboxamide.

In one embodiment, a TetR is codon-optimized for expression in mammalian cells, e.g., murine or human cells. Most amino acids are encoded by more than one codon due to the degeneracy of the genetic code, allowing for substantial variations in the nucleotide sequence of a given nucleic acid without any alteration in the amino acid sequence encoded by the nucleic acid. However, many organisms display differences in codon usage, also known as "codon bias" (i.e., bias for use of a particular codon(s) for a given amino acid). Codon bias often correlates with the presence of a predominant species of tRNA for a particular codon, which in turn increases efficiency of mRNA translation. Accordingly, a coding sequence derived from a particular organism (e.g., a prokaryote) may be tailored for improved expression in a different organism (e.g., a eukaryote) through codon optimization.

Other specific variations of the Tet system include the following "Tet-Off" and "Tet-On" systems. In the Tet-Off system, transcription is inactive in the presence of Tc or Dox. In that system, a tetracycline-controlled transactivator protein (tTA), which is composed of TetR fused to the strong transactivating domain of VP16 from Herpes simplex virus, regulates expression of a target nucleic acid that is under transcriptional control of a tetracycline-responsive promoter element (TRE). The TRE is made up of TetO sequence concatamers fused to a promoter (commonly the minimal promoter sequence derived from the human cytomegalovirus (hCMV) immediate-early promoter). In the absence of Tc or Dox, tTA binds to the TRE and activates transcription of the target gene. In the presence of Tc or Dox, tTA cannot bind to the TRE, and expression from the target gene remains inactive.

Conversely, in the Tet-On system, transcription is active in the presence of Tc or Dox. The Tet-On system is based on a reverse tetacycline-controlled transactivator, rtTA. Like tTA, rtTA is a fusion protein comprised of the TetR repressor and the VP16 transactivation domain. However, a four amino acid change in the TetR DNA binding moiety alters rtTA's binding characteristics such that it can only recognize the tetO sequences in the TRE of the target transgene in the presence of Dox. Thus, in the Tet-On system, transcription of the TRE-regulated target gene is stimulated by rtTA only in the presence of Dox.

Another inducible promoter system is the lac repressor system from *E. coli* (See Brown et al., Cell 49:603-612 (1987)). The lac repressor system functions by regulating transcription of a polynucleotide of interest operably linked to a promoter comprising the lac operator (lacO). The lac repressor (lacR) binds to LacO, thus preventing transcription of the polynucleotide of interest. Expression of the polynucleotide of interest is induced by a suitable inducing agent, e.g., isopropyl-β-D-thiogalactopyranoside (IPTG).

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In some embodiments, there is provided nucleic acid encoding a full-length anti-MUC16 antibody according to any of the full-length anti-MUC16 antibodies described herein. In some embodiments, the nucleic acid comprises one or more nucleic acid sequences encoding the heavy and light chains of the full-length anti-MUC16 antibody. In some embodiments, each of the one or more nucleic acid sequences are contained in separate vectors. In some embodiments, at least some of the nucleic acid sequences are contained in the same vector. In some embodiments, all of the nucleic acid sequences are contained in the same vector. Vectors may be selected, for example, from the group consisting of mammalian expression vectors and viral vectors (such as those derived from retroviruses, adenoviruses, adeno-associated viruses, herpes viruses, and lentiviruses).

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Green and Sambrook (2013, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method of inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution.

For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present technology, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the present technology.

Preparation of Anti-Muc16 Antibody Agents and Anti-Muc16 Antibody Moieties

In some embodiments, the anti-MUC16 antibody agent is a monoclonal antibody or derived from a monoclonal antibody. In some embodiments, the anti-MUC16 antibody agent comprises $V_H$ and $V_L$ domains, or variants thereof, from the monoclonal antibody. In some embodiments, the anti-MUC16 antibody agent further comprises $C_H1$ and $C_L$ domains, or variants thereof, from the monoclonal antibody. Monoclonal antibodies can be prepared, e.g., using known methods in the art, including hybridoma methods, phage display methods, or using recombinant DNA methods. Additionally, exemplary phage display methods are described herein and in the Examples below.

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, California and the American Type Culture Collection, Manassas, Virginia. Human myeloma and mouse-human heteromyeloma cell lines also have been described for the production of human monoclonal antibodies.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

In some embodiments, according to any of the anti-MUC16 antibody agents described herein, the anti-MUC16 antibody agent comprises sequences from a clone selected from an antibody library (such as a phage library presenting scFv or Fab fragments). The clone may be identified by screening combinatorial libraries for antibody fragments with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J. Mol. Biol.* 222: 581-597 (1992); Marks and Bradbury, *Methods in Molecular Biology* 248: 161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as scFv fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The anti-MUC16 antibody agents can be prepared using phage display to screen libraries for anti-MUC16 antibody moieties specific to the target MUC16 (e.g., nMUC16). The library can be a human scFv phage display library having a diversity of at least one×10⁹ (such as at least about any of $1\times10^9$, $2.5\times10^9$, $5\times10^9$, $7.5\times10^9$, $1\times10^{10}$, $2.5\times10^{10}$, $5\times10^{10}$, $7.5\times10^{10}$, or $1\times10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23(3):344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a fully-synthetic phage display library. In some embodiments, the library is a non-human phage display library.

Phage clones that bind to the target MUC16 (e.g., nMUC16) with high affinity can be selected by iterative binding of phage to the target MUC16, which is bound to a solid support (such as, for example, beads for solution panning or mammalian cells for cell panning), followed by removal of non-bound phage and by elution of specifically bound phage. The bound phage clones are then eluted and used to infect an appropriate host cell, such as *E. coli* XL1-Blue, for expression and purification. In an example of cell panning, HEK293 cells over-expressing MUC16 on cell surface are mixed with the phage library, after which the cells are collected and the bound clones are eluted and used to infect an appropriate host cell for expression and purification (all see Examples). The panning can be performed for multiple (such as about any of 2, 3, 4, 5, 6 or more) rounds with solution panning, cell panning, or a combination of both, to enrich for phage clones binding specifically to the target MUC16. Enriched phage clones can be tested for specific binding to the target MUC16 by any methods known in the art, including for example ELISA and FACS.

Monoclonal antibodies can also be made by recombinant DNA methods, such as those described in U.S. Pat. No. 4,816,567. DNA encoding the monoclonal antibodies of the present technology can be readily isolated and sequenced using conventional procedures (e.g., by using oligonucleotide probes that are capable of binding specifically to genes encoding the heavy and light chains of murine antibodies). Hybridoma cells as described above or MUC16-specific phage clones of the present technology can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a non-immunoglobulin polypeptide. Such a non-immunoglobulin polypeptide can be substituted for the constant domains of an antibody agent of the present technology, or can be substituted for the variable domains of one antigen-combining site of an antibody agent of the present technology to create a chimeric bivalent antibody agent.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region (CH1) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism.

Human and Humanized Antibodies

The anti-MUC16 antibody agents (e.g., full-length anti-MUC16 antibodies) or an antigen-binding fragment thereof can be humanized antibody agents or human antibody agents. Humanized forms of non-human (e.g., murine) antibody moieties are chimeric immunoglobulins, immunoglobulin chains, or fragments thereof (such as Fv, Fab, Fab', F(ab')₂, scFv, or other antigen-binding subsequences of antibodies) that typically contain minimal sequence derived from non-human immunoglobulin. Humanized antibody moieties include human immunoglobulins, immunoglobulin chains, or fragments thereof (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibody moieties can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence.

Generally, a humanized antibody agent has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., Nature, 321: 522-525 (1986); Riechmann et al., Nature, 332: 323-327 (1988); Verhoeyen et al., Science, 239: 1534-1536 (1988)), by substituting rodent CDRs or CDR sequences for the corresponding sequences of a human antibody. Accordingly, such "humanized" antibody moieties are antibody moieties (U.S. Pat. No. 4,816,567), wherein substantially less than an intact human variable domain has been substituted by the corresponding sequence from a non-human species. In practice, humanized antibody moieties are typically human antibody moieties in which some CDR residues and possibly some FR residues are substituted by residues from analogous sites in rodent antibodies.

As an alternative to humanization, human antibody moieties can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., PNAS USA, 90:2551 (1993); Jakobovits et al., Nature, 362:255-258 (1993); Bruggemann et al., Year in Immunol., 7:33 (1993); U.S. Pat. Nos. 5,545, 806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; and 5,661,016, and Marks et al., Bio /Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); Lonberg and Huszar, Intern. Rev. Immunol., 13: 65-93 (1995).

Human antibody agents may also be generated by in vitro activated B cells (see U.S. Pat. Nos. 5,567,610 and 5,229, 275) or by using various techniques known in the art, including phage display libraries. Hoogenboom and Winter, J . Mol. Biol., 227:381 (1991); Marks et al., J. Mol. Biol., 222:581 (1991). The techniques of Cole et al. and Boerner et al. are also available for the preparation of human monoclonal antibodies. Cole et al., Monoclonal Antibodies and Cancer Therapy, Alan R. Liss, p. 77 (1985) and Boerner et al., J. Immunol., 147(1): 86-95 (1991).

Anti-Muc16 Antibody Agent Variants

In some embodiments, amino acid sequence variants of the anti-MUC16 antibody agents (e.g., full-length anti-MUC16 antibody) or an antigen-binding fragment thereof provided herein are contemplated. For example, it may be desirable to improve the binding affinity and/or other biological properties of the antibody agent. Amino acid sequence variants of an antibody agent may be prepared by introducing appropriate modifications into the nucleotide sequence encoding the antibody agent, or by peptide synthesis. Such modifications include, for example, deletions from, and/or insertions into and/or substitutions of residues within the amino acid sequences of the antibody agent. Any combination of deletion, insertion, and substitution can be made to arrive at the final construct, provided that the final construct possesses the desired characteristics, e.g., antigen-binding.

In some embodiments, anti-MUC16 antibody agent variants having one or more amino acid substitutions are provided. Sites of interest for substitutional mutagenesis include the HVRs and FRs. Amino acid substitutions may be introduced into an antibody agent of interest and the products screened for a desired activity, e.g., retained/improved antigen binding, decreased immunogenicity, or improved ADCC or CDC.

Conservative substitutions are shown in Table 3 below.

TABLE 3

CONSERVATIVE SUBSTITITIONS

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties: hydrophobic: Norleucine, Met, Ala, Val, Leu, Ile; neutral hydrophilic: Cys, Ser, Thr, Asn, Gln; acidic: Asp, Glu; basic: His, Lys, Arg; residues that influence chain orientation: Gly, Pro; and aromatic: Trp, Tyr, Phe. Non-conservative substitutions involve exchanging a member of one of these classes for another class.

An exemplary substitutional variant is an affinity matured antibody agent, which may be conveniently generated, e.g., using phage display-based affinity maturation techniques. Briefly, one or more CDR residues are mutated and the variant antibody moieties displayed on phage and screened for a particular biological activity (e.g., binding affinity). Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al., in *Methods in Molecular Biology* 178:1-37 (O'Brien et al., ed., Human Press, Totowa, NJ, (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody agent variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody agent to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant VH and VL sequences provided above, each HVR either is unaltered, or contains no more than one, two or three amino acid substitutions.

A useful method for identification of residues or regions of an antibody agent that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody agent with antigen is affected. Further substitutions may be introduced at the amino acid locations demonstrating functional sensitivity to the initial substitutions. Alternatively, or additionally, a crystal structure of an antigen-antibody agent complex can be determined to identify contact points between the antibody agent and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody agent with an N-terminal methionyl residue. Other insertional variants of the antibody agent molecule include the fusion to the N- or C-terminus of the antibody agent to an enzyme (e.g. for ADEPT) or a polypeptide which increases the serum half-life of the antibody agent.

Fc Region Variants

In some embodiments, one or more amino acid modifications may be introduced into the Fc region of an antibody agent (e.g., a full-length anti-MUC16 antibody or anti-MUC16 Fc fusion protein) provided herein, thereby generating an Fc region variant. In some embodiments, the Fc region variant has enhanced ADCC effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al., *J Biol. Chem.* 9(2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., an anti-MUC16 antibody). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII. Binding of the Fc receptor to the Fc region of an antibody results in NK cell activation, release of cytolytic granules and consequent target cell apoptosis. The contribution of ADCC to tumor cell killing can be measured with a specific test that uses NK-92 cells that have been transfected with a high-affinity FcR. Results are compared to wild-type NK-92 cells that do not express the FcR.

In some embodiments, the present technology contemplates an anti-MUC16 antibody agent variant (such as a full-length anti-MUC16 antibody variant) comprising an Fc region that possesses some but not all effector functions, which makes it a desirable candidate for applications in which the half-life of the anti-MUC16 antibody agent in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody agent lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al., *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821, 337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Nat'l Acad. Sci. USA* 95:652-656 (1998). C1q binding assays may also be carried out to confirm that the antibody agent is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody agent variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, there is provided an anti-MUC16 antibody agent (such as a full-length anti-MUC16 antibody) variant comprising a variant Fc region comprising one or more amino acid substitutions which improve ADCC. In some embodiments, the variant Fc region comprises one or more amino acid substitutions which improve ADCC, wherein the substitutions are at positions 298, 333, and/or 334 of the variant Fc region (EU numbering of residues). In some embodiments, the anti-MUC16 antibody agent (e.g., full-length anti-MUC16 antibody) variant comprises the following amino acid substitution in its variant Fc region: S298A, E333A, and K334A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

In some embodiments, there is provided an anti-MUC16 antibody agent (such as a full-length anti-MUC16 antibody) variant comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-MUC16 antibody agents (such as full-length anti-MUC16 antibodies) comprising any of the Fc variants described herein, or combinations thereof, are contemplated.

Glycosylation Variants

In some embodiments, an anti-MUC16 antibody agent (such as a full-length anti-MUC16 antibody) or an antigen-binding fragment thereof provided herein is altered to increase or decrease the extent to which the anti-MUC16 antibody agent is glycosylated. Addition or deletion of glycosylation sites to an anti-MUC16 antibody agent may be conveniently accomplished by altering the amino acid sequence of the anti-MUC16 antibody agent or polypeptide portion thereof such that one or more glycosylation sites is created or removed.

Where the anti-MUC16 antibody agent or an antigen-binding fragment thereof comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-MUC16 antibody agent of the present technology may be made in order to create anti-MUC16 antibody agent variants with certain improved properties.

The N-glycans attached to the CH2 domain of Fc is heterogeneous. Antibodies or Fc fusion proteins generated in CHO cells are fucosylated by fucosyltransferase activity. See Shoji-Hosaka et al., *J. Biochem.* 140:777-83 (2006). Normally, a small percentage of naturally occurring afucosylated IgGs may be detected in human serum. N-glycosylation of the Fc is important for binding to FcγR; and afucosylation of the N-glycan increases Fc's binding capacity to FcγRIIIa. Increased FcγRIIIa binding can enhance ADCC, which can be advantageous in certain antibody agent therapeutic applications in which cytotoxicity is desirable.

In some embodiments, an enhanced effector function can be detrimental when Fc-mediated cytotoxicity is undesirable. In some embodiments, the Fc fragment or CH2 domain is not glycosylated. In some embodiments, the N-glycosylation site in the CH2 domain is mutated to prevent from glycosylation.

In some embodiments, anti-MUC16 antibody agent (such as a full-length anti-MUC16 antibody) variants are provided comprising an Fc region wherein a carbohydrate structure attached to the Fc region has reduced fucose or lacks fucose, which may improve ADCC function. Specifically, anti-MUC16 antibody agents are contemplated herein that have reduced fucose relative to the amount of fucose on the same anti-MUC16 antibody agent produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-MUC16 antibody agent is one wherein less than about 50%, 40%, 30%, 20%, 10%, or 5% of the N-linked glycans thereon comprise fucose. For example, the amount of fucose in such an anti-MUC16 antibody agent may be from 1% to 80%, from 1% to 65%, from 5% to 65% or from 20% to 40%. In some embodiments, the anti-MUC16 antibody agent is one wherein none of the N-linked glycans thereon comprise fucose, i.e., wherein the anti-MUC16 antibody agent is completely without fucose, or has no fucose or is afucosylated. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody agent variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as α-1,6-fucosyltransferase gene, FUT8, knockout CHO cells (see, e.g., Yamane-Ohnuki et al., *Biotech. Bioeng.* 87: 614 (2004); Kanda, Y. et al., *Biotechnol. Bioeng.,* 94(4):680-688 (2006); and WO2003/085107).

Anti-MUC16 antibody agent (such as a full-length anti-MUC16 antibody) variants are further provided with bisected oligosaccharides, e.g., in which a biantennary oligosaccharide attached to the Fc region of the anti-MUC16 antibody agent is bisected by GlcNAc. Such anti-MUC16 antibody agent (such as a full-length anti-MUC16 antibody) variants may have reduced fucosylation and/or improved ADCC function. Examples of such antibody agent variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering,* 93(5): 851-861 (2006). Anti-MUC16 antibody agent (such as full-length anti-MUC16 antibody) variants with at least one galactose residue in the oligosaccharide attached to the Fc region are also provided. Such anti-MUC16 antibody agent variants may have improved CDC function. Such antibody agent variants are described, e.g., in WO 1997/30087 (Patel et al.); WO 1998/58964 (Raju, S.); and WO 1999/22764 (Raju, S.).

In some embodiments, the anti-MUC16 antibody agent (such as a full-length anti-MUC16 antibody) variants comprising an Fc region are capable of binding to an FcγRIII. In some embodiments, the anti-MUC16 antibody agent (such as a full-length anti-MUC16 antibody) variants comprising an Fc region have ADCC activity in the presence of human effector cells (e.g., T cell) or have increased ADCC activity in the presence of human effector cells compared to the otherwise same anti-MUC16 antibody agent (such as a full-length anti-MUC16 antibody) comprising a human wild-type IgG1Fc region.

Cysteine Engineered Variants

In some embodiments, it may be desirable to create cysteine engineered anti-MUC16 antibody agents (such as a full-length anti-MUC16 antibody) or an antigen-binding fragment thereof in which one or more amino acid residues are substituted with cysteine residues. In some embodiments, the substituted residues occur at accessible sites of the anti-MUC16 antibody agent or an antigen-binding fragment thereof. By substituting those residues with cysteine, reactive thiol groups are thereby positioned at accessible sites of the anti-MUC16 antibody agent and may be used to conjugate the anti-MUC16 antibody agent to other moieties, such as drug moieties or linker-drug moieties, to create an anti-MUC16 immunoconjugate, as described further herein. Cysteine engineered anti-MUC16 antibody agents (such as anti-MUC16 antibodies, e.g., full-length anti-MUC16 antibodies) may be generated as described, e.g., in U.S. Pat. No. 7,521,541.

Derivatives

In some embodiments, an anti-MUC16 antibody agent (such as a full-length anti-MUC16 antibody) or an antigen-binding fragment thereof provided herein may be further modified to contain additional non-proteinaceous moieties that are known in the art and readily available. The moieties suitable for derivatization of the anti-MUC16 antibody agent include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolpropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the anti-MUC16 antibody agent may vary, and if more than one polymer are attached, they can be the same or different molecules. In general, the number and/or type of polymers used for derivatization can be determined based on considerations including, but not limited to, the particular properties or functions of the anti-MUC16 antibody agent to be improved, whether the anti-MUC16 antibody agent derivative will be used in a therapy under defined conditions, etc.

In some embodiments, conjugates of an anti-MUC16 antibody agent (such as a full-length anti-MUC16 antibody) or an antigen-binding fragment thereof and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the anti-MUC16 antibody agent-nonproteinaceous moiety are killed.

Antibody Conjugates

In certain embodiments, provided herein are anti-MUC16 antibody agent or antigen-binding fragments thereof conjugates, wherein said anti-MUC16 antibody agent or antigen-binding fragments thereof is conjugated to one or more agents, e.g., an imaging agent or a cytotoxic agent. Also provided herein are bispecific antibody conjugates, wherein said bispecific antibody is conjugated to one or more agent, e.g., an imaging agent or a cytotoxic agent. Also provided herein are antibody heavy chain conjugates, wherein said antibody heavy chain is conjugated to one or more agent, e.g., an imaging agent or a cytotoxic agent. Also provided herein are antibody light chain conjugates, wherein said antibody light chain is conjugated to one or more agent, e.g., an imaging agent or a cytotoxic agent. Also provided herein are fusion protein conjugates, wherein said fusion protein is conjugated to an agent, e.g., an imaging agent or a cytotoxic agent. In certain embodiments, the agent is conjugated covalently or non-covalently.

In certain embodiments, the imaging agent is a detectable label, such as, a chromogenic, enzymatic, radioisotopic, isotopic, fluorescent, toxic, chemiluminescent, nuclear magnetic resonance contrast agent or another label.

The detectable group can be any material having a detectable physical or chemical property. Such detectable labels have been well-developed in the field of immunoassays and imaging. In general, almost any label useful in such methods can be applied to the present technology. Thus, a label is any composition detectable by spectroscopic, photochemical, biochemical, immunochemical, electrical, optical or chemical means. Labels useful in the practice of the present technology include magnetic beads (e.g., Dynabeads™), fluorescent dyes (e.g., fluorescein isothiocyanate, Texas red, rhodamine, and the like), radiolabels (e.g., $^3$H, $^{14}$C, $^{35}$S, $^{125}$I, $^{121}$I, $^{131}$I, $^{112}$In, $^{99}$mTc), other imaging agents such as microbubbles (for ultrasound imaging), $^{18}$F, $^{11}$C, $^{15}$O, $^{89}$Zr, $^{89}$Zr-DFO (for Positron emission tomography), $^{99m}$TC, $^{111}$In (for Single photon emission tomography), enzymes (e.g., horse radish peroxidase, alkaline phosphatase and others commonly used in an ELISA), and calorimetric labels such as colloidal gold or colored glass or plastic (e.g., polystyrene, polypropylene, latex, and the like) beads. Patents that describe the use of such labels include U.S. Pat. Nos. 3,817,837; 3,850,752; 3,939,350; 3,996,345; 4,277,437; 4,275,149; and 4,366,241, each incorporated herein by reference in their entirety and for all purposes. See also Handbook of Fluorescent Probes and Research Chemicals (6$^{th}$ Ed., Molecular Probes, Inc., Eugene OR.).

The label can be coupled directly or indirectly to the desired component of an assay according to methods well known in the art. As indicated above, a wide variety of labels can be used, with the choice of label depending on factors such as required sensitivity, ease of conjugation with the compound, stability requirements, available instrumentation, and disposal provisions.

Non-limiting examples of suitable chromogenic labels include diaminobenzidine and 4-hydroxyazo-benzene-2-carboxylic acid.

Non-limiting examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Suitable radioisotopes are well known to those skilled in the art and include beta-emitters, gamma-emitters, positron-emitters, and x-ray emitters. Non-limiting examples of suitable radioisotopic labels include $^3$H, $^{18}$F, $^{111}$In, $^{125}$I, $^{131}$I, $^{32}$P, $^{33}$P, $^{35}$S, $^{11}$C, $^{14}$C, $^{51}$Cr, $^{57}$To, $^{58}$Co, $^{59}$Fe, $^{75}$Se, $^{152}$Eu, $^{90}$Y $^{67}$Cu, $^{217}$Ci, $^{211}$At, $^{212}$Pb, $^{47}$Sc, $^{223}$Ra, $^{223}$Ra, $^{89}$Zr, $^{177}$Lu, and $^{109}$Pd. In certain embodiments, $^{111}$In is a preferred isotope for in vivo imaging as it avoids the problem of dehalogenation of $^{125}$I or $^{131}$I-labeled anti-MUC16 antibody agents or antigen-binding fragments thereof in the liver. In addition, $^{111}$In has a more favorable gamma emission energy for imaging (Perkins et al, *Eur. J. Nucl. Med.* 70:296-301 (1985); Carasquillo et al., *J. Nucl. Med.* 25:281-287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861-870 (1987)).

Non-limiting examples of suitable non-radioactive isotopic labels include 157Gd, $^{55}$n, $^{162}$Dy, $^{52}$Tr, and $^{56}$Fe.

Non-limiting examples of suitable fluorescent labels include a $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label.

Non-limiting examples of chemiluminescent labels include a luminol label, an isoluminol label, an aromatic acridinium ester label, an imidazole label, an acridinium salt label, an oxalate ester label, a luciferin label, a luciferase label, and an aequorin label.

Non-limiting examples of nuclear magnetic resonance contrasting agents include heavy metal nuclei such as Gd, Mn, and iron.

Techniques known to one of ordinary skill in the art for conjugating the above-described labels to said anti-MUC16 antibody agents or antigen-binding fragments thereof, bispecific antibodies, antibody heavy chains, antibody light chains, and fusion proteins are described in, for example, Kennedy et at., *Clin. CMm. Acta* 70: 1-31 (1976), and Schurs et al, *Clin. CMm. Acta* 81: 1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

Nonlimiting examples of cytotoxic agents include a cytostatic or cytocidal agent, a radioactive metal ion, e.g., alpha-emitters, and toxins, e.g., *pseudomonas* exotoxin, abrin, cholera toxin, ricin A, and diphtheria toxin.

In certain embodiments, the agent is a diagnostic agent. A diagnostic agent is an agent useful in diagnosing or detecting a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In order to load an anti-MUC16 antibody agent or antigen-binding fragment thereof with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, for example, ethylenediaminetetraacetic acid (EDTA), diethylenetriaminepentaacetic acid (DTP A), porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking other, more unusual, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with an anti-MUC16 antibody agent or antigen-binding fragment thereof provided herein.

Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed herein.

Pharmaceutical Compositions

Also provided herein are compositions (such as pharmaceutical compositions, also referred to herein as formulations) comprising an anti-MUC16 antibody agent (such as a full-length anti-MUC16 antibody) or an antigen-binding fragment thereof, nucleic acid encoding the antibody agent, vector comprising the nucleic acid encoding the antibody agent, or host cell comprising the nucleic acid or vector. In some embodiments, there is provided a pharmaceutical composition comprising an anti-MUC16 antibody agent and optionally a pharmaceutically acceptable carrier.

Suitable formulations of the anti-MUC16 antibody agents (such as anti-MUC16 antibodies, e.g., full-length anti-MUC16 antibodies) or an antigen-binding fragment thereof are obtained by mixing an anti-MUC16 antibody agent having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-MUC16 antibody agents of this present technology into cells.

The formulation herein may also contain one or more active compounds in addition to the anti-MUC16 antibody agent (such as a full-length anti-MUC16 antibody) or an antigen-binding fragment thereof as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent in addition to the anti-MUC16 antibody agent or an antigen-binding fragment thereof. Such molecules are suitably present in combination in amounts that are effective for the purpose intended. The effective amount of such other agents depends on the amount of anti-MUC16 antibody agent present in the formulation, the type of disease or disorder or treatment, and other factors discussed above. These are generally used in the same dosages and with administration routes as described herein or about from 1 to 99% of the heretofore employed dosages.

The anti-MUC16 antibody agents (such as anti-MUC16 antibodies, e.g., full-length anti-MUC16 antibodies) or an antigen-binding fragment thereof may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Sustained-release preparations may be prepared.

Sustained-release preparations of the anti-MUC16 antibody agents (such as anti-MUC16 antibodies, e.g., full-length anti-MUC16 antibodies) or an antigen-binding fragment thereof can be prepared. Suitable examples of sustained-release preparations include semipermeable matrices of solid hydrophobic polymers containing the antibody agent (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D (–)-3-hydroxybutyric acid. While polymers such as ethylene-vinyl acetate and lactic acid-glycolic acid enable release of molecules for over 100 days, certain hydro gels release proteins for shorter time periods. When encapsulated antibody agents remain in the body for a long time, they can denature or aggregate as a result of exposure to moisture at 37° C., resulting in a loss of biological activity and possible changes in immunogenicity. Rational strategies can be devised for stabilization of anti-MUC16 antibody agents depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-MUC16 antibody agent (such as a full-length anti-MUC16 antibody) or an antigen-binding fragment thereof is formulated in a buffer comprising a citrate, NaCl, acetate, succinate, glycine, polysorbate 80 (Tween 80), or any combination of the foregoing. In some embodiments, the anti-MUC16 antibody agent or an antigen-binding fragment thereof is formulated in a buffer comprising about 100 mM to about 150 mM glycine. In some embodiments, the anti-MUC16 antibody agent or an antigen-binding fragment thereof is formulated in a buffer comprising about 50 mM to about 100 mM NaCl. In some embodiments, the anti-MUC16 antibody agent or an antigen-binding fragment thereof is formulated in a buffer comprising about 10 mM to about 50 mM acetate. In some embodiments, the anti-MUC16 antibody agent or an antigen-binding fragment thereof is formulated in a buffer comprising about 10 mM to about 50 mM succinate. In some embodiments, the anti-MUC16 antibody agent or an antigen-binding fragment thereof is formulated in a buffer comprising about 0.005% to about 0.02% polysorbate 80. In some embodiments, the anti-MUC16 antibody agent or an antigen-binding fragment thereof is formulated in a buffer having a pH between about 5.1 and 5.6. In some embodiments, the anti-MUC16 antibody agent or an antigen-binding fragment thereof is formulated in a buffer comprising 10 mM citrate, 100 mM NaCl, 100 mM glycine, and 0.01% polysorbate 80, wherein the formulation is at pH 5.5.

The formulations to be used for in vivo administration must be sterile. This is readily accomplished by, e.g., filtration through sterile filtration membranes.

Methods of Treatment Using Anti-Muc16 Antibody Agents

In certain embodiments, provided herein are methods for treating a cancer in a subject, in particular, a MUC16-positive cancer in a subject, comprising administering to the subject in need thereof a therapeutically effective amount of anti-MUC16 antibody agent or an antigen-binding fragment thereof. In some embodiments, the anti-MUC16 antibody agent or antigen-binding fragment thereof is administered at a therapeutically effective dose, such as a dose described herein. In some embodiments, the anti-MUC16 antibody agent or antigen-binding fragment thereof is administered according to a method as described herein. In some embodiments, the anti-MUC16 antibody agent or antigen-binding fragment thereof is administered in combination with one or more additional pharmaceutically active agents.

For use of an anti-MUC16 antibody agent or antigen-binding fragment thereof in a subject of a particular species, an anti-MUC16 antibody agent or antigen-binding fragment thereof is used that binds to MUC16 of that particular species. For example, to treat a human, an anti-MUC16 antibody agent or antigen-binding fragment thereof is used that binds to human MUC16. In some embodiments, the anti-MUC16 antibody agent or antigen-binding fragment thereof is an immunoglobulin.

In addition, for use of an anti-MUC16 antibody agent or antigen-binding fragment thereof in a subject of a particular species, the anti-MUC16 antibody agent, preferably, the constant region of an anti-MUC16 antibody agent or antigen-binding fragment thereof, is derived from that particular species. For example, to treat a human, an anti-MUC16 antibody agent or antigen-binding fragment thereof can comprise an anti-MUC16 antibody agent or antigen-binding fragment thereof that is an immunoglobulin, wherein the immunoglobulin comprises a human constant region. In some embodiments, the subject is a human.

In some embodiments, the MUC16-positive cancer is ovarian cancer, lung cancer, pancreatic cancer, breast cancer, fallopian tube cancer, uterine (e.g., endometrial) cancer, primary peritoneum cancer or cancer of any other tissue that expresses the MUC16 receptor.

In some embodiments, treatment can be to achieve beneficial or desired clinical results including, but not limited to, alleviation of a symptom, diminishment of extent of a disease, stabilizing (i.e., not worsening) of state of a disease, delay or slowing of disease progression, amelioration or palliation of the disease state, and remission (whether partial or total), whether detectable or undetectable. In a specific embodiment, "treatment" can also be to prolong survival as compared to expected survival if not receiving treatment. In some embodiments, the administration of an anti-MUC16 antibody agent or an antigen-binding fragment thereof described herein, or a pharmaceutical composition described herein to a subject with cancer (e.g., ovarian cancer, lung cancer, pancreatic cancer, breast cancer, fallopian tube cancer, uterine (e.g., endometrial) cancer, or primary peritoneum cancer, or cancer of any other tissue that expresses the MUC16 receptor) achieves at least one, two, three, four or more of the following effects: (i) the reduction or amelioration of the severity of one or more symptoms of cancer; (ii) the reduction in the duration of one or more symptoms associated with cancer; (iii) the prevention in the recurrence of a symptom associated with cancer; (iv) the reduction in hospitalization of a subject; (v) a reduction in hospitalization length; (vi) the increase in the survival of a subject; (vii) the enhancement or improvement of the therapeutic effect of another therapy; (viii) the inhibition of the development or onset of one or more symptoms associated with cancer; (ix) the reduction in the number of symptoms associated with cancer; (x) improvement in quality of life as assessed by methods well known in the art; (x) inhibition of the recurrence of a tumor; (xi) the regression of tumors and/or one or more symptoms associated therewith; (xii) the inhibition of the progression of tumors and/or one or more symptoms associated therewith; (xiii) a reduction in the growth of a tumor; (xiv) a decrease in tumor size (e.g., volume or diameter); (xv) a reduction in the formation of a newly formed tumor; (xvi) prevention, eradication, removal, or control of primary, regional and/or metastatic tumors; (xvii) a decrease in the number or size of metastases; (xviii) a reduction in mortality; (xix) an increase in relapse free survival; (xx) the size of the tumor is maintained and does not increase or increases by less than the increase of a tumor after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; and/or (xxi) an increase in the length of remission in patients. Treatment can be to achieve one or more of the foregoing.

A subject treated in accordance with the methods provided herein can be any mammal, such as a rodent, a cat, a canine, a horse, a cow, a pig, a monkey, a primate, or a human, etc. In some embodiments, the subject is a human. In some embodiments, the subject is a canine. As used herein, the terms "subject" and "patient" are used interchangeably.

In certain embodiments, a subject treated in accordance with the methods provided herein has been diagnosed with a MUC16-positive cancer, including but not limited to, ovary, lung, pancreas, breast, uterine, fallopian tube, or primary peritoneum cancer, or cancer of any other tissue that expresses the MUC16.

Diagnostic Uses

In certain embodiments, anti-MUC16 antibody agents or antigen-binding fragments thereof described herein can be used for diagnostic purposes to detect, diagnose, or monitor a condition described herein (e.g., a condition involving MUC16-positive cancer cells). In certain embodiments, anti-MUC16 antibody agents or antigen-binding fragments thereof for use in diagnostic purposes are labeled.

In certain embodiments, provided herein are methods for the detection of a condition described herein comprising (a) assaying the expression of MUC16 or a fragment thereof in cells or a tissue sample of a subject using one or more anti-MUC16 antibody agents or antigen-binding fragments thereof described herein; and (b) comparing the level of MUC16 or the fragment thereof expression with a control level, for example, levels in normal tissue samples (e.g., from a subject not having a condition described herein, or from the same patient before onset of the condition), whereby an increase or decrease in the assayed level of MUC16 or the fragment thereof expression compared to the control level of MUC16 or the fragment thereof expression is indicative of a condition described herein.

Antibodies described herein can be used to assay the levels of MUC16 or a fragment thereof in a biological sample using classical immunohistological methods as described herein or as known to those of skill in the art (e.g., see Jalkanen et al., *J. Cell. Biol.* 101: 976-985 (1985); and Jalkanen et al., *J. Cell. Biol.* 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, 121I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. In some embodiments, the assay labels are conjugated to the anti-MUC16 antibody agents or antigen-binding fragment thereof provided herein for direct detection. In some embodiments, the assay labels are conjugated to a secondary antibody that binds to an anti-MUC16 antibody agents or antigen-binding fragment thereof provided herein. The secondary antibody type is selected according to the class of the primary antibody (e.g., IgG or IgM), the source host, and the kind of label which is preferred. In some embodiments, the secondary antibody is a class or isotype specific antibody (e.g., IgG, IgM, IgA, IgE or IgG). In some embodiments, the secondary antibody is a subclass specific antibody (e.g., IgG1, IgG2, IgG2, IgG4, IgA1, or IgA2). In some embodiments, the secondary antibody binds to one or more classes or subclasses of antibodies. In some embodiments, the secondary antibody binds to the heavy chain of the primary antibody. In some embodiments, the secondary antibody binds to the light chain of the primary antibody. In some embodiments, the secondary antibody binds to a kappa light chain of the primary antibody. In some embodiments, the secondary antibody binds to a lambda light chain of the primary antibody. In some embodiments, the secondary antibody is an anti-Fc or an anti-F(ab) or anti-(Fab')2 fragment antibody. In some embodiments, the secondary antibody is a rabbit, mouse, goat, donkey or chicken antibody.

In certain embodiments, monitoring of a condition described herein (e.g., a MUC16-positive cancer), is carried out by repeating the method for diagnosing for a period of time after initial diagnosis.

Presence of the labeled molecule can be detected in the subject (i.e., in vivo) using methods known in the art for in vivo scanning. Skilled artisans will be able to determine the appropriate method for detecting a particular label. Methods and devices that may be used in the diagnostic methods of the present technology include, but are not limited to, computed tomography (CT), whole body scan such as position emission tomography (PET), magnetic resonance imaging (MRI), and sonography.

Also disclosed herein is a method for detecting cancer in a subject in vivo comprising (a) administering to the subject an effective amount of any of the anti-MUC16 constructs disclosed herein, wherein the anti-MUC16 construct is configured to localize to a cancer cell expressing MUC16 and is labeled with a radioisotope; and (b) detecting the presence of a tumor in the subject by detecting radioactive levels emitted by the anti-MUC16 construct that are higher than a reference value, optionally wherein the radioisotope is $^{89}$Zr-desferri-oxamine B (DFO). In some embodiments, the subject is diagnosed with or is suspected of having cancer. Additionally or alternatively, in some embodiments, the radioactive levels emitted by the anti-MUC16 construct are detected using positron emission tomography or single photon emission computed tomography. In any of the preceding embodiments, the method further comprises administering to the subject an effective amount of an immunoconjugate comprising an anti-MUC16 construct of the present technology conjugated to a radionuclide. The radionuclide may be an alpha particle-emitting isotope, a beta particle-emitting isotope, an Auger-emitter, or any combination thereof.

Delivery of Anti-Muc16 Antibody Agents

An anti-MUC16 antibody agent or antigen-binding fragment thereof as described herein, or composition containing, or cells expressing the antibodies, or antigen-binding fragments thereof, described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray. In one embodiment, an anti-MUC16 antibody agent or antigen-binding fragment thereof, or a composition described herein is administered parenterally to a subject. In some embodiments, said parenteral administration is intravenous, intramuscular, or subcutaneous.

The amount of an anti-MUC16 antibody agent or antigen-binding fragment thereof, or composition which will be effective in the treatment and/or prevention of a condition will depend on the nature of the disease, and can be determined by standard clinical techniques.

The precise dose to be employed in a composition will also depend on the route of administration, and the type of cancer, and should be decided according to the judgment of the practitioner and each subject's circumstances. For example, effective doses may also vary depending upon means of administration, target site, physiological state of the patient (including age, body weight and health), whether the patient is human or animal, other medications administered, or whether treatment is prophylactic or therapeutic. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

For an anti-MUC16 antibody agent or an antigen-binding fragment thereof, the dosage may range from about 0.0001 to 100 mg/kg, and more usually 0.01 to 15 mg/kg, of the patient body weight. For example, dosages can be 1 mg/kg body weight, 10 mg/kg body weight, or within the range of 1-10 mg/kg or in other words, 70 mg or 700 mg or within the range of 70-700 mg, respectively, for a 70 kg patient. Generally, human antibodies have a longer half-life within the human body than antibodies from other species due to the immune response to the foreign polypeptides. Thus, lower dosages of human antibodies and less frequent administration is often possible.

In certain embodiments, such as in the administration of engineered cells expressing the antibodies or antigen-binding fragments thereof, or CARs, a subject is administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges. In some embodiments, the dose of total cells and/or dose of individual sub-populations of cells is within a range of between at or about $10^4$ and at or about $10^9$ cells/kilograms (kg) body weight, such as between $10^5$ and $10^6$ cells/kg body weight, for example, at or about $1 \times 10^5$ cells/kg, $1.5 \times 10^5$ cells/kg, $2 \times 10^5$ cells/kg, or $1 \times 10^6$ cells/kg, $2 \times 10^6$ cells/kg, $5 \times 10^6$ cells/kg, or $10 \times 10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^7$ T cells/kg body weight.

An anti-MUC16 antibody agent or antigen-binding fragment thereof can be administered on multiple occasions. Intervals between single dosages can be 1 week, 2 weeks, 3 weeks, 4 weeks, 1 month, 2 months, 3 months, 6 months, 1 year, or 2 years.

Combination Therapies

In some embodiments, the methods provided herein for treating cancer (e.g., ovarian cancer, pancreatic cancer, lung cancer, breast cancer, fallopian tube cancer, uterine (e.g., endometrial) cancer, or primary peritoneum cancer) in a subject, comprising administering to a subject in need thereof a pharmaceutical composition comprising an anti-MUC16 antibody agent or an antigen-binding fragment thereof described herein, further comprise administering to the subject one or more additional therapeutic agents. In some embodiments, the additional therapeutic agent is for treating the cancer in the subject (e.g., ovarian cancer, pancreatic cancer, lung cancer, breast cancer, fallopian tube cancer, uterine (e.g., endometrial) cancer, and primary peritoneum cancer). In some embodiments, the additional therapeutic agent is for treating any side effects of treatment with an anti-MUC16 antibody agent or an antigen-binding fragment thereof described herein.

In some embodiments, the additional agent is an agent used to treat ovarian cancer. In some embodiments, the additional agent is an agent used to treat pancreatic cancer. In some embodiments, the additional agent is an agent used to treat lung cancer. In some embodiments, the additional agent is an agent used to treat breast cancer. In some embodiments, the additional agent is an agent used to treat fallopian tube cancer. In some embodiments, the additional agent is an agent used to treat uterine (e.g., endometrial) cancer. In some embodiments, the additional agent is an agent used to treat primary peritoneum cancer.

An anti-MUC16 antibody agent or antigen-binding fragment thereof described herein can be administered with an additional therapeutic agent concurrently or sequentially (before and/or after). The antibody or antigen binding fragment thereof and the additional therapeutic agent can be administered in the same or different compositions, and by the same or different routes of administration. A first therapy (which is an anti-MUC16 antibody agent or an antigen-binding fragment thereof described herein, or the additional therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second therapy (the anti-MUC16 antibody agent or an antigen-binding fragment thereof described herein, or the additional therapeutic agent) to a subject with cancer (e.g., ovarian cancer, pancreatic cancer, lung cancer, breast cancer, fallopian tube cancer, uterine (e.g., endometrial) cancer, and primary peritoneum cancer). In certain embodiments, an additional therapeutic agent administered to a subject in combination with an anti-MUC16 antibody agent or an antigen-binding fragment thereof described herein is administered in the same composition (pharmaceutical composition). In other embodiments, an additional therapeutic agent administered in combination with an anti-MUC16 antibody agent or an antigen-binding fragment thereof described herein is administered to a subject in a different composition than the anti-MUC16 antibody agent or an antigen-binding fragment thereof described herein (e.g., two or more pharmaceutical compositions are used).

Articles of Manufacture and Kits

In some embodiments of the present technology, there is provided an article of manufacture containing materials useful for the treatment of a cancer characterized by high MUC16 expression and/or high aerobic glycolysis (e.g., kidney cancer, cervical cancer, or prostate cancer), or for delivering an anti-MUC16 antibody agent (such as a full-length anti-MUC16 antibody) to a cell expressing MUC16 on its surface. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder described herein, and may have a sterile access port (for example the container may be an intravenous solution bag or a vial having a stopper pierceable by a hypodermic injection needle). At least one active agent in the composition is an anti-MUC16 antibody agent of the present technology. The label or package insert indicates that the composition is used for treating the particular condition. The label or package insert will further comprise instructions for administering the anti-MUC16 antibody agent composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating cancer (such as HCC, melanoma, lung squamous cell carcinoma, ovarian carcinoma, yolk sac tumor, choriocarcinoma, neuroblastoma, hepatoblastoma, Wilms' tumor, testicular nonseminomatous germ cell tumor, gastric carcinoma, or liposarcoma).

Additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a cancer characterized by high MUC16 expression and/or high aerobic glycolysis (e.g., kidney cancer, cervical cancer, or prostate cancer), or for delivering an anti-MUC16 antibody agent (such as a full-length anti-MUC16 antibody) to a cell expressing MUC16 on its surface, optionally in combination with the articles of manufacture. Kits of the present technology include one or more containers comprising an anti-MUC16 antibody agent composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the present technology are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-MUC16 antibody agent (such as a full-length anti-MUC16 antibody). In some embodiments, the kit comprises a) a composition comprising an anti-MUC16 antibody agent, and b) an effective amount of at least one other agent, wherein the other agent enhances the effect (e.g., treatment effect, detecting effect) of the anti-MUC16 antibody agent. In some embodiments, the kit comprises a) a composition comprising an anti-MUC16 antibody agent, and b) instructions for administering the anti-MUC16 antibody agent composition to an individual for treatment of a cancer characterized by high MUC16 expression and/or high aerobic glycolysis (e.g., kidney cancer, cervical cancer, or prostate cancer). In some embodiments, the kit comprises a) a composition comprising an anti-MUC16 antibody agent, b) an effective amount of at least one other agent, wherein the other agent enhances the effect (e.g., treatment effect, detecting effect) of the anti-MUC16 antibody agent, and c) instructions for administering the anti-MUC16 antibody agent composition and the other agent(s) to an individual for treatment of a cancer characterized by high MUC16 expression and/or high aerobic glycolysis (e.g., kidney cancer, cervical cancer, or prostate cancer). The anti-MUC16 antibody agent and the other agent(s) can be present in separate containers or in a single container. For example, the kit may comprise one distinct composition or two or more compositions wherein one composition comprises an anti-MUC16 antibody agent and another composition comprises another agent.

In some embodiments, the kit comprises a nucleic acid (or set of nucleic acids) encoding an anti-MUC16 antibody agent (such as a full-length anti-MUC16 antibody). In some embodiments, the kit comprises a) a nucleic acid (or set of nucleic acids) encoding an anti-MUC16 antibody agent, and b) a host cell for expressing the nucleic acid (or set of nucleic acids). In some embodiments, the kit comprises a) a nucleic acid (or set of nucleic acids) encoding an anti-MUC16 antibody agent, and b) instructions for i) expressing the anti-MUC16 antibody agent in a host cell, ii) preparing a composition comprising the anti-MUC16 antibody agent, and iii) administering the composition comprising the anti-MUC16 antibody agent to an individual for the treatment of a cancer characterized by high MUC16 expression and/or high aerobic glycolysis (e.g., kidney cancer, cervical cancer, or prostate cancer). In some embodiments, the kit comprises a) a nucleic acid (or set of nucleic acids) encoding an anti-MUC16 antibody agent, b) a host cell for expressing the nucleic acid (or set of nucleic acids), and c) instructions for i) expressing the anti-MUC16 antibody agent in the host cell, ii) preparing a composition comprising the anti-MUC16 antibody agent, and iii) administering the composition comprising the anti-MUC16 antibody agent to an individual for the treatment of a cancer characterized by high MUC16 expression and/or high aerobic glycolysis (e.g., kidney cancer, cervical cancer, or prostate cancer).

Also disclosed herein are kits comprising an anti-MUC16 construct of the present technology, a murine anti-MUC16 antibody or antigen binding fragment thereof, and instructions for use, wherein the murine anti-MUC16 antibody or antigen binding fragment includes (a) a variable heavy (VH) chain comprising a heavy chain complementarity determining region 1 (HC-CDR1), HC-CDR2, and HC-CDR3 of SEQ ID NOS: 17, 18, and 19, respectively, and a variable light (VL) chain comprising a light chain complementarity determining region 1 (LC-CDR1), LC-CDR2, and LC-CDR3 of SEQ ID NOS: 14, 15, and 16, respectively; or (b) a variable heavy (VH) chain comprising a heavy chain complementarity determining region 1 (HC-CDR1), HC-CDR2, and HC-CDR3 of SEQ ID NOS: 35, 36, and 37, respectively, and a variable light (VL) chain comprising a light chain complementarity determining region 1 (LC-CDR1), LC-CDR2, and LC-CDR3 of SEQ ID NOS: 32, 33, and 34, respectively. The murine anti-MUC16 antibody or antigen binding fragment (e.g., those described in U.S. Pat. No. 9,169,328) may be used to identify a patient that is responsive to treatment with the anti-MUC16 construct. In some embodiments, the murine anti-MUC16 antibody or antigen binding fragment is used to detect MUC16-expressing tumors in a sample obtained from the patient via western blotting, immunohistochemistry, high-performance liquid chromatography (HPLC), liquid chromatography-mass spectrometry (LC/MS), enzyme-linked immunosorbent assay (ELISA), immunoprecipitation, or immunoelectrophoresis.

The kits of the present technology are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-MUC16 antibody agent compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of an anti-MUC16 antibody agent (such as a full-length anti-MUC16 antibody) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-MUC16 antibody agent and pharmaceutical compositions and instructions for use and packaged in quantities sufficient for storage and use in pharmacies, for example, hospital pharmacies and compounding pharmacies.

Those skilled in the art will recognize that several embodiments are possible within the scope and spirit of the present technology. The present technology will now be described in greater detail by reference to the following non-limiting examples. The following examples further illustrate the present technology but, of course, should not be construed as in any way limiting its scope.

EXAMPLES

The present technology is further illustrated by the following Examples, which should not be construed as limiting in any way. The following Examples demonstrate the preparation, characterization, and use of illustrative anti-MUC16 antibodies of the present technology. The following Examples demonstrate the production of human and bispecific antibodies of the present technology, and characterization of their binding specificities and in vivo biological activities.

Example 1: In Vitro Characterization of Antibodies Binding to the Carboxy-Terminus of MUC16

Murine monoclonal antibodies were previously developed against the peptide sequence in the ectodomain (juxtamembrane) portion of the MUC16 carboxy-terminus (called herein "peptide-2"). This example described the testing of six of these murine monoclonal antibodies which showed differential binding to MUC16. The goal of the study was to identify the best antibody candidate for humanization and potential translation in the clinic. The study was divided into three phases. In the first phase, the six antibodies were evaluated based on the results of a comparative in vitro screening process. The objective of this phase of the study was to select two lead candidates for in vivo analyses based on the following 3 parameters: 1) amenability of the antibodies to bioconjugation; 2) outcome of radiolabeling the antibodies, including radiochemical yields and molar activities; and 3) performance of the radioimmunoconjugates in cell-based assays including determination of the immunoreactive fraction, saturation binding, and cellular internalization.

In the second phase of the study, the in vivo tumor-targeting and radiopharmacologic profiles of the two lead candidates identified from the in vitro screening process were evaluated (see Example 2).

Finally, in the third phase of the study, humanization of the lead MUC16 carboxy-terminus binding antibody identified from the preceding phase was performed. The humanized variant was then evaluated for its in vivo tumor-targeting and radiopharmacologic profile (see Example 3).

Three of the antibodies, 9C9, 4H11 and 4A5, that were chosen in in the study had previously demonstrated robust and high affinity binding to the MUC16 carboxy-terminus using various methods of analyses, including enzyme linked immunosorbent assay (ELISA) with supernatants from cultures of their respective hybridomas, Western blotting with purified recombinant pFUSE MUC16c114 containing the 58 amino acid residues of the ectodomain MUC16 carboxy-terminus fused to the human Fc antibody domain, flow cytometry analyses and saturation binding assays with MUC16-expressing OVCAR3 cells. Two other antibodies, 4C7 and 29G9, showed binding to MUC16 via ELISA and western blot analyses. The last antibody, 4A2, showed positivity by ELISA alone.

The ideal characteristics of $^{89}$Zr, including its physical (decay) half-life (ti/2=72.4 h), which matches well with the biological half-life and in vivo pharmacokinetics of tumor-targeting by antibodies, combined with its ability to residualize within cells after internalization, made it an isotope of choice for radiolabeling the various MUC16 carboxy-terminus-binding antibodies and evaluating their in vitro and in vivo radiopharmacologic profiles. $^{89}$Zr was produced at Memorial Sloan Kettering Cancer Center on a TR19/9 cyclotron (Ebco Industries Inc.) via the $^{89}$Y(p,n)$^{89}$Zr reaction and purified to yield $^{89}$Zr with a specific activity of 196-496 MBq/mg. Activity measurements were made using a CRC-15R Dose Calibrator (Capintec). For the quantification of activities, samples were counted on an Automatic Wizard gamma counter (Perkin Elmer). The radiolabeling of ligands was monitored using instant thin-layer chromatography paper (Agilent Technologies) and analyzed on a Bioscan AR-2000 radio-ITLC plate reader using Winscan Radio-TLC software (Bioscan Inc.).

To radiolabel the antibodies with $^{89}$Zr, the isothiocyanate-functionalized variant of desferrioxamine (p-SCN-Bn-DFO) was conjugated to produce DFO-immunoconjugates of all six antibodies using identical reaction conditions. The objective was to facilitate bioconjugation of the bifunctional chelator with epsilon-amine(s) on lysine residues, which are randomly distributed in the structure of the antibody. Briefly, the antibodies were suspended in citrate buffer (25 mM sodium citrate, 150 mM sodium chloride) at an average concentration of 2-3 mg/mL. The antibodies were buffer-exchanged using disposable Sephadex G-25 PD10 desalting columns (17085101; GE Healthcare, Life Sciences) pre-equilibrated with chelexed PBS and concentrated using centrifugal filter units with a 50,000 molecular weight cutoff (Amicon Ultra 4 Centrifugal Filtration Units, Millipore) to obtain a final concentration of 12-15 mg/mL. The pH of the antibody solution was adjusted to 8.5-9.0 using 0.1 M Na$_2$CO$_3$. Thereafter, 10 molar equivalents of isothiocyanato-desferrioxamine (p-SCN-Bn-DFO) (B-705; Macrocyclics, Inc.) dissolved in DMSO (41640; Sigma Aldrich) at a concentration of 10 mg/mL. The reaction was incubated at 37° C. for 1 h on a thermomixer set at 500 rpm. The DFO-conjugated antibodies were purified using PD10 desalting columns and concentrated using centrifugal filter units as described above.

$^{89}$Zr was provided by the Radiochemistry and Molecular Imaging Probes core at MSKCC as [$^{89}$Zr]Zr-oxalate dissolved in 1M oxalic acid. The solution was neutralized with 1M sodium carbonate to reach pH~7. Each immunoconjugate dissolved in chelexed PBS pH 7.4 was incubated with neutralized $^{89}$Zr at 37° C. for 1 hour. The progress of the radiolabeling reactions was monitored via radio-instant thin layer chromatography (radio-ITLC) by spotting 0.5 μL of the crude reaction mixture on a silica-gel impregnated glass-microfiber paper strip (iTLC-SG; Varian) and analyzed on an ITLC scanner (AR-2000; Bioscan Inc.) using 50 mM EDTA pH 5.5 as the solvent for the mobile phase. On the ITLC, the $^{89}$Zr-labeled radioimmunoconjugates complexes remained at the origin, while free $^{89}$Zr was taken up by EDTA in the mobile phase and migrated with the solvent front. Crude radiochemical yields were calculated using the radio-ITLC data. The $^{89}$Zr-radioimmunoconjugates were then purified via size exclusion chromatography using PD10 desalting columns, followed by centrifugal filtration to concentrate the final volume to prepare the tracer doses. The radiochemical purity of the purified radioimmunoconjugates was confirmed via radio-ITLC prior to using them for animal experiments.

The determine serum stability, 100 μL of each of the radioimmunoconjugates was incubated with 900 μL of human serum (H4522; Sigma Aldrich) and agitated constantly on a thermomixer set at 37° C. Samples were taken from each microcentrifuge tube and analyzed via radio-ITLC at day 0, 1, 3, 5, and 7. All samples were analyzed in triplicates. The serum stability of the radioimmunoconjugates was measured as the percentage of $^{89}$Zr retained at the origin of the radio-ITLC strip and reported as % intact.

The immunoreactive fraction of the $^{89}$Zr-DFO-antibodies was determined using a modified cell binding assay following the procedure described by Lindmo et al. (1984) *J ImmunolMethods* 72:77-89) To this end, SKOV3$^{c114}$ cells were suspended in microcentrifuge tubes at concentrations ranging from $5.0 \times 10^5$-$5.0 \times 10^6$ cells/mL in 500 μL PBS supplemented with 1% BSA (pH 7.4). Aliquots of the various radioimmunoconjugates—50 μL of 1 μCi/mL stock were added to each tube before the final volume of the cells and radioimmunoconjugates per tube was made up to 500 μL. The samples were incubated for 60 min on a thermomixer set to 37° C. and 500 rpm. The treated cells were then pelleted via centrifugation (1400 rpm for 4 min), the supernatant was aspirated out and the pellet was washed three times with ice-cold PBS before removing the supernatant and counting the radioactivity associated with the cell pellets. The activity data were background-corrected and compared with the total number of counts in appropriate control samples. Immunoreactive fractions were determined by linear regression analysis of total/bound radioactivity plotted against the inverse of normalized cell concentration. Additionally, the immunoreactivity of the lead antibody [$^{89}$Zr] Zr-DFO-4H11 was evaluated in a bead-based binding assay (see FIG. 5).

To generate SKOV3$^{c114}$ cells, SKOV3 cells purchased from the American Type Cell Culture (ATCC, Manassas, VA) were transfected with a plasmid, phrGFP-MUC16$^{c114}$, encoding the 114 amino acids from the carboxy-terminus of MUC16. Un-transfected SKOV3 (wild type) cells were also cultured and used as a negative control in the experiments. The cells were cultured in RPMI McCoy's 5A Medium, modified to contain 1.5 mM L-glutamine, 100 units/mL penicillin G and 100 g/mL streptomycin and 10% fetal bovine serum and 800 g/mL of geneticin G418. The cells were maintained at 37° C. in water-jacketed incubators and supplied with 5% CO$_2$. The cell lines were sub-cultured by splitting a T-150 flask (1:5) once per week using 0.25% trypsin/0.53 mM EDTA in Hank's Buffered Salt Solution without calcium and magnesium. MUC16-expressing OVCAR3 cells were obtained from ATCC and cultured using RPMI 1640 medium supplemented with heat inactivated fetal bovine serum (20% v/v, GIBCO, Life Technologies), 2 mM L-glutamine, 10 mM HEPES, 1 mM sodium pyruvate, 4.5 g/L glucose, 1.5 g/L sodium bicarbonate, 0.01 mg/mL bovine insulin (Gemini Bio-Products, 700-112P), 100 units/mL penicillin and 100 μg/mL streptomycin.

For saturation binding studies, six concentrations, 0.1, 1, 5, 10, 25, 50 and 100 nM of the $^{89}$Zr-labeled variants of the MUC16 carboxy-terminus binding antibodies were incubated for 1 hour at 37° C. with 500,000 SKOV3$^{c114}$ cells suspended in PBS supplemented with 1% BSA. At the same time, a parallel set up was prepared and analyzed for non-specific binding of the antibody to SKOV3$^{c114}$ cells. The latter was prepared by adding the $^{89}$Zr-radioimmuno-conjugate variant of the MUC16 carboxy-terminus binding antibody and 100 nM of the respective unlabeled antibody to the mixture of SKOV3$^{c114}$ cells. All experiments were carried out in triplicates.

Internalization of the various radioimmunoconjugates was investigated using SKOV3$^{c114}$ cells. Approximately $1 \times 10^5$ cells were seeded in a 12-well plate and incubated overnight. A volume of 2 mL of the radioimmunoconjugates (1 μCi per mL of SKOV3$^{c114}$ medium) was added to each well. The plates were incubated at 37° C. versus 4° C. for 1, 4, 12 and 24 h. Following each incubation period, the cell supernatant was collected, and the cells were rinsed twice with 1 mL of ice-cold phosphate buffered saline (PBS). Surface-bound activity was collected by washing the cells in 1 mL of 100 mM acetic acid+100 mM glycine (1:1, pH 3.5). The adherent cells were then lysed with 1 mL of 1M sodium hydroxide. Each wash was collected and counted for activity. The percent internalized activity was calculated as the ratio of the activity of the lysate and the total activity from the medium, PBS, acid, and base washes.

Despite performing the bioconjugation and radiolabeling of the immunoconjugates under identical conditions, variable radiochemical yields and molar activities of the radioimmunoconjugates ranging from 1.16 MBq/nmol (0.21 mCi/mg) to 31.8 MBq/nmol (5.74 mCi/mg) were obtained (Table 4). One antibody, 4A2, could not be radiolabeled under the same conditions that were used for bioconjugation and radiolabeling of the other five antibodies, and was dropped from further analyses. Antibodies 29G9 and 4A5 yielded low molar activities upon radiolabeling with $^{89}$Zr. Specifically, the extremely low molar activity of [$^{89}$Zr]Zr-DFO-4A5 compared poorly with a radioiodinated variant of the same antibody, which previously demonstrated an efficient binding affinity (KD=7.3±1.1 nM) to MUC16-expressing OVCAR3 cells (Dharma et al. (2010) *Appl Immunohistochem Mol Morphol.* 18:462-472). Plausibly, the lysine residues in 4A5 may not be as solvent accessible and amenable to amine-based conjugation compared to tyrosine residues, which may be more readily accessible for radioiodination of 4A5, thus leading to the differences in radiochemical yields between the two methods used to radiolabel the antibody. The low immunoreactive fraction may be linked to the low molar activity (higher unlabeled fraction), which can block the radiolabeled antibody's access to the target. In sum, owing to their low radiochemical yields and poor molar activities, 29G9 and 4A5, were also not pursued further in this study.

TABLE 4

In vitro characterization of six MUC16 CTD-binding murine monoclonal antibodies

| Antibody | MUC16 Reactivity | Molar Activity (MBq/nmol) | Immunoreactive Fraction (%) | Binding Affinity (nM) | Cellular Internalization (% ID at 24 h) |
|---|---|---|---|---|---|
| 9C9 | ++++ | 24.13 4.35 mCi/mg | 84.6 ± 4.4% | 9.0 ± 1.49 | 11.9 ± 2.21 |
| 4H11 | ++++ | 31.8 5.74 mCi/mg | 88.3 ± 5.9% | 6.4 ± 1.20 | 14.1 ± 1.34 |
| 4C7 | ++ | 17.7 3.19 mCi/mg | 76.3 ± 3.8% | 13.3 ± 2.89 | – |
| 29G9 | ++ | 6.9 1.25 mCi/mg | 62.0 ± 6.6% | – | – |
| 4A5 | ++++ | 1.16 0.21 mCi/mg | 67.2 ± 1.2% | – | – |
| 4A2 | + | – | – | – | – |

++++ indicates positivity for MUC16-binding in ELISA, Western Blot, Flow Cytometry, Saturation Binding ++ indicates positivity for MUC16-binding in ELISA and Western Blot only + indicates positivity for MUC16-binding in ELISA only – indicates not applicable and was not performed.

All data presented are expressed as mean ± SD. When applicable, statistical differences were analyzed by an unpaired, two-tailed Student's t test (with a Welch's correction when mentioned). Differences at the 95% confidence level (P < 0.05) were considered statistically significant, and are indicated by asterisks Among the three antibodies remaining, 9C9, 4H11 and 4C7, the radioimmunoconjugate of 4C7 yielded the least molar activity and displayed the lowest immunoreactive fraction. These outcomes combined with its relatively high binding affinity (>10 nM) derived from saturation binding assays led to the exclusion of 4C7 from the second phase of the screening workflow.

Figure 3A:
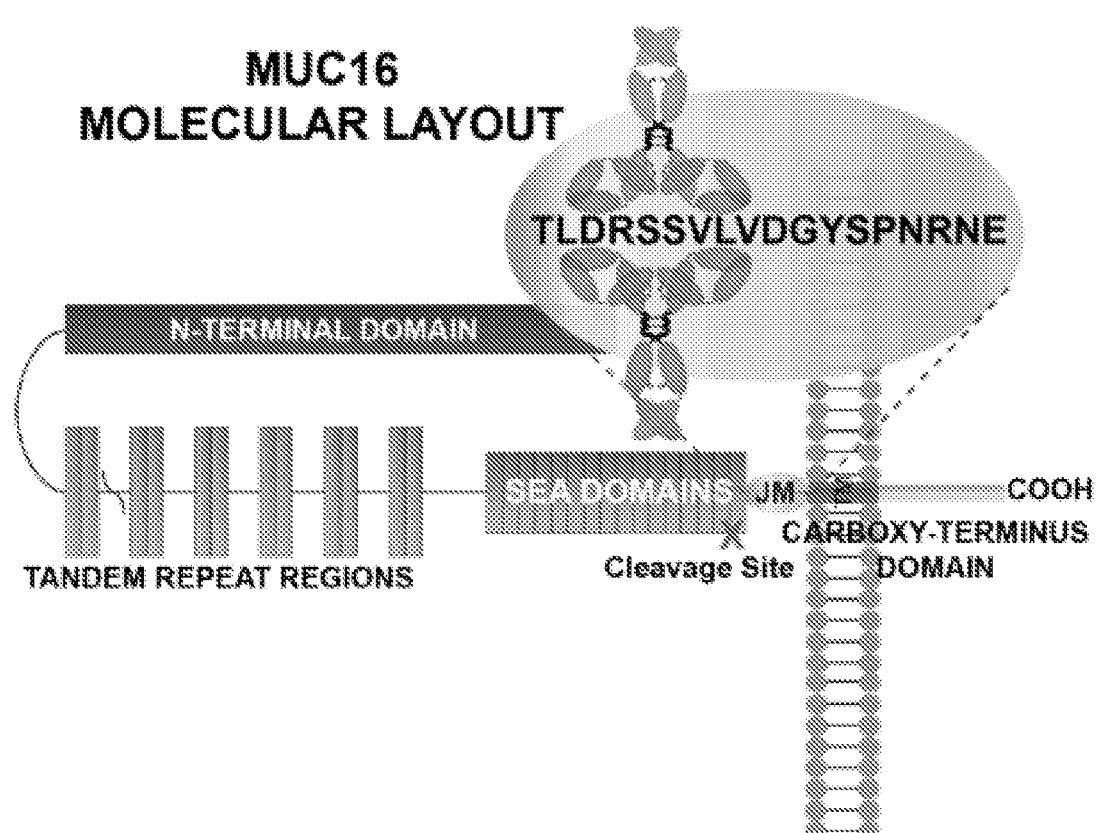
FIGS. 3A-3E illustrate the in vitro characterization of antibodies that bind to the MUC16 carboxy-terminus.
Figure 3B:
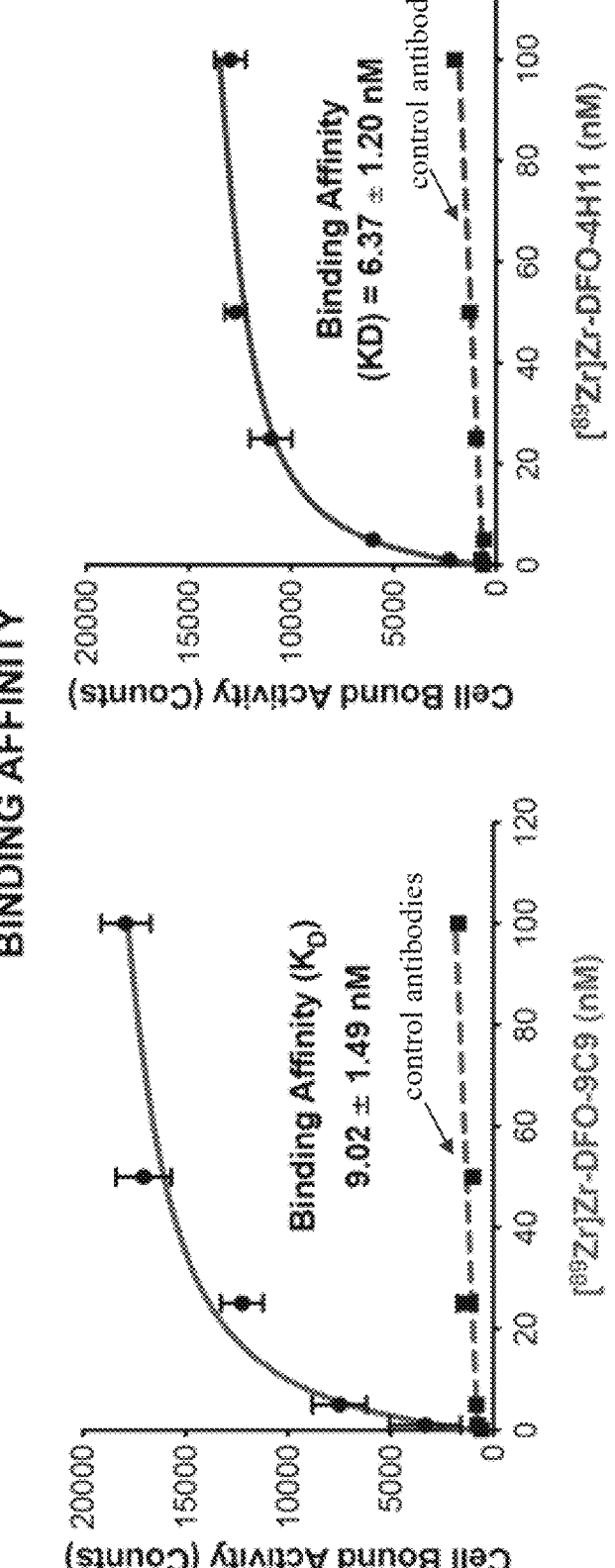

Thus, 9C9 and 4H11 were identified as the two lead MUC16 carboxy-terminus binding antibodies. Their [89]Zr-labeled variants—[[89]Zr]Zr-DFO-9C9 and [[89]Zr]Zr-DFO-4H11 displayed favorable in vitro characteristics including high molar activities, ≥80% immunoreactive fractions and binding affinities in the range of 5-11 nM (Table 4 and FIG. 3B). The binding affinity values derived from saturation binding assays in the present study were concordant with previously reported values obtained in similar experiments carried out with radioiodinated variants of 9C9 and 4H11 (Dharma et al. (2010) *Appl Immunohistochem Mol Morphol.* 18:462-472).

Figure 3C:
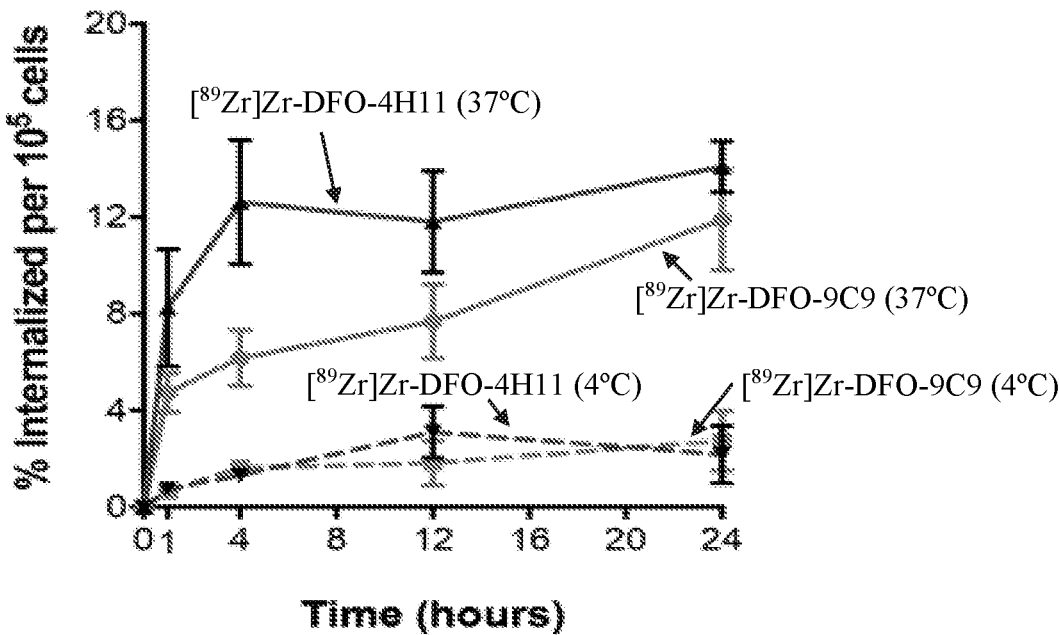
Figure 3D:
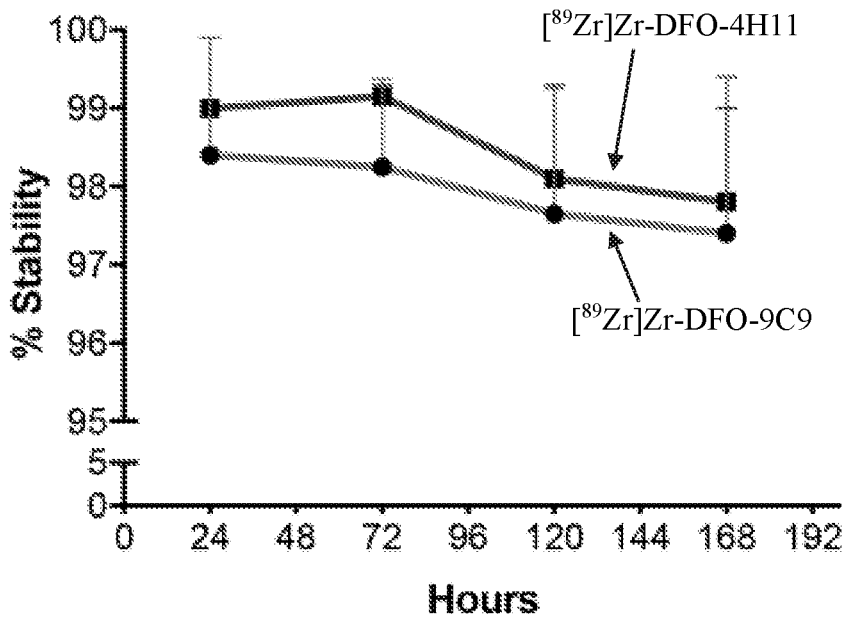
Figure 3E:
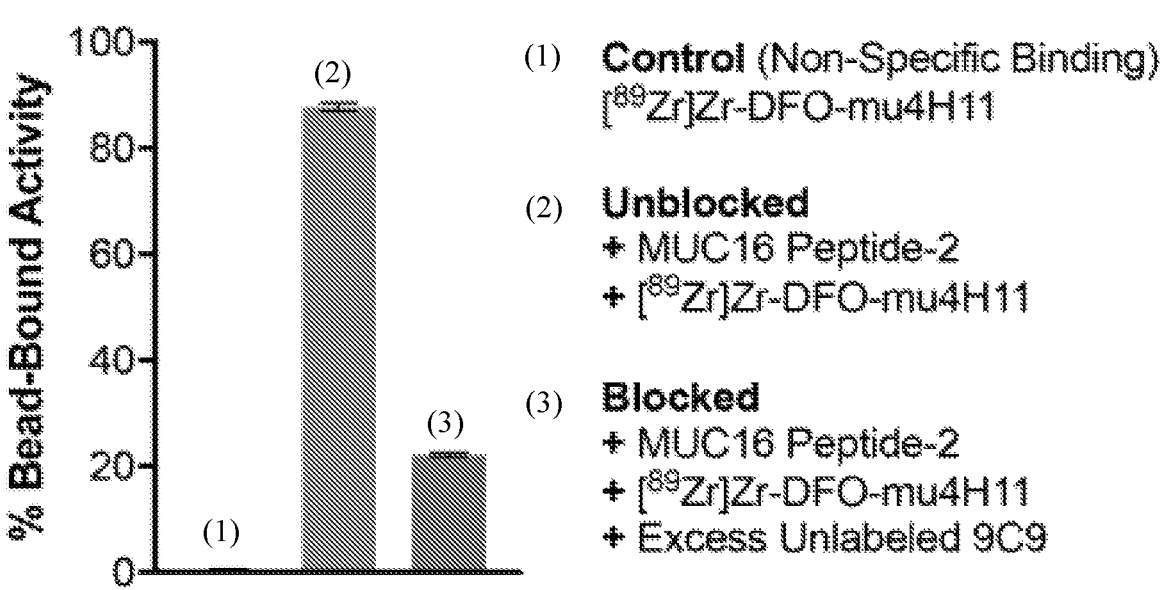

Notably, despite their comparable binding affinity for peptide-2 in the MUC16 carboxy-terminal domain, the [89]Zr-radioimmunoconjugates of 9C9 and 4H11 displayed different rates of cell uptake profiles (FIG. 3C). The binding of both the radioimmunoconjugates to SKOV3[c114] cells was low and comparable at 4° C. However, at 37° C., [[89]Zr]Zr-DFO-4H11 exhibited more uptake of radioactivity with 12.47±3.02% of the normalized applied activity being internalized within 4 hours, followed by a slow accumulation reaching 14.09±1.34% at 24 hours (FIG. 3C). On the other hand, [[89]Zr]Zr-DFO-9C9 displayed relatively slow cell uptake indicated by 5.22±1.34% being internalized by 1 hour, followed by a gradual accumulation that reached 11.89±2.21% at 24 hours. Such differences in the rate of cell uptake and maximal cellular internalization values achieved by the two lead antibody candidates may be attributed to more than one factor including the overall charge of the radioimmunoconjugates, which can be influenced by the composition of amino acids in the antibody class or a difference in the geometry of binding to MUC16 peptide-2, which can be deduced from the crystal structure of the binding pocket(s) of the scFv from 9C9 versus 4H11. The radioimmunoconjugates for both the lead antibody candidates showed comparable and high stability upon incubation in serum (FIG. 3D). Interestingly, an unrelated study aimed at exploring the use of single chain variable fragment (scFv) of 9C9 and 4H11 to develop CAR T-cells revealed that the sequence of scFvs from both these antibodies were identical (data not shown) suggesting that both the antibodies may have an identical molecular footprint on MUC16 by virtue of binding to the same epitope in the peptide-2 sequence within the juxtamembrane region of the MUC16 ectodomain. This was experimentally validated in the present study by achieving the blockade of [[89]Zr]Zr-DFO-mu4H11 binding to biotinylated peptide-2 in the presence of an excess of unlabeled 9C9 antibody (FIG. 3E).

Example 2: In Vivo Characterization of Antibodies Binding to the Carboxy-Terminus of MUC16

Having identified 9C9 and 4H11 as the two lead candidates, the second phase of the study was performed with these antibodies. This second phase involved the in vivo characterization of the tumor-targeting ability and overall radiopharmacologic profiles of these antibodies. To this end, the radioimmunoconjugates, [[89]Zr]Zr-DFO-9C9 and [[89]Zr]Zr-DFO-4H11, were synthesized with high radiochemical purity and high molar activity, and tested via PET imaging and biodistribution studies in mice bearing subcutaneously xenografted SKOV3[c114] tumors.

8-10-week old nu/nu female mice were purchased from Charles River Laboratories. The animals were housed in ventilated cages, were given food and water ad libitum, and allowed to acclimatize for approximately 1 week prior to inoculation with tumor cells. SKOV3[c114] tumors were implanted on the right shoulder of each mouse via subcutaneous injection of 5×10⁶ cells in a 150 µL cell suspension of a 1:1 mixture of fresh media/BD Matrigel (356234, BD Biosciences). Experiments were performed approximately 3 weeks following the injection of the SKOV3[c114] cells. To generate a bilateral tumor model, 5×10⁶ SKOV3 cells were inoculated on the right shoulder followed two weeks later by the inoculation of 5×10⁶ SKOV3[c114] cells on the left shoulder of 8-10-week old female nu/nu mice. 10×10⁶ OVCAR3 cells were implanted in the right shoulder of 6-8-week old female nude mice. Seeds for HGSOC patient-derived xenografts were provided by the MSKCC anti-tumor assessment core and passaged and expanded as subcutaneous xenografts.

PET imaging experiments were conducted on an Inveon PET/CT scanner (Siemens Healthcare). Mice bearing subcutaneously xenografted SKOV3[c114] tumors on their right shoulders were administered the [89]Zr-labeled radioimmunoconjugate variants of the lead MUC16 carboxy-terminus binding antibodies (150-260 µCi; 5.55-9.62 MBq in 200 µL of chelexed PBS) via intravenous tail vein injection. Animals were anesthetized by inhalation of 2% isoflurane (Baxter Healthcare) and medical air gas mixture and placed on the scanner bed. PET data for each mouse were recorded via static scans at various time points after injection of the radioimmunoconjugates. Images were analyzed using ASIPro VM software (Concorde Microsystems). PET images of the bilateral tumor model were acquired using a mouse hotel in the Inveon PET/CT scanner, and the images were analyzed using AMIDE software. Briefly, the 3-dimensional ordered subset expectation maximization (3D OSEM) reconstructed images were calibrated for the injected dose of the tracer and smoothed using a Gaussian function by applying a full width at half maximum (FWHM) value of 1.5 prior to overlaying the PET and CT images.

Biodistribution studies were performed using [89]Zr-labeled variants of the lead MUC16 carboxy-terminus binding antibodies in female nude mice bearing subcutaneous xenografts of SKOV3[c114+] tumors. The mice were administered 21-30 µCi; 0.77-1.11 MBq of each radioimmunoconjugate suspended in 200 µL PBS via lateral tail vein injection. For the blocking arm, animals were co-injected with 50-fold excess of unlabeled antibody. Animals (n=4 per group) were euthanized by CO₂ asphyxiation to analyze biodistribution of the radioimmunoconjugates at various time points following injection in mice. Following euthanasia, vital organs such as the blood, heart, lungs, liver, spleen, stomach, pancreas, large intestine, small intestine, pancreas, reproductive organs inclusive of the ovary, fallopian tubes and uterus, kidneys, bone, muscle, tail, axillary lymph nodes, and the tumor(s) were harvested, weighed, and assayed for radioactivity on a gamma counter calibrated for [89]Zr. Counts were converted into activity using a calibration curve generated from known standards. Count data were background and decay corrected to the time of injection, and the percent injected dose per gram (% ID/g) for each tissue sample was calculated by normalization to the total activity injected per mouse.

Figure 4A:
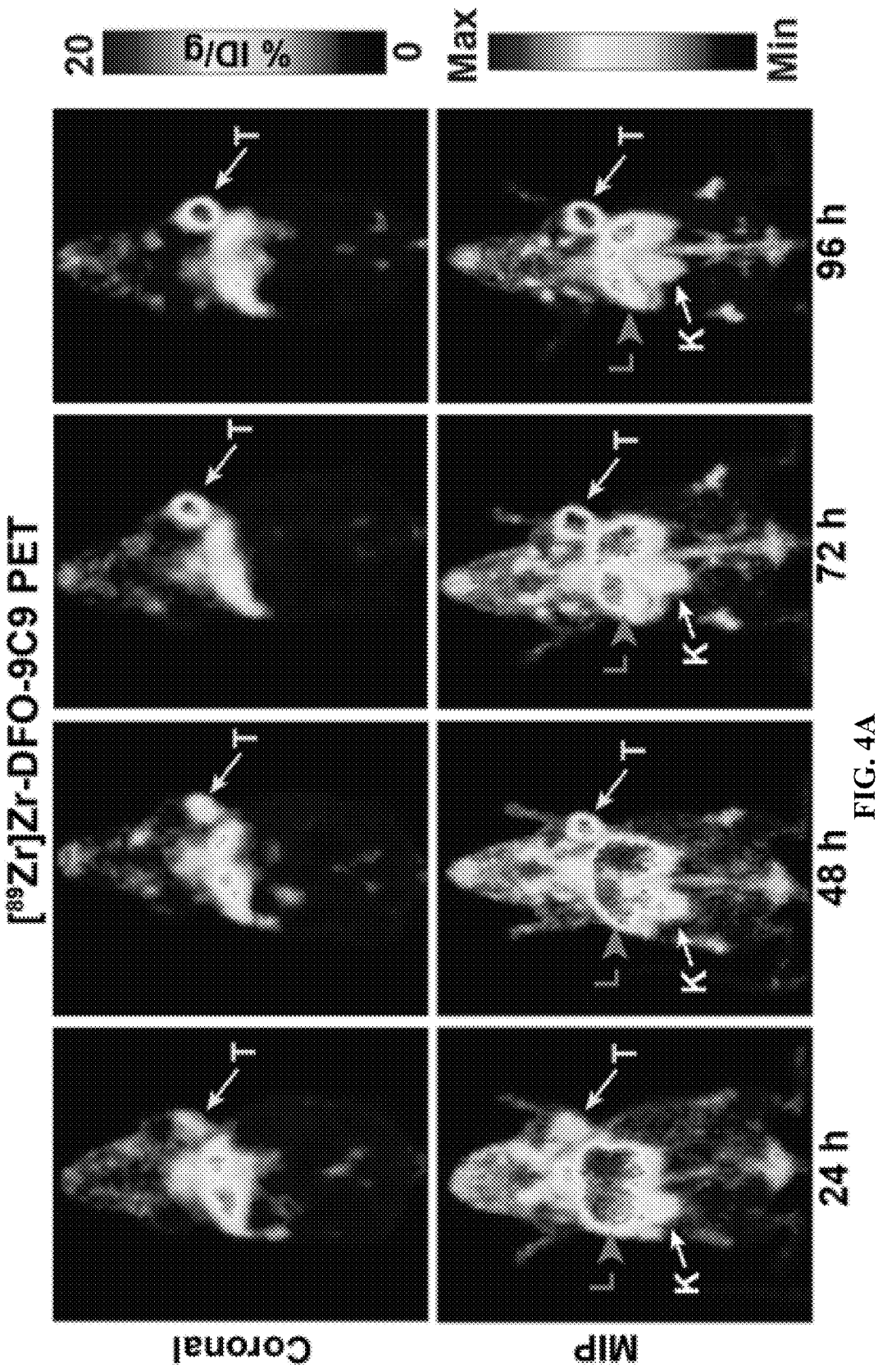
FIGS. 4A-4D illustrates in vivo characterization of the radiopharmacologic profiles of [$^{89}$Zr]Zr-DFO-9C9 and [$^{89}$Zr]Zr-DFO-4H11.
Figure 4B:
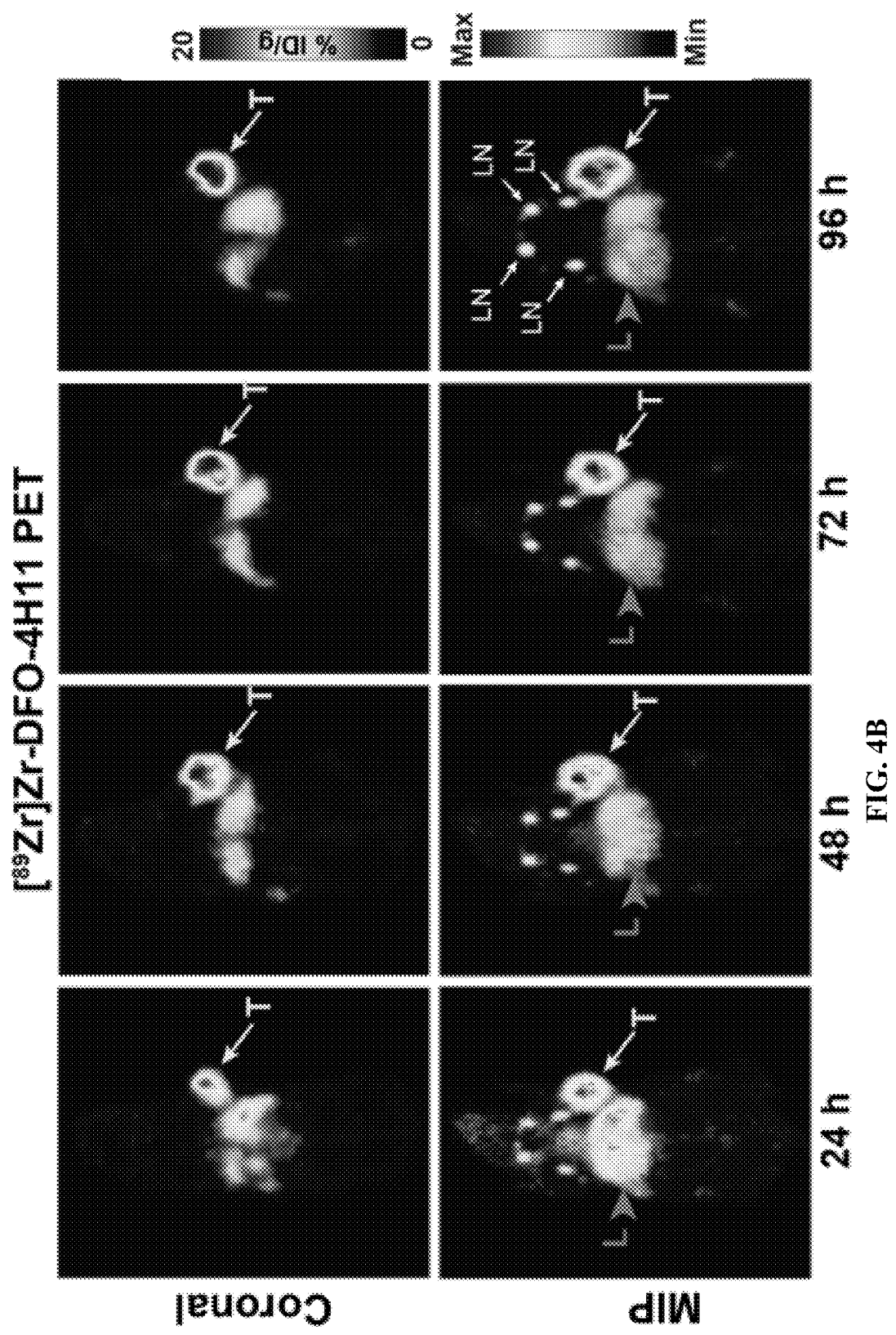

Serial PET imaging of [[89]Zr]Zr-DFO-9C9 (FIG. 4A) at 24 h intervals post injection (p.i.) of the radioimmunoconjugate delineated the subcutaneous tumor at 24 h, followed by a gradual accretion of activity in the tumor with progression of time up to 96 h p.i. [$^{89}$Zr]Zr-DFO-9C9 showed high radioactivity concentration in the liver as early as 24 h p.i., with an apparent wash out of signal from this tissue at later time points. Most notably, [$^{89}$Zr]Zr-DFO-9C9 displayed relatively high radioactivity concentration in the kidneys. This is an unexpected observation for full-length antibody-based radioimmunoconjugates, which have molecular weights that are above the renal filtration cut-off for clearance by the body. Additionally, the kidneys of mice are not known to express MUC16 or an analog of the MUC16 juxtamembrane carboxy-terminus domain to justify the presence of the antibody in this organ. Furthermore, the maximum intensity projection (MIP) images from longitudinal PET studies of mice injected with [$^{89}$Zr]Zr-DFO-9C9 indicate a gradual washout of activity from the kidneys between 24 h-96 h p.i. of the radioimmunoconjugate. Plausibly, the high radioactivity concentration in the liver and kidneys of mice at early time points may result from a combination of these organs being highly perfused and the slow in vivo pharmacokinetics of the 9C9 antibody. The persistence of activity in systemic circulation evidenced by PET signal in the heart and aortic arches seen in the MIP images at 72 and 96 h p.i. of [$^{89}$Zr]Zr-DFO-9C9 suggest a very slow in vivo pharmacokinetic profile for this antibody despite the presence of a target sink provided by the tumor. These in vivo observations corroborate the relatively slow in vitro cell uptake profile demonstrated by the 9C9 antibody in the preceding phase of this study.

Figure 2:
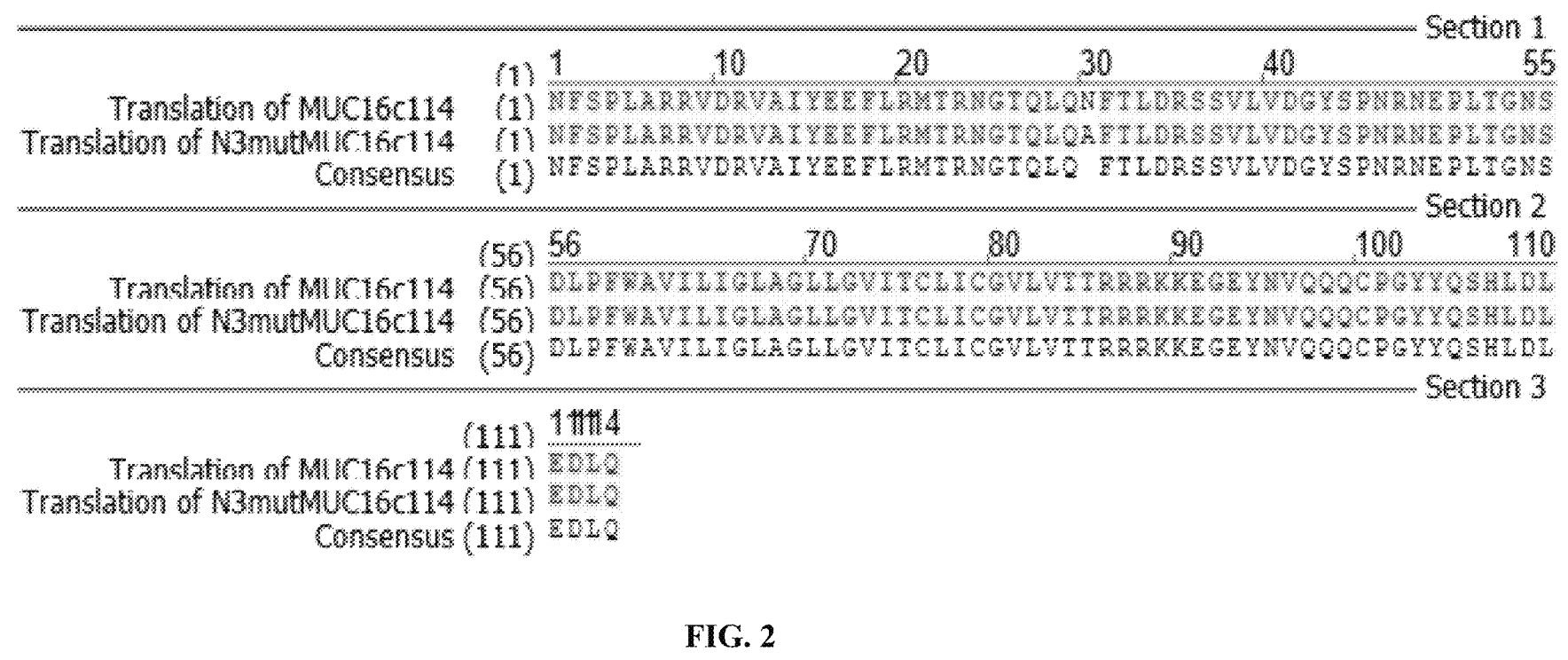

On the other hand, serial PET imaging of [$^{89}$Zr]Zr-DFO-4H11 (FIG. 2B) at 24 h intervals after injection of the radioimmunoconjugate delineated the subcutaneous SKOV3$^{c114}$ tumor at 24 h p.i. A head-to-head comparison of the serial PET images of [$^{89}$Zr]Zr-DFO-9C9 versus [$^{89}$Zr]Zr-DFO-4H11 suggest that the radioactivity concentration of [$^{89}$Zr]Zr-DFO-4H11 in the SKOV3$^{c114}$ tumor at the earliest time point was higher than that of [$^{89}$Zr]Zr-DFO-9C9. [$^{89}$Zr]Zr-DFO-4H11 also showed uptake of radioactivity in the liver at 24 h p.i., however, the activity concentration in this organ decreased at later time points whilst the accretion of activity in the tumor progressively increased up to 96 h p.i. of the radioimmunoconjugate. In addition to the tumor (primary target sink for the antibody), and the liver (site of clearance for exogenous immunoglobulins), the MIP images for mice injected with [$^{89}$Zr]Zr-DFO-4H11 showed bilaterally symmetrical PET foci in the axillary lymph nodes. Apart from this anomaly, the in vivo radiopharmacologic profile of [$^{89}$Zr]Zr-DFO-4H11 was more favorable than its counterpart [$^{89}$Zr]Zr-DFO-9C9. [$^{89}$Zr]Zr-DFO-4H11 yielded high contrast PET images owing to a relatively rapid uptake in the SKOV3$^{c114}$ tumor as early as 24 h, and minimum activity left in the systemic circulation and background organs except the liver at later time points.

Figure 6A:
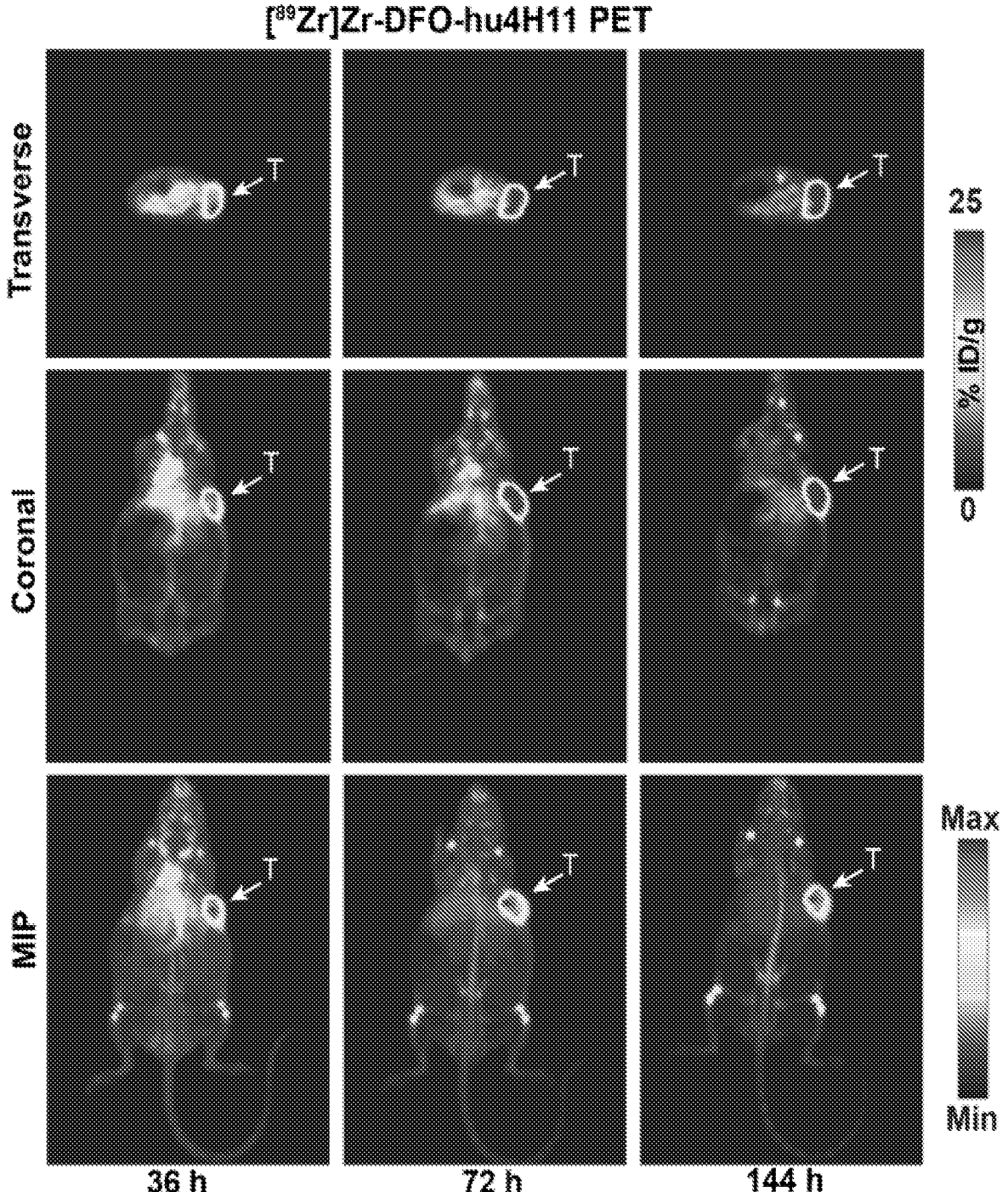
FIGS. 6A-6C illustrate in vivo characterization of the radiopharmacologic profile of humanized 4H11 antibody.
Figure 6B:
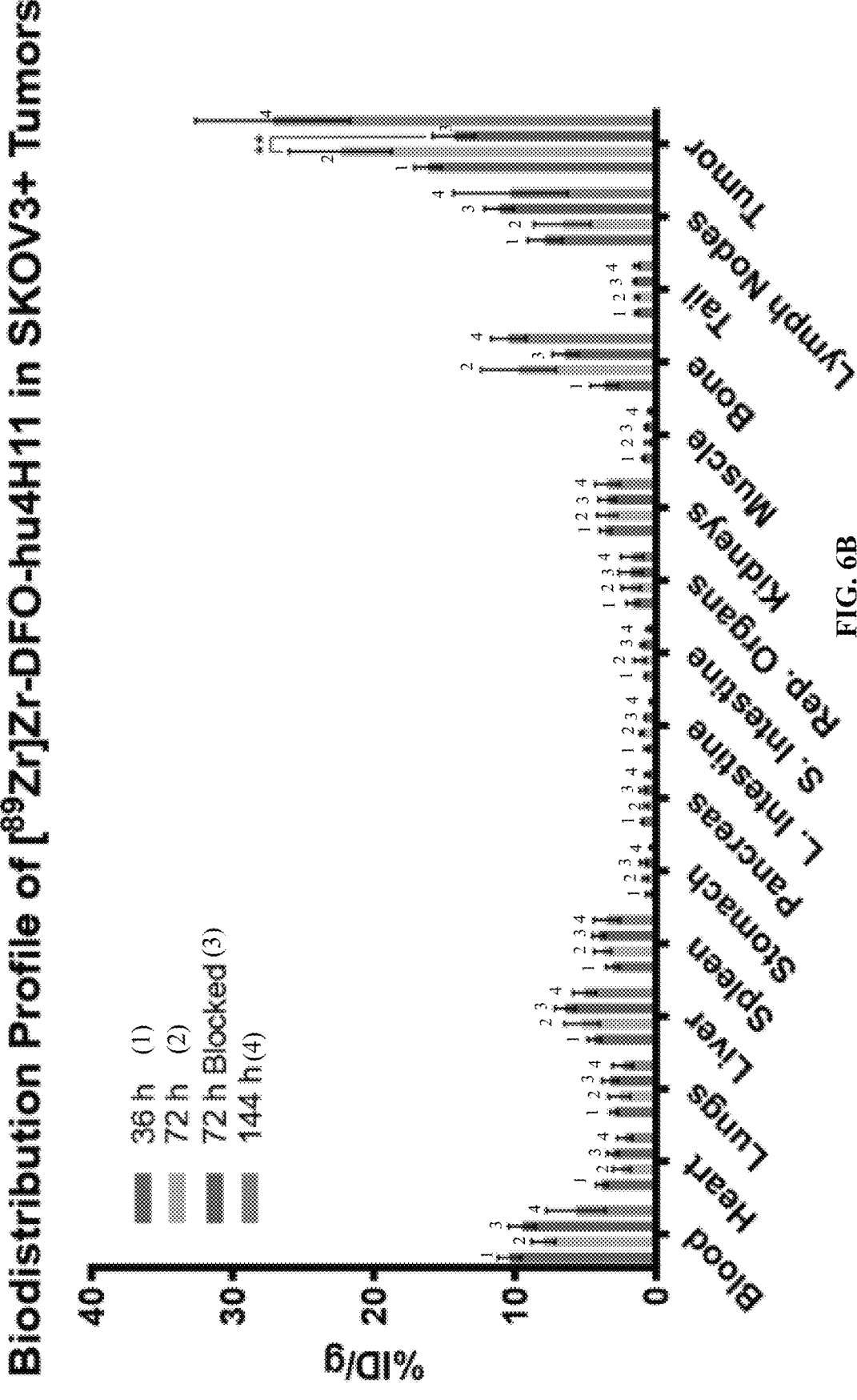
Figure 6C:
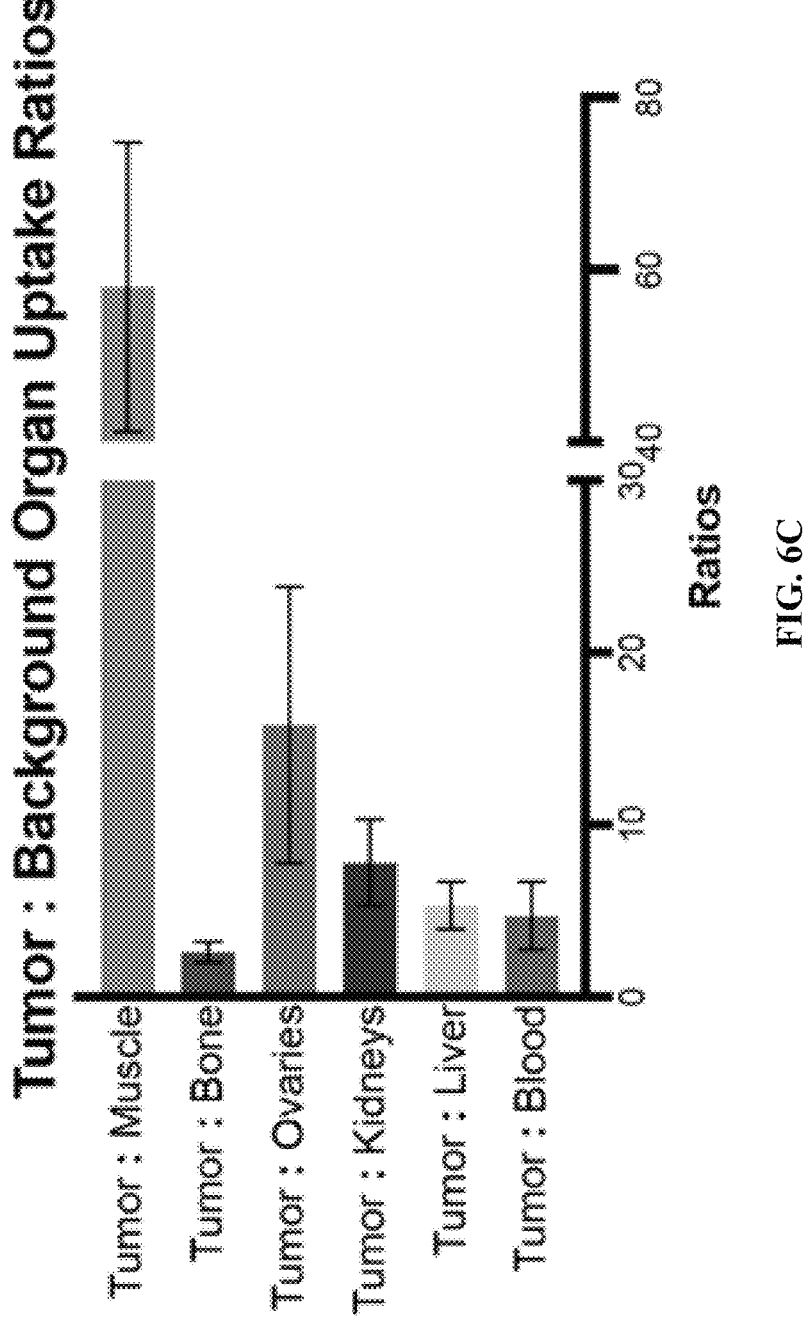

The observations from PET imaging were corroborated by independent biodistribution studies, wherein the tumor and organs of interest were harvested at 96 h p.i. of the radioimmunoconjugates in subcutaneous SKOV3$^{c114}$ xenografts (FIG. 6C). To validate the specificity of antibody binding and activity uptake in the tumor, a blockade arm was included in the in vivo biodistribution study of both the radioimmunoconjugates. Subcutaneous SKOV3$^{c114}$ xenografts were co-injected with a 50-fold excess (mass) of unlabeled 9C9 or 4H11 antibody to block the specific uptake of [$^{89}$Zr]Zr-DFO-9C9 and [$^{89}$Zr]Zr-DFO-4H11 respectively. Whilst target-mediated uptake of the radioimmunoconjugate and its associated activity is expected to decrease, the activity concentration in tissues displaying non-specific uptake is expected to remain unchanged. However, the efficient blockade of target-mediated specific uptake of the radioimmunoconjugate in the tumor may often manifest as slightly increased activity concentrations in well-perfused non-target background organs including the heart, lungs, liver, spleen and kidneys. This may be attributed to a substantial amount of the radioimmunoconjugate persisting in systemic circulation due to blockade of the target-rich sink provided by the tumor.

In sum, the biodistribution profiles of [$^{89}$Zr]Zr-DFO-9C9 and [$^{89}$Zr]Zr-DFO-4H11 were consistent with the PET imaging profiles for both radioimmunoconjugates. The uptake of activity in most non-target background organs barring a few case-specific exceptions noted in PET imaging studies was comparable and low ($\leq$5% ID/g). Specifically, [$^{89}$Zr]Zr-DFO-9C9 showed high activity concentration (11.2±2.35% ID/g) in the kidneys, which was significantly higher than the uptake of [$^{89}$Zr]Zr-DFO-4H11 (4.3±1.00% ID/g; p-value=0.0016) and [$^{89}$Zr]Zr-DFO-Isotype IgG (4.9±0.57% ID/g; p-value=0.002) in this organ. SKOV3$^{c114}$ xenografts co-injected with 50-fold excess of unlabeled 9C9 antibody did not show a blockade in the uptake of activity from [$^{89}$Zr]Zr-DFO-9C9 in the kidneys (13.3±2.64% ID/g), suggesting that the uptake of activity in this organ may be non-specific.

Figure 4C:
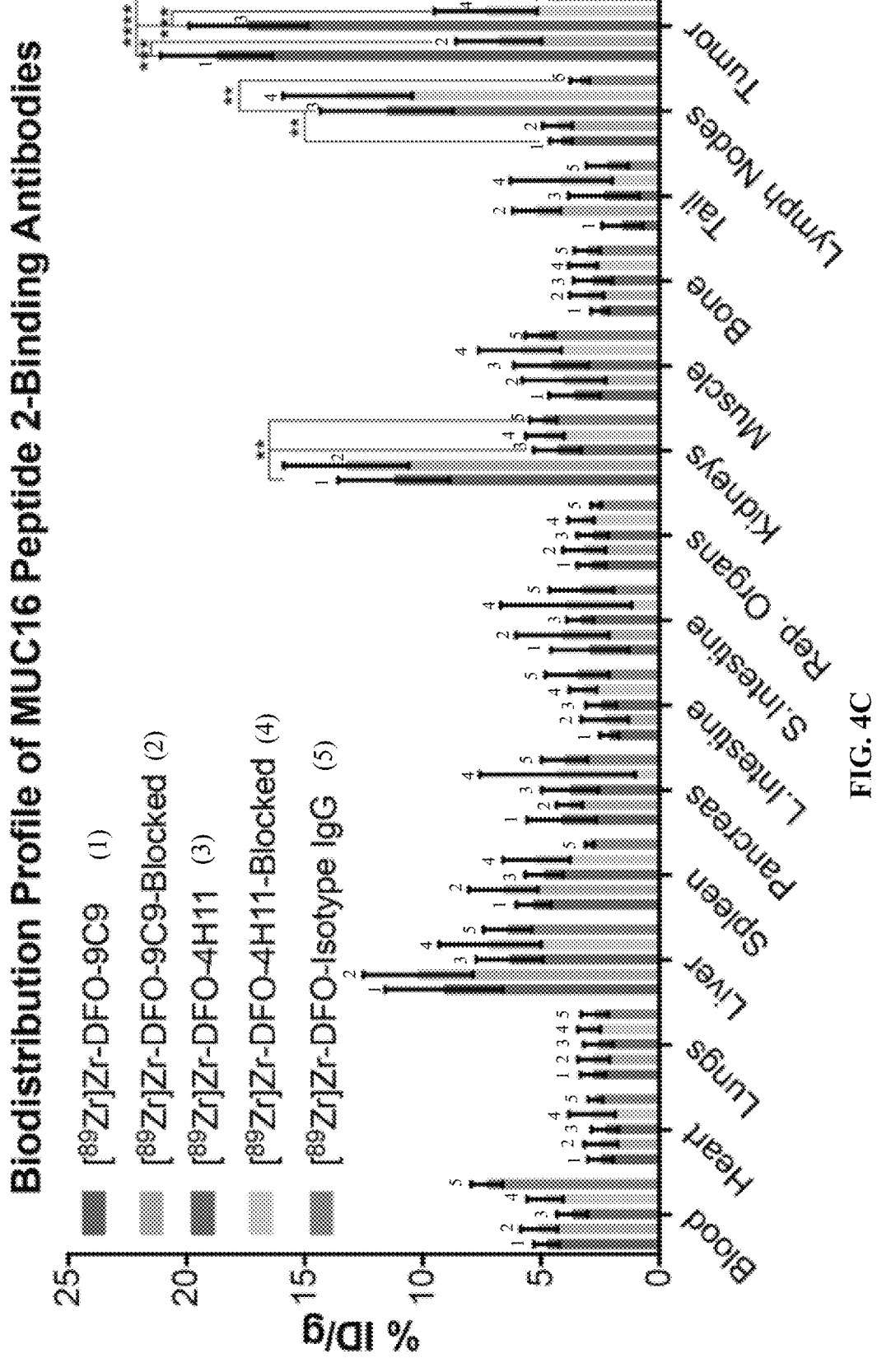

Intriguingly, unlike PET images, comparative biodistribution studies confirmed that the radioactivity concentrations in the liver of SKOV3$^{c114}$ xenografts at 96 h p.i. were not significantly different between the two MUC16-targeting radioimmunoconjugates (9.1±2.49% ID/g for [$^{89}$Zr]Zr-DFO-9C9 versus 6.3±1.41% ID/g for [$^{89}$Zr]Zr-DFO-4H11; p-value=0.099) or the isotype IgG (6.4 1.02% ID/g; p-value=0.091). Despite the elevated concentration of activity (11.5 2.80% ID/g) in the axillary lymph nodes of SKOV3$^{c114}$ xenografts injected with [$^{89}$Zr]Zr-DFO-4H11 versus [$^{89}$Zr]Zr-DFO-9C9 (4.2±0.48% ID/g; p-value=0.002) or isotype IgG (3.4±0.40% ID/g; p-value=0.001), the uptake in these tissues was non-specific since it could not be blocked (13.2±2.72% ID/g p-value=0.43) in mice co-injected with a 50-fold excess of the unlabeled 4H11 antibody. Additional histopathologic analysis of H&E stained sections of harvested PET- and biodistribution-positive lymph nodes from SKOV3$^{c114}$ xenografts injected with [$^{89}$Zr]Zr-DFO-4H11 did not reveal presence of neoplastic cells. Finally, the tumoral uptake of [$^{89}$Zr]Zr-DFO-9C9 (18.7±2.37% ID/g) and [$^{89}$Zr]Zr-DFO-4H11 (17.4±2.51% ID/g) was comparable and significantly higher than isotype IgG (4.7±0.42% ID/g; p-values=0.00002 and 0.00006 respectively). Furthermore, the tumoral uptake of [$^{89}$Zr]Zr-DFO-9C9 and [$^{89}$Zr]Zr-DFO-4H11 could be blocked (6.8±1.81% ID/g and 7.4±2.18% ID/g) when the MUC16-targeted radioimmunoconjugates were co-injected with a 50-fold excess of their respective unlabeled variants (FIG. 4C).

Figure 4D:
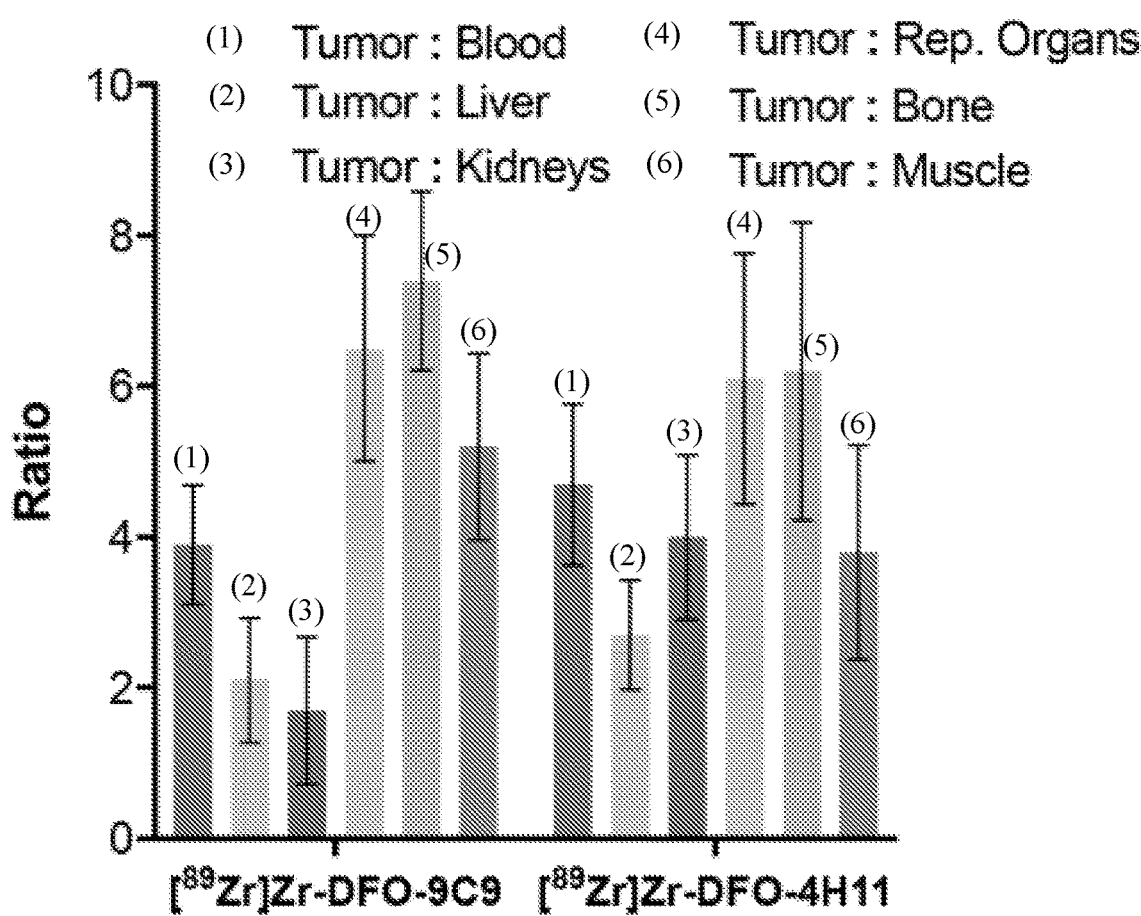

Taken together, the results from in vitro studies and the in vivo evaluation using PET imaging and biodistribution studies to compare the tumor-to-background organ uptake ratios of radioactivity associated with the two lead antibodies targeting the ectodomain of MUC16 in SKOV3$^{c114}$ (FIG. 4D) revealed [$^{89}$Zr]Zr-DFO-4H11 to yield a relatively better in vivo radiopharmacologic profile. These findings lend credibility to the clinical utility of the murine variant of the 4H11 antibody, which previously demonstrated excellent performance in immunohistochemical staining of formalin-fixed paraffin embedded surgical specimens obtained from HGSOC and lobular breast cancer patients.

Example 3: Humanized 4H11 Antibody

Murine 4H11 was humanized to ensure a minimum compromise to the binding affinity of the humanized variant for MUC16 $^{c114}$. The sequence for the humanized heavy chain is provided as SEQ ID NO: 4, and the sequence for the humanized light chain is provided as SEQ ID NO: 2. To validate the retention of in vitro target binding ability and in vivo pharmacologic profile in the preclinical setting, the humanized variant of 4H11 ("hereafter referred to as hu4H11") was conjugated with DFO (FIG. 5A) as previously described for the murine variant. MALDI-ToF analysis of the immunoconjugate revealed ~1 DFO conjugated per antibody. Prior to radiolabeling, the DFO-immunoconjugate was tested for target binding via flow cytometry using SKOV3$^{c114}$ cells versus SKOV3 cells.

Figure 5A:
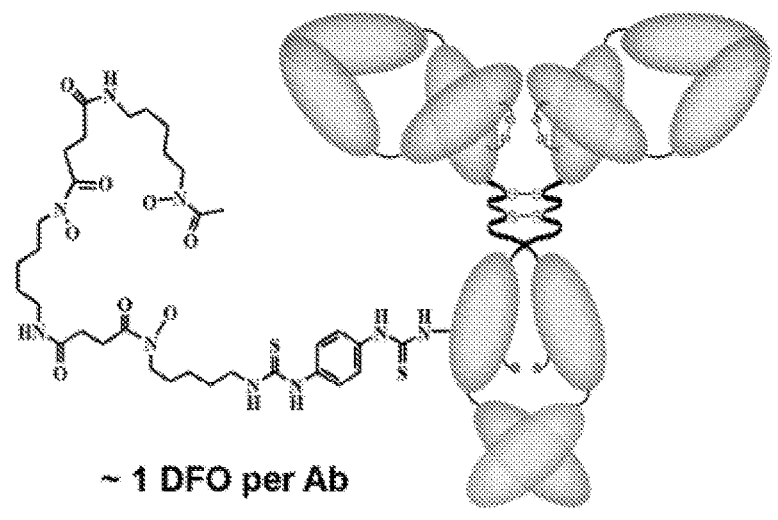
FIGS. 5A-5E illustrate in vitro characterization of humanized 4H11 antibody.
Figure 5B:
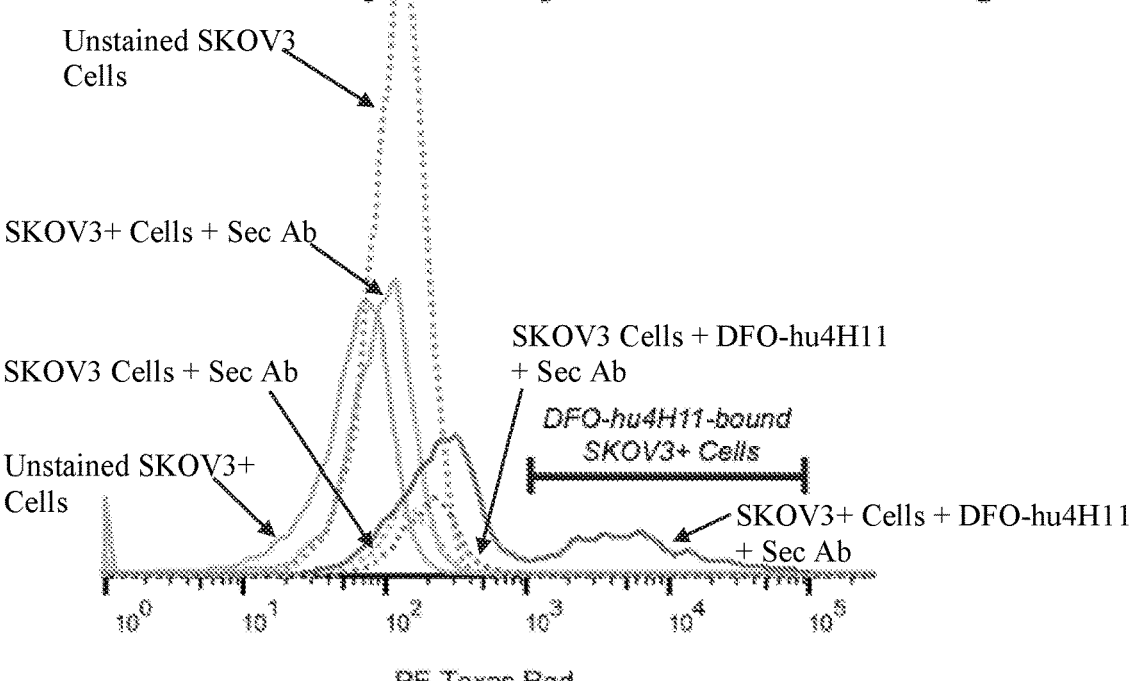
Figure 5C:
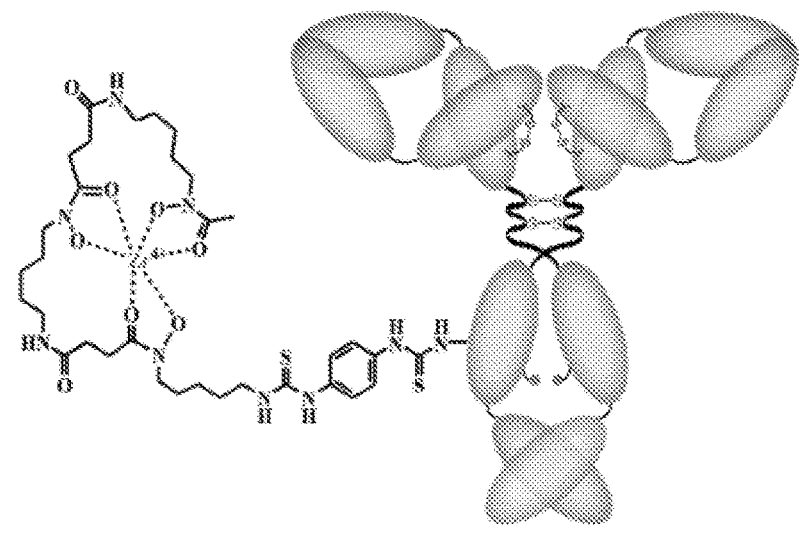
Figure 5D:
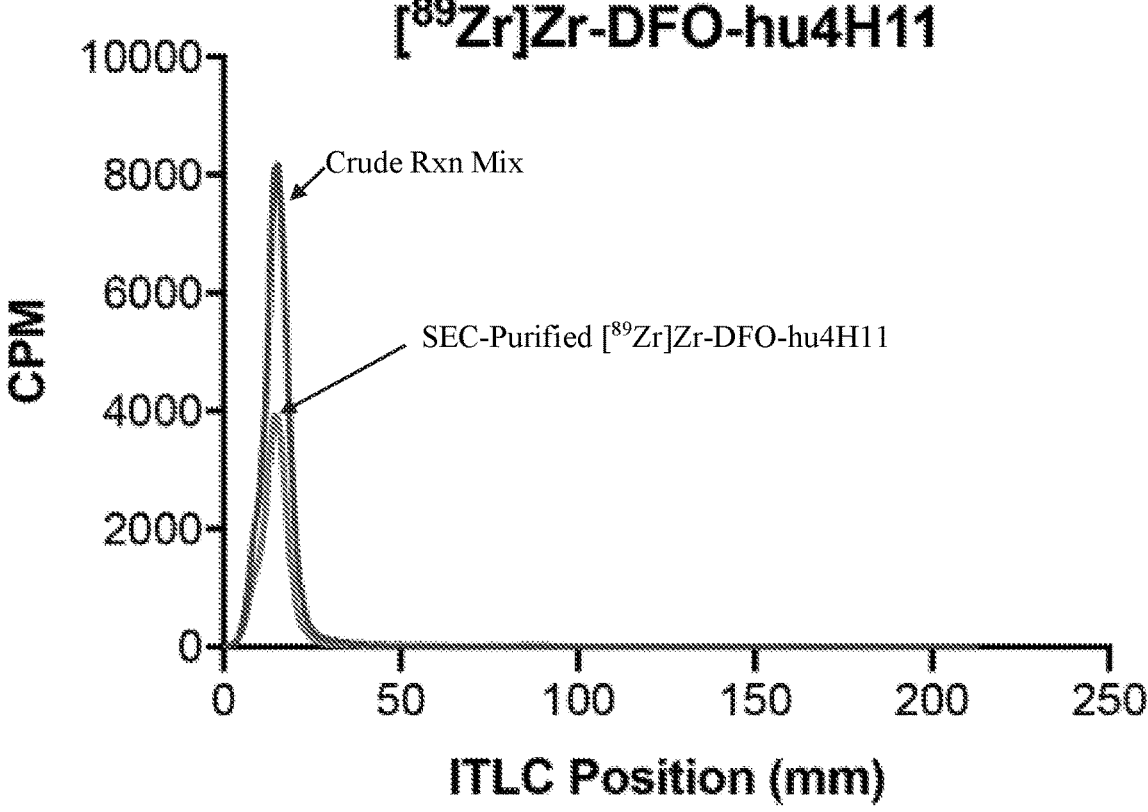
Figure 5E:
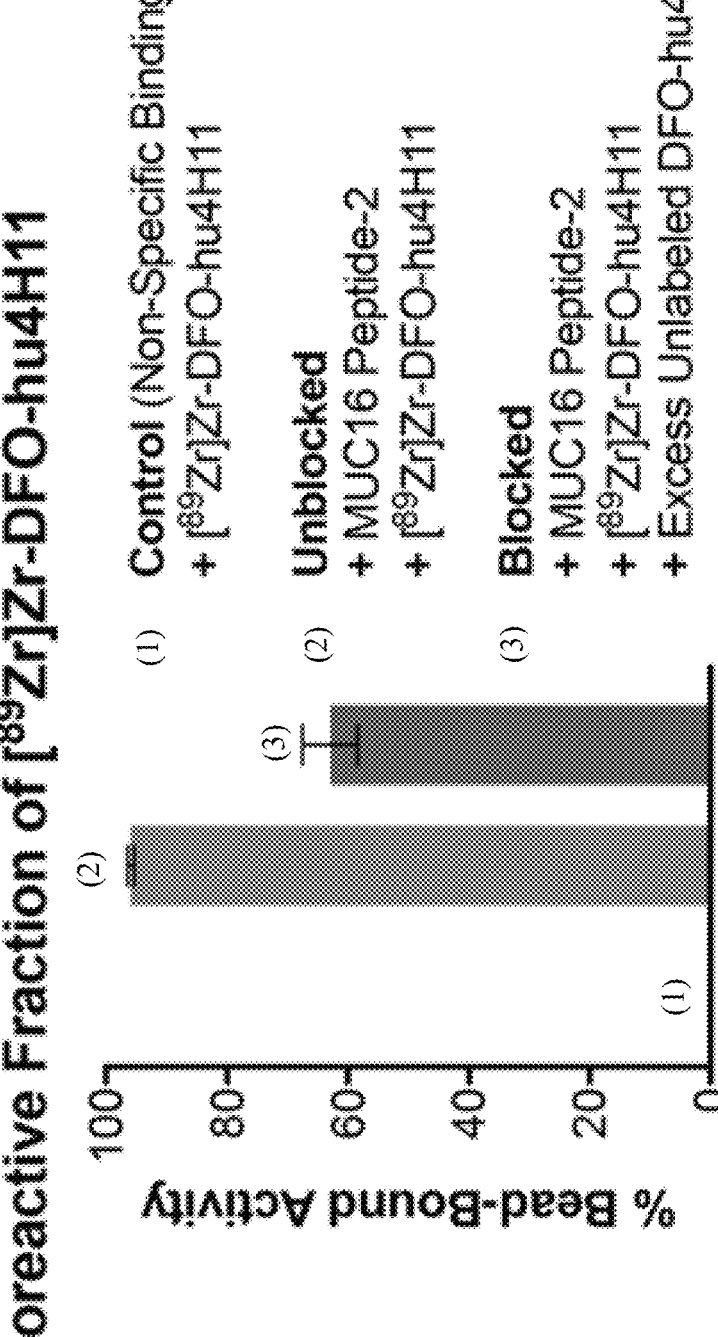

A shift in the fluorescence peak to the right on the X-axis of the histogram indicated positive binding of DFO-hu4H11 immunoconjugate to SKOV3$^{c114}$ cells, whereas the lack of a shift in fluorescence peak compared to unstained cells and cells stained with secondary antibody alone indicated an absence of binding to SKOV3 (wt) cells (FIG. 5B). Notably, the SKOV3 (wt) cell line is more representative of ovarian clear cell carcinomas, an OvCa subtype which is not known to rely on the expression of MUC16. Moving on, the radiolabeling of DFO-hu4H11 with $^{89}$Zr consistently afforded high radiochemical yield and purity of the radioimmunoconjugate with a molar activity of 23.6 MBq/nmol (n=9) (FIGS. 5C-D). The target-binding fraction of [$^{89}$Zr]Zr-DFO-hu4H11 was found to be 96±0.53% and the binding of the radioimmunoconjugate to biotinylated MUC16 peptide-2 captured on the streptavidin magnetic beads could be partially blocked in the presence of a huge excess of unlabeled 4H11 antibody in the bead based radioligand binding assay (FIG. 5E).

Having characterized in vitro target-binding ability, the hu4H11 immunoconjugate was tested further to evaluate its in vivo biodistribution and radiopharmacologic profile. Consistent with the in vivo profile displayed by its murine predecessor longitudinal PET imaging studies, hu4H11 was able to clearly delineate subcutaneously xenografted SKOV3$^{c114}$ tumors at early time points after injection of the radioimmunoconjugate (FIG. 6A). Although persistence of some activity in systemic circulation was observed at the intermediate time point of 72 h p.i., a vast majority of the injected activity was found in the tumor by 144 h p.i. Results from biodistribution studies concurred with the observations from PET images and showed a gradual accretion of activity in SKOV3$^{c114}$ tumors concomitant with a decrease in the background activity in the blood pool (FIG. 6B). The tumoral uptake of [$^{89}$Zr]Zr-DFO-hu4H11 was repressed in the blockade arm wherein mice were co-injected with a 40-fold excess (by mass) of unlabeled hu4H11 antibody and evaluated for in vivo biodistribution at 72 h p.i. (22.4±3.65 versus 14.3±1.50% ID/g; p-value=0.006). Unlike its murine predecessor, [$^{89}$Zr]Zr-DFO-hu4H11 did not show PET-positive axillary lymph nodes in the SKOV3$^{c114}$ xenografts. However, harvesting the bilateral axillary lymph nodes in biodistribution studies revealed activity concentrations ranging between 7.9±1.23% ID/g at 36 h p.i.-10.3±4.04% ID/g at 144 h p.i. Notably, the absence of repressed radioactivity concentration in the axillary lymph nodes at 72 h p.i. of mice in the blockade arm suggested that the uptake in this tissue may be non-specific. As a radiotracer, [$^{89}$Zr]Zr-DFOhu4H11 demonstrated excellent tumor-to-background organ ratios (FIG. 6C). Such a favorable in vivo profile bodes well for the future development of hu4H11-based drugs including radiopharmaceuticals for immunoPET and targeted radiotherapy.

Figure 7A:
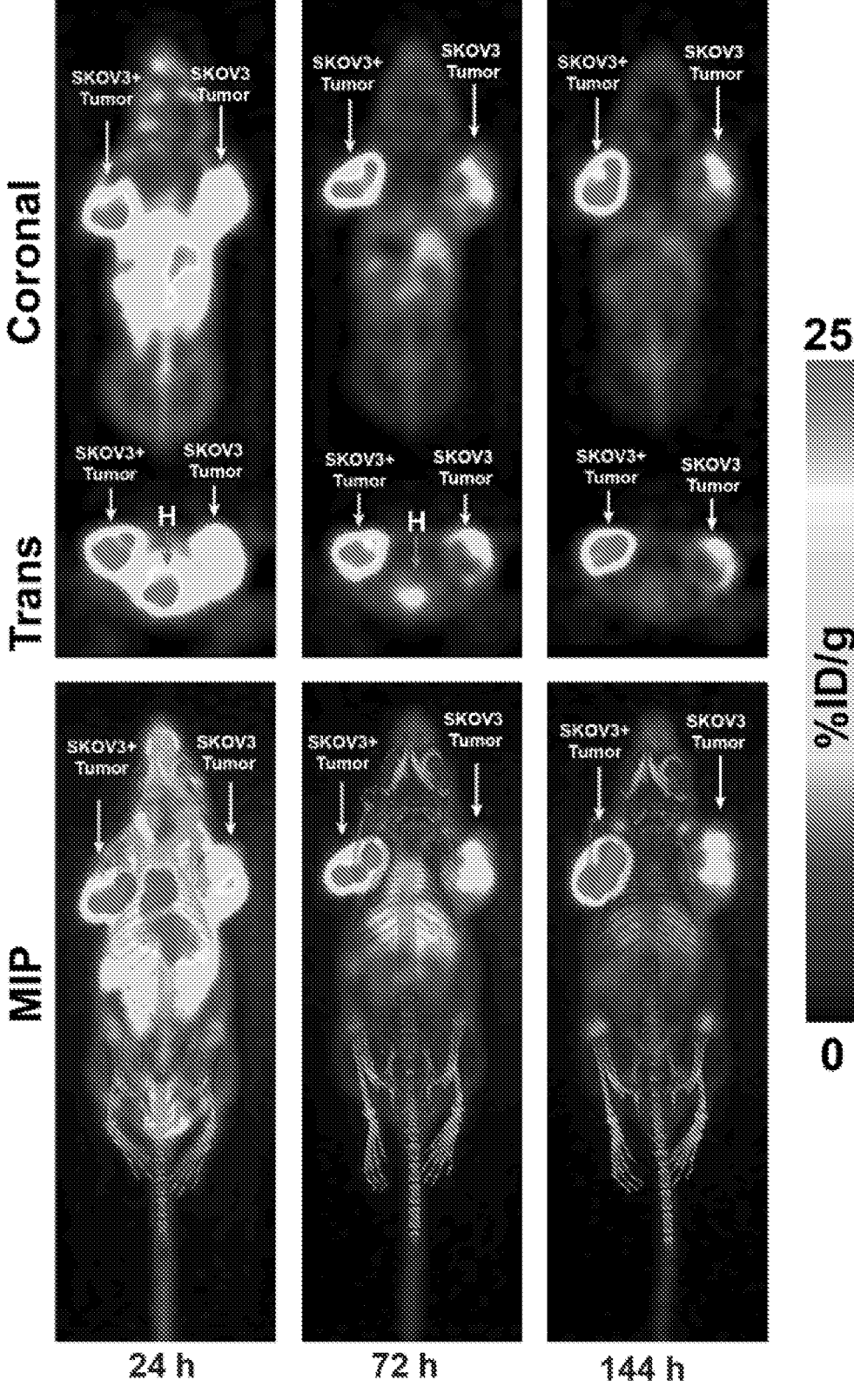
FIGS. 7A-7D illustrate in vivo and ex vivo analyses of the biodistribution of [$^{89}$Zr]Zr-DFO-hu4H11.

Further examination of the in vivo specificity of [$^{89}$Zr] Zr-DFO-hu4H11 binding to MUC16 carboxy-terminus expressing cells was performed in a bilateral tumor model wherein SKOV3$^{c114}$ cells were implanted on the left shoulder of nu/nu mice versus SKOV3 tumors implanted on the right shoulder. [$^{89}$Zr]Zr-DFO-hu4H11 demonstrated excellent specificity for binding to the target expressed by SKOV3$^{c114}$ cells as shown by the high tumoral uptake of radioactivity in this tumor versus minimum non-specific uptake in SKOV3 tumors (FIG. 7A). The latter is commonly attributed to in vivo enhanced permeability and retention of full-length antibody-based imaging agents in poorly vascularized solid tumor tissue.

Figure 7B:
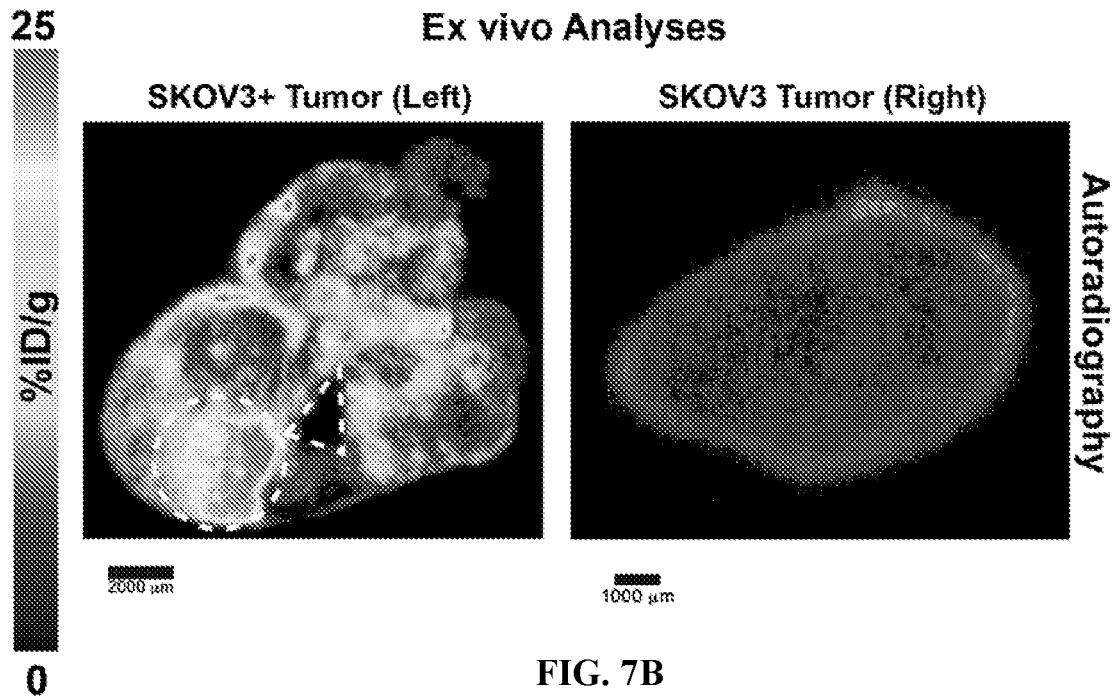
Figure 7C:
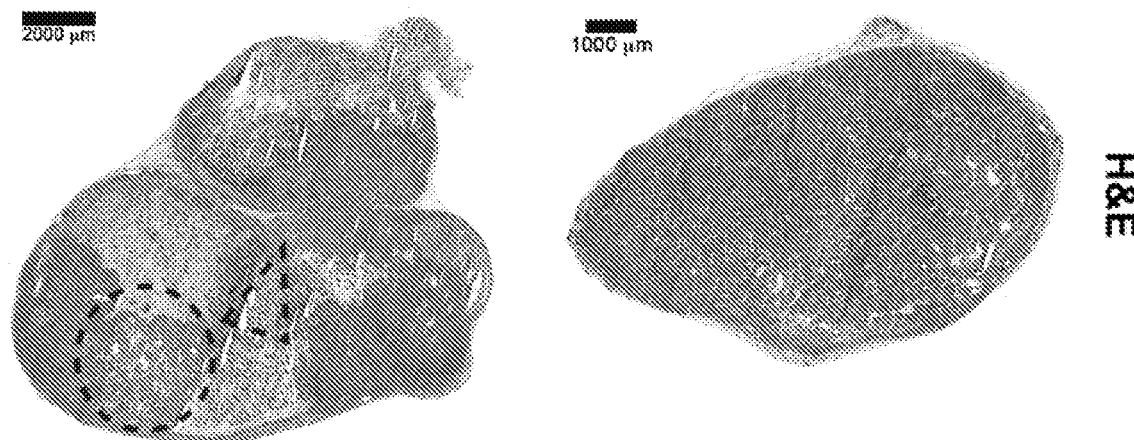
Figure 7D:
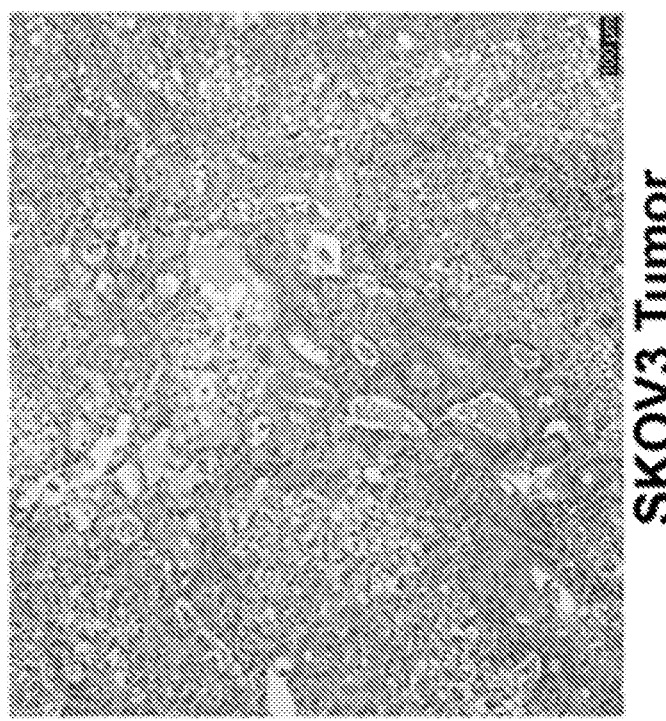
Figure 7D:
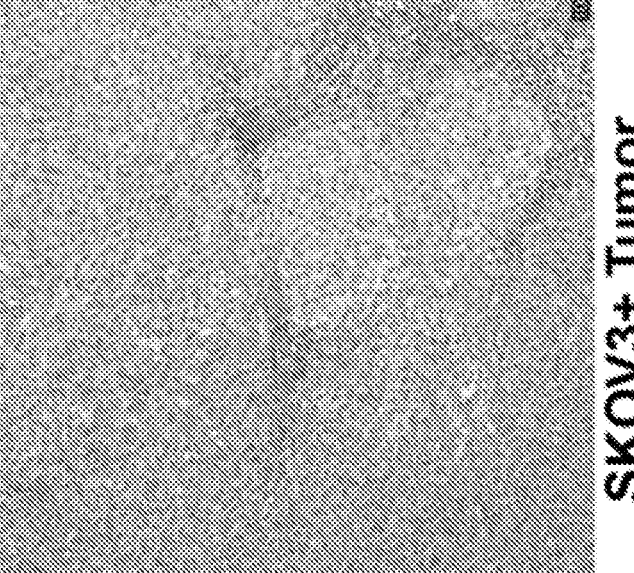

Ex vivo analysis of the bilateral tumors from mice injected with [$^{89}$Zr]Zr-DFO-hu4H11 revealed focal accumulation of radioactivity in the perivascular spaces of the MUC16 carboxy-terminus-expressing SKOV3$^{c114}$ tumor and regions rich in healthy tumor cells (FIGS. 7B and 7C; dashed circle). On the other hand, necrotic regions (FIGS. 7B and 7C; dashed triangle) of the SKOV3$^{c114}$ tumor revealed an absence of radioactivity. Consistent with the PET images of [$^{89}$Zr]Zr-DFO-hu4H11 in the bilateral tumor model, the target-negative SKOV3 tumors showed minimal accumulation of radioactivity (FIG. 7B). Histopathologic analysis via H&E staining of the bilateral tumors revealed SKOV3$^{c114}$ tumors bearing an architecture and morphologic features that were remarkably distinct from the typical cellular morphology of a clear cytoplasm, which is characteristic of SKOV3 cells, a cell line representative of ovarian clear cell carcinoma (FIG. 7D). Previous reports have shown that expression of the carboxy-terminus domain of MUC16 in NIH/3T3 cells induces transformation and potentiates metastatic properties in this cell line, whereas ectopic expression of the carboxy-terminus domain in SKOV3 cells increased in vitro cell motility and invasiveness and in vivo tumorigenicity.

Figure 8A:
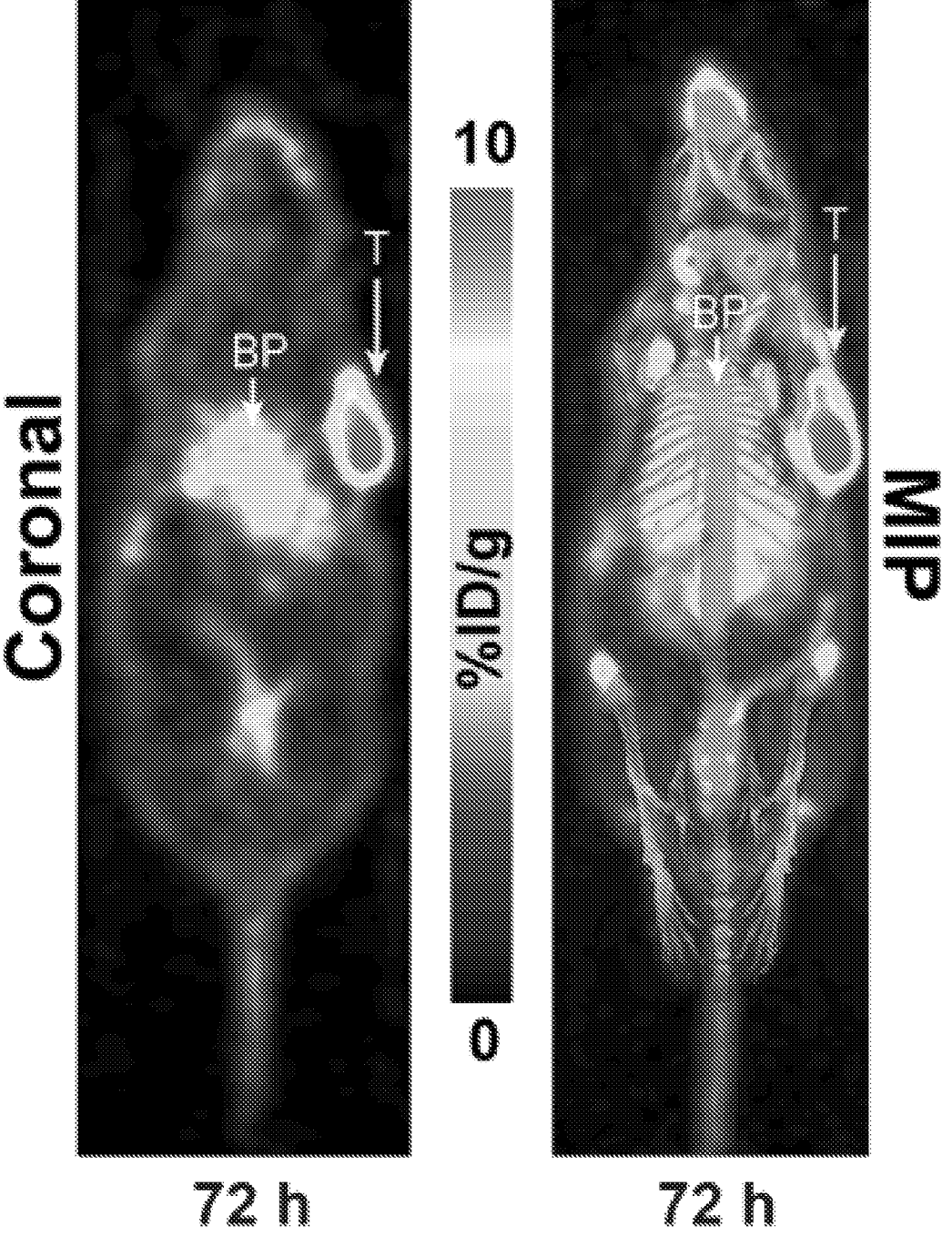
FIGS. 8A-8B illustrate PET imaging of [$^{89}$Zr]Zr-DFO-hu4H11 in a MUC16-expressing cell line and HGSOC patient-derived xenograft model.
Figure 8B:
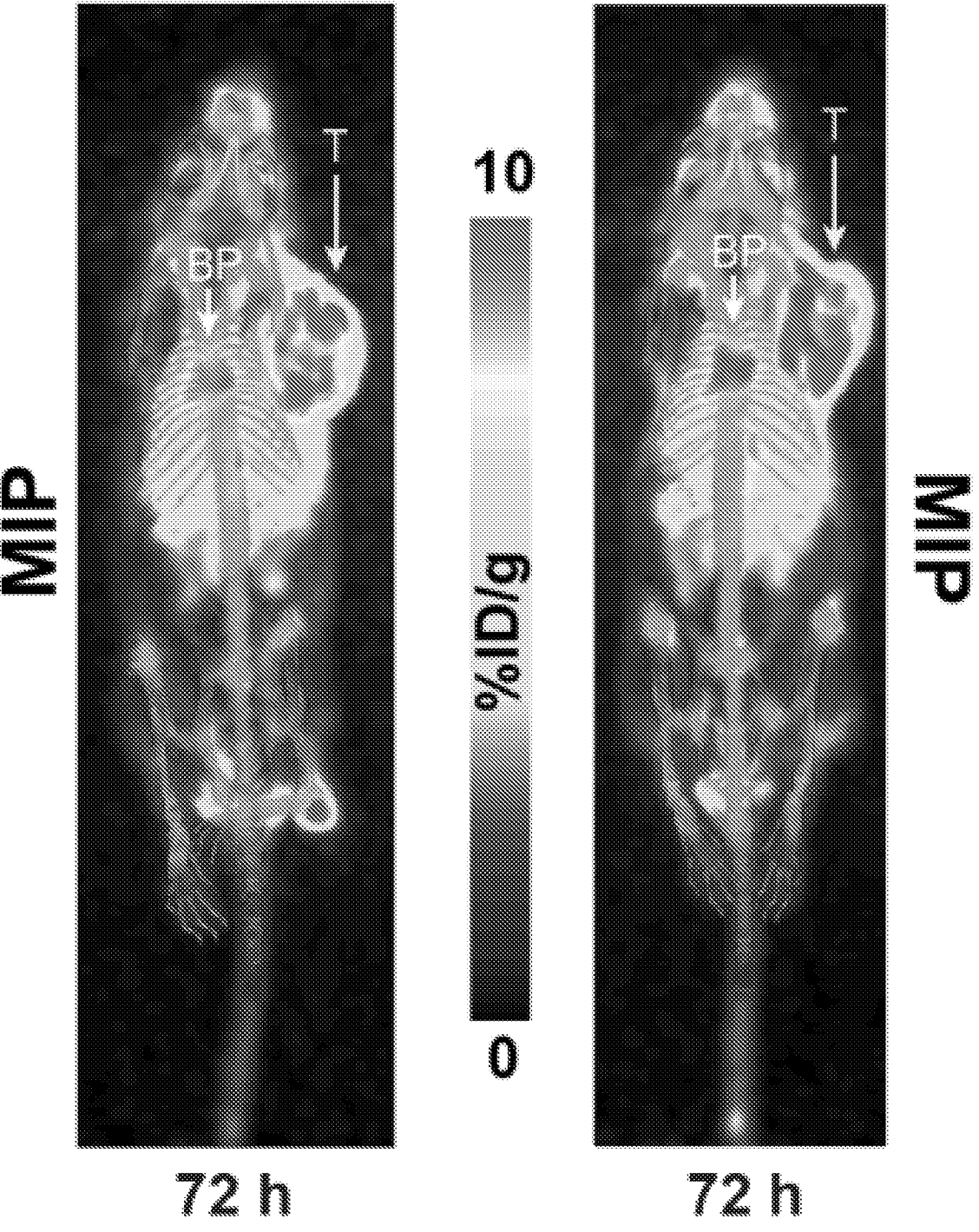

To test the utility of the 4H11-based radiotracer in a model that is not artificially overexpressing the MUC16 peptide-2, we developed a subcutaneous xenograft model using OVCAR3 cells, which is a representative cell line for HGSOC and naturally expresses copious amounts of MUC16. PET images of [$^{89}$Zr]Zr-DFO-hu4H11 in this model demonstrated high radioactivity concentration in the OVCAR3 tumor at the intermediate time point of 72 h p.i. (FIG. 8A). Finally, to explore the feasibility and demonstrate a proof-of-concept for using [$^{89}$Zr]Zr-DFO-hu4H11 as an immunoPET agent in the clinic, we used a patient-derived xenograft (PDX) model representative of HGSOC. PET images of [$^{89}$Zr]Zr-DFO-hu4H11 in this model revealed high radioactivity concentrations in the PDX tumors at 72 h p.i. Notably, the PET images from the OVCAR3 as well as PDX model revealed background activity persisting in the blood pool (BP) inclusive of the heart and descending aorta of mice. This is consistent with observations from previous experiments with the humanized 4H11 antibody (FIGS. 5-7) and appears to be a phenomenon that is independent of the target sink volume provided by the tumor(s). The persistence of activity in systemic circulation may indicate a characteristic feature of the pharmacokinetics and biological half-life of an antibody in vivo.

The study highlighted the utility of radiopharmacologic screening to identify the best candidate during the development of antibody-based drugs. Despite the evolution of several nuclear and label-free biophysical and biochemical methods of analyses to characterize key features of antibodies including their binding affinity and rates of cellular internalization, these techniques remain limited in their ability to predict or characterize the in vivo behavior of lead antibody candidates. The results derived from in vitro radiometric assays can be used in combination with in vivo radiopharmacologic profiles revealed by non-invasive nuclear imaging and biodistribution studies as a strategy that can better screen and characterize lead antibody candidates. Radiopharmacologic screening offers the unique benefit of visualization, traceability and quantitative evaluation of the in vivo pharmacokinetics of antibodies, all of which can be achieved with high sensitivity despite microdosing. Having this information can contribute to a better understanding and characterization of the accessibility and engagement of an antibody with its cognate target to define its potency as a drug while simultaneously outlining any anomalous interactions it may have with non-target organs that may lead to potential toxicities.

Example 4: Surface Plasmon Resonance (SPR) Characterization of Humanized 4H11 Antibodies The relative binding affinities of 4H11 humanized antibodies (H1L1, H1L2, H2L1, H2L2) were compared by surface plasmon resonance using a BIACore-X100 instrument with a Biotin CAP Chip (GE Healthcare). The assay format consisted of capturing the biotinylated MUC16 peptide-2 (TLDRSSVLVDGYSPNRNE; SEQ ID NO: 52) onto a streptavidin coated sensor and flowing over the antibody at various concentrations using single cycle kinetics. Ligand capture was performed by flowing 0.5 g/ml of biotinylated MUC16 peptide-2 at a rate of 5 μl per minute for 65 seconds. The 4H11 humanized antibodies were then flowed over at the various test concentrations (150 nM, 75 nM, 37.5 nM, 18.8 nM, and 9.4 nM). The assay conditions used for measuring the effects of the added antibodies were as follows: association time of 2 minutes, disassociation time of 10 min, and a flow rate of 30 μl per minute.

The relative binding affinities of all 4 antibodies were comparable with 1-3 nM $K_D$ (Table 5). The sensorgram for mouse IgG 4H11 showed similar trend as humanized antibodies (not shown). However, stickiness was observed for kinetic off-step, especially at high concentration.

TABLE 5

| Binding Parameters of 4H11 antibodies | | | |
|---|---|---|---|
| Antibody | $k_a$ [1/Ms] | $k_d$ [1/s] | $K_D$ (nM) |
| 4H11-H1L1 hIgG | $9.27 \times 10^4$ | $1.46 \times 10^{-4}$ | 1.57 |
| 4H11-H1L2 hIgG | $9.04 \times 10^4$ | $1.98 \times 10^{-4}$ | 2.19 |
| 4H11-H2L1 hIgG | $7.61 \times 10^4$ | $1.01 \times 10^{-4}$ | 1.33 |
| 4H11-H2L2 hIgG | $7.38 \times 10^4$ | $1.75 \times 10^{-4}$ | 2.37 |

Example 5: Surface Plasmon Resonance (SPR) Characterization of Humanized 18C6 Antibodies The relative binding affinities of 18C6 humanized antibodies (H1L1, H1L2, H2L1, H2L2) were compared by surface plasmon resonance using a BIACore-X100 instrument with a CM5 Chip (GE Healthcare). The assay format consisted of capturing the four humanized antibodies H1L1, H1L2, H2L1, H2L2 on a CM5 chip coated with anti-mouse IgG or parental mouse 18C6 IgG on a CM5 chip coated with anti-human IgG under near saturating conditions and flowing the MUC16 peptide-2 glycopeptide (TLDRSSVLVDGYSPNRNE; SEQ ID NO: 52) over at various concentrations.

Ligand capture was performed by flowing the humanized anti-Muc16 antibodies 18C6 H1L1, 18C6 H1L2, 18C6 H2L1, 18C6 H2L2) and the parental 18C6 mouse antibody onto the respective chips under saturating conditions. The MUC16 peptide-2 was then flowed over at the various test concentrations (150 nM, 75 nM, 37.5 nM, 18.8 nM, and 9.4 nM). The assay conditions used for measuring the effects of the glycopeptide were as follows: association time of 2 minutes, disassociation time of 10 min, and a flow rate of 30 μl per minute.

The relative binding affinities of all 4 antibodies tested were comparable with each other and similar to parental 18C6 mouse antibody (Table 6).

TABLE 6

| Binding Parameters of 18C6 antibodies | | | |
|---|---|---|---|
| Antibody | $k_a$ [1/MS] | $k_d$ [1/s] | $K_D$ (nM) |
| 18C6 parental mouse IgG | $4.85 \times 10^5$ | $6.8 \times 10^{-3}$ | 14.1 |
| 18C6 H1L1 | $2.87 \times 10^5$ | $1.9 \times 10^{-3}$ | 6.7 |
| 18C6 H1L2 | $2.87 \times 10^5$ | $2.5 \times 10^{-3}$ | 8.7 |
| 18C6 H2L1 | $5.49 \times 10^5$ | $5.4 \times 10^{-3}$ | 9.9 |
| 18C6 H2L2 | $4.33 \times 10^5$ | $4.0 \times 10^{-3}$ | 9.2 |

Example 6: Characterization of Humanized 4H11 and 18C6 Antibodies by Fluorescence Activated Cell Sorting Analysis In this example the ability of the antibodies to bind to MUC16-positive cells (OVCAR3) or cells expressing MUC16 peptides (SKOV3 and A2780 transfectants) was assessed.

OVCAR3, SKOV3, and A2780 cell lines were obtained through the American Type Culture Collection (ATCC, Manassas, VA) and sustained in culture according the supplier's instructions. MUC16 expressing cell lines were created by transfecting MUC16-negative human ovarian cancer cell lines (SKOV3 and A2780) with the sequence elements of the C-terminal MUC16, which are essential for tumor promoting effects, using the Vitality phrGFP vector expression system, which generates green fluorescent protein fusion proteins (Stratagene, LaJolla, CA). (A2780-phrGFP-MUC16c344 and SKOV3-phrGFP-MUC16c344). Stable cell lines were selected using geneticin (G418, Invitrogen, Grand Island, NY) in their respective culture media and isolated by expression of Green Fluorescence Protein. Stable transfectants were routinely maintained in G418 in their culture media, respectively. The ΔMUC16c114 transfectants have cell surface expression of MUC16 protein from the putative cleavage site to the carboxy terminus (amino acids 1776 to 1890). The ΔMUC16c344 transfectants have cell surface expression of MUC16 protein from amino acid 1547 to the carboxy terminus (amino acid 1890).

Figure 9A:
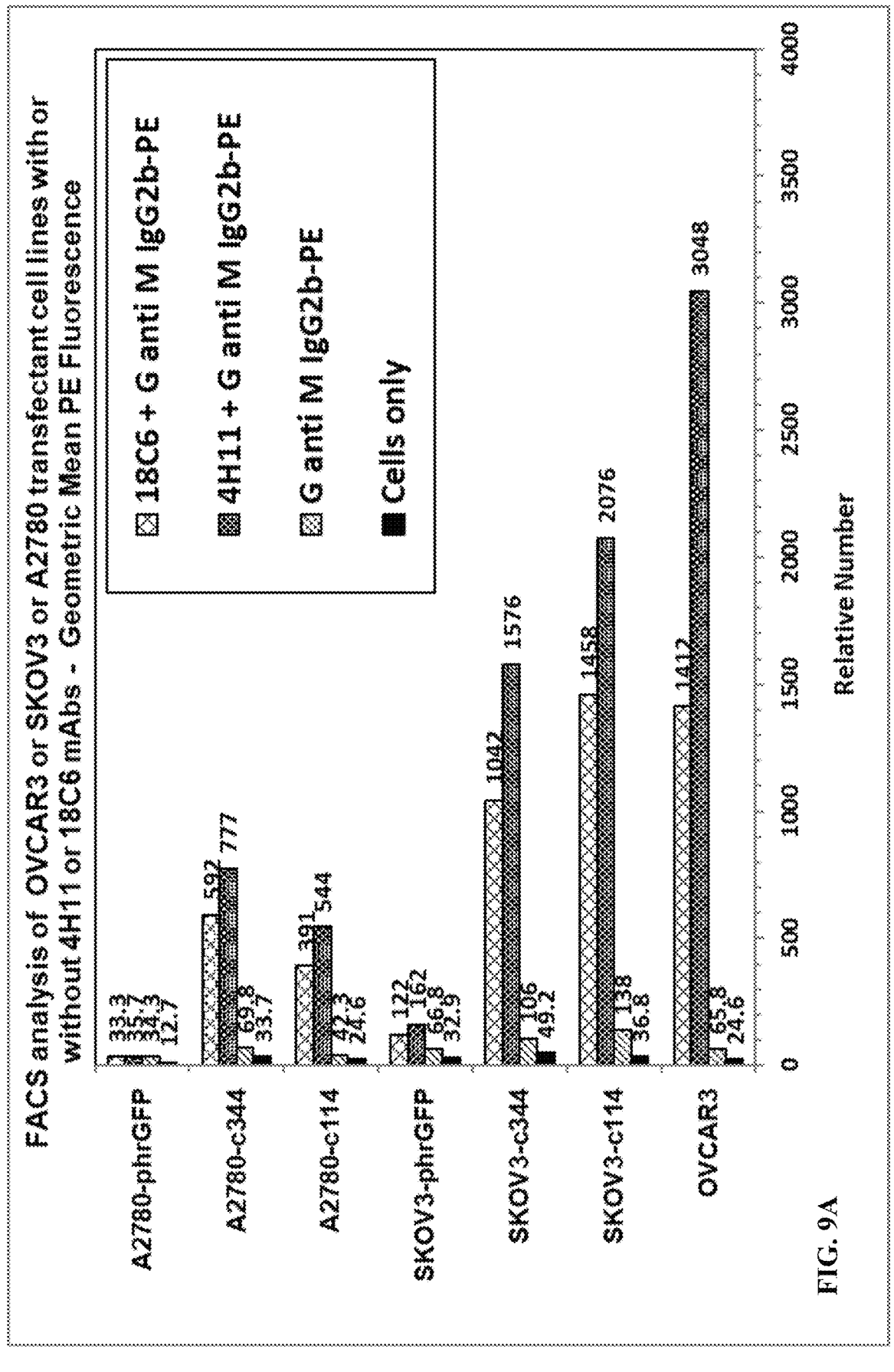
FIGS. 9A-9D illustrate in vitro binding of 4H11 and 18C6 mouse mAbs and humanized antibodies to a MUC16+ OVCAR3 cell line and transfectant cell lines expressing MUC16 c344 and c114 peptides but not to control MUC16$^-$ A2780 and SKOV3 cell line by FACS analysis.
Figure 9B:
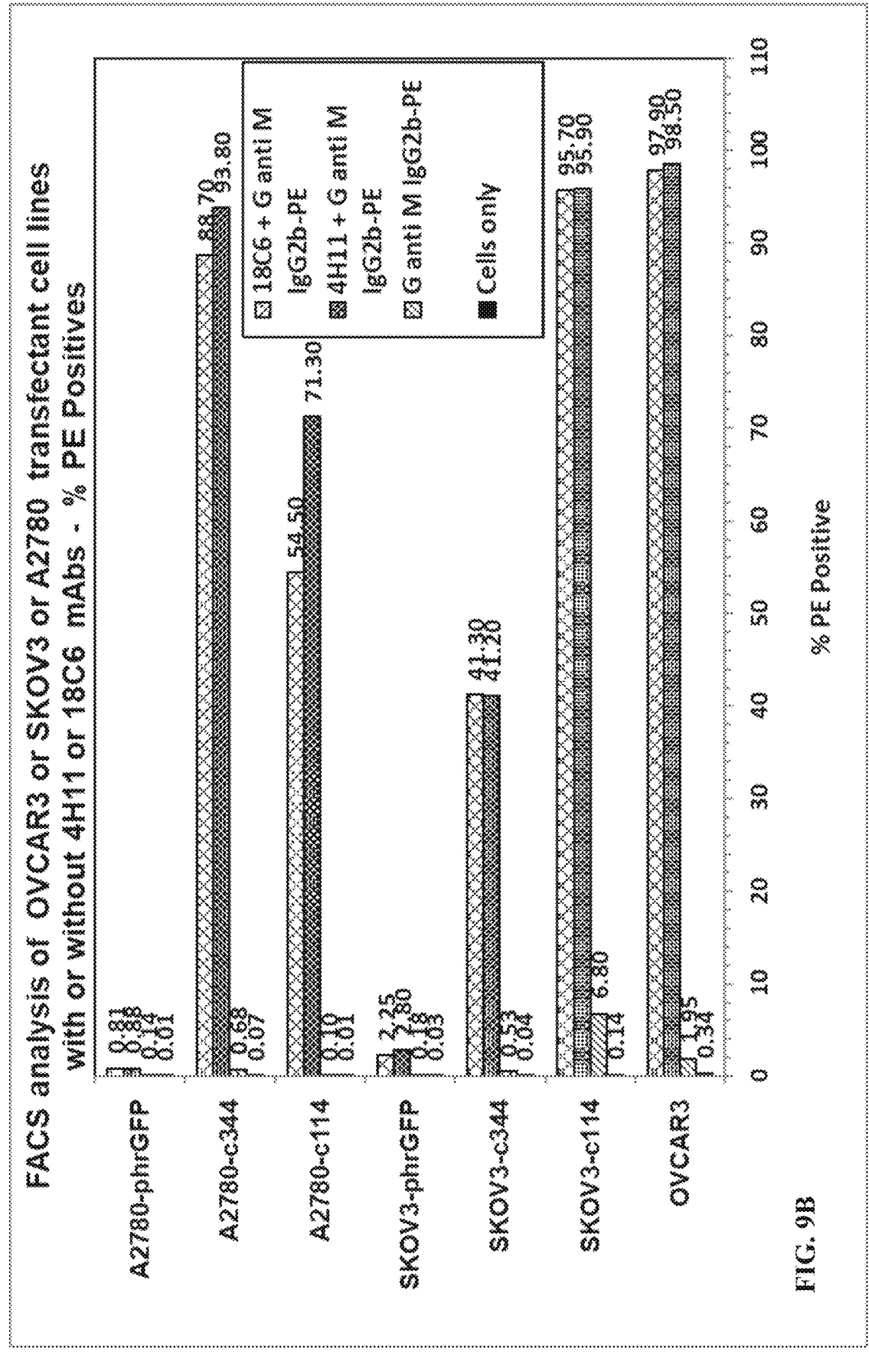
Figure 9C:
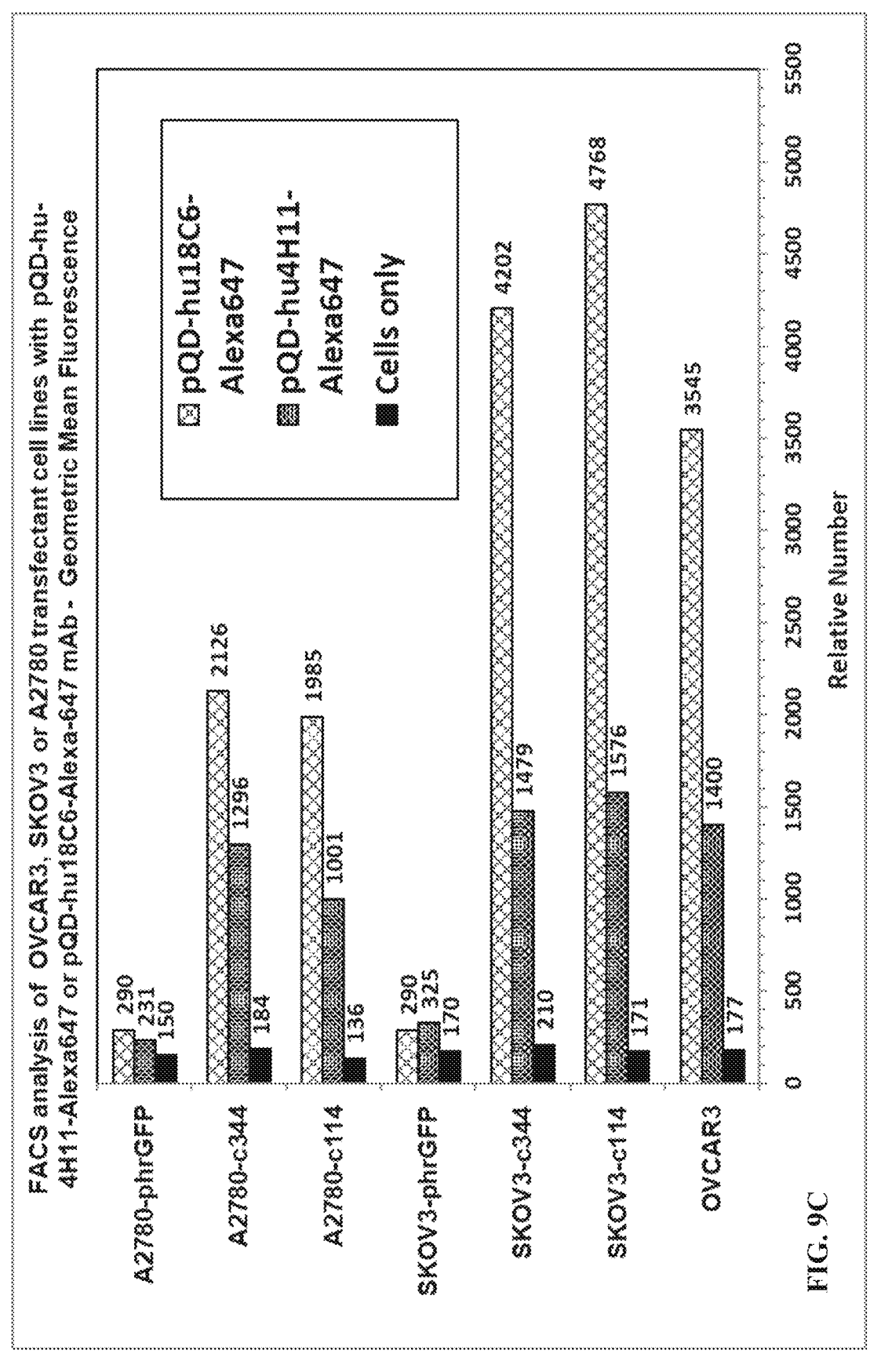
Figure 9D:
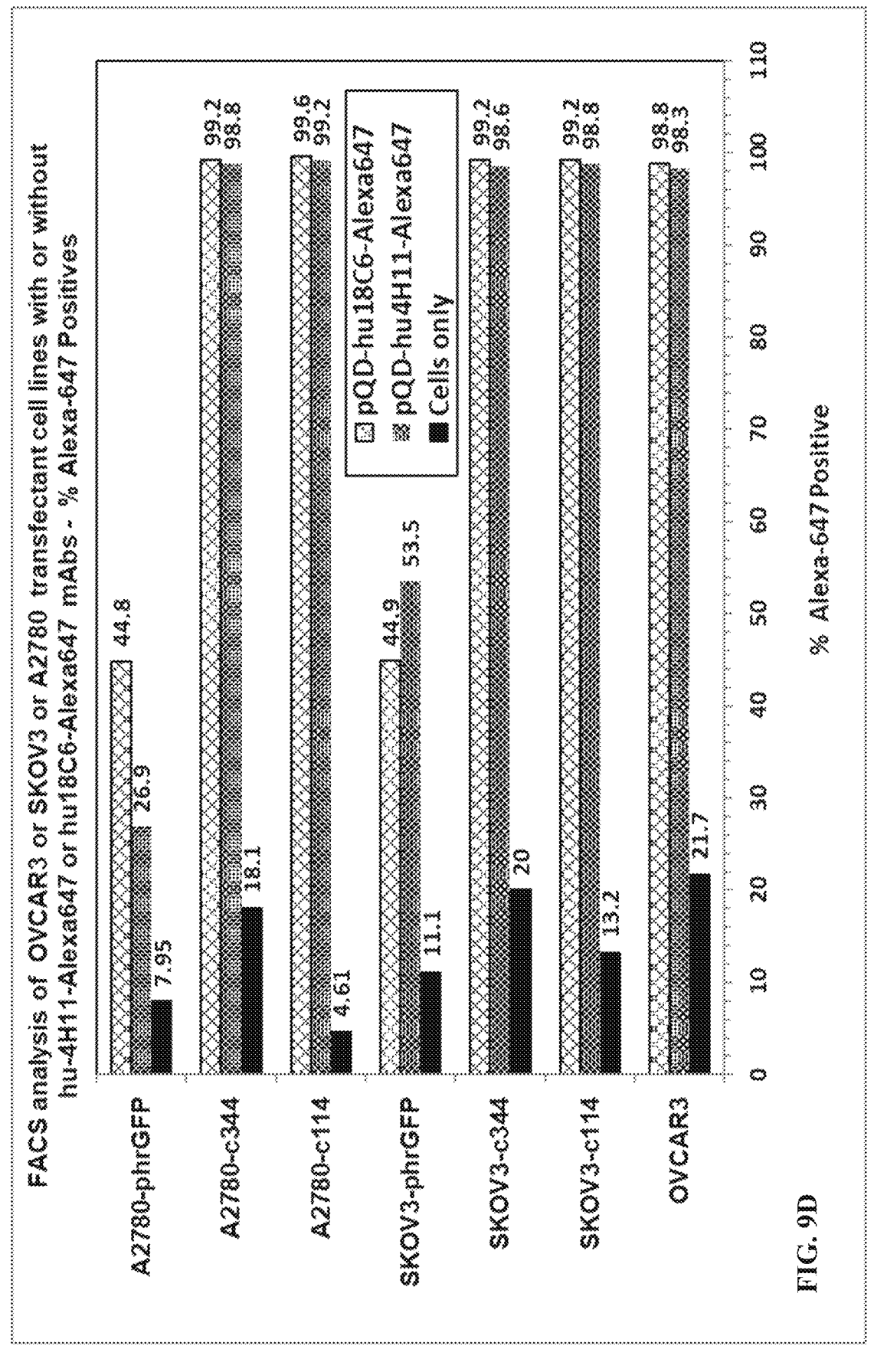

Adherent target cells were removed by 0.05% Trypsin and 0.1% EDTA, washed, and counted by a hemocytometer. Cells were distributed into multiple Eppendorf tubes with at least $0.5-1 \times 10^6$ cells per tube. Cells were washed with phosphate buffered saline (PBS) containing 1% FCS and 0.025% Sodium Azide (FACS buffer). For internal FACS staining, cells in the Eppendorf tubes were permeabilized with 1:10 diluted FACS Permeabilizing Solution 2 (BD BioSciences, San Jose, CA) for 10 minutes at room temperature and then washed twice with ice cold FACS buffer. For surface FACS staining, cells were incubated either without or with 1 mg/tube of 4H11 or 18C6 mouse mAbs or 4H11 or 18C6 humanized antibodies conjugated to Alex Fluor 647 for 30 minutes on ice. All cells were washed 3 times with FACS buffer. Cells labeled with the 4H11 or 18C6 mouse mAbs were further incubated with 1 mg/tube of second antibody Goat anti-mouse IgG2b-PE (phycoerythrin) for 30 minutes on ice and then washed 3 times with FACS buffer. The cells were analyzed by a FACS Calibur machine. Data for mean PE fluorescence and percentage PE positive cells for the 4H11 or 18C6 mouse mAbs assay are shown in FIGS. 9A and 9B. Data for mean Alexa-647 fluorescence and percentage Alexa-647 positive cells for the 4H11 or 18C6 humanized antibody assay are shown in FIGS. 9C and 9D. Data is shown for the H1L2 humanized 4H11 antibody and the H1L1 humanized 18C6 antibody.

Figure 10A:
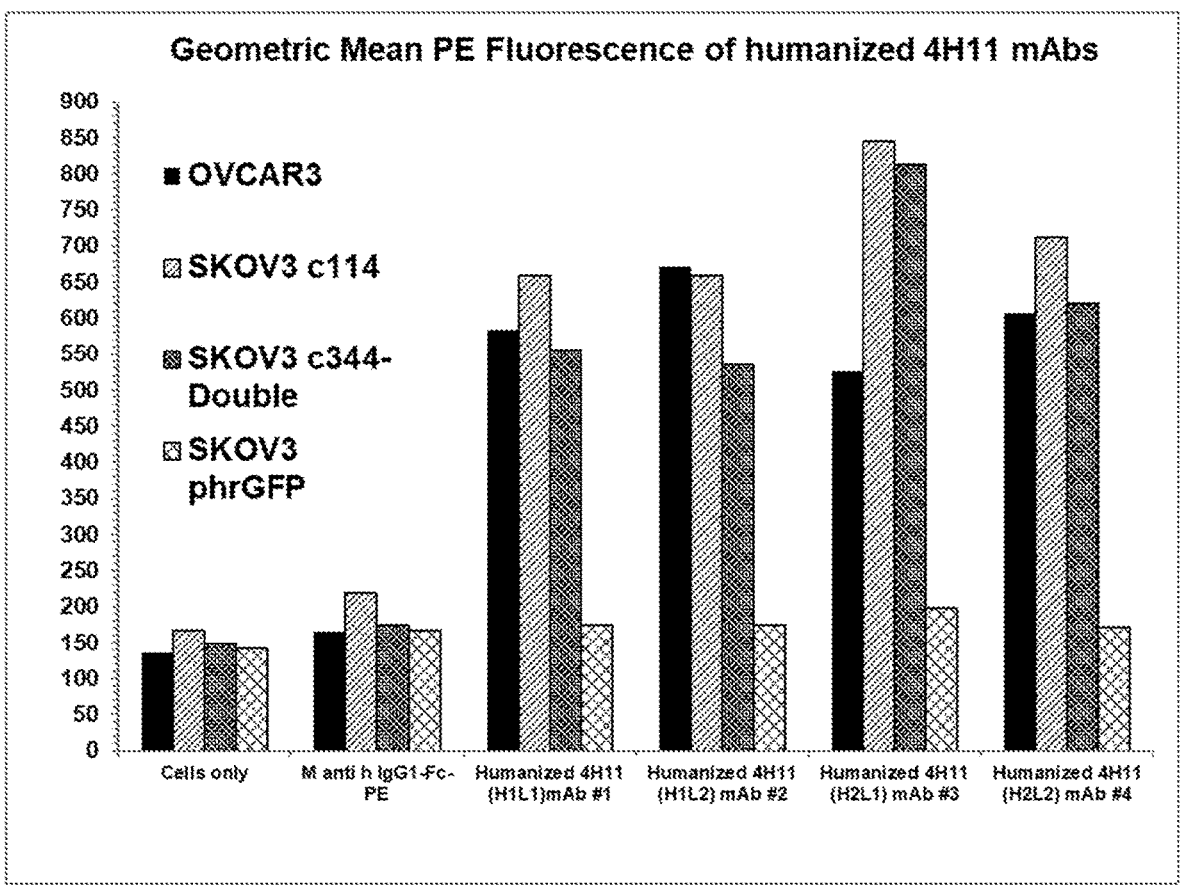
FIGS. 10A and 10B illustrate in vitro binding of 4H11 humanized antibodies to a MUC16+ OVCAR3 cell line and transfectant SKOV3 cell lines expressing MUC16 c344 and c114 peptides but not to control MUC16$^-$ SKOV3 cell line by FACS analysis.
Figure 10B:
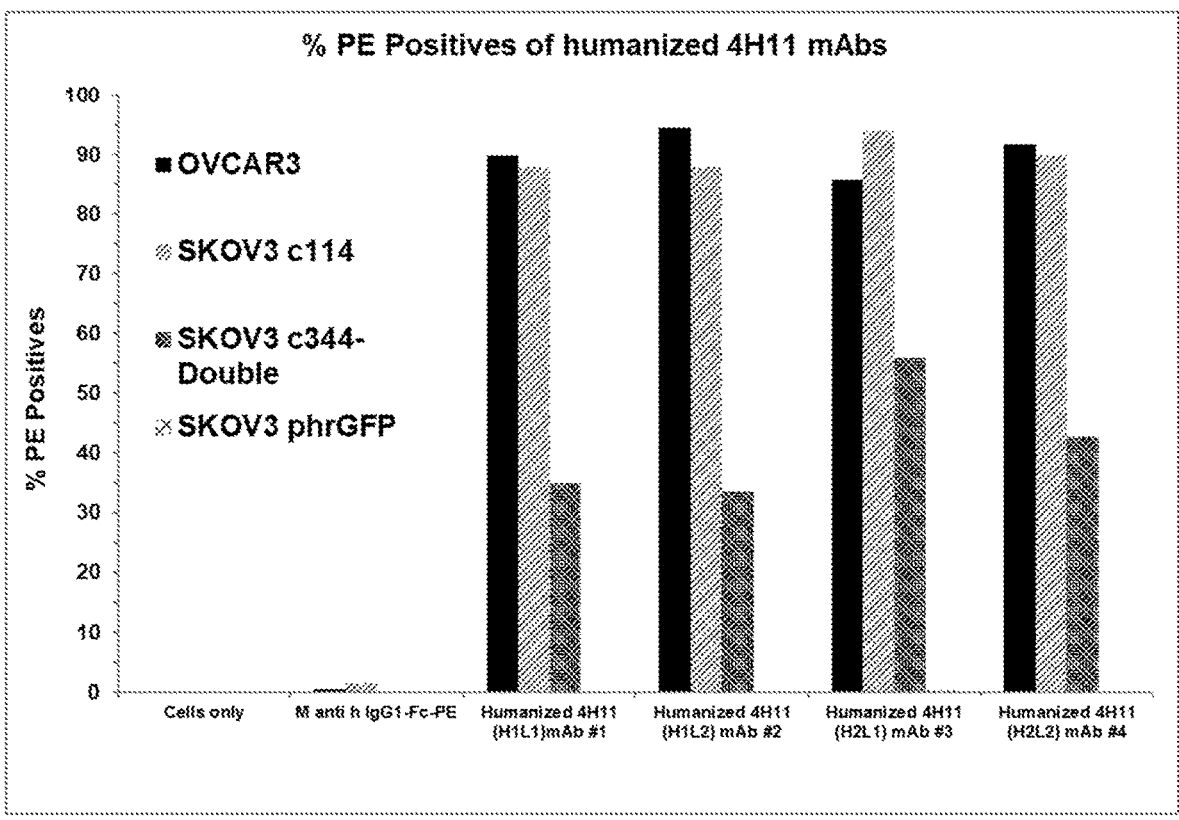

In a separate experiment, full-length humanized 4H11 antibodies (IgG1-Fc) comprising different combinations of humanized heavy and light chain variable regions of the 4H11 antibody were assayed. An anti-human IgG1-Fc-PE antibody was employed for fluorescent staining of MUC16-positive OVCAR3 or SKOV3 transfectant cells expressing MUC16 peptides. FIGS. 10A and 10B provide data for mean PE fluorescence and percentage PE positive cells for the 4H11 H1L1, H1L2, H2L1 and H2L2 antibodies assayed.

Amino acid sequences for the 4H11 L1, L2, H1, and H2, variable regions are provided herein as SEQ ID NOS: 2, 3, 4, and 5, respectively. Amino acid sequences for the 18C6 L1, L2, H1, and H2, variable regions are provided herein as SEQ ID NOS: 20, 21, 22, and 23, respectively.

Figure 11:
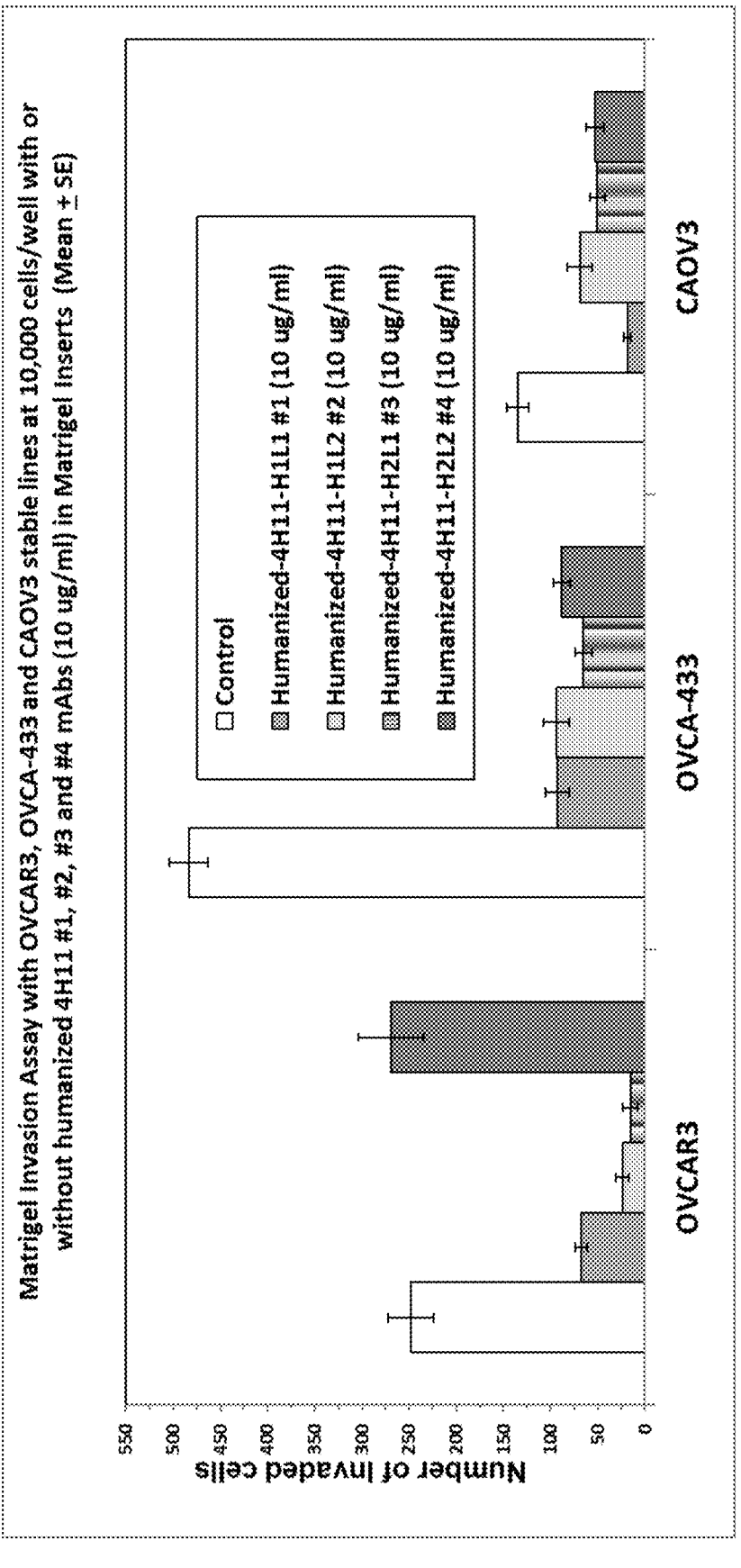
FIG. 11 illustrates 4H11 humanized antibodies inhibit invasion of MUC16+ OVCAR3, OVCA-433 and CAOV3 cell lines as compared to untreated cells in a Matrigel invasion assay.
Figure 12:
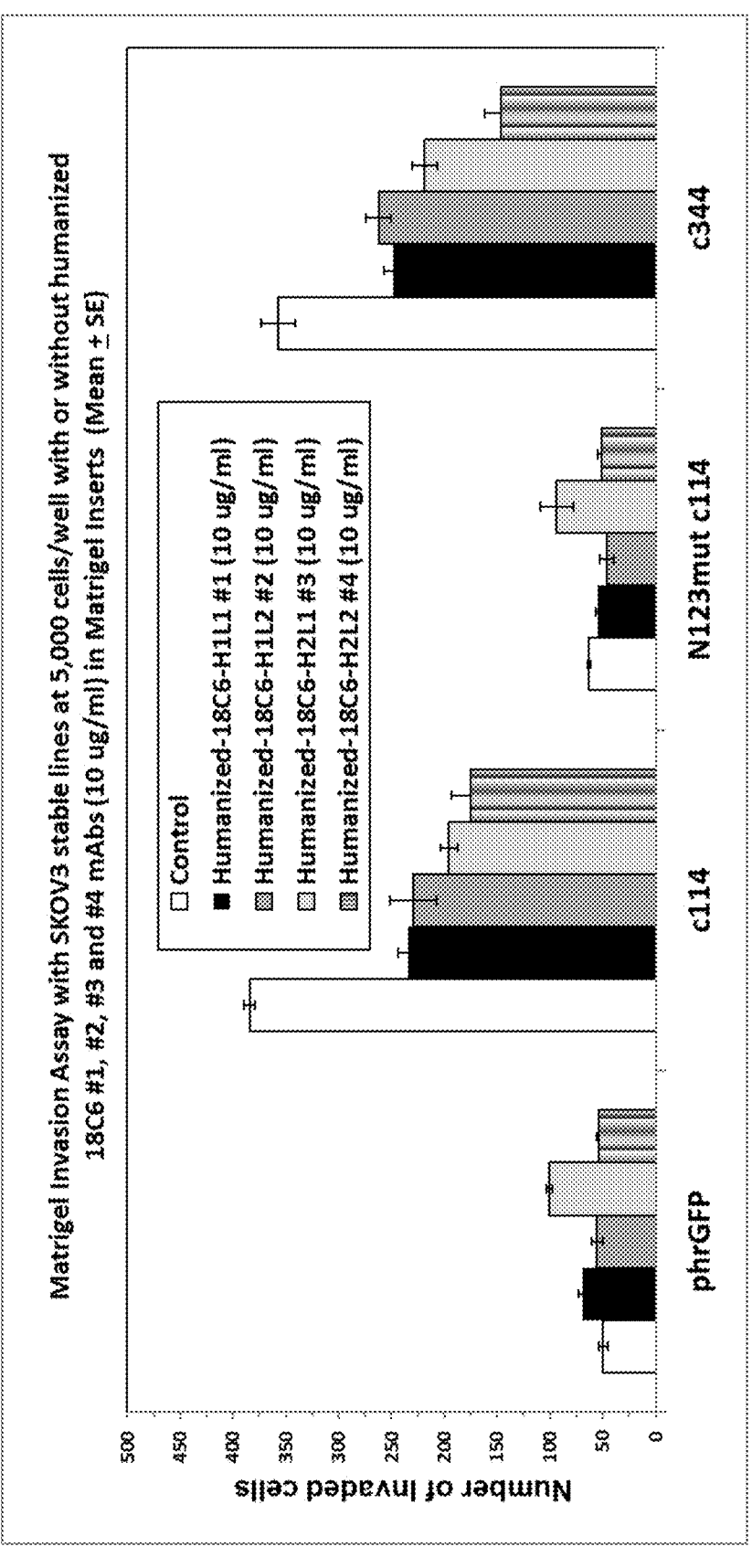
FIG. 12 illustrates 4H11 humanized antibodies inhibit invasion of transfectant SKOV3 cell lines expressing MUC16 c344 and c114 peptides as compared to untreated cells in a Matrigel invasion assay. SKOV3 cell lines expressing the mutant MUC16 peptide N123mut c114 was employed as a negative control for invasion.

Example 7: Characterization of Humanized 4H11 and 18C6 Antibodies by Matrigel Invasion Assay Antibody inhibition of basement membrane invasion was determined in Matrigel invasion chambers as previously described by Rao, et al. (2017) ACS Chem. Biol. 12 (8): 2085-2096, which is incorporated by reference in its entirety. SKOV3 cell lines expressing the C-terminal portions of MUC16 necessary for invasion were generated as described above. The transfected cells as well as wild type MUC16 expressing ovarian cancer cells (OVCAR3, OVCA-433 and CAOV3) were pretreated without or with full-length humanized 4H11 antibodies (IgG1-Fc) comprising different combinations of humanized heavy and light chain variable regions of the 4H11 antibody prior to exposure to the Matrigel® invasion chambers. The number of invading cells was counted. FIG. 11 shows exemplary data for the MUC16-positive OVCAR, VCA-433 and CAOV3 cell lines, and FIG. 12 shows exemplary data for the MUC16-expressing SKOV3 cell lines and parent SKOV3 cell line. A SKOV3 cell line expressing the mutant MUC16 peptide N123mut c114 was employed as a negative control for invasion.

Example 8: Generation of Anti-MUC16 Bispecific Antibodies

This example describes the generation of anti-MUC16 bi-specific antibodies (BsAbs) from the humanized 4H11 and 18C6 anti-MUC16 scFvs. A single-chain BsAb comprising anti-MUC16 scFv at the N-terminal end and an anti-human CD3F scFv of a mouse monoclonal antibody at the C-terminal end is generated. A 4H11 anti-MUC16 BsAb and an 18C6 anti-MUC16 BsAb are generated by cloning DNA fragments encoding the anti-MUC16 scFv and the anti-human CD3P scFv antibody derived from parental clone L2K into an expression vector using standard DNA technology. A hexahistidine (His) tag (SEQ ID NO: 41) is inserted downstream of the anti-MUC16 BsAb at the C-terminal end for antibody purification and detection. Sequences for exemplary 4H11 anti-MUC16 BsAbs are provided in SEQ ID NOS: 44 or 180, 69-71 and 88-91. Sequences for exemplary 18C6 anti-MUC16 BsAbs are provided in SEQ ID NOS: 72-75 and 92-95.

Chinese hamster ovary (CHO) cells are transfected with the anti-MUC16 BsAb expression vector and stable expression is achieved by standard drug selection with methionine sulfoximine (MSX), a glutamine synthetase (GS)-based method (Fan, et al., Biotechnology Bioengineering. 109 (4), 1007-1005 (2012)). CHO cell supernatants containing secreted anti-MUC16 BsAb molecules are collected. Anti-MUC16 BsAbs are purified using HisTrap HP column (GE healthcare) by FPLC AKTA system. Briefly, CHO cell culture is clarified and loaded onto the column with low imidazole concentration (20 mM), and then an isocratic high imidazole concentration elution buffer (500 mM) is used to elute the bound anti-MUC16 bi-specific antibody protein. The bands for the BsAbs are observed by SDS-PAGE, indicating that the BsAbs are successfully purified.

Example 9: Anti-MUC16 BsAb—MUC16+ Cell Specificity

In this example, the specificity of the 4H11 and 18C6 anti-MUC16 BsAbs for binding to cancer cells that express MUC16 is assessed. In one study, two target cell lines are employed, a MUC16+ OVCAR3 cell line and a MUC16− SKOV3 cell line. OVCAR3 and SKOV3 cell lines are obtained through the American Type Culture Collection (ATCC, Manassas, VA) and sustained in culture according to the ATCC literature. FACS analysis of anti-MUC16 antibody binding to the two target cell lines is performed to confirm that antibody binding is observed only with the MUC16+ OVCAR3 cell line. SKOV3 or OVCAR3 cell lines are incubated with the anti-MUC16 Ab followed by a secondary antibody or with a secondary antibody alone as a control. The MUC16+ OVCAR3 cell line are expected to exhibit an increase in binding over the control cells while SKOV3 exhibit low or no signal.

Example 10: Anti-MUC16 BsAb—Directed Cell Cytotoxicity

In this example, the ability of the 4H11 and 18C6 anti-MUC16 BsAbs to induce MUC16-specific cell toxicity is assessed. 4H11 anti-MUC16 BsAb and 18C6 anti-MUC16 BsAb are incubated at a concentration of about 0.2 µg/ml with either the MUC16+ OVCAR3 target cell line or the MUC16− SKOV3 target cell line and human activated T cells at an effector:target (E:T) ratio of 5:1 for 16 hours. The cytotoxicity is measured by lactate dehydrogenase (LDH) release assay. The BsAbs are expected to be able to induce cell lysis of OVCAR3 cells, while cell lysis of SKOV3 is expected to be minimal, indicating that the MUC16+ target specificity is required for the T cell activation. The experiment demonstrates that the 4H11 and 18C6 anti-MUC16 BsAbs can induce potent and specific killing of a MUC16+ cancer cell line.

Example 11: Therapy of Human MUC16⁺ Metastatic Ovarian Cancer in NSG Mice

In this example, the in vivo therapeutic efficacy of the 4H11 and 18C6 anti-MUC16 BsAbs in a mouse xenograft model of metastatic ovarian cancer is assessed. Female NSG mice between 6-8 weeks old are injected on day 0 (DO) intraperitoneally (i.p.) with $3\times10^6$ SKOV3-MUC-CD tumor cells that are modified to express MUC16-C114 and GFP-LUC. These mice are then treated intravenously (i.v.) with $1\times10^7$ human T cells on day 7 (D7) and i.p with 5 µg of the 4H11 or 18C6 anti-MUC16 BsAb. Additional treatments with 5 µg of the BsAb were administered i.p. on D9, D11, D14, D16, and D18 for a total of six BsAb treatments. Animals are imaged on D14, D21, D28, and D42.

Animals treated with the anti-MUC16 BsAb are expected to exhibit delayed disease progression compared to untreated mice or mice treated with T-cells alone. Treatment with the anti-MUC16 BsAb is expected to significantly prolong survival in tumor-bearing mice compared to T-cell-only therapy or no treatment. Tumor-bearing mice treated with T-cells and anti-MUC16 BsAbs are expected to show significantly elevated levels of systemic IL-2 and IFN-γ 7 days after treatment indicating an induction of an anti-tumor immune response. These results demonstrate that administration of anti-MUC16 BsAb delays disease progression and improves survival in a xenogeneic model of MUC16+ metastatic ovarian cancer.

Example 12: Generation of Anti-MUC16 Chimeric Antigen Receptors (CAR)

This example describes the generation of anti-MUC16 Chimeric Antigen Receptors (CARs) from humanized 4H11 and 18C6 anti-MUC16 scFvs. CAR T cells expressing CARs comprising anti-CD19 scFvs have previously been made using standard recombinant techniques and initial publications on the methods to create them and to characterize their activity are described (Brentjens et al., *Sci. Trans. Med.* 5(177):177ra38 (2013), Pegram et al. *Leukemia* 29(2):415-22 (2015)). The 4H11 and 18C6 anti-MUC16 CAR T cell will be made and characterized similarly.

The 4H11 and 18C6 anti-MUC16 scFv sequences (e.g., scFv sequences comprising any one of SEQ ID NOS: 53-56 or 61-64 (4H11) and 57-60 or 65-68 (18C6)) are utilized to generate the antigen binding domain of the CARs. The variable heavy and light chains of the scFv are connected via a $(Gly4Ser)_3$ linker (SEQ ID NO: 179). A leader peptide (e.g., a CD8 signal sequence; e.g., SEQ ID NO: 76) is added to the N-terminus of the scFv for localization. In alternative embodiments, a c-Myc tag can be added to allow detection of the CAR by flow cytometry. A CD8 transmembrane domain (e.g., SEQ ID NO: 77) follows the antigen binding domain. On the cytoplasmic side of the CAR, 4-1BB (e.g., SEQ ID NO: 78) is used as a costimulatory element due to the increased persistence of 4-1BB CAR T cells (Oka et al. PNAS. 101:13885-90 (2004)). The CAR can be optimized to include a spacer domain upstream of the CD8 transmembrane domain if desired. The nucleic acid encoding the CAR can be cloned into an SFG retroviral vector containing the 4-1BB signaling (e.g., SEQ ID NO: 78) and CD3ζ activation domains (e.g., SEQ ID NO: 79), forming a second generation CAR (Brentjens et al. *Clin Cancer Res.* 13(18 Pt 1):5426-35 (2007)). A clinical grade construct, without the c-Myc tag, can also be generated, for which an anti-idiotype mAb to allow detection of the CAR, can be generated.

Stable HEK293T viral producing cell lines are generated, subcloned and used to transduce primary human T cells as described previously (Curran et al. *American Society of Gene Therapy* 23(4):769-78 (2015)). Following transduction, CAR expression is verified by flow cytometry, using an anti-idiotype antibody to detect the anti-MUC16 scFv.

Example 13: Characterization of Anti-MUC16 Chimeric Antigen Receptors (CAR)

In this example, the ability of CART cells expressing a CAR comprising a 4H11 or 18C6 anti-MUC16 scFv to induce MUC16-specific cell toxicity is assessed. Activated 4H111 anti-MUC16 CART cells or 18C6 anti-MUC16 CART cells are incubated with either the MUC16⁺ OVCAR3 target cell line or the MUC16⁻ SKOV3 target cell line at an effector:target (E:T) ratio of 5:1 for 16 hours. The cytotoxicity is measured by lactate dehydrogenase (LDH) release assay. The 4H11 anti-MUC16 CART cells or 18C6 anti-MUC16 CART cells are expected to be able to induce cell lysis of OVCAR3 cells, while cell lysis of SKOV3 is expected to be minimal, indicating that the MUC16⁺ target specificity is required for the T cell activation. The experiment demonstrates that the 4H11 anti-MUC16 CART cells or 18C6 anti-MUC16 CART cells can induce potent and specific killing of a MUC16⁺ cancer cell line.

Example 14: Therapy of Human MUC16⁺ Metastatic Ovarian Cancer in NSG Mice

In this example, the in vivo therapeutic efficacy of CART cells expressing a CAR comprising a 4H11 or 18C6 anti-MUC16 scFv in a mouse xenograft model of metastatic ovarian cancer is assessed. Female NSG mice between 6-8 weeks old are injected on day 0 (DO) intraperitoneally (i.p.) with $3\times10^6$ SKOV3-MUC-CD tumor cells that are modified to express MUC16-C114 and GFP-LUC. These mice are then treated intravenously (i.v.) with $1\times10^7$ 4H11 anti-MUC16 CART cells or 18C6 anti-MUC16 CART cells or control T-cells. Additional treatments with of the 4H11 anti-MUC16 CART cells or 18C6 anti-MUC16 CART cells can be administered intravenously at subsequence interval for multiple treatments. Animals are imaged on D14, D21, D28, and D42.

Animals treated with the 4H11 anti-MUC16 CART cells or 18C6 anti-MUC16 CART cells are expected to exhibit delayed disease progression compared to untreated mice or mice treated with control T-cells. Treatment with the 4H11 anti-MUC16 CART cells or 18C6 anti-MUC16 CART cells is expected to significantly prolong survival in tumor-bearing mice compared to T-cell-only therapy or no treatment. Tumor-bearing mice treated with 4H11 anti-MUC16 CART cells or 18C6 anti-MUC16 CART cells are expected to show significantly elevated levels of systemic IL-2 and IFN-γ 7 days after treatment indicating an induction of an anti-tumor immune response. These results demonstrate that administration of 4H11 anti-MUC16 CART cells or 18C6 anti-MUC16 CART cells delays disease progression and improves survival in a xenogeneic model of MUC16+ metastatic ovarian cancer.

Exemplary Embodiments

The present disclosure may be described in terms of the following non-limiting embodiments:

Embodiment 1: The present application in one aspect provides an anti-mucin 16 (MUC16) construct comprising an antibody moiety that immunospecifically recognizes a mucin 16 (MUC16) polypeptide. In some embodiments, the antibody moiety comprises: (a) (i) a variable heavy (VH) chain comprising a heavy chain complementarity determining region 1 (HC-CDR1), HC-CDR2, and HC-CDR3 of SEQ ID NOS: 17, 18, and 19, respectively, and a heavy chain framework region 1 (HC-FW1), HC-FW2, and HC-FW3 of SEQ ID NOS: 136, 137, and 138, respectively, wherein one or more amino acids selected from amino acid positions 1, 3, 5, 11 and 19 of SEQ ID NO: 136, amino acid positions 5, 7, 8, and 9 of SEQ ID NO: 137, and amino acid positions 12, 14, 18, 22, and 23 of SEQ ID NO: 138 is humanized relative to a mouse HC-FW1, HC-FW2, and HC-FW3 of SEQ ID NOS: 124, 125, and 126, respectively; and (ii) a variable light (VL) chain comprising a light chain complementarity determining region 1 (LC-CDR1), LC-CDR2, and LC-CDR3 of SEQ ID NOS: 14, 15, and 16, respectively, and a light chain framework region 1 (LC-FW1), LC-FW2, LC-FW3, and LC-FW4 of SEQ ID NOS: 120, 121, 122, and 123, respectively, wherein one or more amino acids selected from positions 3, 9, 15, 18, and 22 of SEQ ID NO: 120, amino acid positions 7 and 27 of SEQ ID NO: 122, and amino acid positions 3 and 9 of SEQ ID NO: 123, is humanized relative to a mouse LC-FW1, LC-FW2, LC-FW3, and LC-FW4 of SEQ ID NOS: 104, 105, 106 and 107, respectively; or (b) (i) a variable heavy (VH) chain comprising SEQ ID NO: 4 or 5; and (ii) a variable light (VL) chain comprising SEQ ID NO: 2 or 3; or (c) (i) a variable heavy (VH) chain comprising a heavy chain complementarity determining region 1 (HC-CDR1), HC-CDR2, and HC-CDR3 of SEQ ID NOS: 35, 36, and 37, respectively, and a heavy chain framework region 1 (HC-FW1), HC-FW2, HC-FW3, and HC-FW4 of SEQ ID NOS: 175, 176, 177 and 178, respectively, wherein one or more amino acids selected from amino acid positions 10, 11, 12, 13, 15, 19, and 23 of SEQ ID NO: 175, amino acid positions 5, 14, 16, 18, 22, and 23 of SEQ ID NO: 177, and amino acid position 6 of SEQ ID NO: 178 is humanized relative to a mouse HC-FW1, HC-FW2, HC-FW3, and HC-FW4 of SEQ ID NOS: 159, 160, 161, and 162, respectively; and (ii) a variable light (VL) chain comprising a light chain complementarity determining region 1 (LC-CDR1), LC-CDR2, and LC-CDR3 of SEQ ID NOS: 32, 33, and 34, respectively, and a light chain framework region 1 (LC-FW1), LC-FW2, LC-FW3, and LC-FW4 of SEQ ID NOS: 155, 156, 157, and 158, respectively, wherein one or more amino acids selected from positions 7, 9, 11, and 18 of SEQ ID NO: 155, amino acid position 5 of SEQ ID NO: 156, and amino acid positions 9 and 18 of SEQ ID NO: 157, is humanized relative to a mouse LC-FW1, LC-FW2, LC-FW3, and LC-FW4 of SEQ ID NOS: 139, 140, 141, and 142, respectively; or (d) (i) a variable heavy (VH) chain comprising SEQ ID NO: 22 or 23; and (ii) a variable light (VL) chain comprising SEQ ID NO: 20 or 21.

Embodiment 2: The anti-MUC16 construct of Embodiment 1, wherein HC-FW1 of (a)(i) comprises SEQ ID NO: 130; the HC-FW2 of (a)(i) comprises SEQ ID NO: 131; the HC-FW3 of (a)(i) comprises SEQ ID NO: 132; the LC-FW1 of (a)(ii) comprises SEQ ID NO: 112; the LC-FW2 of (a)(ii) comprises SEQ ID NO: 113; the LC-FW3 of (a)(ii) comprises SEQ ID NO: 114; and/or the LC-FW4 of (a)(ii) comprises SEQ ID NO: 115.

Embodiment 3: The anti-MUC16 construct of Embodiment 1, wherein the HC-FW1 of (a)(i) comprises SEQ ID NO: 130; the HC-FW2 of (a)(i) comprises SEQ ID NO: 131; the HC-FW3 of (a)(i) comprises SEQ ID NO: 132; the LC-FW1 of (a)(ii) comprises SEQ ID NO: 112; the LC-FW2 of (a)(ii) comprises SEQ ID NO: 113; the LC-FW3 of (a)(ii) comprises SEQ ID NO: 114; and the LC-FW4 of (a)(ii) comprises SEQ ID NO: 115.

Embodiment 4: The anti-MUC16 construct of Embodiment 1, wherein the HC-FW1 of (a)(i) comprises SEQ ID NO: 133; the HC-FW2 of (a)(i) comprises SEQ ID NO: 134; the HC-FW3 of (a)(i) comprises SEQ ID NO: 135; the LC-FW1 of (a)(ii) comprises SEQ ID NO: 116; the LC-FW2 of (a)(ii) comprises SEQ ID NO: 117; the LC-FW3 of (a)(ii) comprises SEQ ID NO: 118; and/or the LC-FW4 of (a)(ii) comprises SEQ ID NO: 119.

Embodiment 5: The anti-MUC16 construct of Embodiment 1, wherein the HC-FW1 of (a)(i) comprises SEQ ID NO: 133; the HC-FW2 of (a)(i) comprises SEQ ID NO: 134; the HC-FW3 of (a)(i) comprises SEQ ID NO: 135; the LC-FW1 of (a)(ii) comprises SEQ ID NO: 116; the LC-FW2 of (a)(ii) comprises SEQ ID NO: 117; the LC-FW3 of (a)(ii) comprises SEQ ID NO: 118; and the LC-FW4 of (a)(ii) comprises SEQ ID NO: 119

Embodiment 6: The anti-MUC16 construct of Embodiment 1, wherein the HC-FW1 of (c)(i) comprises SEQ ID NO: 167; the HC-FW2 of (c)(i) comprises SEQ ID NO: 168; the HC-FW3 of (c)(i) comprises SEQ ID NO: 169; the HC-FW4 of (c)(i) comprises SEQ ID NO: 170; the LC-FW1 of (c)(ii) comprises SEQ ID NO: 147; the LC-FW2 of (c)(ii) comprises SEQ ID NO: 148; the LC-FW3 of (c)(ii) comprises SEQ ID NO: 149; and/or the LC-FW4 of (c)(ii) comprises SEQ ID NO: 150.

Embodiment 7: The anti-MUC16 construct of Embodiment 1, wherein the HC-FW1 of (c)(i) comprises SEQ ID NO: 167; the HC-FW2 of (c)(i) comprises SEQ ID NO: 168; the HC-FW3 of (c)(i) comprises SEQ ID NO: 169; the HC-FW4 of (c)(i) comprises SEQ ID NO: 170; the LC-FW1 of (c)(ii) comprises SEQ ID NO: 147; the LC-FW2 of (c)(ii) comprises SEQ ID NO: 148; the LC-FW3 of (c)(ii) comprises SEQ ID NO: 149; and the LC-FW4 of (c)(ii) comprises SEQ ID NO: 150

Embodiment 8: The anti-MUC16 construct of Embodiment 1, the HC-FW1 of (c)(i) comprises SEQ ID NO: 171; the HC-FW2 of (c)(i) comprises SEQ ID NO: 172; the HC-FW3 of (c)(i) comprises SEQ ID NO: 173; the HC-FW4 of (c)(i) comprises SEQ ID NO: 174; the LC-FW1 of (c)(ii) comprises SEQ ID NO: 151; the LC-FW2 of (c)(ii) comprises SEQ ID NO: 152; the LC-FW3 of (c)(ii) comprises SEQ ID NO: 153; and/or the LC-FW4 of (c)(ii) comprises SEQ ID NO: 154.

Embodiment 9: The anti-MUC16 construct of Embodiment 1, wherein the HC-FW1 of (c)(i) comprises SEQ ID NO: 171; the HC-FW2 of (c)(i) comprises SEQ ID NO: 172; the HC-FW3 of (c)(i) comprises SEQ ID NO: 173; the HC-FW4 of (c)(i) comprises SEQ ID NO: 174; the LC-FW1 of (c)(ii) comprises SEQ ID NO: 151; the LC-FW2 of (c)(ii) comprises SEQ ID NO: 152; the LC-FW3 of (c)(ii) comprises SEQ ID NO: 153; and the LC-FW4 of (c)(ii) comprises SEQ ID NO: 154

Embodiment 10: The anti-MUC16 construct of any one of embodiments 1-7, wherein the antibody moiety immunospecifically binds to the ectodomain of MUC16.

Embodiment 11: The anti-MUC16 construct of any one of embodiments 1-9 wherein the MUC16 is a human MUC16.

Embodiment 12: The anti-MUC16 construct of any one of Embodiments 1-11, wherein the antibody moiety is a full-length antibody, a Fab, a Fab', a F(ab')2, an Fv, or a single chain Fv (scFv).

Embodiment 13: The anti-MUC16 construct of Embodiment 12, wherein the antibody moiety is a single chain Fv (scFv), and the scFv comprises any one of SEQ ID NOs: 53-68.

Embodiment 14: The anti-MUC16 construct of any one of Embodiments 1-13, wherein the VH chain and the VL chain are humanized VH chain and VL chain.

Embodiment 15: The anti-MUC16 construct of any one of Embodiments 1-14, wherein the antibody moiety immunospecifically binds to a MUC16 c114 polypeptide comprising the amino acid sequence of SEQ ID NO: 44 or 180.

Embodiment 16: The anti-MUC16 construct of any one of Embodiments 1-15, wherein the anti-MUC16 construct inhibits in vitro invasion of a tumor cell that expresses MUC16 in a Matrigel invasion assay.

Embodiment 17: The anti-MUC16 construct of Embodiment 16, wherein the tumor cell may include an ovarian tumor cell.

Embodiment 18: The anti-MUC16 construct of Embodiment 16 or 17, wherein the MUC16 may be glycosylated.

Embodiment 19: The anti-MUC16 construct of Embodiment 18, wherein the MUC16 is N-glycosylated at N24 or N30 relative to SEQ ID NO: 44 or 180.

Embodiment 20: The anti-MUC16 construct of any one of Embodiments 1-19, wherein the antibody moiety is a monoclonal antibody.

Embodiment 21: The anti-MUC16 construct of any one of Embodiments 1-20, wherein the antibody moiety comprises human-derived heavy and light chain constant regions.

Embodiment 22: The anti-MUC16 construct of Embodiment 21, wherein the heavy chain constant region has an isotype selected from the group consisting of gamma 1, gamma 2, gamma 3, and gamma 4.

Embodiment 23: The anti-MUC16 construct of any one of Embodiment 21 or 22, wherein the light chain constant region has an isotype selected from the group consisting of kappa and lambda.

Embodiment 24: The anti-MUC16 construct of any one of Embodiments 1-23, wherein the antibody moiety is an immunoglobulin comprising two identical heavy chains and two identical light chains.

Embodiment 25: The anti-MUC16 construct of Embodiment 24, wherein the immunoglobulin is an IgG.

Embodiment 26: The anti-MUC16 construct of any one of Embodiments 1-24, wherein the anti-MUC16 construct is monospecific.

Embodiment 27: The anti-MUC16 construct of any one of Embodiments 1-24, wherein the anti-MUC16 construct is multispecific.

Embodiment 28: The anti-MUC16 construct of any one of Embodiments 1-24, wherein the anti-MUC16 construct is multispecific.

Embodiment 29: The anti-MUC16 construct of Embodiment 21 or Embodiment 28, wherein the multispecific or bispecific anti-MUC16 construct further may comprise an anti-CD3 antibody moiety.

Embodiment 30: The anti-MUC16 construct of any one of Embodiments 1-24, wherein the anti-MUC16 construct is a tandem scFv, a diabody (Db), a single chain diabody (scDb), a dual-affinity retargeting (DART) antibody, a F(ab')2, a dual variable domain (DVD) antibody, a knob-into-hole (KiH) antibody, a dock and lock (DNL) antibody, a chemically cross-linked antibody, a heteromultimeric antibody, or a heteroconjugate antibody.

Embodiment 31: The anti-MUC16 construct of Embodiment 30, wherein the construct is a tandem scFv comprising two scFvs linked by a peptide linker.

Embodiment 32: The anti-MUC16 construct of any one of Embodiments 27-31, wherein the antibody moiety that immunospecifically recognizes MUC16 is a first antibody moiety, and wherein the anti-MUC16 construct further comprises a second antibody moiety that immunospecifically recognizes a second antigen.

Embodiment 33: The anti-MUC16 construct of Embodiment 32, wherein the second antigen is an antigen on the surface of a T cell.

Embodiment 34: The anti-MUC16 construct of Embodiment 33, wherein the second antigen is a CD3.

Embodiment 35: The anti-MUC16 construct of Embodiment 34, wherein the second antigen is selected from the group consisting of CD3γ, CD3δ, CD3ε, and CD3ζ.

Embodiment 36: The anti-MUC16 construct of Embodiment 36, wherein the second antigen is CD3R.

Embodiment 37: The anti-MUC16 construct of Embodiment 36, wherein the anti-MUC16 construct comprises any one of SEQ ID NOS: 42, 69-75, and 88-95.

Embodiment 38: The anti-MUC16 construct of any one of Embodiments 1-19, wherein the anti-MUC16 construct is a chimeric antigen receptor (CAR).

Embodiment 39: The anti-MUC16 construct of Embodiment 38, wherein the CAR comprises a co-stimulatory domain.

Embodiment 40: The anti-MUC16 construct of Embodiments 38 or 39, wherein the CAR comprises a CD3 zeta (ζ) chain cytoplasmic signaling domain.

Embodiment 41: The anti-MUC16 construct of any one of Embodiments 38-40, wherein the CAR comprises an scFv of any one of SEQ ID NOS: 53-68.

Embodiment 42: The anti-MUC16 construct of any one of Embodiments 38-41, wherein the CAR comprises any one of SEQ ID NOS: 80-87 and 97-103.

Embodiment 43: The anti-MUC16 construct of any one of Embodiments 1-42 wherein the anti-MUC16 construct is further conjugated to a peptide agent, a detection agent, an imaging agent, a therapeutic agent, or a cytotoxic agent.

Embodiment 44: A polypeptide comprising an amino acid sequence of one or more of SEQ ID NOs: 2-5, 10-13, 20-23 and 28-31, or an amino acid sequence of the anti-MUC16 construct of any one of Embodiments 1-43.

Embodiment 45: A polynucleotide comprising a nucleic acid sequence encoding one or more polypeptides of Embodiment 44.

Embodiment 46: A vector comprising the polynucleotide of Embodiment 45 operably linked to a promoter.

Embodiment 47: A cell comprising the anti-MUC16 construct of any one of Embodiments 1-43, the polypeptide of Embodiment 44, the polynucleotide of Embodiment 45, or the vector of Embodiment 46.

Embodiment 48: The cell of Embodiment 47, wherein the cell is a mammalian cell.

Embodiment 49: The cell of Embodiment 48, wherein the cell is an immune cell.

Embodiment 50: The cell of Embodiment 49, wherein the cell is a lymphocyte.

Embodiment 51: The cell of Embodiment 50, wherein the cell is a T cell or a B cell.

Embodiment 52: A pharmaceutical composition comprising: a therapeutically effective amount of the anti-MUC16 construct of any one of Embodiments 1-43, the polypeptide of Embodiments 31, the polynucleotide of Embodiment 45, the vector of Embodiment 46, or the cell of any one of Embodiments 47-51; and a pharmaceutically acceptable carrier.

Embodiment 53: A method of treating a MUC16-associated disease or disorder in a patient in need thereof, comprising administering to said patient a therapeutically effective amount of the anti-MUC16 construct of any one of Embodiments 1-43 or the pharmaceutical composition of Embodiment 52.

Embodiment 54: The method of Embodiment 53, wherein said MUC16-associated disease or disorder is a cancer.

Embodiment 55: The method of Embodiment 41, wherein said cancer is a cancer of the ovary, lung, pancreas, breast, uterine, fallopian tube, or primary peritoneum.

Embodiment 56: The method of Embodiment 41 or 55, wherein said cancer is a metastatic cancer.

Embodiment 57: The method of any one of Embodiments 53-56, wherein the pharmaceutical composition inhibits or reduces metastasis in the patient.

Embodiment 58: The method of any one of Embodiments 53-57, wherein said patient is a human patient.

Embodiment 59: A method of producing an effector cell, comprising genetically modifying a cell with one or more nucleic acids encoding the anti-MUC16 construct of any one of Embodiments 1-43 or the polypeptide of Embodiment 44.

Embodiment 60: A method of treatment comprising introducing one or more nucleic acids encoding the anti-MUC16 construct of any one of Embodiments 1-43 or the polypeptide of Embodiment 44 into one or more primary cells isolated from a patient and administering cells comprising the one or more nucleic acids to the patient.

Embodiment 61: The method of Embodiment 60, further comprising expanding the cells prior to administering the cells to the patient.

Embodiment 62: The method Embodiment 60 or 61, wherein the primary cells are lymphocytes.

Embodiment 63: The method of Embodiment 62, wherein the primary cells are T cells.

Embodiment 64: The method of any one of Embodiments 53-63, wherein the method further comprises administering a therapeutically effective amount of an additional therapeutic agent to the patient.

Embodiment 65: The method of any one of Embodiments 53-64, wherein the anti-MUC16 construct is the anti-MUC16 construct of any one of Embodiments 1-43.

Embodiment 66: A method of detecting MUC16 in a sample, comprising: (a) contacting the sample with the anti-MUC16 construct of any one of Embodiments 1-31; and (b) detecting the binding, directly or indirectly, between the anti-MUC16 construct and any MUC16 in the sample.

Embodiment 67: The method of Embodiment 66, wherein the anti-MUC16 construct is conjugated to a detectable label.

Embodiment 68: The method of Embodiment 67, wherein the detectable label is a chromogenic, enzymatic, radioisotopic, isotopic, fluorescent, toxic, chemiluminescent, nuclear magnetic resonance contrast agent.

Embodiment 69: The method of Embodiment 67 or 68, wherein the binding between the anti-MUC16 construct and any MUC16 in the sample is detected directly by detecting the detectable label.

Embodiment 70: The method of Embodiment 66, wherein the binding between the anti-MUC16 construct and any MUC16 in the sample is detected indirectly using a secondary antibody.

Embodiment 71: A method of diagnosing an individual suspected of having a MUC16-associated disease or disorder, comprising: a) administering an effective amount of the anti-MUC16 construct of any one of Embodiments 1-31 to the individual; and b) determining the level of the binding, directly or indirectly, between the anti-MUC16 construct and any MUC16 in the individual, wherein a level of the binding above a threshold level indicates that the individual has the MUC16-associated disease or disorder.

Embodiment 72: A method of diagnosing an individual suspected of having a MUC16-associated disease or disorder, comprising: a) contacting a sample comprising cells derived from the individual with the anti-MUC16 construct of any one of Embodiments 1-31; and b) determining the number of cells in the sample bound to the anti-MUC16 construct, wherein a value for the number of cells bound to the anti-MUC16 construct above a threshold level indicates that the individual has the MUC16-associated disease or disorder.

Embodiment 73: Use of the anti-MUC16 construct of any one of Embodiments 1-43, the polypeptide of Embodiment 44, the polynucleotide of Embodiment 45, the vector of Embodiment 46, or the cell of any one of Embodiments 47-51 for the treatment of a disease or disorder associated with positive MUC16 expression.

Embodiment 74: Use of the anti-MUC16 construct of any one of Embodiments 1-43, the polypeptide of Embodiment 44, the polynucleotide of Embodiment 45, the vector of Embodiment 46, or the cell of any one of Embodiments 47-51 in the manufacture of a medicament for the treatment of a disease or disorder associated with positive MUC16 expression.

Embodiment 75: Use of the anti-MUC16 construct of any one of Embodiments 1-31 for the diagnosis of a disease or disorder associated with positive MUC16 expression.

Embodiment 76: The use of any one of Embodiments 62-75, wherein the disease or disorder associated with positive MUC16 expression is a cancer.

Embodiment 77: The use of Embodiment 76, wherein the cancer is ovarian cancer.

Embodiment 78: A kit comprising an anti-MUC16 construct of any one of Embodiments 1-43, a murine anti-MUC16 antibody or antigen binding fragment thereof, and instructions for use, wherein the murine anti-MUC16 antibody or antigen binding fragment includes (a) a variable heavy (VH) chain comprising a heavy chain complementarity determining region 1 (HC-CDR1), HC-CDR2, and HC-CDR3 of SEQ ID NOS: 17, 18, and 19, respectively, and a variable light (VL) chain comprising a light chain complementarity determining region 1 (LC-CDR1), LC-CDR2, and LC-CDR3 of SEQ ID NOS: 14, 15, and 16, respectively; or (b) a variable heavy (VH) chain comprising a heavy chain complementarity determining region 1 (HC-CDR1), HC-CDR2, and HC-CDR3 of SEQ ID NOS: 35, 36, and 37, respectively, and a variable light (VL) chain comprising a light chain complementarity determining region 1 (LC-CDR1), LC-CDR2, and LC-CDR3 of SEQ ID NOS: 32, 33, and 34, respectively.

Embodiment 79: The kit of Embodiment 78, wherein the murine anti-MUC16 antibody or antigen binding fragment is used to identify a patient that is responsive to treatment with the anti-MUC16 construct.

Embodiment 80: The kit of Embodiment 79, wherein the murine anti-MUC16 antibody or antigen binding fragment is used to detect MUC16-expressing tumors in a sample obtained from the patient via western blotting, immunohistochemistry, high-performance liquid chromatography (HPLC), liquid chromatography-mass spectrometry (LC/MS), enzyme-linked immunosorbent assay (ELISA), immunoprecipitation, or immunoelectrophoresis.

Embodiment 81: The anti-MUC16 construct of Embodiment 68, wherein the anti-MUC16 construct is conjugated to an alpha emitter, an Auger-emitter, a beta-emitter, a gamma-emitter, a positron-emitters, or an x-ray emitter, optionally wherein the positron-emitter is [89]Zr-desferrioxamine B (DFO).

Embodiment 82: A method for detecting cancer in a subject in vivo comprising (a) administering to the subject an effective amount of the anti-MUC16 construct of any one of Embodiments 1-31, wherein the anti-MUC16 construct is configured to localize to a cancer cell expressing MUC16 and is labeled with a radioisotope; and (b) detecting the presence of a tumor in the subject by detecting radioactive levels emitted by the anti-MUC16 construct that are higher than a reference value, optionally wherein the radioisotope is [89]Zr-desferrioxamine B (DFO).

Embodiment 83: The method of Embodiment 82, wherein the subject is diagnosed with or is suspected of having cancer.

Embodiment 84: The method of Embodiment 82 or 83, wherein the radioactive levels emitted by the anti-MUC16 construct are detected using positron emission tomography or single photon emission computed tomography.

Embodiment 85: The method of any one of Embodiments 82-84, further comprising administering to the subject an effective amount of an immunoconjugate comprising the anti-MUC16 construct of any one of Embodiments 1-31 conjugated to a radionuclide.

Embodiment 86: The method of any one of Embodiments 82-85, wherein the radionuclide is an alpha particle-emitting isotope, a beta particle-emitting isotope, an Auger-emitter, or any combination thereof.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

TABLE 7

Table of Sequences

| SEQ ID NO | Description | Sequence |
|---|---|---|
| 1 | hMUC16 (Immature) | MLKPSGLPGSSSPTRSLMTGSRSTKATPEMDSGLTGATLSPKTSTGA IVVTEHTLPFTSPDKTLASPTSSVVGRTTQSLGVMSSALPESTSRGM THSEQRTSPSLSPQVNGTPSRNYPATSMVSGLSSPRTRTSSTEGNFT KEASTYTLTVETTSGPVTEKYTVPTETSTTEGDSTETPWDTRYIPVK ITSPMKTFADSTASKENAPVSMTPAETTVTDSHTPGRTNPSFGTLYS SFLDLSPKGTPNSRGETSLELILSTTGYPFSSPEPGSAGHSRISTSAPL SSSASVLDNKISETSIFSGQSLTSPLSPGVPEARASTMPNSAIPFSMTL SNAETSAERVRSTISSLGTPSISTKQTAETILTPHAFAETMDIPSTHIA KTLASEWLGSPGTLGGTSTSALTTTSPSTTLVSEETNTHEISTSGKET EGTLNTSMTPLETSAPGEESEMTATLVPTLGFTTLDSKIRSPSQVSSS HPTRELRTTGSTSGRQSSSTAAHGSSDILRATTSSTSKASSWTSESTA QQFSEPQHTQWVETSPSMKTERPPASTSVAAPITTSVPSVVSGFTTL KTSSTKGIWLEETSADTLIGESTAGPTTHQFAVPTGISMTGGSSTRG SQGTTHLLTRATASSETSADLTLATNGVPVSVSPAVSKTAAGSSPPG GTKPSYTMVSSVIPETSSLQSSAFREGTSLGLTPLNTRHPFSSPEPDS AGHTKISTSIPLLSSASVLEDKVSATSTFSHHKATSSITTGTPEISTKT KPSSAVLSSMTLSNAATSPERVRNATSPLTHPSPSGEETAGSVLTLS TSAETTDSPNIHPTGTLTSESSESPSTLSLPSVSGVKTTFSSSTPSTHLF TSGEETEETSNPSVSQPETSVSRVRTTLASTSVPTPVFPTMDTWPTR SAQFSSSHLVSELRATSSTSVTNSTGSALPKISHLTGTATMSQTNRD TFNDSAAPQSTTWPETSPRFKTGLPSATTTVSTSATSLSATVMVSKF TSPATSSMEATSIREPSTTILTTETTNGPGSMAVASTNIPIGKGYITEG RLDTSHLPIGTTASSETSMDFTMAKESVSMSVSPSQSMDAAGSSTP |

TABLE 7-continued

| | | |
|---|---|---|
| | | Table of Sequences |

| SEQ ID NO | Description | Sequence |
|---|---|---|
| | | GRTSQFVDTFSDDVYHLTSREITIPRDGTSSALTPQMTATHPPSPDP |
| | | GSARSTWLGILSSSPSSPTPKVTMSSTFSTQRVTTSMIMDTVETSRW |
| | | NMPNLPSTTSLTPSNIPTSGAIGKSTLVPLDTPSPATSLEASEGGLPTL |
| | | STYPESTNTPSIHLGAHASSESPSTIKLTMASVVKPGSYTPLTFPSIET |
| | | HIHVSTARMAYSSGSSPEMTAPGETNTGSTWDPTTYITTTDPKDTSS |
| | | AQVSTPHSVRTLRTTENHPKTESATPAAYSGSPKISSSPNLTSPATK |
| | | AWTITDTTEHSTQLHYTKLAEKSSGFETQSAPGPVSVVIPTSPTIGSS |
| | | TLELTSDVPGEPLVLAPSEQTTITLPMATWLSTSLTEEMASTDLDISS |
| | | PSSPMSTFAIFPPMSTPSHELSKSEADTSAIRNTDSTTLDQHLGIRSLG |
| | | RTGDLTTVPITPLTTTWTSVIEHSTQAQDTLSATMSPTHVTQSLKDQ |
| | | TSIPASASPSHLTEVYPELGTQGRSSSEATTFWKPSTDTLSREIETGP |
| | | TNIQSTPPMDNTTTGSSSSGVTLGIAHLPIGTSSPAETSTNMALERRS |
| | | STATVSMAGTMGLLVTSAPGRSISQSLGRVSSVLSESTTEGVTDSSK |
| | | GSSPRLNTQGNTALSSSLEPSYAEGSQMSTSIPLTSSPTTPDVEFIGGS |
| | | TFWTKEVTTVMTSDISKSSARTESSSATLMSTALGSTENTGKEKLR |
| | | TASMDLPSPTPSMEVTPWISLTLSNAPNTTDSLDLSHGVHTSSAGTL |
| | | ATDRSLNTGVTRASRLENGSDTSSKSLSMGNSTHTSMTYTEKSEVS |
| | | SSIHPRPETSAPGAETTLTSTPGNRAISLTLPFSSIPVEEVISTGITSGPD |
| | | INSAPMTHSPITPPTIVWTSTGTIEQSTQPLHAVSSEKVSVQTQSTPY |
| | | VNSVAVSASPTHENSVSSGSSTSSPYSSASLESLDSTISRRNAITSWL |
| | | WDLTTSLPTTTWPSTSLSEALSSGHSGVSNPSSTTTEFPLFSAASTSA |
| | | AKQRNPETETHGPQNTAASTLNTDASSVTGLSETPVGASISSEVPLP |
| | | MAITSRSDVSGLTSESTANPSLGTASSAGTKLTRTISLPTSESLVSFR |
| | | MNKDPWTVSIPLGSHPTTNTETSIPVNSAGPPGLSTVASDVIDTPSD |
| | | GAESIPTVSFSPSPDTEVTTISHFPEKTTHSFRTISSLTHELTSRVTPIP |
| | | GDWMSSAMSTKPTGASPSITLGERRTITSAAPTTSPIVLTASFTETST |
| | | VSLDNETTVKTSDILDARKTNELPSDSSSSSDLINTSIASSTMDVTKT |
| | | ASISPTSISGMTASSSPSLFSSDRPQVPTSTTETNTATSPSVSSNTYSL |
| | | DGGSNVGGTPSTLPPFTITHPVETSSALLAWSRPVRTFSTMVSTDTA |
| | | SGENPTSSNSVVTSVPAPGTWTSVGSTTDLPAMGFLKTSPAGEAHS |
| | | LLASTIEPATAFTPHLSAAVVTGSSATSEASLLTTSESKAIHSSPQTPT |
| | | TPTSGANWETSATPESLLVVTETSDTTLTSKILVTDTILFSTVSTPPS |
| | | KFPSTGTLSGASFPTLLPDTPAIPLTATEPTSSLATSFDSTPLVTIASDS |
| | | LGTVPETTLTMSETSNGDALVLKTVSNPDRSIPGITIQGVTESPLHPS |
| | | STSPSKIVAPRNTTYEGSITVALSTLPAGTTGSLVFSQSSENSETTAL |
| | | VDSSAGLERASVMPLTTGSQGMASSGGIRSGSTHSTGTKTFSSLPLT |
| | | MNPGEVTAMSEITTNRLTATQSTAPKGIPVKPTSAESGLLTPVSASS |
| | | SPSKAFASLTTAPPTWGIPQSTLTFEFSEVPSLDTKSASLPTPGQSLN |
| | | TIPDSDASTASSSLSKSPEKNPRARMMTSTKAISASSFQSTGFTETPE |
| | | GSASPSMAGHEPRVPTSGTGDPRYASESMSYPDPSKASSAMTSTSL |
| | | ASKLTTLFSTGQAARSGSSSSPISLSTEKETSFLSPTASTSRKTSLFLG |
| | | PSMARQPNILVHLQTSALTLSPTSTLNMSQEEPPELTSSQTIAEEEGT |
| | | TAETQTLTFTPSETPTSLLPVSSPTEPTARRKSSPETWASSISVPAKTS |
| | | LVETTDGTLVTTIKMSSQAAQGNSTWPAPAEETGSSPAGTSPGSPE |
| | | MSTTLKIMSSKEPSISPEIRSTVRNSPWKTPETTVPMETTVEPVTLQS |
| | | TALGSGSTSISHLPTGTTSPTKSPTENMLATERVSLSPSPPEAWTNLY |
| | | SGTPGGTRQSLATMSSVSLESPTARSITGTGQQSSPELVSKTTGMEF |
| | | SMWHGSTGGTTGDTHVSLSTSSNILEDPVTSPNSVSSLTDKSKHKT |
| | | ETWVSTTAIPSTVLNNKIMAAEQQTSRSVDEAYSSTSSWSDQTSGS |
| | | DITLGASPDVTNTLYIITSTAQTTSLVSLPSGDQGITSLTNPSGGKTSS |
| | | ASSVTSPSIGLETLRANVSAVKSDIAPTAGHLSQTSSPAEVSILDVTT |
| | | APTPGISTTITTMGTNSISTTTPNPEVGMSTMDSTPATERRTTSTEHP |
| | | STWSSTAASDSWTVTDMTSNLKVARSPGTISTMHTTSFLASSTELD |
| | | SMSTPHGRITVIGTSLVTPSSDASAVKTETSTSERTLSPSDTTASTPIS |
| | | TFSRVQRMSISVPDILSTSWTPSSTEAEDVPVSMVSTDHASTKTDPN |
| | | TPLSTFLFDSLSTLDWDTGRSLSSATATTSAPQGATTPQELTLETMIS |
| | | PATSQLPFSIGHITSAVTPAAMARSSGVTFSRPDPTSKKAEQTSTQLP |
| | | TTTSAHPGQVPRSAATTLDVIPHTAKTPDATFQRQGQTALTTEARA |
| | | TSDSWNEKEKSTPSAPWITEMMNSVSEDTIKEVTSSSSVLRTLNTLD |
| | | INLESGTTSSPSWKSSPYERIAPSESTTDKEAIHPSTNTVETTGWVTS |
| | | SEHASHSTIPAHSASSKLTSPVVTTSTREQAIVSMSTTTWPESTRART |
| | | EPNSFLTIELRDVSPYMDTSSTTQTSIISSPGSTAITKGPRTEITSSKRIS |
| | | SSFLAQSMRSSDSPSEAITRLSNFPAMTESGGMILAMQTSPPGATSL |
| | | SAPTLDTSATASWTGTPLATTQRFTYSEKTTLFSKGPEDTSQPSPPS |
| | | VEETSSSSSLVPIHATTSPSNILLTSQGHSPSSTPPVTSVFLSETSGLG |
| | | KTTDMSRISLEPGTSLPPNLSSTAGEALSTYEASRDTKAIHHSADTA |
| | | VTNMEATSSEYSPIPGHTKPSKATSPLVTSHEVIGDITSSTSVFGSSET |
| | | TEIETVSSVNQGLQERSTSQVASSATETSTVITHVSSGDATTHVTKT |
| | | QATFSSGTSISSPHQFITSTNTFTDVSTNPSTSLIMTESSGVTITTQTGP |
| | | TGAATQGPYLLDTSTMPYLTETPLAVTPDFMQSEKTTLISKGPKDV |
| | | SWTSPPSVAETSYPSSLTPFLVTTIPPATSTLQGQHTSSPVSATSVLTS |
| | | GLVKTTDMLNTSMEPVTNSPQNLNNPSNEILATLAATTDIETIHPSI |
| | | NKAVTNMGTASSAHVLHSTLPVSSEPSTATSPMVPASSMGDALASI |
| | | SIPGSETTDIEGEPTSSLTAGRKENSTLQEMNSTTESNIILSNVSVGAI |

TABLE 7-continued

Table of Sequences

| SEQ ID NO | Description | Sequence |
|-----------|-------------|----------|
| | | TEATKMEVPSFDATFIPTPAQSTKFPDIFSVASSRLSNSPPMTISTHM |
| | | TTTQTGSSGATSKIPLALDTSTLETSAGTPSVVTEGFAHSKITTAMN |
| | | NDVKDVSQTNPPFQDEASSPSSQAPVLVTTLPSSVAFTPQWHSTSSP |
| | | VSMSSVLTSSLVKTAGKVDTSLETVTSSPQSMSNTLDDISVTSAATT |
| | | DIETTHPSINTVVTNVGTTGSAFESHSTVSAYPEPSKVTSPNVTTST |
| | | MEDTTISRSIPKSSKTTRTETETTSSLTPKLRETSISQEITSSTETSTVP |
| | | YKELTGATTEVSRTDVTSSSSTSFPGPDQSTVSLDISTETNTRLSTSPI |
| | | MTESAEITITTQTGPHGATSQDTFTMDPSNTTPQAGIHSAMTHGFSQ |
| | | LDVTTLMSRIPQDVSWTSPPSVDKTSSPSSFLSSPAMTTPSLISSTLPE |
| | | DKLSSPMTSLLTSGLVKITDILRTRLEPVTSSLPNFSSTSDKILATSKD |
| | | SKDTKEIFPSINTEETNVKANNSGHESHSPALADSETPKATTQMVIT |
| | | TTVGDPAPSTSMPVHGSSETTNIKREPTYFLTPRLRETSTSQESSFPT |
| | | DTSFLLSKVPTGTITEVSSTGVNSSSKISTPDHDKSTVPPDTFTGEIPR |
| | | VFTSSIKTKSAEMTITTQASPPESASHSTLPLDTSTTLSQGGTHSTVT |
| | | QGFPYSEVTTLMGMGPGNVSWMTTPPVEETSSVSSLMSSPAMTSPS |
| | | PVSSTSPQSIPSSPLPVTALPTSVLVTTTDVLGTTSPESVTSSPPNLSSI |
| | | THERPATYKDTAHTEAAMHHSTNTAVTNVGTSGSGHKSQSSVLAD |
| | | SETSKATPLMSTTSTLGDTSVSTSTPNISQTNQIQTEPTASLSPRLRES |
| | | STSEKTSSTTETNTAFSYVPTGAITQASRTEISSSRTSISDLDRPTIAPD |
| | | ISTGMITRLFTSPEVITKSAEMTVTTQTTTPGATSQGILPWDTSTTLFQ |
| | | GGTHSTVSQGFPHSEITTLRSRTPGDVSWMTTPPVEETSSGFSLMSP |
| | | SMTSPSPVSSTSPESIPSSPLPVTALLTSVLVTTTNVLGTTSPEPVTSS |
| | | PPNLSSPTQERLTTYKDTAHTEAMHASMHTNTAVANVGTSISGHES |
| | | QSSVPADSHTSKATSPMGITFAMGDTSVSTSTPAFFETRIQTESTSSL |
| | | IPGLRDTRTSEEINTVTETSTVLSEVPTTTTTEVSRTEVITSSRTTISGP |
| | | DHSKMSPYISTETITRLSTFPFVTGSTEMAITNQTGPIGTISQATLTLD |
| | | TSSTASWEGTHSPVTQRFPHSEETTTMSRSTKGVSWQSPPSVEETSS |
| | | PSSPVPLPAITSHSSLYSAVSGSSPTSALPVTSLLTSGRRKTIDMLDT |
| | | HSELVTSSLPSASSFSGEILTSEASTNTETIHFSENTAETNMGTTNSM |
| | | HKLHSSVSIHSQPSGHTPPKVTGSMMEDAIVSTSTPGSPETKNVDRD |
| | | STSPLTPELKEDSTALVMNSTTESNTVFSSVSLDAATEVSRAEVTYY |
| | | DPTFMPASAQSTKSPDISPEASSSHSNSPPLTISTHKTIATQTGPSGVT |
| | | SLGQLTLDTSTIATSAGTPSARTQDFVDSETTSVMNNDLNDVLKTS |
| | | PFSAEEANSLSSQAPLLVTTSPSPVTSTLQEHSTSSLVSVTSVPTPTL |
| | | AKITDMDTNLEPVTRSPQNLRNTLATSEATTDTHTMHPSINTAVAN |
| | | VGTTSSPNEFYFTVSPDSDPYKATSAVVITSTSGDSIVSTSMPRSSAM |
| | | KKIESETTFSLIFRLRETSTSQKIGSSSDTSTVFDKAFTAATTEVSRTE |
| | | LTSSSRTSIQGTEKPTMSPDTSTRSVTMLSTFAGLTKSEERTIATQTG |
| | | PHRATSQGTLTWDTSITTSQAGTHSAMTHGFSQLDLSTLTSRVPEYI |
| | | SGTSPPSVEKTSSSSSLLSLPAITSPSPVPTTLPESRPSSPVHLTSLPTS |
| | | GLVKTTDMLASVASLPPNLGSTSHKIPTTSEDIKDTEKMYPSTNIAV |
| | | TNVGTTTSEKESYSSVPAYSEPPKVTSPMVTSFNIRDTIVSTSMPGSS |
| | | EITRIEMESTFSLAHGLKGTSTSQDPIVSTEKSAVLHKLTTGATETSR |
| | | TEVASSRRTSIPGPDHSTESPDISTEVIPSLPISLGITESSNMTIITRTGP |
| | | PLGSTSQGTFTLDTPTTSSRAGTHSMATQEFPHSEMTTVMNKDPEIL |
| | | SWTIPPSIEKTSFSSSLMPSPAMTSPPVSSTLPKTIHTTPSPMTSLLTPS |
| | | LVMTTDTLGTSPEPTTSSPPNLSSTSHEILTTDEDTTAIEAMHPSTST |
| | | AATNVETTSSGHGSQSSVLADSEKTKATAPMDTTSTMGHTTVSTS |
| | | MSVSSETTKIKRESTYSLTPGLRETSISQNASFSTDTSIVLSEVPTGTT |
| | | AEVSRTEVTSSGRTSIPGPSQSTVLPEISTRTMTRLFASPTMTESAEM |
| | | TIPTQTGPSGSTSQDTLTLDTSTTKSQAKTHSTLTQRFPHSEMTTLM |
| | | SRGPGDMSWQSSPSLENPSSLPSLLSLPATTSPPPISSTLPVTISSSPLP |
| | | VTSLLTSSPVTTTDMLHTSPELVTSSPPKLSHTSDERLTTGKDTTNT |
| | | EAVHPSTNTAASNVEIPSSGHESPSSALADSETSKATSPMFITSTQED |
| | | TTVAISTPHFLETSRIQKESISSLSPKLRETGSSVETSSAIETSAVLSEV |
| | | SIGATTEISRTEVTSSSRTSISGSAESTMLPEISTTRKIIKEPTSPILAESS |
| | | EMTIKTQTSPPGSTSESTFTLDTSTTPSLVITHSTMTQRLPHSEITTLV |
| | | SRGAGDVPRPSSLPVEETSPPSSQLSLSAMISPSPVSSTLPASSHSSSA |
| | | SVTSLLTPGQVKTTEVLDASAEPETSSPPSLSSTSVEILATSEVTTDT |
| | | EKIHPFSNTAVTKVGTSSSGHESPSSVLPDSETTKATSAMGTISIMGD |
| | | TSVSTLTPALSNTRKIQSEPASSLTTRLRETSTSEETSLATEANTVLS |
| | | KVSTGATTEVSRTEAISFSRTSMSGPEQSTMSQDISIGTIPRISASSVL |
| | | TESAKMTITTQTGPSESTLESTLNLNTATTPSWVETHSIVIQGFPHPE |
| | | MTTSMGRGPGGVSWPSPPFVKETSPPSSPLSLPAVTSPHPVSTTFLA |
| | | HIPPSPLPVTSLLTSGPATTTDILGTSTEPGTSSSSSLSTTSHERLTTYK |
| | | DTAHTEAVHPSTNTGGTNVATTSSGYKSQSSVLADSSPMCTTSTM |
| | | GDTSVLTSTPAFLETRRIQTELASSLTPGLRESSGSEGTSSGTKMSTV |
| | | LSKVPTGATTEISKEDVTSIPGPAQSTISPDISTRTVSWFSTSPVMTES |
| | | AEITMNTHTSPLGATTQGTSTLDTSSTTSLTMTHSTISQGFSHSQMS |
| | | TLMRRGPEDVSWMSPPLLEKTRPSFSLMSSPATTSPSPVSSTLPESIS |
| | | SSPLPVTSLLTSGLAKTTDMLHKSSEPVTNSPANLSSTSVEILATSEV |
| | | TTDTEKTHPSSNRTVTDVGTSSSGHESTSFVLADSQTSKVTSPMVIT |
| | | STMEDTSVSTSTPGFFETSRIQTEPTSSLTLGLRKTSSSEGTSLATEM |
| | | STVLSGVPTGATAEVSRTEVTSSSRTSISGFAQLTVSPETSTETITRLP |

TABLE 7-continued

Table of Sequences

| SEQ ID NO | Description | Sequence |
|---|---|---|
| | | TSSIMTESAEMMIKTQTDPPGSTPESTHTVDISTTPNWVETHSTVTQ<br>RFSHSEMTTLVSRSPGDMLWPSQSSVEETSSASSLLSLPATTSPSPVS<br>STLVEDFPSASLPVTSLLNPGLVITTDRMGISREPGTSSTSNLSSTSRE<br>RLTTLEDTVDTEDMQPSTHTAVTNVRTSISGHESQSSVLSDSETPKA<br>TSPMGTTYTMGETSVSISTSDFFETSRIQIEPTSSLTSGLRETSSSERIS<br>SATEGSTVLSEVPSGATTEVSRTEVISSRGTSMSGPDQFTISPDISTEA<br>ITRLSTSPIMTESAESAITIETGSPGATSEGTLTLDTSTTTFWSGTHST<br>ASPGFSHSEMTTLMSRTPGDVPWPSLPSVEEASSVSSSLSSPAMTST<br>SFFSTLPESISSSPHPVTALLTLGPVKTTDMLRTSSEPETSSPPNLSSTS<br>AEILATSEVTKDREKIHPSSNTPVVNVGTVIYKHLSPSSVLADLVTT<br>KPTSPMATTSTLGNTSVSTSTPAFPETMMTQPTSSLTSGLREISTSQE<br>TSSATERSASLSG1VIPTGATTKVSRTEALSLGRTSTPGPAQSTISPEIS<br>TETITRISTPLTTTGSAEMTITPKTGHSGASSQGTFTLDTSSRASWPG<br>THSAATHRSPHSGMTTPMSRGPEDVSWPSRPSVEKTSPPSSLVSLSA<br>VTSPSPLYSTPSESSHSSPLRVTSLFTPVMMKTTDMLDTSLEPVTTSP<br>PSMNITSDESLATSKATMETEAIQLSENTAVTQMGTISARQEFYSSY<br>PGLPEPSKVTSPVVTSSTIKDIVSTTIPASSEITRIEMESTSTLTPTPRET<br>STSQEIHSATKPSTVPYKALTSATIEDSMTQVMSSSRGPSPDQSTMS<br>QDISTEVITRLSTSPIKTESTEMTITTQTGSPGATSRGTLTLDTSTTFM<br>SGTHSTASQGFSHSQMTALMSRTPGDVPWLSHPSVEEASSASFSLSS<br>PVMTSSSPVSSTLPDSIHSSSLPVTSLLTSGLVKTTELLGTSSEPETSS<br>PPNLSSTSAEILAITEVTTDTEKLEMTNVVTSGYTHESPSSVLADSVT<br>TKATSSMGITYPTGDTNVLTSTPAFSDTSRIQTKSKLSLTPGLMETSI<br>SEETSSATEKSTVLSSVPTGATTEVSRTEAISSSRTSIPGPAQSTMSSD<br>TSMETITRISTPLTRKESTDMAITPKTGPSGATSQGTFTLDSSSTASW<br>PGTHSATTQRFPQSVVTTPMSRGPEDVSWPSPLSVEKNSPPSSLVSS<br>SSVTSPSPLYSTPSGSSHSSPVPVTSLFTSIMMKATDMLDASLEPETT<br>SAPNMNITSDESLAASKATTETEAIHVFENTAASHVETTSATEELYS<br>SSPGFSEPTKVISPVVTSSSIRDNMVSTTMPGSSGITRIEIESMSSLTPG<br>LRETRTSQDITSSTETSTVLYKMPSGATPEVSRTEVMPSSRTSIPGPA<br>QSTMSLDISDEVVTRLSTSPIMTESAEITITTQTGYSLATSQVTLPLG<br>TSMTFLSGTHSTMSQGLSHSEMTNLMSRGPESLSWTSPRFVETTRS<br>SSSLTSLPLTTSLSPVSSTLLDSSPSSPLPVTSLILPGLVKTTEVLDTSS<br>EPKTSSSPNLSSTSVEIPATSEIMTDTEKIHPSSNTAVAKVRTSSSVHE<br>SHSSVLADSETTITIPSMGITSAVDDTTVETSNPAFSETRRIPTEPTESL<br>TPGFRETSTSEETTSIITETSAVLYGVPTSATTEVSMTEIMSSNRIHIPD<br>SDQSTMSPDIITEVITRLSSSSMMSESTQMTITTQKSSPGATAQSTLT<br>LATTTAPLARTHSTVPPRFLHSEMTTLMSRSPENPSWKSSLFVEKTS<br>SSSSLLSLPVTTSPSVSSTLPQSIPSSSFSVTSLLTPGMVKTTDTSTEPG<br>TSLSPNLSGTSVEILAASEVTTDTEKIHPSSSMAVTNVGTTSSGHELY<br>SSVSIHSEPSKATYPVGTPSSMAETSISTSMPANFETTGFEAEPFSHL<br>TSGFRKTNMSLDTSSVTPTNTPSSPGSTHLLQSSKTDFTSSAKTSSPD<br>WPPASQYTEIPVDIITPFNASPSITESTGITSFPESRFTMSVTESTHHLS<br>TDLLPSAETISTGTVMPSLSEAMTSFATTGVPRAISGSGSPPFSRTESG<br>PGDATLSTIAESLPSSTPVPFSSSTFTTTDSSTIPALHEITSSSATPYRV<br>DTSLGTESSTTEGRLVMVSTLDTSSQPGRTSSSPILDTRMTESVELG<br>TVTSAYQVPSLSTRLTRTDGIMEHITKIPNEAAHRGTIRPVKGPQTST<br>SPASPKGLHTGGTKRMETTTTALKTTTTALKTTSRATLTTSVYTPTL<br>GTLTPLNASMQMASTIPTEMMITTPYVFPDVPETTSSLATSLGAETS<br>TALPRTTPSVFNRESETTASLVSRSGAERSPVIQTLDVSSSEPDTTAS<br>WVIHPAETIPTVSKTTPNFEHSELDTVSSTATSHGADVSSAIPTNISPS<br>ELDALTPLVTISGTDTSTTEPTLTKSPHETETRTTWLTHPAETSSTIPR<br>TIPNESHHESDATPSIATSPGAETSSAIPEVITVSPGAEDLVTSQVTSSG<br>TDRNMTIPTLTLSPGEPKTIASLVTHPEAQTSSAIPTSTISPAVSRLVT<br>SMVTSLAAKTSTTNRALTNSPGEPATTVSLVTHPAQTSPTVPWTTSI<br>FFHSKSDTTPSMTTSHGAESSSAVPTPTVSTEVPGVVTPLVTSSRAVI<br>STTIPILTLSPGEPETTPSMATSHGEEASSAIPTPTVSPGVPGVVTSLV<br>TSSRAVTSTTIPILTFSLGEPETTPSMATSHGTEAGSAVPTVLPEVPG<br>MVTSLVASSRAVTSTTLPTLTLSPGEPETTPSMATSHGAEASSTVPT<br>VSPEVPGVVTSLVTSSSGVNSTSIPTLILSPGELETTPSMATSHGAEA<br>SSAVPTPTVSPGVSGVVTPLVTSSRAVTSTTIPILTLSSSEPETTPSMA<br>TSHGVEASSAVLTVSPEVPGMVTSLVTSSRAVTSTTIPTLTISSDEPE<br>TTTSLVTHSEAKMISAIPTLAVSPTVQGLVTSLVTSSGSETSAFSNLT<br>VASSQPETIDSWVAHPGTEASSVVPTLTVSTGEPFTNISLVTHPAESS<br>STLPRTTSRFSHSELDTMPSTVTSPEAESSSAISTTISPGIPGVLTSLVT<br>SSGRDISATFPTVPESPHESEATASWVTHPAVTSTTVPRTTPNYSHSE<br>PDTTPSIATSPGAEATSDFPTITVSPDVPDMVTSQVTSSGTDTSITIPT<br>LTLSSGEPETTTSFITYSETHTSSAIPTLPVSPGASKMLTSLVISSGTDS<br>TTTEPTLTETPYEPETTAIQUHPAETNTMVPRTTPKESHSKSDTTLP<br>VAITSPGPEASSAVSTTTISPDMSDLVTSLVPSSGTDTSTTFPTLSETP<br>YEPETTATWLTHPAETSTTVSGTIPNFSHRGSDTAPSMVTSPGVDTR<br>SGVPTTTIPPSIPGVVTSQVTSSATDTSTAIPTLTPSPGEPETTASSAT<br>HPGTQTGFTVPIRTVPSSEPDTMASWVTHPPQTSTPVSRTTSSFSHSS<br>PDATPVMATSPRTEASSAVLTTISPGAPEMVTSQITSSGAATSTTVPT |

TABLE 7-continued

Table of Sequences

| SEQ ID NO | Description | Sequence |
|---|---|---|
| | | LTHSPGMPETTALLSTHPRTETSKTFPASTVFPQVSETTASLTIRPGA |
| | | ETSTALPTQTTSSLFTLLVTGTSRVDLSPTASPGVSAKTAPLSTHPGT |
| | | ETSTMIPTSTLSLGLLETTGLLATSSSAETSTSTLTLTVSPAVSGLSSA |
| | | SITTDKPQTVTSWNTETSPSVTSVGPPEFSRTVTGTTMTLIPSEMPTP |
| | | PKTSHGEGVSPTTILRTTMVEATNLATTGSSPTVAKTTTTFNTLAGS |
| | | LFTPLTTPGMSTLASESVTSRTSYNHRSWISTTSSYNRRYWTPATST |
| | | PVTSTFSPGISTSSIPSSTAATVPFMVPFTLNFTITNLQYEEDMRHPGS |
| | | RKFNATERELQGLLKPLFRNSSLEYLYSGCRLASLRPEKDSSATAV |
| | | DAICTHRPDPEDLGLDRERLYWELSNLTNGIQELGPYTLDRNSLYV |
| | | NGETHRSSMPTTSTPGTSTVDVGTSGTPSSSPSPTTAGPLLMPFTLNF |
| | | TITNLQYEEDMRRTGSRKENTMESVLQGLLKPLEKNTSVGPLYSGC |
| | | RLTLLRPEKDGAATGVDAICTHRLDPKSPGLNREQLYWELSKLTND |
| | | IEELGPYTLDRNSLYVNGFTHQSSVSTTSTPGTSTVDLRTSGTPSSLS |
| | | SPTIMAAGPLLVPFTLNETITNLQYGEDMGHPGSRKENTTERVLQG |
| | | LLGPIFKNTSVGPLYSGCRLTSLRSEKDGAATGVDAICIHHLDPKSP |
| | | GLNRERLYWELSQLTNGIKELGPYTLDRNSLYVNGFTHRTSVPTSS |
| | | TPGTSTVDLGTSGTPFSLPSPATAGPLLVLFTLNFTITNLKYEEDMH |
| | | RPGSRKFNTTERVLQTLLGPMFKNTSVGLLYSGCRLTLLRSEKDGA |
| | | ATGVDAICTHRLDPKSPGVDREQLYWELSQLTNGIKELGPYTLDRN |
| | | SLYVNGFTHWIPVPTSSTPGTSTVDLGSGTPSSLPSPTTAGPLLVPFT |
| | | LNETITNLKYEEDMHCPGSRKENTTERVLQSLLGPMFKNTSVGPLY |
| | | SGCRLTLLRSEKDGAATGVDAICTHRLDPKSPGVDREQLYWELSQL |
| | | TNGIKELGPYTLDRNSLYVNGFTHQTSAPNTSTPGTSTVDLGTSGTP |
| | | SSLPSPTSAGPLLVPFTLNETITNLQYEEDMHHPGSRKENTTERVLQ |
| | | GLLGPMEKNTSVGLLYSGCRLTLLRPEKNGAATGMDAICSHRLDP |
| | | KSPGLNREQLYWELSQLTHGIKELGPYTLDRNSLYVNGFTHRSSVA |
| | | PTSTPGTSTVDLGTSGTPSSLPSPTTAVPLLVPFTLNFTITNLQYGED |
| | | MRHPGSRKFNTTERVLQGLLGPLFKNSSVGPLYSGCRLISLRSEKD |
| | | GAATGVDAICTHHLNPQSPGLDREQLYWQLSQMTNGIKELGPYTL |
| | | DRNSLYVNGFTHRSSGLTTSTPWTSTVDLGTSGTPSPVPSPTTTGPL |
| | | LVPFTLNETITNLQYEENMGHPGSRKFNITESVLQGLLKPLEKSTSV |
| | | GPLYSGCRLTLLRPEKDGVATRVDAICTHRPDPKIPGLDRQQLYWE |
| | | LSQLTHSITELGPYTLDRDSLYVNGFTQRSSVPTTSTPGTFTVQPETS |
| | | ETPSSLPGPTATGPVLLPFTLNFTITNLQYEEDMRRPGSRKFNTTER |
| | | VLQGLLMPLFKNTSVSSLYSGCRLTLLRPEKDGAATRVDAVCTHRP |
| | | DPKSPGLDRERLYWKLSQLTHGITELGPYTLDRHSLYVNGFTHQSS |
| | | MTTTRTPDTSTMHLATSRTPASLSGPMTASPLLVLFTINFTITNLRYE |
| | | ENMHHPGSRKFNTTERVLQGLLRPVFKNTSVGPLYSGCRLTLLRPK |
| | | KDGAATKVDAICTYRPDPKSPGLDREQLYWELSQLTHSITELGPYT |
| | | LDRDSLYVNGFTQRSSVPTTSIPGTPTVDLGTSGTPVSKPGPSAASPL |
| | | LVLFTLNFTITNLRYEENIVIQHPGSRKFNTTERVLQGLLRSLFKSTSV |
| | | GPLYSGCRLTLLRPEKDGTATGVDAICTHHPDPKSPRLDREQLYWE |
| | | LSQLTHNITELGPYALDNDSLFVNGFTHRSSVSTTSTPGTPTVYLGA |
| | | SKTPASIFGPSAASHLLILFTLNFTITNLRYEENIVIWPGSRKFNTTERV |
| | | LQGLLRPLFKNTSVGPLYSGCRLTLLRPEKDGEATGVDAICTHRPD |
| | | PTGPGLDREQLYLELSQLTHSITELGPYTLDRDSLYVNGFTHRSSVP |
| | | TTSTGVVSEEPFTLNFTINNLRYMADMGQPGSLKFNITDNVMQHLL |
| | | SPLFQRSSLGARYTGCRVIALRSVKNGAETRVDLLCTYLQPLSGPG |
| | | LPIKQVFHELSQQTHGITRLGPYSLDKDSLYLNGYNEPGPDEPPTTP |
| | | KPATTFLPPLSEATTAMGYHLKTLTLNFTISNLQYSPDMGKGSATF |
| | | NSTEGVLQHLLRPLFQKSSMGPFYLGCQLISLRPEKDGAATGVDTT |
| | | CTYHPDPVGPGLDIQQLYWELSQLTHGVTQLGFYVLDRDSLFINGY |
| | | APQNLSIRGEYQINFHIVNWNLSNPDPTSSEYITLLRDIQDKVTTLYK |
| | | GSQLHDTFRFCLVTNLTMDSVLVTVKALFSSNLDPSLVEQVFLDKT |
| | | LNASFHWLGSTYQLVDIHVTEMESSVYQPTSSSSTQHFYLNFTITNL |
| | | PYSQDKAQPGTTNYQRNKRNIEDALNQLFRNSSIKSYFSDCQVSTF |
| | | RSVPNRHHTGVDSLCNFSPLARRVDRVAIYEEFLRMTRNGTQLQNF |
| | | TLDRSSVLVDGYSPNRNEPLTGNSDLPFWAVILIGLAGLLGVITCLI |
| | | CGVLVTTRRRKKEGEYNVQQQCPGYYQSHLDLEDLQ |
| 2 | 4H11 humanized light chain variable region L1 | DIELTQSPSSLAVSAGERVTMNCKSSQSLLNSRTRKNQLAWYQQKP GQSPELLIYWASTRQSGVPDRFSGSGSGTDFTLTISSVQAEDVAVYY CQQSYNLLTFGPGTKLEIKR |
| 3 | 4H11 humanized light chain variable region L2 | DIVLTQSPDSLAVSLGERVTMNCKSSQSLLNSRTRKNQLAWYQQK PGQSPELLIYWASTRQSGVPDRFSGSGSGTDFTLTISSVQAEDVAVY YCQQSYNLLTFGQGTKLEIKR |

TABLE 7-continued

Table of Sequences

| SEQ ID NO | Description | Sequence |
|---|---|---|
| 4 | 4H11 humanized heavy chain variable region H1 | EVKLQESGGGFVKPGGSLRVSCAASGFTFSSYAMSWVRLAPEMRL EWVATISSAGGYIFYSDSVQGRFTISRDNAKNSLHLQMGSLRSGDT AMYYCARQGFGNYGDYYAMDYWGQGTTVTVSS |
| 5 | 4H11 humanized heavy chain variable region H2 | EVQLVESGGGLVKPGGSLRVSCAASGFTFSSYAMSWVRLAPGKGL EWVATISSAGGYIFYSDSVQGRFTISRDNAKNSLYLQMNSLRAEDT AMYYCARQGFGNYGDYYAMDYWGQGTLVTVSS |
| 6 | 4H11 light chain constant region L1 | TVAAPSVFIFPPSDEQLKSGTASVVCLLNNFYPREAKVQWKVDNAL QSGNSQESVTEQDSKDSTYSLSSTLTLSKADYEKHKVYACEVTHQ GLSSPVTKSFNRGEC |
| 7 | 4H11 light chain constant region L2 | TVAAPSVFIFPPSDEQLKSGTASVVCLLNNFYPREAKVQWKVDNAL QSGNSQESVTEQDSKDSTYSLSSTLTLSKADYEKHKVYACEVTHQ GLSSPVTKSFNRGEC |
| 8 | 4H11 heavy chain constant region H1 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKRVEPKSCDKTHTCPPCPAPELLGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSRDELTKNQVSLTCLVKGFYPSDIAVEWESNGQPENNYK TTPPVLDSDGSFFLYSKLTVDKSRWQQGNVFSCSVMHEALHNHYT QKSLSLSPGK |
| 9 | 4H11 heavy chain constant region H2 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKRVEPKSCDKTHTCPPCPAPELLGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSRDELTKNQVSLTCLVKGFYPSDIAVEWESNGQPENNYK TTPPVLDSDGSFFLYSKLTVDKSRWQQGNVFSCSVMHEALHNHYT QKSLSLSPGK |
| 10 | 4H11 light chain L1 | DIELTQSPSSLAVSAGERVTMNCKSSQSLLNSRTRKNQLAWYQQKP GQSPELLIYWASTRQSGVPDRFSGSGSGTDFTLTISSVQAEDVAVYY CQQSYNLLTFGPGTKLEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| 11 | 4H11 light chain L2 | DIVLTQSPDSLAVSLGERVTMNCKSSQSLLNSRTRKNQLAWYQQK PGQSPELLIYWASTRQSGVPDRFSGSGSGTDFTLTISSVQAEDVAVY YCQQSYNLLTFGQGTKLEIKRTVAAPSVFIFPPSDEQLKSGTASVVC LLNNFYPREAKVQWKVDNALQSGNSQESVTEQDSKDSTYSLSSTL TLSKADYEKHKVYACEVTHQGLSSPVTKSFNRGEC |
| 12 | 4H11 heavy chain H1 | EVKLQESGGGFVKPGGSLRVSCAASGFTFSSYAMSWVRLAPEMRL EWVATISSAGGYIFYSDSVQGRFTISRDNAKNSLHLQMGSLRSGDT AMYYCARQGFGNYGDYYAMDYWGQGTTVTVSSASTKGPSVFPL APSSKSTSGGTAALGCLVKDYFPEPVTVSWNSGALTSGVHTFPAVL QSSGLYSLSSVVTVPSSSLGTQTYICNVNHKPSNTKVDKRVEPKSC DKTHTCPPCPAPELLGGPSVFLFPPKPKDTLMISRTPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLTCLVKGFYPSDIAVEWESNGQPENNYKTTPPVLDSDGS FFLYSKLTVDKSRWQQGNVFSCSVMHEALHNHYTQKSLSLSPGK |
| 13 | 4H11 heavy chain H2 | EVQLVESGGGLVKPGGSLRVSCAASGFTFSSYAMSWVRLAPGKGL EWVATISSAGGYIFYSDSVQGRFTISRDNAKNSLYLQMNSLRAEDT AMYYCARQGFGNYGDYYAMDYWGQGTLVTVSSASTKGPSVFPL APSSKSTSGGTAALGCLVKDYFPEPVTVSWNSGALTSGVHTFPAVL QSSGLYSLSSVVTVPSSSLGTQTYICNVNHKPSNTKVDKRVEPKSC DKTHTCPPCPAPELLGGPSVFLFPPKPKDTLMISRTPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPSRDE LTKNQVSLTCLVKGFYPSDIAVEWESNGQPENNYKTTPPVLDSDGS FFLYSKLTVDKSRWQQGNVFSCSVMHEALHNHYTQKSLSLSPGK |

TABLE 7-continued

Table of Sequences

| SEQ ID NO | Description | Sequence |
|---|---|---|
| 14 | 4H11 LCDR1 | QSLLNSRTRKNQ |
| 15 | 4H11 LCDR2 | WAS |
| 16 | 4H11 LCDR3 | QQSYNLLT |
| 17 | 4H11 HCDR1 | GFTFSSYA |
| 18 | 4H11 HCDR2 | ISSAGGYI |
| 19 | 4H11 HCDR3 | ARQGFGNYGDYYAMDY |
| 20 | 18C6 humanized light chain variable region L1 | DIVMTQSAPSVPVTPGESVSISCRSSKSLLHSNGNTYLYWFLQKPGQ SPQRLIYYMSNLASGVPDRFSGRGSGTDFTLKISRVEAEDVGVYYC MQSLEYPLTFGGGTKLEIKR |
| 21 | 18C6 humanized light chain variable region L2 | DIVMTQSALSLPVTPGEPVSISCRSSKSLLHSNGNTYLYWFLQKPGQ SPQRLIYYMSNLASGVPDRFSGSGSGTDFTLKISRVEAEDVGVYYC MQSLEYPLTFGGGTKLEIKR |
| 22 | 18C6 heavy chain variable region H1 | QVTLKESGPGILQPTQTLTLTCTFSGFSLSTVGMGVGWSRQPSGKG LEWLAHIWWDDEDKYYNPALKSRLTITKDTSKNQVFLKITNVDTA DTATYYCTRIGTAQATDALDYWGQGTLVTVSS |
| 23 | 18C6 heavy chain variable region H2 | QVTLKESGPTLVKPTQTLTLTCTFSGFSLSTVGMGVGWSRQPSGKG LEWLAHIWWDDEDKYYNPALKSRLTITKDTSKNQVVLTITNVDPV DTATYYCTRIGTAQATDALDYWGQGTLVTVSS |
| 24 | 18C6 light chain constant region L1 | TVAAPSVFIFPPSDEQLKSGTASVVCLLNNFYPREAKVQWKVDNAL QSGNSQESVTEQDSKDSTYSLSSTLTLSKADYEKHKVYACEVTHQ GLSSPVTKSFNRGEC |
| 25 | 18C6 light chain constant region L2 | TVAAPSVFIFPPSDEQLKSGTASVVCLLNNFYPREAKVQWKVDNAL QSGNSQESVTEQDSKDSTYSLSSTLTLSKADYEKHKVYACEVTHQ GLSSPVTKSFNRGEC |
| 26 | 18C6 heavy chain constant region H1 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKRVEPKSCDKTHTCPPCPAPELLGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSRDELTKNQVSLTCLVKGFYPSDIAVEWESNGQPENNYK TTPPVLDSDGSFFLYSKLTVDKSRWQQGNVFSCSVMHEALHNHYT QKSLSLSPGK |
| 27 | 18C6 heavy chain constant region H1 | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKRVEPKSCDKTHTCPPCPAPELLGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSRDELTKNQVSLTCLVKGFYPSDIAVEWESNGQPENNYK TTPPVLDSDGSFFLYSKLTVDKSRWQQGNVFSCSVMHEALHNHYT QKSLSLSPGK |
| 28 | 18C6 light chain L1 | DIVMTQSAPSVPVTPGESVSISCRSSKSLLHSNGNTYLYWFLQKPGQ SPQRLIYYMSNLASGVPDRFSGRGSGTDFTLKISRVEAEDVGVYYC MQSLEYPLTFGGGTKLEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |

TABLE 7-continued

Table of Sequences

| SEQ ID NO | Description | Sequence |
|---|---|---|
| 29 | 18C6 light chain L2 | DIVMTQSALSLPVTPGEPVSISCRSSKSLLHSNGNTYLYWFLQKPGQ<br>SPQRLIYYMSNLASGVPDRFSGSGSGTDFTLKISRVEAEDVGVYYC<br>MQSLEYPLTFGGGTKLEIKRTVAAPSVFIFPPSDEQLKSGTASVVCL<br>LNNFYPREAKVQWKVDNALQSGNSQESVTEQDSKDSTYSLSSTLT<br>LSKADYEKHKVYACEVTHQGLSSPVTKSFNRGEC |
| 30 | 18C6 heavy chain H1 | QVTLKESGPGILQPTQTLTLTCTFSGFSLSTVGMGVGWSRQPSGKG<br>LEWLAHIWWDDEDKYYNPALKSRLTITKDTSKNQVFLKITNVDTA<br>DTATYYCTRIGTAQATDALDYWGQGTLVTVSSASTKGPSVFPLAPS<br>SKSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPELLGGPSVFLFPPKPKDTLMISRTPEVTCVVVDVSHED<br>PEVKFNWYVDGVEVHNAKTKPREEQYNSTYRVVSVLTVLHQDWL<br>NGKEYKCKVSNKALPAPIEKTISKAKGQPREPQVYTLPPSRDELTK<br>NQVSLTCLVKGFYPSDIAVEWESNGQPENNYKTTPPVLDSDGSFFL<br>YSKLTVDKSRWQQGNVFSCSVMHEALHNHYTQKSLSLSPGK |
| 31 | 18C6 heavy chain H2 | QVTLKESGPTLVKPTQTLTLTCTFSGFSLSTVGMGVGWSRQPSGKG<br>LEWLAHIWWDDEDKYYNPALKSRLTITKDTSKNQVVLTITNVDPV<br>DTATYYCTRIGTAQATDALDYWGQGTLVTVSSASTKGPSVFPLAPS<br>SKSTSGGTAALGCLVKDYFPEPVTVSWNSGALTSGVHTFPAVLQSS<br>GLYSLSSVVTVPSSSLGTQTYICNVNHKPSNTKVDKRVEPKSCDKT<br>HTCPPCPAPELLGGPSVFLFPPKPKDTLMISRTPEVTCVVVDVSHED<br>PEVKFNWYVDGVEVHNAKTKPREEQYNSTYRVVSVLTVLHQDWL<br>NGKEYKCKVSNKALPAPIEKTISKAKGQPREPQVYTLPPSRDELTK<br>NQVSLTCLVKGFYPSDIAVEWESNGQPENNYKTTPPVLDSDGSFFL<br>YSKLTVDKSRWQQGNVFSCSVMHEALHNHYTQKSLSLSPGK |
| 32 | 18C6 LCDR1 | KSLLHSNGNTY |
| 33 | 18C6 LCDR2 | YMS |
| 34 | 18C6 LCDR3 | MQSLEYPLT |
| 35 | 18C6 HCDR1 | GFSLSTVGMG |
| 36 | 18C6 HCDR2 | IWWDDEDK |
| 37 | 18C6 HCDR3 | TRIGTAQATDALDY |
| 38 | Leader Sequence | MGWSCIILFLVATATG |
| 179 | GS linker | GGGGSGGGGSGGGGS |
| 39 | Linker | TSGGGGS |
| 40 | L2K (anti-CD3) | DVQLVQSGAEVKKPGASVKVSCKASGYTFTRYTMHWVRQAPGQG<br>LEWIGYINPSRGYTNYADSVKGRFTITTDKSTSTAYMELSSLRSEDT<br>ATYYCARYYDDHYCLDYWGQGTTVTVSSGEGTSTGSGGSGGSGG<br>ADDIVLTQSPATLSLSPGERATLSCRASQSVSYMNWYQQKPGKAP<br>KRWIYDTSKVASGVPARFSGSGSGTDYSLTINSLEAEDAATYYCQQ<br>WSSNPLTFGGGTKVEIK |
| 41 | His tag | HHHHHH |
| 42 | 4H11 L1H1-BsAB | MGWSCIILFLVATATGKLDIELTQSPSSLAVSAGERVTMNCKSSQSL<br>LNSRTRKNQLAWYQQKPGQSPELLIYWASTRQSGVPDRFSGSGSG<br>TDFTLTISSVQAEDVAVYYCQQSYNLLTFGPGTKLEIKRGGGGSGG<br>GGSGGGGSEVKLQESGGGFVKPGGSLRVSCAASGFTFSSYAMSWV<br>RLAPEMRLEWVATISSAGGYIFYSDSVQGRFTISRDNAKNSLHLQM<br>GSLRSGDTAMYYCARQGFGNYGDYYAMDYWGQGTTVTVSSTSG<br>GGGSDVQLVQSGAEVKKPGASVKVSCKASGYTFTRYTMHWVRQA<br>PGQGLEWIGYINPSRGYTNYADSVKGRFTITTDKSTSTAYMELSSLR<br>SEDTATYYCARYYDDHYCLDYWGQGTTVTVSSGEGTSTGSGGSG |

TABLE 7-continued

Table of Sequences

| SEQ ID NO | Description | Sequence |
|---|---|---|
| | | GSGGADDIVLTQSPATLSLSPGERATLSCRASQSVSYMNWYQQKP GKAPKRWIYDTSKVASGVPARFSGSGSGTDYSLTINSLEAEDAATY YCQQWSSNPLTFGGGTKVEIKHHHHHH |
| 43 | MUC16c344 | WELSQLTHGVTQLGFYVLDRDSLFINGYAPQNLSIRGEYQINFHIVN QNLSNPDPTSSEYITLLRDIQDKVTTLYKGSQLHDTFRFCLVTNLTM DSVLVTVKALFSSNLDPSLVEQVFLDKTLNASFHQLGSTYQLVDIH VTEMESSVYQPTSSSSTQHFYLNFTITNLPYSQDKAQPGTTNYQRN KRNIEDALNQLFRNSSIKSYFSDCQVSTFRSVPNRHHTGVDSLCNFS PLARRVDRVAIYEEFLRMTRNGTQLQNFTLDRSSVLVDGYSPNRNE PLTGNSDLPFWAVILIGLAGLLGLITCLICGVLVTTRRRKKEGEYNV QQQCPGYYQSHLDLEDLQ |
| 44 | MUC16c114 | NFSPLARRVDRVAIYEEFLRMTRNGTQLQNFTLDRSSVLVDGYSPN RNEPLTGNSDLPFWAVILIGLAGLLGLITCLICGVLVTTRRRKKEGE YNVQQQCPGYYQSHLDLEDLQ |
| 45 | MUC16c86 | NFSPLARRVDRVAIYEEFLRMDLPFWAVILIGLAGLLGLITCLICGV LVTTRRRKKEGEYNVQQQCPGYYQSHLDLEDLQ |
| 46 | MUC16c80 | NFSPLARRVDRVAIYEEFLRMTRNGTQLQNFTLDRSSVLVDGYSPN RNEPLTGNSDLPFWAVILIGLAGLLGLITCLICGDLEDLQ |
| 47 | IgG1 heavy chain constant region | ASTKGPSVFPLAPSSKSTSGGTAALGCLVKDYFPEPVTVSWNSGAL TSGVHTFPAVLQSSGLYSLSSVVTVPSSSLGTQTYICNVNHKPSNTK VDKKVEPKSCDKTHTCPPCPAPELLGGPSVFLFPPKPKDTLMISRTP EVTCVVVDVSHEDPEVKFNWYVDGVEVHNAKTKPREEQYNSTYR VVSVLTVLHQDWLNGKEYKCKVSNKALPAPIEKTISKAKGQPREP QVYTLPPSREEMTKNQVSLTCLVKGFYPSDIAVEWESNGQPENNY KTTPPVLDSDGSFFLYSKLTVDKSRWQQGNVFSCSVMHEALHNHY TQKSLSLSPGK |
| 48 | IgG4 heavy chain constant region | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTK VDKRVESKYGPPCPSCPAPEFLGGPSVFLFPPKPKDTLMISRTPEVT CVVVDVSQEDPEVQFNWYVDGVEVHNAKTKPREEQFNSTYRVVS VLTVLHQDWLNGKEYKCKVSNKGLPSSIEKTISKAKGQPREPQVYT LPPSQEEMTKNQVSLTCLVKGFYPSDIAVEWESNGQPENNYKTTPP VLDSDGSFFLYSRLTVDKSRWQEGNVFSCSVMHEALHNHYTQKSL SLSLGK |
| 49 | Light chain constant region | QPKANPTVTLFPPSSEELQANKATLVCLISDFYPGAVTVAWKADGS PVKAGVETTKPSKQSNNKYAASSYLSLTPEQWKSHRSYSCQVTHE GSTVEKTVAPTECS |
| 50 | MUC16c114 N30A | NFSPLARRVDRVAIYEEFLRMTRNGTQLQAFTLDRSSVLVDGYSPN RNEPLTGNSDLPFWAVILIGLAGLLGLITCLICGVLVTTRRRKKEGE YNVQQQCPGYYQSHLDLEDLQ |
| 51 | hMUC16 (mature) | DKTLASPTSSVVGRTTQSLGVMSSALPESTSRGMTHSEQRTSPSLSP QVNGTPSRNYPATSMVSGLSSPRTRTSSTEGNFTKEASTYTLTVETT SGPVTEKYTVPTETSTTEGDSTETPWDTRYIPVKITSPMKTFADSTA SKENAPVSMTPAETTVTDSHTPGRTNPSFGTLYSSFLDLSPKGTPNS RGETSLELILSTTGYPFSSPEPGSAGHSRISTSAPLSSSASVLDNKISET SIFSGQSLTSPLSPGVPEARASTMPNSAIPFSMTLSNAETSAERVRSTI SSLGTPSISTKQTAETILTFHAFAETMDIPSTHIAKTLASEWLGSPGT LGGTSTSALTTTSPSTTLVSEETNTHEISTSGKETEGTLNTSMTPLETS APGEESEMTATLVPTLGFTTLDSKIRSPSQVSSSHPTRELRTTGSTSG RQSSSTAAHGSSDILRATTSSTSKASSWTSESTAQQFSEPQHTQWVE TSPSMKTERPPASTSVAAPITTSVPSVVSGFTTLKTSSTKGIWLEETS ADTLIGESTAGPTTHQFAVPTGISMTGGSSTRGSQGTTHLLTRATAS SETSADLTLATNGVPVSVSPAVSKTAAGSSPPGGTKPSYTMVSSVIP ETSSLQSSAFREGTSLGLTPLNTRHPFSSPEPDSAGHTKISTSIPLLSS ASVLEDKVSATSTFSHHKATSSITTGTPEISTKTKPSSAVLSSMTLSN AATSPERVRNATSPLTHPSPSGEETAGSVLTLSTSAETTDSPNIHPTG TLTSESSSESPSTLSLPSVSGVKTTESSSTPSTHLFTSGEETEETSNPSVS QPETSVSRVRTTLASTSVPTPVEPTMDTWPTRSAQESSSHLVSELRA TSSTSVTNSTGSALPKISHLTGTATMSQTNRDTFNDSAAPQSTTWPE TSPREKTGLPSATTTVSTSATSLSATVMVSKFTSPATSSMEATSIREP STTILTTETTNGPGSMAVASTNIPIGKGYITEGRLDTSHLPIGTTASSE TSMDFTMAKESVSMSVSPSQSMDAAGSSTPGRTSQFVDTFSDDVY HLTSREITIPRDGTSSALTPQMTATHPPSPDPGSARSTWLGILSSSPSS PTPKVTMSSTFSTQRVTTSMIMDTVETSRWNMPNLPSTTSLTPSNIP TSGAIGKSTLVPLDTPSPATSLEASEGGLPTLSTYPESTNTPSIHLGA |

TABLE 7-continued

Table of Sequences

| SEQ ID NO | Description | Sequence |
|-----------|-------------|----------|
| | | HASSESPSTIKLTMASVVKPGSYTPLTFPSIETHIHVSTARMAYSSGS |
| | | SPEMTAPGETNTGSTWDPTTYITTTDPKDTSSAQVSTPHSVRTLRTT |
| | | ENHPKTESATPAAYSGSPKISSSPNLTSPATKAWTITDTTEHSTQLH |
| | | YTKLAEKSSGFETQSAPGPVSVVIPTSPTIGSSTLELTSDVPGEPLVL |
| | | APSEQTTITLPMATWLSTSLTEEMASTDLDISSPSSPMSTFAIFPPMS |
| | | TPSHELSKSEADTSAIRNTDSTTLDQHLGIRSLGRTGDLTTVPITPLT |
| | | TTWTSVIEHSTQAQDTLSATMSPTHVTQSLKDQTSIPASASPSHLTE |
| | | VYPELGTQGRSSSEATTFWKPSTDTLSREIETGPTNIQSTPPMDNTTT |
| | | GSSSSGVTLGIAHLPIGTSSPAETSTNMALERRSSTATVSMAGTMGL |
| | | LVTSAPGRSISQSLGRVSSVLSESTTEGVTDSSKGSSPRLNTQGNTA |
| | | LSSSLEPSYAEGSQMSTSIPLTSSPTTPDVEFIGGSTFWTKEVTTVMT |
| | | SDISKSSARTESSSATLMSTALGSTENTGKEKLRTASMDLPSPTPSM |
| | | EVTPWISLTLSNAPNTTDSLDLSHGVHTSSAGTLATDRSLNTGVTR |
| | | ASRLENGSDTSSKSLSMGNSTHTSMTYTEKSEVSSSIHPRPETSAPG |
| | | AETTLTSTPGNRAISLTLPFSSIPVEEVISTGITSGPDINSAPMTHSPITP |
| | | PTIVWTSTGTIEQSTQPLHAVSSEKVSVQTQSTPYVNSVAVSASPTH |
| | | ENSVSSGSSTSSPYSSASLESLDSTISRRNAITSWLWDLTTSLPTTTW |
| | | PSTSLSEALSSGHSGVSNPSSTTTEFPLFSAASTSAAKQRNPETETHG |
| | | PQNTAASTLNTDASSVTGLSETPVGASISSEVPLPMAITSRSDVSGLT |
| | | SESTANPSLGTASSAGTKLTRTISLPTSESLVSFRMNKDPWTVSIPLG |
| | | SHPTTNTETSIPVNSAGPPGLSTVASDVIDTPSDGAESIPTVSFSPSPD |
| | | TEVTTISHFPEKTTHSERTISSLTHELTSRVTPIPGDWMSSAMSTKPT |
| | | GASPSITLGERRTITSAAPTTSPIVLTASFTETSTVSLDNETTVKTSDI |
| | | LDARKTNELPSDSSSSSDLINTSIASSTMDVTKTASISPTSISGMTASS |
| | | SPSLFSSDRPQVPTSTTETNTATSPSVSSNTYSLDGGSNVGGTPSTLP |
| | | PFTITHPVETSSALLAWSRPVRTFSTMVSTDTASGENPTSSNSVVTS |
| | | VPAPGTWTSVGSTTDLPAMGFLKTSPAGEAHSLLASTIEPATAFTPH |
| | | LSAAVVTGSSATSEASLLTTSESKAIHSSPQTPTTPTSGANWETSATP |
| | | ESLLVVTETSDTTLTSKILVTDTILFSTVSTPPSKFPSTGTLSGASFPT |
| | | LLPDTPAIPLTATEPTSSLATSFDSTPLVTIASDSLGTVPETTLTMSET |
| | | SNGDALVLKTVSNPDRSIPGITIQGVTESPLHPSSTSPSKIVAPRNTTY |
| | | EGSITVALSTLPAGTTGSLVFSQSSENSETTALVDSSAGLERASVMP |
| | | LTTGSQGMASSGGIRSGSTHSTGTKTFSSLPLTMNPGEVTAMSEITT |
| | | NRLTATQSTAPKGIPVKPTSAESGLLTPVSASSSPSKAFASLTTAPPT |
| | | WGIPQSTLTFEFSEVPSLDTKSASLPTPGQSLNTIPDSDASTASSSLSK |
| | | SPEKNPRARMMTSTKAISASSFQSTGFTETPEGSASPSMAGHEPRVP |
| | | TSGTGDPRYASESMSYPDPSKASSAMTSTSLASKLTTLFSTGQAARS |
| | | GSSSSPISLSTEKETSFLSPTASTSRKTSLFLGPSMARQPNILVHLQTS |
| | | ALTLSPTSTLNMSQEEPPELTSSQTIAEEEGTTAETQTLTFTPSETPTS |
| | | LLPVSSPTEPTARRKSSPETWASSISVPAKTSLVETTDGTLVTTIKMS |
| | | SQAAQGNSTWPAPAEETGSSPAGTSPGSPEMSTTLKIMSSKEPSISPE |
| | | IRSTVRNSPWKTPETTVPMETTVEPVTLQSTALGSGSTSISHLPTGTT |
| | | SPTKSPTENMLATERVSLSPSPPEAWTNLYSGTPGGTRQSLATMSS |
| | | VSLESPTARSITGTGQQSSPELVSKTTGMEFSMWHGSTGGTTGDTH |
| | | VSLSTSSNILEDPVTSPNSVSSLTDKSKHKTETWVSTTAIPSTVLNNK |
| | | IMAAEQQTSRSVDEAYSSTSSWSDQTSGSDITLGASPDVTNTLYITS |
| | | TAQTTSLVSLPSGDQGITSLTNPSGGKTSSASSVTSPSIGLETLRANV |
| | | SAVKSDIAPTAGHLSQTSSPAEVSILDVTTAPTPGISTTITTMGTNSIS |
| | | TTTPNPEVGMSTMDSTPATERRTTSTEHPSTWSSTAASDSWTVTDM |
| | | TSNLKVARSPGTISTMHTTSFLASSTELDSMSTPHGRITVIGTSLVTP |
| | | SSDASAVKTETSTSERTLSPSDTTASTPISTFSRVQRMSISVPDILSTS |
| | | WTPSSTEAEDVPVSMVSTDHASTKTDPNTPLSTFLFDSLSTLDWDT |
| | | GRSLSSATATTSAPQGATTPQELTLETMISPATSQLPFSIGHITSAVTP |
| | | AAMARSSGVTFSRPDPTSKKAEQTSTQLPTTTSAHPGQVPRSAATT |
| | | LDVIPHTAKTPDATFQRQGQTALTTEARATSDSWNEKEKSTPSAPW |
| | | ITEMMNSVSEDTIKEVTSSSSVLRTLNTLDINLESGTTSSPSWKSSPY |
| | | ERIAPSESTTDKEAIHPSTNTVETTGWVTSSEHASHSTIPAHSASSKL |
| | | TSPVVTTSTREQAIVSMSTTTWPESTRARTEPNSFLTIELRDVSPYM |
| | | DTSSTTQTSIISSPGSTAITKGPRTEITSSKRISSSFLAQSMRSSDSPSE |
| | | AITRLSNFPAMTESGGMILAMQTSPPGATSLSAPTLDTSATASWTGT |
| | | PLATTQRFTYSEKTTLFSKGPEDTSQPSPPSVEETSSSSSLVPIHATTS |
| | | PSNILLTSQGHSPSSTPPVTSVFLSETSGLGKTTDMSRISLEPGTSLPP |
| | | NLSSTAGEALSTYEASRDTKAIHHSADTAVTNMEATSSEYSPIPGHT |
| | | KPSKATSPLVTSHEVIGDITSSTSVFGSSETTEIETVSSVNQGLQERSTS |
| | | QVASSATETSTVITHVSSGDATTHVTKTQATFSSGTSISSPHQFITST |
| | | NTFTDVSTNPSTSLIMTESSGVTITTQTGPTGAATQGPYLLDTSTMP |
| | | YLTETPLAVTPDFMQSEKTTLISKGPKDVSWTSPPSVAETSYPSSLT |
| | | PFLVTTIPPATSTLQGQHTSSPVSATSVLTSGLVKTTDMLNTSMEPV |
| | | TNSPQNLNNPSNEILATLAATTDIETIHPSINKAVTNMGTASSAHVL |
| | | HSTLPVSSEPSTATSPMVPASSMGDALASISIPGSETTDIEGEPTSSLT |
| | | AGRKENSTLQEMNSTTESNIILSNVSVGAITEATKMEVPSFDATFIPT |
| | | PAQSTKFPDIFSVASSRLSNSPPMTISTHMTTTQTGSSGATSKIPLAL |
| | | DTSTLETSAGTPSVVTEGFAHSKITTAMNNDVKDVSQTNPPFQDEA |
| | | SSPSSQAPVLVTTLPSSVAFTPQWHSTSSPVSMSSVLTSSLVKTAGK |

TABLE 7-continued

Table of Sequences

| SEQ ID NO | Description | Sequence |
|---|---|---|
| | | VDTSLETVTSSPQSMSNTLDDISVTSAATTDIETTHPSINTVVTNVGT<br>TGSAFESHSTVSAYPEPSKVTSPNVTTSTMEDTTISRSIPKSSKTTRT<br>ETETTSSLTPKLRETSISQEITSSTETSTVPYKELTGATTEVSRTDVTS<br>SSSTSFPGPDQSTVSLDISTETNTRLSTSPEVITESAEITITTQTGPHGAT<br>SQDTFTMDPSNTTPQAGIHSAMTHGFSQLDVTTLMSRIPQDVSWTS<br>PPSVDKTSSPSSFLSSPAMTTPSLISSTLPEDKLSSPMTSLLTSGLVKI<br>TDILRTRLEPVTSSLPNFSSTSDKILATSKDSKDTKEIFPSINTEETNV<br>KANNSGHESHSPALADSETPKATTQMVITTTVGDPAPSTSMPVHGS<br>SETTNIKREPTYFLTPRLRETSTSQESSEPTDTSELLSKVPTGTITEVSS<br>TGVNSSSKISTPDHDKSTVPPDTFTGEIPRVETSSIKTKSAEMTITTQA<br>SPPESASHSTLPLDTSTTLSQGGTHSTVTQGFPYSEVTTLMGMGPGN<br>VSWMTTPPVEETSSVSSLMSSPAMTSPSPVSSTSPQSIPSSPLPVTAL<br>PTSVLVTTTDVLGTTSPESVTSSPPNLSSITHERPATYKDTAHTEAA<br>MHHSTNTAVTNVGTSGSGHKSQSSVLADSETSKATPLMSTTSTLGD<br>TSVSTSTPNISQTNQIQTEPTASLSPRLRESSTSEKTSSTTETNTAFSY<br>VPTGAITQASRTEISSSRTSISDLDRPTIAPDISTGMITRLFTSPEVITKS<br>AEMTVTTQTTTPGATSQGILPWDTSTTLFQGGTHSTVSQGFPHSEIT<br>TLRSRTPGDVSWMTTPPVEETSSGFSLMSPSMTSPSPVSSTSPESIPSS<br>PLPVTALLTSVLVTTTNVLGTTSPEPVTSSPPNLSSPTQERLTTYKDT<br>AHTEAMHASMHTNTAVANVGTSISGHESQSSVPADSHTSKATSPM<br>GITFAMGDTSVSTSTPAFFETRIQTESTSSLIPGLRDTRTSEEINTVTE<br>TSTVLSEVPTTTTTEVSRTEVITSSRTTISGPDHSKMSPYISTETITRLS<br>TFPFVTGSTEMAITNQTGPIGTISQATLTLDTSSTASWEGTHSPVTQR<br>FPHSEETTTMSRSTKGVSWQSPPSVEETSSPSSPVPLPAITSHSSLYS<br>AVSGSSPTSALPVTSLLTSGRRKTIDMLDTHSELVTSSLPSASSFSGEI<br>LTSEASTNTETIHFSENTAETNMGTTNSMHKLHSSVSIHSQPSGHTP<br>PKVTGSMMEDAIVSTSTPGSPETKNVDRDSTSPLTPELKEDSTALV<br>MNSTTESNTVFSSVSLDAATEVSRAEVTYYDPTFMPASAQSTKSPDI<br>SPEASSSHSNSPPLTISTHKTIATQTGPSGVTSLGQLTLDTSTIATSAG<br>TPSARTQDFVDSETTSVMNNDLNDVLKTSPFSAEEANSLSSQAPLL<br>VTTSPSPVTSTLQEHSTSSLVSVTSVPTPTLAKITDMDTNLEPVTRSP<br>QNLRNTLATSEATTDTHTMHPSINTAVANVGTTSSPNEFYFTVSPDS<br>DPYKATSAVVITSTSGDSIVSTSMPRSSAMKKIESETTFSLIFRLRETS<br>TSQKIGSSSDTSTVFDKAFTAATTEVSRTELTSSSRTSIQGTEKPTMS<br>PDTSTRSVTMLSTFAGLTKSEERTIATQTGPHRATSQGTLTWDTSIT<br>TSQAGTHSAMTHGFSQLDLSTLTSRVPEYISGTSPPSVEKTSSSSSLL<br>SLPAITSPSPVPTTLPESRPSSPVHLTSLPTSGLVKTTDMLASVASLPP<br>NLGSTSHKIPTTSEDIKDTEKMYPSTNIAVTNVGTTTSEKESYSSVPA<br>YSEPPKVTSPMVTSFNIRDTIVSTSMPGSSEITRIEMESTFSLAHGLK<br>GTSTSQDPIVSTEKSAVLHKLTTGATETSRTEVASSRRTSIPGPDHST<br>ESPDISTEVIPSLPISLGITESSNMTIITRTGPPLGSTSQGTFTLDTPTTS<br>SRAGTHSMATQEFPHSEMTTVMNKDPEILSWTIPPSIEKTSFSSSLM<br>PSPAMTSPPVSSTLPKTIHTTPSPMTSLLTPSLVMTTDTLGTSPEPTTS<br>SPPNLSSTSHEILTTDEDTTAIEAMHPSTSTAATNVETTSSGHGSQSS<br>VLADSEKTKATAPMDTTSTMGHTTVSTSMSVSSETTKIKRESTYSL<br>TPGLRETSISQNASFSTDTSIVLSEVPTGTTAEVSRTEVTSSGRTSIPG<br>PSQSTVLPEISTRTMTRLFASPTMTESAEMTIPTQTGPSGSTSQDTLT<br>LDTSTTKSQAKTHSTLTQRFPHSEMTTLMSRGPGDMSWQSSPSLEN<br>PSSLPSLLSLPATTSPPPISSTLPVTISSSPLPVTSLLTSSPVTTTDMLHT<br>SPELVTSSPPKLSHTSDERLTTGKDTTNTEAVHPSTNTAASNVEIPSS<br>GHESPSSALADSETSKATSPMFITSTQEDTTVAISTPHFLETSRIQKES<br>ISSLSPKLRETGSSVETSSAIETSAVLSEVSIGATTEISRTEVTSSSRTSI<br>SGSAESTMLPEISTTRKIIKEPTSPILAESSEMTIKTQTSPPGSTSESTFT<br>LDTSTTPSLVITHSTMTQRLPHSEITTLVSRGAGDVPRPSSLPVEETS<br>PPSSQLSLSAMISPSPVSSTLPASSHSSSASVTSLLTPGQVKTTEVLD<br>ASAEPETSSPPSLSSTSVEILATSEVTTDTEKIHPFSNTAVTKVGTSSS<br>GHESPSSVLPDSETTKATSAMGTISIMGDTSVSTLTPALSNTRKIQSE<br>PASSLTTRLRETSTSEETSLATEANTVLSKVSTGATTEVSRTEAISFS<br>RTSMSGPEQSTMSQDISIGTIPRISASSVLTESAKMTITTQTGPSESTL<br>ESTLNLNTATTPSWVETHSIVIQGFPHPEMTTSMGRGPGGVSWPSPP<br>FVKETSPPSSPLSLPAVTSPHPVSTTFLAHIPPSPLPVTSLLTSGPATTT<br>DILGTSTEPGTSSSSSLSTTSHERLTTYKDTAHTEAVHPSTNTGGTN<br>VATTSSGYKSQSSVLADSSPMCTTSTMGDTSVLTSTPAFLETRRIQT<br>ELASSLTPGLRESSGSEGTSSGTKMSTVLSKVPTGATTEISKEDVTSI<br>PGPAQSTISPDISTRTVSWFSTSPVMTESAEITMNTHTSPLGATTQGT<br>STLDTSTTSLTMTHSTISQGFSHSQMSTLMRRGPEDVSWMSPPLLE<br>KTRPSFSLMSSPATTSPSPVSSTLPESISSSPLPVTSLLTSGLAKTTDM<br>LHKSSEPVTNSPANLSSTSVEILATSEVTTDTEKTHPSSNRTVTDVG<br>TSSSGHESTSFVLADSQTSKVTSPMVITSTMEDTSVSTSTPGFFETSR<br>IQTEPTSSSLTLGLRKTSSSEGTSLATEMSTVLSGVPTGATAEVSRTEV<br>TSSSRTSISGFAQLTVSPETSTETITRLPTSSIMTESAEMMIKTQTDPP<br>GSTPESTHTVDISTTPNWVETHSTVTQRFSHSEMTTLVSRSPGDML<br>WPSQSSVEETSSASSLLSLPATTSPSPVSSTLVEDFPSASLPVTSLLNP<br>GLVITTDRMGISREPGTSSTSNLSSTSHERLTTLEDTVDTEDMQPST |

TABLE 7-continued

Table of Sequences

| SEQ ID NO | Description | Sequence |
|---|---|---|

HTAVTNVRTSISGHESQSSVLSDSETPKATSPMGTTYTMGETSVSIS
TSDFFETSRIQIEPTSSLTSGLRETSSSERISSATEGSTVLSEVPSGATT
EVSRTEVISSRGTSMSGPDQFTISPDISTEAITRLSTSPIMTESAESAITI
ETGSPGATSEGTLTLDTSTTTFWSGTHSTASPGFSHSEMTTLMSRTP
GDVPWPSLPSVEEASSVSSSLSSPAMTSTSFFSTLPESISSSPHPVTAL
LTLGPVKTTDMLRTSSEPETSSPPNLSSTSAEILATSEVTKDREKIHP
SSNTPVVNVGTVIYKHLSPSSVLADLVTTKPTSPMATTSTLGNTSVS
TSTPAFPETMMTQPTSSLTSGLREISTSQETSSATERSASLSGMPTGA
TTKVSRTEALSLGRTSTPGPAQSTISPEISTETITRISTPLTTTGSAEMT
ITPKTGHSGASSQGTFTLDTSSRASWPGTHSAATHRSPHSGMTTPM
SRGPEDVSWPSRPSVEKTSPPSSLVSLSAVTSPSPLYSTPSESSHSSPL
RVTSLFTPVMMKTTDMLDTSLEPVTTSPPSMNITSDESLATSKATM
ETEAIQLSENTAVTQMGTISARQEFYSSYPGLPEPSKVTSPVVTSSTI
KDIVSTTIPASSEITRIEMESTSTLTPTPRETSTSQEIHSATKPSTVPYK
ALTSATIEDSMTQVMSSSRGPSPDQSTMSQDISTEVITRLSTSPIKTES
TEMTITTQTGSPGATSRGTLTLDTSTTFMSGTHSTASQGFSHSQMTA
LMSRTPGDVPWLSHPSVEEASSASFSLSSPVMTSSSPVSSTLPDSIES
SSLPVTSLLTSGLVKTTELLGTSSEPETSSPPNLSSTSAEILAITEVTTD
TEKLEMTNVVTSGYTHESPSSVLADSVTTKATSSMGITYPTGDTNV
LTSTPAFSDTSRIQTKSKLSLTPGLMETSISEETSSATEKSTVLSSVPT
GATTEVSRTEAISSSRTSIPGPAQSTMSSDTSMETITRISTPLTRKEST
DMAITPKTGPSGATSQGTFTLDSSSTASWPGTHSATTQRFPQSVVTT
PMSRGPEDVSWPSPLSVEKNSPPSSLVSSSSVTSPSPLYSTPSGSSHSS
PVPVTSLFTSINIMKATDMLDASLEPETTSAPNMNITSDESLAASKAT
TETEAIHVFENTAASHVETTSATEELYSSSPGFSEPTKVISPVVTSSSI
RDNMVSTTMPGSSGITRIEIESMSSLTPGLRETRTSQDITSSTETSTVL
YKMPSGATPEVSRTEVMPSSRTSIPGPAQSTMSLDISDEVVTRLSTS
PIMTESAEITITTQTGYSLATSQVTLPLGTSMTELSGTHSTMSQGLSH
SEMTNLMSRGPESLSWTSPRFVETTRSSSSLTSLPLTTSLSPVSSTLL
DSSPSSPLPVTSLILPGLVKTTEVLDTSSEPKTSSSPNLSSTSVEIPATS
EEVITDTEKIHPSSNTAVAKVRTSSSVHESHSSVLADSETTITIPSMGIT
SAVDDTTVFTSNPAFSETRRIPTEPTESLTPGFRETSTSEETTSITETSA
VLYGVPTSATTEVSMTEIMSSNRIHIPDSDQSTMSPDIITEVITRLSSS
SMMSESTQMTITTQKSSPGATAQSTLTLATTTAPLARTHSTVPPRFL
HSEMTTLMSRSPENPSWKSSLFVEKTSSSSSLLSLPVTTSPSVSSTLP
QSIPSSSFSVTSLLTPGMVKTTDTSTEPGTSLSPNLSGTSVEILAASEV
TTDTEKIHPSSSMAVTNVGTTSSGHELYSSVSIHSEPSKATYPVGTPS
SMAETSISTSMPANFETTGFEAEPFSHLTSGERKTNMSLDTSSVTPT
NTPSSPGSTHLLQSSKTDFTSSAKTSSPDWPPASQYTEIPVDIITPFNA
SPSITESTGITSFPESRFTMSVTESTHHLSTDLLPSAETISTGTVMPSLS
EAMTSFATTGVPRAISGSGSPFSRTESGPGDATLSTIAESLPSSTPVPF
SSSTFTTTDSSTIPALHEITSSSATPYRVDTSLGTESSTTEGRLVMVST
LDTSSQPGRTSSSPILDTRMTESVELGTVTSAYQVPSLSTRLTRTDGI
MEHITKIPNEAAHRGTIRPVKGPQTSTSPASPKGLHTGGTKRMETTT
TALKTTTTALKTTSRATLTTSVYTPTLGTLTPLNASMQMASTIPTEM
MITTPYVFPDVPETTSSLATSLGAETSTALPRTTPSVFNRESETTASL
VSRSGAERSPVIQTLDVSSSEPDTTASWVIHPAETIPTVSKTTPNFFH
SELDTVSSTATSHGADVSSAIPTNISPSELDALTPLVTISGTDTSTTFP
TLTKSPHETETRTTWLTHPAETSSTIPRTIPNFSHHESDATPSIATSPG
AETSSAIPIMTVSPGAEDLVTSQVTSSGTDRNMTIPTLTLSPGEPKTI
ASLVTHPEAQTSSAIPTSTISPAVSRLVTSMVTSLAAKTSTTNRALTN
SPGEPATTVSLVTHPAQTSPTVPWTTSIFFHSKSDTTPSMTTSHGAES
SSAVPTPTVSTEVPGVVTPLVTSSRAVISTTIPILTLSPGEPETTPSMA
TSHGEEASSAIPTPTVSPGVPGVVTSLVTSSRAVTSTTIPILTFSLGEP
ETTPSMATSHGTEAGSAVPTVLPEVPGMVTSLVASSRAVTSTTLPT
LTLSPGEPETTPSMATSHGAEASSTVPTVSPEVPGVVTSLVTSSSGV
NSTSIPTLILSPGELETTPSMATSHGAEASSAVPTPTVSPGVSGVVTP
LVTSSRAVTSTTIPILTLSSSEPETTPSMATSHGVEASSAVLTVSPEVP
GMVTSLVTSSRAVTSTTIPTLTISSDEPETTTSLVTHSEAKMISAIPTL
AVSPTVQGLVTSLVTSSGSETSAFSNLTVASSQPETIDSWVAHPGTE
ASSVVPTLTVSTGEPFTNISLVTHPAESSSTLPRTTSRFSHSELDTMPS
TVTSPEAESSSAISTTISPGIPGVLTSLVTSSGRDISATEPTVPESPHES
EATASWVTHPAVTSTTVPRTTPNYSHSEPDTTPSIATSPGAEATSDF
PTITVSPDVPDMVTSQVTSSGTDTSITIPTLTLSSGEPETTTSFITYSET
HTSSAIPTLPVSPGASKMLTSLVISSGTDSTTTFPTLTETPYEPETTAI
QLIHPAETNTMVPRTTPKESHSKSDTTLPVAITSPGPEASSAVSTTTIS
PDMSDLVTSLVPSSGTDTSTTFPTLSETPYEPETTATWLTHPAETSTT
VSGTIPNFSHRGSDTAPSMVTSPGVDTRSGVPTTTIPPSIPGVVTSQV
TSSATDTSTAIPTLTPSPGEPETTASSATHPGTQTGFTVPIRTVPSSEP
DTMASWVTHPPQTSTPVSRTTSSFSHSSPDATPVMATSPRTEASSAV
LTTISPGAPEMVTSQITSSGAATSTTVPTLTHSPGMPETTALLSTHPR
TETSKTFPASTVFPQVSETTASLTIRPGAETSTALPTQTTSSLFTLLVT
GTSRVDLSPTASPGVSAKTAPLSTHPGTETSTMIPTSTLSLGLLETTG
LLATSSSAETSTSTLTLTVSPAVSGLSSASITTDKPQTVTSWNTETSP

TABLE 7-continued

Table of Sequences

| SEQ ID NO | Description | Sequence |
|---|---|---|
| | | SVTSVGPPEFSRTVTGTTMTLIPSEMPTPPKTSHGEGVSPTTILRTTM VEATNLATTGSSPTVAKTTTTFNTLAGSLFTPLTTPGMSTLASESVT SRTSYNHRSWISTTSSYNRRYWTPATSTPVTSTFSPGISTSSIPSSTAA TVPFMVPFTLNFTITNLQYEEDMRHPGSRKFNATERELQGLLKPLF RNSSLEYLYSGCRLASLRPEKDSSATAVDAICTHRPDPEDLGLDRER LYWELSNLTNGIQELGPYTLDRNSLYVNGFTHRSSMPTTSTPGTST VDVGTSGTPSSSPSPTTAGPLLMPFTLNFTITNLQYEEDMRRTGSRK FNTMESVLQGLLKPLFKNTSVGPLYSGCRLTLLRPEKDGAATGVD AICTHRLDPKSPGLNREQLYWELSKLTNDIEELGPYTLDRNSLYVN GFTHQSSVSTTSTPGTSTVDLRTSGTPSSLSSPTIMAAGPLLVPFTLN FTITNLQYGEDMGHPGSRKFNTTERVLQGLLGPIFKNTSVGPLYSG CRLTSLRSEKDGAATGVDAICIHEILDPKSPGLNRERLYWELSQLTN GIKELGPYTLDRNSLYVNGFTHRTSVPTSSTPGTSTVDLGTSGTPFS LPSPATAGPLLVLFTLNFTITNLKYEEDMHRPGSRKFNTTERVLQTL LGPMFKNTSVGLLYSGCRLTLLRSEKDGAATGVDAICTHRLDPKSP GVDREQLYWELSQLTNGIKELGPYTLDRNSLYVNGFTHWIPVPTSS TPGTSTVDLGSGTPSSLPSPTTAGPLLVPFTLNFTITNLKYEEDMHCP GSRKFNTTERVLQSLLGPMFKNTSVGPLYSGCRLTLLRSEKDGAAT GVDAICTHRLDPKSPGVDREQLYWELSQLTNGIKELGPYTLDRNSL YVNGFTHQTSAPNTSTPGTSTVDLGTSGTPSSLPSPTSAGPLLVPFTL NFTITNLQYEEDMHHPGSRKFNTTERVLQGLLGPMFKNTSVGLLYS GCRLTLLRPEKNGAATGMDAICSHRLDPKSPGLNREQLYWELSQL THGIKELGPYTLDRNSLYVNGFTHRSSVAPTSTPGTSTVDLGTSGTP SSLPSPTTAVPLLVPFTLNFTITNLQYGEDMRHPGSRKFNTTERVLQ GLLGPLFKNSSVGPLYSGCRLISLRSEKDGAATGVDAICTHHLNPQS PGLDREQLYWQLSQMTNGIKELGPYTLDRNSLYVNGFTHRSSGLT TSTPWTSTVDLGTSGTPSPVPSPTTTGPLLVPFTLNFTITNLQYEENM GHPGSRKFNITESVLQGLLKPLFKSTSVGPLYSGCRLTLLRPEKDGV ATRVDAICTHRPDPKIPGLDRQQLYWELSQLTHSITELGPYTLDRDS LYVNGFTQRSSVPTTSTPGTFTVQPETSETPSSLPGPTATGPVLLPFT LNFTITNLQYEEDMRRPGSRKFNTTERVLQGLLMPLFKNTSVSSLY SGCRLTLLRPEKDGAATRVDAVCTHRPDPKSPGLDRERLYWKLSQ LTHGITELGPYTLDRHSLYVNGFTHQSSMTTTRTPDTSTMHLATSR TPASLSGPMTASPLLVLFTINFTITNLRYEENMHHPGSRKFNTTERV LQGLLRPVFKNTSVGPLYSGCRLTLLRPKKDGAATKVDAICTYRPD PKSPGLDREQLYWELSQLTHSITELGPYTLDRDSLYVNGFTQRSSVP TTSIPGTPTVDLGTSGTPVSKPGPSAASPLLVLFTLNFTITNLRYEEN MQHPGSRKFNTTERVLQGLLRSLFKSTSVGPLYSGCRLTLLRPEKD GTATGVDAICTHHPDPKSPRLDREQLYWELSQLTHNITELGPYALD NDSLFVNGFTHRSSVSTTSTPGTPTVYLGASKTPASIFGPSAASHLLI LFTLNFTITNLRYEENMWPGSRKFNTTERVLQGLLRPLFKNTSVGP LYSGCRLTLLRPEKDGEATGVDAICTHRPDPTGPGLDREQLYLELS QLTHSITELGPYTLDRDSLYVNGFTHRSSVPTTSTGVVSEEPFTLNFT INNLRYMADMGQPGSLKFNITDNVMQHLLSPLFQRSSLGARYTGC RVIALRSVKNGAETRVDLLCTYLQPLSGPGLPIKQVFHELSQQTHGI TRLGPYSLDKDSLYLNGYNEPGPDEPPTTPKPATTFLPPLSEATTAM GYHLKTLTLNFTISNLQYSPDMGKGSATFNSTEGVLQHLLRPLFQK SSMGPFYLGCQLISLRPEKDGAATGVDTTCTYHPDPVGPGLDIQQL YWELSQLTHGVTQLGFYVLDRDSLFINGYAPQNLSIRGEYQINFHIV NWNLSNPDPTSSEYITLLRDIQDKVTTLYKGSQLHDTFRFCLVTNLT MDSVLVTVKALFSSNLDPSLVEQVFLDKTLNASFHWLGSTYQLVDI HVTEMESSVYQPTSSSSTQHFYLNFTITNLPYSQDKAQPGTTNYQR NKRNIEDALNQLFRNSSIKSYFSDCQVSTFRSVPNRHHTGVDSLCNF SPLARRVDRVAIYEEFLRMTRNGTQLQNFTLDRSSVLVDGYSPNRN EPLTGNSDLPFWAVILIGLAGLLGVITCLICGVLVTTRRRKKEGEYN VQQQCPGYYQSHLDLEDLQ |
| 52 | MUC16 peptide-2 | TLDRSSVLVDGYSPNRNE |
| 53 | 4H11 L1H1- scFv | DIELTQSPSSLAVSAGERVTMNCKSSQSLLNSRTRKNQLAWYQQKP GQSPELLIYWASTRQSGVPDRFSGSGSGTDFTLTISSVQAEDVAVYY CQQSYNLLTFGPGTKLEIKRGGGGSGGGGSGGGGSEVKLQESGGG FVKPGGSLRVSCAASGFTFSSYAMSWVRLAPEMRLEWVATISSAG GYIFYSDSVQGRFTISRDNAKNSLHLQMGSLRSGDTAMYYCARQG FGNYGDYYAMDYWGQGTTVTVSS |
| 54 | 4H11 L2H1- scFv | DIVLTQSPDSLAVSLGERVTMNCKSSQSLLNSRTRKNQLAWYQQK PGQSPELLIYWASTRQSGVPDRFSGSGSGTDFTLTISSVQAEDVAVY YCQQSYNLLTFGQGTKLEIKRGGGGSGGGGSGGGGSEVKLQESGG GFVKPGGSLRVSCAASGFTFSSYAMSWVRLAPEMRLEWVATISSA GGYIFYSDSVQGRFTISRDNAKNSLHLQMGSLRSGDTAMYYCARQ GFGNYGDYYAMDYWGQGTTVTVSS |

TABLE 7-continued

Table of Sequences

| SEQ ID NO | Description | Sequence |
|---|---|---|
| 55 | 4H11 L1H2-scFv | DIELTQSPSSLAVSAGERVTMNCKSSQSLLNSRTRKNQLAWYQQKP<br>GQSPELLIYWASTRQSGVPDRFSGSGSGTDFTLTISSVQAEDVAVYY<br>CQQSYNLLTFGPGTKLEIKRGGGGSGGGGSGGGGSEVQLVESGGG<br>LVKPGGSLRVSCAASGFTFSSYAMSWVRLAPGKGLEWVATISSAG<br>GYIFYSDSVQGRFTISRDNAKNSLYLQMNSLRAEDTAMYYCARQG<br>FGNYGDYYAMDYWGQGTLVTVSS |
| 56 | 4H11 L2H2-scFv | DIVLTQSPDSLAVSLGERVTMNCKSSQSLLNSRTRKNQLAWYQQK<br>PGQSPELLIYWASTRQSGVPDRFSGSGSGTDFTLTISSVQAEDVAVY<br>YCQQSYNLLTFGQGTKLEIKRGGGGSGGGGSGGGGSEVQLVESGG<br>GLVKPGGSLRVSCAASGFTFSSYAMSWVRLAPGKGLEWVATISSA<br>GGYIFYSDSVQGRFTISRDNAKNSLYLQMNSLRAEDTAMYYCARQ<br>GFGNYGDYYAMDYWGQGTLVTVSS |
| 57 | 18C6 L1H1-scFv | DIVMTQSAPSVPVTPGESVSISCRSSKSLLHSNGNTYLYWFLQKPGQ<br>SPQRLIYYMSNLASGVPDRFSGRGSGTDFTLKISRVEAEDVGVYYC<br>MQSLEYPLTFGGGTKLEIKRGGGGSGGGGSGGGGSQVTLKESGPGI<br>LQPTQTLTLTCTFSGFSLSTVGMGVGWSRQPSGKGLEWLAHIWWD<br>DEDKYYNPALKSRLTITKDTSKNQVFLKITNVDTADTATYYCTRIG<br>TAQATDALDYWGQGTLVTVSS |
| 58 | 18C6 L2H1-scFv | DIVMTQSALSLPVTPGEPVSISCRSSKSLLHSNGNTYLYWFLQKPGQ<br>SPQRLIYYMSNLASGVPDRFSGSGSGTDFTLKISRVEAEDVGVYYC<br>MQSLEYPLTFGGGTKLEIKRGGGGSGGGGSGGGGSQVTLKESGPGI<br>LQPTQTLTLTCTFSGFSLSTVGMGVGWSRQPSGKGLEWLAHIWWD<br>DEDKYYNPALKSRLTITKDTSKNQVFLKITNVDTADTATYYCTRIG<br>TAQATDALDYWGQGTLVTVSS |
| 59 | 18C6 L1H2-scFv | DIVMTQSAPSVPVTPGESVSISCRSSKSLLHSNGNTYLYWFLQKPGQ<br>SPQRLIYYMSNLASGVPDRFSGRGSGTDFTLKISRVEAEDVGVYYC<br>MQSLEYPLTFGGGTKLEIKRGGGGSGGGGSGGGGSQVTLKESGPTL<br>VKPTQTLTLTCTFSGFSLSTVGMGVGWSRQPSGKGLEWLAHIWWD<br>DEDKYYNPALKSRLTITKDTSKNQVVLTITNVDPVDTATYYCTRIG<br>TAQATDALDYWGQGTLVTVSS |
| 60 | 18C6 L2H2-scFv | DIVMTQSALSLPVTPGEPVSISCRSSKSLLHSNGNTYLYWFLQKPGQ<br>SPQRLIYYMSNLASGVPDRFSGSGSGTDFTLKISRVEAEDVGVYYC<br>MQSLEYPLTFGGGTKLEIKRGGGGSGGGGSGGGGSQVTLKESGPTL<br>VKPTQTLTLTCTFSGFSLSTVGMGVGWSRQPSGKGLEWLAHIWWD<br>DEDKYYNPALKSRLTITKDTSKNQVVLTITNVDPVDTATYYCTRIG<br>TAQATDALDYWGQGTLVTVSS |
| 61 | 4H11 H1L1-scFv | EVKLQESGGGFVKPGGSLRVSCAASGFTFSSYAMSWVRLAPEMRL<br>EWVATISSAGGYIFYSDSVQGRFTISRDNAKNSLHLQMGSLRSGDT<br>AMYYCARQGFGNYGDYYAMDYWGQGTTVTVSSGGGGSGGGGS<br>GGGGSDIELTQSPSSLAVSAGERVTMNCKSSQSLLNSRTRKNQLAW<br>YQQKPGQSPELLIYWASTRQSGVPDRFSGSGSGTDFTLTISSVQAED<br>VAVYYCQQSYNLLTFGPGTKLEIKR |
| 62 | 4H11 H1L2-scFv | EVKLQESGGGFVKPGGSLRVSCAASGFTFSSYAMSWVRLAPEMRL<br>EWVATISSAGGYIFYSDSVQGRFTISRDNAKNSLHLQMGSLRSGDT<br>AMYYCARQGFGNYGDYYAMDYWGQGTTVTVSSGGGGSGGGGS<br>GGGGSDIVLTQSPDSLAVSLGERVTMNCKSSQSLLNSRTRKNQLA<br>WYQQKPGQSPELLIYWASTRQSGVPDRFSGSGSGTDFTLTISSVQA<br>EDVAVYYCQQSYNLLTFGQGTKLEIKR |
| 63 | 4H11 H2L1-scFv | EVQLVESGGGLVKPGGSLRVSCAASGFTFSSYAMSWVRLAPGKGL<br>EWVATISSAGGYIFYSDSVQGRFTISRDNAKNSLYLQMNSLRAEDT<br>AMYYCARQGFGNYGDYYAMDYWGQGTLVTVSSGGGGSGGGGS<br>GGGGSDIELTQSPSSLAVSAGERVTMNCKSSQSLLNSRTRKNQLAW<br>YQQKPGQSPELLIYWASTRQSGVPDRFSGSGSGTDFTLTISSVQAED<br>VAVYYCQQSYNLLTFGPGTKLEIKR |
| 64 | 4H11 H2L2-scFv | EVQLVESGGGLVKPGGSLRVSCAASGFTFSSYAMSWVRLAPGKGL<br>EWVATISSAGGYIFYSDSVQGRFTISRDNAKNSLYLQMNSLRAEDT<br>AMYYCARQGFGNYGDYYAMDYWGQGTLVTVSSGGGGSGGGGS<br>GGGGSDIVLTQSPDSLAVSLGERVTMNCKSSQSLLNSRTRKNQLA<br>WYQQKPGQSPELLIYWASTRQSGVPDRFSGSGSGTDFTLTISSVQA<br>EDVAVYYCQQSYNLLTFGQGTKLEIKR |
| 65 | 18C6 H1L1-scFv | QVTLKESGPGILQPTQTLTLTCTFSGFSLSTVGMGVGWSRQPSGKG<br>LEWLAHIWWDDEDKYYNPALKSRLTITKDTSKNQVFLKITNVDTA<br>DTATYYCTRIGTAQATDALDYWGQGTLVTVSSGGGGSGGGGSGG<br>GGSDIVMTQSAPSVPVTPGESVSISCRSSKSLLHSNGNTYLYWFLQK |

TABLE 7-continued

Table of Sequences

| SEQ ID NO | Description | Sequence |
|---|---|---|
| | | PGQSPQRLIYYMSNLASGVPDRFSGRGSGTDFTLKISRVEAEDVGV<br>YYCMQSLEYPLTFGGGTKLEIKR |
| 66 | 18C6<br>H1L2-scFv | QVTLKESGPGILQPTQTLTLTCTFSGFSLSTVGMGVGWSRQPSGKG<br>LEWLAHIWWDDEDKYYNPALKSRLTITKDTSKNQVFLKITNVDTA<br>DTATYYCTRIGTAQATDALDYWGQGTLVTVSSGGGGSGGGGSGG<br>GGSDIVMTQSALSLPVTPGEPVSISCRSSKSLLHSNGNTYLYWFLQK<br>PGQSPQRLIYYMSNLASGVPDRFSGSGSGTDFTLKISRVEAEDVGV<br>YYCMQSLEYPLTFGGGTKLEIKR |
| 67 | 18C6<br>H2L1-scFv | QVTLKESGPTLVKPTQTLTLTCTFSGFSLSTVGMGVGWSRQPSGKG<br>LEWLAHIWWDDEDKYYNPALKSRLTITKDTSKNQVVLTITNVDPV<br>DTATYYCTRIGTAQATDALDYWGQGTLVTVSSGGGGSGGGGSGG<br>GGSDIVMTQSAPSVPVTPGESVSISCRSSKSLLHSNGNTYLYWFLQK<br>PGQSPQRLIYYMSNLASGVPDRFSGRGSGTDFTLKISRVEAEDVGV<br>YYCMQSLEYPLTFGGGTKLEIKR |
| 68 | 18C6<br>H2L2-scFv | QVTLKESGPTLVKPTQTLTLTCTFSGFSLSTVGMGVGWSRQPSGKG<br>LEWLAHIWWDDEDKYYNPALKSRLTITKDTSKNQVVLTITNVDPV<br>DTATYYCTRIGTAQATDALDYWGQGTLVTVSSGGGGSGGGGSGG<br>GGSDIVMTQSALSLPVTPGEPVSISCRSSKSLLHSNGNTYLYWFLQK<br>PGQSPQRLIYYMSNLASGVPDRFSGSGSGTDFTLKISRVEAEDVGV<br>YYCMQSLEYPLTFGGGTKLEIKR |
| 69 | 4H11 L2H1-<br>BsAB | MGWSCIILFLVATATGKLDIVLTQSPDSLAVSLGERVTMNCKSSQS<br>LLNSRTRKNQLAWYQQKPGQSPELLIYWASTRQSGVPDRFSGSGS<br>GTDFTLTISSVQAEDVAVYYCQQSYNLLTFGQGTKLEIKRGGGGSG<br>GGGSGGGGSEVKLQESGGGFVKPGGSLRVSCAASGFTFSSYAMSW<br>VRLAPEMRLEWVATISSAGGYIFYSDSVQGRFTISRDNAKNSLHLQ<br>MGSLRSGDTAMYYCARQGFGNYGDYYAMDYWGQGTTVTVSSTS<br>GGGGSDVQLVQSGAEVKKPGASVKVSCKASGYTFTRYTMHWVRQ<br>APGQGLEWIGYINPSRGYTNYADSVKGRFTITTDKSTSTAYMELSS<br>LRSEDTATYYCARYYDDHYCLDYWGQGTTVTVSSGEGTSTGSGGS<br>GGSGGADDIVLTQSPATLSLSPGERATLSCRASQSVSYMNWYQQK<br>PGKAPKRWIYDTSKVASGVPARFSGSGSGTDYSLTINSLEAEDAAT<br>YYCQQWSSNPLTFGGGTKVEIKHHHHHH |
| 70 | 4H11 L1H2-<br>BsAB | MGWSCIILFLVATATGKLDIELTQSPSSLAVSAGERVTMNCKSSQSL<br>LNSRTRKNQLAWYQQKPGQSPELLIYWASTRQSGVPDRFSGSGSG<br>TDFTLTISSVQAEDVAVYYCQQSYNLLTFGPGTKLEIKRGGGGSGG<br>GGSGGGGSEVQLVESGGGLVKPGGSLRVSCAASGFTFSSYAMSWV<br>RLAPGKGLEWVATISSAGGYIFYSDSVQGRFTISRDNAKNSLYLQM<br>NSLRAEDTAMYYCARQGFGNYGDYYAMDYWGQGTLVTVSS<br>TSGGGGSDVQLVQSGAEVKKPGASVKVSCKASGYTFTRYTMHWV<br>RQAPGQGLEWIGYINPSRGYTNYADSVKGRFTITTDKSTSTAYMEL<br>SSLRSEDTATYYCARYYDDHYCLDYWGQGTTVTVSSGEGTSTGSG<br>GSGGSGGADDIVLTQSPATLSLSPGERATLSCRASQSVSYMNWYQ<br>QKPGKAPKRWIYDTSKVASGVPARFSGSGSGTDYSLTINSLEAEDA<br>ATYYCQQWSSNPLTFGGGTKVEIKHHHHHH |
| 71 | 4H11 L2H2-<br>BsAB | MGWSCIILFLVATATGKLDIVLTQSPDSLAVSLGERVTMNCKSSQS<br>LLNSRTRKNQLAWYQQKPGQSPELLIYWASTRQSGVPDRFSGSGS<br>GTDFTLTISSVQAEDVAVYYCQQSYNLLTFGQGTKLEIKR<br>GGGGSGGGGSGGGGSEVQLVESGGGLVKPGGSLRVSCAASGFTFS<br>SYAMSWVRLAPGKGLEWVATISSAGGYIFYSDSVQGRFTISRDNAK<br>NSLYLQMNSLRAEDTAMYYCARQGFGNYGDYYAMDYWGQGTL<br>VTVSSTSGGGGSDVQLVQSGAEVKKPGASVKVSCKASGYTFTRYT<br>MIHWVRQAPGQGLEWIGYINPSRGYTNYADSVKGRFTITTDKSTST<br>AYMELSSLRSEDTATYYCARYYDDHYCLDYWGQGTTVTVSSGEG<br>TSTGSGGSGGSGGADDIVLTQSPATLSLSPGERATLSCRASQSVSYM<br>NWYQQKPGKAPKRWIYDTSKVASGVPARFSGSGSGTDYSLTINSLE<br>AEDAATYYCQQWSSNPLTFGGGTKVEIKHHHHHH |
| 72 | 18C6<br>L1H1-BsAB | MGWSCIILFLVATATGKLDIVMTQSAPSVPVTPGESVSISCRSSKSLL<br>HSNGNTYLYWFLQKPGQSPQRLIYYMSNLASGVPDRFSGRGSGTD<br>FTLKISRVEAEDVGVYYCMQSLEYPLTFGGGTKLEIKRGGGGSGGGG<br>GSGGGGGSQVTLKESGPGILQPTQTLTLTCTFSGFSLSTVGMGVGWS<br>RQPSGKGLEWLAHIWWDDEDKYYNPALKSRLTITKDTSKNQVFLK<br>ITNVDTADTATYYCTRIGTAQATDALDYWGQGTLVTVSSTSGGGG<br>SDVQLVQSGAEVKKPGASVKVSCKASGYTFTRYTMHWVRQAPGQ<br>GLEWIGYINPSRGYTNYADSVKGRFTITTDKSTSTAYMELSSLRSED<br>TATYYCARYYDDHYCLDYWGQGTTVTVSSGEGTSTGSGGSGGSG |

TABLE 7-continued

| | | Table of Sequences |
|---|---|---|
| SEQ ID NO | Description | Sequence |

| SEQ ID NO | Description | Sequence |
|---|---|---|
| | | GADDIVLTQSPATLSLSPGERATLSCRASQSVSYMNWYQQKPGKA PKRWIYDTSKVASGVPARFSGSGSGTDYSLTINSLEAEDAATYYCQ QWSSNPLTFGGGTKVEIKHHHHHH |
| 73 | 18C6 L2H1-BsAB | MGWSCIILFLVATATGKLDIVMTQSALSLPVTPGEPVSISCRSSKSLL HSNGNTYLYWFLQKPGQSPQRLIYYMSNLASGVPDRFSGSGSGTDF TLKISRVEAEDVGVYYCMQSLEYPLTFGGGTKLEIKRGGGGSGGG GSGGGGSQVTLKESGPGILQPTQTLTLTCTFSGFSLSTVGMGVGWS RQPSGKGLEWLAHIWWDDEDKYYNPALKSRLTITKDTSKNQVFLK ITNVDTADTATYYCTRIGTAQATDALDYWGQGTLVTVSSTSGGGG SDVQLVQSGAEVKKPGASVKVSCKASGYTFTRYTMHWVRQAPGQ GLEWIGYINPSRGYTNYADSVKGRFTITTDKSTSTAYMELSSLRSED TATYYCARYYDDHYCLDYWGQGTTVTVSSGEGTSTGSGGSGGSG GADDIVLTQSPATLSLSPGERATLSCRASQSVSYMNWYQQKPGKA PKRWIYDTSKVASGVPARFSGSGSGTDYSLTINSLEAEDAATYYCQ QWSSNPLTFGGGTKVEIKHHHHHH |
| 74 | 18C6 L1H2-BsAB | MGWSCIILFLVATATGKLDIVMTQSAPSVPVTPGESVSISCRSSKSLL HSNGNTYLYWFLQKPGQSPQRLIYYMSNLASGVPDRFSGRGSGTD FTLKISRVEAEDVGVYYCMQSLEYPLTFGGGTKLEIKRGGGGSGGG GSGGGGSQVTLKESGPTLVKPTQTLTLTCTFSGFSLSTVGMGVGWS RQPSGKGLEWLAHIWWDDEDKYYNPALKSRLTITKDTSKNQVVLT ITNVDPVDTATYYCTRIGTAQATDALDYWGQGTLVTVSSTSGGGG SDVQLVQSGAEVKKPGASVKVSCKASGYTFTRYTMHWVRQAPGQ GLEWIGYINPSRGYTNYADSVKGRFTITTDKSTSTAYMELSSLRSED TATYYCARYYDDHYCLDYWGQGTTVTVSSGEGTSTGSGGSGGSG GADDIVLTQSPATLSLSPGERATLSCRASQSVSYMNWYQQKPGKA PKRWIYDTSKVASGVPARFSGSGSGTDYSLTINSLEAEDAATYYCQ QWSSNPLTFGGGTKVEIKHHHHHH |
| 75 | 18C6 L2H2-BsAB | MGWSCIILFLVATATGKLDIVMTQSALSLPVTPGEPVSISCRSSKSLL HSNGNTYLYWFLQKPGQSPQRLIYYMSNLASGVPDRFSGSGSGTDF TLKISRVEAEDVGVYYCMQSLEYPLTFGGGTKLEIKRGGGGSGGG GSGGGGSQVTLKESGPTLVKPTQTLTLTCTFSGFSLSTVGMGVGWS RQPSGKGLEWLAHIWWDDEDKYYNPALKSRLTITKDTSKNQVVLT ITNVDPVDTATYYCTRIGTAQATDALDYWGQGTLVTVSSTSGGGG SDVQLVQSGAEVKKPGASVKVSCKASGYTFTRYTMHWVRQAPGQ GLEWIGYINPSRGYTNYADSVKGRFTITTDKSTSTAYMELSSLRSED TATYYCARYYDDHYCLDYWGQGTTVTVSSGEGTSTGSGGSGGSG GADDIVLTQSPATLSLSPGERATLSCRASQSVSYMNWYQQKPGKA PKRWIYDTSKVASGVPARFSGSGSGTDYSLTINSLEAEDAATYYCQ QWSSNPLTFGGGTKVEIKHHHHHH |
| 76 | CD8 signal sequence | MALPVTALLLPLALLLHA |
| 77 | CD8 transmembrane sequence | PTTTPAPRPPTPAPTIASQPLSLRPEACRPAAGGAVHTRGLDFACDIY IWAPLAGTCGVLLLSLVITLYCN |
| 78 | 41BB costimulatory domain | KRGRKKLLYIFKQPFMRPVQTTQEEDGCSCRFPEEEEGGCEL |
| 79 | CD3 zeta chain | RVKFSRSADAPAYQQGQNQLYNELNLGRREEYDVLDKRRGRDPE MGGKPRRKNPQEGLYNELQKDKMAEAYSEIGMKGERRRGKGHD GLYQGLSTATKDTYDALHMQALPPR |
| 80 | 4H11 H1L1-CAR | MALPVTALLLPLALLLHADIELTQSPSSLAVSAGERVTMNCKSSQS LLNSRTRKNQLAWYQQKPGQSPELLIYWASTRQSGVPDRFSGSGS GTDFTLTISSVQAEDVAVYYCQQSYNLLTFGPGTKLEIKRGGGGSG GGGSGGGGSEVKLQESGGGFVKPGGSLRVSCAASGFTFSSYAMSW VRLAPEMRLEWVATISSAGGYIFYSDSVQGRFTISRDNAKNSLHLQ MGSLRSGDTAMYYCARQGFGNYGDYYAMDYWGQGTTVTVSSAA APTTTPAPRPPTPAPTIASQPLSLRPEACRPAAGGAVHTRGLDFACDI YIWAPLAGTCGVLLLSLVITLYCNKRGRKKLLYIFKQPFMRPVQTT QEEDGCSCRFPEEEEGGCELRVKFSRSADAPAYQQGQNQLYNELN LGRREEYDVLDKRRGRDPEMGGKPRRKNPQEGLYNELQKDKMAE AYSEIGMKGERRRGKGHDGLYQGLSTATKDTYDALHMQALPPR |
| 81 | 4H11 H1L2-CAR | MALPVTALLLPLALLLHAEVKLQESGGGFVKPGGSLRVSCAASGFT FSSYAMSWVRLAPEMRLEWVATISSAGGYIFYSDSVQGRFTISRDN AKNSLHLQMGSLRSGDTAMYYCARQGFGNYGDYYAMDYWGQG TTVTVSSGGGGSGGGGSGGGGSDIVLTQSPDSLAVSLGERVTMNC |

TABLE 7-continued

Table of Sequences

| SEQ ID NO | Description | Sequence |
|---|---|---|
| | | KSSQSLLNSRTRKNQLAWYQQKPGQSPELLIYWASTRQSGVPDRFS<br>GSGSGTDFTLTISSVQAEDVAVYYCQQSYNLLTFGQGTKLEIKRAA<br>APTTTPAPRPPTPAPTIASQPLSLRPEACRPAAGGAVHTRGLDFACDI<br>YIWAPLAGTCGVLLLSLVITLYCNKRGRKKLLYIFKQPFMRPVQTT<br>QEEDGCSCRFPEEEEGGCELRVKFSRSADAPAYQQGQNQLYNELN<br>LGRREEYDVLDKRRGRDPEMGGKPRRKNPQEGLYNELQKDKMAE<br>AYSEIGMKGERRRGKGHDGLYQGLSTATKDTYDALHMQALPPR |
| 82 | 4H11 H2L1-CAR | MALPVTALLLPLALLLHAEVQLVESGGGLVKPGGSLRVSCAASGFT<br>FSSYAMSWVRLAPGKGLEWVATISSAGGYIFYSDSVQGRFTISRDN<br>AKNSLYLQMNSLRAEDTAMYYCARQGFGNYGDYYAMDYWGQG<br>TLVTVSSGGGGSGGGGSGGGGSDIELTQSPSSLAVSAGERVTMNCK<br>SSQSLLNSRTRKNQLAWYQQKPGQSPELLIYWASTRQSGVPDRFSG<br>SGSGTDFTLTISSVQAEDVAVYYCQQSYNLLTFGPGTKLEIKRAAA<br>PTTTPAPRPPTPAPTIASQPLSLRPEACRPAAGGAVHTRGLDFACDIY<br>IWAPLAGTCGVLLLSLVITLYCNKRGRKKLLYIFKQPFMRPVQTTQ<br>EEDGCSCRFPEEEEGGCELRVKFSRSADAPAYQQGQNQLYNELNL<br>GRREEYDVLDKRRGRDPEMGGKPRRKNPQEGLYNELQKDKMAEA<br>YSEIGMKGERRRGKGHDGLYQGLSTATKDTYDALHMQALPPR |
| 83 | 4H11 H2L2-CAR | MALPVTALLLPLALLLHAEVQLVESGGGLVKPGGSLRVSCAASGFT<br>FSSYAMSWVRLAPGKGLEWVATISSAGGYIFYSDSVQGRFTISRDN<br>AKNSLYLQMNSLRAEDTAMYYCARQGFGNYGDYYAMDYWGQG<br>TLVTVSSGGGGSGGGGSGGGGSDIVLTQSPDSLAVSLGERVTMNC<br>KSSQSLLNSRTRKNQLAWYQQKPGQSPELLIYWASTRQSGVPDRFS<br>GSGSGTDFTLTISSVQAEDVAVYYCQQSYNLLTFGQGTKLEIKRAA<br>APTTTPAPRPPTPAPTIASQPLSLRPEACRPAAGGAVHTRGLDFACDI<br>YIWAPLAGTCGVLLLSLVITLYCNKRGRKKLLYIFKQPFMRPVQTT<br>QEEDGCSCRFPEEEEGGCELRVKFSRSADAPAYQQGQNQLYNELN<br>LGRREEYDVLDKRRGRDPEMGGKPRRKNPQEGLYNELQKDKMAE<br>AYSEIGMKGERRRGKGHDGLYQGLSTATKDTYDALHMQALPPR |
| 84 | 18C6 H1L1-CAR | MALPVTALLLPLALLLHAQVTLKESGPGILQPTQTLTLTCTFSGFSL<br>STVGMGVGWSRQPSGKGLEWLAHIWWDDEDKYYNPALKSRLTIT<br>KDTSKNQVFLKITNVDTADTATYYCTRIGTAQATDALDYWGQGTL<br>VTVSSGGGGSGGGGSGGGGSDIVMTQSAPSVPVTPGESVSISCRSSK<br>SLLHSNGNTYLYWFLQKPGQSPQRLIYYMSNLASGVPDRFSGRGSG<br>TDFTLKISRVEAEDVGVYYCMQSLEYPLTFGGGTKLEIKRAAAPTT<br>TPAPRPPTPAPTIASQPLSLRPEACRPAAGGAVHTRGLDFACDIYIW<br>APLAGTCGVLLLSLVITLYCNKRGRKKLLYIFKQPFMRPVQTTQEE<br>DGCSCRFPEEEEGGCELRVKFSRSADAPAYQQGQNQLYNELNLGR<br>REEYDVLDKRRGRDPEMGGKPRRKNPQEGLYNELQKDKMAEAYS<br>EIGMKGERRRGKGHDGLYQGLSTATKDTYDALHMQALPPR |
| 85 | 18C6 H1L2-CAR | MALPVTALLLPLALLLHAQVTLKESGPGILQPTQTLTLTCTFSGFSL<br>STVGMGVGWSRQPSGKGLEWLAHIWWDDEDKYYNPALKSRLTIT<br>KDTSKNQVFLKITNVDTADTATYYCTRIGTAQATDALDYWGQGTL<br>VTVSSGGGGSGGGGSGGGGSDIVMTQSALSLPVTPGEPVSISCRSSK<br>SLLHSNGNTYLYWFLQKPGQSPQRLIYYMSNLASGVPDRFSGSGSG<br>TDFTLKISRVEAEDVGVYYCMQSLEYPLTFGGGTKLEIKRAAAPTT<br>TPAPRPPTPAPTIASQPLSLRPEACRPAAGGAVHTRGLDFACDIYIW<br>APLAGTCGVLLLSLVITLYCNKRGRKKLLYIFKQPFMRPVQTTQEE<br>DGCSCRFPEEEEGGCELRVKFSRSADAPAYQQGQNQLYNELNLGR<br>REEYDVLDKRRGRDPEMGGKPRRKNPQEGLYNELQKDKMAEAYS<br>EIGMKGERRRGKGHDGLYQGLSTATKDTYDALHMQALPPR |
| 86 | 18C6 H2L1-CAR | MALPVTALLLPLALLLHAQVTLKESGPTLVKPTQTLTLTCTFSGFSL<br>STVGMGVGWSRQPSGKGLEWLAHIWWDDEDKYYNPALKSRLTIT<br>KDTSKNQVVLTITNVDPVDTATYYCTRIGTAQATDALDYWGQGTL<br>VTVSSGGGGSGGGGSGGGGSDIVMTQSAPSVPVTPGESVSISCRSSK<br>SLLHSNGNTYLYWFLQKPGQSPQRLIYYMSNLASGVPDRFSGRGSG<br>TDFTLKISRVEAEDVGVYYCMQSLEYPLTFGGGTKLEIKRAAAPTT<br>TPAPRPPTPAPTIASQPLSLRPEACRPAAGGAVHTRGLDFACDIYIW<br>APLAGTCGVLLLSLVITLYCNKRGRKKLLYIFKQPFMRPVQTTQEE<br>DGCSCRFPEEEEGGCELRVKFSRSADAPAYQQGQNQLYNELNLGR<br>REEYDVLDKRRGRDPEMGGKPRRKNPQEGLYNELQKDKMAEAYS<br>EIGMKGERRRGKGHDGLYQGLSTATKDTYDALHMQALPPR |
| 87 | 18C6 H2L2-CAR | MALPVTALLLPLALLLHAQVTLKESGPTLVKPTQTLTLTCTFSGFSL<br>STVGMGVGWSRQPSGKGLEWLAHIWWDDEDKYYNPALKSRLTIT<br>KDTSKNQVVLTITNVDPVDTATYYCTRIGTAQATDALDYWGQGTL<br>VTVSSGGGGSGGGGSGGGGSDIVMTQSALSLPVTPGEPVSISCRSSK<br>SLLHSNGNTYLYWFLQKPGQSPQRLIYYMSNLASGVPDRFSGSGSG<br>TDFTLKISRVEAEDVGVYYCMQSLEYPLTFGGGTKLEIKRAAAPTT |

TABLE 7-continued

Table of Sequences

| SEQ ID NO | Description | Sequence |
|-----------|-------------|----------|
| | | TPAPRPPTPAPTIASQPLSLRPEACRPAAGGAVHTRGLDFACDIYIW APLAGTCGVLLLSLVITLYCNKRGRKKLLYIFKQPFMRPVQTTQEE DGCSCRFPEEEEGGCELRVKFSRSADAPAYQQGQNQLYNELNLGR REEYDVLDKRRGRDPEMGGKPRRKNPQEGLYNELQKDKMAEAYS EIGMKGERRRGKGHDGLYQGLSTATKDTYDALHMQALPPR |
| 88 | 4H11 H1L1-BsAb | MGWSCIILFLVATATGKLEVKLQESGGGFVKPGGSLRVSCAASGFT FSSYAMSWVRLAPEMRLEWVATISSAGGYIFYSDSVQGRFTISRDN AKNSLHLQMGSLRSGDTAMYYCARQGFGNYGDYYAMDYWGQG TTVTVSSGGGGSGGGGSGGGGSDIELTQSPSSLAVSAGERVTMNCK SSQSLLNSRTRKNQLAWYQQKPGQSPELLIYWASTRQSGVPDRFSG SGSGTDFTLTISSVQAEDVAVYYCQQSYNLLTFGPGTKLEIKRTSGG GGSDVQLVQSGAEVKKPGASVKVSCKASGYTFTRYTMHWVRQAP GQGLEWIGYINPSRGYTNYADSVKGRFTITTDKSTSTAYMELSSLRS EDTATYYCARYYDDHYCLDYWGQGTTVTVSSGEGTSTGSGGSGG SGGADDIVLTQSPATLSLSPGERATLSCRASQSVSYMNWYQQKPG KAPKRWIYDTSKVASGVPARFSGSGSGTDYSLTINSLEAEDAATYY CQQWSSNPLTFGGGTKVEIKHHHHHH |
| 89 | 4H11 H1L2-BsAb | MGWSCIILFLVATATGKLEVKLQESGGGFVKPGGSLRVSCAASGFT FSSYAMSWVRLAPEMRLEWVATISSAGGYIFYSDSVQGRFTISRDN AKNSLHLQMGSLRSGDTAMYYCARQGFGNYGDYYAMDYWGQG TTVTVSSGGGGSGGGGSGGGGSDIVLTQSPDSLAVSLGERVTMNC KSSQSLLNSRTRKNQLAWYQQKPGQSPELLIYWASTRQSGVPDRFS GSGSGTDFTLTISSVQAEDVAVYYCQQSYNLLTFGQGTKLEIKRTS GGGGSDVQLVQSGAEVKKPGASVKVSCKASGYTFTRYTMHWVRQ APGQGLEWIGYINPSRGYTNYADSVKGRFTITTDKSTSTAYMELSS LRSEDTATYYCARYYDDHYCLDYWGQGTTVTVSSGEGTSTGSGGS GGSGGADDIVLTQSPATLSLSPGERATLSCRASQSVSYMNWYQQK PGKAPKRWIYDTSKVASGVPARFSGSGSGTDYSLTINSLEAEDAAT YYCQQWSSNPLTFGGGTKVEIKHHHHHH |
| 90 | 4H11 H2L1-BsAb | MGWSCIILFLVATATGKLEVQLVESGGGLVKPGGSLRVSCAASGFT FSSYAMSWVRLAPGKGLEWVATISSAGGYIFYSDSVQGRFTISRDN AKNSLYLQMNSLRAEDTAMYYCARQGFGNYGDYYAMDYWGQG TLVTVSSGGGGSGGGGSGGGGSDIELTQSPSSLAVSAGERVTMNCK SSQSLLNSRTRKNQLAWYQQKPGQSPELLIYWASTRQSGVPDRFSG SGSGTDFTLTISSVQAEDVAVYYCQQSYNLLTFGPGTKLEIKRTSGG GGSDVQLVQSGAEVKKPGASVKVSCKASGYTFTRYTMHWVRQAP GQGLEWIGYINPSRGYTNYADSVKGRFTITTDKSTSTAYMELSSLRS EDTATYYCARYYDDHYCLDYWGQGTTVTVSSGEGTSTGSGGSGG SGGADDIVLTQSPATLSLSPGERATLSCRASQSVSYMNWYQQKPG KAPKRWIYDTSKVASGVPARFSGSGSGTDYSLTINSLEAEDAATYY CQQWSSNPLTFGGGTKVEIKHHHHHH |
| 91 | 4H11 H2L2-BsAb | MGWSCIILFLVATATGKLEVQLVESGGGLVKPGGSLRVSCAASGFT FSSYAMSWVRLAPGKGLEWVATISSAGGYIFYSDSVQGRFTISRDN AKNSLYLQMNSLRAEDTAMYYCARQGFGNYGDYYAMDYWGQG TLVTVSSGGGGSGGGGSGGGGSDIVLTQSPDSLAVSLGERVTMNC KSSQSLLNSRTRKNQLAWYQQKPGQSPELLIYWASTRQSGVPDRFS GSGSGTDFTLTISSVQAEDVAVYYCQQSYNLLTFGQGTKLEIKRTS GGGGSDVQLVQSGAEVKKPGASVKVSCKASGYTFTRYTMHWVRQ APGQGLEWIGYINPSRGYTNYADSVKGRFTITTDKSTSTAYMELSS LRSEDTATYYCARYYDDHYCLDYWGQGTTVTVSSGEGTSTGSGGS GGSGGADDIVLTQSPATLSLSPGERATLSCRASQSVSYMNWYQQK PGKAPKRWIYDTSKVASGVPARFSGSGSGTDYSLTINSLEAEDAAT YYCQQWSSNPLTFGGGTKVEIKHHHHHH |
| 92 | 18C6 H1L1-BsAb | MGWSCIILFLVATATGKLQVTLKESGPGILQPTQTLTLTCTFSGFSLS TVGMGVGWSRQPSGKGLEWLAHIWWDDEDKYYNPALKSRLTITK DTSKNQVFLKITNVDTADTATYYCTRIGTAQATDALDYWGQGTLV TVSSGGGGSGGGGSGGGGSDIVMTQSAPSVPVTPGESVSISCRSSKS LLHSNGNTYLYWFLQKPGQSPQRLIYYMSNLASGVPDRFSGRGSG TDFTLKISRVEAEDVGVYYCMQSLEYPLTFGGGTKLEIKRTSGGGG SDVQLVQSGAEVKKPGASVKVSCKASGYTFTRYTMHWVRQAPGQ GLEWIGYINPSRGYTNYADSVKGRFTITTDKSTSTAYMELSSLRSED TATYYCARYYDDHYCLDYWGQGTTVTVSSGEGTSTGSGGSGGSG GADDIVLTQSPATLSLSPGERATLSCRASQSVSYMNWYQQKPGKA PKRWIYDTSKVASGVPARFSGSGSGTDYSLTINSLEAEDAATYYCQ QWSSNPLTFGGGTKVEIKHHHHHH |
| 93 | 18C6 H1L2-BsAb | MGWSCIILFLVATATGKLQVTLKESGPGILQPTQTLTLTCTFSGFSLS TVGMGVGWSRQPSGKGLEWLAHIWWDDEDKYYNPALKSRLTITK DTSKNQVFLKITNVDTADTATYYCTRIGTAQATDALDYWGQGTLV |

TABLE 7-continued

Table of Sequences

| SEQ ID NO | Description | Sequence |
|---|---|---|
| | | TVSSGGGGSGGGGSGGGGSDIVMTQSALSLPVTPGEPVSISCRSSKS<br>LLHSNGNTYLYWFLQKPGQSPQRLIYYMSNLASGVPDRFSGSGSGT<br>DFTLKISRVEAEDVGVYYCMQSLEYPLTFGGGTKLEIKRTSGGGGS<br>DVQLVQSGAEVKKPGASVKVSCKASGYTFTRYTMHWVRQAPGQG<br>LEWIGYINPSRGYTNYADSVKGRFTITTDKSTSTAYMELSSLRSEDT<br>ATYYCARYYDDHYCLDYWGQGTTVTVSSGEGTSTGSGGSGGSGG<br>ADDIVLTQSPATLSLSPGERATLSCRASQSVSYMNWYQQKPGKAP<br>KRWIYDTSKVASGVPARFSGSGSGTDYSLTINSLEAEDAATYYCQQ<br>WSSNPLTFGGGTKVEIKHHHHHH |
| 94 | 18C6<br>H2L1-<br>BsAb | MGWSCIILFLVATATGKLQVTLKESGPTLVKPTQTLTLTCTFSGFSL<br>STVGMGVGWSRQPSGKGLEWLAHIWWDDEDKYYNPALKSRLTIT<br>KDTSKNQVVLTITNVDPVDTATYYCTRIGTAQATDALDYWGQGTL<br>VTVSSGGGGSGGGGSGGGGSDIVMTQSAPSVPVTPGESVSISCRSSK<br>SLLHSNGNTYLYWFLQKPGQSPQRLIYYMSNLASGVPDRFSGRGSG<br>TDFTLKISRVEAEDVGVYYCMQSLEYPLTFGGGTKLEIKRTSGGGG<br>SDVQLVQSGAEVKKPGASVKVSCKASGYTFTRYTMHWVRQAPGQ<br>GLEWIGYINPSRGYTNYADSVKGRFTITTDKSTSTAYMELSSLRSED<br>TATYYCARYYDDHYCLDYWGQGTTVTVSSGEGTSTGSGGSGGSG<br>GADDIVLTQSPATLSLSPGERATLSCRASQSVSYMNWYQQKPGKA<br>PKRWIYDTSKVASGVPARFSGSGSGTDYSLTINSLEAEDAATYYCQ<br>QWSSNPLTFGGGTKVEIKHHHHHH |
| 95 | 18C6<br>H2L2-<br>BsAb | MGWSCIILFLVATATGKLQVTLKESGPTLVKPTQTLTLTCTFSGFSL<br>STVGMGVGWSRQPSGKGLEWLAHIWWDDEDKYYNPALKSRLTIT<br>KDTSKNQVVLTITNVDPVDTATYYCTRIGTAQATDALDYWGQGTL<br>VTVSSGGGGSGGGGSGGGGSDIVMTQSALSLPVTPGEPVSISCRSSK<br>SLLHSNGNTYLYWFLQKPGQSPQRLIYYMSNLASGVPDRFSGSGSG<br>TDFTLKISRVEAEDVGVYYCMQSLEYPLTFGGGTKLEIKRTSGGGG<br>SDVQLVQSGAEVKKPGASVKVSCKASGYTFTRYTMHWVRQAPGQ<br>GLEWIGYINPSRGYTNYADSVKGRFTITTDKSTSTAYMELSSLRSED<br>TATYYCARYYDDHYCLDYWGQGTTVTVSSGEGTSTGSGGSGGSG<br>GADDIVLTQSPATLSLSPGERATLSCRASQSVSYMNWYQQKPGKA<br>PKRWIYDTSKVASGVPARFSGSGSGTDYSLTINSLEAEDAATYYCQ<br>QWSSNPLTFGGGTKVEIKHHHHHH |
| 96 | 4H11 L1H1-<br>CAR | MALPVTALLLPLALLLHADIELTQSPSSLAVSAGERVTMNCKSSQS<br>LLNSRTRKNQLAWYQQKPGQSPELLIYWASTRQSGVPDRFSGSGS<br>GTDFTLTISSVQAEDVAVYYCQQSYNLLTFGPGTKLEIKRGGGGSG<br>GGGSGGGGSEVKLQESGGGFVKPGGSLRVSCAASGFTFSSYAMSW<br>VRLAPEMRLEWVATISSAGGYIFYSDSVQGRFTISRDNAKNSLHLQ<br>MGSLRSGDTAMYYCARQGFGNYGDYYAMDYWGQGTTVTVSSAA<br>APTTTPAPRPPTPAPTIASQPLSLRPEACRPAAGGAVHTRGLDFACDI<br>YIWAPLAGTCGVLLLSLVITLYCNKRGRKKLLYIFKQPFMRPVQTT<br>QEEDGCSCRFPEEEEGGCELRVKFSRSADAPAYQQGQNQLYNELN<br>LGRREEYDVLDKRRGRDPEMGGKPRRKNPQEGLYNELQKDKMAE<br>AYSEIGMKGERRRGKGHDGLYQGLSTATKDTYDALHMQALPPR |
| 97 | 4H11 L2H1-<br>CAR | MALPVTALLLPLALLLHADIVLTQSPDSLAVSLGERVTMNCKSSQS<br>LLNSRTRKNQLAWYQQKPGQSPELLIYWASTRQSGVPDRFSGSGS<br>GTDFTLTISSVQAEDVAVYYCQQSYNLLTFGPGTKLEIKRGGGGSG<br>GGGSGGGGSEVKLQESGGGFVKPGGSLRVSCAASGFTFSSYAMSW<br>VRLAPEMRLEWVATISSAGGYIFYSDSVQGRFTISRDNAKNSLHLQ<br>MGSLRSGDTAMYYCARQGFGNYGDYYAMDYWGQGTTVTVSSAA<br>APTTTPAPRPPTPAPTIASQPLSLRPEACRPAAGGAVHTRGLDFACDI<br>YIWAPLAGTCGVLLLSLVITLYCNKRGRKKLLYIFKQPFMRPVQTT<br>QEEDGCSCRFPEEEEGGCELRVKFSRSADAPAYQQGQNQLYNELN<br>LGRREEYDVLDKRRGRDPEMGGKPRRKNPQEGLYNELQKDKMAE<br>AYSEIGMKGERRRGKGHDGLYQGLSTATKDTYDALHMQALPPR |
| 98 | 4H11 L1H2-<br>CAR | MALPVTALLLPLALLLHADIELTQSPSSLAVSAGERVTMNCKSSQS<br>LLNSRTRKNQLAWYQQKPGQSPELLIYWASTRQSGVPDRFSGSGS<br>GTDFTLTISSVQAEDVAVYYCQQSYNLLTFGPGTKLEIKRGGGGSG<br>GGGSGGGGSEVQLVESGGGLVKPGGSLRVSCAASGFTFSSYAMSW<br>VRLAPGKGLEWVATISSAGGYIFYSDSVQGRFTISRDNAKNSLYLQ<br>MNSLRAEDTAMYYCARQGFGNYGDYYAMDYWGQGTLVTVSSAA<br>APTTTPAPRPPTPAPTIASQPLSLRPEACRPAAGGAVHTRGLDFACDI<br>YIWAPLAGTCGVLLLSLVITLYCNKRGRKKLLYIFKQPFMRPVQTT<br>QEEDGCSCRFPEEEEGGCELRVKFSRSADAPAYQQGQNQLYNELN<br>LGRREEYDVLDKRRGRDPEMGGKPRRKNPQEGLYNELQKDKMAE<br>AYSEIGMKGERRRGKGHDGLYQGLSTATKDTYDALHMQALPPR |
| 99 | 4H11 L2H2-<br>CAR | MALPVTALLLPLALLLHADIVLTQSPDSLAVSLGERVTMNCKSSQS<br>LLNSRTRKNQLAWYQQKPGQSPELLIYWASTRQSGVPDRFSGSGS |

TABLE 7-continued

Table of Sequences

| SEQ ID NO | Description | Sequence |
|---|---|---|
| | | GTDFTLTISSVQAEDVAVYYCQQSYNLLTFGQGTKLEIKRGGGGSG GGGSGGGGSEVQLVESGGGLVKPGGSLRVSCAASGFTFSSYAMSW VRLAPGKGLEWVATISSAGGYIFYSDSVQGRFTISRDNAKNSLYLQ MNSLRAEDTAMYYCARQGFGNYGDYYAMDYWGQGTLVTVSSAA APTTTPAPRPPTPAPTIASQPLSLRPEACRPAAGGAVHTRGLDFACDI YIWAPLAGTCGVLLLSLVITLYCNKRGRKKLLYIFKQPFMRPVQTT QEEDGCSCRFPEEEEGGCELRVKFSRSADAPAYQQGQNQLYNELN LGRREEYDVLDKRRGRDPEMGGKPRRKNPQEGLYNELQKDKMAE AYSEIGMKGERRRGKGHDGLYQGLSTATKDTYDALHMQALPPR |
| 100 | 18C6 L1H1-CAR | MALPVTALLLPLALLLHADIVMTQSAPSVPVTPGESVSISCRSSKSL LHSNGNTYLYWFLQKPGQSPQRLIYYMSNLASGVPDRFSGRGSGT DFTLKISRVEAEDVGVYYCMQSLEYPLTFGGGTKLEIKRGGGGSGG GGSGGGGSQVTLKESGPGILQPTQTLTLTCTFSGFSLSTVGMGVGW SRQPSGKGLEWLAHIWWDDEDKYYNPALKSRLTITKDTSKNQVFL KITNVDTADTATYYCTRIGTAQATDALDYWGQGTLVTVSSAAAPT TTPAPRPPTPAPTIASQPLSLRPEACRPAAGGAVHTRGLDFACDIYI WAPLAGTCGVLLLSLVITLYCNKRGRKKLLYIF'KQPFMRPVQTTQE EDGCSCRFPEEEEGGCELRVKFSRSADAPAYQQGQNQLYNELNLG RREEYDVLDKRRGRDPEMGGKPRRKNPQEGLYNELQKDKMAEAY SEIGMKGERRRGKGHDGLYQGLSTATKDTYDALHMQALPPR |
| 101 | 18C6 L2H1-CAR | MALPVTALLLPLALLLHADIVMTQSALSLPVTPGEPVSISCRSSKSL LHSNGNTYLYWFLQKPGQSPQRLIYYMSNLASGVPDRFSGSGSGT DFTLKISRVEAEDVGVYYCMQSLEYPLTFGGGTKLEIKRGGGGSGG GGSGGGGSQVTLKESGPGILQPTQTLTLTCTFSGFSLSTVGMGVGW SRQPSGKGLEWLAHIWWDDEDKYYNPALKSRLTITKDTSKNQVFL KITNVDTADTATYYCTRIGTAQATDALDYWGQGTLVTVSSAAAPT TTPAPRPPTPAPTIASQPLSLRPEACRPAAGGAVHTRGLDFACDIYI WAPLAGTCGVLLLSLVITLYCNKRGRKKLLYIFKQPFMRPVQTTQE EDGCSCRFPEEEEGGCELRVKFSRSADAPAYQQGQNQLYNELNLG RREEYDVLDKRRGRDPEMGGKPRRKNPQEGLYNELQKDKMAEAY SEIGMKGERRRGKGHDGLYQGLSTATKDTYDALHMQALPPR |
| 102 | 18C6 L1H2-CAR | MALPVTALLLPLALLLHADIVMTQSAPSVPVTPGESVSISCRSSKSL LHSNGNTYLYWFLQKPGQSPQRLIYYMSNLASGVPDRFSGRGSGT DFTLKISRVEAEDVGVYYCMQSLEYPLTFGGGTKLEIKRGGGGSGG GGSGGGGSQVTLKESGPTLVKPTQTLTLTCTFSGFSLSTVGMGVG WSRQPSGKGLEWLAHIWWDDEDKYYNPALKSRLTITKDTSKNQV VLTITNVDPVDTATYYCTRIGTAQATDALDYWGQGTLVTVSSAAA PTTTPAPRPPTPAPTIASQPLSLRPEACRPAAGGAVHTRGLDFACDIY IWAPLAGTCGVLLLSLVITLYCNKRGRKKLLYIFKQPFMRPVQTTQ EEDGCSCRFPEEEEGGCELRVKFSRSADAPAYQQGQNQLYNELNL GRREEYDVLDKRRGRDPEMGGKPRRKNPQEGLYNELQKDKMAEA YSEIGMKGERRRGKGHDGLYQGLSTATKDTYDALHMQALPPR |
| 103 | 18C6 L2H2-CAR | MALPVTALLLPLALLLHADIVMTQSALSLPVTPGEPVSISCRSSKSL LHSNGNTYLYWFLQKPGQSPQRLIYYMSNLASGVPDRFSGSGSGT DFTLKISRVEAEDVGVYYCMQSLEYPLTFGGGTKLEIKRGGGGSGG GGSGGGGSQVTLKESGPTLVKPTQTLTLTCTFSGFSLSTVGMGVG WSRQPSGKGLEWLAHIWWDDEDKYYNPALKSRLTITKDTSKNQV VLTITNVDPVDTATYYCTRIGTAQATDALDYWGQGTLVTVSSAAA PTTTPAPRPPTPAPTIASQPLSLRPEACRPAAGGAVHTRGLDFACDIY IWAPLAGTCGVLLLSLVITLYCNKRGRKKLLYIFKQPFMRPVQTTQ EEDGCSCRFPEEEEGGCELRVKFSRSADAPAYQQGQNQLYNELNL GRREEYDVLDKRRGRDPEMGGKPRRKNPQEGLYNELQKDKMAEA YSEIGMKGERRRGKGHDGLYQGLSTATKDTYDALHMQALPPR |
| 104 | 4H11 LFW1 mouse | DIELTQSPSSLAVSAGEKVTMSC |
| 105 | 4H11 LFW2 mouse | WYQQKPGQSPELLIY |
| 106 | 4H11 LFW3 mouse | GVPDRFTGSGSGTDFTLTISSVQAEDLAVYYC |
| 107 | 4H11 LFW4 mouse | FGPGTKLEVKR |
| 108 | Human IGKV4-1*01 LFW1 | DIVMTQSPDSLAVSL ERATINC |

TABLE 7-continued

| SEQ ID NO | Description | Sequence |
|---|---|---|
| Table of Sequences | | |
| 109 | Human IGKV4-1*01 LFW2 | WYQQKPGQPPKLLIY |
| 110 | Human IGKV4-1*01 LFW3 | GVPDRFSGSGSGTDFTLTISSLQAEDVAVYYC |
| 111 | Human IGKJ2*01 LFW4 | FGQGTKLEIKR |
| 112 | 4H11 L1-FW1 | DIELTQSPSSLAVSAGERVTMNC |
| 113 | 4H11 L1-FW2 | WYQQKPGQSPELLIY |
| 114 | 4H11 L1-FW3 | GVPDRFSGSGSGTDFTLTISSVQAEDVAVYYC |
| 115 | 4H11 L1-FW4 | FGPGTKLEIKR |
| 116 | 4H11 L2-FW1 | DIVLTQSPDSLAVSLGERVTMNC |
| 117 | 4H11 L2-FW2 | WYQQKPGQSPELLIY |
| 118 | 4H11 L2-FW3 | GVPDRFSGSGSGTDFTLTISSVQAEDVAVYYC |
| 119 | 4H11 L2-FW4 | FGQGTKLEIKR |
| 120 | 4H11 LFW1 consensus | DIXLTQSPXSLAVSXGEXVTMXC |
| 121 | 4H11 LFW2 consensus | WYQQKPGQSPELLIY |
| 122 | 4H11 LFW3 consensus | GVPDRFXGSGSGTDFTLTISSVQAEDXAVYYC |
| 123 | 4H11 LFW4 consensus | FGXGTKLEXKR |
| 124 | 4H11 HFW1 mouse | SVKLQESGGGFVKPGGSLKVSCAASGFTFS |
| 125 | 4H11 HFW2 mouse | WVRLSPEMRLEWVA |
| 126 | 4H11 HFW3 mouse | RFTISRDNAKNTLHLQMGSLRSGDTAMYYCAR |
| 127 | Human IGHV3-21*01 HFW1 | EVQLVESGGGLVKPGGSLRLSCAASGFTFS |
| 128 | Human IGHV3-21*01 HFW2 | WVRQAPGKGLEWVS |
| 129 | Human IGHV3-21*01 HFW3 | RFTISRDNAKNSLYLQMNSLRAEDTAVYYCAR |
| 130 | 4H11 H1-FW1 | EVKLQESGGGFVKPGGSLRVSCAASGFTFS |

TABLE 7-continued

| SEQ ID NO | Description | Sequence |
|---|---|---|
| 131 | 4H11 H1-FW2 | WVRLAPEMRLEWVA |
| 132 | 4H11 H1-FW3 | RFTISRDNAKNSLHLQMGSLRSGDTAMYYCAR |
| 133 | 4H11 H2-FW1 | EVQLVESGGGLVKPGGSLRVSCAASGFTFS |
| 134 | 4H11 H2-FW2 | WVRLAPGKGLEWVA |
| 135 | 4H11 H2-FW3 | RFTISRDNAKNSLYLQMNSLRAEDTAMYYCAR |
| 136 | 4H11 HFW1 consensus | XVXLXESGGGXVKPGGSLXVSCAASGFTFS |
| 137 | 4H11 HFW2 consensus | WVRLXPXXXLEWVA |
| 138 | 4H11 HFW3 consensus | RFTISRDNAKNXLXLQMXSLRXXDTAMYYCAR |
| 139 | 18C6 LFW1 mouse | DIVMTQAAPSVPVTPGESVSISC |
| 140 | 18C6 LFW2 mouse | WFLQRPGQSPQRLIY |
| 141 | 18C6 LFW3 mouse | GVPDRFSGRGSGTDFTLRISRVEAEDVGVYYC |
| 142 | 18C6 LFW4 mouse | FGGGTKLEIK |
| 143 | Human KV2-28*01 LFW1 | DIVMTQSPLSLPVTPGEPASISC |
| 144 | Human KV2-28*01 LFW2 | WYLQKPGQSPQLLIY |
| 145 | Human KV2-28*01 LFW3 | GVPDRFSGSGSGTDFTLKISRVEAEDVGVYYC |
| 146 | Human J4*01 LFW4 | FGGGTKVEIK |
| 147 | 18C6 L1-FW1 | DIVMTQSAPSVPVTPGESVSISC |
| 148 | 18C6 L1-FW2 | WFLQKPGQSPQRLIY |
| 149 | 18C6 L1-FW3 | GVPDRFSGRGSGTDFTLKISRVEAEDVGVYYC |
| 150 | 18C6 L1-FW4 | FGGGTKLEIK |
| 151 | 18C6 L2-FW1 | DIVMTQSALSLPVTPGEPVSISC |
| 152 | 18C6 L2-FW2 | WFLQKPGQSPQRLIY |
| 153 | 18C6 L2-FW3 | GVPDRFSGSGSGTDFTLKISRVEAEDVGVYYC |

TABLE 7-continued

| SEQ ID NO | Description | Sequence |
|---|---|---|

Table of Sequences

| SEQ ID NO | Description | Sequence |
|---|---|---|
| 154 | 18C6 L2-FW4 | FGGGTKLEIK |
| 155 | 18C6 LFW1 consensus | DIVMTQXAXSXPVTPGEXVSISC |
| 156 | 18C6 LFW2 consensus | WFLQXPGQSPQRLIY |
| 157 | 18C6 LFW3 consensus | GVPDRFSGXGSGTDFTLXISRVEAEDVGVYYC |
| 158 | 18C6 LFW4 consensus | FGGGTKLEIK |
| 159 | 18C6 HFW1 mouse | QVTLKESGPGILQPSQTLSLTCSFSGFSLS |
| 160 | 18C6 HFW2 mouse | WSRQPSGKGLEWLA |
| 161 | 18C6 HFW3 mouse | RLTISKDTSKNQVFLKIANVDTADTATYYCTR |
| 162 | 18C6 HFW4 mouse | WGQGTSVTVSS |
| 163 | Human HV2-5*09 HFW1 | QVTLKESGPTLVKPTQTLTLTCTFSGFSLS |
| 164 | Human HV2-5*09 HFW2 | WIRQPPGKALEWLA |
| 165 | Human HV2-5*09 HFW3 | RLTITKDTSKNQVVLTMTNMDPVDTATYYCAH |
| 166 | Human J4*01 HFW4 | WGQGTLVTVSS |
| 167 | 18C6 H1-FW1 | QVTLKESGPGILQPTQTLTLTCTFSGFSLS |
| 168 | 18C6 H1-FW2 | WSRQPSGKGLEWLA |
| 169 | 18C6 H1-FW3 | RLTITKDTSKNQVFLKITNVDTADTATYYCTR |
| 170 | 18C6 H1-FW4 | WGQGTLVTVSS |
| 171 | 18C6 H2-FW1 | QVTLKESGPTLVKPTQTLTLTCTFSGFSLS |
| 172 | 18C6 H2-FW2 | WSRQPSGKGLEWLA |
| 173 | 18C6 H2-FW3 | RLTITKDTSKNQVVLTITNVDPVDTATYYCTR |
| 174 | 18C6 H2-FW4 | WGQGTLVTVSS |
| 175 | 18C6 HFW1 consensus | QVTLKESGPXXXXPXQTLXLTCXFSGFSLS |
| 176 | 18C6 HFW2 consensus | WSRQPSGKGLEWLA |

TABLE 7-continued

Table of Sequences

| SEQ ID NO | Description | Sequence |
|---|---|---|
| 177 | 18C6 HFW3 consensus | RLTIXKDTSKNQVXLXIXNVDXXDTATYYCTR |
| 178 | 18C6 HFW4 consensus | WGQGTXVTVSS |

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

What is claimed is:

1. An anti-mucin 16 (MUC16) construct comprising an antibody moiety that immunospecifically recognizes a mucin 16 (MUC16) polypeptide, wherein the antibody moiety comprises:

(a)
    (i) a variable heavy (VH) chain comprising SEQ ID NO: 4 or 5; and
    (ii) a variable light (VL) chain comprising SEQ ID NO: 2 or 3; or (b)
    (i) a variable heavy (VH) chain comprising SEQ ID NO: 22 or 23; and
    (ii) a variable light (VL) chain comprising SEQ ID NO: 20 or 21,
    wherein the VH chain and VL chain are humanized.

2. The anti-MUC16 construct of claim 1, wherein the antibody moiety
    (a) immunospecifically binds to the ectodomain of MUC16, or to a MUC16 c114 polypeptide comprising the amino acid sequence of SEQ ID NO: 44 or 180;

(b) is a full-length antibody, a monoclonal antibody, a Fab, a Fab', a F(ab')2, an a Fv, or a single chain Fv (scFv), wherein the scFv comprises any one of SEQ ID NOs: 53-68;

(c) comprises human-derived heavy and light chain constant regions, wherein the heavy chain constant region has an isotype selected from the group consisting of gamma 1, gamma 2, gamma 3, and gamma 4, or wherein the light chain constant region has an isotype selected from the group consisting of kappa and lambda; or (d) is an immunoglobulin comprising two identical heavy chains and two identical light chains, wherein the immunoglobulin is an IgG.

3. The anti-MUC16 construct of claim 1, wherein the anti-MUC16 construct inhibits in vitro invasion of a MUC16-expressing tumor cell in a gel invasion assay, wherein the MUC16-expressing tumor cell is an ovarian tumor cell; or is monospecific, multispecific, or bispecific, wherein the multispecific or bispecific anti-MUC16 construct comprises an anti-CD3 antibody moiety; or is (i) a tandem scFv, wherein the tandem scFv comprises two scFvs linked by a peptide linker; (ii) a diabody (Db); (iii) a single chain diabody (scDb); (iv) a dual-affinity retargeting (DART) antibody, (v) a F(ab')2; (vi) a dual variable domain (DVD) antibody; (vii) a knob-into-hole (KiH) antibody; (viii) a dock and lock (DNL) antibody; (ix) a chemically cross-linked antibody; (x) a heteromultimeric antibody; or (xi) a heteroconjugate antibody; or is a chimeric antigen receptor (CAR) comprising at least one of: (i) a co-stimulatory domain, (ii) a CD3 zeta ($\zeta$) chain cytoplasmic signaling domain, (iii) an scFv of any a one of SEQ ID NOS: 53-68, or (iv) any one of SEQ ID NOS: 80-87 and 97-103.

4. The anti-MUC16 construct of claim 3, wherein the multispecific or bispecific anti-MUC16 construct comprises a first antibody moiety that immunospecifically recognizes MUC16, and a second antibody moiety that immunospecifically a recognizes a second antigen, wherein the second antigen is a CD3 polypeptide selected from the group consisting of CD3γ, CD3δ, CD3ε, and CD3ζ or wherein the anti-MUC16 construct comprises any one of SEQ ID NOS: 42, 69-75, and 88-95.

5. The anti-MUC16 construct of claim 1, further conjugated to a peptide agent, a detection agent, an imaging agent, a therapeutic agent, a cytotoxic agent, an alpha emitter, an Auger-emitter, a beta-emitter, a gamma-emitter, a positron-emitter, or an x-ray a emitter.

6. A polypeptide comprising an amino acid sequence of the anti-MUC16 construct of claim 1.

7. A polynucleotide or vector comprising a nucleic acid sequence encoding one or more polypeptides of claim 6, wherein the nucleic acid sequence is operably linked to a promoter.

8. A cell comprising the polynucleotide or vector of claim 7, wherein the cell is a mammalian cell, an immune cell, a lymphocyte, a T cell or a B cell.

9. A pharmaceutical composition comprising: a a therapeutically effective amount of the anti-MUC16 construct of claim 1; and a pharmaceutically acceptable carrier.

10. A method of treating a MUC16-associated disease or disorder in a patient in need thereof, comprising administering to said patient a a therapeutically effective amount of the anti-MUC16 construct of claim 1, wherein said MUC16-associated disease or disorder is a metastatic cancer or a cancer of the ovary, lung, pancreas, breast, uterine, fallopian tube, or primary peritoneum.

11. A method of detecting MUC16 in a sample, a comprising: (a) contacting the sample with the anti-MUC16 construct of claim 1; and (b) detecting direct or indirect binding between the anti-MUC16 construct and a MUC16 polypeptide in the sample, wherein the anti-MUC16 construct is conjugated to a detectable label selected from among a chromogenic label, an enzymatic label, a radioisotopic label, an isotopic label, a fluorescent label, a toxic label, a chemiluminescent label, and a nuclear magnetic resonance contrast agent.

12. A method for detecting cancer in a subject in vivo comprising (a) administering to the subject an effective amount of the anti-MUC16 construct a of claim 1, wherein the anti-MUC16 construct is configured to localize to a cancer cell expressing MUC16 and is labeled with a radioisotope; and (b) detecting the presence of a tumor in the subject by detecting radioactive levels emitted by the anti-MUC16 construct that are higher than a reference value, wherein the radioisotope is 89Zr-desferrioxamine B (DFO) or wherein the radioactive levels emitted by the anti-MUC16 construct are detected using positron emission tomography or single photon emission computed tomography.

* * * * *

SEQUENCE LISTING

<160> NUMBER OF SEQ ID NOS: 183

<210> SEQ ID NO 1
<211> LENGTH: 14507
<212> TYPE: PRT
<213> ORGANISM: Homo sapiens

<400> SEQUENCE: 1

Met Leu Lys Pro Ser Gly Leu Pro Gly Ser Ser Ser Pro Thr Arg Ser
1               5                   10                  15

Leu Met Thr Gly Ser Arg Ser Thr Lys Ala Thr Pro Glu Met Asp Ser
            20                  25                  30

Gly Leu Thr Gly Ala Thr Leu Ser Pro Lys Thr Ser Thr Gly Ala Ile
        35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser

```
              115                    120                    125

Pro Arg Thr Arg Thr Ser Ser Thr Glu Gly Asn Phe Thr Lys Glu Ala
    130                    135                    140

Ser Thr Tyr Thr Leu Thr Val Glu Thr Thr Ser Gly Pro Val Thr Glu
145                    150                    155                    160

Lys Tyr Thr Val Pro Thr Glu Thr Ser Thr Thr Glu Gly Asp Ser Thr
                165                    170                    175

Glu Thr Pro Trp Asp Thr Arg Tyr Ile Pro Val Lys Ile Thr Ser Pro
                180                    185                    190

Met Lys Thr Phe Ala Asp Ser Thr Ala Ser Lys Glu Asn Ala Pro Val
                195                    200                    205

Ser Met Thr Pro Ala Glu Thr Thr Val Thr Asp Ser His Thr Pro Gly
    210                    215                    220

Arg Thr Asn Pro Ser Phe Gly Thr Leu Tyr Ser Ser Phe Leu Asp Leu
225                    230                    235                    240

Ser Pro Lys Gly Thr Pro Asn Ser Arg Gly Glu Thr Ser Leu Glu Leu
                245                    250                    255

Ile Leu Ser Thr Thr Gly Tyr Pro Phe Ser Ser Pro Glu Pro Gly Ser
                260                    265                    270

Ala Gly His Ser Arg Ile Ser Thr Ser Ala Pro Leu Ser Ser Ser Ala
    275                    280                    285

Ser Val Leu Asp Asn Lys Ile Ser Glu Thr Ser Ile Phe Ser Gly Gln
    290                    295                    300

Ser Leu Thr Ser Pro Leu Ser Pro Gly Val Pro Glu Ala Arg Ala Ser
305                    310                    315                    320

Thr Met Pro Asn Ser Ala Ile Pro Phe Ser Met Thr Leu Ser Asn Ala
                325                    330                    335

Glu Thr Ser Ala Glu Arg Val Arg Ser Thr Ile Ser Ser Leu Gly Thr
                340                    345                    350

Pro Ser Ile Ser Thr Lys Gln Thr Ala Glu Thr Ile Leu Thr Phe His
                355                    360                    365

Ala Phe Ala Glu Thr Met Asp Ile Pro Ser Thr His Ile Ala Lys Thr
    370                    375                    380

Leu Ala Ser Glu Trp Leu Gly Ser Pro Gly Thr Leu Gly Gly Thr Ser
385                    390                    395                    400

Thr Ser Ala Leu Thr Thr Thr Ser Pro Ser Thr Thr Leu Val Ser Glu
                405                    410                    415

Glu Thr Asn Thr His His Ser Thr Ser Gly Lys Glu Thr Glu Gly Thr
                420                    425                    430

Leu Asn Thr Ser Met Thr Pro Leu Glu Thr Ser Ala Pro Gly Glu Glu
    435                    440                    445

Ser Glu Met Thr Ala Thr Leu Val Pro Thr Leu Gly Phe Thr Thr Leu
    450                    455                    460

Asp Ser Lys Ile Arg Ser Pro Ser Gln Val Ser Ser Ser His Pro Thr
465                    470                    475                    480

Arg Glu Leu Arg Thr Thr Gly Ser Thr Ser Gly Arg Gln Ser Ser Ser
                485                    490                    495

Thr Ala Ala His Gly Ser Ser Asp Ile Leu Arg Ala Thr Thr Ser Ser
                500                    505                    510

Thr Ser Lys Ala Ser Ser Trp Thr Ser Glu Ser Thr Ala Gln Gln Phe
                515                    520                    525

Ser Glu Pro Gln His Thr Gln Trp Val Glu Thr Ser Pro Ser Met Lys
    530                    535                    540
```

-continued

```
Thr Glu Arg Pro Pro Ala Ser Thr Ser Val Ala Ala Pro Ile Thr Thr
545                 550                 555                 560

Ser Val Pro Ser Val Val Ser Gly Phe Thr Thr Leu Lys Thr Ser Ser
                565                 570                 575

Thr Lys Gly Ile Trp Leu Glu Glu Thr Ser Ala Asp Thr Leu Ile Gly
            580                 585                 590

Glu Ser Thr Ala Gly Pro Thr Thr His Gln Phe Ala Val Pro Thr Gly
            595                 600                 605

Ile Ser Met Thr Gly Gly Ser Ser Thr Arg Gly Ser Gln Gly Thr Thr
            610                 615                 620

His Leu Leu Thr Arg Ala Thr Ala Ser Ser Glu Thr Ser Ala Asp Leu
625                 630                 635                 640

Thr Leu Ala Thr Asn Gly Val Pro Val Ser Val Ser Pro Ala Val Ser
                645                 650                 655

Lys Thr Ala Ala Gly Ser Ser Pro Pro Gly Gly Thr Lys Pro Ser Tyr
                660                 665                 670

Thr Met Val Ser Ser Val Ile Pro Glu Thr Ser Ser Leu Gln Ser Ser
                675                 680                 685

Ala Phe Arg Glu Gly Thr Ser Leu Gly Leu Thr Pro Leu Asn Thr Arg
            690                 695                 700

His Pro Phe Ser Ser Pro Glu Pro Asp Ser Ala Gly His Thr Lys Ile
705                 710                 715                 720

Ser Thr Ser Ile Pro Leu Leu Ser Ser Ala Ser Val Leu Glu Asp Lys
                725                 730                 735

Val Ser Ala Thr Ser Thr Phe Ser His His Lys Ala Thr Ser Ser Ile
                740                 745                 750

Thr Thr Gly Thr Pro Glu Ile Ser Thr Lys Thr Lys Pro Ser Ser Ala
            755                 760                 765

Val Leu Ser Ser Met Thr Leu Ser Asn Ala Ala Thr Ser Pro Glu Arg
            770                 775                 780

Val Arg Asn Ala Thr Ser Pro Leu Thr His Pro Ser Pro Ser Gly Glu
785                 790                 795                 800

Glu Thr Ala Gly Ser Val Leu Thr Leu Ser Thr Ser Ala Glu Thr Thr
                805                 810                 815

Asp Ser Pro Asn Ile His Pro Thr Gly Thr Leu Thr Ser Glu Ser Ser
            820                 825                 830

Glu Ser Pro Ser Thr Leu Ser Leu Pro Ser Val Ser Gly Val Lys Thr
            835                 840                 845

Thr Phe Ser Ser Ser Thr Pro Ser Thr His Leu Phe Thr Ser Gly Glu
            850                 855                 860

Glu Thr Glu Glu Thr Ser Asn Pro Ser Val Ser Gln Pro Glu Thr Ser
865                 870                 875                 880

Val Ser Arg Val Arg Thr Thr Leu Ala Ser Thr Ser Val Pro Thr Pro
                885                 890                 895

Val Phe Pro Thr Met Asp Thr Trp Pro Thr Arg Ser Ala Gln Phe Ser
            900                 905                 910

Ser Ser His Leu Val Ser Glu Leu Arg Ala Thr Ser Ser Thr Ser Val
            915                 920                 925

Thr Asn Ser Thr Gly Ser Ala Leu Pro Lys Ile Ser His Leu Thr Gly
            930                 935                 940

Thr Ala Thr Met Ser Gln Thr Asn Arg Asp Thr Phe Asn Asp Ser Ala
945                 950                 955                 960
```

```
Ala Pro Gln Ser Thr Thr Trp Pro Glu Thr Ser Pro Arg Phe Lys Thr
            965                 970                 975

Gly Leu Pro Ser Ala Thr Thr Thr Val Ser Thr Ser Ala Thr Ser Leu
            980                 985                 990

Ser Ala Thr Val Met Val Ser Lys  Phe Thr Ser Pro Ala  Thr Ser Ser
        995                 1000                1005

Met Glu  Ala Thr Ser Ile Arg  Glu Pro Ser Thr Thr  Ile Leu Thr
    1010                1015                1020

Thr Glu  Thr Thr Asn Gly Pro  Gly Ser Met Ala Val  Ala Ser Thr
    1025                1030                1035

Asn Ile  Pro Ile Gly Lys Gly  Tyr Ile Thr Glu Gly  Arg Leu Asp
    1040                1045                1050

Thr Ser  His Leu Pro Ile Gly  Thr Thr Ala Ser Ser  Glu Thr Ser
    1055                1060                1065

Met Asp  Phe Thr Met Ala Lys  Glu Ser Val Ser Met  Ser Val Ser
    1070                1075                1080

Pro Ser  Gln Ser Met Asp Ala  Ala Gly Ser Ser Thr  Pro Gly Arg
    1085                1090                1095

Thr Ser  Gln Phe Val Asp Thr  Phe Ser Asp Asp Val  Tyr His Leu
    1100                1105                1110

Thr Ser  Arg Glu Ile Thr Ile  Pro Arg Asp Gly Thr  Ser Ser Ala
    1115                1120                1125

Leu Thr  Pro Gln Met Thr Ala  Thr His Pro Pro Ser  Pro Asp Pro
    1130                1135                1140

Gly Ser  Ala Arg Ser Thr Trp  Leu Gly Ile Leu Ser  Ser Ser Pro
    1145                1150                1155

Ser Ser  Pro Thr Pro Lys Val  Thr Met Ser Ser Thr  Phe Ser Thr
    1160                1165                1170

Gln Arg  Val Thr Thr Ser Met  Ile Met Asp Thr Val  Glu Thr Ser
    1175                1180                1185

Arg Trp  Asn Met Pro Asn Leu  Pro Ser Thr Thr Ser  Leu Thr Pro
    1190                1195                1200

Ser Asn  Ile Pro Thr Ser Gly  Ala Ile Gly Lys Ser  Thr Leu Val
    1205                1210                1215

Pro Leu  Asp Thr Pro Ser Pro  Ala Thr Ser Leu Glu  Ala Ser Glu
    1220                1225                1230

Gly Gly  Leu Pro Thr Leu Ser  Thr Tyr Pro Glu Ser  Thr Asn Thr
    1235                1240                1245

Pro Ser  Ile His Leu Gly Ala  His Ala Ser Ser Glu  Ser Pro Ser
    1250                1255                1260

Thr Ile  Lys Leu Thr Met Ala  Ser Val Val Lys Pro  Gly Ser Tyr
    1265                1270                1275

Thr Pro  Leu Thr Phe Pro Ser  Ile Glu Thr His Ile  His Val Ser
    1280                1285                1290

Thr Ala  Arg Met Ala Tyr Ser  Ser Gly Ser Ser Pro  Glu Met Thr
    1295                1300                1305

Ala Pro  Gly Glu Thr Asn Thr  Gly Ser Thr Trp Asp  Pro Thr Thr
    1310                1315                1320

Tyr Ile  Thr Thr Thr Asp Pro  Lys Asp Thr Ser Ser  Ala Gln Val
    1325                1330                1335

Ser Thr  Pro His Ser Val Arg  Thr Leu Arg Thr Thr  Glu Asn His
    1340                1345                1350

Pro Lys  Thr Glu Ser Ala Thr  Pro Ala Ala Tyr Ser  Gly Ser Pro
```

-continued

```
     1355                1360                1365

Lys Ile Ser Ser Ser Pro Asn Leu Thr Ser Pro Ala  Thr Lys Ala
     1370                1375                1380

Trp Thr Ile Thr Asp Thr Thr Glu His Ser Thr Gln  Leu His Tyr
     1385                1390                1395

Thr Lys Leu Ala Glu Lys Ser Ser Gly Phe Glu Thr  Gln Ser Ala
     1400                1405                1410

Pro Gly Pro Val Ser Val Val Ile Pro Thr Ser Pro  Thr Ile Gly
     1415                1420                1425

Ser Ser Thr Leu Glu Leu Thr Ser Asp Val Pro Gly  Glu Pro Leu
     1430                1435                1440

Val Leu Ala Pro Ser Glu Gln Thr Thr Ile Thr Leu  Pro Met Ala
     1445                1450                1455

Thr Trp Leu Ser Thr Ser Leu Thr Glu Glu Met Ala  Ser Thr Asp
     1460                1465                1470

Leu Asp Ile Ser Ser Pro Ser Ser Pro Met Ser Thr  Phe Ala Ile
     1475                1480                1485

Phe Pro Pro Met Ser Thr Pro Ser His Glu Leu Ser  Lys Ser Glu
     1490                1495                1500

Ala Asp Thr Ser Ala Ile Arg Asn Thr Asp Ser Thr  Thr Leu Asp
     1505                1510                1515

Gln His Leu Gly Ile Arg Ser Leu Gly Arg Thr Gly  Asp Leu Thr
     1520                1525                1530

Thr Val Pro Ile Thr Pro Leu Thr Thr Thr Trp Thr  Ser Val Ile
     1535                1540                1545

Glu His Ser Thr Gln Ala Gln Asp Thr Leu Ser Ala  Thr Met Ser
     1550                1555                1560

Pro Thr His Val Thr Gln Ser Leu Lys Asp Gln Thr  Ser Ile Pro
     1565                1570                1575

Ala Ser Ala Ser Pro Ser His Leu Thr Glu Val Tyr  Pro Glu Leu
     1580                1585                1590

Gly Thr Gln Gly Arg Ser Ser Ser Glu Ala Thr Thr  Phe Trp Lys
     1595                1600                1605

Pro Ser Thr Asp Thr Leu Ser Arg Glu Ile Glu Thr  Gly Pro Thr
     1610                1615                1620

Asn Ile Gln Ser Thr Pro Pro Met Asp Asn Thr Thr  Thr Gly Ser
     1625                1630                1635

Ser Ser Ser Gly Val Thr Leu Gly Ile Ala His Leu  Pro Ile Gly
     1640                1645                1650

Thr Ser Ser Pro Ala Glu Thr Ser Thr Asn Met Ala  Leu Glu Arg
     1655                1660                1665

Arg Ser Ser Thr Ala Thr Val Ser Met Ala Gly Thr  Met Gly Leu
     1670                1675                1680

Leu Val Thr Ser Ala Pro Gly Arg Ser Ile Ser Gln  Ser Leu Gly
     1685                1690                1695

Arg Val Ser Ser Val Leu Ser Glu Ser Thr Thr Glu  Gly Val Thr
     1700                1705                1710

Asp Ser Ser Lys Gly Ser Ser Pro Arg Leu Asn Thr  Gln Gly Asn
     1715                1720                1725

Thr Ala Leu Ser Ser Ser Leu Glu Pro Ser Tyr Ala  Glu Gly Ser
     1730                1735                1740

Gln Met Ser Thr Ser Ile Pro Leu Thr Ser Ser Pro  Thr Thr Pro
     1745                1750                1755
```

-continued

```
Asp Val Glu Phe Ile Gly Gly Ser Thr Phe Trp Thr Lys Glu Val
    1760            1765            1770

Thr Thr Val Met Thr Ser Asp Ile Ser Lys Ser Ser Ala Arg Thr
    1775            1780            1785

Glu Ser Ser Ser Ala Thr Leu Met Ser Thr Ala Leu Gly Ser Thr
    1790            1795            1800

Glu Asn Thr Gly Lys Glu Lys Leu Arg Thr Ala Ser Met Asp Leu
    1805            1810            1815

Pro Ser Pro Thr Pro Ser Met Glu Val Thr Pro Trp Ile Ser Leu
    1820            1825            1830

Thr Leu Ser Asn Ala Pro Asn Thr Thr Asp Ser Leu Asp Leu Ser
    1835            1840            1845

His Gly Val His Thr Ser Ser Ala Gly Thr Leu Ala Thr Asp Arg
    1850            1855            1860

Ser Leu Asn Thr Gly Val Thr Arg Ala Ser Arg Leu Glu Asn Gly
    1865            1870            1875

Ser Asp Thr Ser Ser Lys Ser Leu Ser Met Gly Asn Ser Thr His
    1880            1885            1890

Thr Ser Met Thr Tyr Thr Glu Lys Ser Glu Val Ser Ser Ser Ile
    1895            1900            1905

His Pro Arg Pro Glu Thr Ser Ala Pro Gly Ala Glu Thr Thr Leu
    1910            1915            1920

Thr Ser Thr Pro Gly Asn Arg Ala Ile Ser Leu Thr Leu Pro Phe
    1925            1930            1935

Ser Ser Ile Pro Val Glu Glu Val Ile Ser Thr Gly Ile Thr Ser
    1940            1945            1950

Gly Pro Asp Ile Asn Ser Ala Pro Met Thr His Ser Pro Ile Thr
    1955            1960            1965

Pro Pro Thr Ile Val Trp Thr Ser Thr Gly Thr Ile Glu Gln Ser
    1970            1975            1980

Thr Gln Pro Leu His Ala Val Ser Ser Glu Lys Val Ser Val Gln
    1985            1990            1995

Thr Gln Ser Thr Pro Tyr Val Asn Ser Val Ala Val Ser Ala Ser
    2000            2005            2010

Pro Thr His Glu Asn Ser Val Ser Ser Gly Ser Ser Thr Ser Ser
    2015            2020            2025

Pro Tyr Ser Ser Ala Ser Leu Glu Ser Leu Asp Ser Thr Ile Ser
    2030            2035            2040

Arg Arg Asn Ala Ile Thr Ser Trp Leu Trp Asp Leu Thr Thr Ser
    2045            2050            2055

Leu Pro Thr Thr Thr Trp Pro Ser Thr Ser Leu Ser Glu Ala Leu
    2060            2065            2070

Ser Ser Gly His Ser Gly Val Ser Asn Pro Ser Ser Thr Thr Thr
    2075            2080            2085

Glu Phe Pro Leu Phe Ser Ala Ala Ser Thr Ser Ala Ala Lys Gln
    2090            2095            2100

Arg Asn Pro Glu Thr Glu Thr His Gly Pro Gln Asn Thr Ala Ala
    2105            2110            2115

Ser Thr Leu Asn Thr Asp Ala Ser Ser Val Thr Gly Leu Ser Glu
    2120            2125            2130

Thr Pro Val Gly Ala Ser Ile Ser Ser Glu Val Pro Leu Pro Met
    2135            2140            2145
```

-continued

```
Ala Ile  Thr Ser Arg Ser Asp  Val Ser Gly Leu Thr  Ser Glu Ser
2150              2155              2160

Thr Ala  Asn Pro Ser Leu Gly  Thr Ala Ser Ser Ala  Gly Thr Lys
2165              2170              2175

Leu Thr  Arg Thr Ile Ser Leu  Pro Thr Ser Glu Ser  Leu Val Ser
2180              2185              2190

Phe Arg  Met Asn Lys Asp Pro  Trp Thr Val Ser Ile  Pro Leu Gly
2195              2200              2205

Ser His  Pro Thr Thr Asn Thr  Glu Thr Ser Ile Pro  Val Asn Ser
2210              2215              2220

Ala Gly  Pro Pro Gly Leu Ser  Thr Val Ala Ser Asp  Val Ile Asp
2225              2230              2235

Thr Pro  Ser Asp Gly Ala Glu  Ser Ile Pro Thr Val  Ser Phe Ser
2240              2245              2250

Pro Ser  Pro Asp Thr Glu Val  Thr Thr Ile Ser His  Phe Pro Glu
2255              2260              2265

Lys Thr  Thr His Ser Phe Arg  Thr Ile Ser Ser Leu  Thr His Glu
2270              2275              2280

Leu Thr  Ser Arg Val Thr Pro  Ile Pro Gly Asp Trp  Met Ser Ser
2285              2290              2295

Ala Met  Ser Thr Lys Pro Thr  Gly Ala Ser Pro Ser  Ile Thr Leu
2300              2305              2310

Gly Glu  Arg Arg Thr Ile Thr  Ser Ala Ala Pro Thr  Thr Ser Pro
2315              2320              2325

Ile Val  Leu Thr Ala Ser Phe  Thr Glu Thr Ser Thr  Val Ser Leu
2330              2335              2340

Asp Asn  Glu Thr Thr Val Lys  Thr Ser Asp Ile Leu  Asp Ala Arg
2345              2350              2355

Lys Thr  Asn Glu Leu Pro Ser  Asp Ser Ser Ser Ser  Ser Asp Leu
2360              2365              2370

Ile Asn  Thr Ser Ile Ala Ser  Ser Thr Met Asp Val  Thr Lys Thr
2375              2380              2385

Ala Ser  Ile Ser Pro Thr Ser  Ile Ser Gly Met Thr  Ala Ser Ser
2390              2395              2400

Ser Pro  Ser Leu Phe Ser Ser  Asp Arg Pro Gln Val  Pro Thr Ser
2405              2410              2415

Thr Thr  Glu Thr Asn Thr Ala  Thr Ser Pro Ser Val  Ser Ser Asn
2420              2425              2430

Thr Tyr  Ser Leu Asp Gly Gly  Ser Asn Val Gly Gly  Thr Pro Ser
2435              2440              2445

Thr Leu  Pro Pro Phe Thr Ile  Thr His Pro Val Glu  Thr Ser Ser
2450              2455              2460

Ala Leu  Leu Ala Trp Ser Arg  Pro Val Arg Thr Phe  Ser Thr Met
2465              2470              2475

Val Ser  Thr Asp Thr Ala Ser  Gly Glu Asn Pro Thr  Ser Ser Asn
2480              2485              2490

Ser Val  Val Thr Ser Val Pro  Ala Pro Gly Thr Trp  Thr Ser Val
2495              2500              2505

Gly Ser  Thr Thr Asp Leu Pro  Ala Met Gly Phe Leu  Lys Thr Ser
2510              2515              2520

Pro Ala  Gly Glu Ala His Ser  Leu Leu Ala Ser Thr  Ile Glu Pro
2525              2530              2535

Ala Thr  Ala Phe Thr Pro His  Leu Ser Ala Ala Val  Val Thr Gly
```

-continued

```
        2540              2545              2550

Ser Ser  Ala Thr Ser Glu Ala  Ser Leu Leu Thr Thr  Ser Glu Ser
    2555              2560              2565

Lys Ala  Ile His Ser Ser Pro  Gln Thr Pro Thr Thr  Pro Thr Ser
    2570              2575              2580

Gly Ala  Asn Trp Glu Thr Ser  Ala Thr Pro Glu Ser  Leu Leu Val
    2585              2590              2595

Val Thr  Glu Thr Ser Asp Thr  Thr Leu Thr Ser Lys  Ile Leu Val
    2600              2605              2610

Thr Asp  Thr Ile Leu Phe Ser  Thr Val Ser Thr Pro  Pro Ser Lys
    2615              2620              2625

Phe Pro  Ser Thr Gly Thr Leu  Ser Gly Ala Ser Phe  Pro Thr Leu
    2630              2635              2640

Leu Pro  Asp Thr Pro Ala Ile  Pro Leu Thr Ala Thr  Glu Pro Thr
    2645              2650              2655

Ser Ser  Leu Ala Thr Ser Phe  Asp Ser Thr Pro Leu  Val Thr Ile
    2660              2665              2670

Ala Ser  Asp Ser Leu Gly Thr  Val Pro Glu Thr Thr  Leu Thr Met
    2675              2680              2685

Ser Glu  Thr Ser Asn Gly Asp  Ala Leu Val Leu Lys  Thr Val Ser
    2690              2695              2700

Asn Pro  Asp Arg Ser Ile Pro  Gly Ile Thr Ile Gln  Gly Val Thr
    2705              2710              2715

Glu Ser  Pro Leu His Pro Ser  Ser Thr Ser Pro Ser  Lys Ile Val
    2720              2725              2730

Ala Pro  Arg Asn Thr Thr Tyr  Glu Gly Ser Ile Thr  Val Ala Leu
    2735              2740              2745

Ser Thr  Leu Pro Ala Gly Thr  Thr Gly Ser Leu Val  Phe Ser Gln
    2750              2755              2760

Ser Ser  Glu Asn Ser Glu Thr  Thr Ala Leu Val Asp  Ser Ser Ala
    2765              2770              2775

Gly Leu  Glu Arg Ala Ser Val  Met Pro Leu Thr Thr  Gly Ser Gln
    2780              2785              2790

Gly Met  Ala Ser Ser Gly Gly  Ile Arg Ser Gly Ser  Thr His Ser
    2795              2800              2805

Thr Gly  Thr Lys Thr Phe Ser  Ser Leu Pro Leu Thr  Met Asn Pro
    2810              2815              2820

Gly Glu  Val Thr Ala Met Ser  Glu Ile Thr Thr Asn  Arg Leu Thr
    2825              2830              2835

Ala Thr  Gln Ser Thr Ala Pro  Lys Gly Ile Pro Val  Lys Pro Thr
    2840              2845              2850

Ser Ala  Glu Ser Gly Leu Leu  Thr Pro Val Ser Ala  Ser Ser Ser
    2855              2860              2865

Pro Ser  Lys Ala Phe Ala Ser  Leu Thr Thr Ala Pro  Pro Thr Trp
    2870              2875              2880

Gly Ile  Pro Gln Ser Thr Leu  Thr Phe Glu Phe Ser  Glu Val Pro
    2885              2890              2895

Ser Leu  Asp Thr Lys Ser Ala  Ser Leu Pro Thr Pro  Gly Gln Ser
    2900              2905              2910

Leu Asn  Thr Ile Pro Asp Ser  Asp Ala Ser Thr Ala  Ser Ser Ser
    2915              2920              2925

Leu Ser  Lys Ser Pro Glu Lys  Asn Pro Arg Ala Arg  Met Met Thr
    2930              2935              2940
```

```
Ser Thr Lys Ala Ile Ser Ala  Ser Ser Phe Gln Ser  Thr Gly Phe
2945                2950              2955

Thr Glu Thr Pro Glu Gly Ser  Ala Ser Pro Ser Met  Ala Gly His
2960                2965              2970

Glu Pro Arg Val Pro Thr Ser  Gly Thr Gly Asp Pro  Arg Tyr Ala
2975                2980              2985

Ser Glu Ser Met Ser Tyr Pro  Asp Pro Ser Lys Ala  Ser Ser Ala
2990                2995              3000

Met Thr Ser Thr Ser Leu Ala  Ser Lys Leu Thr Thr  Leu Phe Ser
3005                3010              3015

Thr Gly Gln Ala Ala Arg Ser  Gly Ser Ser Ser Ser  Pro Ile Ser
3020                3025              3030

Leu Ser Thr Glu Lys Glu Thr  Ser Phe Leu Ser Pro  Thr Ala Ser
3035                3040              3045

Thr Ser Arg Lys Thr Ser Leu  Phe Leu Gly Pro Ser  Met Ala Arg
3050                3055              3060

Gln Pro Asn Ile Leu Val His  Leu Gln Thr Ser Ala  Leu Thr Leu
3065                3070              3075

Ser Pro Thr Ser Thr Leu Asn  Met Ser Gln Glu Glu  Pro Pro Glu
3080                3085              3090

Leu Thr Ser Ser Gln Thr Ile  Ala Glu Glu Glu Gly  Thr Thr Ala
3095                3100              3105

Glu Thr Gln Thr Leu Thr Phe  Thr Pro Ser Glu Thr  Pro Thr Ser
3110                3115              3120

Leu Leu Pro Val Ser Ser Pro  Thr Glu Pro Thr Ala  Arg Arg Lys
3125                3130              3135

Ser Ser Pro Glu Thr Trp Ala  Ser Ser Ile Ser Val  Pro Ala Lys
3140                3145              3150

Thr Ser Leu Val Glu Thr Thr  Asp Gly Thr Leu Val  Thr Thr Ile
3155                3160              3165

Lys Met Ser Ser Gln Ala Ala  Gln Gly Asn Ser Thr  Trp Pro Ala
3170                3175              3180

Pro Ala Glu Glu Thr Gly Ser  Ser Pro Ala Gly Thr  Ser Pro Gly
3185                3190              3195

Ser Pro Glu Met Ser Thr Thr  Leu Lys Ile Met Ser  Ser Lys Glu
3200                3205              3210

Pro Ser Ile Ser Pro Glu Ile  Arg Ser Thr Val Arg  Asn Ser Pro
3215                3220              3225

Trp Lys Thr Pro Glu Thr Thr  Val Pro Met Glu Thr  Thr Val Glu
3230                3235              3240

Pro Val Thr Leu Gln Ser Thr  Ala Leu Gly Ser Gly  Ser Thr Ser
3245                3250              3255

Ile Ser His Leu Pro Thr Gly  Thr Thr Ser Pro Thr  Lys Ser Pro
3260                3265              3270

Thr Glu Asn Met Leu Ala Thr  Glu Arg Val Ser Leu  Ser Pro Ser
3275                3280              3285

Pro Pro Glu Ala Trp Thr Asn  Leu Tyr Ser Gly Thr  Pro Gly Gly
3290                3295              3300

Thr Arg Gln Ser Leu Ala Thr  Met Ser Ser Val Ser  Leu Glu Ser
3305                3310              3315

Pro Thr Ala Arg Ser Ile Thr  Gly Thr Gly Gln Gln  Ser Ser Pro
3320                3325              3330
```

-continued

```
Glu Leu Val Ser Lys Thr Thr  Gly Met Glu Phe Ser  Met Trp His
    3335              3340              3345

Gly Ser  Thr Gly Gly Thr Thr  Gly Asp Thr His Val  Ser Leu Ser
    3350              3355              3360

Thr Ser  Ser Asn Ile Leu Glu  Asp Pro Val Thr Ser  Pro Asn Ser
    3365              3370              3375

Val Ser  Ser Leu Thr Asp Lys  Ser Lys His Lys Thr  Glu Thr Trp
    3380              3385              3390

Val Ser  Thr Thr Ala Ile Pro  Ser Thr Val Leu Asn  Asn Lys Ile
    3395              3400              3405

Met Ala  Ala Glu Gln Gln Thr  Ser Arg Ser Val Asp  Glu Ala Tyr
    3410              3415              3420

Ser Ser  Thr Ser Ser Trp Ser  Asp Gln Thr Ser Gly  Ser Asp Ile
    3425              3430              3435

Thr Leu  Gly Ala Ser Pro Asp  Val Thr Asn Thr Leu  Tyr Ile Thr
    3440              3445              3450

Ser Thr  Ala Gln Thr Thr Ser  Leu Val Ser Leu Pro  Ser Gly Asp
    3455              3460              3465

Gln Gly  Ile Thr Ser Leu Thr  Asn Pro Ser Gly Gly  Lys Thr Ser
    3470              3475              3480

Ser Ala  Ser Ser Val Thr Ser  Pro Ser Ile Gly Leu  Glu Thr Leu
    3485              3490              3495

Arg Ala  Asn Val Ser Ala Val  Lys Ser Asp Ile Ala  Pro Thr Ala
    3500              3505              3510

Gly His  Leu Ser Gln Thr Ser  Ser Pro Ala Glu Val  Ser Ile Leu
    3515              3520              3525

Asp Val  Thr Thr Ala Pro Thr  Pro Gly Ile Ser Thr  Thr Ile Thr
    3530              3535              3540

Thr Met  Gly Thr Asn Ser Ile  Ser Thr Thr Thr Pro  Asn Pro Glu
    3545              3550              3555

Val Gly  Met Ser Thr Met Asp  Ser Thr Pro Ala Thr  Glu Arg Arg
    3560              3565              3570

Thr Thr  Ser Thr Glu His Pro  Ser Thr Trp Ser Ser  Thr Ala Ala
    3575              3580              3585

Ser Asp  Ser Trp Thr Val Thr  Asp Met Thr Ser Asn  Leu Lys Val
    3590              3595              3600

Ala Arg  Ser Pro Gly Thr Ile  Ser Thr Met His Thr  Thr Ser Phe
    3605              3610              3615

Leu Ala  Ser Ser Thr Glu Leu  Asp Ser Met Ser Thr  Pro His Gly
    3620              3625              3630

Arg Ile  Thr Val Ile Gly Thr  Ser Leu Val Thr Pro  Ser Ser Asp
    3635              3640              3645

Ala Ser  Ala Val Lys Thr Glu  Thr Ser Thr Ser Glu  Arg Thr Leu
    3650              3655              3660

Ser Pro  Ser Asp Thr Thr Ala  Ser Thr Pro Ile Ser  Thr Phe Ser
    3665              3670              3675

Arg Val  Gln Arg Met Ser Ile  Ser Val Pro Asp Ile  Leu Ser Thr
    3680              3685              3690

Ser Trp  Thr Pro Ser Ser Thr  Glu Ala Glu Asp Val  Pro Val Ser
    3695              3700              3705

Met Val  Ser Thr Asp His Ala  Ser Thr Lys Thr Asp  Pro Asn Thr
    3710              3715              3720

Pro Leu  Ser Thr Phe Leu Phe  Asp Ser Leu Ser Thr  Leu Asp Trp
```

```
        3725                3730                3735

Asp Thr  Gly Arg Ser Leu Ser  Ser Ala Thr Ala Thr  Thr Ser Ala
    3740                3745                3750

Pro Gln  Gly Ala Thr Thr Pro  Gln Glu Leu Thr Leu  Glu Thr Met
    3755                3760                3765

Ile Ser  Pro Ala Thr Ser Gln  Leu Pro Phe Ser Ile  Gly His Ile
    3770                3775                3780

Thr Ser  Ala Val Thr Pro Ala  Ala Met Ala Arg Ser  Ser Gly Val
    3785                3790                3795

Thr Phe  Ser Arg Pro Asp Pro  Thr Ser Lys Lys Ala  Glu Gln Thr
    3800                3805                3810

Ser Thr  Gln Leu Pro Thr Thr  Thr Ser Ala His Pro  Gly Gln Val
    3815                3820                3825

Pro Arg  Ser Ala Ala Thr Thr  Leu Asp Val Ile Pro  His Thr Ala
    3830                3835                3840

Lys Thr  Pro Asp Ala Thr Phe  Gln Arg Gln Gly Gln  Thr Ala Leu
    3845                3850                3855

Thr Thr  Glu Ala Arg Ala Thr  Ser Asp Ser Trp Asn  Glu Lys Glu
    3860                3865                3870

Lys Ser  Thr Pro Ser Ala Pro  Trp Ile Thr Glu Met  Met Asn Ser
    3875                3880                3885

Val Ser  Glu Asp Thr Ile Lys  Glu Val Thr Ser Ser  Ser Ser Val
    3890                3895                3900

Leu Arg  Thr Leu Asn Thr Leu  Asp Ile Asn Leu Glu  Ser Gly Thr
    3905                3910                3915

Thr Ser  Ser Pro Ser Trp Lys  Ser Ser Pro Tyr Glu  Arg Ile Ala
    3920                3925                3930

Pro Ser  Glu Ser Thr Thr Asp  Lys Glu Ala Ile His  Pro Ser Thr
    3935                3940                3945

Asn Thr  Val Glu Thr Thr Gly  Trp Val Thr Ser Ser  Glu His Ala
    3950                3955                3960

Ser His  Ser Thr Ile Pro Ala  His Ser Ala Ser Ser  Lys Leu Thr
    3965                3970                3975

Ser Pro  Val Val Thr Thr Ser  Thr Arg Glu Gln Ala  Ile Val Ser
    3980                3985                3990

Met Ser  Thr Thr Thr Trp Pro  Glu Ser Thr Arg Ala  Arg Thr Glu
    3995                4000                4005

Pro Asn  Ser Phe Leu Thr Ile  Glu Leu Arg Asp Val  Ser Pro Tyr
    4010                4015                4020

Met Asp  Thr Ser Ser Thr Thr  Gln Thr Ser Ile Ile  Ser Ser Pro
    4025                4030                4035

Gly Ser  Thr Ala Ile Thr Lys  Gly Pro Arg Thr Glu  Ile Thr Ser
    4040                4045                4050

Ser Lys  Arg Ile Ser Ser Ser  Phe Leu Ala Gln Ser  Met Arg Ser
    4055                4060                4065

Ser Asp  Ser Pro Ser Glu Ala  Ile Thr Arg Leu Ser  Asn Phe Pro
    4070                4075                4080

Ala Met  Thr Glu Ser Gly Gly  Met Ile Leu Ala Met  Gln Thr Ser
    4085                4090                4095

Pro Pro  Gly Ala Thr Ser Leu  Ser Ala Pro Thr Leu  Asp Thr Ser
    4100                4105                4110

Ala Thr  Ala Ser Trp Thr Gly  Thr Pro Leu Ala Thr  Thr Gln Arg
    4115                4120                4125
```

-continued

```
Phe Thr Tyr Ser Glu Lys Thr  Thr Leu Phe Ser Lys  Gly Pro Glu
    4130                4135                 4140

Asp Thr Ser Gln Pro Ser Pro  Pro Ser Val Glu Glu  Thr Ser Ser
    4145                4150                 4155

Ser Ser Ser Leu Val Pro Ile  His Ala Thr Thr Ser  Pro Ser Asn
    4160                4165                 4170

Ile Leu Leu Thr Ser Gln Gly  His Ser Pro Ser Ser  Thr Pro Pro
    4175                4180                 4185

Val Thr Ser Val Phe Leu Ser  Glu Thr Ser Gly Leu  Gly Lys Thr
    4190                4195                 4200

Thr Asp Met Ser Arg Ile Ser  Leu Glu Pro Gly Thr  Ser Leu Pro
    4205                4210                 4215

Pro Asn Leu Ser Ser Thr Ala  Gly Glu Ala Leu Ser  Thr Tyr Glu
    4220                4225                 4230

Ala Ser Arg Asp Thr Lys Ala  Ile His His Ser Ala  Asp Thr Ala
    4235                4240                 4245

Val Thr Asn Met Glu Ala Thr  Ser Ser Glu Tyr Ser  Pro Ile Pro
    4250                4255                 4260

Gly His Thr Lys Pro Ser Lys  Ala Thr Ser Pro Leu  Val Thr Ser
    4265                4270                 4275

His Ile Met Gly Asp Ile Thr  Ser Ser Thr Ser Val  Phe Gly Ser
    4280                4285                 4290

Ser Glu Thr Thr Glu Ile Glu  Thr Val Ser Ser Val  Asn Gln Gly
    4295                4300                 4305

Leu Gln Glu Arg Ser Thr Ser  Gln Val Ala Ser Ser  Ala Thr Glu
    4310                4315                 4320

Thr Ser Thr Val Ile Thr His  Val Ser Ser Gly Asp  Ala Thr Thr
    4325                4330                 4335

His Val Thr Lys Thr Gln Ala  Thr Phe Ser Ser Gly  Thr Ser Ile
    4340                4345                 4350

Ser Ser Pro His Gln Phe Ile  Thr Ser Thr Asn Thr  Phe Thr Asp
    4355                4360                 4365

Val Ser Thr Asn Pro Ser Thr  Ser Leu Ile Met Thr  Glu Ser Ser
    4370                4375                 4380

Gly Val Thr Ile Thr Thr Gln  Thr Gly Pro Thr Gly  Ala Ala Thr
    4385                4390                 4395

Gln Gly Pro Tyr Leu Leu Asp  Thr Ser Thr Met Pro  Tyr Leu Thr
    4400                4405                 4410

Glu Thr Pro Leu Ala Val Thr  Pro Asp Phe Met Gln  Ser Glu Lys
    4415                4420                 4425

Thr Thr Leu Ile Ser Lys Gly  Pro Lys Asp Val Ser  Trp Thr Ser
    4430                4435                 4440

Pro Pro Ser Val Ala Glu Thr  Ser Tyr Pro Ser Ser  Leu Thr Pro
    4445                4450                 4455

Phe Leu Val Thr Thr Ile Pro  Pro Ala Thr Ser Thr  Leu Gln Gly
    4460                4465                 4470

Gln His Thr Ser Ser Pro Val  Ser Ala Thr Ser Val  Leu Thr Ser
    4475                4480                 4485

Gly Leu Val Lys Thr Thr Asp  Met Leu Asn Thr Ser  Met Glu Pro
    4490                4495                 4500

Val Thr Asn Ser Pro Gln Asn  Leu Asn Asn Pro Ser  Asn Glu Ile
    4505                4510                 4515
```

-continued

```
Leu Ala  Thr Leu Ala Ala Thr  Thr Asp Ile Glu Thr  Ile His Pro
    4520                  4525                  4530

Ser Ile  Asn Lys Ala Val Thr  Asn Met Gly Thr Ala  Ser Ser Ala
    4535                  4540                  4545

His Val  Leu His Ser Thr Leu  Pro Val Ser Ser Glu  Pro Ser Thr
    4550                  4555                  4560

Ala Thr  Ser Pro Met Val Pro  Ala Ser Ser Met Gly  Asp Ala Leu
    4565                  4570                  4575

Ala Ser  Ile Ser Ile Pro Gly  Ser Glu Thr Thr Asp  Ile Glu Gly
    4580                  4585                  4590

Glu Pro  Thr Ser Ser Leu Thr  Ala Gly Arg Lys Glu  Asn Ser Thr
    4595                  4600                  4605

Leu Gln  Glu Met Asn Ser Thr  Thr Glu Ser Asn Ile  Ile Leu Ser
    4610                  4615                  4620

Asn Val  Ser Val Gly Ala Ile  Thr Glu Ala Thr Lys  Met Glu Val
    4625                  4630                  4635

Pro Ser  Phe Asp Ala Thr Phe  Ile Pro Thr Pro Ala  Gln Ser Thr
    4640                  4645                  4650

Lys Phe  Pro Asp Ile Phe Ser  Val Ala Ser Ser Arg  Leu Ser Asn
    4655                  4660                  4665

Ser Pro  Pro Met Thr Ile Ser  Thr His Met Thr Thr  Thr Gln Thr
    4670                  4675                  4680

Gly Ser  Ser Gly Ala Thr Ser  Lys Ile Pro Leu Ala  Leu Asp Thr
    4685                  4690                  4695

Ser Thr  Leu Glu Thr Ser Ala  Gly Thr Pro Ser Val  Val Thr Glu
    4700                  4705                  4710

Gly Phe  Ala His Ser Lys Ile  Thr Thr Ala Met Asn  Asn Asp Val
    4715                  4720                  4725

Lys Asp  Val Ser Gln Thr Asn  Pro Pro Phe Gln Asp  Glu Ala Ser
    4730                  4735                  4740

Ser Pro  Ser Ser Gln Ala Pro  Val Leu Val Thr Thr  Leu Pro Ser
    4745                  4750                  4755

Ser Val  Ala Phe Thr Pro Gln  Trp His Ser Thr Ser  Ser Pro Val
    4760                  4765                  4770

Ser Met  Ser Ser Val Leu Thr  Ser Ser Leu Val Lys  Thr Ala Gly
    4775                  4780                  4785

Lys Val  Asp Thr Ser Leu Glu  Thr Val Thr Ser Ser  Pro Gln Ser
    4790                  4795                  4800

Met Ser  Asn Thr Leu Asp Asp  Ile Ser Val Thr Ser  Ala Ala Thr
    4805                  4810                  4815

Thr Asp  Ile Glu Thr Thr His  Pro Ser Ile Asn Thr  Val Val Thr
    4820                  4825                  4830

Asn Val  Gly Thr Thr Gly Ser  Ala Phe Glu Ser His  Ser Thr Val
    4835                  4840                  4845

Ser Ala  Tyr Pro Glu Pro Ser  Lys Val Thr Ser Pro  Asn Val Thr
    4850                  4855                  4860

Thr Ser  Thr Met Glu Asp Thr  Thr Ile Ser Arg Ser  Ile Pro Lys
    4865                  4870                  4875

Ser Ser  Lys Thr Thr Arg Thr  Glu Thr Glu Thr Thr  Ser Ser Leu
    4880                  4885                  4890

Thr Pro  Lys Leu Arg Glu Thr  Ser Ile Ser Gln Glu  Ile Thr Ser
    4895                  4900                  4905

Ser Thr  Glu Thr Ser Thr Val  Pro Tyr Lys Glu Leu  Thr Gly Ala
```

```
        4910                    4915                    4920

Thr Thr  Glu Val Ser Arg Thr  Asp Val Thr Ser Ser  Ser Ser Thr
    4925                    4930                    4935

Ser Phe  Pro Gly Pro Asp Gln  Ser Thr Val Ser Leu  Asp Ile Ser
    4940                    4945                    4950

Thr Glu  Thr Asn Thr Arg Leu  Ser Thr Ser Pro Ile  Met Thr Glu
    4955                    4960                    4965

Ser Ala  Glu Ile Thr Ile Thr  Thr Gln Thr Gly Pro  His Gly Ala
    4970                    4975                    4980

Thr Ser  Gln Asp Thr Phe Thr  Met Asp Pro Ser Asn  Thr Thr Pro
    4985                    4990                    4995

Gln Ala  Gly Ile His Ser Ala  Met Thr His Gly Phe  Ser Gln Leu
    5000                    5005                    5010

Asp Val  Thr Thr Leu Met Ser  Arg Ile Pro Gln Asp  Val Ser Trp
    5015                    5020                    5025

Thr Ser  Pro Pro Ser Val Asp  Lys Thr Ser Ser Pro  Ser Ser Phe
    5030                    5035                    5040

Leu Ser  Ser Pro Ala Met Thr  Thr Pro Ser Leu Ile  Ser Ser Thr
    5045                    5050                    5055

Leu Pro  Glu Asp Lys Leu Ser  Ser Pro Met Thr Ser  Leu Leu Thr
    5060                    5065                    5070

Ser Gly  Leu Val Lys Ile Thr  Asp Ile Leu Arg Thr  Arg Leu Glu
    5075                    5080                    5085

Pro Val  Thr Ser Ser Leu Pro  Asn Phe Ser Ser Thr  Ser Asp Lys
    5090                    5095                    5100

Ile Leu  Ala Thr Ser Lys Asp  Ser Lys Asp Thr Lys  Glu Ile Phe
    5105                    5110                    5115

Pro Ser  Ile Asn Thr Glu Glu  Thr Asn Val Lys Ala  Asn Asn Ser
    5120                    5125                    5130

Gly His  Glu Ser His Ser Pro  Ala Leu Ala Asp Ser  Glu Thr Pro
    5135                    5140                    5145

Lys Ala  Thr Thr Gln Met Val  Ile Thr Thr Thr Val  Gly Asp Pro
    5150                    5155                    5160

Ala Pro  Ser Thr Ser Met Pro  Val His Gly Ser Ser  Glu Thr Thr
    5165                    5170                    5175

Asn Ile  Lys Arg Glu Pro Thr  Tyr Phe Leu Thr Pro  Arg Leu Arg
    5180                    5185                    5190

Glu Thr  Ser Thr Ser Gln Glu  Ser Ser Phe Pro Thr  Asp Thr Ser
    5195                    5200                    5205

Phe Leu  Leu Ser Lys Val Pro  Thr Gly Thr Ile Thr  Glu Val Ser
    5210                    5215                    5220

Ser Thr  Gly Val Asn Ser Ser  Ser Lys Ile Ser Thr  Pro Asp His
    5225                    5230                    5235

Asp Lys  Ser Thr Val Pro Pro  Asp Thr Phe Thr Gly  Glu Ile Pro
    5240                    5245                    5250

Arg Val  Phe Thr Ser Ser Ile  Lys Thr Lys Ser Ala  Glu Met Thr
    5255                    5260                    5265

Ile Thr  Thr Gln Ala Ser Pro  Pro Glu Ser Ala Ser  His Ser Thr
    5270                    5275                    5280

Leu Pro  Leu Asp Thr Ser Thr  Thr Leu Ser Gln Gly  Gly Thr His
    5285                    5290                    5295

Ser Thr  Val Thr Gln Gly Phe  Pro Tyr Ser Glu Val  Thr Thr Leu
    5300                    5305                    5310
```

-continued

```
Met Gly Met Gly Pro Gly Asn  Val Ser Trp Met Thr  Thr Pro Pro
5315               5320             5325

Val Glu Glu Thr Ser Ser Val  Ser Ser Leu Met Ser  Ser Pro Ala
5330               5335             5340

Met Thr Ser Pro Ser Pro Val  Ser Ser Thr Ser Pro  Gln Ser Ile
5345               5350             5355

Pro Ser Ser Pro Leu Pro Val  Thr Ala Leu Pro Thr  Ser Val Leu
5360               5365             5370

Val Thr Thr Thr Asp Val Leu  Gly Thr Thr Ser Pro  Glu Ser Val
5375               5380             5385

Thr Ser Ser Pro Pro Asn Leu  Ser Ser Ile Thr His  Glu Arg Pro
5390               5395             5400

Ala Thr Tyr Lys Asp Thr Ala  His Thr Glu Ala Ala  Met His His
5405               5410             5415

Ser Thr Asn Thr Ala Val Thr  Asn Val Gly Thr Ser  Gly Ser Gly
5420               5425             5430

His Lys Ser Gln Ser Ser Val  Leu Ala Asp Ser Glu  Thr Ser Lys
5435               5440             5445

Ala Thr Pro Leu Met Ser Thr  Thr Ser Thr Leu Gly  Asp Thr Ser
5450               5455             5460

Val Ser Thr Ser Thr Pro Asn  Ile Ser Gln Thr Asn  Gln Ile Gln
5465               5470             5475

Thr Glu Pro Thr Ala Ser Leu  Ser Pro Arg Leu Arg  Glu Ser Ser
5480               5485             5490

Thr Ser Glu Lys Thr Ser Ser  Thr Thr Glu Thr Asn  Thr Ala Phe
5495               5500             5505

Ser Tyr Val Pro Thr Gly Ala  Ile Thr Gln Ala Ser  Arg Thr Glu
5510               5515             5520

Ile Ser Ser Ser Arg Thr Ser  Ile Ser Asp Leu Asp  Arg Pro Thr
5525               5530             5535

Ile Ala Pro Asp Ile Ser Thr  Gly Met Ile Thr Arg  Leu Phe Thr
5540               5545             5550

Ser Pro Ile Met Thr Lys Ser  Ala Glu Met Thr Val  Thr Thr Gln
5555               5560             5565

Thr Thr Thr Pro Gly Ala Thr  Ser Gln Gly Ile Leu  Pro Trp Asp
5570               5575             5580

Thr Ser Thr Thr Leu Phe Gln  Gly Gly Thr His Ser  Thr Val Ser
5585               5590             5595

Gln Gly Phe Pro His Ser Glu  Ile Thr Thr Leu Arg  Ser Arg Thr
5600               5605             5610

Pro Gly Asp Val Ser Trp Met  Thr Thr Pro Pro Val  Glu Glu Thr
5615               5620             5625

Ser Ser Gly Phe Ser Leu Met  Ser Pro Ser Met Thr  Ser Pro Ser
5630               5635             5640

Pro Val Ser Ser Thr Ser Pro  Glu Ser Ile Pro Ser  Ser Pro Leu
5645               5650             5655

Pro Val Thr Ala Leu Leu Thr  Ser Val Leu Val Thr  Thr Thr Asn
5660               5665             5670

Val Leu Gly Thr Thr Ser Pro  Glu Pro Val Thr Ser  Ser Pro Pro
5675               5680             5685

Asn Leu Ser Ser Pro Thr Gln  Glu Arg Leu Thr Thr  Tyr Lys Asp
5690               5695             5700
```

-continued

```
Thr Ala His Thr Glu Ala Met   His Ala Ser Met His   Thr Asn Thr
    5705              5710                5715

Ala Val Ala Asn Val Gly Thr   Ser Ile Ser Gly His   Glu Ser Gln
    5720              5725                5730

Ser Ser Val Pro Ala Asp Ser   His Thr Ser Lys Ala   Thr Ser Pro
    5735              5740                5745

Met Gly Ile Thr Phe Ala Met   Gly Asp Thr Ser Val   Ser Thr Ser
    5750              5755                5760

Thr Pro Ala Phe Phe Glu Thr   Arg Ile Gln Thr Glu   Ser Thr Ser
    5765              5770                5775

Ser Leu Ile Pro Gly Leu Arg   Asp Thr Arg Thr Ser   Glu Glu Ile
    5780              5785                5790

Asn Thr Val Thr Glu Thr Ser   Thr Val Leu Ser Glu   Val Pro Thr
    5795              5800                5805

Thr Thr Thr Thr Glu Val Ser   Arg Thr Glu Val Ile   Thr Ser Ser
    5810              5815                5820

Arg Thr Thr Ile Ser Gly Pro   Asp His Ser Lys Met   Ser Pro Tyr
    5825              5830                5835

Ile Ser Thr Glu Thr Ile Thr   Arg Leu Ser Thr Phe   Pro Phe Val
    5840              5845                5850

Thr Gly Ser Thr Glu Met Ala   Ile Thr Asn Gln Thr   Gly Pro Ile
    5855              5860                5865

Gly Thr Ile Ser Gln Ala Thr   Leu Thr Leu Asp Thr   Ser Ser Thr
    5870              5875                5880

Ala Ser Trp Glu Gly Thr His   Ser Pro Val Thr Gln   Arg Phe Pro
    5885              5890                5895

His Ser Glu Glu Thr Thr Thr   Met Ser Arg Ser Thr   Lys Gly Val
    5900              5905                5910

Ser Trp Gln Ser Pro Pro Ser   Val Glu Glu Thr Ser   Ser Pro Ser
    5915              5920                5925

Ser Pro Val Pro Leu Pro Ala   Ile Thr Ser His Ser   Ser Leu Tyr
    5930              5935                5940

Ser Ala Val Ser Gly Ser Ser   Pro Thr Ser Ala Leu   Pro Val Thr
    5945              5950                5955

Ser Leu Leu Thr Ser Gly Arg   Arg Lys Thr Ile Asp   Met Leu Asp
    5960              5965                5970

Thr His Ser Glu Leu Val Thr   Ser Ser Leu Pro Ser   Ala Ser Ser
    5975              5980                5985

Phe Ser Gly Glu Ile Leu Thr   Ser Glu Ala Ser Thr   Asn Thr Glu
    5990              5995                6000

Thr Ile His Phe Ser Glu Asn   Thr Ala Glu Thr Asn   Met Gly Thr
    6005              6010                6015

Thr Asn Ser Met His Lys Leu   His Ser Ser Val Ser   Ile His Ser
    6020              6025                6030

Gln Pro Ser Gly His Thr Pro   Pro Lys Val Thr Gly   Ser Met Met
    6035              6040                6045

Glu Asp Ala Ile Val Ser Thr   Ser Thr Pro Gly Ser   Pro Glu Thr
    6050              6055                6060

Lys Asn Val Asp Arg Asp Ser   Thr Ser Pro Leu Thr   Pro Glu Leu
    6065              6070                6075

Lys Glu Asp Ser Thr Ala Leu   Val Met Asn Ser Thr   Thr Glu Ser
    6080              6085                6090

Asn Thr Val Phe Ser Ser Val   Ser Leu Asp Ala Ala   Thr Glu Val
```

-continued

```
        6095            6100            6105

Ser Arg  Ala Glu Val Thr Tyr  Tyr Asp Pro Thr Phe  Met Pro Ala
    6110            6115            6120

Ser Ala  Gln Ser Thr Lys Ser  Pro Asp Ile Ser Pro  Glu Ala Ser
    6125            6130            6135

Ser Ser  His Ser Asn Ser Pro  Pro Leu Thr Ile Ser  Thr His Lys
    6140            6145            6150

Thr Ile  Ala Thr Gln Thr Gly  Pro Ser Gly Val Thr  Ser Leu Gly
    6155            6160            6165

Gln Leu  Thr Leu Asp Thr Ser  Thr Ile Ala Thr Ser  Ala Gly Thr
    6170            6175            6180

Pro Ser  Ala Arg Thr Gln Asp  Phe Val Asp Ser Glu  Thr Thr Ser
    6185            6190            6195

Val Met  Asn Asn Asp Leu Asn  Asp Val Leu Lys Thr  Ser Pro Phe
    6200            6205            6210

Ser Ala  Glu Glu Ala Asn Ser  Leu Ser Ser Gln Ala  Pro Leu Leu
    6215            6220            6225

Val Thr  Thr Ser Pro Ser Pro  Val Thr Ser Thr Leu  Gln Glu His
    6230            6235            6240

Ser Thr  Ser Ser Leu Val Ser  Val Thr Ser Val Pro  Thr Pro Thr
    6245            6250            6255

Leu Ala  Lys Ile Thr Asp Met  Asp Thr Asn Leu Glu  Pro Val Thr
    6260            6265            6270

Arg Ser  Pro Gln Asn Leu Arg  Asn Thr Leu Ala Thr  Ser Glu Ala
    6275            6280            6285

Thr Thr  Asp Thr His Thr Met  His Pro Ser Ile Asn  Thr Ala Val
    6290            6295            6300

Ala Asn  Val Gly Thr Thr Ser  Ser Pro Asn Glu Phe  Tyr Phe Thr
    6305            6310            6315

Val Ser  Pro Asp Ser Asp Pro  Tyr Lys Ala Thr Ser  Ala Val Val
    6320            6325            6330

Ile Thr  Ser Thr Ser Gly Asp  Ser Ile Val Ser Thr  Ser Met Pro
    6335            6340            6345

Arg Ser  Ser Ala Met Lys Lys  Ile Glu Ser Glu Thr  Thr Phe Ser
    6350            6355            6360

Leu Ile  Phe Arg Leu Arg Glu  Thr Ser Thr Ser Gln  Lys Ile Gly
    6365            6370            6375

Ser Ser  Ser Asp Thr Ser Thr  Val Phe Asp Lys Ala  Phe Thr Ala
    6380            6385            6390

Ala Thr  Thr Glu Val Ser Arg  Thr Glu Leu Thr Ser  Ser Ser Arg
    6395            6400            6405

Thr Ser  Ile Gln Gly Thr Glu  Lys Pro Thr Met Ser  Pro Asp Thr
    6410            6415            6420

Ser Thr  Arg Ser Val Thr Met  Leu Ser Thr Phe Ala  Gly Leu Thr
    6425            6430            6435

Lys Ser  Glu Glu Arg Thr Ile  Ala Thr Gln Thr Gly  Pro His Arg
    6440            6445            6450

Ala Thr  Ser Gln Gly Thr Leu  Thr Trp Asp Thr Ser  Ile Thr Thr
    6455            6460            6465

Ser Gln  Ala Gly Thr His Ser  Ala Met Thr His Gly  Phe Ser Gln
    6470            6475            6480

Leu Asp  Leu Ser Thr Leu Thr  Ser Arg Val Pro Glu  Tyr Ile Ser
    6485            6490            6495
```

-continued

```
Gly Thr Ser Pro Pro Ser Val  Glu Lys Thr Ser Ser  Ser Ser Ser
    6500              6505              6510

Leu Leu Ser Leu Pro Ala Ile  Thr Ser Pro Ser Pro  Val Pro Thr
    6515              6520              6525

Thr Leu Pro Glu Ser Arg Pro  Ser Ser Pro Val His  Leu Thr Ser
    6530              6535              6540

Leu Pro Thr Ser Gly Leu Val  Lys Thr Thr Asp Met  Leu Ala Ser
    6545              6550              6555

Val Ala Ser Leu Pro Pro Asn  Leu Gly Ser Thr Ser  His Lys Ile
    6560              6565              6570

Pro Thr Thr Ser Glu Asp Ile  Lys Asp Thr Glu Lys  Met Tyr Pro
    6575              6580              6585

Ser Thr Asn Ile Ala Val Thr  Asn Val Gly Thr Thr  Thr Ser Glu
    6590              6595              6600

Lys Glu Ser Tyr Ser Ser Val  Pro Ala Tyr Ser Glu  Pro Pro Lys
    6605              6610              6615

Val Thr Ser Pro Met Val Thr  Ser Phe Asn Ile Arg  Asp Thr Ile
    6620              6625              6630

Val Ser Thr Ser Met Pro Gly  Ser Ser Glu Ile Thr  Arg Ile Glu
    6635              6640              6645

Met Glu Ser Thr Phe Ser Leu  Ala His Gly Leu Lys  Gly Thr Ser
    6650              6655              6660

Thr Ser Gln Asp Pro Ile Val  Ser Thr Glu Lys Ser  Ala Val Leu
    6665              6670              6675

His Lys Leu Thr Thr Gly Ala  Thr Glu Thr Ser Arg  Thr Glu Val
    6680              6685              6690

Ala Ser Ser Arg Arg Thr Ser  Ile Pro Gly Pro Asp  His Ser Thr
    6695              6700              6705

Glu Ser Pro Asp Ile Ser Thr  Glu Val Ile Pro Ser  Leu Pro Ile
    6710              6715              6720

Ser Leu Gly Ile Thr Glu Ser  Ser Asn Met Thr Ile  Ile Thr Arg
    6725              6730              6735

Thr Gly Pro Pro Leu Gly Ser  Thr Ser Gln Gly Thr  Phe Thr Leu
    6740              6745              6750

Asp Thr Pro Thr Thr Ser Ser  Arg Ala Gly Thr His  Ser Met Ala
    6755              6760              6765

Thr Gln Glu Phe Pro His Ser  Glu Met Thr Thr Val  Met Asn Lys
    6770              6775              6780

Asp Pro Glu Ile Leu Ser Trp  Thr Ile Pro Pro Ser  Ile Glu Lys
    6785              6790              6795

Thr Ser Phe Ser Ser Ser Leu  Met Pro Ser Pro Ala  Met Thr Ser
    6800              6805              6810

Pro Pro Val Ser Ser Thr Leu  Pro Lys Thr Ile His  Thr Thr Pro
    6815              6820              6825

Ser Pro Met Thr Ser Leu Leu  Thr Pro Ser Leu Val  Met Thr Thr
    6830              6835              6840

Asp Thr Leu Gly Thr Ser Pro  Glu Pro Thr Thr Ser  Ser Pro Pro
    6845              6850              6855

Asn Leu Ser Ser Thr Ser His  Glu Ile Leu Thr Thr  Asp Glu Asp
    6860              6865              6870

Thr Thr Ala Ile Glu Ala Met  His Pro Ser Thr Ser  Thr Ala Ala
    6875              6880              6885
```

```
Thr Asn  Val Glu Thr Thr Ser  Ser Gly His Gly Ser  Gln Ser Ser
    6890                 6895                 6900

Val Leu  Ala Asp Ser Glu Lys  Thr Lys Ala Thr Ala  Pro Met Asp
    6905                 6910                 6915

Thr Thr  Ser Thr Met Gly His  Thr Thr Val Ser Thr  Ser Met Ser
    6920                 6925                 6930

Val Ser  Ser Glu Thr Thr Lys  Ile Lys Arg Glu Ser  Thr Tyr Ser
    6935                 6940                 6945

Leu Thr  Pro Gly Leu Arg Glu  Thr Ser Ile Ser Gln  Asn Ala Ser
    6950                 6955                 6960

Phe Ser  Thr Asp Thr Ser Ile  Val Leu Ser Glu Val  Pro Thr Gly
    6965                 6970                 6975

Thr Thr  Ala Glu Val Ser Arg  Thr Glu Val Thr Ser  Ser Gly Arg
    6980                 6985                 6990

Thr Ser  Ile Pro Gly Pro Ser  Gln Ser Thr Val Leu  Pro Glu Ile
    6995                 7000                 7005

Ser Thr  Arg Thr Met Thr Arg  Leu Phe Ala Ser Pro  Thr Met Thr
    7010                 7015                 7020

Glu Ser  Ala Glu Met Thr Ile  Pro Thr Gln Thr Gly  Pro Ser Gly
    7025                 7030                 7035

Ser Thr  Ser Gln Asp Thr Leu  Thr Leu Asp Thr Ser  Thr Thr Lys
    7040                 7045                 7050

Ser Gln  Ala Lys Thr His Ser  Thr Leu Thr Gln Arg  Phe Pro His
    7055                 7060                 7065

Ser Glu  Met Thr Thr Leu Met  Ser Arg Gly Pro Gly  Asp Met Ser
    7070                 7075                 7080

Trp Gln  Ser Ser Pro Ser Leu  Glu Asn Pro Ser Ser  Leu Pro Ser
    7085                 7090                 7095

Leu Leu  Ser Leu Pro Ala Thr  Thr Ser Pro Pro Pro  Ile Ser Ser
    7100                 7105                 7110

Thr Leu  Pro Val Thr Ile Ser  Ser Ser Pro Leu Pro  Val Thr Ser
    7115                 7120                 7125

Leu Leu  Thr Ser Ser Pro Val  Thr Thr Thr Asp Met  Leu His Thr
    7130                 7135                 7140

Ser Pro  Glu Leu Val Thr Ser  Ser Pro Pro Lys Leu  Ser His Thr
    7145                 7150                 7155

Ser Asp  Glu Arg Leu Thr Thr  Gly Lys Asp Thr Thr  Asn Thr Glu
    7160                 7165                 7170

Ala Val  His Pro Ser Thr Asn  Thr Ala Ala Ser Asn  Val Glu Ile
    7175                 7180                 7185

Pro Ser  Ser Gly His Glu Ser  Pro Ser Ser Ala Leu  Ala Asp Ser
    7190                 7195                 7200

Glu Thr  Ser Lys Ala Thr Ser  Pro Met Phe Ile Thr  Ser Thr Gln
    7205                 7210                 7215

Glu Asp  Thr Thr Val Ala Ile  Ser Thr Pro His Phe  Leu Glu Thr
    7220                 7225                 7230

Ser Arg  Ile Gln Lys Glu Ser  Ile Ser Ser Leu Ser  Pro Lys Leu
    7235                 7240                 7245

Arg Glu  Thr Gly Ser Ser Val  Glu Thr Ser Ser Ala  Ile Glu Thr
    7250                 7255                 7260

Ser Ala  Val Leu Ser Glu Val  Ser Ile Gly Ala Thr  Thr Glu Ile
    7265                 7270                 7275

Ser Arg  Thr Glu Val Thr Ser  Ser Ser Arg Thr Ser  Ile Ser Gly
```

```
        7280              7285              7290

Ser Ala Glu Ser Thr Met Leu Pro Glu Ile Ser Thr  Thr Arg Lys
    7295              7300              7305

Ile Ile Lys Phe Pro Thr Ser Pro Ile Leu Ala Glu  Ser Ser Glu
    7310              7315              7320

Met Thr Ile Lys Thr Gln Thr Ser Pro Pro Gly Ser  Thr Ser Glu
    7325              7330              7335

Ser Thr Phe Thr Leu Asp Thr Ser Thr Thr Pro Ser  Leu Val Ile
    7340              7345              7350

Thr His Ser Thr Met Thr Gln Arg Leu Pro His Ser  Glu Ile Thr
    7355              7360              7365

Thr Leu Val Ser Arg Gly Ala Gly Asp Val Pro Arg  Pro Ser Ser
    7370              7375              7380

Leu Pro Val Glu Glu Thr Ser Pro Pro Ser Ser Gln  Leu Ser Leu
    7385              7390              7395

Ser Ala Met Ile Ser Pro Ser Pro Val Ser Ser Thr  Leu Pro Ala
    7400              7405              7410

Ser Ser His Ser Ser Ser Ala Ser Val Thr Ser Leu  Leu Thr Pro
    7415              7420              7425

Gly Gln Val Lys Thr Thr Glu Val Leu Asp Ala Ser  Ala Glu Pro
    7430              7435              7440

Glu Thr Ser Ser Pro Pro Ser Leu Ser Ser Thr Ser  Val Glu Ile
    7445              7450              7455

Leu Ala Thr Ser Glu Val Thr Thr Asp Thr Glu Lys  Ile His Pro
    7460              7465              7470

Phe Ser Asn Thr Ala Val Thr Lys Val Gly Thr Ser  Ser Ser Gly
    7475              7480              7485

His Glu Ser Pro Ser Ser Val Leu Pro Asp Ser Glu  Thr Thr Lys
    7490              7495              7500

Ala Thr Ser Ala Met Gly Thr Ile Ser Ile Met Gly  Asp Thr Ser
    7505              7510              7515

Val Ser Thr Leu Thr Pro Ala Leu Ser Asn Thr Arg  Lys Ile Gln
    7520              7525              7530

Ser Glu Pro Ala Ser Ser Leu Thr Thr Arg Leu Arg  Glu Thr Ser
    7535              7540              7545

Thr Ser Glu Glu Thr Ser Leu Ala Thr Glu Ala Asn  Thr Val Leu
    7550              7555              7560

Ser Lys Val Ser Thr Gly Ala Thr Thr Glu Val Ser  Arg Thr Glu
    7565              7570              7575

Ala Ile Ser Phe Ser Arg Thr Ser Met Ser Gly Pro  Glu Gln Ser
    7580              7585              7590

Thr Met Ser Gln Asp Ile Ser Ile Gly Thr Ile Pro  Arg Ile Ser
    7595              7600              7605

Ala Ser Ser Val Leu Thr Glu Ser Ala Lys Met Thr  Ile Thr Thr
    7610              7615              7620

Gln Thr Gly Pro Ser Glu Ser Thr Leu Glu Ser Thr  Leu Asn Leu
    7625              7630              7635

Asn Thr Ala Thr Thr Pro Ser Trp Val Glu Thr His  Ser Ile Val
    7640              7645              7650

Ile Gln Gly Phe Pro His Pro Glu Met Thr Thr Ser  Met Gly Arg
    7655              7660              7665

Gly Pro Gly Gly Val Ser Trp Pro Ser Pro Pro Phe  Val Lys Glu
    7670              7675              7680
```

-continued

```
Thr Ser  Pro Pro Ser Ser Pro  Leu Ser Leu Pro Ala  Val Thr Ser
    7685             7690             7695

Pro His  Pro Val Ser Thr Thr  Phe Leu Ala His Ile  Pro Pro Ser
    7700             7705             7710

Pro Leu  Pro Val Thr Ser Leu  Leu Thr Ser Gly Pro  Ala Thr Thr
    7715             7720             7725

Thr Asp  Ile Leu Gly Thr Ser  Thr Glu Pro Gly Thr  Ser Ser Ser
    7730             7735             7740

Ser Ser  Leu Ser Thr Thr Ser  His Glu Arg Leu Thr  Thr Tyr Lys
    7745             7750             7755

Asp Thr  Ala His Thr Glu Ala  Val His Pro Ser Thr  Asn Thr Gly
    7760             7765             7770

Gly Thr  Asn Val Ala Thr Thr  Ser Ser Gly Tyr Lys  Ser Gln Ser
    7775             7780             7785

Ser Val  Leu Ala Asp Ser Ser  Pro Met Cys Thr Thr  Ser Thr Met
    7790             7795             7800

Gly Asp  Thr Ser Val Leu Thr  Ser Thr Pro Ala Phe  Leu Glu Thr
    7805             7810             7815

Arg Arg  Ile Gln Thr Glu Leu  Ala Ser Ser Leu Thr  Pro Gly Leu
    7820             7825             7830

Arg Glu  Ser Ser Gly Ser Glu  Gly Thr Ser Ser Gly  Thr Lys Met
    7835             7840             7845

Ser Thr  Val Leu Ser Lys Val  Pro Thr Gly Ala Thr  Thr Glu Ile
    7850             7855             7860

Ser Lys  Glu Asp Val Thr Ser  Ile Pro Gly Pro Ala  Gln Ser Thr
    7865             7870             7875

Ile Ser  Pro Asp Ile Ser Thr  Arg Thr Val Ser Trp  Phe Ser Thr
    7880             7885             7890

Ser Pro  Val Met Thr Glu Ser  Ala Glu Ile Thr Met  Asn Thr His
    7895             7900             7905

Thr Ser  Pro Leu Gly Ala Thr  Thr Gln Gly Thr Ser  Thr Leu Asp
    7910             7915             7920

Thr Ser  Ser Thr Thr Ser Leu  Thr Met Thr His Ser  Thr Ile Ser
    7925             7930             7935

Gln Gly  Phe Ser His Ser Gln  Met Ser Thr Leu Met  Arg Arg Gly
    7940             7945             7950

Pro Glu  Asp Val Ser Trp Met  Ser Pro Pro Leu Leu  Glu Lys Thr
    7955             7960             7965

Arg Pro  Ser Phe Ser Leu Met  Ser Ser Pro Ala Thr  Thr Ser Pro
    7970             7975             7980

Ser Pro  Val Ser Ser Thr Leu  Pro Glu Ser Ile Ser  Ser Ser Pro
    7985             7990             7995

Leu Pro  Val Thr Ser Leu Leu  Thr Ser Gly Leu Ala  Lys Thr Thr
    8000             8005             8010

Asp Met  Leu His Lys Ser Ser  Glu Pro Val Thr Asn  Ser Pro Ala
    8015             8020             8025

Asn Leu  Ser Ser Thr Ser Val  Glu Ile Leu Ala Thr  Ser Glu Val
    8030             8035             8040

Thr Thr  Asp Thr Glu Lys Thr  His Pro Ser Ser Asn  Arg Thr Val
    8045             8050             8055

Thr Asp  Val Gly Thr Ser Ser  Ser Gly His Glu Ser  Thr Ser Phe
    8060             8065             8070
```

-continued

```
Val Leu  Ala Asp Ser Gln Thr  Ser Lys Val Thr Ser  Pro Met Val
    8075                8080                8085

Ile Thr  Ser Thr Met Glu Asp  Thr Ser Val Ser Thr  Ser Thr Pro
    8090                8095                8100

Gly Phe  Phe Glu Thr Ser Arg  Ile Gln Thr Glu Pro  Thr Ser Ser
    8105                8110                8115

Leu Thr  Leu Gly Leu Arg Lys  Thr Ser Ser Ser Glu  Gly Thr Ser
    8120                8125                8130

Leu Ala  Thr Glu Met Ser Thr  Val Leu Ser Gly Val  Pro Thr Gly
    8135                8140                8145

Ala Thr  Ala Glu Val Ser Arg  Thr Glu Val Thr Ser  Ser Ser Arg
    8150                8155                8160

Thr Ser  Ile Ser Gly Phe Ala  Gln Leu Thr Val Ser  Pro Glu Thr
    8165                8170                8175

Ser Thr  Glu Thr Ile Thr Arg  Leu Pro Thr Ser Ser  Ile Met Thr
    8180                8185                8190

Glu Ser  Ala Glu Met Met Ile  Lys Thr Gln Thr Asp  Pro Pro Gly
    8195                8200                8205

Ser Thr  Pro Glu Ser Thr His  Thr Val Asp Ile Ser  Thr Thr Pro
    8210                8215                8220

Asn Trp  Val Glu Thr His Ser  Thr Val Thr Gln Arg  Phe Ser His
    8225                8230                8235

Ser Glu  Met Thr Thr Leu Val  Ser Arg Ser Pro Gly  Asp Met Leu
    8240                8245                8250

Trp Pro  Ser Gln Ser Ser Val  Glu Glu Thr Ser Ser  Ala Ser Ser
    8255                8260                8265

Leu Leu  Ser Leu Pro Ala Thr  Thr Ser Pro Ser Pro  Val Ser Ser
    8270                8275                8280

Thr Leu  Val Glu Asp Phe Pro  Ser Ala Ser Leu Pro  Val Thr Ser
    8285                8290                8295

Leu Leu  Asn Pro Gly Leu Val  Ile Thr Thr Asp Arg  Met Gly Ile
    8300                8305                8310

Ser Arg  Glu Pro Gly Thr Ser  Ser Thr Ser Asn Leu  Ser Ser Thr
    8315                8320                8325

Ser His  Glu Arg Leu Thr Thr  Leu Glu Asp Thr Val  Asp Thr Glu
    8330                8335                8340

Asp Met  Gln Pro Ser Thr His  Thr Ala Val Thr Asn  Val Arg Thr
    8345                8350                8355

Ser Ile  Ser Gly His Glu Ser  Gln Ser Ser Val Leu  Ser Asp Ser
    8360                8365                8370

Glu Thr  Pro Lys Ala Thr Ser  Pro Met Gly Thr Thr  Tyr Thr Met
    8375                8380                8385

Gly Glu  Thr Ser Val Ser Ile  Ser Thr Ser Asp Phe  Phe Glu Thr
    8390                8395                8400

Ser Arg  Ile Gln Ile Glu Pro  Thr Ser Ser Leu Thr  Ser Gly Leu
    8405                8410                8415

Arg Glu  Thr Ser Ser Ser Glu  Arg Ile Ser Ser Ala  Thr Glu Gly
    8420                8425                8430

Ser Thr  Val Leu Ser Glu Val  Pro Ser Gly Ala Thr  Thr Glu Val
    8435                8440                8445

Ser Arg  Thr Glu Val Ile Ser  Ser Arg Gly Thr Ser  Met Ser Gly
    8450                8455                8460

Pro Asp  Gln Phe Thr Ile Ser  Pro Asp Ile Ser Thr  Glu Ala Ile
```

-continued

```
        8465                    8470                    8475

Thr Arg  Leu Ser Thr Ser Pro  Ile Met Thr Glu Ser  Ala Glu Ser
    8480                    8485                    8490

Ala Ile  Thr Ile Glu Thr Gly  Ser Pro Gly Ala Thr  Ser Glu Gly
    8495                    8500                    8505

Thr Leu  Thr Leu Asp Thr Ser  Thr Thr Thr Phe Trp  Ser Gly Thr
    8510                    8515                    8520

His Ser  Thr Ala Ser Pro Gly  Phe Ser His Ser Glu  Met Thr Thr
    8525                    8530                    8535

Leu Met  Ser Arg Thr Pro Gly  Asp Val Pro Trp Pro  Ser Leu Pro
    8540                    8545                    8550

Ser Val  Glu Glu Ala Ser Ser  Val Ser Ser Ser Leu  Ser Ser Pro
    8555                    8560                    8565

Ala Met  Thr Ser Thr Ser Phe  Phe Ser Thr Leu Pro  Glu Ser Ile
    8570                    8575                    8580

Ser Ser  Ser Pro His Pro Val  Thr Ala Leu Leu Thr  Leu Gly Pro
    8585                    8590                    8595

Val Lys  Thr Thr Asp Met Leu  Arg Thr Ser Ser Glu  Pro Glu Thr
    8600                    8605                    8610

Ser Ser  Pro Pro Asn Leu Ser  Ser Thr Ser Ala Glu  Ile Leu Ala
    8615                    8620                    8625

Thr Ser  Glu Val Thr Lys Asp  Arg Glu Lys Ile His  Pro Ser Ser
    8630                    8635                    8640

Asn Thr  Pro Val Val Asn Val  Gly Thr Val Ile Tyr  Lys His Leu
    8645                    8650                    8655

Ser Pro  Ser Ser Val Leu Ala  Asp Leu Val Thr Thr  Lys Pro Thr
    8660                    8665                    8670

Ser Pro  Met Ala Thr Thr Ser  Thr Leu Gly Asn Thr  Ser Val Ser
    8675                    8680                    8685

Thr Ser  Thr Pro Ala Phe Pro  Glu Thr Met Met Thr  Gln Pro Thr
    8690                    8695                    8700

Ser Ser  Leu Thr Ser Gly Leu  Arg Glu Ile Ser Thr  Ser Gln Glu
    8705                    8710                    8715

Thr Ser  Ser Ala Thr Glu Arg  Ser Ala Ser Leu Ser  Gly Met Pro
    8720                    8725                    8730

Thr Gly  Ala Thr Thr Lys Val  Ser Arg Thr Glu Ala  Leu Ser Leu
    8735                    8740                    8745

Gly Arg  Thr Ser Thr Pro Gly  Pro Ala Gln Ser Thr  Ile Ser Pro
    8750                    8755                    8760

Glu Ile  Ser Thr Glu Thr Ile  Thr Arg Ile Ser Thr  Pro Leu Thr
    8765                    8770                    8775

Thr Thr  Gly Ser Ala Glu Met  Thr Ile Thr Pro Lys  Thr Gly His
    8780                    8785                    8790

Ser Gly  Ala Ser Ser Gln Gly  Thr Phe Thr Leu Asp  Thr Ser Ser
    8795                    8800                    8805

Arg Ala  Ser Trp Pro Gly Thr  His Ser Ala Ala Thr  His Arg Ser
    8810                    8815                    8820

Pro His  Ser Gly Met Thr Thr  Pro Met Ser Arg Gly  Pro Glu Asp
    8825                    8830                    8835

Val Ser  Trp Pro Ser Arg Pro  Ser Val Glu Lys Thr  Ser Pro Pro
    8840                    8845                    8850

Ser Ser  Leu Val Ser Leu Ser  Ala Val Thr Ser Pro  Ser Pro Leu
    8855                    8860                    8865
```

-continued

```
Tyr Ser  Thr Pro Ser Glu Ser  Ser His Ser Ser Pro  Leu Arg Val
    8870             8875              8880

Thr Ser  Leu Phe Thr Pro Val  Met Met Lys Thr Thr  Asp Met Leu
    8885             8890              8895

Asp Thr  Ser Leu Glu Pro Val  Thr Thr Ser Pro Pro  Ser Met Asn
    8900             8905              8910

Ile Thr  Ser Asp Glu Ser Leu  Ala Thr Ser Lys Ala  Thr Met Glu
    8915             8920              8925

Thr Glu  Ala Ile Gln Leu Ser  Glu Asn Thr Ala Val  Thr Gln Met
    8930             8935              8940

Gly Thr  Ile Ser Ala Arg Gln  Glu Phe Tyr Ser Ser  Tyr Pro Gly
    8945             8950              8955

Leu Pro  Glu Pro Ser Lys Val  Thr Ser Pro Val Val  Thr Ser Ser
    8960             8965              8970

Thr Ile  Lys Asp Ile Val Ser  Thr Thr Ile Pro Ala  Ser Ser Glu
    8975             8980              8985

Ile Thr  Arg Ile Glu Met Glu  Ser Thr Ser Thr Leu  Thr Pro Thr
    8990             8995              9000

Pro Arg  Glu Thr Ser Thr Ser  Gln Glu Ile His Ser  Ala Thr Lys
    9005             9010              9015

Pro Ser  Thr Val Pro Tyr Lys  Ala Leu Thr Ser Ala  Thr Ile Glu
    9020             9025              9030

Asp Ser  Met Thr Gln Val Met  Ser Ser Ser Arg Gly  Pro Ser Pro
    9035             9040              9045

Asp Gln  Ser Thr Met Ser Gln  Asp Ile Ser Thr Glu  Val Ile Thr
    9050             9055              9060

Arg Leu  Ser Thr Ser Pro Ile  Lys Thr Glu Ser Thr  Glu Met Thr
    9065             9070              9075

Ile Thr  Thr Gln Thr Gly Ser  Pro Gly Ala Thr Ser  Arg Gly Thr
    9080             9085              9090

Leu Thr  Leu Asp Thr Ser Thr  Thr Phe Met Ser Gly  Thr His Ser
    9095             9100              9105

Thr Ala  Ser Gln Gly Phe Ser  His Ser Gln Met Thr  Ala Leu Met
    9110             9115              9120

Ser Arg  Thr Pro Gly Asp Val  Pro Trp Leu Ser His  Pro Ser Val
    9125             9130              9135

Glu Glu  Ala Ser Ser Ala Ser  Phe Ser Leu Ser Ser  Pro Val Met
    9140             9145              9150

Thr Ser  Ser Ser Pro Val Ser  Ser Thr Leu Pro Asp  Ser Ile His
    9155             9160              9165

Ser Ser  Ser Leu Pro Val Thr  Ser Leu Leu Thr Ser  Gly Leu Val
    9170             9175              9180

Lys Thr  Thr Glu Leu Leu Gly  Thr Ser Ser Glu Pro  Glu Thr Ser
    9185             9190              9195

Ser Pro  Pro Asn Leu Ser Ser  Thr Ser Ala Glu Ile  Leu Ala Ile
    9200             9205              9210

Thr Glu  Val Thr Thr Asp Thr  Glu Lys Leu Glu Met  Thr Asn Val
    9215             9220              9225

Val Thr  Ser Gly Tyr Thr His  Glu Ser Pro Ser Ser  Val Leu Ala
    9230             9235              9240

Asp Ser  Val Thr Thr Lys Ala  Thr Ser Ser Met Gly  Ile Thr Tyr
    9245             9250              9255
```

-continued

```
Pro Thr  Gly Asp Thr Asn Val  Leu Thr Ser Thr Pro  Ala Phe Ser
    9260              9265              9270

Asp Thr  Ser Arg Ile Gln Thr  Lys Ser Lys Leu Ser  Leu Thr Pro
    9275              9280              9285

Gly Leu  Met Glu Thr Ser Ile  Ser Glu Glu Thr Ser  Ser Ala Thr
    9290              9295              9300

Glu Lys  Ser Thr Val Leu Ser  Ser Val Pro Thr Gly  Ala Thr Thr
    9305              9310              9315

Glu Val  Ser Arg Thr Glu Ala  Ile Ser Ser Ser Arg  Thr Ser Ile
    9320              9325              9330

Pro Gly  Pro Ala Gln Ser Thr  Met Ser Ser Asp Thr  Ser Met Glu
    9335              9340              9345

Thr Ile  Thr Arg Ile Ser Thr  Pro Leu Thr Arg Lys  Glu Ser Thr
    9350              9355              9360

Asp Met  Ala Ile Thr Pro Lys  Thr Gly Pro Ser Gly  Ala Thr Ser
    9365              9370              9375

Gln Gly  Thr Phe Thr Leu Asp  Ser Ser Ser Thr Ala  Ser Trp Pro
    9380              9385              9390

Gly Thr  His Ser Ala Thr Thr  Gln Arg Phe Pro Gln  Ser Val Val
    9395              9400              9405

Thr Thr  Pro Met Ser Arg Gly  Pro Glu Asp Val Ser  Trp Pro Ser
    9410              9415              9420

Pro Leu  Ser Val Glu Lys Asn  Ser Pro Pro Ser Ser  Leu Val Ser
    9425              9430              9435

Ser Ser  Ser Val Thr Ser Pro  Ser Pro Leu Tyr Ser  Thr Pro Ser
    9440              9445              9450

Gly Ser  Ser His Ser Ser Pro  Val Pro Val Thr Ser  Leu Phe Thr
    9455              9460              9465

Ser Ile  Met Met Lys Ala Thr  Asp Met Leu Asp Ala  Ser Leu Glu
    9470              9475              9480

Pro Glu  Thr Thr Ser Ala Pro  Asn Met Asn Ile Thr  Ser Asp Glu
    9485              9490              9495

Ser Leu  Ala Ala Ser Lys Ala  Thr Thr Glu Thr Glu  Ala Ile His
    9500              9505              9510

Val Phe  Glu Asn Thr Ala Ala  Ser His Val Glu Thr  Thr Ser Ala
    9515              9520              9525

Thr Glu  Glu Leu Tyr Ser Ser  Ser Pro Gly Phe Ser  Glu Pro Thr
    9530              9535              9540

Lys Val  Ile Ser Pro Val Val  Thr Ser Ser Ser Ile  Arg Asp Asn
    9545              9550              9555

Met Val  Ser Thr Thr Met Pro  Gly Ser Ser Gly Ile  Thr Arg Ile
    9560              9565              9570

Glu Ile  Glu Ser Met Ser Ser  Leu Thr Pro Gly Leu  Arg Glu Thr
    9575              9580              9585

Arg Thr  Ser Gln Asp Ile Thr  Ser Ser Thr Glu Thr  Ser Thr Val
    9590              9595              9600

Leu Tyr  Lys Met Pro Ser Gly  Ala Thr Pro Glu Val  Ser Arg Thr
    9605              9610              9615

Glu Val  Met Pro Ser Ser Arg  Thr Ser Ile Pro Gly  Pro Ala Gln
    9620              9625              9630

Ser Thr  Met Ser Leu Asp Ile  Ser Asp Glu Val Val  Thr Arg Leu
    9635              9640              9645

Ser Thr  Ser Pro Ile Met Thr  Glu Ser Ala Glu Ile  Thr Ile Thr
```

```
        9650                    9655                    9660

Thr Gln  Thr Gly Tyr Ser Leu  Ala Thr Ser Gln Val  Thr Leu Pro
   9665                    9670                    9675

Leu Gly  Thr Ser Met Thr Phe  Leu Ser Gly Thr His  Ser Thr Met
   9680                    9685                    9690

Ser Gln  Gly Leu Ser His Ser  Glu Met Thr Asn Leu  Met Ser Arg
   9695                    9700                    9705

Gly Pro  Glu Ser Leu Ser Trp  Thr Ser Pro Arg Phe  Val Glu Thr
   9710                    9715                    9720

Thr Arg  Ser Ser Ser Ser Leu  Thr Ser Leu Pro Leu  Thr Thr Ser
   9725                    9730                    9735

Leu Ser  Pro Val Ser Ser Thr  Leu Leu Asp Ser Ser  Pro Ser Ser
   9740                    9745                    9750

Pro Leu  Pro Val Thr Ser Leu  Ile Leu Pro Gly Leu  Val Lys Thr
   9755                    9760                    9765

Thr Glu  Val Leu Asp Thr Ser  Ser Glu Pro Lys Thr  Ser Ser Ser
   9770                    9775                    9780

Pro Asn  Leu Ser Ser Thr Ser  Val Glu Ile Pro Ala  Thr Ser Glu
   9785                    9790                    9795

Ile Met  Thr Asp Thr Glu Lys  Ile His Pro Ser Ser  Asn Thr Ala
   9800                    9805                    9810

Val Ala  Lys Val Arg Thr Ser  Ser Ser Val His Glu  Ser His Ser
   9815                    9820                    9825

Ser Val  Leu Ala Asp Ser Glu  Thr Thr Ile Thr Ile  Pro Ser Met
   9830                    9835                    9840

Gly Ile  Thr Ser Ala Val Asp  Asp Thr Thr Val Phe  Thr Ser Asn
   9845                    9850                    9855

Pro Ala  Phe Ser Glu Thr Arg  Arg Ile Pro Thr Glu  Pro Thr Phe
   9860                    9865                    9870

Ser Leu  Thr Pro Gly Phe Arg  Glu Thr Ser Thr Ser  Glu Glu Thr
   9875                    9880                    9885

Thr Ser  Ile Thr Glu Thr Ser  Ala Val Leu Tyr Gly  Val Pro Thr
   9890                    9895                    9900

Ser Ala  Thr Thr Glu Val Ser  Met Thr Glu Ile Met  Ser Ser Asn
   9905                    9910                    9915

Arg Ile  His Ile Pro Asp Ser  Asp Gln Ser Thr Met  Ser Pro Asp
   9920                    9925                    9930

Ile Ile  Thr Glu Val Ile Thr  Arg Leu Ser Ser Ser  Ser Met Met
   9935                    9940                    9945

Ser Glu  Ser Thr Gln Met Thr  Ile Thr Thr Gln Lys  Ser Ser Pro
   9950                    9955                    9960

Gly Ala  Thr Ala Gln Ser Thr  Leu Thr Leu Ala Thr  Thr Thr Ala
   9965                    9970                    9975

Pro Leu  Ala Arg Thr His Ser  Thr Val Pro Pro Arg  Phe Leu His
   9980                    9985                    9990

Ser Glu  Met Thr Thr Leu Met   Ser Arg Ser Pro Glu   Asn Pro Ser
   9995                    10000                    10005

Trp Lys   Ser Ser Leu Phe Val   Glu Lys Thr Ser Ser   Ser Ser Ser
   10010                    10015                    10020

Leu Leu   Ser Leu Pro Val Thr   Thr Ser Pro Ser Val   Ser Ser Thr
   10025                    10030                    10035

Leu Pro   Gln Ser Ile Pro Ser   Ser Ser Phe Ser Val   Thr Ser Leu
   10040                    10045                    10050
```

-continued

```
Leu Thr  Pro Gly Met Val Lys  Thr Thr Asp Thr Ser  Thr Glu Pro
    10055             10060                10065

Gly Thr  Ser Leu Ser Pro Asn  Leu Ser Gly Thr Ser  Val Glu Ile
    10070             10075                10080

Leu Ala  Ala Ser Glu Val Thr  Thr Asp Thr Glu Lys  Ile His Pro
    10085             10090                10095

Ser Ser  Ser Met Ala Val Thr  Asn Val Gly Thr Thr  Ser Ser Gly
    10100             10105                10110

His Glu  Leu Tyr Ser Ser Val  Ser Ile His Ser Glu  Pro Ser Lys
    10115             10120                10125

Ala Thr  Tyr Pro Val Gly Thr  Pro Ser Ser Met Ala  Glu Thr Ser
    10130             10135                10140

Ile Ser  Thr Ser Met Pro Ala  Asn Phe Glu Thr Thr  Gly Phe Glu
    10145             10150                10155

Ala Glu  Pro Phe Ser His Leu  Thr Ser Gly Phe Arg  Lys Thr Asn
    10160             10165                10170

Met Ser  Leu Asp Thr Ser Ser  Val Thr Pro Thr Asn  Thr Pro Ser
    10175             10180                10185

Ser Pro  Gly Ser Thr His Leu  Leu Gln Ser Ser Lys  Thr Asp Phe
    10190             10195                10200

Thr Ser  Ser Ala Lys Thr Ser  Ser Pro Asp Trp Pro  Pro Ala Ser
    10205             10210                10215

Gln Tyr  Thr Glu Ile Pro Val  Asp Ile Ile Thr Pro  Phe Asn Ala
    10220             10225                10230

Ser Pro  Ser Ile Thr Glu Ser  Thr Gly Ile Thr Ser  Phe Pro Glu
    10235             10240                10245

Ser Arg  Phe Thr Met Ser Val  Thr Glu Ser Thr His  His Leu Ser
    10250             10255                10260

Thr Asp  Leu Leu Pro Ser Ala  Glu Thr Ile Ser Thr  Gly Thr Val
    10265             10270                10275

Met Pro  Ser Leu Ser Glu Ala  Met Thr Ser Phe Ala  Thr Thr Gly
    10280             10285                10290

Val Pro  Arg Ala Ile Ser Gly  Ser Gly Ser Pro Phe  Ser Arg Thr
    10295             10300                10305

Glu Ser  Gly Pro Gly Asp Ala  Thr Leu Ser Thr Ile  Ala Glu Ser
    10310             10315                10320

Leu Pro  Ser Ser Thr Pro Val  Pro Phe Ser Ser Ser  Thr Phe Thr
    10325             10330                10335

Thr Thr  Asp Ser Ser Thr Ile  Pro Ala Leu His Glu  Ile Thr Ser
    10340             10345                10350

Ser Ser  Ala Thr Pro Tyr Arg  Val Asp Thr Ser Leu  Gly Thr Glu
    10355             10360                10365

Ser Ser  Thr Thr Glu Gly Arg  Leu Val Met Val Ser  Thr Leu Asp
    10370             10375                10380

Thr Ser  Ser Gln Pro Gly Arg  Thr Ser Ser Ser Pro  Ile Leu Asp
    10385             10390                10395

Thr Arg  Met Thr Glu Ser Val  Glu Leu Gly Thr Val  Thr Ser Ala
    10400             10405                10410

Tyr Gln  Val Pro Ser Leu Ser  Thr Arg Leu Thr Arg  Thr Asp Gly
    10415             10420                10425

Ile Met  Glu His Ile Thr Lys  Ile Pro Asn Glu Ala  Ala His Arg
    10430             10435                10440
```

```
Gly Thr  Ile Arg Pro Val Lys  Gly Pro Gln Thr Ser  Thr Ser Pro
    10445               10450               10455

Ala Ser  Pro Lys Gly Leu His  Thr Gly Gly Thr Lys  Arg Met Glu
    10460               10465               10470

Thr Thr  Thr Thr Ala Leu Lys  Thr Thr Thr Thr Ala  Leu Lys Thr
    10475               10480               10485

Thr Ser  Arg Ala Thr Leu Thr  Thr Ser Val Tyr Thr  Pro Thr Leu
    10490               10495               10500

Gly Thr  Leu Thr Pro Leu Asn  Ala Ser Met Gln Met  Ala Ser Thr
    10505               10510               10515

Ile Pro  Thr Glu Met Met Ile  Thr Thr Pro Tyr Val  Phe Pro Asp
    10520               10525               10530

Val Pro  Glu Thr Thr Ser Ser  Leu Ala Thr Ser Leu  Gly Ala Glu
    10535               10540               10545

Thr Ser  Thr Ala Leu Pro Arg  Thr Thr Pro Ser Val  Phe Asn Arg
    10550               10555               10560

Glu Ser  Glu Thr Thr Ala Ser  Leu Val Ser Arg Ser  Gly Ala Glu
    10565               10570               10575

Arg Ser  Pro Val Ile Gln Thr  Leu Asp Val Ser Ser  Ser Glu Pro
    10580               10585               10590

Asp Thr  Thr Ala Ser Trp Val  Ile His Pro Ala Glu  Thr Ile Pro
    10595               10600               10605

Thr Val  Ser Lys Thr Thr Pro  Asn Phe Phe His Ser  Glu Leu Asp
    10610               10615               10620

Thr Val  Ser Ser Thr Ala Thr  Ser His Gly Ala Asp  Val Ser Ser
    10625               10630               10635

Ala Ile  Pro Thr Asn Ile Ser  Pro Ser Glu Leu Asp  Ala Leu Thr
    10640               10645               10650

Pro Leu  Val Thr Ile Ser Gly  Thr Asp Thr Ser Thr  Thr Phe Pro
    10655               10660               10665

Thr Leu  Thr Lys Ser Pro His  Glu Thr Glu Thr Arg  Thr Thr Trp
    10670               10675               10680

Leu Thr  His Pro Ala Glu Thr  Ser Ser Thr Ile Pro  Arg Thr Ile
    10685               10690               10695

Pro Asn  Phe Ser His His Glu  Ser Asp Ala Thr Pro  Ser Ile Ala
    10700               10705               10710

Thr Ser  Pro Gly Ala Glu Thr  Ser Ser Ala Ile Pro  Ile Met Thr
    10715               10720               10725

Val Ser  Pro Gly Ala Glu Asp  Leu Val Thr Ser Gln  Val Thr Ser
    10730               10735               10740

Ser Gly  Thr Asp Arg Asn Met  Thr Ile Pro Thr Leu  Thr Leu Ser
    10745               10750               10755

Pro Gly  Glu Pro Lys Thr Ile  Ala Ser Leu Val Thr  His Pro Glu
    10760               10765               10770

Ala Gln  Thr Ser Ser Ala Ile  Pro Thr Ser Thr Ile  Ser Pro Ala
    10775               10780               10785

Val Ser  Arg Leu Val Thr Ser  Met Val Thr Ser Leu  Ala Ala Lys
    10790               10795               10800

Thr Ser  Thr Thr Asn Arg Ala  Leu Thr Asn Ser Pro  Gly Glu Pro
    10805               10810               10815

Ala Thr  Thr Val Ser Leu Val  Thr His Pro Ala Gln  Thr Ser Pro
    10820               10825               10830

Thr Val  Pro Trp Thr Thr Ser  Ile Phe Phe His Ser  Lys Ser Asp
```

-continued

```
     10835                10840                10845

Thr Thr  Pro Ser Met Thr Thr  Ser His Gly Ala Glu  Ser Ser Ser
     10850                10855                10860

Ala Val  Pro Thr Pro Thr Val  Ser Thr Glu Val Pro  Gly Val Val
     10865                10870                10875

Thr Pro  Leu Val Thr Ser Ser  Arg Ala Val Ile Ser  Thr Thr Ile
     10880                10885                10890

Pro Ile  Leu Thr Leu Ser Pro  Gly Glu Pro Glu Thr  Thr Pro Ser
     10895                10900                10905

Met Ala  Thr Ser His Gly Glu  Glu Ala Ser Ser Ala  Ile Pro Thr
     10910                10915                10920

Pro Thr  Val Ser Pro Gly Val  Pro Gly Val Val Thr  Ser Leu Val
     10925                10930                10935

Thr Ser  Ser Arg Ala Val Thr  Ser Thr Thr Ile Pro  Ile Leu Thr
     10940                10945                10950

Phe Ser  Leu Gly Glu Pro Glu  Thr Thr Pro Ser Met  Ala Thr Ser
     10955                10960                10965

His Gly  Thr Glu Ala Gly Ser  Ala Val Pro Thr Val  Leu Pro Glu
     10970                10975                10980

Val Pro  Gly Met Val Thr Ser  Leu Val Ala Ser Ser  Arg Ala Val
     10985                10990                10995

Thr Ser  Thr Thr Leu Pro Thr  Leu Thr Leu Ser Pro  Gly Glu Pro
     11000                11005                11010

Glu Thr  Thr Pro Ser Met Ala  Thr Ser His Gly Ala  Glu Ala Ser
     11015                11020                11025

Ser Thr  Val Pro Thr Val Ser  Pro Glu Val Pro Gly  Val Val Thr
     11030                11035                11040

Ser Leu  Val Thr Ser Ser Ser  Gly Val Asn Ser Thr  Ser Ile Pro
     11045                11050                11055

Thr Leu  Ile Leu Ser Pro Gly  Glu Leu Glu Thr Thr  Pro Ser Met
     11060                11065                11070

Ala Thr  Ser His Gly Ala Glu  Ala Ser Ser Ala Val  Pro Thr Pro
     11075                11080                11085

Thr Val  Ser Pro Gly Val Ser  Gly Val Val Thr Pro  Leu Val Thr
     11090                11095                11100

Ser Ser  Arg Ala Val Thr Ser  Thr Thr Ile Pro Ile  Leu Thr Leu
     11105                11110                11115

Ser Ser  Ser Glu Pro Glu Thr  Thr Pro Ser Met Ala  Thr Ser His
     11120                11125                11130

Gly Val  Glu Ala Ser Ser Ala  Val Leu Thr Val Ser  Pro Glu Val
     11135                11140                11145

Pro Gly  Met Val Thr Ser Leu  Val Thr Ser Ser Arg  Ala Val Thr
     11150                11155                11160

Ser Thr  Thr Ile Pro Thr Leu  Thr Ile Ser Ser Asp  Glu Pro Glu
     11165                11170                11175

Thr Thr  Thr Ser Leu Val Thr  His Ser Glu Ala Lys  Met Ile Ser
     11180                11185                11190

Ala Ile  Pro Thr Leu Ala Val  Ser Pro Thr Val Gln  Gly Leu Val
     11195                11200                11205

Thr Ser  Leu Val Thr Ser Ser  Gly Ser Glu Thr Ser  Ala Phe Ser
     11210                11215                11220

Asn Leu  Thr Val Ala Ser Ser  Gln Pro Glu Thr Ile  Asp Ser Trp
     11225                11230                11235
```

-continued

```
Val Ala   His Pro Gly Thr Glu   Ala Ser Ser Val Val   Pro Thr Leu
11240             11245                 11250

Thr Val   Ser Thr Gly Glu Pro   Phe Thr Asn Ile Ser   Leu Val Thr
11255             11260                 11265

His Pro   Ala Glu Ser Ser Ser   Thr Leu Pro Arg Thr   Thr Ser Arg
11270             11275                 11280

Phe Ser   His Ser Glu Leu Asp   Thr Met Pro Ser Thr   Val Thr Ser
11285             11290                 11295

Pro Glu   Ala Glu Ser Ser Ser   Ala Ile Ser Thr Thr   Ile Ser Pro
11300             11305                 11310

Gly Ile   Pro Gly Val Leu Thr   Ser Leu Val Thr Ser   Ser Gly Arg
11315             11320                 11325

Asp Ile   Ser Ala Thr Phe Pro   Thr Val Pro Glu Ser   Pro His Glu
11330             11335                 11340

Ser Glu   Ala Thr Ala Ser Trp   Val Thr His Pro Ala   Val Thr Ser
11345             11350                 11355

Thr Thr   Val Pro Arg Thr Thr   Pro Asn Tyr Ser His   Ser Glu Pro
11360             11365                 11370

Asp Thr   Thr Pro Ser Ile Ala   Thr Ser Pro Gly Ala   Glu Ala Thr
11375             11380                 11385

Ser Asp   Phe Pro Thr Ile Thr   Val Ser Pro Asp Val   Pro Asp Met
11390             11395                 11400

Val Thr   Ser Gln Val Thr Ser   Ser Gly Thr Asp Thr   Ser Ile Thr
11405             11410                 11415

Ile Pro   Thr Leu Thr Leu Ser   Ser Gly Glu Pro Glu   Thr Thr Thr
11420             11425                 11430

Ser Phe   Ile Thr Tyr Ser Glu   Thr His Thr Ser Ser   Ala Ile Pro
11435             11440                 11445

Thr Leu   Pro Val Ser Pro Gly   Ala Ser Lys Met Leu   Thr Ser Leu
11450             11455                 11460

Val Ile   Ser Ser Gly Thr Asp   Ser Thr Thr Thr Phe   Pro Thr Leu
11465             11470                 11475

Thr Glu   Thr Pro Tyr Glu Pro   Glu Thr Thr Ala Ile   Gln Leu Ile
11480             11485                 11490

His Pro   Ala Glu Thr Asn Thr   Met Val Pro Arg Thr   Thr Pro Lys
11495             11500                 11505

Phe Ser   His Ser Lys Ser Asp   Thr Thr Leu Pro Val   Ala Ile Thr
11510             11515                 11520

Ser Pro   Gly Pro Glu Ala Ser   Ser Ala Val Ser Thr   Thr Thr Ile
11525             11530                 11535

Ser Pro   Asp Met Ser Asp Leu   Val Thr Ser Leu Val   Pro Ser Ser
11540             11545                 11550

Gly Thr   Asp Thr Ser Thr Thr   Phe Pro Thr Leu Ser   Glu Thr Pro
11555             11560                 11565

Tyr Glu   Pro Glu Thr Thr Ala   Thr Trp Leu Thr His   Pro Ala Glu
11570             11575                 11580

Thr Ser   Thr Thr Val Ser Gly   Thr Ile Pro Asn Phe   Ser His Arg
11585             11590                 11595

Gly Ser   Asp Thr Ala Pro Ser   Met Val Thr Ser Pro   Gly Val Asp
11600             11605                 11610

Thr Arg   Ser Gly Val Pro Thr   Thr Thr Ile Pro Pro   Ser Ile Pro
11615             11620                 11625
```

Gly Val   Val Thr Ser Gln Val   Thr Ser Ser Ala Thr   Asp Thr Ser
    11630             11635             11640

Thr Ala   Ile Pro Thr Leu Thr   Pro Ser Pro Gly Glu   Pro Glu Thr
    11645             11650             11655

Thr Ala   Ser Ser Ala Thr His   Pro Gly Thr Gln Thr   Gly Phe Thr
    11660             11665             11670

Val Pro   Ile Arg Thr Val Pro   Ser Ser Glu Pro Asp   Thr Met Ala
    11675             11680             11685

Ser Trp   Val Thr His Pro Pro   Gln Thr Ser Thr Pro   Val Ser Arg
    11690             11695             11700

Thr Thr   Ser Ser Phe Ser His   Ser Ser Pro Asp Ala   Thr Pro Val
    11705             11710             11715

Met Ala   Thr Ser Pro Arg Thr   Glu Ala Ser Ser Ala   Val Leu Thr
    11720             11725             11730

Thr Ile   Ser Pro Gly Ala Pro   Glu Met Val Thr Ser   Gln Ile Thr
    11735             11740             11745

Ser Ser   Gly Ala Ala Thr Ser   Thr Thr Val Pro Thr   Leu Thr His
    11750             11755             11760

Ser Pro   Gly Met Pro Glu Thr   Thr Ala Leu Leu Ser   Thr His Pro
    11765             11770             11775

Arg Thr   Glu Thr Ser Lys Thr   Phe Pro Ala Ser Thr   Val Phe Pro
    11780             11785             11790

Gln Val   Ser Glu Thr Thr Ala   Ser Leu Thr Ile Arg   Pro Gly Ala
    11795             11800             11805

Glu Thr   Ser Thr Ala Leu Pro   Thr Gln Thr Thr Ser   Ser Leu Phe
    11810             11815             11820

Thr Leu   Leu Val Thr Gly Thr   Ser Arg Val Asp Leu   Ser Pro Thr
    11825             11830             11835

Ala Ser   Pro Gly Val Ser Ala   Lys Thr Ala Pro Leu   Ser Thr His
    11840             11845             11850

Pro Gly   Thr Glu Thr Ser Thr   Met Ile Pro Thr Ser   Thr Leu Ser
    11855             11860             11865

Leu Gly   Leu Leu Glu Thr Thr   Gly Leu Leu Ala Thr   Ser Ser Ser
    11870             11875             11880

Ala Glu   Thr Ser Thr Ser Thr   Leu Thr Leu Thr Val   Ser Pro Ala
    11885             11890             11895

Val Ser   Gly Leu Ser Ser Ala   Ser Ile Thr Thr Asp   Lys Pro Gln
    11900             11905             11910

Thr Val   Thr Ser Trp Asn Thr   Glu Thr Ser Pro Ser   Val Thr Ser
    11915             11920             11925

Val Gly   Pro Pro Glu Phe Ser   Arg Thr Val Thr Gly   Thr Thr Met
    11930             11935             11940

Thr Leu   Ile Pro Ser Glu Met   Pro Thr Pro Pro Lys   Thr Ser His
    11945             11950             11955

Gly Glu   Gly Val Ser Pro Thr   Thr Ile Leu Arg Thr   Thr Met Val
    11960             11965             11970

Glu Ala   Thr Asn Leu Ala Thr   Thr Gly Ser Ser Pro   Thr Val Ala
    11975             11980             11985

Lys Thr   Thr Thr Thr Phe Asn   Thr Leu Ala Gly Ser   Leu Phe Thr
    11990             11995             12000

Pro Leu   Thr Thr Pro Gly Met   Ser Thr Leu Ala Ser   Glu Ser Val
    12005             12010             12015

Thr Ser   Arg Thr Ser Tyr Asn   His Arg Ser Trp Ile   Ser Thr Thr

-continued

```
        12020                    12025                    12030

Ser Ser  Tyr Asn Arg Arg Tyr  Trp Thr Pro Ala Thr  Ser Thr Pro
    12035                    12040                    12045

Val Thr  Ser Thr Phe Ser Pro  Gly Ile Ser Thr Ser  Ser Ile Pro
    12050                    12055                    12060

Ser Ser  Thr Ala Ala Thr Val  Pro Phe Met Val Pro  Phe Thr Leu
    12065                    12070                    12075

Asn Phe  Thr Ile Thr Asn Leu  Gln Tyr Glu Glu Asp  Met Arg His
    12080                    12085                    12090

Pro Gly  Ser Arg Lys Phe Asn  Ala Thr Glu Arg Glu  Leu Gln Gly
    12095                    12100                    12105

Leu Leu  Lys Pro Leu Phe Arg  Asn Ser Ser Leu Glu  Tyr Leu Tyr
    12110                    12115                    12120

Ser Gly  Cys Arg Leu Ala Ser  Leu Arg Pro Glu Lys  Asp Ser Ser
    12125                    12130                    12135

Ala Thr  Ala Val Asp Ala Ile  Cys Thr His Arg Pro  Asp Pro Glu
    12140                    12145                    12150

Asp Leu  Gly Leu Asp Arg Glu  Arg Leu Tyr Trp Glu  Leu Ser Asn
    12155                    12160                    12165

Leu Thr  Asn Gly Ile Gln Glu  Leu Gly Pro Tyr Thr  Leu Asp Arg
    12170                    12175                    12180

Asn Ser  Leu Tyr Val Asn Gly  Phe Thr His Arg Ser  Ser Met Pro
    12185                    12190                    12195

Thr Thr  Ser Thr Pro Gly Thr  Ser Thr Val Asp Val  Gly Thr Ser
    12200                    12205                    12210

Gly Thr  Pro Ser Ser Ser Pro  Ser Pro Thr Thr Ala  Gly Pro Leu
    12215                    12220                    12225

Leu Met  Pro Phe Thr Leu Asn  Phe Thr Ile Thr Asn  Leu Gln Tyr
    12230                    12235                    12240

Glu Glu  Asp Met Arg Arg Thr  Gly Ser Arg Lys Phe  Asn Thr Met
    12245                    12250                    12255

Glu Ser  Val Leu Gln Gly Leu  Leu Lys Pro Leu Phe  Lys Asn Thr
    12260                    12265                    12270

Ser Val  Gly Pro Leu Tyr Ser  Gly Cys Arg Leu Thr  Leu Leu Arg
    12275                    12280                    12285

Pro Glu  Lys Asp Gly Ala Ala  Thr Gly Val Asp Ala  Ile Cys Thr
    12290                    12295                    12300

His Arg  Leu Asp Pro Lys Ser  Pro Gly Leu Asn Arg  Glu Gln Leu
    12305                    12310                    12315

Tyr Trp  Glu Leu Ser Lys Leu  Thr Asn Asp Ile Glu  Glu Leu Gly
    12320                    12325                    12330

Pro Tyr  Thr Leu Asp Arg Asn  Ser Leu Tyr Val Asn  Gly Phe Thr
    12335                    12340                    12345

His Gln  Ser Ser Val Ser Thr  Thr Ser Thr Pro Gly  Thr Ser Thr
    12350                    12355                    12360

Val Asp  Leu Arg Thr Ser Gly  Thr Pro Ser Ser Leu  Ser Ser Pro
    12365                    12370                    12375

Thr Ile  Met Ala Ala Gly Pro  Leu Leu Val Pro Phe  Thr Leu Asn
    12380                    12385                    12390

Phe Thr  Ile Thr Asn Leu Gln  Tyr Gly Glu Asp Met  Gly His Pro
    12395                    12400                    12405

Gly Ser  Arg Lys Phe Asn Thr  Thr Glu Arg Val Leu  Gln Gly Leu
    12410                    12415                    12420
```

-continued

```
Leu Gly Pro Ile Phe Lys Asn   Thr Ser Val Gly Pro   Leu Tyr Ser
    12425             12430             12435

Gly Cys Arg Leu Thr Ser Leu   Arg Ser Glu Lys Asp   Gly Ala Ala
    12440             12445             12450

Thr Gly Val Asp Ala Ile Cys   Ile His His Leu Asp   Pro Lys Ser
    12455             12460             12465

Pro Gly Leu Asn Arg Glu Arg   Leu Tyr Trp Glu Leu   Ser Gln Leu
    12470             12475             12480

Thr Asn Gly Ile Lys Glu Leu   Gly Pro Tyr Thr Leu   Asp Arg Asn
    12485             12490             12495

Ser Leu Tyr Val Asn Gly Phe   Thr His Arg Thr Ser   Val Pro Thr
    12500             12505             12510

Ser Ser Thr Pro Gly Thr Ser   Thr Val Asp Leu Gly   Thr Ser Gly
    12515             12520             12525

Thr Pro Phe Ser Leu Pro Ser   Pro Ala Thr Ala Gly   Pro Leu Leu
    12530             12535             12540

Val Leu Phe Thr Leu Asn Phe   Thr Ile Thr Asn Leu   Lys Tyr Glu
    12545             12550             12555

Glu Asp Met His Arg Pro Gly   Ser Arg Lys Phe Asn   Thr Thr Glu
    12560             12565             12570

Arg Val Leu Gln Thr Leu Leu   Gly Pro Met Phe Lys   Asn Thr Ser
    12575             12580             12585

Val Gly Leu Leu Tyr Ser Gly   Cys Arg Leu Thr Leu   Leu Arg Ser
    12590             12595             12600

Glu Lys Asp Gly Ala Ala Thr   Gly Val Asp Ala Ile   Cys Thr His
    12605             12610             12615

Arg Leu Asp Pro Lys Ser Pro   Gly Val Asp Arg Glu   Gln Leu Tyr
    12620             12625             12630

Trp Glu Leu Ser Gln Leu Thr   Asn Gly Ile Lys Glu   Leu Gly Pro
    12635             12640             12645

Tyr Thr Leu Asp Arg Asn Ser   Leu Tyr Val Asn Gly   Phe Thr His
    12650             12655             12660

Trp Ile Pro Val Pro Thr Ser   Ser Thr Pro Gly Thr   Ser Thr Val
    12665             12670             12675

Asp Leu Gly Ser Gly Thr Pro   Ser Ser Leu Pro Ser   Pro Thr Thr
    12680             12685             12690

Ala Gly Pro Leu Leu Val Pro   Phe Thr Leu Asn Phe   Thr Ile Thr
    12695             12700             12705

Asn Leu Lys Tyr Glu Glu Asp   Met His Cys Pro Gly   Ser Arg Lys
    12710             12715             12720

Phe Asn Thr Thr Glu Arg Val   Leu Gln Ser Leu Leu   Gly Pro Met
    12725             12730             12735

Phe Lys Asn Thr Ser Val Gly   Pro Leu Tyr Ser Gly   Cys Arg Leu
    12740             12745             12750

Thr Leu Leu Arg Ser Glu Lys   Asp Gly Ala Ala Thr   Gly Val Asp
    12755             12760             12765

Ala Ile Cys Thr His Arg Leu   Asp Pro Lys Ser Pro   Gly Val Asp
    12770             12775             12780

Arg Glu Gln Leu Tyr Trp Glu   Leu Ser Gln Leu Thr   Asn Gly Ile
    12785             12790             12795

Lys Glu Leu Gly Pro Tyr Thr   Leu Asp Arg Asn Ser   Leu Tyr Val
    12800             12805             12810
```

-continued

```
Asn Gly  Phe Thr His Gln Thr  Ser Ala Pro Asn Thr  Ser Thr Pro
    12815             12820             12825

Gly Thr  Ser Thr Val Asp Leu  Gly Thr Ser Gly Thr  Pro Ser Ser
    12830             12835             12840

Leu Pro  Ser Pro Thr Ser Ala  Gly Pro Leu Leu Val  Pro Phe Thr
    12845             12850             12855

Leu Asn  Phe Thr Ile Thr Asn  Leu Gln Tyr Glu Glu  Asp Met His
    12860             12865             12870

His Pro  Gly Ser Arg Lys Phe  Asn Thr Thr Glu Arg  Val Leu Gln
    12875             12880             12885

Gly Leu  Leu Gly Pro Met Phe  Lys Asn Thr Ser Val  Gly Leu Leu
    12890             12895             12900

Tyr Ser  Gly Cys Arg Leu Thr  Leu Leu Arg Pro Glu  Lys Asn Gly
    12905             12910             12915

Ala Ala  Thr Gly Met Asp Ala  Ile Cys Ser His Arg  Leu Asp Pro
    12920             12925             12930

Lys Ser  Pro Gly Leu Asn Arg  Glu Gln Leu Tyr Trp  Glu Leu Ser
    12935             12940             12945

Gln Leu  Thr His Gly Ile Lys  Glu Leu Gly Pro Tyr  Thr Leu Asp
    12950             12955             12960

Arg Asn  Ser Leu Tyr Val Asn  Gly Phe Thr His Arg  Ser Ser Val
    12965             12970             12975

Ala Pro  Thr Ser Thr Pro Gly  Thr Ser Thr Val Asp  Leu Gly Thr
    12980             12985             12990

Ser Gly  Thr Pro Ser Ser Leu  Pro Ser Pro Thr Thr  Ala Val Pro
    12995             13000             13005

Leu Leu  Val Pro Phe Thr Leu  Asn Phe Thr Ile Thr  Asn Leu Gln
    13010             13015             13020

Tyr Gly  Glu Asp Met Arg His  Pro Gly Ser Arg Lys  Phe Asn Thr
    13025             13030             13035

Thr Glu  Arg Val Leu Gln Gly  Leu Leu Gly Pro Leu  Phe Lys Asn
    13040             13045             13050

Ser Ser  Val Gly Pro Leu Tyr  Ser Gly Cys Arg Leu  Ile Ser Leu
    13055             13060             13065

Arg Ser  Glu Lys Asp Gly Ala  Ala Thr Gly Val Asp  Ala Ile Cys
    13070             13075             13080

Thr His  His Leu Asn Pro Gln  Ser Pro Gly Leu Asp  Arg Glu Gln
    13085             13090             13095

Leu Tyr  Trp Gln Leu Ser Gln  Met Thr Asn Gly Ile  Lys Glu Leu
    13100             13105             13110

Gly Pro  Tyr Thr Leu Asp Arg  Asn Ser Leu Tyr Val  Asn Gly Phe
    13115             13120             13125

Thr His  Arg Ser Ser Gly Leu  Thr Thr Ser Thr Pro  Trp Thr Ser
    13130             13135             13140

Thr Val  Asp Leu Gly Thr Ser  Gly Thr Pro Ser Pro  Val Pro Ser
    13145             13150             13155

Pro Thr  Thr Thr Gly Pro Leu  Leu Val Pro Phe Thr  Leu Asn Phe
    13160             13165             13170

Thr Ile  Thr Asn Leu Gln Tyr  Glu Glu Asn Met Gly  His Pro Gly
    13175             13180             13185

Ser Arg  Lys Phe Asn Ile Thr  Glu Ser Val Leu Gln  Gly Leu Leu
    13190             13195             13200

Lys Pro  Leu Phe Lys Ser Thr  Ser Val Gly Pro Leu  Tyr Ser Gly
```

-continued

```
    13205             13210             13215

Cys Arg  Leu Thr Leu Leu Arg  Pro Glu Lys Asp Gly  Val Ala Thr
    13220             13225             13230

Arg Val  Asp Ala Ile Cys Thr  His Arg Pro Asp Pro  Lys Ile Pro
    13235             13240             13245

Gly Leu  Asp Arg Gln Gln Leu  Tyr Trp Glu Leu Ser  Gln Leu Thr
    13250             13255             13260

His Ser  Ile Thr Glu Leu Gly  Pro Tyr Thr Leu Asp  Arg Asp Ser
    13265             13270             13275

Leu Tyr  Val Asn Gly Phe Thr  Gln Arg Ser Ser Val  Pro Thr Thr
    13280             13285             13290

Ser Thr  Pro Gly Thr Phe Thr  Val Gln Pro Glu Thr  Ser Glu Thr
    13295             13300             13305

Pro Ser  Ser Leu Pro Gly Pro  Thr Ala Thr Gly Pro  Val Leu Leu
    13310             13315             13320

Pro Phe  Thr Leu Asn Phe Thr  Ile Thr Asn Leu Gln  Tyr Glu Glu
    13325             13330             13335

Asp Met  Arg Arg Pro Gly Ser  Arg Lys Phe Asn Thr  Thr Glu Arg
    13340             13345             13350

Val Leu  Gln Gly Leu Leu Met  Pro Leu Phe Lys Asn  Thr Ser Val
    13355             13360             13365

Ser Ser  Leu Tyr Ser Gly Cys  Arg Leu Thr Leu Leu  Arg Pro Glu
    13370             13375             13380

Lys Asp  Gly Ala Ala Thr Arg  Val Asp Ala Val Cys  Thr His Arg
    13385             13390             13395

Pro Asp  Pro Lys Ser Pro Gly  Leu Asp Arg Glu Arg  Leu Tyr Trp
    13400             13405             13410

Lys Leu  Ser Gln Leu Thr His  Gly Ile Thr Glu Leu  Gly Pro Tyr
    13415             13420             13425

Thr Leu  Asp Arg His Ser Leu  Tyr Val Asn Gly Phe  Thr His Gln
    13430             13435             13440

Ser Ser  Met Thr Thr Thr Arg  Thr Pro Asp Thr Ser  Thr Met His
    13445             13450             13455

Leu Ala  Thr Ser Arg Thr Pro  Ala Ser Leu Ser Gly  Pro Met Thr
    13460             13465             13470

Ala Ser  Pro Leu Leu Val Leu  Phe Thr Ile Asn Phe  Thr Ile Thr
    13475             13480             13485

Asn Leu  Arg Tyr Glu Glu Asn  Met His His Pro Gly  Ser Arg Lys
    13490             13495             13500

Phe Asn  Thr Thr Glu Arg Val  Leu Gln Gly Leu Leu  Arg Pro Val
    13505             13510             13515

Phe Lys  Asn Thr Ser Val Gly  Pro Leu Tyr Ser Gly  Cys Arg Leu
    13520             13525             13530

Thr Leu  Leu Arg Pro Lys Lys  Asp Gly Ala Ala Thr  Lys Val Asp
    13535             13540             13545

Ala Ile  Cys Thr Tyr Arg Pro  Asp Pro Lys Ser Pro  Gly Leu Asp
    13550             13555             13560

Arg Glu  Gln Leu Tyr Trp Glu  Leu Ser Gln Leu Thr  His Ser Ile
    13565             13570             13575

Thr Glu  Leu Gly Pro Tyr Thr  Leu Asp Arg Asp Ser  Leu Tyr Val
    13580             13585             13590

Asn Gly  Phe Thr Gln Arg Ser  Ser Val Pro Thr Thr  Ser Ile Pro
    13595             13600             13605
```

```
Gly Thr  Pro Thr Val Asp Leu  Gly Thr Ser Gly Thr  Pro Val Ser
    13610             13615                  13620

Lys Pro  Gly Pro Ser Ala Ala  Ser Pro Leu Leu Val  Leu Phe Thr
    13625             13630                  13635

Leu Asn  Phe Thr Ile Thr Asn  Leu Arg Tyr Glu Glu  Asn Met Gln
    13640             13645                  13650

His Pro  Gly Ser Arg Lys Phe  Asn Thr Thr Glu Arg  Val Leu Gln
    13655             13660                  13665

Gly Leu  Leu Arg Ser Leu Phe  Lys Ser Thr Ser Val  Gly Pro Leu
    13670             13675                  13680

Tyr Ser  Gly Cys Arg Leu Thr  Leu Leu Arg Pro Glu  Lys Asp Gly
    13685             13690                  13695

Thr Ala  Thr Gly Val Asp Ala  Ile Cys Thr His His  Pro Asp Pro
    13700             13705                  13710

Lys Ser  Pro Arg Leu Asp Arg  Glu Gln Leu Tyr Trp  Glu Leu Ser
    13715             13720                  13725

Gln Leu  Thr His Asn Ile Thr  Glu Leu Gly Pro Tyr  Ala Leu Asp
    13730             13735                  13740

Asn Asp  Ser Leu Phe Val Asn  Gly Phe Thr His Arg  Ser Ser Val
    13745             13750                  13755

Ser Thr  Thr Ser Thr Pro Gly  Thr Pro Thr Val Tyr  Leu Gly Ala
    13760             13765                  13770

Ser Lys  Thr Pro Ala Ser Ile  Phe Gly Pro Ser Ala  Ala Ser His
    13775             13780                  13785

Leu Leu  Ile Leu Phe Thr Leu  Asn Phe Thr Ile Thr  Asn Leu Arg
    13790             13795                  13800

Tyr Glu  Glu Asn Met Trp Pro  Gly Ser Arg Lys Phe  Asn Thr Thr
    13805             13810                  13815

Glu Arg  Val Leu Gln Gly Leu  Leu Arg Pro Leu Phe  Lys Asn Thr
    13820             13825                  13830

Ser Val  Gly Pro Leu Tyr Ser  Gly Cys Arg Leu Thr  Leu Leu Arg
    13835             13840                  13845

Pro Glu  Lys Asp Gly Glu Ala  Thr Gly Val Asp Ala  Ile Cys Thr
    13850             13855                  13860

His Arg  Pro Asp Pro Thr Gly  Pro Gly Leu Asp Arg  Glu Gln Leu
    13865             13870                  13875

Tyr Leu  Glu Leu Ser Gln Leu  Thr His Ser Ile Thr  Glu Leu Gly
    13880             13885                  13890

Pro Tyr  Thr Leu Asp Arg Asp  Ser Leu Tyr Val Asn  Gly Phe Thr
    13895             13900                  13905

His Arg  Ser Ser Val Pro Thr  Thr Ser Thr Gly Val  Val Ser Glu
    13910             13915                  13920

Glu Pro  Phe Thr Leu Asn Phe  Thr Ile Asn Asn Leu  Arg Tyr Met
    13925             13930                  13935

Ala Asp  Met Gly Gln Pro Gly  Ser Leu Lys Phe Asn  Ile Thr Asp
    13940             13945                  13950

Asn Val  Met Gln His Leu Leu  Ser Pro Leu Phe Gln  Arg Ser Ser
    13955             13960                  13965

Leu Gly  Ala Arg Tyr Thr Gly  Cys Arg Val Ile Ala  Leu Arg Ser
    13970             13975                  13980

Val Lys  Asn Gly Ala Glu Thr  Arg Val Asp Leu Leu  Cys Thr Tyr
    13985             13990                  13995
```

```
Leu Gln  Pro Leu Ser Gly Pro  Gly Leu Pro Ile Lys  Gln Val Phe
    14000                14005                14010

His Glu  Leu Ser Gln Gln Thr  His Gly Ile Thr Arg  Leu Gly Pro
    14015                14020                14025

Tyr Ser  Leu Asp Lys Asp Ser  Leu Tyr Leu Asn Gly  Tyr Asn Glu
    14030                14035                14040

Pro Gly  Pro Asp Glu Pro Pro  Thr Thr Pro Lys Pro  Ala Thr Thr
    14045                14050                14055

Phe Leu  Pro Pro Leu Ser Glu  Ala Thr Thr Ala Met  Gly Tyr His
    14060                14065                14070

Leu Lys  Thr Leu Thr Leu Asn  Phe Thr Ile Ser Asn  Leu Gln Tyr
    14075                14080                14085

Ser Pro  Asp Met Gly Lys Gly  Ser Ala Thr Phe Asn  Ser Thr Glu
    14090                14095                14100

Gly Val  Leu Gln His Leu Leu  Arg Pro Leu Phe Gln  Lys Ser Ser
    14105                14110                14115

Met Gly  Pro Phe Tyr Leu Gly  Cys Gln Leu Ile Ser  Leu Arg Pro
    14120                14125                14130

Glu Lys  Asp Gly Ala Ala Thr  Gly Val Asp Thr Thr  Cys Thr Tyr
    14135                14140                14145

His Pro  Asp Pro Val Gly Pro  Gly Leu Asp Ile Gln  Gln Leu Tyr
    14150                14155                14160

Trp Glu  Leu Ser Gln Leu Thr  His Gly Val Thr Gln  Leu Gly Phe
    14165                14170                14175

Tyr Val  Leu Asp Arg Asp Ser  Leu Phe Ile Asn Gly  Tyr Ala Pro
    14180                14185                14190

Gln Asn  Leu Ser Ile Arg Gly  Glu Tyr Gln Ile Asn  Phe His Ile
    14195                14200                14205

Val Asn  Trp Asn Leu Ser Asn  Pro Asp Pro Thr Ser  Ser Glu Tyr
    14210                14215                14220

Ile Thr  Leu Leu Arg Asp Ile  Gln Asp Lys Val Thr  Thr Leu Tyr
    14225                14230                14235

Lys Gly  Ser Gln Leu His Asp  Thr Phe Arg Phe Cys  Leu Val Thr
    14240                14245                14250

Asn Leu  Thr Met Asp Ser Val  Leu Val Thr Val Lys  Ala Leu Phe
    14255                14260                14265

Ser Ser  Asn Leu Asp Pro Ser  Leu Val Glu Gln Val  Phe Leu Asp
    14270                14275                14280

Lys Thr  Leu Asn Ala Ser Phe  His Trp Leu Gly Ser  Thr Tyr Gln
    14285                14290                14295

Leu Val  Asp Ile His Val Thr  Glu Met Glu Ser Ser  Val Tyr Gln
    14300                14305                14310

Pro Thr  Ser Ser Ser Ser Thr  Gln His Phe Tyr Leu  Asn Phe Thr
    14315                14320                14325

Ile Thr  Asn Leu Pro Tyr Ser  Gln Asp Lys Ala Gln  Pro Gly Thr
    14330                14335                14340

Thr Asn  Tyr Gln Arg Asn Lys  Arg Asn Ile Glu Asp  Ala Leu Asn
    14345                14350                14355

Gln Leu  Phe Arg Asn Ser Ser  Ile Lys Ser Tyr Phe  Ser Asp Cys
    14360                14365                14370

Gln Val  Ser Thr Phe Arg Ser  Val Pro Asn Arg His  His Thr Gly
    14375                14380                14385

Val Asp  Ser Leu Cys Asn Phe  Ser Pro Leu Ala Arg  Arg Val Asp
```

-continued

```
    14390              14395              14400

Arg Val  Ala Ile Tyr Glu Glu  Phe Leu Arg Met Thr  Arg Asn Gly
    14405              14410              14415

Thr Gln  Leu Gln Asn Phe Thr  Leu Asp Arg Ser Ser  Val Leu Val
    14420              14425              14430

Asp Gly  Tyr Ser Pro Asn Arg  Asn Glu Pro Leu Thr  Gly Asn Ser
    14435              14440              14445

Asp Leu  Pro Phe Trp Ala Val  Ile Leu Ile Gly Leu  Ala Gly Leu
    14450              14455              14460

Leu Gly  Val Ile Thr Cys Leu  Ile Cys Gly Val Leu  Val Thr Thr
    14465              14470              14475

Arg Arg  Arg Lys Lys Glu Gly  Glu Tyr Asn Val Gln  Gln Gln Cys
    14480              14485              14490

Pro Gly  Tyr Tyr Gln Ser His  Leu Asp Leu Glu Asp  Leu Gln
    14495              14500              14505
```

<210> SEQ ID NO 2
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Asp Ile Glu Leu Thr Gln Ser Pro Ser Ser Leu Ala Val Ser Ala Gly
1               5                  10                  15

Glu Arg Val Thr Met Asn Cys Lys Ser Ser Gln Ser Leu Leu Asn Ser
            20                  25                  30

Arg Thr Arg Lys Asn Gln Leu Ala Trp Tyr Gln Gln Lys Pro Gly Gln
        35                  40                  45

Ser Pro Glu Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Ser Tyr Asn Leu Leu Thr Phe Gly Pro Gly Thr Lys Leu Glu Ile Lys
            100                 105                 110

Arg
```

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Asp Ile Val Leu Thr Gln Ser Pro Asp Ser Leu Ala Val Ser Leu Gly
1               5                  10                  15

Glu Arg Val Thr Met Asn Cys Lys Ser Ser Gln Ser Leu Leu Asn Ser
            20                  25                  30

Arg Thr Arg Lys Asn Gln Leu Ala Trp Tyr Gln Gln Lys Pro Gly Gln
        35                  40                  45

Ser Pro Glu Leu Leu Ile Tyr Trp Ala Ser Thr Arg Gln Ser Gly Val
    50                  55                  60
```

```
Pro Asp Arg Phe Ser Gly Ser Gly Ser Gly Thr Asp Phe Thr Leu Thr
65              70                  75                  80

Ile Ser Ser Val Gln Ala Glu Asp Val Ala Val Tyr Tyr Cys Gln Gln
                85                  90                  95

Ser Tyr Asn Leu Leu Thr Phe Gly Gln Gly Thr Lys Leu Glu Ile Lys
            100                 105                 110

Arg
```

```
<210> SEQ ID NO 4
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4
```

```
Glu Val Lys Leu Gln Glu Ser Gly Gly Gly Phe Val Lys Pro Gly Gly
1               5                   10                  15

Ser Leu Arg Val Ser Cys Ala Ala Ser Gly Phe Thr Phe Ser Ser Tyr
                20                  25                  30

Ala Met Ser Trp Val Arg Leu Ala Pro Glu Met Arg Leu Glu Trp Val
            35                  40                  45

Ala Thr Ile Ser Ser Ala Gly Gly Tyr Ile Phe Tyr Ser Asp Ser Val
        50                  55                  60

Gln Gly Arg Phe Thr Ile Ser Arg Asp Asn Ala Lys Asn Ser Leu His
65              70                  75                  80

Leu Gln Met Gly Ser Leu Arg Ser Gly Asp Thr Ala Met Tyr Tyr Cys
                85                  90                  95

Ala Arg Gln Gly Phe Gly Asn Tyr Gly Asp Tyr Tyr Ala Met Asp Tyr
            100                 105                 110

Trp Gly Gln Gly Thr Thr Val Thr Val Ser Ser
        115                 120
```

```
<210> SEQ ID NO 5
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

```
Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Ser Tyr
                20                  25                  30

Ala Met Ser Trp Val Arg Leu Ala Pro Gly Lys Gly Leu Glu Trp Val
            35                  40                  45

Ala Thr Ile Ser Ser Ala Gly Gly Tyr Ile Phe Tyr Ser Asp Ser Val
        50                  55                  60

Gln Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Met Tyr Tyr Cys
                85                  90                  95

Ala Arg Gln Gly Phe Gly Asn Tyr Gly Asp Tyr Tyr Ala Met Asp Tyr
            100                 105                 110
```

-continued

```
Trp Gly Gln Gly Thr Leu Val Thr Val Ser Ser
      115                 120

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 7
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 8
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ser Thr Lys Gly Pro Ser Val Phe Pro Leu Ala Pro Ser Ser Lys
```

-continued

```
1               5                    10                   15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 9
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Ala Ser Thr Lys Gly Pro Ser Val Phe Pro Leu Ala Pro Ser Ser Lys
1               5                    10                   15

Ser Thr Ser Gly Gly Thr Ala Ala Leu Gly Cys Leu Val Lys Asp Tyr
            20                  25                  30
```

-continued

```
Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
            85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```

```
<210> SEQ ID NO 10
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10
```

```
Asp Ile Glu Leu Thr Gln Ser Pro Ser Ser Leu Ala Val Ser Ala Gly
1               5               10              15

Glu Arg Val Thr Met Asn Cys Lys Ser Ser Gln Ser Leu Leu Asn Ser
            20              25              30

Arg Thr Arg Lys Asn Gln Leu Ala Trp Tyr Gln Gln Lys Pro Gly Gln
        35              40              45

Ser Pro Glu Leu Leu Ile Tyr Trp Ala Ser Thr Arg Gln Ser Gly Val
    50              55              60
```

-continued

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Ser Tyr Asn Leu Leu Thr Phe Gly Pro Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 11
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Val Leu Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ser
            20                  25                  30

Arg Thr Arg Lys Asn Gln Leu Ala Trp Tyr Gln Gln Lys Pro Gly Gln
            35                  40                  45

Ser Pro Glu Leu Leu Ile Tyr Trp Ala Ser Thr Arg Gln Ser Gly Val
        50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Ser Tyr Asn Leu Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser

-continued

```
             195                200                205

Pro Val Thr Lys Ser Phe Asn Arg Gly Glu Cys
    210                215

<210> SEQ ID NO 12
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Lys Leu Gln Glu Ser Gly Gly Gly Phe Val Lys Pro Gly Gly
1               5                   10                  15

Ser Leu Arg Val Ser Cys Ala Ala Ser Gly Phe Thr Phe Ser Ser Tyr
            20                  25                  30

Ala Met Ser Trp Val Arg Leu Ala Pro Glu Met Arg Leu Glu Trp Val
        35                  40                  45

Ala Thr Ile Ser Ser Ala Gly Gly Tyr Ile Phe Tyr Ser Asp Ser Val
    50                  55                  60

Gln Gly Arg Phe Thr Ile Ser Arg Asp Asn Ala Lys Asn Ser Leu His
65                  70                  75                  80

Leu Gln Met Gly Ser Leu Arg Ser Gly Asp Thr Ala Met Tyr Tyr Cys
                85                  90                  95

Ala Arg Gln Gly Phe Gly Asn Tyr Gly Asp Tyr Tyr Ala Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
            340             345             350

Gln Val Tyr Thr Leu Pro Pro Ser Arg Asp Glu Leu Thr Lys Asn Gln
            355             360             365

Val Ser Leu Thr Cys Leu Val Lys Gly Phe Tyr Pro Ser Asp Ile Ala
    370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Lys Leu
            405             410             415

Thr Val Asp Lys Ser Arg Trp Gln Gln Gly Asn Val Phe Ser Cys Ser
            420             425             430

Val Met His Glu Ala Leu His Asn His Tyr Thr Gln Lys Ser Leu Ser
            435             440             445

Leu Ser Pro Gly Lys
    450

<210> SEQ ID NO 13
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Lys Pro Gly Gly
1               5               10              15

Ser Leu Arg Val Ser Cys Ala Ala Ser Gly Phe Thr Phe Ser Ser Tyr
            20              25              30

Ala Met Ser Trp Val Arg Leu Ala Pro Gly Lys Gly Leu Glu Trp Val
            35              40              45

Ala Thr Ile Ser Ser Ala Gly Gly Tyr Ile Phe Tyr Ser Asp Ser Val
    50              55              60

Gln Gly Arg Phe Thr Ile Ser Arg Asp Asn Ala Lys Asn Ser Leu Tyr
65              70              75              80

Leu Gln Met Asn Ser Leu Arg Ala Glu Asp Thr Ala Met Tyr Tyr Cys
            85              90              95

Ala Arg Gln Gly Phe Gly Asn Tyr Gly Asp Tyr Tyr Ala Met Asp Tyr
            100             105             110

Trp Gly Gln Gly Thr Leu Val Thr Val Ser Ser Ala Ser Thr Lys Gly
            115             120             125

Pro Ser Val Phe Pro Leu Ala Pro Ser Ser Lys Ser Thr Ser Gly Gly
    130             135             140

Thr Ala Ala Leu Gly Cys Leu Val Lys Asp Tyr Phe Pro Glu Pro Val
145             150             155             160

Thr Val Ser Trp Asn Ser Gly Ala Leu Thr Ser Gly Val His Thr Phe
            165             170             175

Pro Ala Val Leu Gln Ser Ser Gly Leu Tyr Ser Leu Ser Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Arg Val Glu Pro Lys
    210             215             220

Ser Cys Asp Lys Thr His Thr Cys Pro Pro Cys Pro Ala Pro Glu Leu
225             230             235             240
```

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys
    450

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Leu Leu Asn Ser Arg Thr Arg Lys Asn Gln
1               5                   10

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Ala Ser
1

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Ser Tyr Asn Leu Leu Thr
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Phe Thr Phe Ser Ser Tyr Ala
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Ser Ser Ala Gly Gly Tyr Ile
1               5

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Arg Gln Gly Phe Gly Asn Tyr Gly Asp Tyr Tyr Ala Met Asp Tyr
1               5                   10                  15

<210> SEQ ID NO 20
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Ser Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Arg Leu Ile Tyr Tyr Met Ser Asn Leu Ala Ser Gly Val Pro
    50                  55                  60

Asp Arg Phe Ser Gly Arg Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Tyr Pro Leu Thr Phe Gly Gly Gly Thr Lys Leu Glu Ile Lys
            100                 105                 110

Arg

<210> SEQ ID NO 21
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Val Met Thr Gln Ser Ala Leu Ser Leu Pro Val Thr Pro Gly
1               5                   10                  15

Glu Pro Val Ser Ile Ser Cys Arg Ser Ser Lys Ser Leu Leu His Ser
                20                  25                  30

Asn Gly Asn Thr Tyr Leu Tyr Trp Phe Leu Gln Lys Pro Gly Gln Ser
            35                  40                  45

Pro Gln Arg Leu Ile Tyr Tyr Met Ser Asn Leu Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Tyr Pro Leu Thr Phe Gly Gly Gly Thr Lys Leu Glu Ile Lys
            100                 105                 110

Arg

<210> SEQ ID NO 22
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Thr Leu Lys Glu Ser Gly Pro Gly Ile Leu Gln Pro Thr Gln
1               5                   10                  15

Thr Leu Thr Leu Thr Cys Thr Phe Ser Gly Phe Ser Leu Ser Thr Val
                20                  25                  30

Gly Met Gly Val Gly Trp Ser Arg Gln Pro Ser Gly Lys Gly Leu Glu
            35                  40                  45

Trp Leu Ala His Ile Trp Trp Asp Asp Glu Asp Lys Tyr Tyr Asn Pro
        50                  55                  60

Ala Leu Lys Ser Arg Leu Thr Ile Thr Lys Asp Thr Ser Lys Asn Gln
65                  70                  75                  80

Val Phe Leu Lys Ile Thr Asn Val Asp Thr Ala Asp Thr Ala Thr Tyr
                85                  90                  95

Tyr Cys Thr Arg Ile Gly Thr Ala Gln Ala Thr Asp Ala Leu Asp Tyr
            100                 105                 110

Trp Gly Gln Gly Thr Leu Val Thr Val Ser Ser
        115                 120

<210> SEQ ID NO 23
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Val
            20                  25                  30

Gly Met Gly Val Gly Trp Ser Arg Gln Pro Ser Gly Lys Gly Leu Glu
        35                  40                  45

Trp Leu Ala His Ile Trp Trp Asp Asp Glu Asp Lys Tyr Tyr Asn Pro
    50                  55                  60

Ala Leu Lys Ser Arg Leu Thr Ile Thr Lys Asp Thr Ser Lys Asn Gln
65                  70                  75                  80

Val Val Leu Thr Ile Thr Asn Val Asp Pro Val Asp Thr Ala Thr Tyr
                85                  90                  95

Tyr Cys Thr Arg Ile Gly Thr Ala Gln Ala Thr Asp Ala Leu Asp Tyr
            100                 105                 110

Trp Gly Gln Gly Thr Leu Val Thr Val Ser Ser
        115                 120
```

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 25
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45
```

```
Gly Asn Ser Gln Glu Ser Val Thr Glu Gln Asp Ser Lys Asp Ser Thr
    50              55              60

Tyr Ser Leu Ser Ser Thr Leu Thr Leu Ser Lys Ala Asp Tyr Glu Lys
65              70              75              80

His Lys Val Tyr Ala Cys Glu Val Thr His Gln Gly Leu Ser Ser Pro
                85              90              95

Val Thr Lys Ser Phe Asn Arg Gly Glu Cys
            100             105

<210> SEQ ID NO 26
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
        260             265             270

Asn Tyr Lys Thr Thr Pro Pro Val Leu Asp Ser Asp Gly Ser Phe Phe
    275             280             285

Leu Tyr Ser Lys Leu Thr Val Asp Lys Ser Arg Trp Gln Gln Gly Asn
```

```
        290              295              300

Val Phe Ser Cys Ser Val Met His Glu Ala Leu His Asn His Tyr Thr
305                 310              315                 320

Gln Lys Ser Leu Ser Leu Ser Pro Gly Lys
                325              330

<210> SEQ ID NO 27
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Ser Thr Lys Gly Pro Ser Val Phe Pro Leu Ala Pro Ser Ser Lys
1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly Lys
                325                     330

<210> SEQ ID NO 28
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Val Met Thr Gln Ser Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Arg Leu Ile Tyr Tyr Met Ser Asn Leu Ala Ser Gly Val Pro
    50                  55                  60

Asp Arg Phe Ser Gly Arg Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Tyr Pro Leu Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 29
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Met Thr Gln Ser Ala Leu Ser Leu Pro Val Thr Pro Gly
1               5                   10                  15

Glu Pro Val Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
        35                  40                  45

Pro Gln Arg Leu Ile Tyr Tyr Met Ser Asn Leu Ala Ser Gly Val Pro
    50                  55                  60
```

-continued

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Tyr Pro Leu Thr Phe Gly Gly Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 30
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30
```

```
Gln Val Thr Leu Lys Glu Ser Gly Pro Gly Ile Leu Gln Pro Thr Gln
1               5                   10                  15

Thr Leu Thr Leu Thr Cys Thr Phe Ser Gly Phe Ser Leu Ser Thr Val
            20                  25                  30

Gly Met Gly Val Gly Trp Ser Arg Gln Pro Ser Gly Lys Gly Leu Glu
        35                  40                  45

Trp Leu Ala His Ile Trp Trp Asp Asp Glu Asp Lys Tyr Tyr Asn Pro
    50                  55                  60

Ala Leu Lys Ser Arg Leu Thr Ile Thr Lys Asp Thr Ser Lys Asn Gln
65                  70                  75                  80

Val Phe Leu Lys Ile Thr Asn Val Asp Thr Ala Asp Thr Ala Thr Tyr
                85                  90                  95

Tyr Cys Thr Arg Ile Gly Thr Ala Gln Ala Thr Asp Ala Leu Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205
```

-continued

```
Asn His Lys Pro Ser Asn Thr Lys Val Asp Lys Arg Val Glu Pro Lys
    210             215             220
```

```
Ser Cys Asp Lys Thr His Thr Cys Pro Pro Cys Pro Ala Pro Glu Leu
225             230             235             240
```

```
Leu Gly Gly Pro Ser Val Phe Leu Phe Pro Pro Lys Pro Lys Asp Thr
            245             250             255
```

```
Leu Met Ile Ser Arg Thr Pro Glu Val Thr Cys Val Val Val Asp Val
            260             265             270
```

```
Ser His Glu Asp Pro Glu Val Lys Phe Asn Trp Tyr Val Asp Gly Val
            275             280             285
```

```
Glu Val His Asn Ala Lys Thr Lys Pro Arg Glu Glu Gln Tyr Asn Ser
    290             295             300
```

```
Thr Tyr Arg Val Val Ser Val Leu Thr Val Leu His Gln Asp Trp Leu
305             310             315             320
```

```
Asn Gly Lys Glu Tyr Lys Cys Lys Val Ser Asn Lys Ala Leu Pro Ala
            325             330             335
```

```
Pro Ile Glu Lys Thr Ile Ser Lys Ala Lys Gly Gln Pro Arg Glu Pro
            340             345             350
```

```
Gln Val Tyr Thr Leu Pro Pro Ser Arg Asp Glu Leu Thr Lys Asn Gln
            355             360             365
```

```
Val Ser Leu Thr Cys Leu Val Lys Gly Phe Tyr Pro Ser Asp Ile Ala
    370             375             380
```

```
Val Glu Trp Glu Ser Asn Gly Gln Pro Glu Asn Asn Tyr Lys Thr Thr
385             390             395             400
```

```
Pro Pro Val Leu Asp Ser Asp Gly Ser Phe Phe Leu Tyr Ser Lys Leu
            405             410             415
```

```
Thr Val Asp Lys Ser Arg Trp Gln Gln Gly Asn Val Phe Ser Cys Ser
            420             425             430
```

```
Val Met His Glu Ala Leu His Asn His Tyr Thr Gln Lys Ser Leu Ser
    435             440             445
```

```
Leu Ser Pro Gly Lys
    450
```

<210> SEQ ID NO 31
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Gln Val Thr Leu Lys Glu Ser Gly Pro Thr Leu Val Lys Pro Thr Gln
1               5               10              15
```

```
Thr Leu Thr Leu Thr Cys Thr Phe Ser Gly Phe Ser Leu Ser Thr Val
            20              25              30
```

```
Gly Met Gly Val Gly Trp Ser Arg Gln Pro Ser Gly Lys Gly Leu Glu
        35              40              45
```

```
Trp Leu Ala His Ile Trp Trp Asp Asp Glu Asp Lys Tyr Tyr Asn Pro
    50              55              60
```

```
Ala Leu Lys Ser Arg Leu Thr Ile Thr Lys Asp Thr Ser Lys Asn Gln
65              70              75              80
```

```
Val Val Leu Thr Ile Thr Asn Val Asp Pro Val Asp Thr Ala Thr Tyr
            85              90              95
```

```
Tyr Cys Thr Arg Ile Gly Thr Ala Gln Ala Thr Asp Ala Leu Asp Tyr
```

```
              100              105              110
Trp Gly Gln Gly Thr Leu Val Thr Val Ser Ser Ala Ser Thr Lys Gly
        115              120              125

Pro Ser Val Phe Pro Leu Ala Pro Ser Ser Lys Ser Thr Ser Gly Gly
    130              135              140

Thr Ala Ala Leu Gly Cys Leu Val Lys Asp Tyr Phe Pro Glu Pro Val
145              150              155              160

Thr Val Ser Trp Asn Ser Gly Ala Leu Thr Ser Gly Val His Thr Phe
            165              170              175

Pro Ala Val Leu Gln Ser Ser Gly Leu Tyr Ser Leu Ser Ser Val Val
            180              185              190

Thr Val Pro Ser Ser Ser Leu Gly Thr Gln Thr Tyr Ile Cys Asn Val
        195              200              205

Asn His Lys Pro Ser Asn Thr Lys Val Asp Lys Arg Val Glu Pro Lys
    210              215              220

Ser Cys Asp Lys Thr His Thr Cys Pro Pro Cys Pro Ala Pro Glu Leu
225              230              235              240

Leu Gly Gly Pro Ser Val Phe Leu Phe Pro Pro Lys Pro Lys Asp Thr
            245              250              255

Leu Met Ile Ser Arg Thr Pro Glu Val Thr Cys Val Val Val Asp Val
            260              265              270

Ser His Glu Asp Pro Glu Val Lys Phe Asn Trp Tyr Val Asp Gly Val
            275              280              285

Glu Val His Asn Ala Lys Thr Lys Pro Arg Glu Glu Gln Tyr Asn Ser
    290              295              300

Thr Tyr Arg Val Val Ser Val Leu Thr Val Leu His Gln Asp Trp Leu
305              310              315              320

Asn Gly Lys Glu Tyr Lys Cys Lys Val Ser Asn Lys Ala Leu Pro Ala
            325              330              335

Pro Ile Glu Lys Thr Ile Ser Lys Ala Lys Gly Gln Pro Arg Glu Pro
            340              345              350

Gln Val Tyr Thr Leu Pro Pro Ser Arg Asp Glu Leu Thr Lys Asn Gln
            355              360              365

Val Ser Leu Thr Cys Leu Val Lys Gly Phe Tyr Pro Ser Asp Ile Ala
    370              375              380

Val Glu Trp Glu Ser Asn Gly Gln Pro Glu Asn Asn Tyr Lys Thr Thr
385              390              395              400

Pro Pro Val Leu Asp Ser Asp Gly Ser Phe Phe Leu Tyr Ser Lys Leu
            405              410              415

Thr Val Asp Lys Ser Arg Trp Gln Gln Gly Asn Val Phe Ser Cys Ser
            420              425              430

Val Met His Glu Ala Leu His Asn His Tyr Thr Gln Lys Ser Leu Ser
        435              440              445

Leu Ser Pro Gly Lys
    450
```

```
<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

```
Lys Ser Leu Leu His Ser Asn Gly Asn Thr Tyr
1               5                   10

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Met Ser
1

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Gln Ser Leu Glu Tyr Pro Leu Thr
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Phe Ser Leu Ser Thr Val Gly Met Gly
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Trp Trp Asp Asp Glu Asp Lys
1               5

<210> SEQ ID NO 37
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Thr Arg Ile Gly Thr Ala Gln Ala Thr Asp Ala Leu Asp Tyr
1               5                   10

<210> SEQ ID NO 38
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 38

Met Gly Trp Ser Cys Ile Ile Leu Phe Leu Val Ala Thr Ala Thr Gly
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Thr Ser Gly Gly Gly Gly Ser
1               5

<210> SEQ ID NO 40
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
        50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys

```
<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 41

His His His His His His
1               5

<210> SEQ ID NO 42
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Met Gly Trp Ser Cys Ile Ile Leu Phe Leu Val Ala Thr Ala Thr Gly
1               5                   10                  15

Lys Leu Asp Ile Glu Leu Thr Gln Ser Pro Ser Ser Leu Ala Val Ser
                20                  25                  30

Ala Gly Glu Arg Val Thr Met Asn Cys Lys Ser Ser Gln Ser Leu Leu
            35                  40                  45

Asn Ser Arg Thr Arg Lys Asn Gln Leu Ala Trp Tyr Gln Gln Lys Pro
        50                  55                  60

Gly Gln Ser Pro Glu Leu Leu Ile Tyr Trp Ala Ser Thr Arg Gln Ser
65                  70                  75                  80

Gly Val Pro Asp Arg Phe Ser Gly Ser Gly Ser Gly Thr Asp Phe Thr
                85                  90                  95

Leu Thr Ile Ser Ser Val Gln Ala Glu Asp Val Ala Val Tyr Tyr Cys
                100                 105                 110

Gln Gln Ser Tyr Asn Leu Leu Thr Phe Gly Pro Gly Thr Lys Leu Glu
            115                 120                 125

Ile Lys Arg Gly Gly Gly Gly Ser Gly Gly Gly Gly Ser Gly Gly Gly
        130                 135                 140

Gly Ser Glu Val Lys Leu Gln Glu Ser Gly Gly Gly Phe Val Lys Pro
145                 150                 155                 160

Gly Gly Ser Leu Arg Val Ser Cys Ala Ala Ser Gly Phe Thr Phe Ser
                165                 170                 175

Ser Tyr Ala Met Ser Trp Val Arg Leu Ala Pro Glu Met Arg Leu Glu
                180                 185                 190

Trp Val Ala Thr Ile Ser Ser Ala Gly Gly Tyr Ile Phe Tyr Ser Asp
            195                 200                 205

Ser Val Gln Gly Arg Phe Thr Ile Ser Arg Asp Asn Ala Lys Asn Ser
        210                 215                 220

Leu His Leu Gln Met Gly Ser Leu Arg Ser Gly Asp Thr Ala Met Tyr
225                 230                 235                 240

Tyr Cys Ala Arg Gln Gly Phe Gly Asn Tyr Gly Asp Tyr Tyr Ala Met
                245                 250                 255

Asp Tyr Trp Gly Gln Gly Thr Thr Val Thr Val Ser Ser Thr Ser Gly
            260                 265                 270

Gly Gly Gly Ser Asp Val Gln Leu Val Gln Ser Gly Ala Glu Val Lys
            275                 280                 285
```

```
Lys Pro Gly Ala Ser Val Lys Val Ser Cys Lys Ala Ser Gly Tyr Thr
    290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
                325                 330                 335

Ala Asp Ser Val Lys Gly Arg Phe Thr Ile Thr Thr Asp Lys Ser Thr
                340                 345                 350

Ser Thr Ala Tyr Met Glu Leu Ser Ser Leu Arg Ser Glu Asp Thr Ala
            355                 360                 365

Thr Tyr Tyr Cys Ala Arg Tyr Tyr Asp Asp His Tyr Cys Leu Asp Tyr
    370                 375                 380

Trp Gly Gln Gly Thr Thr Val Thr Val Ser Ser Gly Glu Gly Thr Ser
385                 390                 395                 400

Thr Gly Ser Gly Gly Ser Gly Gly Ser Gly Gly Ala Asp Asp Ile Val
                405                 410                 415

Leu Thr Gln Ser Pro Ala Thr Leu Ser Leu Ser Pro Gly Glu Arg Ala
                420                 425                 430

Thr Leu Ser Cys Arg Ala Ser Gln Ser Val Ser Tyr Met Asn Trp Tyr
            435                 440                 445

Gln Gln Lys Pro Gly Lys Ala Pro Lys Arg Trp Ile Tyr Asp Thr Ser
    450                 455                 460

Lys Val Ala Ser Gly Val Pro Ala Arg Phe Ser Gly Ser Gly Ser Gly
465                 470                 475                 480

Thr Asp Tyr Ser Leu Thr Ile Asn Ser Leu Glu Ala Glu Asp Ala Ala
                485                 490                 495

Thr Tyr Tyr Cys Gln Gln Trp Ser Ser Asn Pro Leu Thr Phe Gly Gly
                500                 505                 510

Gly Thr Lys Val Glu Ile Lys His His His His His
            515                 520                 525
```

```
<210> SEQ ID NO 43
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Trp Glu Leu Ser Gln Leu Thr His Gly Val Thr Gln Leu Gly Phe Tyr
1               5                   10                  15

Val Leu Asp Arg Asp Ser Leu Phe Ile Asn Gly Tyr Ala Pro Gln Asn
            20                  25                  30

Leu Ser Ile Arg Gly Glu Tyr Gln Ile Asn Phe His Ile Val Asn Gln
        35                  40                  45

Asn Leu Ser Asn Pro Asp Pro Thr Ser Ser Glu Tyr Ile Thr Leu Leu
    50                  55                  60

Arg Asp Ile Gln Asp Lys Val Thr Thr Leu Tyr Lys Gly Ser Gln Leu
65                  70                  75                  80

His Asp Thr Phe Arg Phe Cys Leu Val Thr Asn Leu Thr Met Asp Ser
                85                  90                  95

Val Leu Val Thr Val Lys Ala Leu Phe Ser Ser Asn Leu Asp Pro Ser
            100                 105                 110

Leu Val Glu Gln Val Phe Leu Asp Lys Thr Leu Asn Ala Ser Phe His
```

-continued

```
              115                 120                 125
Gln Leu Gly Ser Thr Tyr Gln Leu Val Asp Ile His Val Thr Glu Met
    130                 135                 140
Glu Ser Ser Val Tyr Gln Pro Thr Ser Ser Ser Ser Thr Gln His Phe
145                 150                 155                 160
Tyr Leu Asn Phe Thr Ile Thr Asn Leu Pro Tyr Ser Gln Asp Lys Ala
                165                 170                 175
Gln Pro Gly Thr Thr Asn Tyr Gln Arg Asn Lys Arg Asn Ile Glu Asp
                180                 185                 190
Ala Leu Asn Gln Leu Phe Arg Asn Ser Ser Ile Lys Ser Tyr Phe Ser
                195                 200                 205
Asp Cys Gln Val Ser Thr Phe Arg Ser Val Pro Asn Arg His His Thr
    210                 215                 220
Gly Val Asp Ser Leu Cys Asn Phe Ser Pro Leu Ala Arg Arg Val Asp
225                 230                 235                 240
Arg Val Ala Ile Tyr Glu Glu Phe Leu Arg Met Thr Arg Asn Gly Thr
                245                 250                 255
Gln Leu Gln Asn Phe Thr Leu Asp Arg Ser Ser Val Leu Val Asp Gly
                260                 265                 270
Tyr Ser Pro Asn Arg Asn Glu Pro Leu Thr Gly Asn Ser Asp Leu Pro
                275                 280                 285
Phe Trp Ala Val Ile Leu Ile Gly Leu Ala Gly Leu Leu Gly Leu Ile
    290                 295                 300
Thr Cys Leu Ile Cys Gly Val Leu Val Thr Thr Arg Arg Arg Lys Lys
305                 310                 315                 320
Glu Gly Glu Tyr Asn Val Gln Gln Cys Pro Gly Tyr Tyr Gln Ser
                325                 330                 335
His Leu Asp Leu Glu Asp Leu Gln
        340

<210> SEQ ID NO 44
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asn Phe Ser Pro Leu Ala Arg Arg Val Asp Arg Val Ala Ile Tyr Glu
1               5                  10                  15
Glu Phe Leu Arg Met Thr Arg Asn Gly Thr Gln Leu Gln Asn Phe Thr
                20                  25                  30
Leu Asp Arg Ser Ser Val Leu Val Asp Gly Tyr Ser Pro Asn Arg Asn
        35                  40                  45
Glu Pro Leu Thr Gly Asn Ser Asp Leu Pro Phe Trp Ala Val Ile Leu
    50                  55                  60
Ile Gly Leu Ala Gly Leu Leu Gly Leu Ile Thr Cys Leu Ile Cys Gly
65                  70                  75                  80
Val Leu Val Thr Thr Arg Arg Arg Lys Lys Glu Gly Glu Tyr Asn Val
                85                  90                  95
Gln Gln Gln Cys Pro Gly Tyr Tyr Gln Ser His Leu Asp Leu Glu Asp
                100                 105                 110
Leu Gln
```

-continued

```
<210> SEQ ID NO 45
<211> LENGTH: 80
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asn Phe Ser Pro Leu Ala Arg Arg Val Asp Arg Val Ala Ile Tyr Glu
1               5                   10                  15

Glu Phe Leu Arg Met Asp Leu Pro Phe Trp Ala Val Ile Leu Ile Gly
            20                  25                  30

Leu Ala Gly Leu Leu Gly Leu Ile Thr Cys Leu Ile Cys Gly Val Leu
        35                  40                  45

Val Thr Thr Arg Arg Arg Lys Lys Glu Gly Glu Tyr Asn Val Gln Gln
    50                  55                  60

Gln Cys Pro Gly Tyr Tyr Gln Ser His Leu Asp Leu Glu Asp Leu Gln
65                  70                  75                  80

<210> SEQ ID NO 46
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro Phe Trp Ala Val Ile Leu
    50                  55                  60

Ile Gly Leu Ala Gly Leu Leu Gly Leu Ile Thr Cys Leu Ile Cys Gly
65                  70                  75                  80

Asp Leu Glu Asp Leu Gln
                85

<210> SEQ ID NO 47
<211> LENGTH: 330
<212> TYPE: PRT
<213> ORGANISM: Homo sapiens

<400> SEQUENCE: 47

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

-continued

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 48
<211> LENGTH: 327
<212> TYPE: PRT
<213> ORGANISM: Homo sapiens

<400> SEQUENCE: 48

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
```

```
         130              135              140

Asp Val Ser Gln Glu Asp Pro Glu Val Gln Phe Asn Trp Tyr Val Asp
145              150              155              160

Gly Val Glu Val His Asn Ala Lys Thr Lys Pro Arg Glu Glu Gln Phe
                 165              170              175

Asn Ser Thr Tyr Arg Val Val Ser Val Leu Thr Val Leu His Gln Asp
                 180              185              190

Trp Leu Asn Gly Lys Glu Tyr Lys Cys Lys Val Ser Asn Lys Gly Leu
             195              200              205

Pro Ser Ser Ile Glu Lys Thr Ile Ser Lys Ala Lys Gly Gln Pro Arg
         210              215              220

Glu Pro Gln Val Tyr Thr Leu Pro Pro Ser Gln Glu Glu Met Thr Lys
225              230              235              240

Asn Gln Val Ser Leu Thr Cys Leu Val Lys Gly Phe Tyr Pro Ser Asp
                 245              250              255

Ile Ala Val Glu Trp Glu Ser Asn Gly Gln Pro Glu Asn Asn Tyr Lys
                 260              265              270

Thr Thr Pro Pro Val Leu Asp Ser Asp Gly Ser Phe Phe Leu Tyr Ser
                 275              280              285

Arg Leu Thr Val Asp Lys Ser Arg Trp Gln Glu Gly Asn Val Phe Ser
         290              295              300

Cys Ser Val Met His Glu Ala Leu His Asn His Tyr Thr Gln Lys Ser
305              310              315              320

Leu Ser Leu Ser Leu Gly Lys
                 325
```

```
<210> SEQ ID NO 49
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Pro Lys Ala Asn Pro Thr Val Thr Leu Phe Pro Pro Ser Ser Glu
1               5               10              15

Glu Leu Gln Ala Asn Lys Ala Thr Leu Val Cys Leu Ile Ser Asp Phe
                20              25              30

Tyr Pro Gly Ala Val Thr Val Ala Trp Lys Ala Asp Gly Ser Pro Val
         35              40              45

Lys Ala Gly Val Glu Thr Thr Lys Pro Ser Lys Gln Ser Asn Asn Lys
     50              55              60

Tyr Ala Ala Ser Ser Tyr Leu Ser Leu Thr Pro Glu Gln Trp Lys Ser
65              70              75              80

His Arg Ser Tyr Ser Cys Gln Val Thr His Glu Gly Ser Thr Val Glu
                 85              90              95

Lys Thr Val Ala Pro Thr Glu Cys Ser
                 100              105
```

```
<210> SEQ ID NO 50
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 50

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Ala Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro Phe Trp Ala Val Ile Leu
    50                  55                  60

Ile Gly Leu Ala Gly Leu Leu Gly Leu Ile Thr Cys Leu Ile Cys Gly
65                  70                  75                  80

Val Leu Val Thr Thr Arg Arg Arg Lys Lys Glu Gly Glu Tyr Asn Val
                85                  90                  95

Gln Gln Gln Cys Pro Gly Tyr Tyr Gln Ser His Leu Asp Leu Glu Asp
            100                 105                 110

Leu Gln

<210> SEQ ID NO 51
<211> LENGTH: 14447
<212> TYPE: PRT
<213> ORGANISM: Homo sapiens

<400> SEQUENCE: 51

Asp Lys Thr Leu Ala Ser Pro Thr Ser Ser Val Val Gly Arg Thr Thr
1               5                   10                  15

Gln Ser Leu Gly Val Met Ser Ser Ala Leu Pro Glu Ser Thr Ser Arg
            20                  25                  30

Gly Met Thr His Ser Glu Gln Arg Thr Ser Pro Ser Leu Ser Pro Gln
        35                  40                  45

Val Asn Gly Thr Pro Ser Arg Asn Tyr Pro Ala Thr Ser Met Val Ser
    50                  55                  60

Gly Leu Ser Ser Pro Arg Thr Arg Thr Ser Ser Thr Glu Gly Asn Phe
65                  70                  75                  80

Thr Lys Glu Ala Ser Thr Tyr Thr Leu Thr Val Glu Thr Thr Ser Gly
                85                  90                  95

Pro Val Thr Glu Lys Tyr Thr Val Pro Thr Glu Thr Ser Thr Thr Glu
            100                 105                 110

Gly Asp Ser Thr Glu Thr Pro Trp Asp Thr Arg Tyr Ile Pro Val Lys
            115                 120                 125

Ile Thr Ser Pro Met Lys Thr Phe Ala Asp Ser Thr Ala Ser Lys Glu
    130                 135                 140

Asn Ala Pro Val Ser Met Thr Pro Ala Glu Thr Thr Val Thr Asp Ser
145                 150                 155                 160

His Thr Pro Gly Arg Thr Asn Pro Ser Phe Gly Thr Leu Tyr Ser Ser
                165                 170                 175

Phe Leu Asp Leu Ser Pro Lys Gly Thr Pro Asn Ser Arg Gly Glu Thr
            180                 185                 190

Ser Leu Glu Leu Ile Leu Ser Thr Thr Gly Tyr Pro Phe Ser Ser Pro
        195                 200                 205

Glu Pro Gly Ser Ala Gly His Ser Arg Ile Ser Thr Ser Ala Pro Leu
    210                 215                 220

Ser Ser Ser Ala Ser Val Leu Asp Asn Lys Ile Ser Glu Thr Ser Ile
225                 230                 235                 240

Phe Ser Gly Gln Ser Leu Thr Ser Pro Leu Ser Pro Gly Val Pro Glu

-continued

```
                    245              250              255

Ala Arg Ala Ser Thr Met Pro Asn Ser Ala Ile Pro Phe Ser Met Thr
            260              265              270

Leu Ser Asn Ala Glu Thr Ser Ala Glu Arg Val Arg Ser Thr Ile Ser
            275              280              285

Ser Leu Gly Thr Pro Ser Ile Ser Thr Lys Gln Thr Ala Glu Thr Ile
            290              295              300

Leu Thr Phe His Ala Phe Ala Glu Thr Met Asp Ile Pro Ser Thr His
305              310              315              320

Ile Ala Lys Thr Leu Ala Ser Glu Trp Leu Gly Ser Pro Gly Thr Leu
                325              330              335

Gly Gly Thr Ser Thr Ser Ala Leu Thr Thr Thr Ser Pro Ser Thr Thr
                340              345              350

Leu Val Ser Glu Glu Thr Asn Thr His His Ser Thr Ser Gly Lys Glu
            355              360              365

Thr Glu Gly Thr Leu Asn Thr Ser Met Thr Pro Leu Glu Thr Ser Ala
            370              375              380

Pro Gly Glu Glu Ser Glu Met Thr Ala Thr Leu Val Pro Thr Leu Gly
385              390              395              400

Phe Thr Thr Leu Asp Ser Lys Ile Arg Ser Pro Ser Gln Val Ser Ser
                405              410              415

Ser His Pro Thr Arg Glu Leu Arg Thr Thr Gly Ser Thr Ser Gly Arg
                420              425              430

Gln Ser Ser Ser Thr Ala Ala His Gly Ser Ser Asp Ile Leu Arg Ala
            435              440              445

Thr Thr Ser Ser Thr Ser Lys Ala Ser Ser Trp Thr Ser Glu Ser Thr
            450              455              460

Ala Gln Gln Phe Ser Glu Pro Gln His Thr Gln Trp Val Glu Thr Ser
465              470              475              480

Pro Ser Met Lys Thr Glu Arg Pro Pro Ala Ser Thr Ser Val Ala Ala
                485              490              495

Pro Ile Thr Thr Ser Val Pro Ser Val Val Ser Gly Phe Thr Thr Leu
                500              505              510

Lys Thr Ser Ser Thr Lys Gly Ile Trp Leu Glu Glu Thr Ser Ala Asp
            515              520              525

Thr Leu Ile Gly Glu Ser Thr Ala Gly Pro Thr Thr His Gln Phe Ala
            530              535              540

Val Pro Thr Gly Ile Ser Met Thr Gly Gly Ser Ser Thr Arg Gly Ser
545              550              555              560

Gln Gly Thr Thr His Leu Leu Thr Arg Ala Thr Ala Ser Ser Glu Thr
                565              570              575

Ser Ala Asp Leu Thr Leu Ala Thr Asn Gly Val Pro Val Ser Val Ser
                580              585              590

Pro Ala Val Ser Lys Thr Ala Ala Gly Ser Ser Pro Pro Gly Gly Thr
            595              600              605

Lys Pro Ser Tyr Thr Met Val Ser Ser Val Ile Pro Glu Thr Ser Ser
            610              615              620

Leu Gln Ser Ser Ala Phe Arg Glu Gly Thr Ser Leu Gly Leu Thr Pro
625              630              635              640

Leu Asn Thr Arg His Pro Phe Ser Ser Pro Glu Pro Asp Ser Ala Gly
                645              650              655

His Thr Lys Ile Ser Thr Ser Ile Pro Leu Leu Ser Ser Ala Ser Val
            660              665              670
```

Leu Glu Asp Lys Val Ser Ala Thr Ser Thr Phe Ser His His Lys Ala
        675             680             685

Thr Ser Ser Ile Thr Thr Gly Thr Pro Glu Ile Ser Thr Lys Thr Lys
    690             695             700

Pro Ser Ser Ala Val Leu Ser Ser Met Thr Leu Ser Asn Ala Ala Thr
705             710             715             720

Ser Pro Glu Arg Val Arg Asn Ala Thr Ser Pro Leu Thr His Pro Ser
            725             730             735

Pro Ser Gly Glu Glu Thr Ala Gly Ser Val Leu Thr Leu Ser Thr Ser
            740             745             750

Ala Glu Thr Thr Asp Ser Pro Asn Ile His Pro Thr Gly Thr Leu Thr
        755             760             765

Ser Glu Ser Ser Glu Ser Pro Ser Thr Leu Ser Leu Pro Ser Val Ser
    770             775             780

Gly Val Lys Thr Thr Phe Ser Ser Ser Thr Pro Ser Thr His Leu Phe
785             790             795             800

Thr Ser Gly Glu Glu Thr Glu Glu Thr Ser Asn Pro Ser Val Ser Gln
            805             810             815

Pro Glu Thr Ser Val Ser Arg Val Arg Thr Thr Leu Ala Ser Thr Ser
        820             825             830

Val Pro Thr Pro Val Phe Pro Thr Met Asp Thr Trp Pro Thr Arg Ser
        835             840             845

Ala Gln Phe Ser Ser Ser His Leu Val Ser Glu Leu Arg Ala Thr Ser
    850             855             860

Ser Thr Ser Val Thr Asn Ser Thr Gly Ser Ala Leu Pro Lys Ile Ser
865             870             875             880

His Leu Thr Gly Thr Ala Thr Met Ser Gln Thr Asn Arg Asp Thr Phe
            885             890             895

Asn Asp Ser Ala Ala Pro Gln Ser Thr Thr Trp Pro Glu Thr Ser Pro
            900             905             910

Arg Phe Lys Thr Gly Leu Pro Ser Ala Thr Thr Thr Val Ser Thr Ser
        915             920             925

Ala Thr Ser Leu Ser Ala Thr Val Met Val Ser Lys Phe Thr Ser Pro
    930             935             940

Ala Thr Ser Ser Met Glu Ala Thr Ser Ile Arg Glu Pro Ser Thr Thr
945             950             955             960

Ile Leu Thr Thr Glu Thr Thr Asn Gly Pro Gly Ser Met Ala Val Ala
            965             970             975

Ser Thr Asn Ile Pro Ile Gly Lys Gly Tyr Ile Thr Glu Gly Arg Leu
            980             985             990

Asp Thr Ser His Leu Pro Ile Gly  Thr Thr Ala Ser Ser  Glu Thr Ser
        995             1000                1005

Met Asp  Phe Thr Met Ala Lys  Glu Ser Val Ser Met  Ser Val Ser
    1010            1015                1020

Pro Ser  Gln Ser Met Asp Ala  Ala Gly Ser Ser Thr  Pro Gly Arg
    1025            1030                1035

Thr Ser  Gln Phe Val Asp Thr  Phe Ser Asp Asp Val  Tyr His Leu
    1040            1045                1050

Thr Ser  Arg Glu Ile Thr Ile  Pro Arg Asp Gly Thr  Ser Ser Ala
    1055            1060                1065

Leu Thr  Pro Gln Met Thr Ala  Thr His Pro Pro Ser  Pro Asp Pro
    1070            1075                1080

```
Gly Ser Ala Arg Ser Thr Trp Leu Gly Ile Leu Ser Ser Ser Pro
    1085                1090            1095

Ser Ser Pro Thr Pro Lys Val Thr Met Ser Ser Thr Phe Ser Thr
    1100                1105            1110

Gln Arg Val Thr Thr Ser Met Ile Met Asp Thr Val Glu Thr Ser
    1115                1120            1125

Arg Trp Asn Met Pro Asn Leu Pro Ser Thr Thr Ser Leu Thr Pro
    1130                1135            1140

Ser Asn Ile Pro Thr Ser Gly Ala Ile Gly Lys Ser Thr Leu Val
    1145                1150            1155

Pro Leu Asp Thr Pro Ser Pro Ala Thr Ser Leu Glu Ala Ser Glu
    1160                1165            1170

Gly Gly Leu Pro Thr Leu Ser Thr Tyr Pro Glu Ser Thr Asn Thr
    1175                1180            1185

Pro Ser Ile His Leu Gly Ala His Ala Ser Ser Glu Ser Pro Ser
    1190                1195            1200

Thr Ile Lys Leu Thr Met Ala Ser Val Val Lys Pro Gly Ser Tyr
    1205                1210            1215

Thr Pro Leu Thr Phe Pro Ser Ile Glu Thr His Ile His Val Ser
    1220                1225            1230

Thr Ala Arg Met Ala Tyr Ser Ser Gly Ser Ser Pro Glu Met Thr
    1235                1240            1245

Ala Pro Gly Glu Thr Asn Thr Gly Ser Thr Trp Asp Pro Thr Thr
    1250                1255            1260

Tyr Ile Thr Thr Thr Asp Pro Lys Asp Thr Ser Ser Ala Gln Val
    1265                1270            1275

Ser Thr Pro His Ser Val Arg Thr Leu Arg Thr Thr Glu Asn His
    1280                1285            1290

Pro Lys Thr Glu Ser Ala Thr Pro Ala Ala Tyr Ser Gly Ser Pro
    1295                1300            1305

Lys Ile Ser Ser Ser Pro Asn Leu Thr Ser Pro Ala Thr Lys Ala
    1310                1315            1320

Trp Thr Ile Thr Asp Thr Thr Glu His Ser Thr Gln Leu His Tyr
    1325                1330            1335

Thr Lys Leu Ala Glu Lys Ser Ser Gly Phe Glu Thr Gln Ser Ala
    1340                1345            1350

Pro Gly Pro Val Ser Val Val Ile Pro Thr Ser Pro Thr Ile Gly
    1355                1360            1365

Ser Ser Thr Leu Glu Leu Thr Ser Asp Val Pro Gly Glu Pro Leu
    1370                1375            1380

Val Leu Ala Pro Ser Glu Gln Thr Thr Ile Thr Leu Pro Met Ala
    1385                1390            1395

Thr Trp Leu Ser Thr Ser Leu Thr Glu Glu Met Ala Ser Thr Asp
    1400                1405            1410

Leu Asp Ile Ser Ser Pro Ser Ser Pro Met Ser Thr Phe Ala Ile
    1415                1420            1425

Phe Pro Pro Met Ser Thr Pro Ser His Glu Leu Ser Lys Ser Glu
    1430                1435            1440

Ala Asp Thr Ser Ala Ile Arg Asn Thr Asp Ser Thr Thr Leu Asp
    1445                1450            1455

Gln His Leu Gly Ile Arg Ser Leu Gly Arg Thr Gly Asp Leu Thr
    1460                1465            1470

Thr Val Pro Ile Thr Pro Leu Thr Thr Thr Trp Thr Ser Val Ile
```

-continued

```
       1475            1480             1485

Glu His  Ser Thr Gln Ala Gln  Asp Thr Leu Ser Ala  Thr Met Ser
   1490                1495              1500

Pro Thr  His Val Thr Gln Ser  Leu Lys Asp Gln Thr  Ser Ile Pro
   1505                1510              1515

Ala Ser  Ala Ser Pro Ser His  Leu Thr Glu Val Tyr  Pro Glu Leu
   1520                1525              1530

Gly Thr  Gln Gly Arg Ser Ser  Ser Glu Ala Thr Thr  Phe Trp Lys
   1535                1540              1545

Pro Ser  Thr Asp Thr Leu Ser  Arg Glu Ile Glu Thr  Gly Pro Thr
   1550                1555              1560

Asn Ile  Gln Ser Thr Pro Pro  Met Asp Asn Thr Thr  Thr Gly Ser
   1565                1570              1575

Ser Ser  Ser Gly Val Thr Leu  Gly Ile Ala His Leu  Pro Ile Gly
   1580                1585              1590

Thr Ser  Ser Pro Ala Glu Thr  Ser Thr Asn Met Ala  Leu Glu Arg
   1595                1600              1605

Arg Ser  Ser Thr Ala Thr Val  Ser Met Ala Gly Thr  Met Gly Leu
   1610                1615              1620

Leu Val  Thr Ser Ala Pro Gly  Arg Ser Ile Ser Gln  Ser Leu Gly
   1625                1630              1635

Arg Val  Ser Ser Val Leu Ser  Glu Ser Thr Thr Glu  Gly Val Thr
   1640                1645              1650

Asp Ser  Ser Lys Gly Ser Ser  Pro Arg Leu Asn Thr  Gln Gly Asn
   1655                1660              1665

Thr Ala  Leu Ser Ser Ser Leu  Glu Pro Ser Tyr Ala  Glu Gly Ser
   1670                1675              1680

Gln Met  Ser Thr Ser Ile Pro  Leu Thr Ser Ser Pro  Thr Thr Pro
   1685                1690              1695

Asp Val  Glu Phe Ile Gly Gly  Ser Thr Phe Trp Thr  Lys Glu Val
   1700                1705              1710

Thr Thr  Val Met Thr Ser Asp  Ile Ser Lys Ser Ser  Ala Arg Thr
   1715                1720              1725

Glu Ser  Ser Ser Ala Thr Leu  Met Ser Thr Ala Leu  Gly Ser Thr
   1730                1735              1740

Glu Asn  Thr Gly Lys Glu Lys  Leu Arg Thr Ala Ser  Met Asp Leu
   1745                1750              1755

Pro Ser  Pro Thr Pro Ser Met  Glu Val Thr Pro Trp  Ile Ser Leu
   1760                1765              1770

Thr Leu  Ser Asn Ala Pro Asn  Thr Thr Asp Ser Leu  Asp Leu Ser
   1775                1780              1785

His Gly  Val His Thr Ser Ser  Ala Gly Thr Leu Ala  Thr Asp Arg
   1790                1795              1800

Ser Leu  Asn Thr Gly Val Thr  Arg Ala Ser Arg Leu  Glu Asn Gly
   1805                1810              1815

Ser Asp  Thr Ser Ser Lys Ser  Leu Ser Met Gly Asn  Ser Thr His
   1820                1825              1830

Thr Ser  Met Thr Tyr Thr Glu  Lys Ser Glu Val Ser  Ser Ser Ile
   1835                1840              1845

His Pro  Arg Pro Glu Thr Ser  Ala Pro Gly Ala Glu  Thr Thr Leu
   1850                1855              1860

Thr Ser  Thr Pro Gly Asn Arg  Ala Ile Ser Leu Thr  Leu Pro Phe
   1865                1870              1875
```

-continued

```
Ser Ser  Ile Pro Val Glu Glu  Val Ile Ser Thr Gly  Ile Thr Ser
    1880             1885            1890

Gly Pro  Asp Ile Asn Ser Ala  Pro Met Thr His Ser  Pro Ile Thr
    1895             1900            1905

Pro Pro  Thr Ile Val Trp Thr  Ser Thr Gly Thr Ile  Glu Gln Ser
    1910             1915            1920

Thr Gln  Pro Leu His Ala Val  Ser Ser Glu Lys Val  Ser Val Gln
    1925             1930            1935

Thr Gln  Ser Thr Pro Tyr Val  Asn Ser Val Ala Val  Ser Ala Ser
    1940             1945            1950

Pro Thr  His Glu Asn Ser Val  Ser Ser Gly Ser Ser  Thr Ser Ser
    1955             1960            1965

Pro Tyr  Ser Ser Ala Ser Leu  Glu Ser Leu Asp Ser  Thr Ile Ser
    1970             1975            1980

Arg Arg  Asn Ala Ile Thr Ser  Trp Leu Trp Asp Leu  Thr Thr Ser
    1985             1990            1995

Leu Pro  Thr Thr Thr Trp Pro  Ser Thr Ser Leu Ser  Glu Ala Leu
    2000             2005            2010

Ser Ser  Gly His Ser Gly Val  Ser Asn Pro Ser Ser  Thr Thr Thr
    2015             2020            2025

Glu Phe  Pro Leu Phe Ser Ala  Ala Ser Thr Ser Ala  Ala Lys Gln
    2030             2035            2040

Arg Asn  Pro Glu Thr Glu Thr  His Gly Pro Gln Asn  Thr Ala Ala
    2045             2050            2055

Ser Thr  Leu Asn Thr Asp Ala  Ser Ser Val Thr Gly  Leu Ser Glu
    2060             2065            2070

Thr Pro  Val Gly Ala Ser Ile  Ser Ser Glu Val Pro  Leu Pro Met
    2075             2080            2085

Ala Ile  Thr Ser Arg Ser Asp  Val Ser Gly Leu Thr  Ser Glu Ser
    2090             2095            2100

Thr Ala  Asn Pro Ser Leu Gly  Thr Ala Ser Ser Ala  Gly Thr Lys
    2105             2110            2115

Leu Thr  Arg Thr Ile Ser Leu  Pro Thr Ser Glu Ser  Leu Val Ser
    2120             2125            2130

Phe Arg  Met Asn Lys Asp Pro  Trp Thr Val Ser Ile  Pro Leu Gly
    2135             2140            2145

Ser His  Pro Thr Thr Asn Thr  Glu Thr Ser Ile Pro  Val Asn Ser
    2150             2155            2160

Ala Gly  Pro Pro Gly Leu Ser  Thr Val Ala Ser Asp  Val Ile Asp
    2165             2170            2175

Thr Pro  Ser Asp Gly Ala Glu  Ser Ile Pro Thr Val  Ser Phe Ser
    2180             2185            2190

Pro Ser  Pro Asp Thr Glu Val  Thr Thr Ile Ser His  Phe Pro Glu
    2195             2200            2205

Lys Thr  Thr His Ser Phe Arg  Thr Ile Ser Ser Leu  Thr His Glu
    2210             2215            2220

Leu Thr  Ser Arg Val Thr Pro  Ile Pro Gly Asp Trp  Met Ser Ser
    2225             2230            2235

Ala Met  Ser Thr Lys Pro Thr  Gly Ala Ser Pro Ser  Ile Thr Leu
    2240             2245            2250

Gly Glu  Arg Arg Thr Ile Thr  Ser Ala Ala Pro Thr  Thr Ser Pro
    2255             2260            2265
```

```
Ile Val  Leu Thr Ala Ser Phe  Thr Glu Thr Ser  Thr Val Ser Leu
    2270                 2275                2280

Asp Asn  Glu Thr Thr Val Lys  Thr Ser Asp Ile Leu  Asp Ala Arg
    2285                 2290                2295

Lys Thr  Asn Glu Leu Pro Ser  Asp Ser Ser Ser Ser  Ser Asp Leu
    2300                 2305                2310

Ile Asn  Thr Ser Ile Ala Ser  Ser Thr Met Asp Val  Thr Lys Thr
    2315                 2320                2325

Ala Ser  Ile Ser Pro Thr Ser  Ile Ser Gly Met Thr  Ala Ser Ser
    2330                 2335                2340

Ser Pro  Ser Leu Phe Ser Ser  Asp Arg Pro Gln Val  Pro Thr Ser
    2345                 2350                2355

Thr Thr  Glu Thr Asn Thr Ala  Thr Ser Pro Ser Val  Ser Ser Asn
    2360                 2365                2370

Thr Tyr  Ser Leu Asp Gly Gly  Ser Asn Val Gly Gly  Thr Pro Ser
    2375                 2380                2385

Thr Leu  Pro Pro Phe Thr Ile  Thr His Pro Val Glu  Thr Ser Ser
    2390                 2395                2400

Ala Leu  Leu Ala Trp Ser Arg  Pro Val Arg Thr Phe  Ser Thr Met
    2405                 2410                2415

Val Ser  Thr Asp Thr Ala Ser  Gly Glu Asn Pro Thr  Ser Ser Asn
    2420                 2425                2430

Ser Val  Val Thr Ser Val Pro  Ala Pro Gly Thr Trp  Thr Ser Val
    2435                 2440                2445

Gly Ser  Thr Thr Asp Leu Pro  Ala Met Gly Phe Leu  Lys Thr Ser
    2450                 2455                2460

Pro Ala  Gly Glu Ala His Ser  Leu Leu Ala Ser Thr  Ile Glu Pro
    2465                 2470                2475

Ala Thr  Ala Phe Thr Pro His  Leu Ser Ala Ala Val  Val Thr Gly
    2480                 2485                2490

Ser Ser  Ala Thr Ser Glu Ala  Ser Leu Leu Thr Thr  Ser Glu Ser
    2495                 2500                2505

Lys Ala  Ile His Ser Ser Pro  Gln Thr Pro Thr Thr  Pro Thr Ser
    2510                 2515                2520

Gly Ala  Asn Trp Glu Thr Ser  Ala Thr Pro Glu Ser  Leu Leu Val
    2525                 2530                2535

Val Thr  Glu Thr Ser Asp Thr  Thr Leu Thr Ser Lys  Ile Leu Val
    2540                 2545                2550

Thr Asp  Thr Ile Leu Phe Ser  Thr Val Ser Thr Pro  Pro Ser Lys
    2555                 2560                2565

Phe Pro  Ser Thr Gly Thr Leu  Ser Gly Ala Ser Phe  Pro Thr Leu
    2570                 2575                2580

Leu Pro  Asp Thr Pro Ala Ile  Pro Leu Thr Ala Thr  Glu Pro Thr
    2585                 2590                2595

Ser Ser  Leu Ala Thr Ser Phe  Asp Ser Thr Pro Leu  Val Thr Ile
    2600                 2605                2610

Ala Ser  Asp Ser Leu Gly Thr  Val Pro Glu Thr Thr  Leu Thr Met
    2615                 2620                2625

Ser Glu  Thr Ser Asn Gly Asp  Ala Leu Val Leu Lys  Thr Val Ser
    2630                 2635                2640

Asn Pro  Asp Arg Ser Ile Pro  Gly Ile Thr Ile Gln  Gly Val Thr
    2645                 2650                2655

Glu Ser  Pro Leu His Pro Ser  Ser Thr Ser Pro Ser  Lys Ile Val
```

```
            2660              2665              2670

Ala Pro  Arg Asn Thr Thr Tyr  Glu Gly Ser Ile Thr  Val Ala Leu
    2675              2680              2685

Ser Thr  Leu Pro Ala Gly Thr  Thr Gly Ser Leu Val  Phe Ser Gln
    2690              2695              2700

Ser Ser  Glu Asn Ser Glu Thr  Thr Ala Leu Val Asp  Ser Ser Ala
    2705              2710              2715

Gly Leu  Glu Arg Ala Ser Val  Met Pro Leu Thr Thr  Gly Ser Gln
    2720              2725              2730

Gly Met  Ala Ser Ser Gly Gly  Ile Arg Ser Gly Ser  Thr His Ser
    2735              2740              2745

Thr Gly  Thr Lys Thr Phe Ser  Ser Leu Pro Leu Thr  Met Asn Pro
    2750              2755              2760

Gly Glu  Val Thr Ala Met Ser  Glu Ile Thr Thr Asn  Arg Leu Thr
    2765              2770              2775

Ala Thr  Gln Ser Thr Ala Pro  Lys Gly Ile Pro Val  Lys Pro Thr
    2780              2785              2790

Ser Ala  Glu Ser Gly Leu Leu  Thr Pro Val Ser Ala  Ser Ser Ser
    2795              2800              2805

Pro Ser  Lys Ala Phe Ala Ser  Leu Thr Thr Ala Pro  Pro Thr Trp
    2810              2815              2820

Gly Ile  Pro Gln Ser Thr Leu  Thr Phe Glu Phe Ser  Glu Val Pro
    2825              2830              2835

Ser Leu  Asp Thr Lys Ser Ala  Ser Leu Pro Thr Pro  Gly Gln Ser
    2840              2845              2850

Leu Asn  Thr Ile Pro Asp Ser  Asp Ala Ser Thr Ala  Ser Ser Ser
    2855              2860              2865

Leu Ser  Lys Ser Pro Glu Lys  Asn Pro Arg Ala Arg  Met Met Thr
    2870              2875              2880

Ser Thr  Lys Ala Ile Ser Ala  Ser Ser Phe Gln Ser  Thr Gly Phe
    2885              2890              2895

Thr Glu  Thr Pro Glu Gly Ser  Ala Ser Pro Ser Met  Ala Gly His
    2900              2905              2910

Glu Pro  Arg Val Pro Thr Ser  Gly Thr Gly Asp Pro  Arg Tyr Ala
    2915              2920              2925

Ser Glu  Ser Met Ser Tyr Pro  Asp Pro Ser Lys Ala  Ser Ser Ala
    2930              2935              2940

Met Thr  Ser Thr Ser Leu Ala  Ser Lys Leu Thr Thr  Leu Phe Ser
    2945              2950              2955

Thr Gly  Gln Ala Ala Arg Ser  Gly Ser Ser Ser Ser  Pro Ile Ser
    2960              2965              2970

Leu Ser  Thr Glu Lys Glu Thr  Ser Phe Leu Ser Pro  Thr Ala Ser
    2975              2980              2985

Thr Ser  Arg Lys Thr Ser Leu  Phe Leu Gly Pro Ser  Met Ala Arg
    2990              2995              3000

Gln Pro  Asn Ile Leu Val His  Leu Gln Thr Ser Ala  Leu Thr Leu
    3005              3010              3015

Ser Pro  Thr Ser Thr Leu Asn  Met Ser Gln Glu Glu  Pro Pro Glu
    3020              3025              3030

Leu Thr  Ser Ser Gln Thr Ile  Ala Glu Glu Glu Gly  Thr Thr Ala
    3035              3040              3045

Glu Thr  Gln Thr Leu Thr Phe  Thr Pro Ser Glu Thr  Pro Thr Ser
    3050              3055              3060
```

-continued

```
Leu Leu Pro Val Ser Ser Pro  Thr Glu Pro Thr Ala  Arg Arg Lys
    3065              3070          3075

Ser Ser Pro Glu Thr Trp Ala  Ser Ser Ile Ser Val  Pro Ala Lys
    3080              3085          3090

Thr Ser Leu Val Glu Thr Thr  Asp Gly Thr Leu Val  Thr Thr Ile
    3095              3100          3105

Lys Met Ser Ser Gln Ala Ala  Gln Gly Asn Ser Thr  Trp Pro Ala
    3110              3115          3120

Pro Ala Glu Glu Thr Gly Ser  Ser Pro Ala Gly Thr  Ser Pro Gly
    3125              3130          3135

Ser Pro Glu Met Ser Thr Thr  Leu Lys Ile Met Ser  Ser Lys Glu
    3140              3145          3150

Pro Ser Ile Ser Pro Glu Ile  Arg Ser Thr Val Arg  Asn Ser Pro
    3155              3160          3165

Trp Lys Thr Pro Glu Thr Thr  Val Pro Met Glu Thr  Thr Val Glu
    3170              3175          3180

Pro Val Thr Leu Gln Ser Thr  Ala Leu Gly Ser Gly  Ser Thr Ser
    3185              3190          3195

Ile Ser His Leu Pro Thr Gly  Thr Thr Ser Pro Thr  Lys Ser Pro
    3200              3205          3210

Thr Glu Asn Met Leu Ala Thr  Glu Arg Val Ser Leu  Ser Pro Ser
    3215              3220          3225

Pro Pro Glu Ala Trp Thr Asn  Leu Tyr Ser Gly Thr  Pro Gly Gly
    3230              3235          3240

Thr Arg Gln Ser Leu Ala Thr  Met Ser Ser Val Ser  Leu Glu Ser
    3245              3250          3255

Pro Thr Ala Arg Ser Ile Thr  Gly Thr Gly Gln Gln  Ser Ser Pro
    3260              3265          3270

Glu Leu Val Ser Lys Thr Thr  Gly Met Glu Phe Ser  Met Trp His
    3275              3280          3285

Gly Ser Thr Gly Gly Thr Thr  Gly Asp Thr His Val  Ser Leu Ser
    3290              3295          3300

Thr Ser Ser Asn Ile Leu Glu  Asp Pro Val Thr Ser  Pro Asn Ser
    3305              3310          3315

Val Ser Ser Leu Thr Asp Lys  Ser Lys His Lys Thr  Glu Thr Trp
    3320              3325          3330

Val Ser Thr Thr Ala Ile Pro  Ser Thr Val Leu Asn  Asn Lys Ile
    3335              3340          3345

Met Ala Ala Glu Gln Gln Thr  Ser Arg Ser Val Asp  Glu Ala Tyr
    3350              3355          3360

Ser Ser Thr Ser Ser Trp Ser  Asp Gln Thr Ser Gly  Ser Asp Ile
    3365              3370          3375

Thr Leu Gly Ala Ser Pro Asp  Val Thr Asn Thr Leu  Tyr Ile Thr
    3380              3385          3390

Ser Thr Ala Gln Thr Thr Ser  Leu Val Ser Leu Pro  Ser Gly Asp
    3395              3400          3405

Gln Gly Ile Thr Ser Leu Thr  Asn Pro Ser Gly Gly  Lys Thr Ser
    3410              3415          3420

Ser Ala Ser Ser Val Thr Ser  Pro Ser Ile Gly Leu  Glu Thr Leu
    3425              3430          3435

Arg Ala Asn Val Ser Ala Val  Lys Ser Asp Ile Ala  Pro Thr Ala
    3440              3445          3450
```

-continued

```
Gly His Leu Ser Gln Thr Ser  Ser Pro Ala Glu Val  Ser Ile Leu
3455              3460              3465

Asp Val Thr Thr Ala Pro Thr  Pro Gly Ile Ser Thr  Thr Ile Thr
3470              3475              3480

Thr Met Gly Thr Asn Ser Ile  Ser Thr Thr Thr Pro  Asn Pro Glu
3485              3490              3495

Val Gly Met Ser Thr Met Asp  Ser Thr Pro Ala Thr  Glu Arg Arg
3500              3505              3510

Thr Thr Ser Thr Glu His Pro  Ser Thr Trp Ser Ser  Thr Ala Ala
3515              3520              3525

Ser Asp Ser Trp Thr Val Thr  Asp Met Thr Ser Asn  Leu Lys Val
3530              3535              3540

Ala Arg Ser Pro Gly Thr Ile  Ser Thr Met His Thr  Thr Ser Phe
3545              3550              3555

Leu Ala Ser Ser Thr Glu Leu  Asp Ser Met Ser Thr  Pro His Gly
3560              3565              3570

Arg Ile Thr Val Ile Gly Thr  Ser Leu Val Thr Pro  Ser Ser Asp
3575              3580              3585

Ala Ser Ala Val Lys Thr Glu  Thr Ser Thr Ser Glu  Arg Thr Leu
3590              3595              3600

Ser Pro Ser Asp Thr Thr Ala  Ser Thr Pro Ile Ser  Thr Phe Ser
3605              3610              3615

Arg Val Gln Arg Met Ser Ile  Ser Val Pro Asp Ile  Leu Ser Thr
3620              3625              3630

Ser Trp Thr Pro Ser Ser Thr  Glu Ala Glu Asp Val  Pro Val Ser
3635              3640              3645

Met Val Ser Thr Asp His Ala  Ser Thr Lys Thr Asp  Pro Asn Thr
3650              3655              3660

Pro Leu Ser Thr Phe Leu Phe  Asp Ser Leu Ser Thr  Leu Asp Trp
3665              3670              3675

Asp Thr Gly Arg Ser Leu Ser  Ser Ala Thr Ala Thr  Thr Ser Ala
3680              3685              3690

Pro Gln Gly Ala Thr Thr Pro  Gln Glu Leu Thr Leu  Glu Thr Met
3695              3700              3705

Ile Ser Pro Ala Thr Ser Gln  Leu Pro Phe Ser Ile  Gly His Ile
3710              3715              3720

Thr Ser Ala Val Thr Pro Ala  Ala Met Ala Arg Ser  Ser Gly Val
3725              3730              3735

Thr Phe Ser Arg Pro Asp Pro  Thr Ser Lys Lys Ala  Glu Gln Thr
3740              3745              3750

Ser Thr Gln Leu Pro Thr Thr  Thr Ser Ala His Pro  Gly Gln Val
3755              3760              3765

Pro Arg Ser Ala Ala Thr Thr  Leu Asp Val Ile Pro  His Thr Ala
3770              3775              3780

Lys Thr Pro Asp Ala Thr Phe  Gln Arg Gln Gly Gln  Thr Ala Leu
3785              3790              3795

Thr Thr Glu Ala Arg Ala Thr  Ser Asp Ser Trp Asn  Glu Lys Glu
3800              3805              3810

Lys Ser Thr Pro Ser Ala Pro  Trp Ile Thr Glu Met  Met Asn Ser
3815              3820              3825

Val Ser Glu Asp Thr Ile Lys  Glu Val Thr Ser Ser  Ser Ser Val
3830              3835              3840

Leu Arg Thr Leu Asn Thr Leu  Asp Ile Asn Leu Glu  Ser Gly Thr
```

```
            3845                3850                3855

Thr Ser  Ser Pro Ser Trp Lys  Ser Ser Pro Tyr Glu  Arg Ile Ala
    3860                3865                3870

Pro Ser  Glu Ser Thr Thr Asp  Lys Glu Ala Ile His  Pro Ser Thr
    3875                3880                3885

Asn Thr  Val Glu Thr Thr Gly  Trp Val Thr Ser Ser  Glu His Ala
    3890                3895                3900

Ser His  Ser Thr Ile Pro Ala  His Ser Ala Ser Ser  Lys Leu Thr
    3905                3910                3915

Ser Pro  Val Val Thr Thr Ser  Thr Arg Glu Gln Ala  Ile Val Ser
    3920                3925                3930

Met Ser  Thr Thr Thr Trp Pro  Glu Ser Thr Arg Ala  Arg Thr Glu
    3935                3940                3945

Pro Asn  Ser Phe Leu Thr Ile  Glu Leu Arg Asp Val  Ser Pro Tyr
    3950                3955                3960

Met Asp  Thr Ser Ser Thr Thr  Gln Thr Ser Ile Ile  Ser Ser Pro
    3965                3970                3975

Gly Ser  Thr Ala Ile Thr Lys  Gly Pro Arg Thr Glu  Ile Thr Ser
    3980                3985                3990

Ser Lys  Arg Ile Ser Ser Ser  Phe Leu Ala Gln Ser  Met Arg Ser
    3995                4000                4005

Ser Asp  Ser Pro Ser Glu Ala  Ile Thr Arg Leu Ser  Asn Phe Pro
    4010                4015                4020

Ala Met  Thr Glu Ser Gly Gly  Met Ile Leu Ala Met  Gln Thr Ser
    4025                4030                4035

Pro Pro  Gly Ala Thr Ser Leu  Ser Ala Pro Thr Leu  Asp Thr Ser
    4040                4045                4050

Ala Thr  Ala Ser Trp Thr Gly  Thr Pro Leu Ala Thr  Thr Gln Arg
    4055                4060                4065

Phe Thr  Tyr Ser Glu Lys Thr  Thr Leu Phe Ser Lys  Gly Pro Glu
    4070                4075                4080

Asp Thr  Ser Gln Pro Ser Pro  Pro Ser Val Glu Glu  Thr Ser Ser
    4085                4090                4095

Ser Ser  Ser Leu Val Pro Ile  His Ala Thr Thr Ser  Pro Ser Asn
    4100                4105                4110

Ile Leu  Leu Thr Ser Gln Gly  His Ser Pro Ser Ser  Thr Pro Pro
    4115                4120                4125

Val Thr  Ser Val Phe Leu Ser  Glu Thr Ser Gly Leu  Gly Lys Thr
    4130                4135                4140

Thr Asp  Met Ser Arg Ile Ser  Leu Glu Pro Gly Thr  Ser Leu Pro
    4145                4150                4155

Pro Asn  Leu Ser Ser Thr Ala  Gly Glu Ala Leu Ser  Thr Tyr Glu
    4160                4165                4170

Ala Ser  Arg Asp Thr Lys Ala  Ile His His Ser Ala  Asp Thr Ala
    4175                4180                4185

Val Thr  Asn Met Glu Ala Thr  Ser Ser Glu Tyr Ser  Pro Ile Pro
    4190                4195                4200

Gly His  Thr Lys Pro Ser Lys  Ala Thr Ser Pro Leu  Val Thr Ser
    4205                4210                4215

His Ile  Met Gly Asp Ile Thr  Ser Ser Thr Ser Val  Phe Gly Ser
    4220                4225                4230

Ser Glu  Thr Thr Glu Ile Glu  Thr Val Ser Ser Val  Asn Gln Gly
    4235                4240                4245
```

```
Leu Gln  Glu Arg Ser Thr Ser  Gln Val Ala Ser Ser  Ala Thr Glu
    4250                4255                4260

Thr Ser  Thr Val Ile Thr His  Val Ser Ser Gly Asp  Ala Thr Thr
    4265                4270                4275

His Val  Thr Lys Thr Gln Ala  Thr Phe Ser Ser Gly  Thr Ser Ile
    4280                4285                4290

Ser Ser  Pro His Gln Phe Ile  Thr Ser Thr Asn Thr  Phe Thr Asp
    4295                4300                4305

Val Ser  Thr Asn Pro Ser Thr  Ser Leu Ile Met Thr  Glu Ser Ser
    4310                4315                4320

Gly Val  Thr Ile Thr Thr Gln  Thr Gly Pro Thr Gly  Ala Ala Thr
    4325                4330                4335

Gln Gly  Pro Tyr Leu Leu Asp  Thr Ser Thr Met Pro  Tyr Leu Thr
    4340                4345                4350

Glu Thr  Pro Leu Ala Val Thr  Pro Asp Phe Met Gln  Ser Glu Lys
    4355                4360                4365

Thr Thr  Leu Ile Ser Lys Gly  Pro Lys Asp Val Ser  Trp Thr Ser
    4370                4375                4380

Pro Pro  Ser Val Ala Glu Thr  Ser Tyr Pro Ser Ser  Leu Thr Pro
    4385                4390                4395

Phe Leu  Val Thr Thr Ile Pro  Pro Ala Thr Ser Thr  Leu Gln Gly
    4400                4405                4410

Gln His  Thr Ser Ser Pro Val  Ser Ala Thr Ser Val  Leu Thr Ser
    4415                4420                4425

Gly Leu  Val Lys Thr Thr Asp  Met Leu Asn Thr Ser  Met Glu Pro
    4430                4435                4440

Val Thr  Asn Ser Pro Gln Asn  Leu Asn Asn Pro Ser  Asn Glu Ile
    4445                4450                4455

Leu Ala  Thr Leu Ala Ala Thr  Thr Asp Ile Glu Thr  Ile His Pro
    4460                4465                4470

Ser Ile  Asn Lys Ala Val Thr  Asn Met Gly Thr Ala  Ser Ser Ala
    4475                4480                4485

His Val  Leu His Ser Thr Leu  Pro Val Ser Ser Glu  Pro Ser Thr
    4490                4495                4500

Ala Thr  Ser Pro Met Val Pro  Ala Ser Ser Met Gly  Asp Ala Leu
    4505                4510                4515

Ala Ser  Ile Ser Ile Pro Gly  Ser Glu Thr Thr Asp  Ile Glu Gly
    4520                4525                4530

Glu Pro  Thr Ser Ser Leu Thr  Ala Gly Arg Lys Glu  Asn Ser Thr
    4535                4540                4545

Leu Gln  Glu Met Asn Ser Thr  Thr Glu Ser Asn Ile  Ile Leu Ser
    4550                4555                4560

Asn Val  Ser Val Gly Ala Ile  Thr Glu Ala Thr Lys  Met Glu Val
    4565                4570                4575

Pro Ser  Phe Asp Ala Thr Phe  Ile Pro Thr Pro Ala  Gln Ser Thr
    4580                4585                4590

Lys Phe  Pro Asp Ile Phe Ser  Val Ala Ser Ser Arg  Leu Ser Asn
    4595                4600                4605

Ser Pro  Pro Met Thr Ile Ser  Thr His Met Thr Thr  Thr Gln Thr
    4610                4615                4620

Gly Ser  Ser Gly Ala Thr Ser  Lys Ile Pro Leu Ala  Leu Asp Thr
    4625                4630                4635
```

```
Ser Thr  Leu Glu Thr Ser Ala  Gly Thr Pro Ser Val  Val Thr Glu
    4640              4645          4650

Gly Phe  Ala His Ser Lys Ile  Thr Thr Ala Met Asn  Asn Asp Val
    4655              4660          4665

Lys Asp  Val Ser Gln Thr Asn  Pro Pro Phe Gln Asp  Glu Ala Ser
    4670              4675          4680

Ser Pro  Ser Ser Gln Ala Pro  Val Leu Val Thr Thr  Leu Pro Ser
    4685              4690          4695

Ser Val  Ala Phe Thr Pro Gln  Trp His Ser Thr Ser  Ser Pro Val
    4700              4705          4710

Ser Met  Ser Ser Val Leu Thr  Ser Ser Leu Val Lys  Thr Ala Gly
    4715              4720          4725

Lys Val  Asp Thr Ser Leu Glu  Thr Val Thr Ser Ser  Pro Gln Ser
    4730              4735          4740

Met Ser  Asn Thr Leu Asp Asp  Ile Ser Val Thr Ser  Ala Ala Thr
    4745              4750          4755

Thr Asp  Ile Glu Thr Thr His  Pro Ser Ile Asn Thr  Val Val Thr
    4760              4765          4770

Asn Val  Gly Thr Thr Gly Ser  Ala Phe Glu Ser His  Ser Thr Val
    4775              4780          4785

Ser Ala  Tyr Pro Glu Pro Ser  Lys Val Thr Ser Pro  Asn Val Thr
    4790              4795          4800

Thr Ser  Thr Met Glu Asp Thr  Thr Ile Ser Arg Ser  Ile Pro Lys
    4805              4810          4815

Ser Ser  Lys Thr Thr Arg Thr  Glu Thr Glu Thr Thr  Ser Ser Leu
    4820              4825          4830

Thr Pro  Lys Leu Arg Glu Thr  Ser Ile Ser Gln Glu  Ile Thr Ser
    4835              4840          4845

Ser Thr  Glu Thr Ser Thr Val  Pro Tyr Lys Glu Leu  Thr Gly Ala
    4850              4855          4860

Thr Thr  Glu Val Ser Arg Thr  Asp Val Thr Ser Ser  Ser Ser Thr
    4865              4870          4875

Ser Phe  Pro Gly Pro Asp Gln  Ser Thr Val Ser Leu  Asp Ile Ser
    4880              4885          4890

Thr Glu  Thr Asn Thr Arg Leu  Ser Thr Ser Pro Ile  Met Thr Glu
    4895              4900          4905

Ser Ala  Glu Ile Thr Ile Thr  Thr Gln Thr Gly Pro  His Gly Ala
    4910              4915          4920

Thr Ser  Gln Asp Thr Phe Thr  Met Asp Pro Ser Asn  Thr Thr Pro
    4925              4930          4935

Gln Ala  Gly Ile His Ser Ala  Met Thr His Gly Phe  Ser Gln Leu
    4940              4945          4950

Asp Val  Thr Thr Leu Met Ser  Arg Ile Pro Gln Asp  Val Ser Trp
    4955              4960          4965

Thr Ser  Pro Pro Ser Val Asp  Lys Thr Ser Ser Pro  Ser Ser Phe
    4970              4975          4980

Leu Ser  Ser Pro Ala Met Thr  Thr Pro Ser Leu Ile  Ser Ser Thr
    4985              4990          4995

Leu Pro  Glu Asp Lys Leu Ser  Ser Pro Met Thr Ser  Leu Leu Thr
    5000              5005          5010

Ser Gly  Leu Val Lys Ile Thr  Asp Ile Leu Arg Thr  Arg Leu Glu
    5015              5020          5025

Pro Val  Thr Ser Ser Leu Pro  Asn Phe Ser Ser Thr  Ser Asp Lys
```

-continued

```
          5030              5035                5040

Ile Leu  Ala Thr Ser Lys Asp  Ser Lys Asp Thr Lys  Glu Ile Phe
    5045              5050                5055

Pro Ser  Ile Asn Thr Glu Glu  Thr Asn Val Lys Ala  Asn Asn Ser
    5060              5065                5070

Gly His  Glu Ser His Ser Pro  Ala Leu Ala Asp Ser  Glu Thr Pro
    5075              5080                5085

Lys Ala  Thr Thr Gln Met Val  Ile Thr Thr Thr Val  Gly Asp Pro
    5090              5095                5100

Ala Pro  Ser Thr Ser Met Pro  Val His Gly Ser Ser  Glu Thr Thr
    5105              5110                5115

Asn Ile  Lys Arg Glu Pro Thr  Tyr Phe Leu Thr Pro  Arg Leu Arg
    5120              5125                5130

Glu Thr  Ser Thr Ser Gln Glu  Ser Ser Phe Pro Thr  Asp Thr Ser
    5135              5140                5145

Phe Leu  Leu Ser Lys Val Pro  Thr Gly Thr Ile Thr  Glu Val Ser
    5150              5155                5160

Ser Thr  Gly Val Asn Ser Ser  Ser Lys Ile Ser Thr  Pro Asp His
    5165              5170                5175

Asp Lys  Ser Thr Val Pro Pro  Asp Thr Phe Thr Gly  Glu Ile Pro
    5180              5185                5190

Arg Val  Phe Thr Ser Ser Ile  Lys Thr Lys Ser Ala  Glu Met Thr
    5195              5200                5205

Ile Thr  Thr Gln Ala Ser Pro  Pro Glu Ser Ala Ser  His Ser Thr
    5210              5215                5220

Leu Pro  Leu Asp Thr Ser Thr  Thr Leu Ser Gln Gly  Gly Thr His
    5225              5230                5235

Ser Thr  Val Thr Gln Gly Phe  Pro Tyr Ser Glu Val  Thr Thr Leu
    5240              5245                5250

Met Gly  Met Gly Pro Gly Asn  Val Ser Trp Met Thr  Thr Pro Pro
    5255              5260                5265

Val Glu  Glu Thr Ser Ser Val  Ser Ser Leu Met Ser  Ser Pro Ala
    5270              5275                5280

Met Thr  Ser Pro Ser Pro Val  Ser Ser Thr Ser Pro  Gln Ser Ile
    5285              5290                5295

Pro Ser  Ser Pro Leu Pro Val  Thr Ala Leu Pro Thr  Ser Val Leu
    5300              5305                5310

Val Thr  Thr Thr Asp Val Leu  Gly Thr Thr Ser Pro  Glu Ser Val
    5315              5320                5325

Thr Ser  Ser Pro Pro Asn Leu  Ser Ser Ile Thr His  Glu Arg Pro
    5330              5335                5340

Ala Thr  Tyr Lys Asp Thr Ala  His Thr Glu Ala Ala  Met His His
    5345              5350                5355

Ser Thr  Asn Thr Ala Val Thr  Asn Val Gly Thr Ser  Gly Ser Gly
    5360              5365                5370

His Lys  Ser Gln Ser Ser Val  Leu Ala Asp Ser Glu  Thr Ser Lys
    5375              5380                5385

Ala Thr  Pro Leu Met Ser Thr  Thr Ser Thr Leu Gly  Asp Thr Ser
    5390              5395                5400

Val Ser  Thr Ser Thr Pro Asn  Ile Ser Gln Thr Asn  Gln Ile Gln
    5405              5410                5415

Thr Glu  Pro Thr Ala Ser Leu  Ser Pro Arg Leu Arg  Glu Ser Ser
    5420              5425                5430
```

```
Thr Ser  Glu Lys Thr Ser Ser  Thr Thr Glu Thr Asn  Thr Ala Phe
    5435             5440             5445

Ser Tyr  Val Pro Thr Gly Ala  Ile Thr Gln Ala Ser  Arg Thr Glu
    5450             5455             5460

Ile Ser  Ser Ser Arg Thr Ser  Ile Ser Asp Leu Asp  Arg Pro Thr
    5465             5470             5475

Ile Ala  Pro Asp Ile Ser Thr  Gly Met Ile Thr Arg  Leu Phe Thr
    5480             5485             5490

Ser Pro  Ile Met Thr Lys Ser  Ala Glu Met Thr Val  Thr Thr Gln
    5495             5500             5505

Thr Thr  Thr Pro Gly Ala Thr  Ser Gln Gly Ile Leu  Pro Trp Asp
    5510             5515             5520

Thr Ser  Thr Thr Leu Phe Gln  Gly Gly Thr His Ser  Thr Val Ser
    5525             5530             5535

Gln Gly  Phe Pro His Ser Glu  Ile Thr Thr Leu Arg  Ser Arg Thr
    5540             5545             5550

Pro Gly  Asp Val Ser Trp Met  Thr Thr Pro Pro Val  Glu Glu Thr
    5555             5560             5565

Ser Ser  Gly Phe Ser Leu Met  Ser Pro Ser Met Thr  Ser Pro Ser
    5570             5575             5580

Pro Val  Ser Ser Thr Ser Pro  Glu Ser Ile Pro Ser  Ser Pro Leu
    5585             5590             5595

Pro Val  Thr Ala Leu Leu Thr  Ser Val Leu Val Thr  Thr Thr Asn
    5600             5605             5610

Val Leu  Gly Thr Thr Ser Pro  Glu Pro Val Thr Ser  Ser Pro Pro
    5615             5620             5625

Asn Leu  Ser Ser Pro Thr Gln  Glu Arg Leu Thr Thr  Tyr Lys Asp
    5630             5635             5640

Thr Ala  His Thr Glu Ala Met  His Ala Ser Met His  Thr Asn Thr
    5645             5650             5655

Ala Val  Ala Asn Val Gly Thr  Ser Ile Ser Gly His  Glu Ser Gln
    5660             5665             5670

Ser Ser  Val Pro Ala Asp Ser  His Thr Ser Lys Ala  Thr Ser Pro
    5675             5680             5685

Met Gly  Ile Thr Phe Ala Met  Gly Asp Thr Ser Val  Ser Thr Ser
    5690             5695             5700

Thr Pro  Ala Phe Phe Glu Thr  Arg Ile Gln Thr Glu  Ser Thr Ser
    5705             5710             5715

Ser Leu  Ile Pro Gly Leu Arg  Asp Thr Arg Thr Ser  Glu Glu Ile
    5720             5725             5730

Asn Thr  Val Thr Glu Thr Ser  Thr Val Leu Ser Glu  Val Pro Thr
    5735             5740             5745

Thr Thr  Thr Thr Glu Val Ser  Arg Thr Glu Val Ile  Thr Ser Ser
    5750             5755             5760

Arg Thr  Thr Ile Ser Gly Pro  Asp His Ser Lys Met  Ser Pro Tyr
    5765             5770             5775

Ile Ser  Thr Glu Thr Ile Thr  Arg Leu Ser Thr Phe  Pro Phe Val
    5780             5785             5790

Thr Gly  Ser Thr Glu Met Ala  Ile Thr Asn Gln Thr  Gly Pro Ile
    5795             5800             5805

Gly Thr  Ile Ser Gln Ala Thr  Leu Thr Leu Asp Thr  Ser Ser Thr
    5810             5815             5820
```

-continued

```
Ala Ser  Trp Glu Gly Thr His  Ser Pro Val Thr Gln  Arg Phe Pro
    5825                  5830              5835

His Ser  Glu Glu Thr Thr Thr  Met Ser Arg Ser Thr  Lys Gly Val
    5840                  5845              5850

Ser Trp  Gln Ser Pro Pro Ser  Val Glu Glu Thr Ser  Ser Pro Ser
    5855                  5860              5865

Ser Pro  Val Pro Leu Pro Ala  Ile Thr Ser His Ser  Ser Leu Tyr
    5870                  5875              5880

Ser Ala  Val Ser Gly Ser Ser  Pro Thr Ser Ala Leu  Pro Val Thr
    5885                  5890              5895

Ser Leu  Leu Thr Ser Gly Arg  Arg Lys Thr Ile Asp  Met Leu Asp
    5900                  5905              5910

Thr His  Ser Glu Leu Val Thr  Ser Ser Leu Pro Ser  Ala Ser Ser
    5915                  5920              5925

Phe Ser  Gly Glu Ile Leu Thr  Ser Glu Ala Ser Thr  Asn Thr Glu
    5930                  5935              5940

Thr Ile  His Phe Ser Glu Asn  Thr Ala Glu Thr Asn  Met Gly Thr
    5945                  5950              5955

Thr Asn  Ser Met His Lys Leu  His Ser Ser Val Ser  Ile His Ser
    5960                  5965              5970

Gln Pro  Ser Gly His Thr Pro  Pro Lys Val Thr Gly  Ser Met Met
    5975                  5980              5985

Glu Asp  Ala Ile Val Ser Thr  Ser Thr Pro Gly Ser  Pro Glu Thr
    5990                  5995              6000

Lys Asn  Val Asp Arg Asp Ser  Thr Ser Pro Leu Thr  Pro Glu Leu
    6005                  6010              6015

Lys Glu  Asp Ser Thr Ala Leu  Val Met Asn Ser Thr  Thr Glu Ser
    6020                  6025              6030

Asn Thr  Val Phe Ser Ser Val  Ser Leu Asp Ala Ala  Thr Glu Val
    6035                  6040              6045

Ser Arg  Ala Glu Val Thr Tyr  Tyr Asp Pro Thr Phe  Met Pro Ala
    6050                  6055              6060

Ser Ala  Gln Ser Thr Lys Ser  Pro Asp Ile Ser Pro  Glu Ala Ser
    6065                  6070              6075

Ser Ser  His Ser Asn Ser Pro  Pro Leu Thr Ile Ser  Thr His Lys
    6080                  6085              6090

Thr Ile  Ala Thr Gln Thr Gly  Pro Ser Gly Val Thr  Ser Leu Gly
    6095                  6100              6105

Gln Leu  Thr Leu Asp Thr Ser  Thr Ile Ala Thr Ser  Ala Gly Thr
    6110                  6115              6120

Pro Ser  Ala Arg Thr Gln Asp  Phe Val Asp Ser Glu  Thr Thr Ser
    6125                  6130              6135

Val Met  Asn Asn Asp Leu Asn  Asp Val Leu Lys Thr  Ser Pro Phe
    6140                  6145              6150

Ser Ala  Glu Glu Ala Asn Ser  Leu Ser Ser Gln Ala  Pro Leu Leu
    6155                  6160              6165

Val Thr  Thr Ser Pro Ser Pro  Val Thr Ser Thr Leu  Gln Glu His
    6170                  6175              6180

Ser Thr  Ser Ser Leu Val Ser  Val Thr Ser Val Pro  Thr Pro Thr
    6185                  6190              6195

Leu Ala  Lys Ile Thr Asp Met  Asp Thr Asn Leu Glu  Pro Val Thr
    6200                  6205              6210

Arg Ser  Pro Gln Asn Leu Arg  Asn Thr Leu Ala Thr  Ser Glu Ala
```

```
      6215                6220                6225

Thr Thr Asp Thr His Thr Met His Pro Ser Ile Asn Thr Ala Val
    6230                6235                6240

Ala Asn Val Gly Thr Thr Ser Ser Pro Asn Glu Phe Tyr Phe Thr
    6245                6250                6255

Val Ser Pro Asp Ser Asp Pro Tyr Lys Ala Thr Ser Ala Val Val
    6260                6265                6270

Ile Thr Ser Thr Ser Gly Asp Ser Ile Val Ser Thr Ser Met Pro
    6275                6280                6285

Arg Ser Ser Ala Met Lys Lys Ile Glu Ser Glu Thr Thr Phe Ser
    6290                6295                6300

Leu Ile Phe Arg Leu Arg Glu Thr Ser Thr Ser Gln Lys Ile Gly
    6305                6310                6315

Ser Ser Ser Asp Thr Ser Thr Val Phe Asp Lys Ala Phe Thr Ala
    6320                6325                6330

Ala Thr Thr Glu Val Ser Arg Thr Glu Leu Thr Ser Ser Ser Arg
    6335                6340                6345

Thr Ser Ile Gln Gly Thr Glu Lys Pro Thr Met Ser Pro Asp Thr
    6350                6355                6360

Ser Thr Arg Ser Val Thr Met Leu Ser Thr Phe Ala Gly Leu Thr
    6365                6370                6375

Lys Ser Glu Glu Arg Thr Ile Ala Thr Gln Thr Gly Pro His Arg
    6380                6385                6390

Ala Thr Ser Gln Gly Thr Leu Thr Trp Asp Thr Ser Ile Thr Thr
    6395                6400                6405

Ser Gln Ala Gly Thr His Ser Ala Met Thr His Gly Phe Ser Gln
    6410                6415                6420

Leu Asp Leu Ser Thr Leu Thr Ser Arg Val Pro Glu Tyr Ile Ser
    6425                6430                6435

Gly Thr Ser Pro Pro Ser Val Glu Lys Thr Ser Ser Ser Ser Ser
    6440                6445                6450

Leu Leu Ser Leu Pro Ala Ile Thr Ser Pro Ser Pro Val Pro Thr
    6455                6460                6465

Thr Leu Pro Glu Ser Arg Pro Ser Ser Pro Val His Leu Thr Ser
    6470                6475                6480

Leu Pro Thr Ser Gly Leu Val Lys Thr Thr Asp Met Leu Ala Ser
    6485                6490                6495

Val Ala Ser Leu Pro Pro Asn Leu Gly Ser Thr Ser His Lys Ile
    6500                6505                6510

Pro Thr Thr Ser Glu Asp Ile Lys Asp Thr Glu Lys Met Tyr Pro
    6515                6520                6525

Ser Thr Asn Ile Ala Val Thr Asn Val Gly Thr Thr Thr Ser Glu
    6530                6535                6540

Lys Glu Ser Tyr Ser Ser Val Pro Ala Tyr Ser Glu Pro Pro Lys
    6545                6550                6555

Val Thr Ser Pro Met Val Thr Ser Phe Asn Ile Arg Asp Thr Ile
    6560                6565                6570

Val Ser Thr Ser Met Pro Gly Ser Ser Glu Ile Thr Arg Ile Glu
    6575                6580                6585

Met Glu Ser Thr Phe Ser Leu Ala His Gly Leu Lys Gly Thr Ser
    6590                6595                6600

Thr Ser Gln Asp Pro Ile Val Ser Thr Glu Lys Ser Ala Val Leu
    6605                6610                6615
```

-continued

```
His Lys Leu Thr Thr Gly Ala  Thr Glu Thr Ser Arg  Thr Glu Val
    6620              6625              6630

Ala Ser  Ser Arg Arg Thr Ser  Ile Pro Gly Pro Asp  His Ser Thr
    6635              6640              6645

Glu Ser  Pro Asp Ile Ser Thr  Glu Val Ile Pro Ser  Leu Pro Ile
    6650              6655              6660

Ser Leu  Gly Ile Thr Glu Ser  Ser Asn Met Thr Ile  Ile Thr Arg
    6665              6670              6675

Thr Gly  Pro Pro Leu Gly Ser  Thr Ser Gln Gly Thr  Phe Thr Leu
    6680              6685              6690

Asp Thr  Pro Thr Thr Ser Ser  Arg Ala Gly Thr His  Ser Met Ala
    6695              6700              6705

Thr Gln  Glu Phe Pro His Ser  Glu Met Thr Thr Val  Met Asn Lys
    6710              6715              6720

Asp Pro  Glu Ile Leu Ser Trp  Thr Ile Pro Pro Ser  Ile Glu Lys
    6725              6730              6735

Thr Ser  Phe Ser Ser Ser Leu  Met Pro Ser Pro Ala  Met Thr Ser
    6740              6745              6750

Pro Pro  Val Ser Ser Thr Leu  Pro Lys Thr Ile His  Thr Thr Pro
    6755              6760              6765

Ser Pro  Met Thr Ser Leu Leu  Thr Pro Ser Leu Val  Met Thr Thr
    6770              6775              6780

Asp Thr  Leu Gly Thr Ser Pro  Glu Pro Thr Thr Ser  Ser Pro Pro
    6785              6790              6795

Asn Leu  Ser Ser Thr Ser His  Glu Ile Leu Thr Thr  Asp Glu Asp
    6800              6805              6810

Thr Thr  Ala Ile Glu Ala Met  His Pro Ser Thr Ser  Thr Ala Ala
    6815              6820              6825

Thr Asn  Val Glu Thr Thr Ser  Ser Gly His Gly Ser  Gln Ser Ser
    6830              6835              6840

Val Leu  Ala Asp Ser Glu Lys  Thr Lys Ala Thr Ala  Pro Met Asp
    6845              6850              6855

Thr Thr  Ser Thr Met Gly His  Thr Thr Val Ser Thr  Ser Met Ser
    6860              6865              6870

Val Ser  Ser Glu Thr Thr Lys  Ile Lys Arg Glu Ser  Thr Tyr Ser
    6875              6880              6885

Leu Thr  Pro Gly Leu Arg Glu  Thr Ser Ile Ser Gln  Asn Ala Ser
    6890              6895              6900

Phe Ser  Thr Asp Thr Ser Ile  Val Leu Ser Glu Val  Pro Thr Gly
    6905              6910              6915

Thr Thr  Ala Glu Val Ser Arg  Thr Glu Val Thr Ser  Ser Gly Arg
    6920              6925              6930

Thr Ser  Ile Pro Gly Pro Ser  Gln Ser Thr Val Leu  Pro Glu Ile
    6935              6940              6945

Ser Thr  Arg Thr Met Thr Arg  Leu Phe Ala Ser Pro  Thr Met Thr
    6950              6955              6960

Glu Ser  Ala Glu Met Thr Ile  Pro Thr Gln Thr Gly  Pro Ser Gly
    6965              6970              6975

Ser Thr  Ser Gln Asp Thr Leu  Thr Leu Asp Thr Ser  Thr Thr Lys
    6980              6985              6990

Ser Gln  Ala Lys Thr His Ser  Thr Leu Thr Gln Arg  Phe Pro His
    6995              7000              7005
```

-continued

```
Ser Glu  Met Thr Thr Leu Met  Ser Arg Gly Pro Gly  Asp Met Ser
    7010                 7015              7020

Trp Gln  Ser Ser Pro Ser Leu  Glu Asn Pro Ser Ser  Leu Pro Ser
    7025                 7030              7035

Leu Leu  Ser Leu Pro Ala Thr  Thr Ser Pro Pro Pro  Ile Ser Ser
    7040                 7045              7050

Thr Leu  Pro Val Thr Ile Ser  Ser Ser Pro Leu Pro  Val Thr Ser
    7055                 7060              7065

Leu Leu  Thr Ser Ser Pro Val  Thr Thr Thr Asp Met  Leu His Thr
    7070                 7075              7080

Ser Pro  Glu Leu Val Thr Ser  Ser Pro Pro Lys Leu  Ser His Thr
    7085                 7090              7095

Ser Asp  Glu Arg Leu Thr Thr  Gly Lys Asp Thr Thr  Asn Thr Glu
    7100                 7105              7110

Ala Val  His Pro Ser Thr Asn  Thr Ala Ala Ser Asn  Val Glu Ile
    7115                 7120              7125

Pro Ser  Ser Gly His Glu Ser  Pro Ser Ser Ala Leu  Ala Asp Ser
    7130                 7135              7140

Glu Thr  Ser Lys Ala Thr Ser  Pro Met Phe Ile Thr  Ser Thr Gln
    7145                 7150              7155

Glu Asp  Thr Thr Val Ala Ile  Ser Thr Pro His Phe  Leu Glu Thr
    7160                 7165              7170

Ser Arg  Ile Gln Lys Glu Ser  Ile Ser Ser Leu Ser  Pro Lys Leu
    7175                 7180              7185

Arg Glu  Thr Gly Ser Ser Val  Glu Thr Ser Ser Ala  Ile Glu Thr
    7190                 7195              7200

Ser Ala  Val Leu Ser Glu Val  Ser Ile Gly Ala Thr  Thr Glu Ile
    7205                 7210              7215

Ser Arg  Thr Glu Val Thr Ser  Ser Ser Arg Thr Ser  Ile Ser Gly
    7220                 7225              7230

Ser Ala  Glu Ser Thr Met Leu  Pro Glu Ile Ser Thr  Thr Arg Lys
    7235                 7240              7245

Ile Ile  Lys Phe Pro Thr Ser  Pro Ile Leu Ala Glu  Ser Ser Glu
    7250                 7255              7260

Met Thr  Ile Lys Thr Gln Thr  Ser Pro Pro Gly Ser  Thr Ser Glu
    7265                 7270              7275

Ser Thr  Phe Thr Leu Asp Thr  Ser Thr Thr Pro Ser  Leu Val Ile
    7280                 7285              7290

Thr His  Ser Thr Met Thr Gln  Arg Leu Pro His Ser  Glu Ile Thr
    7295                 7300              7305

Thr Leu  Val Ser Arg Gly Ala  Gly Asp Val Pro Arg  Pro Ser Ser
    7310                 7315              7320

Leu Pro  Val Glu Glu Thr Ser  Pro Pro Ser Ser Gln  Leu Ser Leu
    7325                 7330              7335

Ser Ala  Met Ile Ser Pro Ser  Pro Val Ser Ser Thr  Leu Pro Ala
    7340                 7345              7350

Ser Ser  His Ser Ser Ser Ala  Ser Val Thr Ser Leu  Leu Thr Pro
    7355                 7360              7365

Gly Gln  Val Lys Thr Thr Glu  Val Leu Asp Ala Ser  Ala Glu Pro
    7370                 7375              7380

Glu Thr  Ser Ser Pro Pro Ser  Leu Ser Ser Thr Ser  Val Glu Ile
    7385                 7390              7395

Leu Ala  Thr Ser Glu Val Thr  Thr Asp Thr Glu Lys  Ile His Pro
```

```
          7400              7405              7410

Phe Ser  Asn Thr Ala Val Thr  Lys Val Gly Thr Ser  Ser Ser Gly
    7415              7420              7425

His Glu  Ser Pro Ser Ser Val  Leu Pro Asp Ser Glu  Thr Thr Lys
    7430              7435              7440

Ala Thr  Ser Ala Met Gly Thr  Ile Ser Ile Met Gly  Asp Thr Ser
    7445              7450              7455

Val Ser  Thr Leu Thr Pro Ala  Leu Ser Asn Thr Arg  Lys Ile Gln
    7460              7465              7470

Ser Glu  Pro Ala Ser Ser Leu  Thr Thr Arg Leu Arg  Glu Thr Ser
    7475              7480              7485

Thr Ser  Glu Glu Thr Ser Leu  Ala Thr Glu Ala Asn  Thr Val Leu
    7490              7495              7500

Ser Lys  Val Ser Thr Gly Ala  Thr Thr Glu Val Ser  Arg Thr Glu
    7505              7510              7515

Ala Ile  Ser Phe Ser Arg Thr  Ser Met Ser Gly Pro  Glu Gln Ser
    7520              7525              7530

Thr Met  Ser Gln Asp Ile Ser  Ile Gly Thr Ile Pro  Arg Ile Ser
    7535              7540              7545

Ala Ser  Ser Val Leu Thr Glu  Ser Ala Lys Met Thr  Ile Thr Thr
    7550              7555              7560

Gln Thr  Gly Pro Ser Glu Ser  Thr Leu Glu Ser Thr  Leu Asn Leu
    7565              7570              7575

Asn Thr  Ala Thr Thr Pro Ser  Trp Val Glu Thr His  Ser Ile Val
    7580              7585              7590

Ile Gln  Gly Phe Pro His Pro  Glu Met Thr Thr Ser  Met Gly Arg
    7595              7600              7605

Gly Pro  Gly Gly Val Ser Trp  Pro Ser Pro Pro Phe  Val Lys Glu
    7610              7615              7620

Thr Ser  Pro Pro Ser Ser Pro  Leu Ser Leu Pro Ala  Val Thr Ser
    7625              7630              7635

Pro His  Pro Val Ser Thr Thr  Phe Leu Ala His Ile  Pro Pro Ser
    7640              7645              7650

Pro Leu  Pro Val Thr Ser Leu  Leu Thr Ser Gly Pro  Ala Thr Thr
    7655              7660              7665

Thr Asp  Ile Leu Gly Thr Ser  Thr Glu Pro Gly Thr  Ser Ser Ser
    7670              7675              7680

Ser Ser  Leu Ser Thr Thr Ser  His Glu Arg Leu Thr  Thr Tyr Lys
    7685              7690              7695

Asp Thr  Ala His Thr Glu Ala  Val His Pro Ser Thr  Asn Thr Gly
    7700              7705              7710

Gly Thr  Asn Val Ala Thr Thr  Ser Ser Gly Tyr Lys  Ser Gln Ser
    7715              7720              7725

Ser Val  Leu Ala Asp Ser Ser  Pro Met Cys Thr Thr  Ser Thr Met
    7730              7735              7740

Gly Asp  Thr Ser Val Leu Thr  Ser Thr Pro Ala Phe  Leu Glu Thr
    7745              7750              7755

Arg Arg  Ile Gln Thr Glu Leu  Ala Ser Ser Leu Thr  Pro Gly Leu
    7760              7765              7770

Arg Glu  Ser Ser Gly Ser Glu  Gly Thr Ser Ser Gly  Thr Lys Met
    7775              7780              7785

Ser Thr  Val Leu Ser Lys Val  Pro Thr Gly Ala Thr  Thr Glu Ile
    7790              7795              7800
```

-continued

```
Ser Lys Glu Asp Val Thr Ser  Ile Pro Gly Pro Ala  Gln Ser Thr
    7805                7810              7815

Ile Ser Pro Asp Ile Ser Thr  Arg Thr Val Ser Trp  Phe Ser Thr
    7820                7825              7830

Ser Pro Val Met Thr Glu Ser  Ala Glu Ile Thr Met  Asn Thr His
    7835                7840              7845

Thr Ser Pro Leu Gly Ala Thr  Thr Gln Gly Thr Ser  Thr Leu Asp
    7850                7855              7860

Thr Ser Ser Thr Thr Ser Leu  Thr Met Thr His Ser  Thr Ile Ser
    7865                7870              7875

Gln Gly Phe Ser His Ser Gln  Met Ser Thr Leu Met  Arg Arg Gly
    7880                7885              7890

Pro Glu Asp Val Ser Trp Met  Ser Pro Pro Leu Leu  Glu Lys Thr
    7895                7900              7905

Arg Pro Ser Phe Ser Leu Met  Ser Ser Pro Ala Thr  Thr Ser Pro
    7910                7915              7920

Ser Pro Val Ser Ser Thr Leu  Pro Glu Ser Ile Ser  Ser Ser Pro
    7925                7930              7935

Leu Pro Val Thr Ser Leu Leu  Thr Ser Gly Leu Ala  Lys Thr Thr
    7940                7945              7950

Asp Met Leu His Lys Ser Ser  Glu Pro Val Thr Asn  Ser Pro Ala
    7955                7960              7965

Asn Leu Ser Ser Thr Ser Val  Glu Ile Leu Ala Thr  Ser Glu Val
    7970                7975              7980

Thr Thr Asp Thr Glu Lys Thr  His Pro Ser Ser Asn  Arg Thr Val
    7985                7990              7995

Thr Asp Val Gly Thr Ser Ser  Ser Gly His Glu Ser  Thr Ser Phe
    8000                8005              8010

Val Leu Ala Asp Ser Gln Thr  Ser Lys Val Thr Ser  Pro Met Val
    8015                8020              8025

Ile Thr Ser Thr Met Glu Asp  Thr Ser Val Ser Thr  Ser Thr Pro
    8030                8035              8040

Gly Phe Phe Glu Thr Ser Arg  Ile Gln Thr Glu Pro  Thr Ser Ser
    8045                8050              8055

Leu Thr Leu Gly Leu Arg Lys  Thr Ser Ser Ser Glu  Gly Thr Ser
    8060                8065              8070

Leu Ala Thr Glu Met Ser Thr  Val Leu Ser Gly Val  Pro Thr Gly
    8075                8080              8085

Ala Thr Ala Glu Val Ser Arg  Thr Glu Val Thr Ser  Ser Ser Arg
    8090                8095              8100

Thr Ser Ile Ser Gly Phe Ala  Gln Leu Thr Val Ser  Pro Glu Thr
    8105                8110              8115

Ser Thr Glu Thr Ile Thr Arg  Leu Pro Thr Ser Ser  Ile Met Thr
    8120                8125              8130

Glu Ser Ala Glu Met Met Ile  Lys Thr Gln Thr Asp  Pro Pro Gly
    8135                8140              8145

Ser Thr Pro Glu Ser Thr His  Thr Val Asp Ile Ser  Thr Thr Pro
    8150                8155              8160

Asn Trp Val Glu Thr His Ser  Thr Val Thr Gln Arg  Phe Ser His
    8165                8170              8175

Ser Glu Met Thr Thr Leu Val  Ser Arg Ser Pro Gly  Asp Met Leu
    8180                8185              8190
```

-continued

```
Trp Pro Ser Gln Ser Ser Val Glu Glu Thr Ser Ser Ala Ser Ser
    8195                8200            8205

Leu Leu Ser Leu Pro Ala Thr Thr Ser Pro Ser Pro Val Ser Ser
    8210                8215            8220

Thr Leu Val Glu Asp Phe Pro Ser Ala Ser Leu Pro Val Thr Ser
    8225                8230            8235

Leu Leu Asn Pro Gly Leu Val Ile Thr Thr Asp Arg Met Gly Ile
    8240                8245            8250

Ser Arg Glu Pro Gly Thr Ser Ser Thr Ser Asn Leu Ser Ser Thr
    8255                8260            8265

Ser His Glu Arg Leu Thr Thr Leu Glu Asp Thr Val Asp Thr Glu
    8270                8275            8280

Asp Met Gln Pro Ser Thr His Thr Ala Val Thr Asn Val Arg Thr
    8285                8290            8295

Ser Ile Ser Gly His Glu Ser Gln Ser Ser Val Leu Ser Asp Ser
    8300                8305            8310

Glu Thr Pro Lys Ala Thr Ser Pro Met Gly Thr Thr Tyr Thr Met
    8315                8320            8325

Gly Glu Thr Ser Val Ser Ile Ser Thr Ser Asp Phe Phe Glu Thr
    8330                8335            8340

Ser Arg Ile Gln Ile Glu Pro Thr Ser Ser Leu Thr Ser Gly Leu
    8345                8350            8355

Arg Glu Thr Ser Ser Ser Glu Arg Ile Ser Ser Ala Thr Glu Gly
    8360                8365            8370

Ser Thr Val Leu Ser Glu Val Pro Ser Gly Ala Thr Thr Glu Val
    8375                8380            8385

Ser Arg Thr Glu Val Ile Ser Ser Arg Gly Thr Ser Met Ser Gly
    8390                8395            8400

Pro Asp Gln Phe Thr Ile Ser Pro Asp Ile Ser Thr Glu Ala Ile
    8405                8410            8415

Thr Arg Leu Ser Thr Ser Pro Ile Met Thr Glu Ser Ala Glu Ser
    8420                8425            8430

Ala Ile Thr Ile Glu Thr Gly Ser Pro Gly Ala Thr Ser Glu Gly
    8435                8440            8445

Thr Leu Thr Leu Asp Thr Ser Thr Thr Thr Phe Trp Ser Gly Thr
    8450                8455            8460

His Ser Thr Ala Ser Pro Gly Phe Ser His Ser Glu Met Thr Thr
    8465                8470            8475

Leu Met Ser Arg Thr Pro Gly Asp Val Pro Trp Pro Ser Leu Pro
    8480                8485            8490

Ser Val Glu Glu Ala Ser Ser Val Ser Ser Ser Leu Ser Ser Pro
    8495                8500            8505

Ala Met Thr Ser Thr Ser Phe Phe Ser Thr Leu Pro Glu Ser Ile
    8510                8515            8520

Ser Ser Ser Pro His Pro Val Thr Ala Leu Leu Thr Leu Gly Pro
    8525                8530            8535

Val Lys Thr Thr Asp Met Leu Arg Thr Ser Ser Glu Pro Glu Thr
    8540                8545            8550

Ser Ser Pro Pro Asn Leu Ser Ser Thr Ser Ala Glu Ile Leu Ala
    8555                8560            8565

Thr Ser Glu Val Thr Lys Asp Arg Glu Lys Ile His Pro Ser Ser
    8570                8575            8580

Asn Thr Pro Val Val Asn Val Gly Thr Val Ile Tyr Lys His Leu
```

-continued

```
        8585                8590                8595

Ser Pro Ser Ser Val Leu Ala  Asp Leu Val Thr Thr  Lys Pro Thr
    8600                8605                8610

Ser Pro Met Ala Thr Thr Ser  Thr Leu Gly Asn Thr  Ser Val Ser
    8615                8620                8625

Thr Ser Thr Pro Ala Phe Pro  Glu Thr Met Met Thr  Gln Pro Thr
    8630                8635                8640

Ser Ser Leu Thr Ser Gly Leu  Arg Glu Ile Ser Thr  Ser Gln Glu
    8645                8650                8655

Thr Ser Ser Ala Thr Glu Arg  Ser Ala Ser Leu Ser  Gly Met Pro
    8660                8665                8670

Thr Gly Ala Thr Thr Lys Val  Ser Arg Thr Glu Ala  Leu Ser Leu
    8675                8680                8685

Gly Arg Thr Ser Thr Pro Gly  Pro Ala Gln Ser Thr  Ile Ser Pro
    8690                8695                8700

Glu Ile Ser Thr Glu Thr Ile  Thr Arg Ile Ser Thr  Pro Leu Thr
    8705                8710                8715

Thr Thr Gly Ser Ala Glu Met  Thr Ile Thr Pro Lys  Thr Gly His
    8720                8725                8730

Ser Gly Ala Ser Ser Gln Gly  Thr Phe Thr Leu Asp  Thr Ser Ser
    8735                8740                8745

Arg Ala Ser Trp Pro Gly Thr  His Ser Ala Ala Thr  His Arg Ser
    8750                8755                8760

Pro His Ser Gly Met Thr Thr  Pro Met Ser Arg Gly  Pro Glu Asp
    8765                8770                8775

Val Ser Trp Pro Ser Arg Pro  Ser Val Glu Lys Thr  Ser Pro Pro
    8780                8785                8790

Ser Ser Leu Val Ser Leu Ser  Ala Val Thr Ser Pro  Ser Pro Leu
    8795                8800                8805

Tyr Ser Thr Pro Ser Glu Ser  Ser His Ser Ser Pro  Leu Arg Val
    8810                8815                8820

Thr Ser Leu Phe Thr Pro Val  Met Met Lys Thr Thr  Asp Met Leu
    8825                8830                8835

Asp Thr Ser Leu Glu Pro Val  Thr Thr Ser Pro Pro  Ser Met Asn
    8840                8845                8850

Ile Thr Ser Asp Glu Ser Leu  Ala Thr Ser Lys Ala  Thr Met Glu
    8855                8860                8865

Thr Glu Ala Ile Gln Leu Ser  Glu Asn Thr Ala Val  Thr Gln Met
    8870                8875                8880

Gly Thr Ile Ser Ala Arg Gln  Glu Phe Tyr Ser Ser  Tyr Pro Gly
    8885                8890                8895

Leu Pro Glu Pro Ser Lys Val  Thr Ser Pro Val Val  Thr Ser Ser
    8900                8905                8910

Thr Ile Lys Asp Ile Val Ser  Thr Thr Ile Pro Ala  Ser Ser Glu
    8915                8920                8925

Ile Thr Arg Ile Glu Met Glu  Ser Thr Ser Thr Leu  Thr Pro Thr
    8930                8935                8940

Pro Arg Glu Thr Ser Thr Ser  Gln Glu Ile His Ser  Ala Thr Lys
    8945                8950                8955

Pro Ser Thr Val Pro Tyr Lys  Ala Leu Thr Ser Ala  Thr Ile Glu
    8960                8965                8970

Asp Ser Met Thr Gln Val Met  Ser Ser Ser Arg Gly  Pro Ser Pro
    8975                8980                8985
```

-continued

```
Asp Gln Ser Thr Met Ser Gln  Asp Ile Ser Thr Glu  Val Ile Thr
    8990            8995            9000

Arg Leu Ser Thr Ser Pro Ile  Lys Thr Glu Ser Thr  Glu Met Thr
    9005            9010            9015

Ile Thr  Thr Gln Thr Gly Ser  Pro Gly Ala Thr Ser  Arg Gly Thr
    9020            9025            9030

Leu Thr  Leu Asp Thr Ser Thr  Thr Phe Met Ser Gly  Thr His Ser
    9035            9040            9045

Thr Ala  Ser Gln Gly Phe Ser  His Ser Gln Met Thr  Ala Leu Met
    9050            9055            9060

Ser Arg  Thr Pro Gly Asp Val  Pro Trp Leu Ser His  Pro Ser Val
    9065            9070            9075

Glu Glu  Ala Ser Ser Ala Ser  Phe Ser Leu Ser Ser  Pro Val Met
    9080            9085            9090

Thr Ser  Ser Ser Pro Val Ser  Ser Thr Leu Pro Asp  Ser Ile His
    9095            9100            9105

Ser Ser  Ser Leu Pro Val Thr  Ser Leu Leu Thr Ser  Gly Leu Val
    9110            9115            9120

Lys Thr  Thr Glu Leu Leu Gly  Thr Ser Ser Glu Pro  Glu Thr Ser
    9125            9130            9135

Ser Pro  Pro Asn Leu Ser Ser  Thr Ser Ala Glu Ile  Leu Ala Ile
    9140            9145            9150

Thr Glu  Val Thr Thr Asp Thr  Glu Lys Leu Glu Met  Thr Asn Val
    9155            9160            9165

Val Thr  Ser Gly Tyr Thr His  Glu Ser Pro Ser Ser  Val Leu Ala
    9170            9175            9180

Asp Ser  Val Thr Thr Lys Ala  Thr Ser Ser Met Gly  Ile Thr Tyr
    9185            9190            9195

Pro Thr  Gly Asp Thr Asn Val  Leu Thr Ser Thr Pro  Ala Phe Ser
    9200            9205            9210

Asp Thr  Ser Arg Ile Gln Thr  Lys Ser Lys Leu Ser  Leu Thr Pro
    9215            9220            9225

Gly Leu  Met Glu Thr Ser Ile  Ser Glu Glu Thr Ser  Ser Ala Thr
    9230            9235            9240

Glu Lys  Ser Thr Val Leu Ser  Ser Val Pro Thr Gly  Ala Thr Thr
    9245            9250            9255

Glu Val  Ser Arg Thr Glu Ala  Ile Ser Ser Ser Arg  Thr Ser Ile
    9260            9265            9270

Pro Gly  Pro Ala Gln Ser Thr  Met Ser Ser Asp Thr  Ser Met Glu
    9275            9280            9285

Thr Ile  Thr Arg Ile Ser Thr  Pro Leu Thr Arg Lys  Glu Ser Thr
    9290            9295            9300

Asp Met  Ala Ile Thr Pro Lys  Thr Gly Pro Ser Gly  Ala Thr Ser
    9305            9310            9315

Gln Gly  Thr Phe Thr Leu Asp  Ser Ser Ser Thr Ala  Ser Trp Pro
    9320            9325            9330

Gly Thr  His Ser Ala Thr Thr  Gln Arg Phe Pro Gln  Ser Val Val
    9335            9340            9345

Thr Thr  Pro Met Ser Arg Gly  Pro Glu Asp Val Ser  Trp Pro Ser
    9350            9355            9360

Pro Leu  Ser Val Glu Lys Asn  Ser Pro Pro Ser Ser  Leu Val Ser
    9365            9370            9375
```

-continued

```
Ser Ser  Ser Val Thr Ser Pro  Ser Pro Leu Tyr Ser  Thr Pro Ser
    9380              9385              9390

Gly Ser  Ser His Ser Ser Pro  Val Pro Val Thr Ser  Leu Phe Thr
    9395              9400              9405

Ser Ile  Met Met Lys Ala Thr  Asp Met Leu Asp Ala  Ser Leu Glu
    9410              9415              9420

Pro Glu  Thr Thr Ser Ala Pro  Asn Met Asn Ile Thr  Ser Asp Glu
    9425              9430              9435

Ser Leu  Ala Ala Ser Lys Ala  Thr Thr Glu Thr Glu  Ala Ile His
    9440              9445              9450

Val Phe  Glu Asn Thr Ala Ala  Ser His Val Glu Thr  Thr Ser Ala
    9455              9460              9465

Thr Glu  Glu Leu Tyr Ser Ser  Ser Pro Gly Phe Ser  Glu Pro Thr
    9470              9475              9480

Lys Val  Ile Ser Pro Val Val  Thr Ser Ser Ser Ile  Arg Asp Asn
    9485              9490              9495

Met Val  Ser Thr Thr Met Pro  Gly Ser Ser Gly Ile  Thr Arg Ile
    9500              9505              9510

Glu Ile  Glu Ser Met Ser Ser  Leu Thr Pro Gly Leu  Arg Glu Thr
    9515              9520              9525

Arg Thr  Ser Gln Asp Ile Thr  Ser Ser Thr Glu Thr  Ser Thr Val
    9530              9535              9540

Leu Tyr  Lys Met Pro Ser Gly  Ala Thr Pro Glu Val  Ser Arg Thr
    9545              9550              9555

Glu Val  Met Pro Ser Ser Arg  Thr Ser Ile Pro Gly  Pro Ala Gln
    9560              9565              9570

Ser Thr  Met Ser Leu Asp Ile  Ser Asp Glu Val Val  Thr Arg Leu
    9575              9580              9585

Ser Thr  Ser Pro Ile Met Thr  Glu Ser Ala Glu Ile  Thr Ile Thr
    9590              9595              9600

Thr Gln  Thr Gly Tyr Ser Leu  Ala Thr Ser Gln Val  Thr Leu Pro
    9605              9610              9615

Leu Gly  Thr Ser Met Thr Phe  Leu Ser Gly Thr His  Ser Thr Met
    9620              9625              9630

Ser Gln  Gly Leu Ser His Ser  Glu Met Thr Asn Leu  Met Ser Arg
    9635              9640              9645

Gly Pro  Glu Ser Leu Ser Trp  Thr Ser Pro Arg Phe  Val Glu Thr
    9650              9655              9660

Thr Arg  Ser Ser Ser Ser Leu  Thr Ser Leu Pro Leu  Thr Thr Ser
    9665              9670              9675

Leu Ser  Pro Val Ser Ser Thr  Leu Leu Asp Ser Ser  Pro Ser Ser
    9680              9685              9690

Pro Leu  Pro Val Thr Ser Leu  Ile Leu Pro Gly Leu  Val Lys Thr
    9695              9700              9705

Thr Glu  Val Leu Asp Thr Ser  Ser Glu Pro Lys Thr  Ser Ser Ser
    9710              9715              9720

Pro Asn  Leu Ser Ser Thr Ser  Val Glu Ile Pro Ala  Thr Ser Glu
    9725              9730              9735

Ile Met  Thr Asp Thr Glu Lys  Ile His Pro Ser Ser  Asn Thr Ala
    9740              9745              9750

Val Ala  Lys Val Arg Thr Ser  Ser Ser Val His Glu  Ser His Ser
    9755              9760              9765

Ser Val  Leu Ala Asp Ser Glu  Thr Thr Ile Thr Ile  Pro Ser Met
```

-continued

```
      9770                9775                9780

Gly Ile  Thr Ser Ala Val Asp  Asp Thr Thr Val Phe  Thr Ser Asn
  9785                9790                9795

Pro Ala  Phe Ser Glu Thr Arg  Arg Ile Pro Thr Glu  Pro Thr Phe
  9800                9805                9810

Ser Leu  Thr Pro Gly Phe Arg  Glu Thr Ser Thr Ser  Glu Glu Thr
  9815                9820                9825

Thr Ser  Ile Thr Glu Thr Ser  Ala Val Leu Tyr Gly  Val Pro Thr
  9830                9835                9840

Ser Ala  Thr Thr Glu Val Ser  Met Thr Glu Ile Met  Ser Ser Asn
  9845                9850                9855

Arg Ile  His Ile Pro Asp Ser  Asp Gln Ser Thr Met  Ser Pro Asp
  9860                9865                9870

Ile Ile  Thr Glu Val Ile Thr  Arg Leu Ser Ser Ser  Ser Met Met
  9875                9880                9885

Ser Glu  Ser Thr Gln Met Thr  Ile Thr Thr Gln Lys  Ser Ser Pro
  9890                9895                9900

Gly Ala  Thr Ala Gln Ser Thr  Leu Thr Leu Ala Thr  Thr Thr Ala
  9905                9910                9915

Pro Leu  Ala Arg Thr His Ser  Thr Val Pro Pro Arg  Phe Leu His
  9920                9925                9930

Ser Glu  Met Thr Thr Leu Met  Ser Arg Ser Pro Glu  Asn Pro Ser
  9935                9940                9945

Trp Lys  Ser Ser Leu Phe Val  Glu Lys Thr Ser Ser  Ser Ser Ser
  9950                9955                9960

Leu Leu  Ser Leu Pro Val Thr  Thr Ser Pro Ser Val  Ser Ser Thr
  9965                9970                9975

Leu Pro  Gln Ser Ile Pro Ser  Ser Ser Phe Ser Val  Thr Ser Leu
  9980                9985                9990

Leu Thr  Pro Gly Met Val Lys   Thr Thr Asp Thr Ser   Thr Glu Pro
  9995                10000                 10005

Gly Thr   Ser Leu Ser Pro Asn   Leu Ser Gly Thr Ser   Val Glu Ile
  10010                10015                 10020

Leu Ala   Ala Ser Glu Val Thr   Thr Asp Thr Glu Lys   Ile His Pro
  10025                10030                 10035

Ser Ser   Ser Met Ala Val Thr   Asn Val Gly Thr Thr   Ser Ser Gly
  10040                10045                 10050

His Glu   Leu Tyr Ser Ser Val   Ser Ile His Ser Glu   Pro Ser Lys
  10055                10060                 10065

Ala Thr   Tyr Pro Val Gly Thr   Pro Ser Ser Met Ala   Glu Thr Ser
  10070                10075                 10080

Ile Ser   Thr Ser Met Pro Ala   Asn Phe Glu Thr Thr   Gly Phe Glu
  10085                10090                 10095

Ala Glu   Pro Phe Ser His Leu   Thr Ser Gly Phe Arg   Lys Thr Asn
  10100                10105                 10110

Met Ser   Leu Asp Thr Ser Ser   Val Thr Pro Thr Asn   Thr Pro Ser
  10115                10120                 10125

Ser Pro   Gly Ser Thr His Leu   Leu Gln Ser Ser Lys   Thr Asp Phe
  10130                10135                 10140

Thr Ser   Ser Ala Lys Thr Ser   Ser Pro Asp Trp Pro   Pro Ala Ser
  10145                10150                 10155

Gln Tyr   Thr Glu Ile Pro Val   Asp Ile Ile Thr Pro   Phe Asn Ala
  10160                10165                 10170
```

-continued

```
Ser Pro   Ser Ile Thr Glu Ser   Thr Gly Ile Thr Ser   Phe Pro Glu
    10175             10180                10185

Ser Arg   Phe Thr Met Ser Val   Thr Glu Ser Thr His   His Leu Ser
    10190             10195                10200

Thr Asp   Leu Leu Pro Ser Ala   Glu Thr Ile Ser Thr   Gly Thr Val
    10205             10210                10215

Met Pro   Ser Leu Ser Glu Ala   Met Thr Ser Phe Ala   Thr Thr Gly
    10220             10225                10230

Val Pro   Arg Ala Ile Ser Gly   Ser Gly Ser Pro Phe   Ser Arg Thr
    10235             10240                10245

Glu Ser   Gly Pro Gly Asp Ala   Thr Leu Ser Thr Ile   Ala Glu Ser
    10250             10255                10260

Leu Pro   Ser Ser Thr Pro Val   Pro Phe Ser Ser Ser   Thr Phe Thr
    10265             10270                10275

Thr Thr   Asp Ser Ser Thr Ile   Pro Ala Leu His Glu   Ile Thr Ser
    10280             10285                10290

Ser Ser   Ala Thr Pro Tyr Arg   Val Asp Thr Ser Leu   Gly Thr Glu
    10295             10300                10305

Ser Ser   Thr Thr Glu Gly Arg   Leu Val Met Val Ser   Thr Leu Asp
    10310             10315                10320

Thr Ser   Ser Gln Pro Gly Arg   Thr Ser Ser Ser Pro   Ile Leu Asp
    10325             10330                10335

Thr Arg   Met Thr Glu Ser Val   Glu Leu Gly Thr Val   Thr Ser Ala
    10340             10345                10350

Tyr Gln   Val Pro Ser Leu Ser   Thr Arg Leu Thr Arg   Thr Asp Gly
    10355             10360                10365

Ile Met   Glu His Ile Thr Lys   Ile Pro Asn Glu Ala   Ala His Arg
    10370             10375                10380

Gly Thr   Ile Arg Pro Val Lys   Gly Pro Gln Thr Ser   Thr Ser Pro
    10385             10390                10395

Ala Ser   Pro Lys Gly Leu His   Thr Gly Gly Thr Lys   Arg Met Glu
    10400             10405                10410

Thr Thr   Thr Thr Ala Leu Lys   Thr Thr Thr Thr Ala   Leu Lys Thr
    10415             10420                10425

Thr Ser   Arg Ala Thr Leu Thr   Thr Ser Val Tyr Thr   Pro Thr Leu
    10430             10435                10440

Gly Thr   Leu Thr Pro Leu Asn   Ala Ser Met Gln Met   Ala Ser Thr
    10445             10450                10455

Ile Pro   Thr Glu Met Met Ile   Thr Thr Pro Tyr Val   Phe Pro Asp
    10460             10465                10470

Val Pro   Glu Thr Thr Ser Ser   Leu Ala Thr Ser Leu   Gly Ala Glu
    10475             10480                10485

Thr Ser   Thr Ala Leu Pro Arg   Thr Thr Pro Ser Val   Phe Asn Arg
    10490             10495                10500

Glu Ser   Glu Thr Thr Ala Ser   Leu Val Ser Arg Ser   Gly Ala Glu
    10505             10510                10515

Arg Ser   Pro Val Ile Gln Thr   Leu Asp Val Ser Ser   Ser Glu Pro
    10520             10525                10530

Asp Thr   Thr Ala Ser Trp Val   Ile His Pro Ala Glu   Thr Ile Pro
    10535             10540                10545

Thr Val   Ser Lys Thr Thr Pro   Asn Phe Phe His Ser   Glu Leu Asp
    10550             10555                10560
```

-continued

```
Thr Val   Ser Ser Thr Ala Thr   Ser His Gly Ala Asp   Val Ser Ser
    10565             10570                 10575

Ala Ile   Pro Thr Asn Ile Ser   Pro Ser Glu Leu Asp   Ala Leu Thr
    10580             10585                 10590

Pro Leu   Val Thr Ile Ser Gly   Thr Asp Thr Ser Thr   Thr Phe Pro
    10595             10600                 10605

Thr Leu   Thr Lys Ser Pro His   Glu Thr Glu Thr Arg   Thr Thr Trp
    10610             10615                 10620

Leu Thr   His Pro Ala Glu Thr   Ser Ser Thr Ile Pro   Arg Thr Ile
    10625             10630                 10635

Pro Asn   Phe Ser His His Glu   Ser Asp Ala Thr Pro   Ser Ile Ala
    10640             10645                 10650

Thr Ser   Pro Gly Ala Glu Thr   Ser Ser Ala Ile Pro   Ile Met Thr
    10655             10660                 10665

Val Ser   Pro Gly Ala Glu Asp   Leu Val Thr Ser Gln   Val Thr Ser
    10670             10675                 10680

Ser Gly   Thr Asp Arg Asn Met   Thr Ile Pro Thr Leu   Thr Leu Ser
    10685             10690                 10695

Pro Gly   Glu Pro Lys Thr Ile   Ala Ser Leu Val Thr   His Pro Glu
    10700             10705                 10710

Ala Gln   Thr Ser Ser Ala Ile   Pro Thr Ser Thr Ile   Ser Pro Ala
    10715             10720                 10725

Val Ser   Arg Leu Val Thr Ser   Met Val Thr Ser Leu   Ala Ala Lys
    10730             10735                 10740

Thr Ser   Thr Thr Asn Arg Ala   Leu Thr Asn Ser Pro   Gly Glu Pro
    10745             10750                 10755

Ala Thr   Thr Val Ser Leu Val   Thr His Pro Ala Gln   Thr Ser Pro
    10760             10765                 10770

Thr Val   Pro Trp Thr Thr Ser   Ile Phe Phe His Ser   Lys Ser Asp
    10775             10780                 10785

Thr Thr   Pro Ser Met Thr Thr   Ser His Gly Ala Glu   Ser Ser Ser
    10790             10795                 10800

Ala Val   Pro Thr Pro Thr Val   Ser Thr Glu Val Pro   Gly Val Val
    10805             10810                 10815

Thr Pro   Leu Val Thr Ser Ser   Arg Ala Val Ile Ser   Thr Thr Ile
    10820             10825                 10830

Pro Ile   Leu Thr Leu Ser Pro   Gly Glu Pro Glu Thr   Thr Pro Ser
    10835             10840                 10845

Met Ala   Thr Ser His Gly Glu   Glu Ala Ser Ser Ala   Ile Pro Thr
    10850             10855                 10860

Pro Thr   Val Ser Pro Gly Val   Pro Gly Val Val Thr   Ser Leu Val
    10865             10870                 10875

Thr Ser   Ser Arg Ala Val Thr   Ser Thr Thr Ile Pro   Ile Leu Thr
    10880             10885                 10890

Phe Ser   Leu Gly Glu Pro Glu   Thr Thr Pro Ser Met   Ala Thr Ser
    10895             10900                 10905

His Gly   Thr Glu Ala Gly Ser   Ala Val Pro Thr Val   Leu Pro Glu
    10910             10915                 10920

Val Pro   Gly Met Val Thr Ser   Leu Val Ala Ser Ser   Arg Ala Val
    10925             10930                 10935

Thr Ser   Thr Thr Leu Pro Thr   Leu Thr Leu Ser Pro   Gly Glu Pro
    10940             10945                 10950

Glu Thr   Thr Pro Ser Met Ala   Thr Ser His Gly Ala   Glu Ala Ser
```

-continued

```
     10955              10960              10965

Ser Thr  Val Pro Thr Val Ser  Pro Glu Val Pro Gly  Val Val Thr
     10970              10975              10980

Ser Leu  Val Thr Ser Ser Ser  Gly Val Asn Ser Thr  Ser Ile Pro
     10985              10990              10995

Thr Leu  Ile Leu Ser Pro Gly  Glu Leu Glu Thr Thr  Pro Ser Met
     11000              11005              11010

Ala Thr  Ser His Gly Ala Glu  Ala Ser Ser Ala Val  Pro Thr Pro
     11015              11020              11025

Thr Val  Ser Pro Gly Val Ser  Gly Val Val Thr Pro  Leu Val Thr
     11030              11035              11040

Ser Ser  Arg Ala Val Thr Ser  Thr Thr Ile Pro Ile  Leu Thr Leu
     11045              11050              11055

Ser Ser  Ser Glu Pro Glu Thr  Thr Pro Ser Met Ala  Thr Ser His
     11060              11065              11070

Gly Val  Glu Ala Ser Ser Ala  Val Leu Thr Val Ser  Pro Glu Val
     11075              11080              11085

Pro Gly  Met Val Thr Ser Leu  Val Thr Ser Ser Arg  Ala Val Thr
     11090              11095              11100

Ser Thr  Thr Ile Pro Thr Leu  Thr Ile Ser Ser Asp  Glu Pro Glu
     11105              11110              11115

Thr Thr  Thr Ser Leu Val Thr  His Ser Glu Ala Lys  Met Ile Ser
     11120              11125              11130

Ala Ile  Pro Thr Leu Ala Val  Ser Pro Thr Val Gln  Gly Leu Val
     11135              11140              11145

Thr Ser  Leu Val Thr Ser Ser  Gly Ser Glu Thr Ser  Ala Phe Ser
     11150              11155              11160

Asn Leu  Thr Val Ala Ser Ser  Gln Pro Glu Thr Ile  Asp Ser Trp
     11165              11170              11175

Val Ala  His Pro Gly Thr Glu  Ala Ser Ser Val Val  Pro Thr Leu
     11180              11185              11190

Thr Val  Ser Thr Gly Glu Pro  Phe Thr Asn Ile Ser  Leu Val Thr
     11195              11200              11205

His Pro  Ala Glu Ser Ser Ser  Thr Leu Pro Arg Thr  Thr Ser Arg
     11210              11215              11220

Phe Ser  His Ser Glu Leu Asp  Thr Met Pro Ser Thr  Val Thr Ser
     11225              11230              11235

Pro Glu  Ala Glu Ser Ser Ser  Ala Ile Ser Thr Thr  Ile Ser Pro
     11240              11245              11250

Gly Ile  Pro Gly Val Leu Thr  Ser Leu Val Thr Ser  Ser Gly Arg
     11255              11260              11265

Asp Ile  Ser Ala Thr Phe Pro  Thr Val Pro Glu Ser  Pro His Glu
     11270              11275              11280

Ser Glu  Ala Thr Ala Ser Trp  Val Thr His Pro Ala  Val Thr Ser
     11285              11290              11295

Thr Thr  Val Pro Arg Thr Thr  Pro Asn Tyr Ser His  Ser Glu Pro
     11300              11305              11310

Asp Thr  Thr Pro Ser Ile Ala  Thr Ser Pro Gly Ala  Glu Ala Thr
     11315              11320              11325

Ser Asp  Phe Pro Thr Ile Thr  Val Ser Pro Asp Val  Pro Asp Met
     11330              11335              11340

Val Thr  Ser Gln Val Thr Ser  Ser Gly Thr Asp Thr  Ser Ile Thr
     11345              11350              11355
```

-continued

```
Ile Pro   Thr Leu Thr Leu Ser   Ser Gly Glu Pro Glu   Thr Thr Thr
    11360             11365               11370

Ser Phe   Ile Thr Tyr Ser Glu   Thr His Thr Ser Ser   Ala Ile Pro
    11375             11380               11385

Thr Leu   Pro Val Ser Pro Gly   Ala Ser Lys Met Leu   Thr Ser Leu
    11390             11395               11400

Val Ile   Ser Ser Gly Thr Asp   Ser Thr Thr Thr Phe   Pro Thr Leu
    11405             11410               11415

Thr Glu   Thr Pro Tyr Glu Pro   Glu Thr Thr Ala Ile   Gln Leu Ile
    11420             11425               11430

His Pro   Ala Glu Thr Asn Thr   Met Val Pro Arg Thr   Thr Pro Lys
    11435             11440               11445

Phe Ser   His Ser Lys Ser Asp   Thr Thr Leu Pro Val   Ala Ile Thr
    11450             11455               11460

Ser Pro   Gly Pro Glu Ala Ser   Ser Ala Val Ser Thr   Thr Thr Ile
    11465             11470               11475

Ser Pro   Asp Met Ser Asp Leu   Val Thr Ser Leu Val   Pro Ser Ser
    11480             11485               11490

Gly Thr   Asp Thr Ser Thr Thr   Phe Pro Thr Leu Ser   Glu Thr Pro
    11495             11500               11505

Tyr Glu   Pro Glu Thr Thr Ala   Thr Trp Leu Thr His   Pro Ala Glu
    11510             11515               11520

Thr Ser   Thr Thr Val Ser Gly   Thr Ile Pro Asn Phe   Ser His Arg
    11525             11530               11535

Gly Ser   Asp Thr Ala Pro Ser   Met Val Thr Ser Pro   Gly Val Asp
    11540             11545               11550

Thr Arg   Ser Gly Val Pro Thr   Thr Thr Ile Pro Pro   Ser Ile Pro
    11555             11560               11565

Gly Val   Val Thr Ser Gln Val   Thr Ser Ser Ala Thr   Asp Thr Ser
    11570             11575               11580

Thr Ala   Ile Pro Thr Leu Thr   Pro Ser Pro Gly Glu   Pro Glu Thr
    11585             11590               11595

Thr Ala   Ser Ser Ala Thr His   Pro Gly Thr Gln Thr   Gly Phe Thr
    11600             11605               11610

Val Pro   Ile Arg Thr Val Pro   Ser Ser Glu Pro Asp   Thr Met Ala
    11615             11620               11625

Ser Trp   Val Thr His Pro Pro   Gln Thr Ser Thr Pro   Val Ser Arg
    11630             11635               11640

Thr Thr   Ser Ser Phe Ser His   Ser Ser Pro Asp Ala   Thr Pro Val
    11645             11650               11655

Met Ala   Thr Ser Pro Arg Thr   Glu Ala Ser Ser Ala   Val Leu Thr
    11660             11665               11670

Thr Ile   Ser Pro Gly Ala Pro   Glu Met Val Thr Ser   Gln Ile Thr
    11675             11680               11685

Ser Ser   Gly Ala Ala Thr Ser   Thr Thr Val Pro Thr   Leu Thr His
    11690             11695               11700

Ser Pro   Gly Met Pro Glu Thr   Thr Ala Leu Leu Ser   Thr His Pro
    11705             11710               11715

Arg Thr   Glu Thr Ser Lys Thr   Phe Pro Ala Ser Thr   Val Phe Pro
    11720             11725               11730

Gln Val   Ser Glu Thr Thr Ala   Ser Leu Thr Ile Arg   Pro Gly Ala
    11735             11740               11745
```

-continued

```
Glu Thr  Ser Thr Ala Leu Pro  Thr Gln Thr Thr Ser  Ser Leu Phe
    11750             11755             11760

Thr Leu  Leu Val Thr Gly Thr  Ser Arg Val Asp Leu  Ser Pro Thr
    11765             11770             11775

Ala Ser  Pro Gly Val Ser Ala  Lys Thr Ala Pro Leu  Ser Thr His
    11780             11785             11790

Pro Gly  Thr Glu Thr Ser Thr  Met Ile Pro Thr Ser  Thr Leu Ser
    11795             11800             11805

Leu Gly  Leu Leu Glu Thr Thr  Gly Leu Leu Ala Thr  Ser Ser Ser
    11810             11815             11820

Ala Glu  Thr Ser Thr Ser Thr  Leu Thr Leu Thr Val  Ser Pro Ala
    11825             11830             11835

Val Ser  Gly Leu Ser Ser Ala  Ser Ile Thr Thr Asp  Lys Pro Gln
    11840             11845             11850

Thr Val  Thr Ser Trp Asn Thr  Glu Thr Ser Pro Ser  Val Thr Ser
    11855             11860             11865

Val Gly  Pro Pro Glu Phe Ser  Arg Thr Val Thr Gly  Thr Thr Met
    11870             11875             11880

Thr Leu  Ile Pro Ser Glu Met  Pro Thr Pro Pro Lys  Thr Ser His
    11885             11890             11895

Gly Glu  Gly Val Ser Pro Thr  Thr Ile Leu Arg Thr  Thr Met Val
    11900             11905             11910

Glu Ala  Thr Asn Leu Ala Thr  Thr Gly Ser Ser Pro  Thr Val Ala
    11915             11920             11925

Lys Thr  Thr Thr Thr Phe Asn  Thr Leu Ala Gly Ser  Leu Phe Thr
    11930             11935             11940

Pro Leu  Thr Thr Pro Gly Met  Ser Thr Leu Ala Ser  Glu Ser Val
    11945             11950             11955

Thr Ser  Arg Thr Ser Tyr Asn  His Arg Ser Trp Ile  Ser Thr Thr
    11960             11965             11970

Ser Ser  Tyr Asn Arg Arg Tyr  Trp Thr Pro Ala Thr  Ser Thr Pro
    11975             11980             11985

Val Thr  Ser Thr Phe Ser Pro  Gly Ile Ser Thr Ser  Ser Ile Pro
    11990             11995             12000

Ser Ser  Thr Ala Ala Thr Val  Pro Phe Met Val Pro  Phe Thr Leu
    12005             12010             12015

Asn Phe  Thr Ile Thr Asn Leu  Gln Tyr Glu Glu Asp  Met Arg His
    12020             12025             12030

Pro Gly  Ser Arg Lys Phe Asn  Ala Thr Glu Arg Glu  Leu Gln Gly
    12035             12040             12045

Leu Leu  Lys Pro Leu Phe Arg  Asn Ser Ser Leu Glu  Tyr Leu Tyr
    12050             12055             12060

Ser Gly  Cys Arg Leu Ala Ser  Leu Arg Pro Glu Lys  Asp Ser Ser
    12065             12070             12075

Ala Thr  Ala Val Asp Ala Ile  Cys Thr His Arg Pro  Asp Pro Glu
    12080             12085             12090

Asp Leu  Gly Leu Asp Arg Glu  Arg Leu Tyr Trp Glu  Leu Ser Asn
    12095             12100             12105

Leu Thr  Asn Gly Ile Gln Glu  Leu Gly Pro Tyr Thr  Leu Asp Arg
    12110             12115             12120

Asn Ser  Leu Tyr Val Asn Gly  Phe Thr His Arg Ser  Ser Met Pro
    12125             12130             12135

Thr Thr  Ser Thr Pro Gly Thr  Ser Thr Val Asp Val  Gly Thr Ser
```

```
     12140                    12145                    12150

Gly Thr  Pro Ser Ser Ser Pro  Ser Pro Thr Thr Ala  Gly Pro Leu
     12155                    12160                    12165

Leu Met  Pro Phe Thr Leu Asn  Phe Thr Ile Thr Asn  Leu Gln Tyr
     12170                    12175                    12180

Glu Glu  Asp Met Arg Arg Thr  Gly Ser Arg Lys Phe  Asn Thr Met
     12185                    12190                    12195

Glu Ser  Val Leu Gln Gly Leu  Leu Lys Pro Leu Phe  Lys Asn Thr
     12200                    12205                    12210

Ser Val  Gly Pro Leu Tyr Ser  Gly Cys Arg Leu Thr  Leu Leu Arg
     12215                    12220                    12225

Pro Glu  Lys Asp Gly Ala Ala  Thr Gly Val Asp Ala  Ile Cys Thr
     12230                    12235                    12240

His Arg  Leu Asp Pro Lys Ser  Pro Gly Leu Asn Arg  Glu Gln Leu
     12245                    12250                    12255

Tyr Trp  Glu Leu Ser Lys Leu  Thr Asn Asp Ile Glu  Glu Leu Gly
     12260                    12265                    12270

Pro Tyr  Thr Leu Asp Arg Asn  Ser Leu Tyr Val Asn  Gly Phe Thr
     12275                    12280                    12285

His Gln  Ser Ser Val Ser Thr  Thr Ser Thr Pro Gly  Thr Ser Thr
     12290                    12295                    12300

Val Asp  Leu Arg Thr Ser Gly  Thr Pro Ser Ser Leu  Ser Ser Pro
     12305                    12310                    12315

Thr Ile  Met Ala Ala Gly Pro  Leu Leu Val Pro Phe  Thr Leu Asn
     12320                    12325                    12330

Phe Thr  Ile Thr Asn Leu Gln  Tyr Gly Glu Asp Met  Gly His Pro
     12335                    12340                    12345

Gly Ser  Arg Lys Phe Asn Thr  Thr Glu Arg Val Leu  Gln Gly Leu
     12350                    12355                    12360

Leu Gly  Pro Ile Phe Lys Asn  Thr Ser Val Gly Pro  Leu Tyr Ser
     12365                    12370                    12375

Gly Cys  Arg Leu Thr Ser Leu  Arg Ser Glu Lys Asp  Gly Ala Ala
     12380                    12385                    12390

Thr Gly  Val Asp Ala Ile Cys  Ile His His Leu Asp  Pro Lys Ser
     12395                    12400                    12405

Pro Gly  Leu Asn Arg Glu Arg  Leu Tyr Trp Glu Leu  Ser Gln Leu
     12410                    12415                    12420

Thr Asn  Gly Ile Lys Glu Leu  Gly Pro Tyr Thr Leu  Asp Arg Asn
     12425                    12430                    12435

Ser Leu  Tyr Val Asn Gly Phe  Thr His Arg Thr Ser  Val Pro Thr
     12440                    12445                    12450

Ser Ser  Thr Pro Gly Thr Ser  Thr Val Asp Leu Gly  Thr Ser Gly
     12455                    12460                    12465

Thr Pro  Phe Ser Leu Pro Ser  Pro Ala Thr Ala Gly  Pro Leu Leu
     12470                    12475                    12480

Val Leu  Phe Thr Leu Asn Phe  Thr Ile Thr Asn Leu  Lys Tyr Glu
     12485                    12490                    12495

Glu Asp  Met His Arg Pro Gly  Ser Arg Lys Phe Asn  Thr Thr Glu
     12500                    12505                    12510

Arg Val  Leu Gln Thr Leu Leu  Gly Pro Met Phe Lys  Asn Thr Ser
     12515                    12520                    12525

Val Gly  Leu Leu Tyr Ser Gly  Cys Arg Leu Thr Leu  Leu Arg Ser
     12530                    12535                    12540
```

Glu Lys Asp Gly Ala Ala Thr   Gly Val Asp Ala Ile   Cys Thr His
    12545              12550             12555

Arg Leu Asp Pro Lys Ser Pro   Gly Val Asp Arg Glu   Gln Leu Tyr
    12560              12565             12570

Trp Glu Leu Ser Gln Leu Thr   Asn Gly Ile Lys Glu   Leu Gly Pro
    12575              12580             12585

Tyr Thr Leu Asp Arg Asn Ser   Leu Tyr Val Asn Gly   Phe Thr His
    12590              12595             12600

Trp Ile Pro Val Pro Thr Ser   Ser Thr Pro Gly Thr   Ser Thr Val
    12605              12610             12615

Asp Leu Gly Ser Gly Thr Pro   Ser Ser Leu Pro Ser   Pro Thr Thr
    12620              12625             12630

Ala Gly Pro Leu Leu Val Pro   Phe Thr Leu Asn Phe   Thr Ile Thr
    12635              12640             12645

Asn Leu Lys Tyr Glu Glu Asp   Met His Cys Pro Gly   Ser Arg Lys
    12650              12655             12660

Phe Asn Thr Thr Glu Arg Val   Leu Gln Ser Leu Leu   Gly Pro Met
    12665              12670             12675

Phe Lys Asn Thr Ser Val Gly   Pro Leu Tyr Ser Gly   Cys Arg Leu
    12680              12685             12690

Thr Leu Leu Arg Ser Glu Lys   Asp Gly Ala Ala Thr   Gly Val Asp
    12695              12700             12705

Ala Ile Cys Thr His Arg Leu   Asp Pro Lys Ser Pro   Gly Val Asp
    12710              12715             12720

Arg Glu Gln Leu Tyr Trp Glu   Leu Ser Gln Leu Thr   Asn Gly Ile
    12725              12730             12735

Lys Glu Leu Gly Pro Tyr Thr   Leu Asp Arg Asn Ser   Leu Tyr Val
    12740              12745             12750

Asn Gly Phe Thr His Gln Thr   Ser Ala Pro Asn Thr   Ser Thr Pro
    12755              12760             12765

Gly Thr Ser Thr Val Asp Leu   Gly Thr Ser Gly Thr   Pro Ser Ser
    12770              12775             12780

Leu Pro Ser Pro Thr Ser Ala   Gly Pro Leu Leu Val   Pro Phe Thr
    12785              12790             12795

Leu Asn Phe Thr Ile Thr Asn   Leu Gln Tyr Glu Glu   Asp Met His
    12800              12805             12810

His Pro Gly Ser Arg Lys Phe   Asn Thr Thr Glu Arg   Val Leu Gln
    12815              12820             12825

Gly Leu Leu Gly Pro Met Phe   Lys Asn Thr Ser Val   Gly Leu Leu
    12830              12835             12840

Tyr Ser Gly Cys Arg Leu Thr   Leu Leu Arg Pro Glu   Lys Asn Gly
    12845              12850             12855

Ala Ala Thr Gly Met Asp Ala   Ile Cys Ser His Arg   Leu Asp Pro
    12860              12865             12870

Lys Ser Pro Gly Leu Asn Arg   Glu Gln Leu Tyr Trp   Glu Leu Ser
    12875              12880             12885

Gln Leu Thr His Gly Ile Lys   Glu Leu Gly Pro Tyr   Thr Leu Asp
    12890              12895             12900

Arg Asn Ser Leu Tyr Val Asn   Gly Phe Thr His Arg   Ser Ser Val
    12905              12910             12915

Ala Pro Thr Ser Thr Pro Gly   Thr Ser Thr Val Asp   Leu Gly Thr
    12920              12925             12930

-continued

```
Ser Gly  Thr Pro Ser Ser Leu  Pro Ser Pro Thr Thr  Ala Val Pro
    12935              12940              12945

Leu Leu  Val Pro Phe Thr Leu  Asn Phe Thr Ile Thr  Asn Leu Gln
    12950              12955              12960

Tyr Gly  Glu Asp Met Arg His  Pro Gly Ser Arg Lys  Phe Asn Thr
    12965              12970              12975

Thr Glu  Arg Val Leu Gln Gly  Leu Leu Gly Pro Leu  Phe Lys Asn
    12980              12985              12990

Ser Ser  Val Gly Pro Leu Tyr  Ser Gly Cys Arg Leu  Ile Ser Leu
    12995              13000              13005

Arg Ser  Glu Lys Asp Gly Ala  Ala Thr Gly Val Asp  Ala Ile Cys
    13010              13015              13020

Thr His  His Leu Asn Pro Gln  Ser Pro Gly Leu Asp  Arg Glu Gln
    13025              13030              13035

Leu Tyr  Trp Gln Leu Ser Gln  Met Thr Asn Gly Ile  Lys Glu Leu
    13040              13045              13050

Gly Pro  Tyr Thr Leu Asp Arg  Asn Ser Leu Tyr Val  Asn Gly Phe
    13055              13060              13065

Thr His  Arg Ser Ser Gly Leu  Thr Thr Ser Thr Pro  Trp Thr Ser
    13070              13075              13080

Thr Val  Asp Leu Gly Thr Ser  Gly Thr Pro Ser Pro  Val Pro Ser
    13085              13090              13095

Pro Thr  Thr Thr Gly Pro Leu  Leu Val Pro Phe Thr  Leu Asn Phe
    13100              13105              13110

Thr Ile  Thr Asn Leu Gln Tyr  Glu Glu Asn Met Gly  His Pro Gly
    13115              13120              13125

Ser Arg  Lys Phe Asn Ile Thr  Glu Ser Val Leu Gln  Gly Leu Leu
    13130              13135              13140

Lys Pro  Leu Phe Lys Ser Thr  Ser Val Gly Pro Leu  Tyr Ser Gly
    13145              13150              13155

Cys Arg  Leu Thr Leu Leu Arg  Pro Glu Lys Asp Gly  Val Ala Thr
    13160              13165              13170

Arg Val  Asp Ala Ile Cys Thr  His Arg Pro Asp Pro  Lys Ile Pro
    13175              13180              13185

Gly Leu  Asp Arg Gln Gln Leu  Tyr Trp Glu Leu Ser  Gln Leu Thr
    13190              13195              13200

His Ser  Ile Thr Glu Leu Gly  Pro Tyr Thr Leu Asp  Arg Asp Ser
    13205              13210              13215

Leu Tyr  Val Asn Gly Phe Thr  Gln Arg Ser Ser Val  Pro Thr Thr
    13220              13225              13230

Ser Thr  Pro Gly Thr Phe Thr  Val Gln Pro Glu Thr  Ser Glu Thr
    13235              13240              13245

Pro Ser  Ser Leu Pro Gly Pro  Thr Ala Thr Gly Pro  Val Leu Leu
    13250              13255              13260

Pro Phe  Thr Leu Asn Phe Thr  Ile Thr Asn Leu Gln  Tyr Glu Glu
    13265              13270              13275

Asp Met  Arg Arg Pro Gly Ser  Arg Lys Phe Asn Thr  Thr Glu Arg
    13280              13285              13290

Val Leu  Gln Gly Leu Leu Met  Pro Leu Phe Lys Asn  Thr Ser Val
    13295              13300              13305

Ser Ser  Leu Tyr Ser Gly Cys  Arg Leu Thr Leu Leu  Arg Pro Glu
    13310              13315              13320

Lys Asp  Gly Ala Ala Thr Arg  Val Asp Ala Val Cys  Thr His Arg
```

-continued

```
      13325                13330                13335

Pro Asp  Pro Lys Ser Pro Gly  Leu Asp Arg Glu Arg  Leu Tyr Trp
    13340                13345                13350

Lys Leu  Ser Gln Leu Thr His  Gly Ile Thr Glu Leu  Gly Pro Tyr
    13355                13360                13365

Thr Leu  Asp Arg His Ser Leu  Tyr Val Asn Gly Phe  Thr His Gln
    13370                13375                13380

Ser Ser  Met Thr Thr Thr Arg  Thr Pro Asp Thr Ser  Thr Met His
    13385                13390                13395

Leu Ala  Thr Ser Arg Thr Pro  Ala Ser Leu Ser Gly  Pro Met Thr
    13400                13405                13410

Ala Ser  Pro Leu Leu Val Leu  Phe Thr Ile Asn Phe  Thr Ile Thr
    13415                13420                13425

Asn Leu  Arg Tyr Glu Glu Asn  Met His His Pro Gly  Ser Arg Lys
    13430                13435                13440

Phe Asn  Thr Thr Glu Arg Val  Leu Gln Gly Leu Leu  Arg Pro Val
    13445                13450                13455

Phe Lys  Asn Thr Ser Val Gly  Pro Leu Tyr Ser Gly  Cys Arg Leu
    13460                13465                13470

Thr Leu  Leu Arg Pro Lys Lys  Asp Gly Ala Ala Thr  Lys Val Asp
    13475                13480                13485

Ala Ile  Cys Thr Tyr Arg Pro  Asp Pro Lys Ser Pro  Gly Leu Asp
    13490                13495                13500

Arg Glu  Gln Leu Tyr Trp Glu  Leu Ser Gln Leu Thr  His Ser Ile
    13505                13510                13515

Thr Glu  Leu Gly Pro Tyr Thr  Leu Asp Arg Asp Ser  Leu Tyr Val
    13520                13525                13530

Asn Gly  Phe Thr Gln Arg Ser  Ser Val Pro Thr Thr  Ser Ile Pro
    13535                13540                13545

Gly Thr  Pro Thr Val Asp Leu  Gly Thr Ser Gly Thr  Pro Val Ser
    13550                13555                13560

Lys Pro  Gly Pro Ser Ala Ala  Ser Pro Leu Leu Val  Leu Phe Thr
    13565                13570                13575

Leu Asn  Phe Thr Ile Thr Asn  Leu Arg Tyr Glu Glu  Asn Met Gln
    13580                13585                13590

His Pro  Gly Ser Arg Lys Phe  Asn Thr Thr Glu Arg  Val Leu Gln
    13595                13600                13605

Gly Leu  Leu Arg Ser Leu Phe  Lys Ser Thr Ser Val  Gly Pro Leu
    13610                13615                13620

Tyr Ser  Gly Cys Arg Leu Thr  Leu Leu Arg Pro Glu  Lys Asp Gly
    13625                13630                13635

Thr Ala  Thr Gly Val Asp Ala  Ile Cys Thr His His  Pro Asp Pro
    13640                13645                13650

Lys Ser  Pro Arg Leu Asp Arg  Glu Gln Leu Tyr Trp  Glu Leu Ser
    13655                13660                13665

Gln Leu  Thr His Asn Ile Thr  Glu Leu Gly Pro Tyr  Ala Leu Asp
    13670                13675                13680

Asn Asp  Ser Leu Phe Val Asn  Gly Phe Thr His Arg  Ser Ser Val
    13685                13690                13695

Ser Thr  Thr Ser Thr Pro Gly  Thr Pro Thr Val Tyr  Leu Gly Ala
    13700                13705                13710

Ser Lys  Thr Pro Ala Ser Ile  Phe Gly Pro Ser Ala  Ala Ser His
    13715                13720                13725
```

Leu Leu  Ile Leu Phe Thr Leu  Asn Phe Thr Ile Thr  Asn Leu Arg
    13730             13735             13740

Tyr Glu  Glu Asn Met Trp Pro  Gly Ser Arg Lys Phe  Asn Thr Thr
    13745             13750             13755

Glu Arg  Val Leu Gln Gly Leu  Leu Arg Pro Leu Phe  Lys Asn Thr
    13760             13765             13770

Ser Val  Gly Pro Leu Tyr Ser  Gly Cys Arg Leu Thr  Leu Leu Arg
    13775             13780             13785

Pro Glu  Lys Asp Gly Glu Ala  Thr Gly Val Asp Ala  Ile Cys Thr
    13790             13795             13800

His Arg  Pro Asp Pro Thr Gly  Pro Gly Leu Asp Arg  Glu Gln Leu
    13805             13810             13815

Tyr Leu  Glu Leu Ser Gln Leu  Thr His Ser Ile Thr  Glu Leu Gly
    13820             13825             13830

Pro Tyr  Thr Leu Asp Arg Asp  Ser Leu Tyr Val Asn  Gly Phe Thr
    13835             13840             13845

His Arg  Ser Ser Val Pro Thr  Thr Ser Thr Gly Val  Val Ser Glu
    13850             13855             13860

Glu Pro  Phe Thr Leu Asn Phe  Thr Ile Asn Asn Leu  Arg Tyr Met
    13865             13870             13875

Ala Asp  Met Gly Gln Pro Gly  Ser Leu Lys Phe Asn  Ile Thr Asp
    13880             13885             13890

Asn Val  Met Gln His Leu Leu  Ser Pro Leu Phe Gln  Arg Ser Ser
    13895             13900             13905

Leu Gly  Ala Arg Tyr Thr Gly  Cys Arg Val Ile Ala  Leu Arg Ser
    13910             13915             13920

Val Lys  Asn Gly Ala Glu Thr  Arg Val Asp Leu Leu  Cys Thr Tyr
    13925             13930             13935

Leu Gln  Pro Leu Ser Gly Pro  Gly Leu Pro Ile Lys  Gln Val Phe
    13940             13945             13950

His Glu  Leu Ser Gln Gln Thr  His Gly Ile Thr Arg  Leu Gly Pro
    13955             13960             13965

Tyr Ser  Leu Asp Lys Asp Ser  Leu Tyr Leu Asn Gly  Tyr Asn Glu
    13970             13975             13980

Pro Gly  Pro Asp Glu Pro Pro  Thr Thr Pro Lys Pro  Ala Thr Thr
    13985             13990             13995

Phe Leu  Pro Pro Leu Ser Glu  Ala Thr Thr Ala Met  Gly Tyr His
    14000             14005             14010

Leu Lys  Thr Leu Thr Leu Asn  Phe Thr Ile Ser Asn  Leu Gln Tyr
    14015             14020             14025

Ser Pro  Asp Met Gly Lys Gly  Ser Ala Thr Phe Asn  Ser Thr Glu
    14030             14035             14040

Gly Val  Leu Gln His Leu Leu  Arg Pro Leu Phe Gln  Lys Ser Ser
    14045             14050             14055

Met Gly  Pro Phe Tyr Leu Gly  Cys Gln Leu Ile Ser  Leu Arg Pro
    14060             14065             14070

Glu Lys  Asp Gly Ala Ala Thr  Gly Val Asp Thr Thr  Cys Thr Tyr
    14075             14080             14085

His Pro  Asp Pro Val Gly Pro  Gly Leu Asp Ile Gln  Gln Leu Tyr
    14090             14095             14100

Trp Glu  Leu Ser Gln Leu Thr  His Gly Val Thr Gln  Leu Gly Phe
    14105             14110             14115

-continued

```
Tyr Val   Leu Asp Arg Asp Ser   Leu Phe Ile Asn Gly   Tyr Ala Pro
    14120             14125              14130

Gln Asn   Leu Ser Ile Arg Gly   Glu Tyr Gln Ile Asn   Phe His Ile
    14135             14140              14145

Val Asn   Trp Asn Leu Ser Asn   Pro Asp Pro Thr Ser   Ser Glu Tyr
    14150             14155              14160

Ile Thr   Leu Leu Arg Asp Ile   Gln Asp Lys Val Thr   Thr Leu Tyr
    14165             14170              14175

Lys Gly   Ser Gln Leu His Asp   Thr Phe Arg Phe Cys   Leu Val Thr
    14180             14185              14190

Asn Leu   Thr Met Asp Ser Val   Leu Val Thr Val Lys   Ala Leu Phe
    14195             14200              14205

Ser Ser   Asn Leu Asp Pro Ser   Leu Val Glu Gln Val   Phe Leu Asp
    14210             14215              14220

Lys Thr   Leu Asn Ala Ser Phe   His Trp Leu Gly Ser   Thr Tyr Gln
    14225             14230              14235

Leu Val   Asp Ile His Val Thr   Glu Met Glu Ser Ser   Val Tyr Gln
    14240             14245              14250

Pro Thr   Ser Ser Ser Ser Thr   Gln His Phe Tyr Leu   Asn Phe Thr
    14255             14260              14265

Ile Thr   Asn Leu Pro Tyr Ser   Gln Asp Lys Ala Gln   Pro Gly Thr
    14270             14275              14280

Thr Asn   Tyr Gln Arg Asn Lys   Arg Asn Ile Glu Asp   Ala Leu Asn
    14285             14290              14295

Gln Leu   Phe Arg Asn Ser Ser   Ile Lys Ser Tyr Phe   Ser Asp Cys
    14300             14305              14310

Gln Val   Ser Thr Phe Arg Ser   Val Pro Asn Arg His   His Thr Gly
    14315             14320              14325

Val Asp   Ser Leu Cys Asn Phe   Ser Pro Leu Ala Arg   Arg Val Asp
    14330             14335              14340

Arg Val   Ala Ile Tyr Glu Glu   Phe Leu Arg Met Thr   Arg Asn Gly
    14345             14350              14355

Thr Gln   Leu Gln Asn Phe Thr   Leu Asp Arg Ser Ser   Val Leu Val
    14360             14365              14370

Asp Gly   Tyr Ser Pro Asn Arg   Asn Glu Pro Leu Thr   Gly Asn Ser
    14375             14380              14385

Asp Leu   Pro Phe Trp Ala Val   Ile Leu Ile Gly Leu   Ala Gly Leu
    14390             14395              14400

Leu Gly   Val Ile Thr Cys Leu   Ile Cys Gly Val Leu   Val Thr Thr
    14405             14410              14415

Arg Arg   Arg Lys Lys Glu Gly   Glu Tyr Asn Val Gln   Gln Gln Cys
    14420             14425              14430

Pro Gly   Tyr Tyr Gln Ser His   Leu Asp Leu Glu Asp   Leu Gln
    14435             14440              14445
```

```
<210> SEQ ID NO 52
<211> LENGTH: 18
<212> TYPE: PRT
<213> ORGANISM: Homo sapiens

<400> SEQUENCE: 52

Thr Leu Asp Arg Ser Ser Val Leu Val Asp Gly Tyr Ser Pro Asn Arg
1               5                   10                  15

Asn Glu
```

-continued

```
<210> SEQ ID NO 53
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Glu Leu Thr Gln Ser Pro Ser Ser Leu Ala Val Ser Ala Gly
1               5                   10                  15

Glu Arg Val Thr Met Asn Cys Lys Ser Ser Gln Ser Leu Leu Asn Ser
            20                  25                  30

Arg Thr Arg Lys Asn Gln Leu Ala Trp Tyr Gln Gln Lys Pro Gly Gln
        35                  40                  45

Ser Pro Glu Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Ser Tyr Asn Leu Leu Thr Phe Gly Pro Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Glu Val Lys Leu Gln Glu Ser Gly Gly Gly Phe Val Lys Pro Gly Gly
    130                 135                 140

Ser Leu Arg Val Ser Cys Ala Ala Ser Gly Phe Thr Phe Ser Ser Tyr
145                 150                 155                 160

Ala Met Ser Trp Val Arg Leu Ala Pro Glu Met Arg Leu Glu Trp Val
                165                 170                 175

Ala Thr Ile Ser Ser Ala Gly Gly Tyr Ile Phe Tyr Ser Asp Ser Val
                180                 185                 190

Gln Gly Arg Phe Thr Ile Ser Arg Asp Asn Ala Lys Asn Ser Leu His
            195                 200                 205

Leu Gln Met Gly Ser Leu Arg Ser Gly Asp Thr Ala Met Tyr Tyr Cys
        210                 215                 220

Ala Arg Gln Gly Phe Gly Asn Tyr Gly Asp Tyr Tyr Ala Met Asp Tyr
225                 230                 235                 240

Trp Gly Gln Gly Thr Thr Val Thr Val Ser Ser
                245                 250

<210> SEQ ID NO 54
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Val Leu Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ser
            20                  25                  30

Arg Thr Arg Lys Asn Gln Leu Ala Trp Tyr Gln Gln Lys Pro Gly Gln
        35                  40                  45
```

```
Ser Pro Glu Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Ser Tyr Asn Leu Leu Thr Phe Gly Gln Gly Thr Lys Leu Glu Ile Lys
                100                 105                 110

Arg Gly Gly Gly Gly Ser Gly Gly Gly Gly Ser Gly Gly Gly Gly Ser
                115                 120                 125

Glu Val Lys Leu Gln Glu Ser Gly Gly Gly Phe Val Lys Pro Gly Gly
    130                 135                 140

Ser Leu Arg Val Ser Cys Ala Ala Ser Gly Phe Thr Phe Ser Ser Tyr
145                 150                 155                 160

Ala Met Ser Trp Val Arg Leu Ala Pro Glu Met Arg Leu Glu Trp Val
                165                 170                 175

Ala Thr Ile Ser Ser Ala Gly Gly Tyr Ile Phe Tyr Ser Asp Ser Val
                180                 185                 190

Gln Gly Arg Phe Thr Ile Ser Arg Asp Asn Ala Lys Asn Ser Leu His
                195                 200                 205

Leu Gln Met Gly Ser Leu Arg Ser Gly Asp Thr Ala Met Tyr Tyr Cys
    210                 215                 220

Ala Arg Gln Gly Phe Gly Asn Tyr Gly Asp Tyr Tyr Ala Met Asp Tyr
225                 230                 235                 240

Trp Gly Gln Gly Thr Thr Val Thr Val Ser Ser
                245                 250
```

```
<210> SEQ ID NO 55
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Glu Leu Thr Gln Ser Pro Ser Ser Leu Ala Val Ser Ala Gly
1               5                   10                  15

Glu Arg Val Thr Met Asn Cys Lys Ser Ser Gln Ser Leu Leu Asn Ser
                20                  25                  30

Arg Thr Arg Lys Asn Gln Leu Ala Trp Tyr Gln Gln Lys Pro Gly Gln
            35                  40                  45

Ser Pro Glu Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Ser Tyr Asn Leu Leu Thr Phe Gly Pro Gly Thr Lys Leu Glu Ile Lys
                100                 105                 110

Arg Gly Gly Gly Gly Ser Gly Gly Gly Gly Ser Gly Gly Gly Gly Ser
                115                 120                 125

Glu Val Gln Leu Val Glu Ser Gly Gly Gly Leu Val Lys Pro Gly Gly
    130                 135                 140

Ser Leu Arg Val Ser Cys Ala Ala Ser Gly Phe Thr Phe Ser Ser Tyr
145                 150                 155                 160
```

-continued

```
Ala Met Ser Trp Val Arg Leu Ala Pro Gly Lys Gly Leu Glu Trp Val
            165                 170                 175

Ala Thr Ile Ser Ser Ala Gly Gly Tyr Ile Phe Tyr Ser Asp Ser Val
            180                 185                 190

Gln Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Met Tyr Tyr Cys
    210                 215                 220

Ala Arg Gln Gly Phe Gly Asn Tyr Gly Asp Tyr Tyr Ala Met Asp Tyr
225                 230                 235                 240

Trp Gly Gln Gly Thr Leu Val Thr Val Ser Ser
            245                 250
```

```
<210> SEQ ID NO 56
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56
```

```
Asp Ile Val Leu Thr Gln Ser Pro Asp Ser Leu Ala Val Ser Leu Gly
1               5                   10                  15

Glu Arg Val Thr Met Asn Cys Lys Ser Ser Gln Ser Leu Leu Asn Ser
            20                  25                  30

Arg Thr Arg Lys Asn Gln Leu Ala Trp Tyr Gln Gln Lys Pro Gly Gln
        35                  40                  45

Ser Pro Glu Leu Leu Ile Tyr Trp Ala Ser Thr Arg Gln Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Ser Tyr Asn Leu Leu Thr Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Glu Val Gln Leu Val Glu Ser Gly Gly Gly Leu Val Lys Pro Gly Gly
    130                 135                 140

Ser Leu Arg Val Ser Cys Ala Ala Ser Gly Phe Thr Phe Ser Ser Tyr
145                 150                 155                 160

Ala Met Ser Trp Val Arg Leu Ala Pro Gly Lys Gly Leu Glu Trp Val
            165                 170                 175

Ala Thr Ile Ser Ser Ala Gly Gly Tyr Ile Phe Tyr Ser Asp Ser Val
            180                 185                 190

Gln Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Met Tyr Tyr Cys
    210                 215                 220

Ala Arg Gln Gly Phe Gly Asn Tyr Gly Asp Tyr Tyr Ala Met Asp Tyr
225                 230                 235                 240

Trp Gly Gln Gly Thr Leu Val Thr Val Ser Ser
            245                 250
```

<210> SEQ ID NO 57
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Asp Ile Val Met Thr Gln Ser Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Lys Pro Gly Gln Ser
            35                  40                  45

Pro Gln Arg Leu Ile Tyr Tyr Met Ser Asn Leu Ala Ser Gly Val Pro
        50                  55                  60

Asp Arg Phe Ser Gly Arg Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Tyr Pro Leu Thr Phe Gly Gly Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Thr Leu Lys Glu Ser Gly Pro Gly Ile Leu Gln Pro Thr Gln
    130                 135                 140

Thr Leu Thr Leu Thr Cys Thr Phe Ser Gly Phe Ser Leu Ser Thr Val
145                 150                 155                 160

Gly Met Gly Val Gly Trp Ser Arg Gln Pro Ser Gly Lys Gly Leu Glu
                165                 170                 175

Trp Leu Ala His Ile Trp Trp Asp Asp Glu Asp Lys Tyr Tyr Asn Pro
            180                 185                 190

Ala Leu Lys Ser Arg Leu Thr Ile Thr Lys Asp Thr Ser Lys Asn Gln
        195                 200                 205

Val Phe Leu Lys Ile Thr Asn Val Asp Thr Ala Asp Thr Ala Thr Tyr
    210                 215                 220

Tyr Cys Thr Arg Ile Gly Thr Ala Gln Ala Thr Asp Ala Leu Asp Tyr
225                 230                 235                 240

Trp Gly Gln Gly Thr Leu Val Thr Val Ser Ser
            245                 250
```

<210> SEQ ID NO 58
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Asp Ile Val Met Thr Gln Ser Ala Leu Ser Leu Pro Val Thr Pro Gly
1               5                   10                  15

Glu Pro Val Ser Ile Ser Cys Arg Ser Ser Lys Ser Leu Leu His Ser
                20                  25                  30

Asn Gly Asn Thr Tyr Leu Tyr Trp Phe Leu Gln Lys Pro Gly Gln Ser
            35                  40                  45

Pro Gln Arg Leu Ile Tyr Tyr Met Ser Asn Leu Ala Ser Gly Val Pro
```

-continued

```
     50               55               60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Tyr Pro Leu Thr Phe Gly Gly Gly Thr Lys Leu Glu Ile Lys
                100                 105                 110

Arg Gly Gly Gly Gly Ser Gly Gly Gly Gly Ser Gly Gly Gly Gly Ser
                115                 120                 125

Gln Val Thr Leu Lys Glu Ser Gly Pro Gly Ile Leu Gln Pro Thr Gln
        130                 135                 140

Thr Leu Thr Leu Thr Cys Thr Phe Ser Gly Phe Ser Leu Ser Thr Val
145                 150                 155                 160

Gly Met Gly Val Gly Trp Ser Arg Gln Pro Ser Gly Lys Gly Leu Glu
                165                 170                 175

Trp Leu Ala His Ile Trp Trp Asp Asp Glu Asp Lys Tyr Tyr Asn Pro
                180                 185                 190

Ala Leu Lys Ser Arg Leu Thr Ile Thr Lys Asp Thr Ser Lys Asn Gln
            195                 200                 205

Val Phe Leu Lys Ile Thr Asn Val Asp Thr Ala Asp Thr Ala Thr Tyr
        210                 215                 220

Tyr Cys Thr Arg Ile Gly Thr Ala Gln Ala Thr Asp Ala Leu Asp Tyr
225                 230                 235                 240

Trp Gly Gln Gly Thr Leu Val Thr Val Ser Ser
                245                 250
```

```
<210> SEQ ID NO 59
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Val Met Thr Gln Ser Ala Pro Ser Val Pro Val Thr Pro Gly
1               5                   10                  15

Glu Ser Val Ser Ile Ser Cys Arg Ser Ser Lys Ser Leu Leu His Ser
                20                  25                  30

Asn Gly Asn Thr Tyr Leu Tyr Trp Phe Leu Gln Lys Pro Gly Gln Ser
            35                  40                  45

Pro Gln Arg Leu Ile Tyr Tyr Met Ser Asn Leu Ala Ser Gly Val Pro
        50                  55                  60

Asp Arg Phe Ser Gly Arg Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Tyr Pro Leu Thr Phe Gly Gly Gly Thr Lys Leu Glu Ile Lys
                100                 105                 110

Arg Gly Gly Gly Gly Ser Gly Gly Gly Gly Ser Gly Gly Gly Gly Ser
            115                 120                 125

Gln Val Thr Leu Lys Glu Ser Gly Pro Thr Leu Val Lys Pro Thr Gln
        130                 135                 140

Thr Leu Thr Leu Thr Cys Thr Phe Ser Gly Phe Ser Leu Ser Thr Val
145                 150                 155                 160
```

```
Gly Met Gly Val Gly Trp Ser Arg Gln Pro Ser Gly Lys Gly Leu Glu
                165                 170                 175

Trp Leu Ala His Ile Trp Trp Asp Asp Glu Asp Lys Tyr Tyr Asn Pro
            180                 185                 190

Ala Leu Lys Ser Arg Leu Thr Ile Thr Lys Asp Thr Ser Lys Asn Gln
            195                 200                 205

Val Val Leu Thr Ile Thr Asn Val Asp Pro Val Asp Thr Ala Thr Tyr
            210                 215                 220

Tyr Cys Thr Arg Ile Gly Thr Ala Gln Ala Thr Asp Ala Leu Asp Tyr
225                 230                 235                 240

Trp Gly Gln Gly Thr Leu Val Thr Val Ser Ser
                245                 250
```

<210> SEQ ID NO 60
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Asp Ile Val Met Thr Gln Ser Ala Leu Ser Leu Pro Val Thr Pro Gly
1               5                   10                  15

Glu Pro Val Ser Ile Ser Cys Arg Ser Ser Lys Ser Leu Leu His Ser
            20                  25                  30

Asn Gly Asn Thr Tyr Leu Tyr Trp Phe Leu Gln Lys Pro Gly Gln Ser
            35                  40                  45

Pro Gln Arg Leu Ile Tyr Tyr Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Leu Glu Tyr Pro Leu Thr Phe Gly Gly Gly Thr Lys Leu Glu Ile Lys
            100                 105                 110

Arg Gly Gly Gly Gly Ser Gly Gly Gly Gly Ser Gly Gly Gly Gly Ser
            115                 120                 125

Gln Val Thr Leu Lys Glu Ser Gly Pro Thr Leu Val Lys Pro Thr Gln
    130                 135                 140

Thr Leu Thr Leu Thr Cys Thr Phe Ser Gly Phe Ser Leu Ser Thr Val
145                 150                 155                 160

Gly Met Gly Val Gly Trp Ser Arg Gln Pro Ser Gly Lys Gly Leu Glu
                165                 170                 175

Trp Leu Ala His Ile Trp Trp Asp Asp Glu Asp Lys Tyr Tyr Asn Pro
            180                 185                 190

Ala Leu Lys Ser Arg Leu Thr Ile Thr Lys Asp Thr Ser Lys Asn Gln
            195                 200                 205

Val Val Leu Thr Ile Thr Asn Val Asp Pro Val Asp Thr Ala Thr Tyr
            210                 215                 220

Tyr Cys Thr Arg Ile Gly Thr Ala Gln Ala Thr Asp Ala Leu Asp Tyr
225                 230                 235                 240

Trp Gly Gln Gly Thr Leu Val Thr Val Ser Ser
                245                 250
```

<210> SEQ ID NO 61

```
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Lys Leu Gln Glu Ser Gly Gly Gly Phe Val Lys Pro Gly Gly
1               5                   10                  15

Ser Leu Arg Val Ser Cys Ala Ala Ser Gly Phe Thr Phe Ser Ser Tyr
            20                  25                  30

Ala Met Ser Trp Val Arg Leu Ala Pro Glu Met Arg Leu Glu Trp Val
        35                  40                  45

Ala Thr Ile Ser Ser Ala Gly Gly Tyr Ile Phe Tyr Ser Asp Ser Val
    50                  55                  60

Gln Gly Arg Phe Thr Ile Ser Arg Asp Asn Ala Lys Asn Ser Leu His
65                  70                  75                  80

Leu Gln Met Gly Ser Leu Arg Ser Gly Asp Thr Ala Met Tyr Tyr Cys
                85                  90                  95

Ala Arg Gln Gly Phe Gly Asn Tyr Gly Asp Tyr Tyr Ala Met Asp Tyr
            100                 105                 110

Trp Gly Gln Gly Thr Thr Val Thr Val Ser Ser Gly Gly Gly Gly Ser
        115                 120                 125

Gly Gly Gly Gly Ser Gly Gly Gly Ser Asp Ile Glu Leu Thr Gln
    130                 135                 140

Ser Pro Ser Ser Leu Ala Val Ser Ala Gly Glu Arg Val Thr Met Asn
145                 150                 155                 160

Cys Lys Ser Ser Gln Ser Leu Leu Asn Ser Arg Thr Arg Lys Asn Gln
            165                 170                 175

Leu Ala Trp Tyr Gln Gln Lys Pro Gly Gln Ser Pro Glu Leu Leu Ile
            180                 185                 190

Tyr Trp Ala Ser Thr Arg Gln Ser Gly Val Pro Asp Arg Phe Ser Gly
        195                 200                 205

Ser Gly Ser Gly Thr Asp Phe Thr Leu Thr Ile Ser Ser Val Gln Ala
    210                 215                 220

Glu Asp Val Ala Val Tyr Tyr Cys Gln Gln Ser Tyr Asn Leu Leu Thr
225                 230                 235                 240

Phe Gly Pro Gly Thr Lys Leu Glu Ile Lys Arg
                245                 250

<210> SEQ ID NO 62
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Lys Leu Gln Glu Ser Gly Gly Gly Phe Val Lys Pro Gly Gly
1               5                   10                  15

Ser Leu Arg Val Ser Cys Ala Ala Ser Gly Phe Thr Phe Ser Ser Tyr
            20                  25                  30

Ala Met Ser Trp Val Arg Leu Ala Pro Glu Met Arg Leu Glu Trp Val
        35                  40                  45

Ala Thr Ile Ser Ser Ala Gly Gly Tyr Ile Phe Tyr Ser Asp Ser Val
    50                  55                  60
```

```
Gln Gly Arg Phe Thr Ile Ser Arg Asp Asn Ala Lys Asn Ser Leu His
65                  70                  75                  80

Leu Gln Met Gly Ser Leu Arg Ser Gly Asp Thr Ala Met Tyr Tyr Cys
                85                  90                  95

Ala Arg Gln Gly Phe Gly Asn Tyr Gly Asp Tyr Tyr Ala Met Asp Tyr
                100                 105                 110

Trp Gly Gln Gly Thr Thr Val Thr Val Ser Ser Gly Gly Gly Gly Ser
            115                 120                 125

Gly Gly Gly Gly Ser Gly Gly Gly Gly Ser Asp Ile Val Leu Thr Gln
        130                 135                 140

Ser Pro Asp Ser Leu Ala Val Ser Leu Gly Glu Arg Val Thr Met Asn
145                 150                 155                 160

Cys Lys Ser Ser Gln Ser Leu Leu Asn Ser Arg Thr Arg Lys Asn Gln
                165                 170                 175

Leu Ala Trp Tyr Gln Gln Lys Pro Gly Gln Ser Pro Glu Leu Leu Ile
            180                 185                 190

Tyr Trp Ala Ser Thr Arg Gln Ser Gly Val Pro Asp Arg Phe Ser Gly
            195                 200                 205

Ser Gly Ser Gly Thr Asp Phe Thr Leu Thr Ile Ser Ser Val Gln Ala
        210                 215                 220

Glu Asp Val Ala Val Tyr Tyr Cys Gln Gln Ser Tyr Asn Leu Leu Thr
225                 230                 235                 240

Phe Gly Gln Gly Thr Lys Leu Glu Ile Lys Arg
                245                 250
```

<210> SEQ ID NO 63
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

```
Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser Ser Tyr
                20                  25                  30

Ala Met Ser Trp Val Arg Leu Ala Pro Gly Lys Gly Leu Glu Trp Val
            35                  40                  45

Ala Thr Ile Ser Ser Ala Gly Gly Tyr Ile Phe Tyr Ser Asp Ser Val
        50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Met Tyr Tyr Cys
                85                  90                  95

Ala Arg Gln Gly Phe Gly Asn Tyr Gly Asp Tyr Tyr Ala Met Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Asp Ile Glu Leu Thr Gln
        130                 135                 140

Ser Pro Ser Ser Leu Ala Val Ser Ala Gly Glu Arg Val Thr Met Asn
145                 150                 155                 160

Cys Lys Ser Ser Gln Ser Leu Leu Asn Ser Arg Thr Arg Lys Asn Gln
```

-continued

```
                165                     170                     175

Leu Ala Trp Tyr Gln Gln Lys Pro Gly Gln Ser Pro Glu Leu Leu Ile
            180                     185                     190

Tyr Trp Ala Ser Thr Arg Gln Ser Gly Val Pro Asp Arg Phe Ser Gly
        195                     200                     205

Ser Gly Ser Gly Thr Asp Phe Thr Leu Thr Ile Ser Ser Val Gln Ala
    210                     215                     220

Glu Asp Val Ala Val Tyr Tyr Cys Gln Gln Ser Tyr Asn Leu Leu Thr
225                     230                     235                     240

Phe Gly Pro Gly Thr Lys Leu Glu Ile Lys Arg
                245                     250

<210> SEQ ID NO 64
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Val Gln Leu Val Glu Ser Gly Gly Gly Leu Val Lys Pro Gly Gly
1                   5                       10                      15

Ser Leu Arg Val Ser Cys Ala Ala Ser Gly Phe Thr Phe Ser Ser Tyr
            20                      25                      30

Ala Met Ser Trp Val Arg Leu Ala Pro Gly Lys Gly Leu Glu Trp Val
        35                      40                      45

Ala Thr Ile Ser Ser Ala Gly Gly Tyr Ile Phe Tyr Ser Asp Ser Val
    50                      55                      60

Gln Gly Arg Phe Thr Ile Ser Arg Asp Asn Ala Lys Asn Ser Leu Tyr
65                      70                      75                      80

Leu Gln Met Asn Ser Leu Arg Ala Glu Asp Thr Ala Met Tyr Tyr Cys
                85                      90                      95

Ala Arg Gln Gly Phe Gly Asn Tyr Gly Asp Tyr Tyr Ala Met Asp Tyr
            100                     105                     110

Trp Gly Gln Gly Thr Leu Val Thr Val Ser Ser Gly Gly Gly Gly Ser
        115                     120                     125

Gly Gly Gly Gly Ser Gly Gly Gly Gly Ser Asp Ile Val Leu Thr Gln
    130                     135                     140

Ser Pro Asp Ser Leu Ala Val Ser Leu Gly Glu Arg Val Thr Met Asn
145                     150                     155                     160

Cys Lys Ser Ser Gln Ser Leu Leu Asn Ser Arg Thr Arg Lys Asn Gln
                165                     170                     175

Leu Ala Trp Tyr Gln Gln Lys Pro Gly Gln Ser Pro Glu Leu Leu Ile
            180                     185                     190

Tyr Trp Ala Ser Thr Arg Gln Ser Gly Val Pro Asp Arg Phe Ser Gly
        195                     200                     205

Ser Gly Ser Gly Thr Asp Phe Thr Leu Thr Ile Ser Ser Val Gln Ala
    210                     215                     220

Glu Asp Val Ala Val Tyr Tyr Cys Gln Gln Ser Tyr Asn Leu Leu Thr
225                     230                     235                     240

Phe Gly Gln Gly Thr Lys Leu Glu Ile Lys Arg
                245                     250

<210> SEQ ID NO 65
<211> LENGTH: 251
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Thr Leu Lys Glu Ser Gly Pro Gly Ile Leu Gln Pro Thr Gln
1               5                   10                  15

Thr Leu Thr Leu Thr Cys Thr Phe Ser Gly Phe Ser Leu Ser Thr Val
            20                  25                  30

Gly Met Gly Val Gly Trp Ser Arg Gln Pro Ser Gly Lys Gly Leu Glu
        35                  40                  45

Trp Leu Ala His Ile Trp Trp Asp Asp Glu Asp Lys Tyr Tyr Asn Pro
    50                  55                  60

Ala Leu Lys Ser Arg Leu Thr Ile Thr Lys Asp Thr Ser Lys Asn Gln
65                  70                  75                  80

Val Phe Leu Lys Ile Thr Asn Val Asp Thr Ala Asp Thr Ala Thr Tyr
                85                  90                  95

Tyr Cys Thr Arg Ile Gly Thr Ala Gln Ala Thr Asp Ala Leu Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Asp Ile Val Met Thr Gln
    130                 135                 140

Ser Ala Pro Ser Val Pro Val Thr Pro Gly Glu Ser Val Ser Ile Ser
145                 150                 155                 160

Cys Arg Ser Ser Lys Ser Leu Leu His Ser Asn Gly Asn Thr Tyr Leu
                165                 170                 175

Tyr Trp Phe Leu Gln Lys Pro Gly Gln Ser Pro Gln Arg Leu Ile Tyr
            180                 185                 190

Tyr Met Ser Asn Leu Ala Ser Gly Val Pro Asp Arg Phe Ser Gly Arg
        195                 200                 205

Gly Ser Gly Thr Asp Phe Thr Leu Lys Ile Ser Arg Val Glu Ala Glu
    210                 215                 220

Asp Val Gly Val Tyr Tyr Cys Met Gln Ser Leu Glu Tyr Pro Leu Thr
225                 230                 235                 240

Phe Gly Gly Gly Thr Lys Leu Glu Ile Lys Arg
            245                 250

<210> SEQ ID NO 66
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Thr Leu Lys Glu Ser Gly Pro Gly Ile Leu Gln Pro Thr Gln
1               5                   10                  15

Thr Leu Thr Leu Thr Cys Thr Phe Ser Gly Phe Ser Leu Ser Thr Val
            20                  25                  30

Gly Met Gly Val Gly Trp Ser Arg Gln Pro Ser Gly Lys Gly Leu Glu
        35                  40                  45

Trp Leu Ala His Ile Trp Trp Asp Asp Glu Asp Lys Tyr Tyr Asn Pro
    50                  55                  60

-continued

```
Ala Leu Lys Ser Arg Leu Thr Ile Thr Lys Asp Thr Ser Lys Asn Gln
65                  70                  75                  80

Val Phe Leu Lys Ile Thr Asn Val Asp Thr Ala Asp Thr Ala Thr Tyr
                85                  90                  95

Tyr Cys Thr Arg Ile Gly Thr Ala Gln Ala Thr Asp Ala Leu Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Val Met Thr Gln
        130                 135                 140

Ser Ala Leu Ser Leu Pro Val Thr Pro Gly Glu Pro Val Ser Ile Ser
145                 150                 155                 160

Cys Arg Ser Ser Lys Ser Leu Leu His Ser Asn Gly Asn Thr Tyr Leu
                165                 170                 175

Tyr Trp Phe Leu Gln Lys Pro Gly Gln Ser Pro Gln Arg Leu Ile Tyr
                180                 185                 190

Tyr Met Ser Asn Leu Ala Ser Gly Val Pro Asp Arg Phe Ser Gly Ser
                195                 200                 205

Gly Ser Gly Thr Asp Phe Thr Leu Lys Ile Ser Arg Val Glu Ala Glu
        210                 215                 220

Asp Val Gly Val Tyr Tyr Cys Met Gln Ser Leu Glu Tyr Pro Leu Thr
225                 230                 235                 240

Phe Gly Gly Gly Thr Lys Leu Glu Ile Lys Arg
                245                 250
```

```
<210> SEQ ID NO 67
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67
```

```
Gln Val Thr Leu Lys Glu Ser Gly Pro Thr Leu Val Lys Pro Thr Gln
1                   5                   10                  15

Thr Leu Thr Leu Thr Cys Thr Phe Ser Gly Phe Ser Leu Ser Thr Val
                20                  25                  30

Gly Met Gly Val Gly Trp Ser Arg Gln Pro Ser Gly Lys Gly Leu Glu
        35                  40                  45

Trp Leu Ala His Ile Trp Trp Asp Asp Glu Asp Lys Tyr Tyr Asn Pro
    50                  55                  60

Ala Leu Lys Ser Arg Leu Thr Ile Thr Lys Asp Thr Ser Lys Asn Gln
65                  70                  75                  80

Val Val Leu Thr Ile Thr Asn Val Asp Pro Val Asp Thr Ala Thr Tyr
                85                  90                  95

Tyr Cys Thr Arg Ile Gly Thr Ala Gln Ala Thr Asp Ala Leu Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Val Met Thr Gln
        130                 135                 140

Ser Ala Pro Ser Val Pro Val Thr Pro Gly Glu Ser Val Ser Ile Ser
145                 150                 155                 160

Cys Arg Ser Ser Lys Ser Leu Leu His Ser Asn Gly Asn Thr Tyr Leu
                165                 170                 175
```

-continued

```
Tyr Trp Phe Leu Gln Lys Pro Gly Gln Ser Pro Gln Arg Leu Ile Tyr
            180                 185                 190

Tyr Met Ser Asn Leu Ala Ser Gly Val Pro Asp Arg Phe Ser Gly Arg
            195                 200                 205

Gly Ser Gly Thr Asp Phe Thr Leu Lys Ile Ser Arg Val Glu Ala Glu
    210                 215                 220

Asp Val Gly Val Tyr Tyr Cys Met Gln Ser Leu Glu Tyr Pro Leu Thr
225                 230                 235                 240

Phe Gly Gly Gly Thr Lys Leu Glu Ile Lys Arg
                245                 250

<210> SEQ ID NO 68
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Val
            20                  25                  30

Gly Met Gly Val Gly Trp Ser Arg Gln Pro Ser Gly Lys Gly Leu Glu
            35                  40                  45

Trp Leu Ala His Ile Trp Trp Asp Asp Glu Asp Lys Tyr Tyr Asn Pro
    50                  55                  60

Ala Leu Lys Ser Arg Leu Thr Ile Thr Lys Asp Thr Ser Lys Asn Gln
65                  70                  75                  80

Val Val Leu Thr Ile Thr Asn Val Asp Pro Val Asp Thr Ala Thr Tyr
            85                  90                  95

Tyr Cys Thr Arg Ile Gly Thr Ala Gln Ala Thr Asp Ala Leu Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Asp Ile Val Met Thr Gln
    130                 135                 140

Ser Ala Leu Ser Leu Pro Val Thr Pro Gly Glu Pro Val Ser Ile Ser
145                 150                 155                 160

Cys Arg Ser Ser Lys Ser Leu Leu His Ser Asn Gly Asn Thr Tyr Leu
            165                 170                 175

Tyr Trp Phe Leu Gln Lys Pro Gly Gln Ser Pro Gln Arg Leu Ile Tyr
            180                 185                 190

Tyr Met Ser Asn Leu Ala Ser Gly Val Pro Asp Arg Phe Ser Gly Ser
            195                 200                 205

Gly Ser Gly Thr Asp Phe Thr Leu Lys Ile Ser Arg Val Glu Ala Glu
    210                 215                 220

Asp Val Gly Val Tyr Tyr Cys Met Gln Ser Leu Glu Tyr Pro Leu Thr
225                 230                 235                 240

Phe Gly Gly Gly Thr Lys Leu Glu Ile Lys Arg
                245                 250

<210> SEQ ID NO 69
<211> LENGTH: 525
<212> TYPE: PRT
```

-continued

```
<213> ORGANISM: Artificial Sequence
<220> FEATURE:
<223> OTHER INFORMATION: Description of Artificial Sequence: Synthetic
      polypeptide

<400> SEQUENCE: 69

Met Gly Trp Ser Cys Ile Ile Leu Phe Leu Val Ala Thr Ala Thr Gly
1               5                   10                  15

Lys Leu Asp Ile Val Leu Thr Gln Ser Pro Asp Ser Leu Ala Val Ser
                20                  25                  30

Leu Gly Glu Arg Val Thr Met Asn Cys Lys Ser Ser Gln Ser Leu Leu
            35                  40                  45

Asn Ser Arg Thr Arg Lys Asn Gln Leu Ala Trp Tyr Gln Gln Lys Pro
        50                  55                  60

Gly Gln Ser Pro Glu Leu Leu Ile Tyr Trp Ala Ser Thr Arg Gln Ser
65                  70                  75                  80

Gly Val Pro Asp Arg Phe Ser Gly Ser Gly Ser Gly Thr Asp Phe Thr
                85                  90                  95

Leu Thr Ile Ser Ser Val Gln Ala Glu Asp Val Ala Val Tyr Tyr Cys
                100                 105                 110

Gln Gln Ser Tyr Asn Leu Leu Thr Phe Gly Gln Gly Thr Lys Leu Glu
            115                 120                 125

Ile Lys Arg Gly Gly Gly Gly Ser Gly Gly Gly Gly Ser Gly Gly Gly
        130                 135                 140

Gly Ser Glu Val Lys Leu Gln Glu Ser Gly Gly Gly Phe Val Lys Pro
145                 150                 155                 160

Gly Gly Ser Leu Arg Val Ser Cys Ala Ala Ser Gly Phe Thr Phe Ser
                165                 170                 175

Ser Tyr Ala Met Ser Trp Val Arg Leu Ala Pro Glu Met Arg Leu Glu
            180                 185                 190

Trp Val Ala Thr Ile Ser Ser Ala Gly Gly Tyr Ile Phe Tyr Ser Asp
        195                 200                 205

Ser Val Gln Gly Arg Phe Thr Ile Ser Arg Asp Asn Ala Lys Asn Ser
    210                 215                 220

Leu His Leu Gln Met Gly Ser Leu Arg Ser Gly Asp Thr Ala Met Tyr
225                 230                 235                 240

Tyr Cys Ala Arg Gln Gly Phe Gly Asn Tyr Gly Asp Tyr Tyr Ala Met
            245                 250                 255

Asp Tyr Trp Gly Gln Gly Thr Thr Val Thr Val Ser Ser Thr Ser Gly
            260                 265                 270

Gly Gly Gly Ser Asp Val Gln Leu Val Gln Ser Gly Ala Glu Val Lys
        275                 280                 285

Lys Pro Gly Ala Ser Val Lys Val Ser Cys Lys Ala Ser Gly Tyr Thr
    290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
            325                 330                 335

Ala Asp Ser Val Lys Gly Arg Phe Thr Ile Thr Thr Asp Lys Ser Thr
            340                 345                 350

Ser Thr Ala Tyr Met Glu Leu Ser Ser Leu Arg Ser Glu Asp Thr Ala
        355                 360                 365

Thr Tyr Tyr Cys Ala Arg Tyr Tyr Asp Asp His Tyr Cys Leu Asp Tyr
    370                 375                 380
```

-continued

```
Trp Gly Gln Gly Thr Thr Val Thr Val Ser Ser Gly Glu Gly Thr Ser
385                 390                 395                 400

Thr Gly Ser Gly Gly Ser Gly Gly Ser Gly Gly Ala Asp Asp Ile Val
                405                 410                 415

Leu Thr Gln Ser Pro Ala Thr Leu Ser Leu Ser Pro Gly Glu Arg Ala
                420                 425                 430

Thr Leu Ser Cys Arg Ala Ser Gln Ser Val Ser Tyr Met Asn Trp Tyr
                435                 440                 445

Gln Gln Lys Pro Gly Lys Ala Pro Lys Arg Trp Ile Tyr Asp Thr Ser
                450                 455                 460

Lys Val Ala Ser Gly Val Pro Ala Arg Phe Ser Gly Ser Gly Ser Gly
465                 470                 475                 480

Thr Asp Tyr Ser Leu Thr Ile Asn Ser Leu Glu Ala Glu Asp Ala Ala
                485                 490                 495

Thr Tyr Tyr Cys Gln Gln Trp Ser Ser Asn Pro Leu Thr Phe Gly Gly
                500                 505                 510

Gly Thr Lys Val Glu Ile Lys His His His His His His
                515                 520                 525

<210> SEQ ID NO 70
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Met Gly Trp Ser Cys Ile Ile Leu Phe Leu Val Ala Thr Ala Thr Gly
1               5                   10                  15

Lys Leu Asp Ile Glu Leu Thr Gln Ser Pro Ser Ser Leu Ala Val Ser
                20                  25                  30

Ala Gly Glu Arg Val Thr Met Asn Cys Lys Ser Ser Gln Ser Leu Leu
                35                  40                  45

Asn Ser Arg Thr Arg Lys Asn Gln Leu Ala Trp Tyr Gln Gln Lys Pro
                50                  55                  60

Gly Gln Ser Pro Glu Leu Leu Ile Tyr Trp Ala Ser Thr Arg Gln Ser
65                  70                  75                  80

Gly Val Pro Asp Arg Phe Ser Gly Ser Gly Ser Gly Thr Asp Phe Thr
                85                  90                  95

Leu Thr Ile Ser Ser Val Gln Ala Glu Asp Val Ala Val Tyr Tyr Cys
                100                 105                 110

Gln Gln Ser Tyr Asn Leu Leu Thr Phe Gly Pro Gly Thr Lys Leu Glu
                115                 120                 125

Ile Lys Arg Gly Gly Gly Ser Gly Gly Gly Gly Ser Gly Gly Gly
                130                 135                 140

Gly Ser Glu Val Gln Leu Val Glu Ser Gly Gly Gly Leu Val Lys Pro
145                 150                 155                 160

Gly Gly Ser Leu Arg Val Ser Cys Ala Ala Ser Gly Phe Thr Phe Ser
                165                 170                 175

Ser Tyr Ala Met Ser Trp Val Arg Leu Ala Pro Gly Lys Gly Leu Glu
                180                 185                 190

Trp Val Ala Thr Ile Ser Ser Ala Gly Gly Tyr Ile Phe Tyr Ser Asp
                195                 200                 205

Ser Val Gln Gly Arg Phe Thr Ile Ser Arg Asp Asn Ala Lys Asn Ser
                210                 215                 220
```

```
Leu Tyr Leu Gln Met Asn Ser Leu Arg Ala Glu Asp Thr Ala Met Tyr
225                 230                 235                 240

Tyr Cys Ala Arg Gln Gly Phe Gly Asn Tyr Gly Asp Tyr Tyr Ala Met
                245                 250                 255

Asp Tyr Trp Gly Gln Gly Thr Leu Val Thr Val Ser Ser Thr Ser Gly
            260                 265                 270

Gly Gly Gly Ser Asp Val Gln Leu Val Gln Ser Gly Ala Glu Val Lys
        275                 280                 285

Lys Pro Gly Ala Ser Val Lys Val Ser Cys Lys Ala Ser Gly Tyr Thr
    290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
                325                 330                 335

Ala Asp Ser Val Lys Gly Arg Phe Thr Ile Thr Thr Asp Lys Ser Thr
            340                 345                 350

Ser Thr Ala Tyr Met Glu Leu Ser Ser Leu Arg Ser Glu Asp Thr Ala
        355                 360                 365

Thr Tyr Tyr Cys Ala Arg Tyr Tyr Asp Asp His Tyr Cys Leu Asp Tyr
    370                 375                 380

Trp Gly Gln Gly Thr Thr Val Thr Val Ser Ser Gly Glu Gly Thr Ser
385                 390                 395                 400

Thr Gly Ser Gly Gly Ser Gly Gly Ser Gly Gly Ala Asp Asp Ile Val
            405                 410                 415

Leu Thr Gln Ser Pro Ala Thr Leu Ser Leu Ser Pro Gly Glu Arg Ala
            420                 425                 430

Thr Leu Ser Cys Arg Ala Ser Gln Ser Val Ser Tyr Met Asn Trp Tyr
            435                 440                 445

Gln Gln Lys Pro Gly Lys Ala Pro Lys Arg Trp Ile Tyr Asp Thr Ser
    450                 455                 460

Lys Val Ala Ser Gly Val Pro Ala Arg Phe Ser Gly Ser Gly Ser Gly
465                 470                 475                 480

Thr Asp Tyr Ser Leu Thr Ile Asn Ser Leu Glu Ala Glu Asp Ala Ala
            485                 490                 495

Thr Tyr Tyr Cys Gln Gln Trp Ser Ser Asn Pro Leu Thr Phe Gly Gly
            500                 505                 510

Gly Thr Lys Val Glu Ile Lys His His His His His
        515                 520                 525
```

```
<210> SEQ ID NO 71
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71
```

```
Met Gly Trp Ser Cys Ile Ile Leu Phe Leu Val Ala Thr Ala Thr Gly
1               5                   10                  15

Lys Leu Asp Ile Val Leu Thr Gln Ser Pro Asp Ser Leu Ala Val Ser
            20                  25                  30

Leu Gly Glu Arg Val Thr Met Asn Cys Lys Ser Ser Gln Ser Leu Leu
        35                  40                  45

Asn Ser Arg Thr Arg Lys Asn Gln Leu Ala Trp Tyr Gln Gln Lys Pro
```

-continued

```
              50              55              60

Gly Gln Ser Pro Glu Leu Leu Ile Tyr Trp Ala Ser Thr Arg Gln Ser
65              70              75              80

Gly Val Pro Asp Arg Phe Ser Gly Ser Gly Ser Gly Thr Asp Phe Thr
                85              90              95

Leu Thr Ile Ser Ser Val Gln Ala Glu Asp Val Ala Val Tyr Tyr Cys
            100             105             110

Gln Gln Ser Tyr Asn Leu Leu Thr Phe Gly Gln Gly Thr Lys Leu Glu
        115             120             125

Ile Lys Arg Gly Gly Gly Ser Gly Gly Gly Gly Ser Gly Gly Gly
        130             135             140

Gly Ser Glu Val Gln Leu Val Glu Ser Gly Gly Gly Leu Val Lys Pro
145             150             155             160

Gly Gly Ser Leu Arg Val Ser Cys Ala Ala Ser Gly Phe Thr Phe Ser
                165             170             175

Ser Tyr Ala Met Ser Trp Val Arg Leu Ala Pro Gly Lys Gly Leu Glu
                180             185             190

Trp Val Ala Thr Ile Ser Ser Ala Gly Gly Tyr Ile Phe Tyr Ser Asp
            195             200             205

Ser Val Gln Gly Arg Phe Thr Ile Ser Arg Asp Asn Ala Lys Asn Ser
        210             215             220

Leu Tyr Leu Gln Met Asn Ser Leu Arg Ala Glu Asp Thr Ala Met Tyr
225             230             235             240

Tyr Cys Ala Arg Gln Gly Phe Gly Asn Tyr Gly Asp Tyr Tyr Ala Met
                245             250             255

Asp Tyr Trp Gly Gln Gly Thr Leu Val Thr Val Ser Ser Thr Ser Gly
            260             265             270

Gly Gly Gly Ser Asp Val Gln Leu Val Gln Ser Gly Ala Glu Val Lys
        275             280             285

Lys Pro Gly Ala Ser Val Lys Val Ser Cys Lys Ala Ser Gly Tyr Thr
        290             295             300

Phe Thr Arg Tyr Thr Met His Trp Val Arg Gln Ala Pro Gly Gln Gly
305             310             315             320

Leu Glu Trp Ile Gly Tyr Ile Asn Pro Ser Arg Gly Tyr Thr Asn Tyr
            325             330             335

Ala Asp Ser Val Lys Gly Arg Phe Thr Ile Thr Thr Asp Lys Ser Thr
            340             345             350

Ser Thr Ala Tyr Met Glu Leu Ser Ser Leu Arg Ser Glu Asp Thr Ala
        355             360             365

Thr Tyr Tyr Cys Ala Arg Tyr Tyr Asp Asp His Tyr Cys Leu Asp Tyr
    370             375             380

Trp Gly Gln Gly Thr Thr Val Thr Val Ser Ser Gly Glu Gly Thr Ser
385             390             395             400

Thr Gly Ser Gly Gly Ser Gly Gly Ser Gly Gly Ala Asp Asp Ile Val
                405             410             415

Leu Thr Gln Ser Pro Ala Thr Leu Ser Leu Ser Pro Gly Glu Arg Ala
            420             425             430

Thr Leu Ser Cys Arg Ala Ser Gln Ser Val Ser Tyr Met Asn Trp Tyr
            435             440             445

Gln Gln Lys Pro Gly Lys Ala Pro Lys Arg Trp Ile Tyr Asp Thr Ser
    450             455             460

Lys Val Ala Ser Gly Val Pro Ala Arg Phe Ser Gly Ser Gly Ser Gly
465             470             475             480
```

-continued

```
Thr Asp Tyr Ser Leu Thr Ile Asn Ser Leu Glu Ala Glu Asp Ala Ala
                485                 490                 495

Thr Tyr Tyr Cys Gln Gln Trp Ser Ser Asn Pro Leu Thr Phe Gly Gly
            500                 505                 510

Gly Thr Lys Val Glu Ile Lys His His His His His His
        515                 520                 525

<210> SEQ ID NO 72
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Met Gly Trp Ser Cys Ile Ile Leu Phe Leu Val Ala Thr Ala Thr Gly
1               5                   10                  15

Lys Leu Asp Ile Val Met Thr Gln Ser Ala Pro Ser Val Pro Val Thr
            20                  25                  30

Pro Gly Glu Ser Val Ser Ile Ser Cys Arg Ser Ser Lys Ser Leu Leu
        35                  40                  45

His Ser Asn Gly Asn Thr Tyr Leu Tyr Trp Phe Leu Gln Lys Pro Gly
    50                  55                  60

Gln Ser Pro Gln Arg Leu Ile Tyr Tyr Met Ser Asn Leu Ala Ser Gly
65                  70                  75                  80

Val Pro Asp Arg Phe Ser Gly Arg Gly Ser Gly Thr Asp Phe Thr Leu
                85                  90                  95

Lys Ile Ser Arg Val Glu Ala Glu Asp Val Gly Val Tyr Tyr Cys Met
            100                 105                 110

Gln Ser Leu Glu Tyr Pro Leu Thr Phe Gly Gly Gly Thr Lys Leu Glu
        115                 120                 125

Ile Lys Arg Gly Gly Gly Gly Ser Gly Gly Gly Gly Ser Gly Gly Gly
        130                 135                 140

Gly Ser Gln Val Thr Leu Lys Glu Ser Gly Pro Gly Ile Leu Gln Pro
145                 150                 155                 160

Thr Gln Thr Leu Thr Leu Thr Cys Thr Phe Ser Gly Phe Ser Leu Ser
                165                 170                 175

Thr Val Gly Met Gly Val Gly Trp Ser Arg Gln Pro Ser Gly Lys Gly
            180                 185                 190

Leu Glu Trp Leu Ala His Ile Trp Trp Asp Asp Glu Asp Lys Tyr Tyr
        195                 200                 205

Asn Pro Ala Leu Lys Ser Arg Leu Thr Ile Thr Lys Asp Thr Ser Lys
    210                 215                 220

Asn Gln Val Phe Leu Lys Ile Thr Asn Val Asp Thr Ala Asp Thr Ala
225                 230                 235                 240

Thr Tyr Tyr Cys Thr Arg Ile Gly Thr Ala Gln Ala Thr Asp Ala Leu
                245                 250                 255

Asp Tyr Trp Gly Gln Gly Thr Leu Val Thr Val Ser Ser Thr Ser Gly
            260                 265                 270

Gly Gly Gly Ser Asp Val Gln Leu Val Gln Ser Gly Ala Glu Val Lys
        275                 280                 285

Lys Pro Gly Ala Ser Val Lys Val Ser Cys Lys Ala Ser Gly Tyr Thr
    290                 295                 300

Phe Thr Arg Tyr Thr Met His Trp Val Arg Gln Ala Pro Gly Gln Gly
```

-continued

```
305              310              315              320

Leu Glu Trp Ile Gly Tyr Ile Asn Pro Ser Arg Gly Tyr Thr Asn Tyr
                 325              330              335

Ala Asp Ser Val Lys Gly Arg Phe Thr Ile Thr Thr Asp Lys Ser Thr
                 340              345              350

Ser Thr Ala Tyr Met Glu Leu Ser Ser Leu Arg Ser Glu Asp Thr Ala
                 355              360              365

Thr Tyr Tyr Cys Ala Arg Tyr Tyr Asp Asp His Tyr Cys Leu Asp Tyr
        370              375              380

Trp Gly Gln Gly Thr Thr Val Thr Val Ser Ser Gly Glu Gly Thr Ser
385              390              395              400

Thr Gly Ser Gly Gly Ser Gly Gly Ser Gly Gly Ala Asp Asp Ile Val
                 405              410              415

Leu Thr Gln Ser Pro Ala Thr Leu Ser Leu Ser Pro Gly Glu Arg Ala
                 420              425              430

Thr Leu Ser Cys Arg Ala Ser Gln Ser Val Ser Tyr Met Asn Trp Tyr
                 435              440              445

Gln Gln Lys Pro Gly Lys Ala Pro Lys Arg Trp Ile Tyr Asp Thr Ser
        450              455              460

Lys Val Ala Ser Gly Val Pro Ala Arg Phe Ser Gly Ser Gly Ser Gly
465              470              475              480

Thr Asp Tyr Ser Leu Thr Ile Asn Ser Leu Glu Ala Glu Asp Ala Ala
                 485              490              495

Thr Tyr Tyr Cys Gln Gln Trp Ser Ser Asn Pro Leu Thr Phe Gly Gly
                 500              505              510

Gly Thr Lys Val Glu Ile Lys His His His His His His
                 515              520              525
```

<210> SEQ ID NO 73
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Met Gly Trp Ser Cys Ile Ile Leu Phe Leu Val Ala Thr Ala Thr Gly
1               5               10              15

Lys Leu Asp Ile Val Met Thr Gln Ser Ala Leu Ser Leu Pro Val Thr
                20              25              30

Pro Gly Glu Pro Val Ser Ile Ser Cys Arg Ser Ser Lys Ser Leu Leu
        35              40              45

His Ser Asn Gly Asn Thr Tyr Leu Tyr Trp Phe Leu Gln Lys Pro Gly
        50              55              60

Gln Ser Pro Gln Arg Leu Ile Tyr Tyr Met Ser Asn Leu Ala Ser Gly
65              70              75              80

Val Pro Asp Arg Phe Ser Gly Ser Gly Ser Gly Thr Asp Phe Thr Leu
                85              90              95

Lys Ile Ser Arg Val Glu Ala Glu Asp Val Gly Val Tyr Tyr Cys Met
                100             105             110

Gln Ser Leu Glu Tyr Pro Leu Thr Phe Gly Gly Gly Thr Lys Leu Glu
        115             120             125

Ile Lys Arg Gly Gly Gly Gly Ser Gly Gly Gly Gly Ser Gly Gly Gly
        130             135             140
```

```
Gly Ser Gln Val Thr Leu Lys Glu Ser Gly Pro Gly Ile Leu Gln Pro
145                 150                 155                 160

Thr Gln Thr Leu Thr Leu Thr Cys Thr Phe Ser Gly Phe Ser Leu Ser
                165                 170                 175

Thr Val Gly Met Gly Val Gly Trp Ser Arg Gln Pro Ser Gly Lys Gly
            180                 185                 190

Leu Glu Trp Leu Ala His Ile Trp Trp Asp Asp Glu Asp Lys Tyr Tyr
        195                 200                 205

Asn Pro Ala Leu Lys Ser Arg Leu Thr Ile Thr Lys Asp Thr Ser Lys
    210                 215                 220

Asn Gln Val Phe Leu Lys Ile Thr Asn Val Asp Thr Ala Asp Thr Ala
225                 230                 235                 240

Thr Tyr Tyr Cys Thr Arg Ile Gly Thr Ala Gln Ala Thr Asp Ala Leu
                245                 250                 255

Asp Tyr Trp Gly Gln Gly Thr Leu Val Thr Val Ser Ser Thr Ser Gly
            260                 265                 270

Gly Gly Gly Ser Asp Val Gln Leu Val Gln Ser Gly Ala Glu Val Lys
            275                 280                 285

Lys Pro Gly Ala Ser Val Lys Val Ser Cys Lys Ala Ser Gly Tyr Thr
    290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
                325                 330                 335

Ala Asp Ser Val Lys Gly Arg Phe Thr Ile Thr Thr Asp Lys Ser Thr
            340                 345                 350

Ser Thr Ala Tyr Met Glu Leu Ser Ser Leu Arg Ser Glu Asp Thr Ala
        355                 360                 365

Thr Tyr Tyr Cys Ala Arg Tyr Tyr Asp Asp His Tyr Cys Leu Asp Tyr
    370                 375                 380

Trp Gly Gln Gly Thr Thr Val Thr Val Ser Ser Gly Glu Gly Thr Ser
385                 390                 395                 400

Thr Gly Ser Gly Gly Ser Gly Gly Ser Gly Gly Ala Asp Asp Ile Val
                405                 410                 415

Leu Thr Gln Ser Pro Ala Thr Leu Ser Leu Ser Pro Gly Glu Arg Ala
            420                 425                 430

Thr Leu Ser Cys Arg Ala Ser Gln Ser Val Ser Tyr Met Asn Trp Tyr
        435                 440                 445

Gln Gln Lys Pro Gly Lys Ala Pro Lys Arg Trp Ile Tyr Asp Thr Ser
    450                 455                 460

Lys Val Ala Ser Gly Val Pro Ala Arg Phe Ser Gly Ser Gly Ser Gly
465                 470                 475                 480

Thr Asp Tyr Ser Leu Thr Ile Asn Ser Leu Glu Ala Glu Asp Ala Ala
            485                 490                 495

Thr Tyr Tyr Cys Gln Gln Trp Ser Ser Asn Pro Leu Thr Phe Gly Gly
            500                 505                 510

Gly Thr Lys Val Glu Ile Lys His His His His His
            515                 520                 525
```

<210> SEQ ID NO 74
<211> LENGTH: 525
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Met Gly Trp Ser Cys Ile Ile Leu Phe Leu Val Ala Thr Ala Thr Gly
1               5                   10                  15

Lys Leu Asp Ile Val Met Thr Gln Ser Ala Pro Ser Val Pro Val Thr
            20                  25                  30

Pro Gly Glu Ser Val Ser Ile Ser Cys Arg Ser Ser Lys Ser Leu Leu
        35                  40                  45

His Ser Asn Gly Asn Thr Tyr Leu Tyr Trp Phe Leu Gln Lys Pro Gly
    50                  55                  60

Gln Ser Pro Gln Arg Leu Ile Tyr Tyr Met Ser Asn Leu Ala Ser Gly
65                  70                  75                  80

Val Pro Asp Arg Phe Ser Gly Arg Gly Ser Gly Thr Asp Phe Thr Leu
                85                  90                  95

Lys Ile Ser Arg Val Glu Ala Glu Asp Val Gly Val Tyr Tyr Cys Met
            100                 105                 110

Gln Ser Leu Glu Tyr Pro Leu Thr Phe Gly Gly Gly Thr Lys Leu Glu
        115                 120                 125

Ile Lys Arg Gly Gly Gly Ser Gly Gly Gly Ser Gly Gly Gly
    130                 135                 140

Gly Ser Gln Val Thr Leu Lys Glu Ser Gly Pro Thr Leu Val Lys Pro
145                 150                 155                 160

Thr Gln Thr Leu Thr Leu Thr Cys Thr Phe Ser Gly Phe Ser Leu Ser
                165                 170                 175

Thr Val Gly Met Gly Val Gly Trp Ser Arg Gln Pro Ser Gly Lys Gly
            180                 185                 190

Leu Glu Trp Leu Ala His Ile Trp Trp Asp Asp Glu Asp Lys Tyr Tyr
        195                 200                 205

Asn Pro Ala Leu Lys Ser Arg Leu Thr Ile Thr Lys Asp Thr Ser Lys
    210                 215                 220

Asn Gln Val Val Leu Thr Ile Thr Asn Val Asp Pro Val Asp Thr Ala
225                 230                 235                 240

Thr Tyr Tyr Cys Thr Arg Ile Gly Thr Ala Gln Ala Thr Asp Ala Leu
                245                 250                 255

Asp Tyr Trp Gly Gln Gly Thr Leu Val Thr Val Ser Ser Thr Ser Gly
            260                 265                 270

Gly Gly Gly Ser Asp Val Gln Leu Val Gln Ser Gly Ala Glu Val Lys
        275                 280                 285

Lys Pro Gly Ala Ser Val Lys Val Ser Cys Lys Ala Ser Gly Tyr Thr
    290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
                325                 330                 335

Ala Asp Ser Val Lys Gly Arg Phe Thr Ile Thr Thr Asp Lys Ser Thr
            340                 345                 350

Ser Thr Ala Tyr Met Glu Leu Ser Ser Leu Arg Ser Glu Asp Thr Ala
        355                 360                 365

Thr Tyr Tyr Cys Ala Arg Tyr Tyr Asp Asp His Tyr Cys Leu Asp Tyr
    370                 375                 380

Trp Gly Gln Gly Thr Thr Val Thr Val Ser Ser Gly Glu Gly Thr Ser
385                 390                 395                 400

```
Thr Gly Ser Gly Gly Ser Gly Gly Ser Gly Gly Ala Asp Asp Ile Val
            405             410             415

Leu Thr Gln Ser Pro Ala Thr Leu Ser Leu Ser Pro Gly Glu Arg Ala
            420             425             430

Thr Leu Ser Cys Arg Ala Ser Gln Ser Val Ser Tyr Met Asn Trp Tyr
            435             440             445

Gln Gln Lys Pro Gly Lys Ala Pro Lys Arg Trp Ile Tyr Asp Thr Ser
        450             455             460

Lys Val Ala Ser Gly Val Pro Ala Arg Phe Ser Gly Ser Gly Ser Gly
465             470             475             480

Thr Asp Tyr Ser Leu Thr Ile Asn Ser Leu Glu Ala Glu Asp Ala Ala
            485             490             495

Thr Tyr Tyr Cys Gln Gln Trp Ser Ser Asn Pro Leu Thr Phe Gly Gly
            500             505             510

Gly Thr Lys Val Glu Ile Lys His His His His His His
            515             520             525
```

```
<210> SEQ ID NO 75
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75
```

```
Met Gly Trp Ser Cys Ile Ile Leu Phe Leu Val Ala Thr Ala Thr Gly
1               5               10              15

Lys Leu Asp Ile Val Met Thr Gln Ser Ala Leu Ser Leu Pro Val Thr
            20              25              30

Pro Gly Glu Pro Val Ser Ile Ser Cys Arg Ser Ser Lys Ser Leu Leu
            35              40              45

His Ser Asn Gly Asn Thr Tyr Leu Tyr Trp Phe Leu Gln Lys Pro Gly
        50              55              60

Gln Ser Pro Gln Arg Leu Ile Tyr Tyr Met Ser Asn Leu Ala Ser Gly
65              70              75              80

Val Pro Asp Arg Phe Ser Gly Ser Gly Ser Gly Thr Asp Phe Thr Leu
            85              90              95

Lys Ile Ser Arg Val Glu Ala Glu Asp Val Gly Val Tyr Tyr Cys Met
            100             105             110

Gln Ser Leu Glu Tyr Pro Leu Thr Phe Gly Gly Gly Thr Lys Leu Glu
            115             120             125

Ile Lys Arg Gly Gly Gly Ser Gly Gly Gly Gly Ser Gly Gly Gly
        130             135             140

Gly Ser Gln Val Thr Leu Lys Glu Ser Gly Pro Thr Leu Val Lys Pro
145             150             155             160

Thr Gln Thr Leu Thr Leu Thr Cys Thr Phe Ser Gly Phe Ser Leu Ser
            165             170             175

Thr Val Gly Met Gly Val Gly Trp Ser Arg Gln Pro Ser Gly Lys Gly
            180             185             190

Leu Glu Trp Leu Ala His Ile Trp Trp Asp Asp Glu Asp Lys Tyr Tyr
            195             200             205

Asn Pro Ala Leu Lys Ser Arg Leu Thr Ile Thr Lys Asp Thr Ser Lys
        210             215             220

Asn Gln Val Val Leu Thr Ile Thr Asn Val Asp Pro Val Asp Thr Ala
225             230             235             240
```

```
Thr Tyr Tyr Cys Thr Arg Ile Gly Thr Ala Gln Ala Thr Asp Ala Leu
            245                 250                 255

Asp Tyr Trp Gly Gln Gly Thr Leu Val Thr Val Ser Ser Thr Ser Gly
            260                 265                 270

Gly Gly Gly Ser Asp Val Gln Leu Val Gln Ser Gly Ala Glu Val Lys
            275                 280                 285

Lys Pro Gly Ala Ser Val Lys Val Ser Cys Lys Ala Ser Gly Tyr Thr
     290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
            325                 330                 335

Ala Asp Ser Val Lys Gly Arg Phe Thr Ile Thr Thr Asp Lys Ser Thr
            340                 345                 350

Ser Thr Ala Tyr Met Glu Leu Ser Ser Leu Arg Ser Glu Asp Thr Ala
            355                 360                 365

Thr Tyr Tyr Cys Ala Arg Tyr Tyr Asp Asp His Tyr Cys Leu Asp Tyr
     370                 375                 380

Trp Gly Gln Gly Thr Thr Val Thr Val Ser Ser Gly Glu Gly Thr Ser
385                 390                 395                 400

Thr Gly Ser Gly Gly Ser Gly Gly Ser Gly Gly Ala Asp Asp Ile Val
            405                 410                 415

Leu Thr Gln Ser Pro Ala Thr Leu Ser Leu Ser Pro Gly Glu Arg Ala
            420                 425                 430

Thr Leu Ser Cys Arg Ala Ser Gln Ser Val Ser Tyr Met Asn Trp Tyr
            435                 440                 445

Gln Gln Lys Pro Gly Lys Ala Pro Lys Arg Trp Ile Tyr Asp Thr Ser
     450                 455                 460

Lys Val Ala Ser Gly Val Pro Ala Arg Phe Ser Gly Ser Gly Ser Gly
465                 470                 475                 480

Thr Asp Tyr Ser Leu Thr Ile Asn Ser Leu Glu Ala Glu Asp Ala Ala
            485                 490                 495

Thr Tyr Tyr Cys Gln Gln Trp Ser Ser Asn Pro Leu Thr Phe Gly Gly
            500                 505                 510

Gly Thr Lys Val Glu Ile Lys His His His His His His
            515                 520                 525
```

```
<210> SEQ ID NO 76
<211> LENGTH: 18
<212> TYPE: PRT
<213> ORGANISM: Unknown
<220> FEATURE:
<223> OTHER INFORMATION: Description of Unknown:
      CD8 signal sequence

<400> SEQUENCE: 76

Met Ala Leu Pro Val Thr Ala Leu Leu Leu Pro Leu Ala Leu Leu Leu
1               5                   10                  15

His Ala

<210> SEQ ID NO 77
<211> LENGTH: 71
<212> TYPE: PRT
<213> ORGANISM: Unknown
<220> FEATURE:
<223> OTHER INFORMATION: Description of Unknown:
      CD8 transmembrane sequence
```

<400> SEQUENCE: 77

Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
                20                  25                  30

Gly Gly Ala Val His Thr Arg Gly Leu Asp Phe Ala Cys Asp Ile Tyr
            35                  40                  45

Ile Trp Ala Pro Leu Ala Gly Thr Cys Gly Val Leu Leu Leu Ser Leu
        50                  55                  60

Val Ile Thr Leu Tyr Cys Asn
65                  70

<210> SEQ ID NO 78
<211> LENGTH: 42
<212> TYPE: PRT
<213> ORGANISM: Unknown
<220> FEATURE:
<223> OTHER INFORMATION: Description of Unknown:
      41BB costimulatory domain

<400> SEQUENCE: 78

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 79
<211> LENGTH: 112
<212> TYPE: PRT
<213> ORGANISM: Unknown
<220> FEATURE:
<223> OTHER INFORMATION: Description of Unknown:
      CD3 zeta chain

<400> SEQUENCE: 79

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 80
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 80

Met Ala Leu Pro Val Thr Ala Leu Leu Leu Pro Leu Ala Leu Leu Leu
1               5                   10                  15

His Ala Asp Ile Glu Leu Thr Gln Ser Pro Ser Ser Leu Ala Val Ser
            20                  25                  30

Ala Gly Glu Arg Val Thr Met Asn Cys Lys Ser Ser Gln Ser Leu Leu
        35                  40                  45

Asn Ser Arg Thr Arg Lys Asn Gln Leu Ala Trp Tyr Gln Gln Lys Pro
    50                  55                  60

Gly Gln Ser Pro Glu Leu Leu Ile Tyr Trp Ala Ser Thr Arg Gln Ser
65                  70                  75                  80

Gly Val Pro Asp Arg Phe Ser Gly Ser Gly Ser Gly Thr Asp Phe Thr
                85                  90                  95

Leu Thr Ile Ser Ser Val Gln Ala Glu Asp Val Ala Val Tyr Tyr Cys
            100                 105                 110

Gln Gln Ser Tyr Asn Leu Leu Thr Phe Gly Pro Gly Thr Lys Leu Glu
        115                 120                 125

Ile Lys Arg Gly Gly Gly Gly Ser Gly Gly Gly Gly Ser Gly Gly Gly
    130                 135                 140

Gly Ser Glu Val Lys Leu Gln Glu Ser Gly Gly Gly Phe Val Lys Pro
145                 150                 155                 160

Gly Gly Ser Leu Arg Val Ser Cys Ala Ala Ser Gly Phe Thr Phe Ser
                165                 170                 175

Ser Tyr Ala Met Ser Trp Val Arg Leu Ala Pro Glu Met Arg Leu Glu
            180                 185                 190

Trp Val Ala Thr Ile Ser Ser Ala Gly Gly Tyr Ile Phe Tyr Ser Asp
        195                 200                 205

Ser Val Gln Gly Arg Phe Thr Ile Ser Arg Asp Asn Ala Lys Asn Ser
    210                 215                 220

Leu His Leu Gln Met Gly Ser Leu Arg Ser Gly Asp Thr Ala Met Tyr
225                 230                 235                 240

Tyr Cys Ala Arg Gln Gly Phe Gly Asn Tyr Gly Asp Tyr Tyr Ala Met
                245                 250                 255

Asp Tyr Trp Gly Gln Gly Thr Thr Val Thr Val Ser Ser Ala Ala Ala
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Asn Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415
```

-continued

```
Tyr Asp Val Leu Asp Lys Arg Arg Gly Arg Asp Pro Glu Met Gly Gly
            420             425             430

Lys Pro Arg Arg Lys Asn Pro Gln Glu Gly Leu Tyr Asn Glu Leu Gln
            435             440             445

Lys Asp Lys Met Ala Glu Ala Tyr Ser Glu Ile Gly Met Lys Gly Glu
            450             455             460

Arg Arg Arg Gly Lys Gly His Asp Gly Leu Tyr Gln Gly Leu Ser Thr
465             470             475             480

Ala Thr Lys Asp Thr Tyr Asp Ala Leu His Met Gln Ala Leu Pro Pro
                485             490             495

Arg
```

<210> SEQ ID NO 81
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Met Ala Leu Pro Val Thr Ala Leu Leu Leu Pro Leu Ala Leu Leu Leu
1               5               10              15

His Ala Glu Val Lys Leu Gln Glu Ser Gly Gly Gly Phe Val Lys Pro
                20              25              30

Gly Gly Ser Leu Arg Val Ser Cys Ala Ala Ser Gly Phe Thr Phe Ser
            35              40              45

Ser Tyr Ala Met Ser Trp Val Arg Leu Ala Pro Glu Met Arg Leu Glu
    50              55              60

Trp Val Ala Thr Ile Ser Ser Ala Gly Gly Tyr Ile Phe Tyr Ser Asp
65              70              75              80

Ser Val Gln Gly Arg Phe Thr Ile Ser Arg Asp Asn Ala Lys Asn Ser
                85              90              95

Leu His Leu Gln Met Gly Ser Leu Arg Ser Gly Asp Thr Ala Met Tyr
                100             105             110

Tyr Cys Ala Arg Gln Gly Phe Gly Asn Tyr Gly Asp Tyr Tyr Ala Met
            115             120             125

Asp Tyr Trp Gly Gln Gly Thr Thr Val Thr Val Ser Ser Gly Gly Gly
    130             135             140

Gly Ser Gly Gly Gly Gly Ser Gly Gly Gly Gly Ser Asp Ile Val Leu
145             150             155             160

Thr Gln Ser Pro Asp Ser Leu Ala Val Ser Leu Gly Glu Arg Val Thr
                165             170             175

Met Asn Cys Lys Ser Ser Gln Ser Leu Leu Asn Ser Arg Thr Arg Lys
                180             185             190

Asn Gln Leu Ala Trp Tyr Gln Gln Lys Pro Gly Gln Ser Pro Glu Leu
            195             200             205

Leu Ile Tyr Trp Ala Ser Thr Arg Gln Ser Gly Val Pro Asp Arg Phe
    210             215             220

Ser Gly Ser Gly Ser Gly Thr Asp Phe Thr Leu Thr Ile Ser Ser Val
225             230             235             240

Gln Ala Glu Asp Val Ala Val Tyr Tyr Cys Gln Gln Ser Tyr Asn Leu
                245             250             255

Leu Thr Phe Gly Gln Gly Thr Lys Leu Glu Ile Lys Arg Ala Ala Ala
            260             265             270
```

```
Pro Thr Thr Thr Pro Ala Pro Arg Pro Pro Thr Pro Ala Pro Thr Ile
    275             280             285

Ala Ser Gln Pro Leu Ser Leu Arg Pro Glu Ala Cys Arg Pro Ala Ala
    290             295             300

Gly Gly Ala Val His Thr Arg Gly Leu Asp Phe Ala Cys Asp Ile Tyr
305             310             315             320

Ile Trp Ala Pro Leu Ala Gly Thr Cys Gly Val Leu Leu Leu Ser Leu
            325             330             335

Val Ile Thr Leu Tyr Cys Asn Lys Arg Gly Arg Lys Lys Leu Leu Tyr
            340             345             350

Ile Phe Lys Gln Pro Phe Met Arg Pro Val Gln Thr Thr Gln Glu Glu
            355             360             365

Asp Gly Cys Ser Cys Arg Phe Pro Glu Glu Glu Glu Gly Gly Cys Glu
    370             375             380

Leu Arg Val Lys Phe Ser Arg Ser Ala Asp Ala Pro Ala Tyr Gln Gln
385             390             395             400

Gly Gln Asn Gln Leu Tyr Asn Glu Leu Asn Leu Gly Arg Arg Glu Glu
            405             410             415

Tyr Asp Val Leu Asp Lys Arg Arg Gly Arg Asp Pro Glu Met Gly Gly
            420             425             430

Lys Pro Arg Arg Lys Asn Pro Gln Glu Gly Leu Tyr Asn Glu Leu Gln
            435             440             445

Lys Asp Lys Met Ala Glu Ala Tyr Ser Glu Ile Gly Met Lys Gly Glu
    450             455             460

Arg Arg Arg Gly Lys Gly His Asp Gly Leu Tyr Gln Gly Leu Ser Thr
465             470             475             480

Ala Thr Lys Asp Thr Tyr Asp Ala Leu His Met Gln Ala Leu Pro Pro
            485             490             495

Arg
```

```
<210> SEQ ID NO 82
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Ala Leu Pro Val Thr Ala Leu Leu Leu Pro Leu Ala Leu Leu Leu
1               5               10              15

His Ala Glu Val Gln Leu Val Glu Ser Gly Gly Gly Leu Val Lys Pro
            20              25              30

Gly Gly Ser Leu Arg Val Ser Cys Ala Ala Ser Gly Phe Thr Phe Ser
            35              40              45

Ser Tyr Ala Met Ser Trp Val Arg Leu Ala Pro Gly Lys Gly Leu Glu
    50              55              60

Trp Val Ala Thr Ile Ser Ser Ala Gly Gly Tyr Ile Phe Tyr Ser Asp
65              70              75              80

Ser Val Gln Gly Arg Phe Thr Ile Ser Arg Asp Asn Ala Lys Asn Ser
            85              90              95

Leu Tyr Leu Gln Met Asn Ser Leu Arg Ala Glu Asp Thr Ala Met Tyr
            100             105             110

Tyr Cys Ala Arg Gln Gly Phe Gly Asn Tyr Gly Asp Tyr Tyr Ala Met
            115             120             125
```

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Glu Leu
145                 150                 155                 160

Thr Gln Ser Pro Ser Ser Leu Ala Val Ser Ala Gly Glu Arg Val Thr
                165                 170                 175

Met Asn Cys Lys Ser Ser Gln Ser Leu Leu Asn Ser Arg Thr Arg Lys
            180                 185                 190

Asn Gln Leu Ala Trp Tyr Gln Gln Lys Pro Gly Gln Ser Pro Glu Leu
        195                 200                 205

Leu Ile Tyr Trp Ala Ser Thr Arg Gln Ser Gly Val Pro Asp Arg Phe
    210                 215                 220

Ser Gly Ser Gly Ser Gly Thr Asp Phe Thr Leu Thr Ile Ser Ser Val
225                 230                 235                 240

Gln Ala Glu Asp Val Ala Val Tyr Tyr Cys Gln Gln Ser Tyr Asn Leu
                245                 250                 255

Leu Thr Phe Gly Pro Gly Thr Lys Leu Glu Ile Lys Arg Ala Ala Ala
            260                 265                 270

Pro Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Asn Lys Arg Gly Arg Lys Lys Leu Leu Tyr
            340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 83
<211> LENGTH: 497
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 83

```
Met Ala Leu Pro Val Thr Ala Leu Leu Leu Pro Leu Ala Leu Leu Leu
1               5                   10                  15

His Ala Glu Val Gln Leu Val Glu Ser Gly Gly Gly Leu Val Lys Pro
                20                  25                  30

Gly Gly Ser Leu Arg Val Ser Cys Ala Ala Ser Gly Phe Thr Phe Ser
            35                  40                  45

Ser Tyr Ala Met Ser Trp Val Arg Leu Ala Pro Gly Lys Gly Leu Glu
        50                  55                  60

Trp Val Ala Thr Ile Ser Ser Ala Gly Gly Tyr Ile Phe Tyr Ser Asp
65                  70                  75                  80

Ser Val Gln Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Met Tyr
            100                 105                 110

Tyr Cys Ala Arg Gln Gly Phe Gly Asn Tyr Gly Asp Tyr Tyr Ala Met
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Val Leu
145                 150                 155                 160

Thr Gln Ser Pro Asp Ser Leu Ala Val Ser Leu Gly Glu Arg Val Thr
                165                 170                 175

Met Asn Cys Lys Ser Ser Gln Ser Leu Leu Asn Ser Arg Thr Arg Lys
            180                 185                 190

Asn Gln Leu Ala Trp Tyr Gln Gln Lys Pro Gly Gln Ser Pro Glu Leu
        195                 200                 205

Leu Ile Tyr Trp Ala Ser Thr Arg Gln Ser Gly Val Pro Asp Arg Phe
    210                 215                 220

Ser Gly Ser Gly Ser Gly Thr Asp Phe Thr Leu Thr Ile Ser Ser Val
225                 230                 235                 240

Gln Ala Glu Asp Val Ala Val Tyr Tyr Cys Gln Gln Ser Tyr Asn Leu
                245                 250                 255

Leu Thr Phe Gly Gln Gly Thr Lys Leu Glu Ile Lys Arg Ala Ala Ala
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Asn Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400
```

-continued

```
Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
        450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 84
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Met Ala Leu Pro Val Thr Ala Leu Leu Leu Pro Leu Ala Leu Leu Leu
1               5                   10                  15

His Ala Gln Val Thr Leu Lys Glu Ser Gly Pro Gly Ile Leu Gln Pro
                20                  25                  30

Thr Gln Thr Leu Thr Leu Thr Cys Thr Phe Ser Gly Phe Ser Leu Ser
            35                  40                  45

Thr Val Gly Met Gly Val Gly Trp Ser Arg Gln Pro Ser Gly Lys Gly
        50                  55                  60

Leu Glu Trp Leu Ala His Ile Trp Trp Asp Asp Glu Asp Lys Tyr Tyr
65                  70                  75                  80

Asn Pro Ala Leu Lys Ser Arg Leu Thr Ile Thr Lys Asp Thr Ser Lys
                85                  90                  95

Asn Gln Val Phe Leu Lys Ile Thr Asn Val Asp Thr Ala Asp Thr Ala
                100                 105                 110

Thr Tyr Tyr Cys Thr Arg Ile Gly Thr Ala Gln Ala Thr Asp Ala Leu
            115                 120                 125

Asp Tyr Trp Gly Gln Gly Thr Leu Val Thr Val Ser Ser Gly Gly Gly
        130                 135                 140

Gly Ser Gly Gly Gly Gly Ser Gly Gly Gly Gly Ser Asp Ile Val Met
145                 150                 155                 160

Thr Gln Ser Ala Pro Ser Val Pro Val Thr Pro Gly Glu Ser Val Ser
                165                 170                 175

Ile Ser Cys Arg Ser Ser Lys Ser Leu Leu His Ser Asn Gly Asn Thr
                180                 185                 190

Tyr Leu Tyr Trp Phe Leu Gln Lys Pro Gly Gln Ser Pro Gln Arg Leu
            195                 200                 205

Ile Tyr Tyr Met Ser Asn Leu Ala Ser Gly Val Pro Asp Arg Phe Ser
        210                 215                 220

Gly Arg Gly Ser Gly Thr Asp Phe Thr Leu Lys Ile Ser Arg Val Glu
225                 230                 235                 240

Ala Glu Asp Val Gly Val Tyr Tyr Cys Met Gln Ser Leu Glu Tyr Pro
                245                 250                 255
```

Leu Thr Phe Gly Gly Gly Thr Lys Leu Glu Ile Lys Arg Ala Ala Ala
260 265 270

Pro Thr Thr Thr Pro Ala Pro Arg Pro Pro Thr Pro Ala Pro Thr Ile
275 280 285

Ala Ser Gln Pro Leu Ser Leu Arg Pro Glu Ala Cys Arg Pro Ala Ala
290 295 300

Gly Gly Ala Val His Thr Arg Gly Leu Asp Phe Ala Cys Asp Ile Tyr
305 310 315 320

Ile Trp Ala Pro Leu Ala Gly Thr Cys Gly Val Leu Leu Leu Ser Leu
325 330 335

Val Ile Thr Leu Tyr Cys Asn Lys Arg Gly Arg Lys Leu Leu Tyr
340 345 350

Ile Phe Lys Gln Pro Phe Met Arg Pro Val Gln Thr Thr Gln Glu Glu
355 360 365

Asp Gly Cys Ser Cys Arg Phe Pro Glu Glu Glu Glu Gly Gly Cys Glu
370 375 380

Leu Arg Val Lys Phe Ser Arg Ser Ala Asp Ala Pro Ala Tyr Gln Gln
385 390 395 400

Gly Gln Asn Gln Leu Tyr Asn Glu Leu Asn Leu Gly Arg Arg Glu Glu
405 410 415

Tyr Asp Val Leu Asp Lys Arg Arg Gly Arg Asp Pro Glu Met Gly Gly
420 425 430

Lys Pro Arg Arg Lys Asn Pro Gln Glu Gly Leu Tyr Asn Glu Leu Gln
435 440 445

Lys Asp Lys Met Ala Glu Ala Tyr Ser Glu Ile Gly Met Lys Gly Glu
450 455 460

Arg Arg Arg Gly Lys Gly His Asp Gly Leu Tyr Gln Gly Leu Ser Thr
465 470 475 480

Ala Thr Lys Asp Thr Tyr Asp Ala Leu His Met Gln Ala Leu Pro Pro
485 490 495

Arg

<210> SEQ ID NO 85
<211> LENGTH: 497
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 85

Met Ala Leu Pro Val Thr Ala Leu Leu Leu Pro Leu Ala Leu Leu Leu
1 5 10 15

His Ala Gln Val Thr Leu Lys Glu Ser Gly Pro Gly Ile Leu Gln Pro
20 25 30

Thr Gln Thr Leu Thr Leu Thr Cys Thr Phe Ser Gly Phe Ser Leu Ser
35 40 45

Thr Val Gly Met Gly Val Gly Trp Ser Arg Gln Pro Ser Gly Lys Gly
50 55 60

Leu Glu Trp Leu Ala His Ile Trp Trp Asp Asp Glu Asp Lys Tyr Tyr
65 70 75 80

Asn Pro Ala Leu Lys Ser Arg Leu Thr Ile Thr Lys Asp Thr Ser Lys
85 90 95

Asn Gln Val Phe Leu Lys Ile Thr Asn Val Asp Thr Ala Asp Thr Ala
100 105 110

-continued

```
Thr Tyr Tyr Cys Thr Arg Ile Gly Thr Ala Gln Ala Thr Asp Ala Leu
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Ala Leu Ser Leu Pro Val Thr Pro Gly Glu Pro Val Ser
                165                 170                 175

Ile Ser Cys Arg Ser Ser Lys Ser Leu Leu His Ser Asn Gly Asn Thr
                180                 185                 190

Tyr Leu Tyr Trp Phe Leu Gln Lys Pro Gly Gln Ser Pro Gln Arg Leu
            195                 200                 205

Ile Tyr Tyr Met Ser Asn Leu Ala Ser Gly Val Pro Asp Arg Phe Ser
        210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Met Gln Ser Leu Glu Tyr Pro
                245                 250                 255

Leu Thr Phe Gly Gly Gly Thr Lys Leu Glu Ile Lys Arg Ala Ala Ala
                260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Asn Lys Arg Gly Arg Lys Lys Leu Leu Tyr
            340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Glu Gly Gly Cys Glu
        370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
        450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 86
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Met Ala Leu Pro Val Thr Ala Leu Leu Leu Pro Leu Ala Leu Leu Leu
1               5                   10                  15

His Ala Gln Val Thr Leu Lys Glu Ser Gly Pro Thr Leu Val Lys Pro
            20                  25                  30

Thr Gln Thr Leu Thr Leu Thr Cys Thr Phe Ser Gly Phe Ser Leu Ser
        35                  40                  45

Thr Val Gly Met Gly Val Gly Trp Ser Arg Gln Pro Ser Gly Lys Gly
    50                  55                  60

Leu Glu Trp Leu Ala His Ile Trp Trp Asp Asp Glu Asp Lys Tyr Tyr
65                  70                  75                  80

Asn Pro Ala Leu Lys Ser Arg Leu Thr Ile Thr Lys Asp Thr Ser Lys
                85                  90                  95

Asn Gln Val Val Leu Thr Ile Thr Asn Val Asp Pro Val Asp Thr Ala
            100                 105                 110

Thr Tyr Tyr Cys Thr Arg Ile Gly Thr Ala Gln Ala Thr Asp Ala Leu
            115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Ala Pro Ser Val Pro Val Thr Pro Gly Glu Ser Val Ser
                165                 170                 175

Ile Ser Cys Arg Ser Ser Lys Ser Leu Leu His Ser Asn Gly Asn Thr
            180                 185                 190

Tyr Leu Tyr Trp Phe Leu Gln Lys Pro Gly Gln Ser Pro Gln Arg Leu
            195                 200                 205

Ile Tyr Tyr Met Ser Asn Leu Ala Ser Gly Val Pro Asp Arg Phe Ser
    210                 215                 220

Gly Arg Gly Ser Gly Thr Asp Phe Thr Leu Lys Ile Ser Arg Val Glu
225                 230                 235                 240

Ala Glu Asp Val Gly Val Tyr Tyr Cys Met Gln Ser Leu Glu Tyr Pro
                245                 250                 255

Leu Thr Phe Gly Gly Gly Thr Lys Leu Glu Ile Lys Arg Ala Ala Ala
            260                 265                 270

Pro Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
            325                 330                 335

Val Ile Thr Leu Tyr Cys Asn Lys Arg Gly Arg Lys Lys Leu Leu Tyr
            340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
```

-continued

```
385                 390                 395                 400

Gly Gln Asn Gln Leu Tyr Asn Glu Leu Asn Leu Gly Arg Arg Glu Glu
            405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 87
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Met Ala Leu Pro Val Thr Ala Leu Leu Leu Pro Leu Ala Leu Leu Leu
1               5                   10                  15

His Ala Gln Val Thr Leu Lys Glu Ser Gly Pro Thr Leu Val Lys Pro
                20                  25                  30

Thr Gln Thr Leu Thr Leu Thr Cys Thr Phe Ser Gly Phe Ser Leu Ser
        35                  40                  45

Thr Val Gly Met Gly Val Gly Trp Ser Arg Gln Pro Ser Gly Lys Gly
    50                  55                  60

Leu Glu Trp Leu Ala His Ile Trp Trp Asp Asp Glu Asp Lys Tyr Tyr
65                  70                  75                  80

Asn Pro Ala Leu Lys Ser Arg Leu Thr Ile Thr Lys Asp Thr Ser Lys
                85                  90                  95

Asn Gln Val Val Leu Thr Ile Thr Asn Val Asp Pro Val Asp Thr Ala
                100                 105                 110

Thr Tyr Tyr Cys Thr Arg Ile Gly Thr Ala Gln Ala Thr Asp Ala Leu
            115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Ala Leu Ser Leu Pro Val Thr Pro Gly Glu Pro Val Ser
                165                 170                 175

Ile Ser Cys Arg Ser Ser Lys Ser Leu Leu His Ser Asn Gly Asn Thr
                180                 185                 190

Tyr Leu Tyr Trp Phe Leu Gln Lys Pro Gly Gln Ser Pro Gln Arg Leu
            195                 200                 205

Ile Tyr Tyr Met Ser Asn Leu Ala Ser Gly Val Pro Asp Arg Phe Ser
    210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Met Gln Ser Leu Glu Tyr Pro
```

-continued

```
              245              250              255
Leu Thr Phe Gly Gly Gly Thr Lys Leu Glu Ile Lys Arg Ala Ala Ala
              260              265              270

Pro Thr Thr Thr Pro Ala Pro Arg Pro Pro Thr Pro Ala Pro Thr Ile
              275              280              285

Ala Ser Gln Pro Leu Ser Leu Arg Pro Glu Ala Cys Arg Pro Ala Ala
              290              295              300

Gly Gly Ala Val His Thr Arg Gly Leu Asp Phe Ala Cys Asp Ile Tyr
305              310              315              320

Ile Trp Ala Pro Leu Ala Gly Thr Cys Gly Val Leu Leu Leu Ser Leu
              325              330              335

Val Ile Thr Leu Tyr Cys Asn Lys Arg Gly Arg Lys Lys Leu Leu Tyr
              340              345              350

Ile Phe Lys Gln Pro Phe Met Arg Pro Val Gln Thr Thr Gln Glu Glu
              355              360              365

Asp Gly Cys Ser Cys Arg Phe Pro Glu Glu Glu Glu Gly Gly Cys Glu
              370              375              380

Leu Arg Val Lys Phe Ser Arg Ser Ala Asp Ala Pro Ala Tyr Gln Gln
385              390              395              400

Gly Gln Asn Gln Leu Tyr Asn Glu Leu Asn Leu Gly Arg Arg Glu Glu
              405              410              415

Tyr Asp Val Leu Asp Lys Arg Arg Gly Arg Asp Pro Glu Met Gly Gly
              420              425              430

Lys Pro Arg Arg Lys Asn Pro Gln Glu Gly Leu Tyr Asn Glu Leu Gln
              435              440              445

Lys Asp Lys Met Ala Glu Ala Tyr Ser Glu Ile Gly Met Lys Gly Glu
              450              455              460

Arg Arg Arg Gly Lys Gly His Asp Gly Leu Tyr Gln Gly Leu Ser Thr
465              470              475              480

Ala Thr Lys Asp Thr Tyr Asp Ala Leu His Met Gln Ala Leu Pro Pro
              485              490              495

Arg
```

```
<210> SEQ ID NO 88
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88
```

```
Met Gly Trp Ser Cys Ile Ile Leu Phe Leu Val Ala Thr Ala Thr Gly
1               5               10              15

Lys Leu Glu Val Lys Leu Gln Glu Ser Gly Gly Gly Phe Val Lys Pro
              20              25              30

Gly Gly Ser Leu Arg Val Ser Cys Ala Ala Ser Gly Phe Thr Phe Ser
              35              40              45

Ser Tyr Ala Met Ser Trp Val Arg Leu Ala Pro Glu Met Arg Leu Glu
              50              55              60

Trp Val Ala Thr Ile Ser Ser Ala Gly Gly Tyr Ile Phe Tyr Ser Asp
65              70              75              80

Ser Val Gln Gly Arg Phe Thr Ile Ser Arg Asp Asn Ala Lys Asn Ser
              85              90              95

Leu His Leu Gln Met Gly Ser Leu Arg Ser Gly Asp Thr Ala Met Tyr
```

-continued

```
                100              105             110

Tyr Cys Ala Arg Gln Gly Phe Gly Asn Tyr Gly Asp Tyr Tyr Ala Met
            115             120             125

Asp Tyr Trp Gly Gln Gly Thr Thr Val Thr Val Ser Ser Gly Gly Gly
    130             135             140

Gly Ser Gly Gly Gly Gly Ser Gly Gly Gly Ser Asp Ile Glu Leu
145             150             155             160

Thr Gln Ser Pro Ser Ser Leu Ala Val Ser Ala Gly Glu Arg Val Thr
            165             170             175

Met Asn Cys Lys Ser Ser Gln Ser Leu Leu Asn Ser Arg Thr Arg Lys
            180             185             190

Asn Gln Leu Ala Trp Tyr Gln Gln Lys Pro Gly Gln Ser Pro Glu Leu
    195             200             205

Leu Ile Tyr Trp Ala Ser Thr Arg Gln Ser Gly Val Pro Asp Arg Phe
    210             215             220

Ser Gly Ser Gly Ser Gly Thr Asp Phe Thr Leu Thr Ile Ser Ser Val
225             230             235             240

Gln Ala Glu Asp Val Ala Val Tyr Tyr Cys Gln Gln Ser Tyr Asn Leu
            245             250             255

Leu Thr Phe Gly Pro Gly Thr Lys Leu Glu Ile Lys Arg Thr Ser Gly
            260             265             270

Gly Gly Gly Ser Asp Val Gln Leu Val Gln Ser Gly Ala Glu Val Lys
            275             280             285

Lys Pro Gly Ala Ser Val Lys Val Ser Cys Lys Ala Ser Gly Tyr Thr
    290             295             300

Phe Thr Arg Tyr Thr Met His Trp Val Arg Gln Ala Pro Gly Gln Gly
305             310             315             320

Leu Glu Trp Ile Gly Tyr Ile Asn Pro Ser Arg Gly Tyr Thr Asn Tyr
            325             330             335

Ala Asp Ser Val Lys Gly Arg Phe Thr Ile Thr Thr Asp Lys Ser Thr
            340             345             350

Ser Thr Ala Tyr Met Glu Leu Ser Ser Leu Arg Ser Glu Asp Thr Ala
            355             360             365

Thr Tyr Tyr Cys Ala Arg Tyr Tyr Asp Asp His Tyr Cys Leu Asp Tyr
    370             375             380

Trp Gly Gln Gly Thr Thr Val Thr Val Ser Ser Gly Glu Gly Thr Ser
385             390             395             400

Thr Gly Ser Gly Gly Ser Gly Gly Ser Gly Gly Ala Asp Asp Ile Val
            405             410             415

Leu Thr Gln Ser Pro Ala Thr Leu Ser Leu Ser Pro Gly Glu Arg Ala
            420             425             430

Thr Leu Ser Cys Arg Ala Ser Gln Ser Val Ser Tyr Met Asn Trp Tyr
            435             440             445

Gln Gln Lys Pro Gly Lys Ala Pro Lys Arg Trp Ile Tyr Asp Thr Ser
    450             455             460

Lys Val Ala Ser Gly Val Pro Ala Arg Phe Ser Gly Ser Gly Ser Gly
465             470             475             480

Thr Asp Tyr Ser Leu Thr Ile Asn Ser Leu Glu Ala Glu Asp Ala Ala
            485             490             495

Thr Tyr Tyr Cys Gln Gln Trp Ser Ser Asn Pro Leu Thr Phe Gly Gly
            500             505             510

Gly Thr Lys Val Glu Ile Lys His His His His His
            515             520             525
```

-continued

```
<210> SEQ ID NO 89
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Met Gly Trp Ser Cys Ile Ile Leu Phe Leu Val Ala Thr Ala Thr Gly
1               5                   10                  15

Lys Leu Glu Val Lys Leu Gln Glu Ser Gly Gly Gly Phe Val Lys Pro
            20                  25                  30

Gly Gly Ser Leu Arg Val Ser Cys Ala Ala Ser Gly Phe Thr Phe Ser
        35                  40                  45

Ser Tyr Ala Met Ser Trp Val Arg Leu Ala Pro Glu Met Arg Leu Glu
    50                  55                  60

Trp Val Ala Thr Ile Ser Ser Ala Gly Gly Tyr Ile Phe Tyr Ser Asp
65                  70                  75                  80

Ser Val Gln Gly Arg Phe Thr Ile Ser Arg Asp Asn Ala Lys Asn Ser
                85                  90                  95

Leu His Leu Gln Met Gly Ser Leu Arg Ser Gly Asp Thr Ala Met Tyr
            100                 105                 110

Tyr Cys Ala Arg Gln Gly Phe Gly Asn Tyr Gly Asp Tyr Tyr Ala Met
            115                 120                 125

Asp Tyr Trp Gly Gln Gly Thr Thr Val Thr Val Ser Ser Gly Gly Gly
        130                 135                 140

Gly Ser Gly Gly Gly Gly Ser Gly Gly Gly Gly Ser Asp Ile Val Leu
145                 150                 155                 160

Thr Gln Ser Pro Asp Ser Leu Ala Val Ser Leu Gly Glu Arg Val Thr
                165                 170                 175

Met Asn Cys Lys Ser Ser Gln Ser Leu Leu Asn Ser Arg Thr Arg Lys
            180                 185                 190

Asn Gln Leu Ala Trp Tyr Gln Gln Lys Pro Gly Gln Ser Pro Glu Leu
            195                 200                 205

Leu Ile Tyr Trp Ala Ser Thr Arg Gln Ser Gly Val Pro Asp Arg Phe
        210                 215                 220

Ser Gly Ser Gly Ser Gly Thr Asp Phe Thr Leu Thr Ile Ser Ser Val
225                 230                 235                 240

Gln Ala Glu Asp Val Ala Val Tyr Tyr Cys Gln Gln Ser Tyr Asn Leu
                245                 250                 255

Leu Thr Phe Gly Gln Gly Thr Lys Leu Glu Ile Lys Arg Thr Ser Gly
            260                 265                 270

Gly Gly Gly Ser Asp Val Gln Leu Val Gln Ser Gly Ala Glu Val Lys
        275                 280                 285

Lys Pro Gly Ala Ser Val Lys Val Ser Cys Lys Ala Ser Gly Tyr Thr
    290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
                325                 330                 335

Ala Asp Ser Val Lys Gly Arg Phe Thr Ile Thr Thr Asp Lys Ser Thr
            340                 345                 350

Ser Thr Ala Tyr Met Glu Leu Ser Ser Leu Arg Ser Glu Asp Thr Ala
```

-continued

```
                355                 360                 365
Thr Tyr Tyr Cys Ala Arg Tyr Tyr Asp Asp His Tyr Cys Leu Asp Tyr
    370                 375                 380

Trp Gly Gln Gly Thr Thr Val Thr Val Ser Ser Gly Glu Gly Thr Ser
385                 390                 395                 400

Thr Gly Ser Gly Gly Ser Gly Gly Ser Gly Ala Asp Asp Ile Val
                405                 410                 415

Leu Thr Gln Ser Pro Ala Thr Leu Ser Leu Ser Pro Gly Glu Arg Ala
                420                 425                 430

Thr Leu Ser Cys Arg Ala Ser Gln Ser Val Ser Tyr Met Asn Trp Tyr
                435                 440                 445

Gln Gln Lys Pro Gly Lys Ala Pro Lys Arg Trp Ile Tyr Asp Thr Ser
    450                 455                 460

Lys Val Ala Ser Gly Val Pro Ala Arg Phe Ser Gly Ser Gly Ser Gly
465                 470                 475                 480

Thr Asp Tyr Ser Leu Thr Ile Asn Ser Leu Glu Ala Glu Asp Ala Ala
                485                 490                 495

Thr Tyr Tyr Cys Gln Gln Trp Ser Ser Asn Pro Leu Thr Phe Gly Gly
                500                 505                 510

Gly Thr Lys Val Glu Ile Lys His His His His His His
                515                 520                 525

<210> SEQ ID NO 90
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Gly Trp Ser Cys Ile Ile Leu Phe Leu Val Ala Thr Ala Thr Gly
1               5                   10                  15

Lys Leu Glu Val Gln Leu Val Glu Ser Gly Gly Gly Leu Val Lys Pro
                20                  25                  30

Gly Gly Ser Leu Arg Val Ser Cys Ala Ala Ser Gly Phe Thr Phe Ser
            35                  40                  45

Ser Tyr Ala Met Ser Trp Val Arg Leu Ala Pro Gly Lys Gly Leu Glu
    50                  55                  60

Trp Val Ala Thr Ile Ser Ser Ala Gly Gly Tyr Ile Phe Tyr Ser Asp
65                  70                  75                  80

Ser Val Gln Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Met Tyr
                100                 105                 110

Tyr Cys Ala Arg Gln Gly Phe Gly Asn Tyr Gly Asp Tyr Tyr Ala Met
            115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Ser Asp Ile Glu Leu
145                 150                 155                 160

Thr Gln Ser Pro Ser Ser Leu Ala Val Ser Ala Gly Glu Arg Val Thr
                165                 170                 175

Met Asn Cys Lys Ser Ser Gln Ser Leu Leu Asn Ser Arg Thr Arg Lys
            180                 185                 190
```

-continued

```
Asn Gln Leu Ala Trp Tyr Gln Gln Lys Pro Gly Gln Ser Pro Glu Leu
        195                 200                 205

Leu Ile Tyr Trp Ala Ser Thr Arg Gln Ser Gly Val Pro Asp Arg Phe
        210                 215                 220

Ser Gly Ser Gly Ser Gly Thr Asp Phe Thr Leu Thr Ile Ser Ser Val
225                 230                 235                 240

Gln Ala Glu Asp Val Ala Val Tyr Tyr Cys Gln Gln Ser Tyr Asn Leu
                245                 250                 255

Leu Thr Phe Gly Pro Gly Thr Lys Leu Glu Ile Lys Arg Thr Ser Gly
                260                 265                 270

Gly Gly Gly Ser Asp Val Gln Leu Val Gln Ser Gly Ala Glu Val Lys
                275                 280                 285

Lys Pro Gly Ala Ser Val Lys Val Ser Cys Lys Ala Ser Gly Tyr Thr
        290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
                325                 330                 335

Ala Asp Ser Val Lys Gly Arg Phe Thr Ile Thr Thr Asp Lys Ser Thr
                340                 345                 350

Ser Thr Ala Tyr Met Glu Leu Ser Ser Leu Arg Ser Glu Asp Thr Ala
                355                 360                 365

Thr Tyr Tyr Cys Ala Arg Tyr Tyr Asp Asp His Tyr Cys Leu Asp Tyr
        370                 375                 380

Trp Gly Gln Gly Thr Thr Val Thr Val Ser Ser Gly Glu Gly Thr Ser
385                 390                 395                 400

Thr Gly Ser Gly Gly Ser Gly Gly Ser Gly Gly Ala Asp Asp Ile Val
                405                 410                 415

Leu Thr Gln Ser Pro Ala Thr Leu Ser Leu Ser Pro Gly Glu Arg Ala
                420                 425                 430

Thr Leu Ser Cys Arg Ala Ser Gln Ser Val Ser Tyr Met Asn Trp Tyr
        435                 440                 445

Gln Gln Lys Pro Gly Lys Ala Pro Lys Arg Trp Ile Tyr Asp Thr Ser
        450                 455                 460

Lys Val Ala Ser Gly Val Pro Ala Arg Phe Ser Gly Ser Gly Ser Gly
465                 470                 475                 480

Thr Asp Tyr Ser Leu Thr Ile Asn Ser Leu Glu Ala Glu Asp Ala Ala
                485                 490                 495

Thr Tyr Tyr Cys Gln Gln Trp Ser Ser Asn Pro Leu Thr Phe Gly Gly
                500                 505                 510

Gly Thr Lys Val Glu Ile Lys His His His His His His
                515                 520                 525
```

```
<210> SEQ ID NO 91
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Met Gly Trp Ser Cys Ile Ile Leu Phe Leu Val Ala Thr Ala Thr Gly
1                   5                   10                  15

Lys Leu Glu Val Gln Leu Val Glu Ser Gly Gly Gly Leu Val Lys Pro
                20                  25                  30
```

-continued

```
Gly Gly Ser Leu Arg Val Ser Cys Ala Ala Ser Gly Phe Thr Phe Ser
        35                  40                  45

Ser Tyr Ala Met Ser Trp Val Arg Leu Ala Pro Gly Lys Gly Leu Glu
    50                  55                  60

Trp Val Ala Thr Ile Ser Ser Ala Gly Gly Tyr Ile Phe Tyr Ser Asp
65                  70                  75                  80

Ser Val Gln Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Met Tyr
            100                 105                 110

Tyr Cys Ala Arg Gln Gly Phe Gly Asn Tyr Gly Asp Tyr Tyr Ala Met
            115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Val Leu
145                 150                 155                 160

Thr Gln Ser Pro Asp Ser Leu Ala Val Ser Leu Gly Glu Arg Val Thr
                165                 170                 175

Met Asn Cys Lys Ser Ser Gln Ser Leu Leu Asn Ser Arg Thr Arg Lys
            180                 185                 190

Asn Gln Leu Ala Trp Tyr Gln Gln Lys Pro Gly Gln Ser Pro Glu Leu
        195                 200                 205

Leu Ile Tyr Trp Ala Ser Thr Arg Gln Ser Gly Val Pro Asp Arg Phe
    210                 215                 220

Ser Gly Ser Gly Ser Gly Thr Asp Phe Thr Leu Thr Ile Ser Ser Val
225                 230                 235                 240

Gln Ala Glu Asp Val Ala Val Tyr Tyr Cys Gln Gln Ser Tyr Asn Leu
                245                 250                 255

Leu Thr Phe Gly Gln Gly Thr Lys Leu Glu Ile Lys Arg Thr Ser Gly
            260                 265                 270

Gly Gly Gly Ser Asp Val Gln Leu Val Gln Ser Gly Ala Glu Val Lys
        275                 280                 285

Lys Pro Gly Ala Ser Val Lys Val Ser Cys Lys Ala Ser Gly Tyr Thr
    290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
                325                 330                 335

Ala Asp Ser Val Lys Gly Arg Phe Thr Ile Thr Thr Asp Lys Ser Thr
            340                 345                 350

Ser Thr Ala Tyr Met Glu Leu Ser Ser Leu Arg Ser Glu Asp Thr Ala
        355                 360                 365

Thr Tyr Tyr Cys Ala Arg Tyr Tyr Asp Asp His Tyr Cys Leu Asp Tyr
    370                 375                 380

Trp Gly Gln Gly Thr Thr Val Thr Val Ser Ser Gly Glu Gly Thr Ser
385                 390                 395                 400

Thr Gly Ser Gly Gly Ser Gly Gly Ser Gly Gly Ala Asp Asp Ile Val
                405                 410                 415

Leu Thr Gln Ser Pro Ala Thr Leu Ser Leu Ser Pro Gly Glu Arg Ala
            420                 425                 430

Thr Leu Ser Cys Arg Ala Ser Gln Ser Val Ser Tyr Met Asn Trp Tyr
        435                 440                 445
```

```
Gln Gln Lys Pro Gly Lys Ala Pro Lys Arg Trp Ile Tyr Asp Thr Ser
    450             455             460

Lys Val Ala Ser Gly Val Pro Ala Arg Phe Ser Gly Ser Gly Ser Gly
465             470             475             480

Thr Asp Tyr Ser Leu Thr Ile Asn Ser Leu Glu Ala Glu Asp Ala Ala
            485             490             495

Thr Tyr Tyr Cys Gln Gln Trp Ser Ser Asn Pro Leu Thr Phe Gly Gly
            500             505             510

Gly Thr Lys Val Glu Ile Lys His His His His His
        515             520             525

<210> SEQ ID NO 92
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Gly Trp Ser Cys Ile Ile Leu Phe Leu Val Ala Thr Ala Thr Gly
1               5               10              15

Lys Leu Gln Val Thr Leu Lys Glu Ser Gly Pro Gly Ile Leu Gln Pro
            20              25              30

Thr Gln Thr Leu Thr Leu Thr Cys Thr Phe Ser Gly Phe Ser Leu Ser
        35              40              45

Thr Val Gly Met Gly Val Gly Trp Ser Arg Gln Pro Ser Gly Lys Gly
        50              55              60

Leu Glu Trp Leu Ala His Ile Trp Trp Asp Asp Glu Asp Lys Tyr Tyr
65              70              75              80

Asn Pro Ala Leu Lys Ser Arg Leu Thr Ile Thr Lys Asp Thr Ser Lys
            85              90              95

Asn Gln Val Phe Leu Lys Ile Thr Asn Val Asp Thr Ala Asp Thr Ala
            100             105             110

Thr Tyr Tyr Cys Thr Arg Ile Gly Thr Ala Gln Ala Thr Asp Ala Leu
            115             120             125

Asp Tyr Trp Gly Gln Gly Thr Leu Val Thr Val Ser Ser Gly Gly Gly
        130             135             140

Gly Ser Gly Gly Gly Gly Ser Gly Gly Gly Gly Ser Asp Ile Val Met
145             150             155             160

Thr Gln Ser Ala Pro Ser Val Pro Val Thr Pro Gly Glu Ser Val Ser
            165             170             175

Ile Ser Cys Arg Ser Ser Lys Ser Leu Leu His Ser Asn Gly Asn Thr
            180             185             190

Tyr Leu Tyr Trp Phe Leu Gln Lys Pro Gly Gln Ser Pro Gln Arg Leu
            195             200             205

Ile Tyr Tyr Met Ser Asn Leu Ala Ser Gly Val Pro Asp Arg Phe Ser
        210             215             220

Gly Arg Gly Ser Gly Thr Asp Phe Thr Leu Lys Ile Ser Arg Val Glu
225             230             235             240

Ala Glu Asp Val Gly Val Tyr Tyr Cys Met Gln Ser Leu Glu Tyr Pro
            245             250             255

Leu Thr Phe Gly Gly Gly Thr Lys Leu Glu Ile Lys Arg Thr Ser Gly
            260             265             270

Gly Gly Gly Ser Asp Val Gln Leu Val Gln Ser Gly Ala Glu Val Lys
        275             280             285
```

```
Lys Pro Gly Ala Ser Val Lys Val Ser Cys Lys Ala Ser Gly Tyr Thr
    290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
                325                 330                 335

Ala Asp Ser Val Lys Gly Arg Phe Thr Ile Thr Thr Asp Lys Ser Thr
                340                 345                 350

Ser Thr Ala Tyr Met Glu Leu Ser Ser Leu Arg Ser Glu Asp Thr Ala
            355                 360                 365

Thr Tyr Tyr Cys Ala Arg Tyr Tyr Asp Asp His Tyr Cys Leu Asp Tyr
    370                 375                 380

Trp Gly Gln Gly Thr Thr Val Thr Val Ser Ser Gly Glu Gly Thr Ser
385                 390                 395                 400

Thr Gly Ser Gly Gly Ser Gly Gly Ser Gly Gly Ala Asp Asp Ile Val
                405                 410                 415

Leu Thr Gln Ser Pro Ala Thr Leu Ser Leu Ser Pro Gly Glu Arg Ala
                420                 425                 430

Thr Leu Ser Cys Arg Ala Ser Gln Ser Val Ser Tyr Met Asn Trp Tyr
            435                 440                 445

Gln Gln Lys Pro Gly Lys Ala Pro Lys Arg Trp Ile Tyr Asp Thr Ser
    450                 455                 460

Lys Val Ala Ser Gly Val Pro Ala Arg Phe Ser Gly Ser Gly Ser Gly
465                 470                 475                 480

Thr Asp Tyr Ser Leu Thr Ile Asn Ser Leu Glu Ala Glu Asp Ala Ala
                485                 490                 495

Thr Tyr Tyr Cys Gln Gln Trp Ser Ser Asn Pro Leu Thr Phe Gly Gly
                500                 505                 510

Gly Thr Lys Val Glu Ile Lys His His His His His
            515                 520                 525
```

```
<210> SEQ ID NO 93
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93
```

```
Met Gly Trp Ser Cys Ile Ile Leu Phe Leu Val Ala Thr Ala Thr Gly
1               5                   10                  15

Lys Leu Gln Val Thr Leu Lys Glu Ser Gly Pro Gly Ile Leu Gln Pro
                20                  25                  30

Thr Gln Thr Leu Thr Leu Thr Cys Thr Phe Ser Gly Phe Ser Leu Ser
            35                  40                  45

Thr Val Gly Met Gly Val Gly Trp Ser Arg Gln Pro Ser Gly Lys Gly
    50                  55                  60

Leu Glu Trp Leu Ala His Ile Trp Trp Asp Asp Glu Asp Lys Tyr Tyr
65                  70                  75                  80

Asn Pro Ala Leu Lys Ser Arg Leu Thr Ile Thr Lys Asp Thr Ser Lys
                85                  90                  95

Asn Gln Val Phe Leu Lys Ile Thr Asn Val Asp Thr Ala Asp Thr Ala
                100                 105                 110

Thr Tyr Tyr Cys Thr Arg Ile Gly Thr Ala Gln Ala Thr Asp Ala Leu
```

-continued

```
              115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Ala Leu Ser Leu Pro Val Thr Pro Gly Glu Pro Val Ser
                165                 170                 175

Ile Ser Cys Arg Ser Ser Lys Ser Leu Leu His Ser Asn Gly Asn Thr
                180                 185                 190

Tyr Leu Tyr Trp Phe Leu Gln Lys Pro Gly Gln Ser Pro Gln Arg Leu
            195                 200                 205

Ile Tyr Tyr Met Ser Asn Leu Ala Ser Gly Val Pro Asp Arg Phe Ser
    210                 215                 220

Gly Ser Gly Ser Gly Thr Asp Phe Thr Leu Lys Ile Ser Arg Val Glu
225                 230                 235                 240

Ala Glu Asp Val Gly Val Tyr Tyr Cys Met Gln Ser Leu Glu Tyr Pro
                245                 250                 255

Leu Thr Phe Gly Gly Gly Thr Lys Leu Glu Ile Lys Arg Thr Ser Gly
                260                 265                 270

Gly Gly Gly Ser Asp Val Gln Leu Val Gln Ser Gly Ala Glu Val Lys
            275                 280                 285

Lys Pro Gly Ala Ser Val Lys Val Ser Cys Lys Ala Ser Gly Tyr Thr
    290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
                325                 330                 335

Ala Asp Ser Val Lys Gly Arg Phe Thr Ile Thr Thr Asp Lys Ser Thr
            340                 345                 350

Ser Thr Ala Tyr Met Glu Leu Ser Ser Leu Arg Ser Glu Asp Thr Ala
            355                 360                 365

Thr Tyr Tyr Cys Ala Arg Tyr Tyr Asp Asp His Tyr Cys Leu Asp Tyr
    370                 375                 380

Trp Gly Gln Gly Thr Thr Val Thr Val Ser Ser Gly Glu Gly Thr Ser
385                 390                 395                 400

Thr Gly Ser Gly Gly Ser Gly Gly Ser Gly Gly Ala Asp Asp Ile Val
            405                 410                 415

Leu Thr Gln Ser Pro Ala Thr Leu Ser Leu Ser Pro Gly Glu Arg Ala
            420                 425                 430

Thr Leu Ser Cys Arg Ala Ser Gln Ser Val Ser Tyr Met Asn Trp Tyr
            435                 440                 445

Gln Gln Lys Pro Gly Lys Ala Pro Lys Arg Trp Ile Tyr Asp Thr Ser
    450                 455                 460

Lys Val Ala Ser Gly Val Pro Ala Arg Phe Ser Gly Ser Gly Ser Gly
465                 470                 475                 480

Thr Asp Tyr Ser Leu Thr Ile Asn Ser Leu Glu Ala Glu Asp Ala Ala
            485                 490                 495

Thr Tyr Tyr Cys Gln Gln Trp Ser Ser Asn Pro Leu Thr Phe Gly Gly
            500                 505                 510

Gly Thr Lys Val Glu Ile Lys His His His His His
            515                 520                 525
```

<210> SEQ ID NO 94

```
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Gly Trp Ser Cys Ile Ile Leu Phe Leu Val Ala Thr Ala Thr Gly
1               5                   10                  15

Lys Leu Gln Val Thr Leu Lys Glu Ser Gly Pro Thr Leu Val Lys Pro
            20                  25                  30

Thr Gln Thr Leu Thr Leu Thr Cys Thr Phe Ser Gly Phe Ser Leu Ser
        35                  40                  45

Thr Val Gly Met Gly Val Gly Trp Ser Arg Gln Pro Ser Gly Lys Gly
    50                  55                  60

Leu Glu Trp Leu Ala His Ile Trp Trp Asp Asp Glu Asp Lys Tyr Tyr
65                  70                  75                  80

Asn Pro Ala Leu Lys Ser Arg Leu Thr Ile Thr Lys Asp Thr Ser Lys
                85                  90                  95

Asn Gln Val Val Leu Thr Ile Thr Asn Val Asp Pro Val Asp Thr Ala
            100                 105                 110

Thr Tyr Tyr Cys Thr Arg Ile Gly Thr Ala Gln Ala Thr Asp Ala Leu
            115                 120                 125

Asp Tyr Trp Gly Gln Gly Thr Leu Val Thr Val Ser Ser Gly Gly Gly
        130                 135                 140

Gly Ser Gly Gly Gly Gly Ser Gly Gly Gly Gly Ser Asp Ile Val Met
145                 150                 155                 160

Thr Gln Ser Ala Pro Ser Val Pro Val Thr Pro Gly Glu Ser Val Ser
                165                 170                 175

Ile Ser Cys Arg Ser Ser Lys Ser Leu Leu His Ser Asn Gly Asn Thr
            180                 185                 190

Tyr Leu Tyr Trp Phe Leu Gln Lys Pro Gly Gln Ser Pro Gln Arg Leu
            195                 200                 205

Ile Tyr Tyr Met Ser Asn Leu Ala Ser Gly Val Pro Asp Arg Phe Ser
        210                 215                 220

Gly Arg Gly Ser Gly Thr Asp Phe Thr Leu Lys Ile Ser Arg Val Glu
225                 230                 235                 240

Ala Glu Asp Val Gly Val Tyr Tyr Cys Met Gln Ser Leu Glu Tyr Pro
                245                 250                 255

Leu Thr Phe Gly Gly Gly Thr Lys Leu Glu Ile Lys Arg Thr Ser Gly
            260                 265                 270

Gly Gly Gly Ser Asp Val Gln Leu Val Gln Ser Gly Ala Glu Val Lys
            275                 280                 285

Lys Pro Gly Ala Ser Val Lys Val Ser Cys Lys Ala Ser Gly Tyr Thr
        290                 295                 300

Phe Thr Arg Tyr Thr Met His Trp Val Arg Gln Ala Pro Gly Gln Gly
305                 310                 315                 320

Leu Glu Trp Ile Gly Tyr Ile Asn Pro Ser Arg Gly Tyr Thr Asn Tyr
                325                 330                 335

Ala Asp Ser Val Lys Gly Arg Phe Thr Ile Thr Thr Asp Lys Ser Thr
            340                 345                 350

Ser Thr Ala Tyr Met Glu Leu Ser Ser Leu Arg Ser Glu Asp Thr Ala
        355                 360                 365

Thr Tyr Tyr Cys Ala Arg Tyr Tyr Asp Asp His Tyr Cys Leu Asp Tyr
```

```
      370                375                380
Trp Gly Gln Gly Thr Thr Val Thr Val Ser Ser Gly Glu Gly Thr Ser
385                390                395                400

Thr Gly Ser Gly Gly Ser Gly Gly Ser Gly Gly Ala Asp Asp Ile Val
              405                410                415

Leu Thr Gln Ser Pro Ala Thr Leu Ser Leu Ser Pro Gly Glu Arg Ala
              420                425                430

Thr Leu Ser Cys Arg Ala Ser Gln Ser Val Ser Tyr Met Asn Trp Tyr
              435                440                445

Gln Gln Lys Pro Gly Lys Ala Pro Lys Arg Trp Ile Tyr Asp Thr Ser
          450                455                460

Lys Val Ala Ser Gly Val Pro Ala Arg Phe Ser Gly Ser Gly Ser Gly
465                470                475                480

Thr Asp Tyr Ser Leu Thr Ile Asn Ser Leu Glu Ala Glu Asp Ala Ala
              485                490                495

Thr Tyr Tyr Cys Gln Gln Trp Ser Ser Asn Pro Leu Thr Phe Gly Gly
              500                505                510

Gly Thr Lys Val Glu Ile Lys His His His His His His
          515                520                525

<210> SEQ ID NO 95
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Met Gly Trp Ser Cys Ile Ile Leu Phe Leu Val Ala Thr Ala Thr Gly
1                5                10                15

Lys Leu Gln Val Thr Leu Lys Glu Ser Gly Pro Thr Leu Val Lys Pro
              20                25                30

Thr Gln Thr Leu Thr Leu Thr Cys Thr Phe Ser Gly Phe Ser Leu Ser
          35                40                45

Thr Val Gly Met Gly Val Gly Trp Ser Arg Gln Pro Ser Gly Lys Gly
          50                55                60

Leu Glu Trp Leu Ala His Ile Trp Trp Asp Asp Glu Asp Lys Tyr Tyr
65                70                75                80

Asn Pro Ala Leu Lys Ser Arg Leu Thr Ile Thr Lys Asp Thr Ser Lys
              85                90                95

Asn Gln Val Val Leu Thr Ile Thr Asn Val Asp Pro Val Asp Thr Ala
              100                105                110

Thr Tyr Tyr Cys Thr Arg Ile Gly Thr Ala Gln Ala Thr Asp Ala Leu
              115                120                125

Asp Tyr Trp Gly Gln Gly Thr Leu Val Thr Val Ser Ser Gly Gly Gly
          130                135                140

Gly Ser Gly Gly Gly Gly Ser Gly Gly Gly Gly Ser Asp Ile Val Met
145                150                155                160

Thr Gln Ser Ala Leu Ser Leu Pro Val Thr Pro Gly Glu Pro Val Ser
              165                170                175

Ile Ser Cys Arg Ser Ser Lys Ser Leu Leu His Ser Asn Gly Asn Thr
              180                185                190

Tyr Leu Tyr Trp Phe Leu Gln Lys Pro Gly Gln Ser Pro Gln Arg Leu
          195                200                205
```

```
Ile Tyr Tyr Met Ser Asn Leu Ala Ser Gly Val Pro Asp Arg Phe Ser
    210             215             220

Gly Ser Gly Ser Gly Thr Asp Phe Thr Leu Lys Ile Ser Arg Val Glu
225             230             235             240

Ala Glu Asp Val Gly Val Tyr Tyr Cys Met Gln Ser Leu Glu Tyr Pro
            245             250             255

Leu Thr Phe Gly Gly Gly Thr Lys Leu Glu Ile Lys Arg Thr Ser Gly
            260             265             270

Gly Gly Gly Ser Asp Val Gln Leu Val Gln Ser Gly Ala Glu Val Lys
            275             280             285

Lys Pro Gly Ala Ser Val Lys Val Ser Cys Lys Ala Ser Gly Tyr Thr
    290             295             300

Phe Thr Arg Tyr Thr Met His Trp Val Arg Gln Ala Pro Gly Gln Gly
305             310             315             320

Leu Glu Trp Ile Gly Tyr Ile Asn Pro Ser Arg Gly Tyr Thr Asn Tyr
            325             330             335

Ala Asp Ser Val Lys Gly Arg Phe Thr Ile Thr Thr Asp Lys Ser Thr
            340             345             350

Ser Thr Ala Tyr Met Glu Leu Ser Ser Leu Arg Ser Glu Asp Thr Ala
            355             360             365

Thr Tyr Tyr Cys Ala Arg Tyr Tyr Asp Asp His Tyr Cys Leu Asp Tyr
    370             375             380

Trp Gly Gln Gly Thr Thr Val Thr Val Ser Ser Gly Glu Gly Thr Ser
385             390             395             400

Thr Gly Ser Gly Gly Ser Gly Gly Ser Gly Gly Ala Asp Asp Ile Val
            405             410             415

Leu Thr Gln Ser Pro Ala Thr Leu Ser Leu Ser Pro Gly Glu Arg Ala
            420             425             430

Thr Leu Ser Cys Arg Ala Ser Gln Ser Val Ser Tyr Met Asn Trp Tyr
            435             440             445

Gln Gln Lys Pro Gly Lys Ala Pro Lys Arg Trp Ile Tyr Asp Thr Ser
    450             455             460

Lys Val Ala Ser Gly Val Pro Ala Arg Phe Ser Gly Ser Gly Ser Gly
465             470             475             480

Thr Asp Tyr Ser Leu Thr Ile Asn Ser Leu Glu Ala Glu Asp Ala Ala
            485             490             495

Thr Tyr Tyr Cys Gln Gln Trp Ser Ser Asn Pro Leu Thr Phe Gly Gly
            500             505             510

Gly Thr Lys Val Glu Ile Lys His His His His His
            515             520             525
```

```
<210> SEQ ID NO 96
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96
```

```
Met Ala Leu Pro Val Thr Ala Leu Leu Leu Pro Leu Ala Leu Leu Leu
1               5               10              15

His Ala Asp Ile Glu Leu Thr Gln Ser Pro Ser Ser Leu Ala Val Ser
            20              25              30

Ala Gly Glu Arg Val Thr Met Asn Cys Lys Ser Ser Gln Ser Leu Leu
            35              40              45
```

```
Asn Ser Arg Thr Arg Lys Asn Gln Leu Ala Trp Tyr Gln Gln Lys Pro
    50              55              60

Gly Gln Ser Pro Glu Leu Leu Ile Tyr Trp Ala Ser Thr Arg Gln Ser
65              70              75              80

Gly Val Pro Asp Arg Phe Ser Gly Ser Gly Ser Gly Thr Asp Phe Thr
            85              90              95

Leu Thr Ile Ser Ser Val Gln Ala Glu Asp Val Ala Val Tyr Tyr Cys
            100             105             110

Gln Gln Ser Tyr Asn Leu Leu Thr Phe Gly Pro Gly Thr Lys Leu Glu
        115             120             125

Ile Lys Arg Gly Gly Gly Ser Gly Gly Gly Gly Ser Gly Gly Gly
    130             135             140

Gly Ser Glu Val Lys Leu Gln Glu Ser Gly Gly Gly Phe Val Lys Pro
145             150             155             160

Gly Gly Ser Leu Arg Val Ser Cys Ala Ala Ser Gly Phe Thr Phe Ser
            165             170             175

Ser Tyr Ala Met Ser Trp Val Arg Leu Ala Pro Glu Met Arg Leu Glu
            180             185             190

Trp Val Ala Thr Ile Ser Ser Ala Gly Gly Tyr Ile Phe Tyr Ser Asp
            195             200             205

Ser Val Gln Gly Arg Phe Thr Ile Ser Arg Asp Asn Ala Lys Asn Ser
    210             215             220

Leu His Leu Gln Met Gly Ser Leu Arg Ser Gly Asp Thr Ala Met Tyr
225             230             235             240

Tyr Cys Ala Arg Gln Gly Phe Gly Asn Tyr Gly Asp Tyr Tyr Ala Met
            245             250             255

Asp Tyr Trp Gly Gln Gly Thr Thr Val Thr Val Ser Ser Ala Ala Ala
            260             265             270

Pro Thr Thr Thr Pro Ala Pro Arg Pro Pro Thr Pro Ala Pro Thr Ile
    275             280             285

Ala Ser Gln Pro Leu Ser Leu Arg Pro Glu Ala Cys Arg Pro Ala Ala
    290             295             300

Gly Gly Ala Val His Thr Arg Gly Leu Asp Phe Ala Cys Asp Ile Tyr
305             310             315             320

Ile Trp Ala Pro Leu Ala Gly Thr Cys Gly Val Leu Leu Leu Ser Leu
            325             330             335

Val Ile Thr Leu Tyr Cys Asn Lys Arg Gly Arg Lys Lys Leu Leu Tyr
            340             345             350

Ile Phe Lys Gln Pro Phe Met Arg Pro Val Gln Thr Thr Gln Glu Glu
        355             360             365

Asp Gly Cys Ser Cys Arg Phe Pro Glu Glu Glu Glu Gly Gly Cys Glu
    370             375             380

Leu Arg Val Lys Phe Ser Arg Ser Ala Asp Ala Pro Ala Tyr Gln Gln
385             390             395             400

Gly Gln Asn Gln Leu Tyr Asn Glu Leu Asn Leu Gly Arg Arg Glu Glu
            405             410             415

Tyr Asp Val Leu Asp Lys Arg Arg Gly Arg Asp Pro Glu Met Gly Gly
            420             425             430

Lys Pro Arg Arg Lys Asn Pro Gln Glu Gly Leu Tyr Asn Glu Leu Gln
        435             440             445

Lys Asp Lys Met Ala Glu Ala Tyr Ser Glu Ile Gly Met Lys Gly Glu
    450             455             460
```

```
Arg Arg Arg Gly Lys Gly His Asp Gly Leu Tyr Gln Gly Leu Ser Thr
465             470                 475                 480

Ala Thr Lys Asp Thr Tyr Asp Ala Leu His Met Gln Ala Leu Pro Pro
                485             490                 495

Arg

<210> SEQ ID NO 97
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Met Ala Leu Pro Val Thr Ala Leu Leu Leu Pro Leu Ala Leu Leu Leu
1               5                   10                  15

His Ala Asp Ile Val Leu Thr Gln Ser Pro Asp Ser Leu Ala Val Ser
                20                  25                  30

Leu Gly Glu Arg Val Thr Met Asn Cys Lys Ser Ser Gln Ser Leu Leu
        35                  40                  45

Asn Ser Arg Thr Arg Lys Asn Gln Leu Ala Trp Tyr Gln Gln Lys Pro
    50                  55                  60

Gly Gln Ser Pro Glu Leu Leu Ile Tyr Trp Ala Ser Thr Arg Gln Ser
65                  70                  75                  80

Gly Val Pro Asp Arg Phe Ser Gly Ser Gly Ser Gly Thr Asp Phe Thr
                85                  90                  95

Leu Thr Ile Ser Ser Val Gln Ala Glu Asp Val Ala Val Tyr Tyr Cys
            100                 105                 110

Gln Gln Ser Tyr Asn Leu Leu Thr Phe Gly Gln Gly Thr Lys Leu Glu
        115                 120                 125

Ile Lys Arg Gly Gly Gly Gly Ser Gly Gly Gly Gly Ser Gly Gly Gly
    130                 135                 140

Gly Ser Glu Val Lys Leu Gln Glu Ser Gly Gly Gly Phe Val Lys Pro
145                 150                 155                 160

Gly Gly Ser Leu Arg Val Ser Cys Ala Ala Ser Gly Phe Thr Phe Ser
                165                 170                 175

Ser Tyr Ala Met Ser Trp Val Arg Leu Ala Pro Glu Met Arg Leu Glu
            180                 185                 190

Trp Val Ala Thr Ile Ser Ser Ala Gly Gly Tyr Ile Phe Tyr Ser Asp
        195                 200                 205

Ser Val Gln Gly Arg Phe Thr Ile Ser Arg Asp Asn Ala Lys Asn Ser
    210                 215                 220

Leu His Leu Gln Met Gly Ser Leu Arg Ser Gly Asp Thr Ala Met Tyr
225                 230                 235                 240

Tyr Cys Ala Arg Gln Gly Phe Gly Asn Tyr Gly Asp Tyr Tyr Ala Met
                245                 250                 255

Asp Tyr Trp Gly Gln Gly Thr Thr Val Thr Val Ser Ser Ala Ala Ala
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320
```

-continued

```
Ile Trp Ala Pro Leu Ala Gly Thr Cys Gly Val Leu Leu Leu Ser Leu
                325                 330                 335

Val Ile Thr Leu Tyr Cys Asn Lys Arg Gly Arg Lys Lys Leu Leu Tyr
            340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Glu Gly Gly Cys Glu
        370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
        450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

```
<210> SEQ ID NO 98
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Ala Leu Pro Val Thr Ala Leu Leu Leu Pro Leu Ala Leu Leu Leu
1               5                   10                  15

His Ala Asp Ile Glu Leu Thr Gln Ser Pro Ser Ser Leu Ala Val Ser
            20                  25                  30

Ala Gly Glu Arg Val Thr Met Asn Cys Lys Ser Ser Gln Ser Leu Leu
        35                  40                  45

Asn Ser Arg Thr Arg Lys Asn Gln Leu Ala Trp Tyr Gln Gln Lys Pro
    50                  55                  60

Gly Gln Ser Pro Glu Leu Leu Ile Tyr Trp Ala Ser Thr Arg Gln Ser
65                  70                  75                  80

Gly Val Pro Asp Arg Phe Ser Gly Ser Gly Ser Gly Thr Asp Phe Thr
                85                  90                  95

Leu Thr Ile Ser Ser Val Gln Ala Glu Asp Val Ala Val Tyr Tyr Cys
            100                 105                 110

Gln Gln Ser Tyr Asn Leu Leu Thr Phe Gly Pro Gly Thr Lys Leu Glu
            115                 120                 125

Ile Lys Arg Gly Gly Gly Gly Ser Gly Gly Gly Ser Gly Gly Gly
        130                 135                 140

Gly Ser Glu Val Gln Leu Val Glu Ser Gly Gly Gly Leu Val Lys Pro
145                 150                 155                 160

Gly Gly Ser Leu Arg Val Ser Cys Ala Ala Ser Gly Phe Thr Phe Ser
                165                 170                 175
```

-continued

```
Ser Tyr Ala Met Ser Trp Val Arg Leu Ala Pro Gly Lys Gly Leu Glu
            180                 185                 190

Trp Val Ala Thr Ile Ser Ser Ala Gly Gly Tyr Ile Phe Tyr Ser Asp
        195                 200                 205

Ser Val Gln Gly Arg Phe Thr Ile Ser Arg Asp Asn Ala Lys Asn Ser
    210                 215                 220

Leu Tyr Leu Gln Met Asn Ser Leu Arg Ala Glu Asp Thr Ala Met Tyr
225                 230                 235                 240

Tyr Cys Ala Arg Gln Gly Phe Gly Asn Tyr Gly Asp Tyr Tyr Ala Met
                245                 250                 255

Asp Tyr Trp Gly Gln Gly Thr Leu Val Thr Val Ser Ser Ala Ala Ala
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
            325                 330                 335

Val Ile Thr Leu Tyr Cys Asn Lys Arg Gly Arg Lys Lys Leu Leu Tyr
            340                 345                 350

Ile Phe Lys Gln Pro Phe Met Arg Pro Val Gln Thr Thr Gln Glu Glu
            355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
            435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
            485                 490                 495

Arg
```

```
<210> SEQ ID NO 99
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Ala Leu Pro Val Thr Ala Leu Leu Leu Pro Leu Ala Leu Leu Leu
1               5                   10                  15

His Ala Asp Ile Val Leu Thr Gln Ser Pro Asp Ser Leu Ala Val Ser
            20                  25                  30
```

-continued

```
Leu Gly Glu Arg Val Thr Met Asn Cys Lys Ser Ser Gln Ser Leu Leu
        35              40              45

Asn Ser Arg Thr Arg Lys Asn Gln Leu Ala Trp Tyr Gln Gln Lys Pro
    50              55              60

Gly Gln Ser Pro Glu Leu Leu Ile Tyr Trp Ala Ser Thr Arg Gln Ser
65              70              75              80

Gly Val Pro Asp Arg Phe Ser Gly Ser Gly Ser Gly Thr Asp Phe Thr
                85              90              95

Leu Thr Ile Ser Ser Val Gln Ala Glu Asp Val Ala Val Tyr Tyr Cys
            100             105             110

Gln Gln Ser Tyr Asn Leu Leu Thr Phe Gly Gln Gly Thr Lys Leu Glu
        115             120             125

Ile Lys Arg Gly Gly Gly Gly Ser Gly Gly Gly Gly Ser Gly Gly Gly
    130             135             140

Gly Ser Glu Val Gln Leu Val Glu Ser Gly Gly Gly Leu Val Lys Pro
145             150             155             160

Gly Gly Ser Leu Arg Val Ser Cys Ala Ala Ser Gly Phe Thr Phe Ser
                165             170             175

Ser Tyr Ala Met Ser Trp Val Arg Leu Ala Pro Gly Lys Gly Leu Glu
            180             185             190

Trp Val Ala Thr Ile Ser Ser Ala Gly Gly Tyr Ile Phe Tyr Ser Asp
            195             200             205

Ser Val Gln Gly Arg Phe Thr Ile Ser Arg Asp Asn Ala Lys Asn Ser
    210             215             220

Leu Tyr Leu Gln Met Asn Ser Leu Arg Ala Glu Asp Thr Ala Met Tyr
225             230             235             240

Tyr Cys Ala Arg Gln Gly Phe Gly Asn Tyr Gly Asp Tyr Tyr Ala Met
            245             250             255

Asp Tyr Trp Gly Gln Gly Thr Leu Val Thr Val Ser Ser Ala Ala Ala
            260             265             270

Pro Thr Thr Thr Pro Ala Pro Arg Pro Pro Thr Pro Ala Pro Thr Ile
            275             280             285

Ala Ser Gln Pro Leu Ser Leu Arg Pro Glu Ala Cys Arg Pro Ala Ala
    290             295             300

Gly Gly Ala Val His Thr Arg Gly Leu Asp Phe Ala Cys Asp Ile Tyr
305             310             315             320

Ile Trp Ala Pro Leu Ala Gly Thr Cys Gly Val Leu Leu Leu Ser Leu
                325             330             335

Val Ile Thr Leu Tyr Cys Asn Lys Arg Gly Arg Lys Lys Leu Leu Tyr
            340             345             350

Ile Phe Lys Gln Pro Phe Met Arg Pro Val Gln Thr Thr Gln Glu Glu
        355             360             365

Asp Gly Cys Ser Cys Arg Phe Pro Glu Glu Glu Glu Gly Gly Cys Glu
    370             375             380

Leu Arg Val Lys Phe Ser Arg Ser Ala Asp Ala Pro Ala Tyr Gln Gln
385             390             395             400

Gly Gln Asn Gln Leu Tyr Asn Glu Leu Asn Leu Gly Arg Arg Glu Glu
                405             410             415

Tyr Asp Val Leu Asp Lys Arg Arg Gly Arg Asp Pro Glu Met Gly Gly
            420             425             430

Lys Pro Arg Arg Lys Asn Pro Gln Glu Gly Leu Tyr Asn Glu Leu Gln
            435             440             445

Lys Asp Lys Met Ala Glu Ala Tyr Ser Glu Ile Gly Met Lys Gly Glu
```

-continued

```
       450          455          460

Arg Arg Arg Gly Lys Gly His Asp Gly Leu Tyr Gln Gly Leu Ser Thr
465          470          475          480

Ala Thr Lys Asp Thr Tyr Asp Ala Leu His Met Gln Ala Leu Pro Pro
             485          490          495

Arg

<210> SEQ ID NO 100
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Ala Leu Pro Val Thr Ala Leu Leu Leu Pro Leu Ala Leu Leu Leu
1               5                   10                  15

His Ala Asp Ile Val Met Thr Gln Ser Ala Pro Ser Val Pro Val Thr
                20                  25                  30

Pro Gly Glu Ser Val Ser Ile Ser Cys Arg Ser Ser Lys Ser Leu Leu
            35                  40                  45

His Ser Asn Gly Asn Thr Tyr Leu Tyr Trp Phe Leu Gln Lys Pro Gly
        50                  55                  60

Gln Ser Pro Gln Arg Leu Ile Tyr Tyr Met Ser Asn Leu Ala Ser Gly
65                  70                  75                  80

Val Pro Asp Arg Phe Ser Gly Arg Gly Ser Gly Thr Asp Phe Thr Leu
                85                  90                  95

Lys Ile Ser Arg Val Glu Ala Glu Asp Val Gly Val Tyr Tyr Cys Met
            100                 105                 110

Gln Ser Leu Glu Tyr Pro Leu Thr Phe Gly Gly Gly Thr Lys Leu Glu
        115                 120                 125

Ile Lys Arg Gly Gly Gly Gly Ser Gly Gly Gly Gly Ser Gly Gly Gly
        130                 135                 140

Gly Ser Gln Val Thr Leu Lys Glu Ser Gly Pro Gly Ile Leu Gln Pro
145                 150                 155                 160

Thr Gln Thr Leu Thr Leu Thr Cys Thr Phe Ser Gly Phe Ser Leu Ser
                165                 170                 175

Thr Val Gly Met Gly Val Gly Trp Ser Arg Gln Pro Ser Gly Lys Gly
                180                 185                 190

Leu Glu Trp Leu Ala His Ile Trp Trp Asp Asp Glu Asp Lys Tyr Tyr
            195                 200                 205

Asn Pro Ala Leu Lys Ser Arg Leu Thr Ile Thr Lys Asp Thr Ser Lys
        210                 215                 220

Asn Gln Val Phe Leu Lys Ile Thr Asn Val Asp Thr Ala Asp Thr Ala
225                 230                 235                 240

Thr Tyr Tyr Cys Thr Arg Ile Gly Thr Ala Gln Ala Thr Asp Ala Leu
                245                 250                 255

Asp Tyr Trp Gly Gln Gly Thr Leu Val Thr Val Ser Ser Ala Ala Ala
            260                 265                 270

Pro Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Ile Tyr
```

-continued

```
305             310             315             320

Ile Trp Ala Pro Leu Ala Gly Thr Cys Gly Val Leu Leu Ser Leu
                325             330             335

Val Ile Thr Leu Tyr Cys Asn Lys Arg Gly Arg Lys Leu Leu Tyr
            340             345             350

Ile Phe Lys Gln Pro Phe Met Arg Pro Val Gln Thr Thr Gln Glu Glu
        355             360             365

Asp Gly Cys Ser Cys Arg Phe Pro Glu Glu Glu Glu Gly Gly Cys Glu
        370             375             380

Leu Arg Val Lys Phe Ser Arg Ser Ala Asp Ala Pro Ala Tyr Gln Gln
385             390             395             400

Gly Gln Asn Gln Leu Tyr Asn Glu Leu Asn Leu Gly Arg Arg Glu Glu
            405             410             415

Tyr Asp Val Leu Asp Lys Arg Arg Gly Arg Asp Pro Glu Met Gly Gly
            420             425             430

Lys Pro Arg Arg Lys Asn Pro Gln Glu Gly Leu Tyr Asn Glu Leu Gln
            435             440             445

Lys Asp Lys Met Ala Glu Ala Tyr Ser Glu Ile Gly Met Lys Gly Glu
            450             455             460

Arg Arg Arg Gly Lys Gly His Asp Gly Leu Tyr Gln Gly Leu Ser Thr
465             470             475             480

Ala Thr Lys Asp Thr Tyr Asp Ala Leu His Met Gln Ala Leu Pro Pro
            485             490             495

Arg
```

```
<210> SEQ ID NO 101
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Ala Leu Pro Val Thr Ala Leu Leu Leu Pro Leu Ala Leu Leu Leu
1               5               10              15

His Ala Asp Ile Val Met Thr Gln Ser Ala Leu Ser Leu Pro Val Thr
                20              25              30

Pro Gly Glu Pro Val Ser Ile Ser Cys Arg Ser Ser Lys Ser Leu Leu
            35              40              45

His Ser Asn Gly Asn Thr Tyr Leu Tyr Trp Phe Leu Gln Lys Pro Gly
        50              55              60

Gln Ser Pro Gln Arg Leu Ile Tyr Tyr Met Ser Asn Leu Ala Ser Gly
65              70              75              80

Val Pro Asp Arg Phe Ser Gly Ser Gly Ser Gly Thr Asp Phe Thr Leu
                85              90              95

Lys Ile Ser Arg Val Glu Ala Glu Asp Val Gly Val Tyr Tyr Cys Met
            100             105             110

Gln Ser Leu Glu Tyr Pro Leu Thr Phe Gly Gly Gly Thr Lys Leu Glu
        115             120             125

Ile Lys Arg Gly Gly Gly Gly Ser Gly Gly Gly Gly Ser Gly Gly Gly
        130             135             140

Gly Ser Gln Val Thr Leu Lys Glu Ser Gly Pro Gly Ile Leu Gln Pro
145             150             155             160

Thr Gln Thr Leu Thr Leu Thr Cys Thr Phe Ser Gly Phe Ser Leu Ser
```

-continued

```
              165                 170                 175
Thr Val Gly Met Gly Val Gly Trp Ser Arg Gln Pro Ser Gly Lys Gly
              180                 185                 190

Leu Glu Trp Leu Ala His Ile Trp Trp Asp Glu Asp Lys Tyr Tyr
              195                 200                 205

Asn Pro Ala Leu Lys Ser Arg Leu Thr Ile Thr Lys Asp Thr Ser Lys
              210                 215                 220

Asn Gln Val Phe Leu Lys Ile Thr Asn Val Asp Thr Ala Asp Thr Ala
225                 230                 235                 240

Thr Tyr Tyr Cys Thr Arg Ile Gly Thr Ala Gln Ala Thr Asp Ala Leu
                  245                 250                 255

Asp Tyr Trp Gly Gln Gly Thr Leu Val Thr Val Ser Ser Ala Ala Ala
                  260                 265                 270

Pro Thr Thr Thr Pro Ala Pro Arg Pro Pro Thr Pro Ala Pro Thr Ile
                  275                 280                 285

Ala Ser Gln Pro Leu Ser Leu Arg Pro Glu Ala Cys Arg Pro Ala Ala
                  290                 295                 300

Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                  325                 330                 335

Val Ile Thr Leu Tyr Cys Asn Lys Arg Gly Arg Lys Lys Leu Leu Tyr
                  340                 345                 350

Ile Phe Lys Gln Pro Phe Met Arg Pro Val Gln Thr Thr Gln Glu Glu
                  355                 360                 365

Asp Gly Cys Ser Cys Arg Phe Pro Glu Glu Glu Glu Gly Gly Cys Glu
                  370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                  405                 410                 415

Tyr Asp Val Leu Asp Lys Arg Arg Gly Arg Asp Pro Glu Met Gly Gly
                  420                 425                 430

Lys Pro Arg Arg Lys Asn Pro Gln Glu Gly Leu Tyr Asn Glu Leu Gln
                  435                 440                 445

Lys Asp Lys Met Ala Glu Ala Tyr Ser Glu Ile Gly Met Lys Gly Glu
                  450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                  485                 490                 495

Arg
```

<210> SEQ ID NO 102
<211> LENGTH: 497
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 102

```
Met Ala Leu Pro Val Thr Ala Leu Leu Leu Pro Leu Ala Leu Leu Leu
1               5                   10                  15

His Ala Asp Ile Val Met Thr Gln Ser Ala Pro Ser Val Pro Val Thr
```

-continued

```
                20              25              30
Pro Gly Glu Ser Val Ser Ile Ser Cys Arg Ser Ser Lys Ser Leu Leu
        35              40              45

His Ser Asn Gly Asn Thr Tyr Leu Tyr Trp Phe Leu Gln Lys Pro Gly
    50              55              60

Gln Ser Pro Gln Arg Leu Ile Tyr Tyr Met Ser Asn Leu Ala Ser Gly
65              70              75              80

Val Pro Asp Arg Phe Ser Gly Arg Gly Ser Gly Thr Asp Phe Thr Leu
                85              90              95

Lys Ile Ser Arg Val Glu Ala Glu Asp Val Gly Val Tyr Tyr Cys Met
            100             105             110

Gln Ser Leu Glu Tyr Pro Leu Thr Phe Gly Gly Gly Thr Lys Leu Glu
        115             120             125

Ile Lys Arg Gly Gly Gly Gly Ser Gly Gly Gly Ser Gly Gly Gly Gly
        130             135             140

Gly Ser Gln Val Thr Leu Lys Glu Ser Gly Pro Thr Leu Val Lys Pro
145             150             155             160

Thr Gln Thr Leu Thr Leu Thr Cys Thr Phe Ser Gly Phe Ser Leu Ser
                165             170             175

Thr Val Gly Met Gly Val Gly Trp Ser Arg Gln Pro Ser Gly Lys Gly
            180             185             190

Leu Glu Trp Leu Ala His Ile Trp Trp Asp Asp Glu Asp Lys Tyr Tyr
            195             200             205

Asn Pro Ala Leu Lys Ser Arg Leu Thr Ile Thr Lys Asp Thr Ser Lys
        210             215             220

Asn Gln Val Val Leu Thr Ile Thr Asn Val Asp Pro Val Asp Thr Ala
225             230             235             240

Thr Tyr Tyr Cys Thr Arg Ile Gly Thr Ala Gln Ala Thr Asp Ala Leu
                245             250             255

Asp Tyr Trp Gly Gln Gly Thr Leu Val Thr Val Ser Ser Ala Ala Ala
            260             265             270

Pro Thr Thr Thr Pro Ala Pro Arg Pro Pro Thr Pro Ala Pro Thr Ile
        275             280             285

Ala Ser Gln Pro Leu Ser Leu Arg Pro Glu Ala Cys Arg Pro Ala Ala
        290             295             300

Gly Gly Ala Val His Thr Arg Gly Leu Asp Phe Ala Cys Asp Ile Tyr
305             310             315             320

Ile Trp Ala Pro Leu Ala Gly Thr Cys Gly Val Leu Leu Leu Ser Leu
            325             330             335

Val Ile Thr Leu Tyr Cys Asn Lys Arg Gly Arg Lys Lys Leu Leu Tyr
            340             345             350

Ile Phe Lys Gln Pro Phe Met Arg Pro Val Gln Thr Thr Gln Glu Glu
        355             360             365

Asp Gly Cys Ser Cys Arg Phe Pro Glu Glu Glu Glu Gly Gly Cys Glu
        370             375             380

Leu Arg Val Lys Phe Ser Arg Ser Ala Asp Ala Pro Ala Tyr Gln Gln
385             390             395             400

Gly Gln Asn Gln Leu Tyr Asn Glu Leu Asn Leu Gly Arg Arg Glu Glu
                405             410             415

Tyr Asp Val Leu Asp Lys Arg Arg Gly Arg Asp Pro Glu Met Gly Gly
            420             425             430

Lys Pro Arg Arg Lys Asn Pro Gln Glu Gly Leu Tyr Asn Glu Leu Gln
        435             440             445
```

-continued

```
Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 103
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Met Ala Leu Pro Val Thr Ala Leu Leu Leu Pro Leu Ala Leu Leu Leu
1               5                   10                  15

His Ala Asp Ile Val Met Thr Gln Ser Ala Leu Ser Leu Pro Val Thr
                20                  25                  30

Pro Gly Glu Pro Val Ser Ile Ser Cys Arg Ser Ser Lys Ser Leu Leu
            35                  40                  45

His Ser Asn Gly Asn Thr Tyr Leu Tyr Trp Phe Leu Gln Lys Pro Gly
    50                  55                  60

Gln Ser Pro Gln Arg Leu Ile Tyr Tyr Met Ser Asn Leu Ala Ser Gly
65                  70                  75                  80

Val Pro Asp Arg Phe Ser Gly Ser Gly Ser Gly Thr Asp Phe Thr Leu
                85                  90                  95

Lys Ile Ser Arg Val Glu Ala Glu Asp Val Gly Val Tyr Tyr Cys Met
            100                 105                 110

Gln Ser Leu Glu Tyr Pro Leu Thr Phe Gly Gly Gly Thr Lys Leu Glu
        115                 120                 125

Ile Lys Arg Gly Gly Gly Gly Ser Gly Gly Gly Gly Ser Gly Gly Gly
    130                 135                 140

Gly Ser Gln Val Thr Leu Lys Glu Ser Gly Pro Thr Leu Val Lys Pro
145                 150                 155                 160

Thr Gln Thr Leu Thr Leu Thr Cys Thr Phe Ser Gly Phe Ser Leu Ser
                165                 170                 175

Thr Val Gly Met Gly Val Gly Trp Ser Arg Gln Pro Ser Gly Lys Gly
            180                 185                 190

Leu Glu Trp Leu Ala His Ile Trp Trp Asp Asp Glu Asp Lys Tyr Tyr
        195                 200                 205

Asn Pro Ala Leu Lys Ser Arg Leu Thr Ile Thr Lys Asp Thr Ser Lys
    210                 215                 220

Asn Gln Val Val Leu Thr Ile Thr Asn Val Asp Pro Val Asp Thr Ala
225                 230                 235                 240

Thr Tyr Tyr Cys Thr Arg Ile Gly Thr Ala Gln Ala Thr Asp Ala Leu
                245                 250                 255

Asp Tyr Trp Gly Gln Gly Thr Leu Val Thr Val Ser Ser Ala Ala Ala
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300
```

-continued

```
Gly Gly Ala Val His Thr Arg Gly Leu Asp Phe Ala Cys Asp Ile Tyr
305                 310                 315                 320

Ile Trp Ala Pro Leu Ala Gly Thr Cys Gly Val Leu Leu Leu Ser Leu
                325                 330                 335

Val Ile Thr Leu Tyr Cys Asn Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445

Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

```
<210> SEQ ID NO 104
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asp Ile Glu Leu Thr Gln Ser Pro Ser Ser Leu Ala Val Ser Ala Gly
1               5                   10                  15

Glu Lys Val Thr Met Ser Cys
            20
```

```
<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Trp Tyr Gln Gln Lys Pro Gly Gln Ser Pro Glu Leu Leu Ile Tyr
1               5                   10                  15
```

```
<210> SEQ ID NO 106
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 106

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Phe Gly Pro Gly Thr Lys Leu Glu Val Lys Arg
1               5                   10

<210> SEQ ID NO 108
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Trp Tyr Gln Gln Lys Pro Gly Gln Pro Pro Lys Leu Leu Ile Tyr
1               5                   10                  15

<210> SEQ ID NO 110
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 111

Phe Gly Gln Gly Thr Lys Leu Glu Ile Lys Arg
1               5                   10

<210> SEQ ID NO 112
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Ile Glu Leu Thr Gln Ser Pro Ser Ser Leu Ala Val Ser Ala Gly
1               5                   10                  15

Glu Arg Val Thr Met Asn Cys
            20

<210> SEQ ID NO 113
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Trp Tyr Gln Gln Lys Pro Gly Gln Ser Pro Glu Leu Leu Ile Tyr
1               5                   10                  15

<210> SEQ ID NO 114
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gly Val Pro Asp Arg Phe Ser Gly Ser Gly Ser Gly Thr Asp Phe Thr
1               5                   10                  15

Leu Thr Ile Ser Ser Val Gln Ala Glu Asp Val Ala Val Tyr Tyr Cys
            20                  25                  30

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Phe Gly Pro Gly Thr Lys Leu Glu Ile Lys Arg
1               5                   10

<210> SEQ ID NO 116
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Ile Val Leu Thr Gln Ser Pro Asp Ser Leu Ala Val Ser Leu Gly
```

-continued

```
1              5              10             15

Glu Arg Val Thr Met Asn Cys
                20
```

<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Trp Tyr Gln Gln Lys Pro Gly Gln Ser Pro Glu Leu Leu Ile Tyr
1              5              10             15
```

<210> SEQ ID NO 118
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Gly Val Pro Asp Arg Phe Ser Gly Ser Gly Ser Gly Thr Asp Phe Thr
1              5              10             15

Leu Thr Ile Ser Ser Val Gln Ala Glu Asp Val Ala Val Tyr Tyr Cys
                20             25             30
```

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Phe Gly Gln Gly Thr Lys Leu Glu Ile Lys Arg
1              5              10
```

<210> SEQ ID NO 120
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (22)..(22)
<223> OTHER INFORMATION: Any amino acid

```
<400> SEQUENCE: 120

Asp Ile Xaa Leu Thr Gln Ser Pro Xaa Ser Leu Ala Val Ser Xaa Gly
1               5                   10                  15

Glu Xaa Val Thr Met Xaa Cys
            20

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Trp Tyr Gln Gln Lys Pro Gly Gln Ser Pro Glu Leu Leu Ile Tyr
1               5                   10                  15

<210> SEQ ID NO 122
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (27)..(27)
<223> OTHER INFORMATION: Any amino acid

<400> SEQUENCE: 122

Gly Val Pro Asp Arg Phe Xaa Gly Ser Gly Ser Gly Thr Asp Phe Thr
1               5                   10                  15

Leu Thr Ile Ser Ser Val Gln Ala Glu Asp Xaa Ala Val Tyr Tyr Cys
            20                  25                  30

<210> SEQ ID NO 123
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (9)..(9)
<223> OTHER INFORMATION: Any amino acid

<400> SEQUENCE: 123

Phe Gly Xaa Gly Thr Lys Leu Glu Xaa Lys Arg
1               5                   10

<210> SEQ ID NO 124
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124
```

```
Ser Val Lys Leu Gln Glu Ser Gly Gly Gly Phe Val Lys Pro Gly Gly
1               5                   10                  15

Ser Leu Lys Val Ser Cys Ala Ala Ser Gly Phe Thr Phe Ser
            20                  25                  30

<210> SEQ ID NO 125
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Trp Val Arg Leu Ser Pro Glu Met Arg Leu Glu Trp Val Ala
1               5                   10

<210> SEQ ID NO 126
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Arg Phe Thr Ile Ser Arg Asp Asn Ala Lys Asn Thr Leu His Leu Gln
1               5                   10                  15

Met Gly Ser Leu Arg Ser Gly Asp Thr Ala Met Tyr Tyr Cys Ala Arg
            20                  25                  30

<210> SEQ ID NO 127
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Trp Val Arg Gln Ala Pro Gly Lys Gly Leu Glu Trp Val Ser
1               5                   10

<210> SEQ ID NO 129
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129
```

```
Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 130
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Lys Leu Gln Glu Ser Gly Gly Gly Phe Val Lys Pro Gly Gly
1               5                   10                  15

Ser Leu Arg Val Ser Cys Ala Ala Ser Gly Phe Thr Phe Ser
            20                  25                  30

<210> SEQ ID NO 131
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Trp Val Arg Leu Ala Pro Glu Met Arg Leu Glu Trp Val Ala
1               5                   10

<210> SEQ ID NO 132
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Arg Phe Thr Ile Ser Arg Asp Asn Ala Lys Asn Ser Leu His Leu Gln
1               5                   10                  15

Met Gly Ser Leu Arg Ser Gly Asp Thr Ala Met Tyr Tyr Cys Ala Arg
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Glu Ser Gly Gly Gly Leu Val Lys Pro Gly Gly
1               5                   10                  15

Ser Leu Arg Val Ser Cys Ala Ala Ser Gly Phe Thr Phe Ser
            20                  25                  30

<210> SEQ ID NO 134
<211> LENGTH: 14
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 134

Trp Val Arg Leu Ala Pro Gly Lys Gly Leu Glu Trp Val Ala
1               5                   10

<210> SEQ ID NO 135
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Met Tyr Tyr Cys Ala Arg
            20                  25                  30

<210> SEQ ID NO 136
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (19)..(19)
<223> OTHER INFORMATION: Any amino acid

<400> SEQUENCE: 136

Xaa Val Xaa Leu Xaa Glu Ser Gly Gly Gly Xaa Val Lys Pro Gly Gly
1               5                   10                  15

Ser Leu Xaa Val Ser Cys Ala Ala Ser Gly Phe Thr Phe Ser
            20                  25                  30

<210> SEQ ID NO 137
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(9)
<223> OTHER INFORMATION: Any amino acid

<400> SEQUENCE: 137

Trp Val Arg Leu Xaa Pro Xaa Xaa Xaa Leu Glu Trp Val Ala
1               5                   10

<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (22)..(23)
<223> OTHER INFORMATION: Any amino acid

<400> SEQUENCE: 138

Arg Phe Thr Ile Ser Arg Asp Asn Ala Lys Asn Xaa Leu Xaa Leu Gln
1               5                   10                  15

Met Xaa Ser Leu Arg Xaa Xaa Asp Thr Ala Met Tyr Tyr Cys Ala Arg
            20                  25                  30

<210> SEQ ID NO 139
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Ile Val Met Thr Gln Ala Ala Pro Ser Val Pro Val Thr Pro Gly
1               5                   10                  15

Glu Ser Val Ser Ile Ser Cys
            20

<210> SEQ ID NO 140
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Trp Phe Leu Gln Arg Pro Gly Gln Ser Pro Gln Arg Leu Ile Tyr
1               5                   10                  15

<210> SEQ ID NO 141
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Gly Val Pro Asp Arg Phe Ser Gly Arg Gly Ser Gly Thr Asp Phe Thr
1               5                   10                  15

Leu Arg Ile Ser Arg Val Glu Ala Glu Asp Val Gly Val Tyr Tyr Cys
            20                  25                  30
```

```
<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Phe Gly Gly Gly Thr Lys Leu Glu Ile Lys
1               5                   10
```

```
<210> SEQ ID NO 143
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Ile Val Met Thr Gln Ser Pro Leu Ser Leu Pro Val Thr Pro Gly
1               5                   10                  15

Glu Pro Ala Ser Ile Ser Cys
            20
```

```
<210> SEQ ID NO 144
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Trp Tyr Leu Gln Lys Pro Gly Gln Ser Pro Gln Leu Leu Ile Tyr
1               5                   10                  15
```

```
<210> SEQ ID NO 145
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30
```

```
<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146
```

-continued

```
Phe Gly Gly Gly Thr Lys Val Glu Ile Lys
1               5                   10

<210> SEQ ID NO 147
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Ile Val Met Thr Gln Ser Ala Pro Ser Val Pro Val Thr Pro Gly
1               5                   10                  15

Glu Ser Val Ser Ile Ser Cys
            20

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Trp Phe Leu Gln Lys Pro Gly Gln Ser Pro Gln Arg Leu Ile Tyr
1               5                   10                  15

<210> SEQ ID NO 149
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Gly Val Pro Asp Arg Phe Ser Gly Arg Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Phe Gly Gly Gly Thr Lys Leu Glu Ile Lys
1               5                   10

<210> SEQ ID NO 151
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asp Ile Val Met Thr Gln Ser Ala Leu Ser Leu Pro Val Thr Pro Gly
1               5                   10                  15
```

-continued

```
Glu Pro Val Ser Ile Ser Cys
        20

<210> SEQ ID NO 152
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Trp Phe Leu Gln Lys Pro Gly Gln Ser Pro Gln Arg Leu Ile Tyr
1               5                   10                  15

<210> SEQ ID NO 153
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Phe Gly Gly Gly Thr Lys Leu Glu Ile Lys
1               5                   10

<210> SEQ ID NO 155
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (18)..(18)
<223> OTHER INFORMATION: Any amino acid

<400> SEQUENCE: 155

Asp Ile Val Met Thr Gln Xaa Ala Xaa Ser Xaa Pro Val Thr Pro Gly
1               5                   10                  15

Glu Xaa Val Ser Ile Ser Cys
```

20

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 156

Trp Phe Leu Gln Xaa Pro Gly Gln Ser Pro Gln Arg Leu Ile Tyr
1               5                   10                  15

<210> SEQ ID NO 157
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Any amino acid
<220> FEATURE:
<221> NAME/KEY: MOD_RES
<222> LOCATION: (18)..(18)
<223> OTHER INFORMATION: Any amino acid

<400> SEQUENCE: 157

Gly Val Pro Asp Arg Phe Ser Gly Xaa Gly Ser Gly Thr Asp Phe Thr
1               5                   10                  15

Leu Xaa Ile Ser Arg Val Glu Ala Glu Asp Val Gly Val Tyr Tyr Cys
            20                  25                  30

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Phe Gly Gly Gly Thr Lys Leu Glu Ile Lys
1               5                   10

<210> SEQ ID NO 159
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser
            20                  25                  30

<210> SEQ ID NO 160
<211> LENGTH: 14

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Trp Ser Arg Gln Pro Ser Gly Lys Gly Leu Glu Trp Leu Ala
1               5                   10

<210> SEQ ID NO 161
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Arg Leu Thr Ile Ser Lys Asp Thr Ser Lys Asn Gln Val Phe Leu Lys
1               5                   10                  15

Ile Ala Asn Val Asp Thr Ala Asp Thr Ala Thr Tyr Tyr Cys Thr Arg
            20                  25                  30

<210> SEQ ID NO 162
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Trp Gly Gln Gly Thr Ser Val Thr Val Ser Ser
1               5                   10

<210> SEQ ID NO 163
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 164
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Trp Ile Arg Gln Pro Pro Gly Lys Ala Leu Glu Trp Leu Ala
1               5                   10

<210> SEQ ID NO 165
<211> LENGTH: 32
<212> TYPE: PRT
<213> ORGANISM: Artificial Sequence
<220> FEATURE:

-continued

<223> OTHER INFORMATION: Description of Artificial Sequence: Synthetic
      polypeptide

<400> SEQUENCE: 165

Arg Leu Thr Ile Thr Lys Asp Thr Ser Lys Asn Gln Val Val Leu Thr
1               5                   10                  15

Met Thr Asn Met Asp Pro Val Asp Thr Ala Thr Tyr Tyr Cys Ala His
            20                  25                  30

<210> SEQ ID NO 166
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Trp Gly Gln Gly Thr Leu Val Thr Val Ser Ser
1               5                   10

<210> SEQ ID NO 167
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Thr Leu Lys Glu Ser Gly Pro Gly Ile Leu Gln Pro Thr Gln
1               5                   10                  15

Thr Leu Thr Leu Thr Cys Thr Phe Ser Gly Phe Ser Leu Ser
            20                  25                  30

<210> SEQ ID NO 168
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Trp Ser Arg Gln Pro Ser Gly Lys Gly Leu Glu Trp Leu Ala
1               5                   10

<210> SEQ ID NO 169
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Arg Leu Thr Ile Thr Lys Asp Thr Ser Lys Asn Gln Val Phe Leu Lys
1               5                   10                  15

Ile Thr Asn Val Asp Thr Ala Asp Thr Ala Thr Tyr Tyr Cys Thr Arg
            20                  25                  30

<210> SEQ ID NO 170
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 170

Trp Gly Gln Gly Thr Leu Val Thr Val Ser Ser
1               5                   10

<210> SEQ ID NO 171
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 172
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Trp Ser Arg Gln Pro Ser Gly Lys Gly Leu Glu Trp Leu Ala
1               5                   10

<210> SEQ ID NO 173
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Arg Leu Thr Ile Thr Lys Asp Thr Ser Lys Asn Gln Val Val Leu Thr
1               5                   10                  15

Ile Thr Asn Val Asp Pro Val Asp Thr Ala Thr Tyr Tyr Cys Thr Arg
            20                  25                  30

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Trp Gly Gln Gly Thr Leu Val Thr Val Ser Ser
1               5                   10

<210> SEQ ID NO 175
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<221> NAME/KEY: MOD_RES
<222> LOCATION: (10)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid
<220> FEATURE:
<221> NAME/KEY: MOD_RES
<222> LOCATION: (19)..(19)
<223> OTHER INFORMATION: Any amino acid
<220> FEATURE:
<221> NAME/KEY: MOD_RES
<222> LOCATION: (23)..(23)
<223> OTHER INFORMATION: Any amino acid

<400> SEQUENCE: 175

Gln Val Thr Leu Lys Glu Ser Gly Pro Xaa Xaa Xaa Xaa Pro Xaa Gln
1               5                   10                  15

Thr Leu Xaa Leu Thr Cys Xaa Phe Ser Gly Phe Ser Leu Ser
            20                  25                  30

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Trp Ser Arg Gln Pro Ser Gly Lys Gly Leu Glu Trp Leu Ala
1               5                   10

<210> SEQ ID NO 177
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (18)..(18)
<223> OTHER INFORMATION: Any amino acid
<220> FEATURE:
<221> NAME/KEY: MOD_RES
<222> LOCATION: (22)..(23)
<223> OTHER INFORMATION: Any amino acid

<400> SEQUENCE: 177

Arg Leu Thr Ile Xaa Lys Asp Thr Ser Lys Asn Gln Val Xaa Leu Xaa
1               5                   10                  15

Ile Xaa Asn Val Asp Xaa Xaa Asp Thr Ala Thr Tyr Tyr Cys Thr Arg
            20                  25                  30

<210> SEQ ID NO 178
<211> LENGTH: 11
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid

<400> SEQUENCE: 178

Trp Gly Gln Gly Thr Xaa Val Thr Val Ser Ser
1               5                   10

<210> SEQ ID NO 179
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Gly Gly Gly Gly Ser Gly Gly Gly Gly Ser Gly Gly Gly Gly Ser
1               5                   10                  15

<210> SEQ ID NO 180
<211> LENGTH: 114
<212> TYPE: PRT
<213> ORGANISM: Homo sapiens

<400> SEQUENCE: 180

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Asn Phe Thr
            20                  25                  30

Leu Asp Arg Ser Ser Val Leu Val Asp Gly Tyr Ser Pro Asn Arg Asn
        35                  40                  45

Glu Pro Leu Thr Gly Asn Ser Asp Leu Pro Phe Trp Ala Val Ile Leu
    50                  55                  60

Ile Gly Leu Ala Gly Leu Leu Gly Val Ile Thr Cys Leu Ile Cys Gly
65                  70                  75                  80

Val Leu Val Thr Thr Arg Arg Arg Lys Lys Glu Gly Glu Tyr Asn Val
                85                  90                  95

Gln Gln Gln Cys Pro Gly Tyr Tyr Gln Ser His Leu Asp Leu Glu Asp
            100                 105                 110

Leu Gln

<210> SEQ ID NO 181
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Asn Phe Ser Pro Leu Ala Arg Arg Val Asp Arg Val Ala Ile Tyr Glu
1               5                   10                  15

Glu Phe Leu Arg Met Thr Arg Asn Gly Thr Gln Leu Gln Ala Phe Thr
            20                  25                  30

Leu Asp Arg Ser Ser Val Leu Val Asp Gly Tyr Ser Pro Asn Arg Asn
        35                  40                  45
```

-continued

```
Glu Pro Leu Thr Gly Asn Ser Asp Leu Pro Phe Trp Ala Val Ile Leu
    50              55              60

Ile Gly Leu Ala Gly Leu Leu Gly Val Ile Thr Cys Leu Ile Cys Gly
65              70              75              80

Val Leu Val Thr Thr Arg Arg Arg Lys Lys Glu Gly Glu Tyr Asn Val
                85              90              95

Gln Gln Gln Cys Pro Gly Tyr Tyr Gln Ser His Leu Asp Leu Glu Asp
            100             105             110

Leu Gln
```

```
<210> SEQ ID NO 182
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (30)..(30)
<223> OTHER INFORMATION: Asn or Ala

<400> SEQUENCE: 182
```

```
Asn Phe Ser Pro Leu Ala Arg Arg Val Asp Arg Val Ala Ile Tyr Glu
1               5               10              15

Glu Phe Leu Arg Met Thr Arg Asn Gly Thr Gln Leu Gln Xaa Phe Thr
                20              25              30

Leu Asp Arg Ser Ser Val Leu Val Asp Gly Tyr Ser Pro Asn Arg Asn
        35              40              45

Glu Pro Leu Thr Gly Asn Ser Asp Leu Pro Phe Trp Ala Val Ile Leu
    50              55              60

Ile Gly Leu Ala Gly Leu Leu Gly Val Ile Thr Cys Leu Ile Cys Gly
65              70              75              80

Val Leu Val Thr Thr Arg Arg Arg Lys Lys Glu Gly Glu Tyr Asn Val
                85              90              95

Gln Gln Gln Cys Pro Gly Tyr Tyr Gln Ser His Leu Asp Leu Glu Asp
            100             105             110

Leu Gln
```

```
<210> SEQ ID NO 183
<211> LENGTH: 18
<212> TYPE: PRT
<213> ORGANISM: Homo sapiens

<400> SEQUENCE: 183
```

```
Thr Leu Asp Arg Ser Ser Val Leu Val Asp Gly Tyr Ser Pro Asn Arg
1               5               10              15

Asn Glu
```